US006197963B1

(12) United States Patent
Hirschmann et al.

(10) Patent No.: US 6,197,963 B1
(45) Date of Patent: Mar. 6, 2001

(54) NON-PEPTIDE PEPTIDOMIMETICS

(75) Inventors: Ralph Hirschmann, Blue Bell, PA (US); John Hynes, Jr., Irvine, CA (US); Maria A. Cichy-Knight, West Chester; Rachel D. van Rijn, Philadelphia, both of PA (US); Paul A. Sprengeler, El Granada, CA (US); P. Grant Spoors, Exton, PA (US); William C. Shakespeare, Watertown, MA (US); Sherrie Pietranico-Cole, West Milford, NJ (US); Amos B. Smith, III, Merion, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/133,546

(22) Filed: Aug. 13, 1998

(51) Int. Cl.$^7$ .................... C07D 209/10; C07D 209/56; C07D 309/04; C07D 405/16

(52) U.S. Cl. ...................... 546/282.1; 548/468; 548/517; 549/417

(58) Field of Search .............................. 548/311.1, 315.7, 548/466, 468, 952, 517; 549/414, 418, 417; 546/282.1

(56) References Cited

U.S. PATENT DOCUMENTS 5,552,534 * 9/1996 Hirschmann et al. .

OTHER PUBLICATIONS

B.H. Arison et al. Inferences about the conformation of somatostatin at a biologic receptor based on NMR studies, *Bioorganic Chemistry*, vol. 7, pp. 447–451, 1978.
B.H. Arison et al. On the low energy solution conformation of somatostatin, *Biochemical and Biophysical Research Communications*, vol. 100(3), pp. 1148–1153, 1981.
W. Bauer et al., A very potent and selective octapeptide analogue of somatostatin with prolonged action, *Life Sciences*, vol. 31, pp. 1133–1140, 1982.
S.F. Brady et al., Approaches to Peptidomimetics which serve as surrogates for the cis amide bond: Novel dsulfide–constrained bicyclic hexapeptide analogs of somatostatin, *Tetrahedron*, vol. 49, pp. 3449–3466, 1993.
P. Brazaeu et al., Hypothalamic polypeptide that inhibits the secretion of immunoreactive pituitary growth hormone, *Science*, vol. 179, pp. 77–79, 1972.
P. Bazeau et al. Isolation of Somatostatin (a somatotropin release inhbiting factor of ovine hypothalamic origin), *Can. J. Biochem.*, vol. 52, pp. 1067–1072, 1974.
T.Q. Dinh et al. Design, synthesis, and evaluation of the multidrug resistance–reversing activity of D–glucose mimetics of hapalosin, *J. Med. Chem.*, vol. 41, pp. 981–987, 1998.

Y. He et al., Syntheses and conformation of somatostain–related cyclic hexapeptides incorporating specific α–and β–methylated residues, *J. Am. Chem Soc.*, vol. 115, pp. 8066–8072, 1993.
H. He et al., Purification of a putative brain somatostatin receptor, *Proc. Natl. Acad. Sci., USA*, vol. 86, pp. 1480–1484, 1989.
R. Hirschmann et al., Nonpetidal petidomimetics with a β–D–Glucose scaffoliding. A partial somatostatin agonist bearing a close structural relationship to a potent, selective substance P antagonist, *J. Am. Chem. Soc.*, vol. 114, pp. 9217–9218, 1992.
R. Hirschmann et al., Modulation of receptor and receptor subtype affinities using diastereomeric and enantiomeric monosaccharide scaffolds as a means to structural and biological diversity. A new route to ether synthesis, *J. Med. Chem.*, vol. 41, 1382–1391, 1998.
R. Hirschmann, "Some recent developments in the chemistry and biology of somatostatin—related peptides", In Chemistry of Natural Products: The Proceedings of Sino–American Symposium on Chemistry of Natuaral Products, W. Yu, ed. Gordon and Breach Science Publishers, New York, pp. 44–54, 1982.
R. Hirschmann et al. Synthesis of potent cyclic hexapeptide NK–1 antagonists. Use of a minilibrary in transforming a peptidal somatostatin receptor ligand into an NK–1 receptor ligand via a polyvalent peptidomimetic, *J. Med. Chem.*, vol. 39, pp. 2441–2448, 1996.
R. Hirschmann et al. De novo design and synthesis of somatostatin non–peptide peptidomimetics utilizing β–D–glucose as a novel scaffolding, *J. Am. Chem. Soc.*, vol. 115, pp. 12550–12568, 1993.
R. Hirschmann et al., "Peptide related research, A means to further biological and chemical understanding", Peptides 1996—Proceedings of the 24$^{th}$ European Peptide Symposium, R. Ramage and R. Epton, eds. Gordon and Breach, Science Publishers, New York, pp. 3–17, 1996.

(List continued on next page.)

Primary Examiner—Cecilia Tsang
Assistant Examiner—Taofiq A. Solola
(74) Attorney, Agent, or Firm—Woodcock Washburn Kurtz Mackiewicz & Norris LLP

(57) ABSTRACT

Compounds are provided which are crossreactive with peptides such as those which bind G-protein-linked receptors, together with preparative and therapeutic methods therefor. The compounds have the general structure:

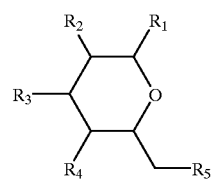

wherein at least one of $R_1$, $R_2$, $R_3$, $R_4$, or $R_5$ comprises a functional group which is chemically similar to that found in the peptide of interest.

15 Claims, No Drawings

OTHER PUBLICATIONS

Z. Huang et al., Cyclic hexapeptide analogs of somatostatin containing bridge modifications, *Int. J. Peptide Protein Res.*, vol. 42, pp. 352–365, 1993.

Z. Huang et al., Main chain and side chain chiral methylated somatostatin analogs: syntheses and conformational analyses, *J. Am. Chem. Soc.*, vol. 114, 9390–9401, 1992.

N. Kimura et al. Characterization of 17-β–estradiol–dependent and –independent somatostatin receptor subtypes in rat anterior pituitary*, *J. Biol. Chem.*, vol. 264, pp. 7033–7040, 1989.

S. Lamberts et al., Octreotide, *New England Journal of Medicine*, vol. 334, pp. 246–254, 1996.

T. LeDiguarher et al., Synthesis of potential peptidomimetics based on highly substituted glucose and allose scaffolds, *Biorganic & Medicinal Chemistry Letters*, vol. 6, pp. 1983–1988, 1996.

K.C. Nicolaou[a] et al., "Design and synthesis of a peptidomimetic employing β–D–glucose for scaffolding" in Peptides, Chemistry, Structure and Biology: Proceedings of the 11th American Peptide Symposium, Rivier and Marshall, eds. ESCOM, pp. 881–884, 1990.

K.C. Nicolau[a] et al., Design synthesis and biological evaluation of carbohydrate–based mimetics of cRGDFV, *Tetrahedron*, vol. 53, pp. 8751–8778, 1997.

C. Papageorgiou* et al., Design, synthesis, and binding affinity of a non peptide mimic of somatostatin, *Bioorganic & Medicinal Chemistry Letters*, vol. 2, pp. 135–140, 1992.

E. Pohl et al., Structure of Octretide, a somatostatin analogue, *Acta Cryst.* Sec. D51, pp. 48–59, 1995.

K. Raynor et al., Analogs of somatostatin selectively label distinct subtypes of somatostatin receptors in rat brain[1], *J. Pharmacol. and Exper. Therapeut.*, vol. 251, pp. 510–517, 1989.

K. Raynor et al., Cloned somatostatin receptors: Identification of subtype–selective peptides and demonstration of high affinity binding of linear peptides, *Molecular Pharamcology*, vol. 43, pp. 838–844, 1993.

T.D. Reisine et al., The localization of receptor binding sites in the *substantia nigra* and striatum of the rat, *Brain Research*, vol. 177, pp. 241–252, 1979.

S. Rens–Domiano et al. Pharmacological properties of two cloned somatostatin receptors, *Molecular Pharmacology*, vol. 42, pp. 28–34, 1992.

D. H. Rich, "Inhibitors of aspartic proteinases", Research monographs in cell and tissue physiology, vol. 12, Dingle and Gordon Eds., Elsevier, New York, pp. 178–217, 1986.

J. Rivier, Somatostain. Total solid Phase synthesis, *J. Am. Chem. Soc.*, vol. 96, pp. 2986–2992, 1974.

J. Rivier, D–Trp[8]–Somatostatin: An analog of somatostatin more potent than the native molecule, *Biochemical and Biophysical Research Communications*, vol. 65, pp. 746–751, 1975.

W.J. Rossowski et al., Specific inhibition of rat pancreatic insulin or glucagon release by receptor–selective somatostatin analogs, *Biochemical and Biophysical Research Communications*, vol. 265, pp. 341–346, 1994.

G. Sassolas, Medical thereapy with somatostain analogues for acromegaly, *European J. of Endocrinology*, vol. 133, pp. 675–677, 1995.

D.B. Sherman et al. Compatibility of thioamides with reverse turn features: synthesis and conformational analysis of two model cyclic pseudopeptides containing thioamides as backbone modifications[1], *J. Am. Chem. Soc.*, vol. 112, pp. 433–441, 1990.

S.P. Sreedharan et al., Distinct subsets of somatostatin receptors on cultured human lymphocytes*, *J. Biol. Chem.*, vol. 264, pp. 949–952, 1989.

E.D. Thorsett et al., Dipeptide mimics. Conformationally restricted inhibitors of angiotensin–converting enzyme, *Biochemical and Biophysical Research Communications*, vol. 111, pp. 166–171, 1983.

D.F. Veber et al., Conformationally restricted bicyclic analogs of somatostatin, *Proc. Natl. Acad. Sci. USA*, pp. 2636–2640, 1978.

D.F. Veber et al., A super active cyclic hexapeptide analog of somatostatin, *Life Sciences*, vol. 34, pp. 1371–1378, 1984.

D.F. Veber et al., A potent cyclic hexapeptide analogue of somatostatin, *Nature*, vol. 292, pp. 55–58, 1981.

E. von Roedern et al., Synthesis and conformational analysis of linear and cyclic peptides containing sugar amino acids, *J. Am. Chem. Soc.*, vol. 118, pp. 10156–10167, 1996.

* cited by examiner

NON-PEPTIDE PEPTIDOMIMETICS

GOVERNMENT SUPPORT

Certain of the inventors have been supported by National Institute of Mental Health Grant 45533 and National Institutes of Health Grant GM-41821.

FIELD OF THE INVENTION

This invention relates to synthetic compounds which mimic or inhibit the biological and/or chemical activity of peptides, including compounds which bind G-protein-linked receptors, like the somatostatin (SRIF) receptors, and NK-1 receptors.

BACKGROUND OF THE INVENTION

Peptides are implicated in a wide variety of biochemical processes in humans and other mammals. For example, it is known that a number of hormones and neurotransmitters are controlled by receptor-mediated stimulation of one or more of a family of guanine nucleotide-binding regulatory proteins, known as G-proteins. G-proteins activate or inhibit different effector enzymes, modulating the levels of intracellular second messengers. At least 50 sub-types of G-protein-linked (G-protein coupled) receptors have been identified, among them the α-adrenergic, β-adrenergic, muscarinic, cholinergic, dopamine, histamine, adenosine, serotonin, prostaglandin, leukotriene, thromboxane, prostacyclin, PAF, cAMP, enkephalin, endorphin, cholecystokinin, bombesin, substance K, substance P, neuromedin, bradykinin, FMLP, C5a, C3a, vasopressin, oxytocin, angiotensin, VIP, parathyroid hormone, calcitonin, neurotensin, TRH, somatostatin, rhodopsin, epinephrine, norepinephrine, acetylcholine, S-hydroxytryptamine, thyrotropin, thyrotropin releasing hormone, follicle stimulating, lutropin, choriogonadotropin, thrombin, retinal, and olfactory receptors. Nine or more G-proteins and at least seven effector systems have also been described. All of the G-protein-linked receptors analyzed to date contain from one to three potential sites of asparagine-linked glycosylation.

The transmembrane signaling pathway used by G-protein-linked receptors represents one of the major mechanism of signal transduction in cellular systems. It is known, for example, that substance P acts as a vasodilator, a depressant, stimulates salivation, and produces increased capillary permeability. Substance P is a naturally occurring undecapeptide belonging to the tachykinin family of peptides, the latter being so-named because of their prompt contractile action on extravascular smooth muscle tissue. In addition to substance P (neurokinin-1 receptor, NK-1), the known mammalian tachykinins include neurokinin A (NK-2 receptor) and neurokinin B (NK-3). The tachykinins have been implicated in gastrointestinal (GI) disorders and diseases of the GI tract, such as inflammatory bowel disease, ulcerative colitis and Crohn's disease.

Substance P is known to produce both analgesia and hyperalgesia in animals, depending on dose and pain responsiveness of the animal and plays a role in sensory transmission and pain perception. Substance P also is believed to be involved in the inflammatory response in diseases such as rheumatoid arthritis and osteoarthritis. Other disease areas where the tachykinins are believed to be involved include allergic conditions, immunoregulation, bronchospasm, reflex or neuronal control of the viscera, and Alzheimer's disease and Downs Syndrome.

Somatostatin, a cyclic tetradecapeptide, has attracted attention for its therapeutic potential. Brazeau et al., Science 1973, 179, 77–79. Brazeau et al., *Can. J. Biochem.* 1974, 52, 1067–1072; Rivier et al., *J. Am. Chem. Soc.* 1974, 96,2986–2992;] Hirschmann et al. "Some Recent Developments in the Chemistry and Biology of Somatostatin-Related Peptides". In *Chemistry of Natural Products: The Proceedings of Sino-American Symposium on Chemistry of Natural Products*; Yu, W., Ed.; Gordon and Breach, Science Publishers: New York, 1982; pp 44–54 and references cited therein. Indeed the parenteral peptidal drug octreotide has been approved for clinical use; see: Bauer, W.; Briner, U.; Doepfner, W.; Haller, R.; Huguenin, R.; Marbach, P.; Petcher, T. J.; Pless, J. *Life Sciences* 1982, 31, 1133–1140. Lamberts, S. W.; van der Lely, A.-J.; de Herder, W. W.; Hofland, L. J. Octreotide. *New Engl. J. Med.* 1996, 334, 246–254. Sassolas, G. *Eur. J. Endocrinology* 1995, 133, 675–677. It has been demonstrated that Phe[7] of somatostatin has an axial disposition.

To date, there have been limited therapeutic applications involving peptides, due in considerable part to lack of oral bioavailability and to proteolytic degradation. Typically, for example, peptides are rapidly degraded in vivo by exo- and endopeptidases, resulting in generally very short biological half-lives. Another deficiency of peptides as potential therapeutic agents is their lack of bioavailability via oral administration. Degradation of the peptides by proteolytic enzymes in the gastrointestinal tract is likely an important contributing factor. The problem is, however, more complicated, because it has been recognized that even small, cyclic peptides which are not subject to rapid metabolic inactivation nevertheless exhibit poor oral bioavailability. This likely is due to poor transport across the intestinal membrane and rapid clearance from the blood by hepatic extraction with subsequent excretion into the intestine. These observations suggest that multiple amide bonds may interfere with oral bioavailability.

The design of peptide mimics which are resistant to degradation by proteolytic enzymes has become of increasing interest to peptide chemists, both for hormone agonist/antagonist and for enzyme inhibitor design. A primary goal has been to reduce the susceptibility of mimics to cleavage and inactivation by peptidases. In one approach, such as disclosed by Sherman and Spatola, *J. Am. Chem. Soc.*, 112, 1990, 433, one or more amide bonds have been replaced in an essentially isosteric manner by a variety of chemical functional groups. This stepwise approach has met with some success in that active analogs have been obtained. In some instances, these analogs have been shown to possess longer biological half-lives than their naturally-occurring counterparts. Nevertheless, this approach has limitations. Successful replacement of more than one amide bond has been rare. Consequently, the resulting analogs have remained susceptible to enzymatic inactivation elsewhere in the molecule. Moreover, this approach does not permit generalizations between chemically unrelated peptides concerning permissible amide mimic substitutions.

In another approach, a variety of uncoded or modified amino acids such as D-amino acids and N-methyl amino acids have been used to modify mammalian peptides. Alternatively, a presumed bioactive conformation has been stabilized by a covalent modification, such as cyclization or by incorporation of y-lactam or other types of bridges. See, e.g., Veber and Hirschmann, et al., *Proc. Natl. Acad. Sci. USA*, 1978 75 2636 and Thorsett, et al., *Biochem Biophys. Res. Comm.*, 1983, 111, 166. The primary purpose of such manipulations has not been to avoid metabolism or to enhance oral bioavailability but rather to constrain a bioactive conformation to enhance potency or to induce greater specificity for a receptor subtype.

Another approach, disclosed by Rich, D. H. in *Protease Inhibitors*, Barrett and Selveson, eds., Elsevier, p. 179–217 (1986), has been to design peptide mimics through the application of the transition state analog concept in enzyme inhibitor design. For example, it is known that the secondary alcohol of statine mimics the tetrahedral transition state of the scissile amide bond of the pepsin substrate. Again, increased potency rather than decreased susceptibility to peptidases or increased bioavailability was the principal objective. Moreover, the transition state analog concept has no apparent relevance to hormone agonist/antagonist design.

Nicolaou and Hirschmann, et al., *Design and synthesis of a peptidomimetic employing β-D-glucose for scaffolding*, in Peptides, Chemistry, Structure and Biology: Proceedings of the 11th American Peptide Symposium, Rivier and Marshall, eds., ESCOM (1990), p. 881–884, disclosed non-peptide somatostatin mimics having structures (III-4a) and (III-5a), wherein Bn is benzyl.

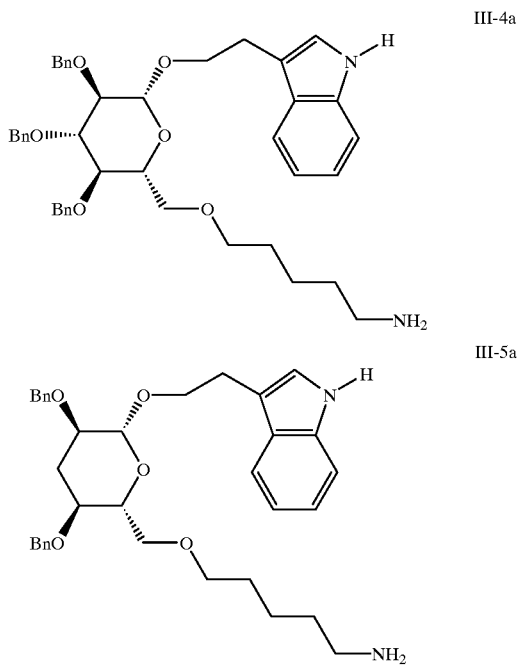

III-4a

III-5a

These mimics bound somatostatin receptors of AtT-20 cells with $IC_{50}$ of about $15 \times 10^{-6}$ M and about $10 \times 10^{-6}$ M, respectively, compared with an $IC_{50}$ of about 9.3 nM ($9.3 \times 10^{-9}$ M) for somatostatin itself. Significantly, the mimics failed to bind other G-protein-linked receptors at clinically acceptable concentrations. For example, while it was found that the β-adrenergic receptor, which is also found in AtT-20 cells, bound mimic (III-4a), it required a five fold higher concentration to do so than was required for the somatostatin receptor. The goal of the authors was to increase the specificity of the mimics for the somatostatin receptor, not to develop compounds which would be bound by G-protein-linked receptors. Indeed, the authors suggested increasing the potency of the compounds as a means for enhancing this specificity.

Accordingly, there remains a long-felt need for metabolically stable chemical compounds which exhibit both good bioavailability and the capacity to bind a variety of G-protein-linked receptors.

OBJECTS OF THE INVENTION

It is one object of the present invention to provide compositions of matter which mimic or inhibit the biological and/or chemical activity of peptides.

It is another object to provide compositions which are chemically more stable than naturally-occurring peptides, particularly under conditions such as found in the human body.

It is a further object to provide compositions which function as hormone agonists or hormone antagonists.

It is a further object to provide compositions which effectively bind G-protein-linked receptors, especially the substance P receptor and the somatostatin receptor.

It is still a further object to provide prophylactic, diagnostic, and therapeutic uses for peptide analogs.

SUMMARY OF THE INVENTION

These and other objects are accomplished by the present invention, which provides compounds, known as peptide analogs, which contain no peptide bonds yet which mimic or inhibit the chemical and/or biological activity of peptides.

It has been discovered that diasteriomeric, enantiomeric, and other sugar congeners can be employed to modulate receptor and receptor subtype affinities and that unexpectedly diverse sugar scaffolds can be used in a library mode to gain information about the bioactive conformation of peptides. Hirschmann et al., *J. Med. Chem.* 1998, 41, 1382–1391. It has also been discovered that the flow of information between peptoide and peptidomimetic can be bidirectional. Id. Further, it has been observed that the stereochemical diversity of readily available monosaccharides represents an improtant advantage of carbohydrate-based scaffolds over hydrocarbon scaffolds. Id.

In general, the peptide analogs of the invention have structure (3):

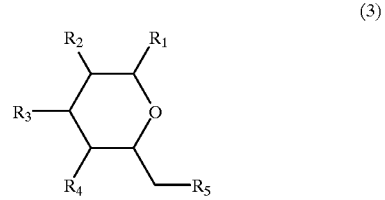

(3)

wherein at least one of $R_1$, $R_2$, $R_3$, $R_4$, or $R_5$ comprises a chemical functional group which causes the compounds to be crossreactive with the peptide of interest.

In certain preferred embodiments, peptide analogs of the invention may have the following structures:

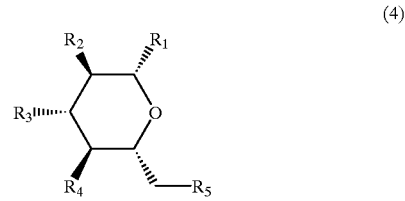

(4)

(5)

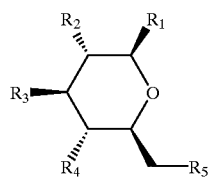

(6)

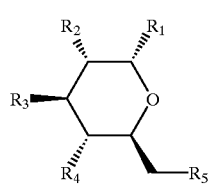

(7)

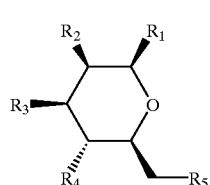

(8)

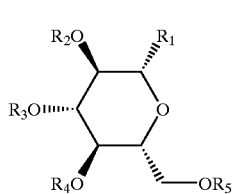

(9)

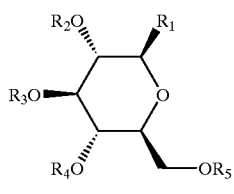

(10)

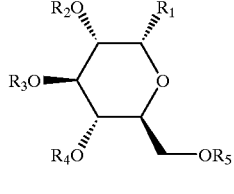

(11)

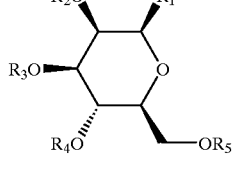

Compounds having these structures have been found to effectively bind a number of G-protein-linked receptors. It has also been found that the stereochemistry of the sugar scaffold can be employed to influence receptor and receptor subtype affinities. This represents an important advantage of carbohydrate-based scaffolds over hydrocarbon scaffolds.

The peptide analogs of the invention can be employed to mediate the chemical and/or biological effects of hormone agonists/antagonists or other peptides. These compounds are believed to possess beneficial properties such as increased half-life, lack of immunogenicity, and the ability to cross the blood-brain barrier; they are believed to be useful for the development of pharmaceutical, therapeutic, and diagnostic techniques. Accordingly, the invention also provides methods for producing a prophylactic or therapeutic response in a mammal by administering to the mammal a pharmaceutically effective amount of one or more peptide analogs of the invention. In accordance with preferred embodiments, the present invention provides methods for producing such responses by modulating the activity of at least one mammalian G-protein-linked receptor by administering an effective amount of one or more peptide analogs of the invention.

DETAILED DESCRIPTION OF THE INVENTION

It has been found in accordance with the present invention that non-peptide compounds which mimic or inhibit the chemical and/or biological activity of a variety of peptides can be produced by appending to certain core species, such as the tetrahydropyranyl ring of structure (3), chemical functional groups which cause the compounds to be at least partially crossreactive with the peptide. It has further been found that enantiomers, diastereoisomers and regioisomers of such core species (3) can be employed to influence receptor and receptor subtype affinities. As will be recognized, compounds which mimic or inhibit peptides are to varying degrees crossreactive therewith. In accordance with the present invention, crossreactive moieties are those which compete with one another in binding G-protein-linked receptors through one of the many chemical reaction phenomena known in the art such as, for example, complexation, crystallization, or ionic, hydrogen, or covalent bonding. Thus, it is intended that the term "crossreactive" include both agonism and antagonism. Those skilled in the art recognize that a substance which competes with a G-protein in binding to a cell receptor is described as an agonist if the response of the cell is the same as or mimics the action of the peptide ligand. A substance that competes with the G-protein in binding to a receptor is referred to as antagonist if it blocks or inhibits the action of the cell to the action of the G-protein.

There exists a wide variety of useful analytical techniques for elucidating the precise structure of a peptide. These techniques include amino acid sequencing, x-ray crystallography, mass spectroscopy, nuclear magnetic resonance spectroscopy, computer-assisted molecular modeling, peptide mapping, and combinations thereof. Structural analysis of a peptide generally provides a large body of data which in preferred embodiments comprises the amino acid sequence of the peptide as well as the three-dimensional positioning of its atomic components. It is believed that only certain of these components, which are known both individually and collectively as chemical functionality, participate in any given reaction phenomena. It will be appreciated that the participation of a chemical functional group in peptide reactivity is manifested by the linkage or coordination of the functional group with at least a portion of a complementary reactive moiety such as a hormone receptor. Such linkage or binding may be effected through a covalent, ionic, or hydrogen bond or some weaker atomic coordination effect such as complexation or crystallization.

In accordance with the present invention, peptide chemical functionality which participates in binding is identified by one of the many techniques known in the art. For example, such identification can be effected through a stepwise process wherein one or more peptide analogs are prepared. For example, peptide analogs having structure (3) can be prepared by substitution at certain of the positions R₁–R₅ with chemical functionalities which are crossreactive with functionalities found in the peptide. The activity of the analog in a binding assay is then compared with that of the peptide. The degree to which the binding of the analog corresponds with that of the peptide indicates the degree to which the substituents participate in the binding phenomena. Accordingly, one important criterion in preparing peptide analogs according to the present invention is the respective chemical similarity of the side chains found in the peptide and any potential substitutes therefor appended to the core structure in the analog. In general, it is desired that the chemical functional group in the peptide of interest and its substitute in at least one of the peptide analogs be somewhat chemically dissimilar. Where the substitute is chemically dissimilar from the peptide side chain, it will generally be easier to elucidate the contribution, if any, of side chain to activity of the peptide.

For example, it is believed that the bioactive conformation of somatostatin (also known as somatotropin release inhibiting factor or SRIF) includes a β-turn involving residues 7–10 (Phe⁷-Trp⁸-Lys⁹-Thr¹⁰). These four amino acids have been shown to be necessary and sufficient for receptor recognition and activation, so long as they are held in the proper orientation. Somatostatin accomplishes this proper orientation through its ten remaining amino acids and the cystine bridge contained therein. In a number of active cyclic hexapeptide analogs for somatostatin, proper orientation of the four amino acids is maintained via dipeptide segments. For example, the cyclic hexapeptide L-363,301 (structure (9a)), disclosed by Veber and Hirschmann, et al., *Life Sciences*, 1984, 34, 1371 and the cyclic hexapeptide MK-678 (structure (9b)), disclosed by Veber and Hirschmann, et al., *Nature*, 1981, 292, 55–58, accomplish the proper orientation via the segments Phe-N-Me-Ala or Phe-Pro, respectively.

(9a)

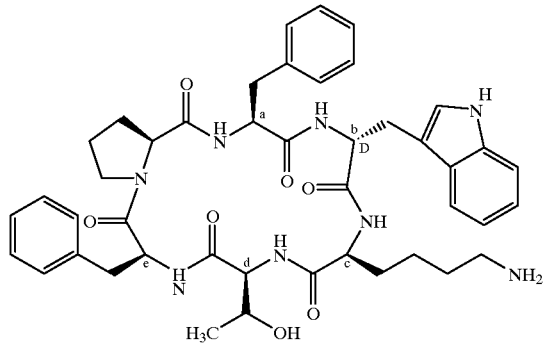

(9b)

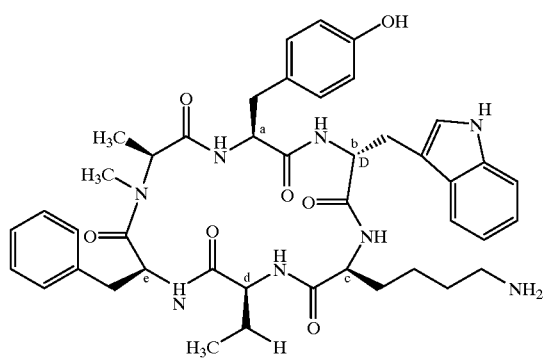

It is believed that the solution conformation of somatostatin involves a type I β-turn for residues 7–10 and that of the significantly more potent D-Trp diastereomer involves a type II' β-turn. While these two turns differ in the φ and ψ angles of the amide backbone, they are believed to assume similar orientations of the side chains at the receptor. In the cyclic hexapeptides, the Phe-N-Me-Ala sequence and the Phe-Pro sequence are believed to be part of a type VI β-turn. Of particular significance is the high activity found for a modified retro-enantiomeric cyclic hexapeptide wherein the amide backbone is reversed. This demonstrates that proper side chain topography is important for activity but that the amide backbone may not be.

In accordance with the present invention, peptide analogs having structure (3) were further simplified by including only three adjacent side chains of the four amino acids of the β-turn. These side chains are attached to rigid frameworks devoid of peptide bonds. The frameworks were developed through molecular modeling to orient the side chains appropriately and/or to permit the receptor to induce the proper fit.

While a proper β-turn requires the fourth amino acid of the β-turn—Thr in somatostatin and several cyclic hexapeptides and Val in the superactive cyclic hexapeptide—it is believed that neither the Thr nor the Val side chains are required for binding. This assumption is based on the fact that highly active somatostatin analogs are known which have either Val, Thr, Ser, α-aminobutyric acid, or Gly in the fourth position of the β-turn. Such non-specificity suggests a conformational rather than a binding role for that amino acid of the β-turn.

The phenylalanine residue in the dipeptide segments Phe-N-Me-Ala or Phe-Pro appears to add an important hydrophobic binding element. For this reason, the present synthetic analogs of somatostatin contain a corresponding aromatic residue. Increased hydrophobicity also should prove helpful in improving the duration of action and activity via oral administration of such compounds.

It is now believed that for the L-363,301 hexapeptide, structure (9a), the β-turn is important and the three groups extending from carbons a, b, and c—benzyl, indole, and alkylamino, respectively—are necessary for binding. Whereas the substituent at carbon d appears to be required to stabilize the β-turn rather than be required for binding, a benzyl group attached at carbon e of the skeleton is believed to be an important binding ligand which improves the activity of analogs. The compounds of the invention have been useful in elucidating the conformation of hexapeptide L-306,301 (see Example 104).

It has now been discovered that a new class of therapeutic agents can be formulated having activity in a broad spectrum of utilities, especially those related to the G-protein-linked receptors.

One member of the class is represented by structure (10a (III-4A) and 10b (III-4d)), respectively).

III-4a

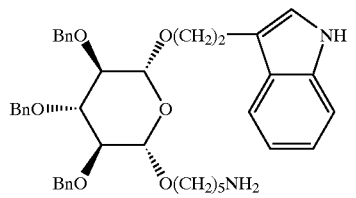

III-4d

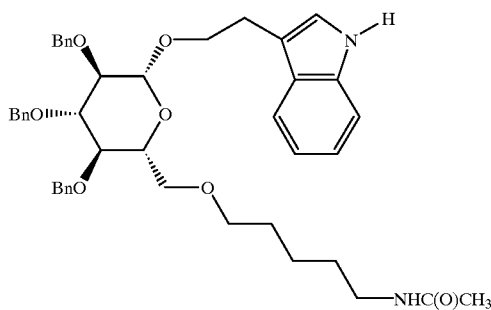

The calculated bond distances for structure (10b (III-4d)) and the cyclic hexapeptide suggest close geometrical similarities. Furthermore, overlaying models of the designed structure (10b (III-4d)) and the cyclic hexapeptide (9a) shows close correspondence of the important functionalities, particularly the phenylalanine, tryptophan and lysine residues.

The present invention, however, is not limited to embodiments wherein benzyl, indole, or alkylamino groups participate in binding. Participatory chemical functionality according to the present invention includes any of the wide variety of functional groups known in the art. The side chains of naturally-occurring amino acids provide examples of suitable participatory functionality. Representative participatory chemical functionality which may be contained within groups $R_1$–$R_5$ of structure (3) is set forth in Table 1. For example, one or more of R1–R5 can have the structure Z—$(CH_2)_y$— or Z—O—, where y is from 0 to about 6 and Z is one of the side chains of Table 1.

TABLE 1

| | |
|---|---|
| H— | $CH_3$—$CH_2$—S—$CH_2$—$CH_2$—(OH)—$CH_2$—$CH_2$— |
| $CH_3$— | $CH_3$—CH(OH)— |
| HO—$CH_2$— | $HO_2C$—$CH_2$—$NH_2C(O)$—$CH_2$— |
| $C_6H_5$—$CH_2$— |  |
| HO—$C_6H_5$—$CH_2$— | $HCO_2$—$CH_2$—$CH_2$— |
| 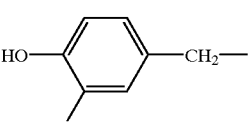 | $NH_2C(O)$—$CH_2$—$CH_2$— |
| 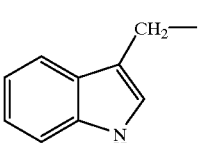 | $(CH_3)_2$—CH— |
| 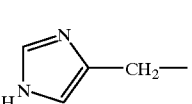 | $(CH_3)_2$—CH—$CH_2$— |
| | $CH_3$—$CH_2$—$CH_2$— |
| | $H_2N$—$CH_2$—$CH_2$—$CH_2$— |
| | $H_2N$—C(NH)—NH—$CH_2$—$CH_2$—$CH_2$— |
| | $H_2N$—C(O)—NH—$CH_2$—$CH_2$—$CH_2$— |
| | $CH_3$—$CH_2$—CH($CH_3$)— |

TABLE 1-continued

```
                                    CH₃—CH₂—CH₂—CH₂—
                                    H₂N—CH₃—CH₂—CH₂—CH₂—
                                    HO—CH₂—CH₂—CH₂—CH₂—CH₂—NH—
                                    HO—CH₂—CH₂—CH₂—CH₂—CH₂—NH—
                                    H₂N—CH₂—CH₂—CH₂—CH₂—CH₂—CH₂—
                                    H₂N—CH₂—CH₂—CH₂—CH₂—CH₂—
                                    CH₃—(O)—C—NH—CH₂—CH₂—CH₂—CH₂—
HS—CH₂—                             CH₂—H₂N—CH₃—(O)—C—NH—CH₂—CH₂—
HO₂C—CH(NH₂)—CH₂—S—S—CH₂—           CH₂—CH₂—CH₂—CH₂—NH—
CH₃—CH₂—                            H₂N—CH₂—CH₂—CH₂—CH₂—CH₂—NH—
CH₃—S—CH₂—CH₂—                      H₂N—CH₂—CH₂—CH₂—CH₂—CH₂—CH₂—NH—
``` tetrazole-CH₂

X = halogen

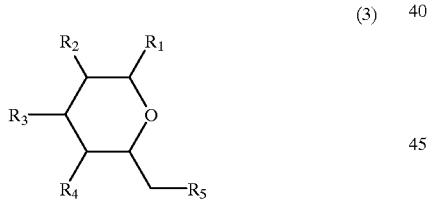

In accordance with the present invention, non-peptide analogs preferably possess the general structure (3):

(3)

wherein:
$R_1$ is H, —O(CH₂)$_n$R$_A$, —OC(O)(CH₂)$_n$R$_A$, —(CH₂)$_n$R$_A$, —C(O)(CH₂)$_n$R$_A$, —(CH₂)$_n$NHR$_A$ where R$_A$ is —H, alkyl or alkenyl having from about 1 to about 14 carbon atoms and up to about 4 nitrogen atoms, or aryl having from about 6 to about 14 carbon atoms and up to about 4 nitrogen atoms, and n is an integer from 0 to about 12;

at least one of $R_2$, $R_3$, and $R_4$, independently, is H, —O(CH₂)$_m$R$_B$, —OC(O)(CH₂)$_m$R$_B$, —(CH₂)$_m$R$_B$ or —C(O)(CH₂)$_m$R$_B$ (CH₂)$_n$NHR$_A$ where R$_B$ is —H, aryl having from about 5 to about 14 carbon atoms and up to about 4 nitrogen atoms, or haloaryl having from about 6 to about 14 carbon atoms, and m is an integer from 0 to about 6; and $R_5$ is H, O(CH₂)$_p$NHR$_C$, OC(O)(CH₂)$_p$NHR$_C$, (CH₂)$_p$NHR$_C$, NH(CH₂)$_p$OH, NH(CH₂)$_p$NHC(O)CH₃, NH(CH₂)$_p$NH₂, O(CH₂)$_p$R$_c$, O(CH₂)$_p$NHC(O)CH₃, O(CH₂)$_p$NH₂, O(CH₂)$_p$R$_D$, OC(O)(CH₂)$_p$R$_D$, (CH₂)$_p$NHR$_C$, C(O)(CH₂)$_p$NHR$_C$, (CH₂)$_p$R$_D$ or C(O)(CH₂)$_p$R$_D$, where:

p is an integer from 0 to about 10;
R$_C$ is —R$_E$ or —C(O)R$_E$;
R$_D$ is —H, —OR$_E$, or —C(O)R$_E$;
R$_E$ is —H, alkyl or alkenyl having from about 1 to about 14 carbon atoms and up to about 4 nitrogen atoms, or aryl having from about 6 to about 14 carbon atoms and up to about 4 nitrogen atoms; or a pharmaceutically acceptable salt thereof.

It will be understood that the terms "alkyl" and "alkenyl" as employed herein are intended to include cyclic as well as straight chain moieties. In certain embodiments, the peptide analogs of the invention possess structures 4–11, with $R_1$–$R_5$ defined as above.

As will be recognized, the precise identity of $R_1$–$R_5$ depends intimately upon the peptide of interest whose biological and/or chemical activity is to be mimicked or inhibited. The particular sterochemistry of the monosaccharide will also depend on the biological target. In general, certain preferred peptide analogs have the structures identified below:

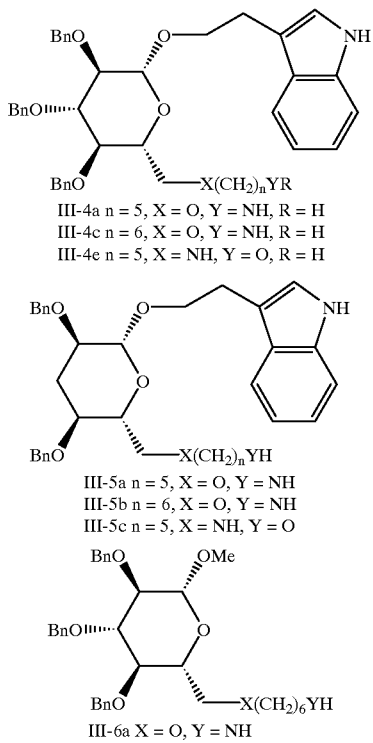

III-4a n = 5, X = O, Y = NH, R = H
III-4c n = 6, X = O, Y = NH, R = H
III-4e n = 5, X = NH, Y = O, R = H

III-5a n = 5, X = O, Y = NH
III-5b n = 6, X = O, Y = NH
III-5c n = 5, X = NH, Y = O

III-6a X = O, Y = NH

These peptide analogs are preferred to the extent that they selectively and effectively bind G-proteins-linked receptors, such as the somatostatin receptor, and the NK-1 receptor, although to different degrees. It will be recognized that the degree to which a compound binds a receptor is known as its binding activity or potency. The potency of a compound commonly is expressed as its inhibitory concentration (IC), the concentration at which the compound is able to displace a predetermined portion—typically 50%—of another compound which is already bound to a particular receptor. In the case of ligand-binding studies, the compound that is displaced is a radioactive agonist or antagonist at the receptor under study. It is preferred in accordance with the present invention that a peptide analog possess a clinically effective $IC_{50}$ in at least one mammal, that is, a concentration which is low enough to inhibit binding of radioactive agonist or antagonist of a given G-protein-linked receptor while causing a minimum of unacceptable side effects in the mammal. As will be recognized, clinically effective inhibitory concentrations vary depending on a number of factors, such as the pharmacokinetic characteristics and stability of the compound under study and thus must be determined empirically for each analog and each factor. For example, the clinically effective concentration for the human somatostatin receptor is about 50–500 nM, but for the in vitro system the potency is about 1–10 nM. In general, it is desired that the potency of a compound of the invention be as great as possible, preferably greater than or equal to the native protein.

Selectivity or specificity is manifested for a compound of the present invention by its tendency to bind one particular G-protein-linked receptor but not other G-protein-linked receptors or to have a preferential affinity for the receptor over another. In an experimental context, selectivity is manifested where a compound is bound by a particular receptor when placed in contact or close proximity with a medium containing at least one other receptor. Typically, specificity is expressed as a ratio of the potency or activity of a compound for two different receptors. Thus, a compound having an $IC_{50}$ of 100 μm for compound A and $IC_{50}$ of 200 μM for compound B can be said be two times more selective for compound A. In general, the selectivity of the peptide analogs of the present invention should be as great as possible. Selectivities greater than about 50–100 fold are preferred and selectivities greater than about 500 fold even more preferred.

In certain other preferred embodiments, wherein the core structure is (3),

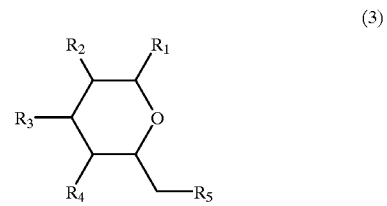

(3)

the compounds of the invention comprise those wherein $R_1$, $R_2$, $R_3$, $R_4$, and $R_5$ are H, OH, $OCH_3$, O—$(CH_2)_n NH_2$, O—$(CH_2)_n OH$, O—$(CH_2)_n NHC(O)CH_3$, O—$(CH_2)_n$-indole, O—(benzyl), O—$(CH_2)_n$(imidazole), pyridine, p-fluoro-benzyl, $CH_2$-β-naphthyl, $CH_2$-α-naphthyl, —$(CH_2)_n$-indole, —$CH_2$ Php-OH, —$CH_2$-picolyl, —NH$(CH_2)_5 NH_2$, —NH$(CH_2)_3 NHC(O)CH_3$, wherein n is 1, 2, 3, 4, 5, or 6, or —NH$(CH_2)_5 OH$, —NH$(CH_2)_6 OH$.

In certain other more preferred embodiments where the structure is (3), the compounds of the invention comprise those wherein:

(a) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_6$—$NH_2$;

(b) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_5$—$NH_2$;

(c) $R_1$ is methoxy, $R_2$ is O—$(CH_2)$-(imidazole), $R_3$ is O-(benzyl) $R_4$ is O-(benzyl), $R_5$ is O—$(CH_2)_5$—$NH_2$;

(d) $R_1$ is methoxy, $R_2$ is O—$(CH_2)$-(imidazole), $R_3$ is O-(benzyl) $R_4$ is O-(benzyl), $R_5$ is O—$(CH_2)_6$—$NH_2$;

(e) $R_1$ is methoxy, $R_2$ is O-(benzyl), $R_3$ is (O)—$(CH_2)$-(imidazole), $R_4$ is O-(benzyl), $R_5$ is O—$(CH_2)_5$—$NH_2$;

(f) $R_1$ is methoxy, $R_2$ is O-(benzyl), $R_3$ is (O)—$(CH_2)$-(imidazole), $R_4$ is O-(benzyl), $R_5$ is O—$(CH_2)_6$—$NH_2$;

(g) $R_1$ is (O)—$(CH_2)_2$-(indole), $R_2$ is O-(benzyl), $R_3$ is O-(benzyl), $R_4$ is O-(benzyl), $R_5$ is $NH(CH_2)_5 OH$;

(h) $R_1$ is (O)$(CH_2)_2$-(indole), $R_2$ is O-(benzyl), $R_3$ is O-(benzyl), $R_4$ is O-(benzyl), $R_5$ is $NH(CH_2)_6 OH$;

(i) $R_1$ is (O)$(CH_2)_2$-(indole), $R_2$ is O-(benzyl), $R_3$ is O-(benzyl), $R_4$ is O-(benzyl), $R_5$ is NH—$(CH_2)_5 NH_2$;

(j) $R_1$ is (O)$(CH_2)_2$-(indole), $R_2$ is O-(benzyl), $R_3$ is O-(benzyl), $R_4$ is O-(benzyl), $R_5$ is NH—$(CH_2)_6 NH_2$;

(k) $R_1$ is (O)$(CH_2)_2$-(indole), O—$CH_2$-β-naphthyl, $R_3$ is O-(benzyl), $R_4$ is O-(benzyl), $R_5$ is O-(p-fluorobenzyl);

(l) $R_1$ is (O)$(CH_2)_2$-(indole), $R_2$ is O-p-fluorobenzyl, $R_3$ is O-(benzyl), $R_4$ is O-(benzyl), $R_5$ is O—$(CH_2)_5$—NHC(O)$CH_3$;

(m) $R_1$ is (O)$(CH_2)_2$-(indole), $R_2$ is O-p-fluorobenzyl, $R_3$ is O-(benzyl), $R_4$ is O-(benzyl), $R_5$ is O—$(CH_2)_6$—NHC(O)$CH_3$;

(n) $R_1$ is (O)—$(CH_2)_2$-(indole), $R_2$ is O—$CH_2$-β-naphthyl, $R_3$ is O-(benzyl), $R_4$ is O-(benzyl), $R_5$ is O—$(CH_2)_5 NHC(O)CH_3$;

(o) $R_1$ is (O)—$(CH_2)_2$-(indole), $R_2$ is O—$CH_2$-β-naphthyl, $R_3$ is O-(benzyl) also O—$CH_2$-α-naphthyl, $R_4$ is O-(benzyl), $R_5$ is O—$(CH_2)_6NHC(O)CH_3$;

(p) $R_1$ is (O)—$(CH_2)_2$-(indole), $R_2$ is O-p-fluorobenzyl, $R_3$ is O-(benzyl), $R_4$ is O-(benzyl), $R_5$ is O—$(CH_2$-β-naphthyl);

(q) $R_1$ is $(CH_2)_2$-(indole), $R_2$ is O-(benzyl), $R_3$ is O-(benzyl), $R_4$ is O-(benzyl), $R_5$ is O—$(CH_2)$—NHC(O)$CH_3$;

(r) $R_1$ is methoxy, $R_2$ is O—$CH_2$-(imidazole), $R_3$ is O-(benzyl), $R_4$ is O-(benzyl), $R_5$ is O—$(CH_2)_5NH_2$;

(s) $R_1$ is methoxy, $R_2$ is O-(benzyl), $R_3$ is O—$CH_2$-(imidazole), $R_4$ is O-(benzyl), $R_5$ is O—$(CH_2)_5NH_2$;

(t) $R_1$ is methoxy, $R_2$ is O-(benzyl), $R_3$ is O—$CH_2$-(imidazole), $R_4$ is O-(benzyl), $R_5$ is O—$(CH_2)_6NH_2$.

In certain other preferred embodiments, wherein the core structure is (4):

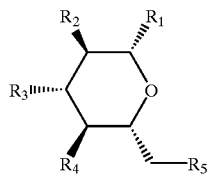

(4)

the compounds of the invention comprise those wherein $R_1$, $R_2$, $R_3$, $R_4$, and $R_5$ are H, OH, $OCH_3$, O—$(CH_2)_nNH_2$, O—$(CH_2)_nOH$, O—$(CH_2)_nNHC(O)CH_3$, O—$(CH_2)_n$-indole, O-(benzyl), O—$(CH_2)_n$(imidazole), pyridine, p-fluoro-benzyl, $CH_2$-β-naphthyl, $CH_2$-α-naphthyl, —$(CH_2)_n$-indole, —$CH_2$ Php-$OH_1$—$CH_2$-picolyl, —NH$(CH_2)_6NH_2$, —NH$(CH_2)_3NH(CO)CH_3$, or —NH$(CH_2)_5OH$, —NH$(CH_2)_6OH$, wherein n is 1, 2, 3, 4, 5, or 6.

In certain other more preferred embodiments where the structure is (4), the compounds of the invention comprise those wherein:

(a) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_6$—$NH_2$;

(b) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_5$—$NH_2$;

(c) $R_1$ is methoxy, $R_2$ is O—$(CH_2)$-(imidazole), $R_3$ is O-(benzyl) $R_4$ is O-(benzyl), $R_5$ is O—$(CH_2)_5$—$NH_2$;

(d) $R_1$ is methoxy, $R_2$ is O—$(CH_2)$-(imidazole), $R_3$ is O-(benzyl) $R_4$ is O-(benzyl), $R_5$ is O—$(CH_2)_6$—$NH_2$;

(e) $R_1$ is methoxy, $R_2$ is O-(benzyl), $R_3$ is O—$CH_2$-(imidazole), $R_4$ is O-(benzyl), $R_5$ is O—$(CH_2)_5NH_2$;

(f) $R_1$ is O—$(CH_2)_2$-indole, $R_2$ is O-(benzyl), $R_3$ is O-(benzyl), $R_4$ is O-(benzyl), $R_5$ is NH$(CH_2)_5NH_2$;

(g) $R_1$ is O—$(CH_2)_2$-indole, $R_2$ is O-(benzyl), $R_3$ is O-(benzyl), $R_4$ is O-(benzyl), $R_5$ is O—$(CH_2)_5NH_2$;

(h) $R_1$ is O—$(CH_2)_2$-indole, $R_2$ is p-fluoro-(benzyl), $R_3$ is O-(benzyl), $R_4$ is O-(benzyl), $R_5$ is O—$(CH_2)_5NHC(O)CH_3$;

(i) $R_1$ is O—$(CH_2)_2$-indole, $R_2$ is O-(benzyl), $R_3$ is O-(benzyl), $R_4$ is OH, $R_5$ is O—$(CH_2)_5NHC(O)CH_3$;

(j) $R_1$ is O—$(CH_2)_2$-indole, $R_2$ is O-(imidazole), $R_3$ is H, $R_4$ is O-(benzyl), $R_5$ is O—$(CH_2)_5NH_2$;

(k) $R_1$ is O—$(CH_2)_2$-indole, $R_2$ is O-(p-fluorobenzyl), $R_3$ is O-(benzyl), $R_4$ is OH, $R_5$ is $(CH_2)_5NHC(O)CH_3$;

(l) $R_1$ is O—$(CH_2)_2$-indole, $R_2$ is O-(benzyl), $R_3$ is O-(benzyl), $R_4$ is O-(benzyl), $R_5$ is —NH$(CH_2)_6OH$;

(m) $R_1$ is O—$(CH_2)_2$-indole, $R_2$ is O-(benzyl), $R_3$ is O-(benzyl), $R_4$ is O-(benzyl), $R_5$ is —NH$(CH_2)_6OH$.

In certain other preferred embodiments, wherein the core structure is (5):

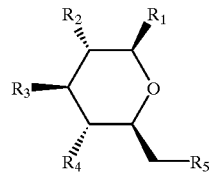

(5)

the compounds of the invention comprise those wherein $R_1$, $R_2$, $R_3$, $R_4$, and $R_5$, are H, OH, $OCH_3$, O—$(CH_2)_nNH_2$, O—$(CH_2)_nOH$, O—$(CH_2)_nNHC(O)CH_3$, O—$(CH_2)_n$-indole, O-(benzyl), O—$(CH_2)_n$(imidazole), pyridine, p-fluoro-benzyl, $CH_2$-β-naphthyl, $CH_2$-α-naphthyl, —$_2)_n$-indole, —$CH_2$ Php-OH, —$CH_2$-picolyl, —NH$(CH_2)_5NH_2$, —NH$(CH_2)_3NH(CO)CH_3$, or —NH$(CH_2)_5OH$, —NH$(CH_2)_6OH$, wherein n is 1, 2, 3, 4, 5, or 6.

In certain other more preferred embodiments where the core structure is (5), the compounds of the invention comprise those wherein (a) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_6$—$NH_2$;

(b) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_5$—$NH_2$;

(c) $R_1$ is methoxy, $R_2$ is O—$(CH_2)$-(imidazole), $R_3$ is O-(benzyl) $R_4$ is O-(benzyl), $R_5$ is O—$(CH_2)_6$—$NH_2$;

(d) $R_1$ is methoxy, $R_2$ is O—$(CH_2)$-(imidazole), $R_3$ is O-(benzyl) $R_4$ is O-(benzyl), $R_5$ is O—$(CH_2)_6$—$NH_2$;

(e) $R_1$ is O—$(CH_2)_2$-(indole), $R_2$ is $(CH_2)$-(imidazole), $R_3$ is H, $R_4$ is O-(benzyl), $R_5$ is O—$(CH_2)_6$—$NH_2$;

(f) $R_1$ is O—$(CH_2)_2$-(indole), $R_2$ is $(CH_2)$-(imidazole), $R_3$ is H, $R_4$ is O-(benzyl), $R_5$ is O—$(CH_2)_5$—$NH_2$;

(g) $R_1$ is methoxy, $R_2$ is O—$(CH_2)$-(imidazole), $R_3$ is O-(benzyl) $R_4$ is O-(benzyl), $R_5$ is O—$(CH_2)_5$—$NH_2$;

(h) $R_1$ is methoxy, $R_2$ is O—$(CH_2)$-(imidazole), $R_3$ is O-(benzyl) $R_4$ is O-(benzyl), $R_5$ is O—$(CH_2)_6$—$NH_2$;

(i) $R_1$ is methoxy, $R_2$ is O-(benzyl), $R_3$ is (O)—$(CH_2)$-(imidazole), $R_4$ is O-(benzyl), $R_5$ is O—$(CH_2)_5$—$NH_2$;

(j) $R_1$ is methoxy, $R_2$ is O-(benzyl), $R_3$ is (O)—$(CH_2)$-(imidazole) $R_4$ is O-(benzyl), $R_5$ is O—$(CH_2)_6$—$NH_2$;

(k) $R_1$ is (O)—$(CH_2)_2$-(indole), $R_2$ is O-(benzyl), $R_3$ is O-(benzyl), $R_4$ is O-(benzyl), $R_5$ is NH$(CH_2)_5OH$;

(l) $R_1$ is (O)$(CH_2)_2$-(indole), $R_2$ is O-(benzyl), $R_3$ is O-(benzyl), $R_4$ is O-(benzyl), $R_5$ is NH$(CH_2)_6OH$;

(m) $R_1$ is (O)$(CH_2)_2$-(indole), $R_2$ is O-(benzyl), $R_3$ is O-(benzyl), $R_4$ is O-(benzyl), $R_5$ is NH—$(CH_2)_5NH_2$;

(n) $R_1$ is (O)$(CH_2)_2$-(indole), $R_2$ is O-(benzyl), $R_3$ is O-(benzyl), $R_4$ is O-(benzyl), $R_5$ is NH—$(CH_2)_6NH_2$;

(o) $R_1$ is (O)$(CH_2)_2$-(indole), O—$CH_2$-β-naphthyl, $R_3$ is O-(benzyl), O—$CH_2$-α-naphthyl $R_4$ is O-(benzyl), $R_5$ is O-(p-fluorobenzyl);

(p) $R_1$ is (O)$(CH_2)_2$-(indole), $R_2$ is O-p-fluorobenzyl, $R_3$ is O-(benzyl), $R_4$ is O-(benzyl), $R_5$ is O—$(CH_2)_5$—NHC(O)$CH_3$;

(q) $R_1$ is (O)$(CH_2)_2$-(indole), $R_2$ is O-p-fluorobenzyl, $R_3$ is O-(benzyl), $R_4$ is O-(benzyl), $R_5$ is O—$(CH_2)_6$—NHC(O)$CH_3$;

(r) $R_1$ is (O)—$(CH_2)_2$-(indole), $R_2$ is O—$CH_2$-β-naphthyl, $R_3$ is O-(benzyl) $R_4$ is O-(benzyl), $R_5$ is O—$(CH_2)_5NHC(O)CH_3$;

(s) $R_1$ is (O)—$(CH_2)_2$-(indole), $R_2$ is O—$CH_2$-β-naphthyl, $R_3$ is O-(benzyl) $R_4$ is O-(benzyl), $R_5$ is O—$(CH_2)_6NHC(O)CH_3$;

(t) $R_1$ is (O)—$(CH_2)_2$-(indole), $R_2$ is O-p-fluorobenzyl, $R_3$ is O-(benzyl), $R_4$ is O-(benzyl), $R_5$ is O—$(CH_2$-β-naphthyl);

(u) $R_1$ is $(CH_2)_2$-(indole), $R_2$ is O-(benzyl), $R_3$ is O-(benzyl), $R_4$ is O-(benzyl), $R_5$ is O—$(CH_2)$—NHC(O)$CH_3$;

(v) $R_1$ is methoxy, $R_2$ is O—$CH_2$-(imidazole), $R_3$ is O-(benzyl), $R_4$ is O-(benzyl), $R_5$ is O—$(CH_2)_5NH_2$;

(w) $R_1$ is methoxy, $R_2$ is O-(benzyl), $R_3$ is O—$CH_2$-(imidazole), $R_4$ is O-(benzyl), $R_5$ is O—$(CH_2)_5NH_2$;

(x) $R_1$ is methoxy, $R_2$ is O-(benzyl), $R_3$ is O—$CH_2$-(imidazole), $R_4$ is O-(benzyl), $R_5$ is O—$(CH_2)_6NH_2$;

(y) $R_1$ is O—$(CH_2)_2$-indole, $R_2$ is O—$CH_2$-(imidazole), $R_3$ is O-(benzyl), $R_4$ is O-(benzyl), $R_5$ is O—$(CH_2)_5NH_2$;

(z) $R_1$ is methoxy, $R_2$ is O-(benzyl), $R_3$ is O-(benzyl), $R_4$ is O-(benzyl), $R_5$ is O—$(CH_2)_5NH_2$.

(aa) $R_1$ is $O(CH_2)_5NH_2$, $R_2$ is O-(benzyl), $R_3$ is O-(benzyl), $R_4$ is O-(benzyl), $R_5$ is methoxy.

In certain other preferred embodiments, wherein the core structure is (6)

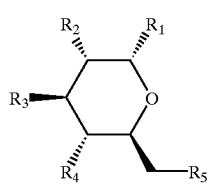

(6)

the compounds of the invention comprise those wherein $R_1$, $R_2$, $R_3$, $R_4$, and $R_5$ are H, OH, $OCH_3$, O—$(CH_2)_nNH_2$, O—$(CH_2)_nOH$, O—$(CH_2)_nNHC(O)CH_3$, O—$(CH_2)_n$-indole, O-(benzyl), O—$(CH_2)_n$(imidazole), pyridine, p-fluoro-benzyl, O—$CH_2$-β-naphthyl, O—$CH_2$-α-naphthyl, O—$(CH_2)_n$-indole, —$CH_2$ Php-OH, —$CH_2$-picolyl, —NH$(CH_2)_6NH_2$, —NH$(CH_2)_3NH(CO)CH_3$, or —NH$(CH_2)_5OH$, —NH$(CH_2)_6OH$, wherein n is 1, 2, 3, 4, 5, or 6.

In certain other more preferred embodiments, the compounds of the invention comprise those wherein:

(a) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_6$—$NH_2$;

(b) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_5$—$NH_2$;

(c) $R_1$ is methoxy, $R_2$ is O—$(CH_2)$-(imidazole), $R_3$ is O-(benzyl) $R_4$ is O-(benzyl), $R_5$ is O—$(CH_2)_5$—$NH_2$;

(d) $R_1$ is methoxy, $R_2$ is O—$(CH_2)$-(imidazole), $R_3$ is O-(benzyl) $R_4$ is O-(benzyl), $R_5$ is O—$(CH_2)_6$—$NH_2$;

(e) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_6$—$NH_2$;

(f) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_5$—$NH_2$;

(g) $R_1$ is methoxy, $R_2$ is O—$(CH_2)$-(imidazole), $R_3$ is O-(benzyl) $R_4$ is O-(benzyl), $R_5$ is O—$(CH_2)_5$—$NH_2$;

(h) $R_1$ is methoxy, $R_2$ is O—$(CH_2)$-(imidazole), $R_3$ is O-(benzyl) $R_4$ is O-(benzyl), $R_5$ is O—$(CH_2)_6$—$NH_2$;

(i) $R_1$ is methoxy, $R_2$ is O-(benzyl), $R_3$ is (O)—$(CH_2)$-(imidazole), $R_4$ is O-(benzyl), $R_5$ is O—$(CH_2)_5$—$NH_2$;

(j) $R_1$ is methoxy, $R_2$ is O-(benzyl), $R_3$ is (O)—$(CH_2)$-(imidazole), $R_4$ is O-(benzyl), $R_5$ is O—$(CH_2)_6$—$NH_2$;

(k) $R_1$ is (O)—$(CH_2)_2$-(indole), $R_2$ is O-(benzyl), $R_3$ is O-(benzyl), $R_4$ is O-(benzyl), $R_5$ is NH$(CH_2)_5OH$;

(l) $R_1$ is (O)$(CH_2)_2$-(indole), $R_2$ is O-(benzyl), $R_3$ is O-(benzyl), $R_4$ is O-(benzyl), $R_5$ is NH$(CH_2)_6OH$;

(m) $R_1$ is (O)$(CH_2)_2$-(indole), $R_2$ is O-(benzyl), $R_3$ is O-(benzyl), $R_4$ is O-(benzyl), $R_5$ is NH—$(CH_2)_5NH_2$;

(n) $R_1$ is (O)$(CH_2)_2$-(indole) $R_2$ is O-(benzyl), $R_3$ is O-(benzyl), $R_4$ is O-(benzyl), $R_5$ is NH—$(CH_2)_6NH_2$;

(o) $R_1$ is (O)$(CH_2)_2$-(indole), O—$CH_2$-β-naphthyl, $R_3$ is O-(benzyl), $R_4$ is O-(benzyl), $R_5$ is O-(p-fluorobenzyl);

(p) $R_1$ is (O)$(CH_2)_2$-(indole), $R_2$ is O-p-fluorobenzyl, $R_3$ is O-(benzyl), $R_4$ is O-(benzyl), $R_5$ is O—$(CH_2)_5$—NHC(O)$CH_3$;

(q) $R_1$ is (O)$(CH_2)_2$-(indole), $R_2$ is O-p-fluorobenzyl, $R_3$ is O-(benzyl), $R_4$ is O-(benzyl), $R_5$ is O—$(CH_2)_6$—NHC(O)$CH_3$;

(r) $R_1$ is (O)—$(CH_2)_2$-(indole), $R_2$ is O—$CH_2$-β-naphthyl, $R_3$ is O-(benzyl), $R_4$ is O-(benzyl), $R_5$ is O—$(CH_2)_5NHC(O)CH_3$;

(s) $R_1$ is (O)—$(CH_2)_2$-(indole), $R_2$ is O—$CH_2$-β-naphthyl, $R_3$ is O-(benzyl), $R_4$ is O-(benzyl), $R_5$ is O—$(CH_2)_6NHC(O)CH_3$;

(t) $R_1$ is (O)—$(CH_2)_2$-(indole), $R_2$ is O-p-fluorobenzyl, $R_3$ is O-(benzyl), $R_4$ is O-(benzyl), $R_5$ is O—$(CH_2$-β-naphthyl);

(u) $R_1$ is $(CH_2)_2$-(indole), $R_2$ is O-(benzyl), $R_3$ is O-(benzyl), $R_4$ is O-(benzyl), $R_5$ is O—$(CH_2)$—NHC(O)$CH_3$;

(v) $R_1$ is methoxy, $R_2$ is O—$CH_2$-(imidazole), $R_3$ is O-(benzyl), $R_4$ is O-(benzyl), $R_5$ is O—$(CH_2)_5NH_2$;

(w) $R_1$ is methoxy, $R_2$ is O-(benzyl), $R_3$ is O—$CH_2$-(imidazole), $R_4$ is O-(benzyl), $R_5$ is O—$(CH_2)_5NH_2$;

(x) $R_1$ is methoxy, $R_2$ is O-(benzyl), $R_3$ is O—$CH_2$-(imidazole), $R_4$ is O-(benzyl), $R_5$ is O—$(CH_2)_6NH_2$;

(y) $R_1$ is O—$(CH2)2$-indole, $R_2$ is O—$CH_2$-(imidazole), $R_3$ is O-(benzyl), $R_4$ is O-(benzyl), $R_5$ is O—$(CH_2)_5NH_2$.

In certain other preferred embodiments, wherein the core structure is (7)

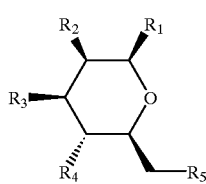

(7)

the compounds of the invention comprise those wherein $R_1$, $R_2$, $R_3$, $R_4$, and $R_5$ are H, OH, $OCH_3$, O—$(CH_2)_nNH_2$, O—$(CH_2)_nOH$, O—$(CH_2)_nNHC(O)CH_3$, O—$(CH_2)_n$-indole, O-(benzyl), O—$(CH_2)_n$(imidazole), pyridine, p-fluoro-benzyl, $CH_2$-β-naphthyl, $CH_2$-α-naphthyl, —$(_2)_n$-indole, —$CH_2$ Php-OH, —$CH_2$-picolyl, —NH$(CH_2)_5NH_2$, —NH$(CH_2)_3NH(CO)CH_3$, or —NH$(CH_2)_5OH$, —NH$(CH_2)_6OH$, wherein n is 1, 2, 3, 4, 5, or 6.

In certain other more preferred embodiments where the core structure is 7, the compounds of the invention comprise those wherein:

(a) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_6$—$NH_2$;

(b) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_5$—$NH_2$;

(c) $R_1$ is methoxy, $R_2$ is O—$(CH_2)$-(imidazole), $R_3$ is O-(benzyl) $R_4$ is O-(benzyl), $R_5$ is O—$(CH_2)_5$—$NH_2$;

(d) $R_1$ is methoxy, $R_2$ is O—$(CH_2)$-(imidazole), $R_3$ is O-(benzyl) $R_4$ is O-(benzyl), $R_5$ is O—$(CH_2)_6$—$NH_2$;

(e) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_6$—$NH_2$;

(f) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_6$—$NH_2$;

(g) $R_1$ is methoxy, $R_2$ is O—$(CH_2)$-(imidazole), $R_3$ is O-(benzyl) $R_4$ is O-(benzyl), $R_5$ is O—$(CH_2)_5$—$NH_2$;

(h) $R_1$ is methoxy, $R_2$ is O—$(CH_2)$-(imidazole), $R_3$ is O-(benzyl) $R_4$ is O-(benzyl), $R_5$ is O—$(CH_2)_6$—$NH_2$;

(i) $R_1$ is methoxy, $R_2$ is O-(benzyl), $R_3$ is (O)—$(CH_2)$-(imidazole), $R_4$ is O-(benzyl), $R_5$ is O—$(CH_2)_5$—$NH_2$;

(j) $R_1$ is methoxy, $R_2$ is O-(benzyl), $R_3$ is (O)—$(CH_2)$-(imidazole), $R_4$ is O-(benzyl), $R_5$ is O—$(CH_2)_6$—$NH_2$;

(k) $R_1$ is (O)—$(CH_2)_2$-(indole), $R_2$ is O-(benzyl), $R_3$ is O-(benzyl), $R_4$ is O-(benzyl), $R_5$ is $NH(CH_2)_5OH$;

(l) $R_1$ is (O)$(CH_2)_2$-(indole), $R_2$ is O-(benzyl), $R_3$ is O-(benzyl), $R_4$ is O-(benzyl), $R_5$ is $NH(CH_2)_6OH$;

(m) $R_1$ is (O)$(CH_2)_2$-(indole), $R_2$ is O-(benzyl), $R_3$ is O-(benzyl), $R_4$ is O-(benzyl), $R_5$ is NH—$(CH_2)_5NH_2$;

(n) $R_1$ is (O)$(CH_2)_2$-(indole), $R_2$ is O-(benzyl), $R_3$ is O-(benzyl), $R_4$ is O-(benzyl), $R_5$ is NH—$(CH_2)_6NH_2$;

(o) $R_1$ is (O)$(CH_2)_2$-(indole), O—$CH_2$-β-naphthyl, $R_3$ is O-(benzyl), $R_4$ is O-(benzyl), $R_5$ is O-(p-fluorobenzyl);

(p) $R_1$ is (O)$(CH_2)_2$-(indole), $R_2$ is O-p-fluorobenzyl, $R_3$ is O-(benzyl), $R_4$ is O-(benzyl), $R_5$ is O—$(CH_2)_5$—$NHC(O)CH_3$;

(q) $R_1$ is (O)$(CH_2)_2$-(indole), $R_2$ is O-p-fluorobenzyl, $R_3$ is O-(benzyl), $R_4$ is O-(benzyl), $R_5$ is O—$(CH_2)_6$—$NHC(O)CH_3$;

(r) $R_1$ is (O)—$(CH_2)_2$-(indole), $R_2$ is O—$CH_2$-β-naphthyl, $R_3$ is O-(benzyl) $R_4$ is O-(benzyl), $R_5$ is O—$(CH_2)_5NHC(O)CH_3$;

(s) $R_1$ is (O)—$(CH_2)_2$-(indole), $R_2$ is O—$CH_2$-β-naphthyl, $R_3$ is O-(benzyl), $R_4$ is O-(benzyl), $R_5$ is O—$(CH_2)_6NHC(O)CH_3$;

(t) $R_1$ is (O)—$(CH_2)_2$-(indole), $R_2$ is O-p-fluorobenzyl, $R_3$ is O-(benzyl), $R_4$ is O-(benzyl), $R_5$ is O—$(CH_2$-β-naphthyl);

(u) $R_1$ is $(CH_2)_2$-(indole), $R_2$ is O-(benzyl), $R_3$ is O-(benzyl), $R_4$ is O-(benzyl), $R_5$ is O—$(CH_2)$—NHC(O)$CH_3$;

(v) $R_1$ is methoxy, $R_2$ is O—$CH_2$-(imidazole), $R_3$ is O-(benzyl), $R_4$ is O-(benzyl), $R_5$ is O—$(CH_2)_5NH_2$;

(w) $R_1$ is methoxy, $R_2$ is O-(benzyl), $R_3$ is O—$CH_2$-(imidazole), $R_4$ is O-(benzyl), $R_5$ is O—$(CH_2)_5NH_2$;

(x) $R_1$ is methoxy, $R_2$ is O-(benzyl), $R_3$ is O—$CH_2$-(imidazole), $R_4$ is O-(benzyl), $R_5$ is O—$(CH_2)_6NH_2$;

(y) $R_1$ is O—(CH2)2-indole, $R_2$ is O—$CH_2$-(imidazole), $R_3$ is O-(benzyl), $R_4$ is O-(benzyl), $R_5$ is O—$(CH_2)_5NH_2$;

(z) $R_1$ is O—$(CH_2)_2$ indole, $R_2$ is O—$(OH_2)$(imidazole), $R_3$ is O-(benzyl), $R_4$ is O-(benzyl), $R_5$ is O—$(CH_2)_6NH_2$.

In certain other preferred embodiments, wherein the core structure is (8):

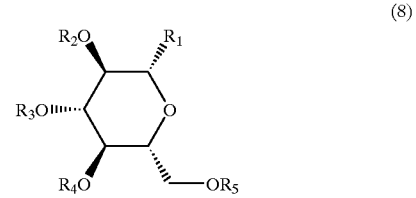

(8)

the compounds of the invention comprise those wherein $R_1$ is H, OH, $OCH_3$, O—$(CH_2)_nNH_2$, O—$(CH_2)_nOH$, O—$(CH_2)_nNHC(O)CH_3$, O—$(CH_2)$-indole, O-(benzyl), pyridine, p-fluoro-benzyl, $CH_2$-β-naphthyl, and $(CH_2)_n$(imidazole);

$R_2$, $R_3$, $R_4$, $R_5$ are H, $CH_3$, $(CH_2)_nNH_2$, $(CH_2)_nOH$, $(CH_2)_nNHC(O)CH_3$, $(CH_2)$-indole, benzyl, pyridine, p-fluoro-benzyl, $CH_2$-β-naphthyl, and $(CH_2)_n$(imidazole); $CH_2$-α-naphthyl, —$(CH_2)_n$-indole, —$CH_2$Php-OH, —$CH_2$-picolyl, —$NH(CH_2)_5NH_2$, —NH$(CH_2)_3NH(CO)CH_3$, or —$NH(CH_2)_5OH$, —$NH(CH_2)_6OH$; and wherein n is 0, 1, 2, 3, 4, 5, or 6.

In certain other more preferred embodiments where the core structure is (8), the compounds of the invention comprise those wherein:

(a) $R_1$ is O—$(CH_2)_2$-(indole), $R_2$ is $(CH_2)$-(imidazole), $R_3$ is H, $R_4$ is (benzyl), $R_5$ is $(CH_2)_6$—$NH_2$;

(b) $R_1$ is $(CH_2)_2$-(indole), $R_2$ is $(CH_2)$-(imidazole), $R_3$ is H, $R_4$ is (benzyl), $R_5$ is $(CH_2)_5$—$NH_2$;

(c) $R_1$ is methoxy, $R_2$ is $(CH_2)$-(imidazole), $R_3$ is (benzyl) $R_4$ is (benzyl), $R_5$ is $(CH_2)_5$—$NH_2$;

(d) $R_1$ is methoxy, $R_2$ is $(CH_2)$-(imidazole), $R_3$ is (benzyl) $R_4$ is (benzyl), $R_5$ is $(CH_2)_6$—$NH_2$;

(e) $R_1$ is O—$(CH_2)_2$-(indole), $R_2$ is $(CH_2)$-(imidazole), $R_3$ is H, $R_4$ is (benzyl), $R_5$ is $(CH_2)_6$—$NH_2$;

(f) $R_1$ is O—$(CH_2)_2$-(indole), $R_2$ is $(CH_2)$-(imidazole), $R_3$ is H, $R_4$ is (benzyl), $R_5$ is $(CH_2)_5$—$NH_2$;

(g) $R_1$ is methoxy, $R_2$ is $(CH_2)$-(imidazole), $R_3$ is (benzyl) $R_4$ is (benzyl), $R_5$ is $(CH_2)_5$—$NH_2$;

(h) $R_1$ is methoxy, $R_2$ is $(CH_2)$-(imidazole), $R_3$ is (benzyl) $R_4$ is (benzyl), $R_5$ is $(CH_2)_6$—$NH_2$;

(i) $R_1$ is methoxy, $R_2$ is (benzyl), $R_3$ is $(CH_2)$-(imidazole), $R_4$ is (benzyl), $R_5$ is $(CH_2)_5$—$NH_2$;

(j) $R_1$ is methoxy, $R_2$ is (benzyl), $R_3$ is $(CH_2)$-(imidazole), $R_4$ is (benzyl), $R_5$ is $(CH_2)_6$—$NH_2$;

(k) $R_1$ is O—$(CH_2)_2$-(indole), $R_2$ is (benzyl), $R_3$ (benzyl), $R_4$ is (benzyl), $R_5$ is $NH(CH_2)_5OH$;

(l) $R_1$ is (O)$(CH_2)_2$-(indole), $R_2$ is (benzyl), $R_3$ is (benzyl), $R_4$ is (benzyl), $R_5$ is $NH(CH_2)_6OH$;

(m) $R_1$ is (O)$(CH_2)_2$-(indole), $R_2$ is (benzyl), $R_3$ is (benzyl) $R_4$ is (benzyl), $R_5$ is NH—$(CH_2)_5NH_2$;

(n) $R_1$ is (O)$(CH_2)_2$-(indole), $R_2$ is (benzyl), $R_3$ is (benzyl), $R_4$ is (benzyl), $R_5$ is NH—$(CH_2)_6NH_2$;

(o) $R_1$ is (O)$(CH_2)_2$-(indole), $CH_2$-β-naphthyl, $R_3$ is (benzyl), $R_4$ is (benzyl), $R_5$ is (p-fluorobenzyl);

(p) $R_1$ is (O)$(CH_2)_2$-(indole), $R_2$ is p-fluorobenzyl, $R_3$ is (benzyl), $R_4$ is (benzyl), $R_5$ is $(CH_2)_5$—$NHC(O)CH_3$;

(q) $R_1$ is (O)$(CH_2)_2$-(indole), $R_2$ is p-fluorobenzyl, $R_3$ is (benzyl), $R_4$ is (benzyl), $R_5$ is $(CH_2)_6$—$NHC(O)CH_3$;

(r) $R_1$ is (O)—$(CH_2)_2$-(indole), $R_2$ is $CH_2$-β-naphthyl, $R_3$ is (benzyl), $R_4$ is (benzyl), $R_5$ is $(CH_2)_5NHC(O)CH_3$;

(s) $R_1$ is (O)—$(CH_2)_2$-(indole), $R_2$ is $CH_2$-β-naphthyl, $R_3$ is (benzyl), $R_4$ is (benzyl), $R_5$ is $(CH_2)6NHC(O)CH_3$;

(t) $R_1$ is (O)—$(CH_2)_2$-(indole), $R_2$ is p-fluorobenzyl, $R_3$ is (benzyl), $R_4$ is (benzyl), $R_5$ is $(CH_2$-β-naphthyl);

(u) $R_1$ is $(CH_2)_2$-(indole), $R_2$ is (benzyl), $R_3$ is (benzyl), $R_4$ is (benzyl), $R_5$ is $(CH_2)_n$—$NHC(O)CH_3$;

(v) $R_1$ is methoxy, $R_2$ is $CH_2$-(imidazole), $R_3$ is (benzyl), $R_4$ is (benzyl), $R_5$ is $(CH_2)_5NH_2$;

(w) $R_1$ is methoxy, $R_2$ is (benzyl), $R_3$ is $CH_2$-(imidazole), $R_4$ is (benzyl), $R_5$ is $(CH_2)_5NH_2$;

(x) $R_1$ is methoxy, $R_2$ is (benzyl), $R_3$ is $CH_2$-(imidazole), $R_4$ is (benzyl), $R_5$ is $(CH_2)_6NH_2$;

(y) $R_1$ is $(CH_2)_2$-indole, $R_2$ is $CH_2$-(imidazole), $R_3$ is (benzyl), $R_4$ is (benzyl), $R_5$ is $(CH_2)_5NH_2$;

(z) $R_1$ is methoxy, $R_2$ is (benzyl), $R_3$ is (benzyl), $R_4$ is (benzyl), $R_5$ is $(CH_2)_5NH_2$;

(aa) $R_1$ is $(CH_2)_2$-indole, $R_2$ is (benzyl), $R_3$ is (benzyl), $R_4$ is (benzyl), $R_5$ is $(CH_2)_5NH_2$.

In certain other preferred embodiments, wherein the core structure is (9):

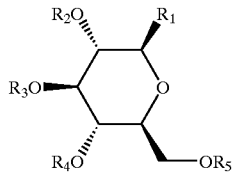

(9)

the compounds of the invention comprise those wherein $R_1$ is H, OH, $OCH_3$, O—$(CH_2)_nNH_2$, O—$(CH_2)_nOH$, O—$(CH_2)_nNHC(O)CH_3$, O—$(CH_2)$-indole, O-(benzyl), pyridine, p-fluoro-benzyl, $CH_2$-β-naphthyl, and $(CH_2)_n$ (imidazole);

$R_2$, $R_3$, $R_4$, $R_5$ are H, $CH_3$, $(CH_2)_nNH_2$, $(CH_2)_nOH$, $(CH_2)_nNHC(O)CH_3$, $(CH_2)_n$-indole, benzyl, pyridine, p-fluoro-benzyl, $CH_2$-β-naphthyl, $(CH_2)_n$(imidazole); $CH_2$-α-naphthyl, —$(CH_2)_n$-indole, —$CH_2$ Php-OH, —$CH_2$-picolyl, —$NH(CH_2)_5NH_2$, —$NH(CH_2)_3NH(CO)CH_3$, or —$NH(CH_2)_5OH$, —$NH(CH_2)_6OH$; and wherein n is 0, 1, 2, 3, 4, 5, or 6.

In certain other more preferred embodiments where the core structure is (9), the compounds of the invention comprise those wherein:

(a) $R_1$ is O—$(CH_2)_2$-(indole), $R_2$ is $(CH_2)$-(imidazole), $R_3$ is H, $R_4$ is (benzyl), $R_5$ is $(CH_2)_6$—$NH_2$;

(b) $R_1$ is O—$(CH_2)_2$-(indole), $R_2$ is $(CH_2)$-(imidazole), $R_3$ is H, $R_4$ is (benzyl), $R_5$ is $(CH_2)_5$—$NH_2$;

(c) $R_1$ is methoxy, $R_2$ is $(CH_2)$-(imidazole), $R_3$ is (benzyl) $R_4$ is (benzyl), $R_5$ is $(CH_2)_5$—$NH_2$;

(d) $R_1$ is methoxy, $R_2$ is $(CH_2)$-(imidazole), $R_3$ is (benzyl) $R_4$ is (benzyl), $R_5$ is $(CH_2)_6$—$NH_2$;

(e) $R_1$ is O—$(CH_2)_2$-(indole), $R_2$ is $(CH_2)$-(imidazole), $R_3$ is H, $R_4$ is (benzyl), $R_5$ is $(CH_2)_6$—$NH_2$;

(f) $R_1$ is O—$(CH_2)_2$-(indole), $R_2$ is $(CH_2)$-(imidazole), $R_3$ is H, $R_4$ is (benzyl), $R_5$ is $(CH_2)_5$—$NH_2$;

(g) $R_1$ is methoxy, $R_2$ is $(CH_2)$-(imidazole), $R_3$ is (benzyl) $R_4$ is (benzyl), $R_5$ is $(CH_2)_5$—$NH_2$;

(h) $R_1$ is methoxy, $R_2$ is $(CH_2)$-(imidazole), $R_3$ is (benzyl) $R_4$ is (benzyl), $R_5$ is $(CH_2)_6$—$NH_2$;

(i) $R_1$ is methoxy, $R_2$ is (benzyl), $R_3$ is $(CH_2)$-(imidazole), $R_4$ is (benzyl), $R_5$ is $(CH_2)_5$—$NH_2$;

(j) $R_1$ is methoxy, $R_2$ is (benzyl), $R_3$ is $(CH_2)$-(imidazole), $R_4$ is (benzyl), $R_5$ is $(CH_2)_6$—$NH_2$;

(k) $R_1$ is (O)—$(CH_2)_2$-(indole), $R_2$ is (benzyl), $R_3$ is (benzyl), $R_4$ is (benzyl), $R_5$ is $NH(CH_2)_5OH$;

(l) $R_1$ is (O)$(CH_2)_2$-(indole), $R_2$ is (benzyl), $R_3$ is (benzyl), $R_4$ is (benzyl), $R_5$ is $NH(CH_2)_6OH$;

(m) $R_1$ is (O)$(CH_2)_2$-(indole), $R_2$ is (benzyl), $R_3$ is (benzyl), $R_4$ is (benzyl), $R_5$ is NH—$(CH_2)_5NH_2$;

(n) $R_1$ is (O)$(CH_2)_2$-(indole), $R_2$ is (benzyl), $R_3$ is (benzyl), $R_4$ is (benzyl), $R_5$ is NH—$(CH_2)_6NH_2$;

(o) $R_1$ is (O)$(CH_2)_2$-(indole), $CH_2$-β-naphthyl, $R_3$ is (benzyl), $R_4$ is (benzyl), $R_5$ is (p-fluorobenzyl);

(p) $R_1$ is (O)$(CH_2)_2$-(indole), $R_2$ is p-fluorobenzyl, $R_3$ is (benzyl), $R_4$ is (benzyl), $R_5$ is $(CH_2)_5$—$NHC(O)CH_3$;

(q) $R_1$ is (O)$(CH_2)_2$-(indole), $R_2$ is p-fluorobenzyl, $R_3$ is (benzyl), $R_4$ is (benzyl), $R_5$ is $(CH_2)_6$—$NHC(O)CH_3$;

(r) $R_1$ is (O)—$(CH_2)_2$-(indole), $R_2$ is $CH_2$-β-naphthyl, $R_3$ is (benzyl), $R_4$ is (benzyl), $R_5$ is $(CH_2)_5NHC(O)CH_3$;

(s) $R_1$ is (O)—$(CH_2)_2$-(indole), $R_2$ is $CH_2$-β-naphthyl, $R_3$ is (benzyl), $R_4$ is (benzyl), $R_5$ is $(CH_2)_6NHC(O)CH_3$;

(t) $R_1$ is (O)—$(CH_2)_2$-(indole), $R_2$ is p-fluorobenzyl, $R_3$ is (benzyl), $R_4$ is (benzyl), $R_5$ is $(CH_2$-β-naphthyl);

(u) $R_1$ is $(CH_2)_2$-(indole), $R_2$ is (benzyl), $R_3$ is (benzyl), $R_4$ is (benzyl), $R_5$ is $(CH_2)$—$NHC(O)CH_3$;

(v) $R_1$ is methoxy, $R_2$ is $CH_2$-(imidazole), $R_3$ is (benzyl), $R_4$ is (benzyl), $R_5$ is $(CH_2)_5NH_2$;

(w) $R_1$ is methoxy, $R_2$ is (benzyl), $R_3$ is $CH_2$-(imidazole), $R_4$ is (benzyl), $R_5$ is $(CH_2)_5NH_2$;

(x) $R_1$ is methoxy, $R_2$ is (benzyl), $R_3$ is $CH_2$-(imidazole), $R_4$ is (benzyl), $R_5$ is $(CH_2)_6NH_2$;

(y) $R_1$ is O—$(CH_2)_2$-indole, $R_2$ is $CH_2$-(imidazole), $R_3$ is (benzyl), $R_4$ is (benzyl), $R_5$ is $(CH_2)_5NH_2$;

(z) $R_1$ is methoxy, $R_2$ is (benzyl), $R_3$ is (benzyl), $R_4$ is (benzyl), $R_5$ is $(CH_2)_5NH_2$;

(aa) $R_1$ is $(CH_2)_2$-indole, $R_2$ is (benzyl), $R_3$ is (benzyl), $R_4$ is (benzyl), $R_5$ is $(CH_2)_5NH_2$.

In certain other preferred embodiments, wherein the core structure is (10):

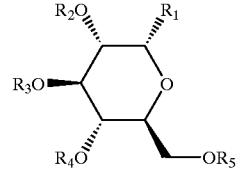

(10)

the compounds of the invention comprise those wherein $R_1$, $R_2$, $R_3$, $R_4$, and $R_5$ are H, OH, $OCH_3$, O—$(CH_2)_nNH_2$, O—$(CH_2)_nOH$, O—$(CH_2)_nNHC(O)CH_3$, O—$(CH_2)$-indole, O-(benzyl), pyridine, p-fluoro-benzyl, $CH_2$-β-naphthyl, $CH_2$-α-naphthyl, —$(CH_2)_n$-indole, -$CH_2$ Php-OH, —$CH_2$-picolyl, —$NH(CH_2)_5NH_2$, —$NH(CH_2)_3NH(CO)CH_3$, or —$NH(CH_2)_5OH$, —$NH(CH_2)_6OH$, wherein n is 1, 2, 3, 4, 5, or 6.

In certain other more preferred embodiments where the core structure is (10), the compounds of the invention comprise those wherein:

(a) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_6$—$NH_2$;

(b) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_5$—$NH_2$;

(c) $R_1$ is methoxy, $R_2$ is O—$(CH_2)$-(imidazole), $R_3$ is O-(benzyl) $R_4$ is O-(benzyl), $R_5$ is O—$(CH_2)_5$—$NH_2$;

(d) $R_1$ is methoxy, $R_2$ is O—$(CH_2)$-(imidazole), $R_3$ is O-(benzyl) $R_4$ is O-(benzyl), $R_5$ is O—$(CH_2)_6$—$NH_2$;

(e) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_6$—$NH_2$;

(f) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_5$—$NH_2$;

(g) $R_1$ is methoxy, $R_2$ is O—$(CH_2)$-(imidazole), $R_3$ is O-(benzyl) $R_4$ is O-(benzyl), $R_5$ is O—$(CH_2)_5$—$NH_2$;

(h) $R_1$ is methoxy, $R_2$ is O—$(CH_2)$-(imidazole), $R_3$ is O-(benzyl) $R_4$ is O-(benzyl), $R_5$ is O—$(CH_2)_6$—$NH_2$;

(i) $R_1$ is methoxy, $R_2$ is O-(benzyl), $R_3$ is (O)—$(CH_2)$-(imidazole), $R_4$ is O-(benzyl), $R_5$ is O—$(CH_2)_5$—$NH_2$;

(j) $R_1$ is methoxy, $R_2$ is O-(benzyl), $R_3$ is (O)—$(CH_2)$-(imidazole), $R_4$ is O-(benzyl), $R_5$ is O—$(CH_2)_6$—$NH_2$;

(k) $R_1$ is (O)—$(CH_2)_2$-(indole), $R_2$ is O-(benzyl), $R_3$ is O-(benzyl), $R_4$ is O-(benzyl), $R_5$ is $NH(CH_2)_5OH$;

(l) $R_1$ is $(O)(CH_2)_2$-(indole), $R_2$ is O-(benzyl), $R_3$ is O-(benzyl), $R_4$ is O-(benzyl), $R_5$ is $NH(CH_2)_6OH$;

(m) $R_1$ is $(O)(CH_2)_2$-(indole), $R_2$ is O-(benzyl), $R_3$ is O-(benzyl), $R_4$ is O-(benzyl), $R_5$ is NH—$(CH_2)_5NH_2$;

(n) $R_1$ is $(O)(CH_2)_2$-(indole), $R_2$ is O-(benzyl), $R_3$ is O-(benzyl), $R_4$ is O-(benzyl), $R_5$ is NH—$(CH_2)_6NH_2$;

(o) $R_1$ is $(O)(CH_2)_2$-(indole), O—$CH_2$-β-naphthyl, $R_3$ is O-(benzyl), $R_4$ is O-(benzyl), $R_5$ is O-(p-fluorobenzyl);

(p) $R_1$ is $(O)(CH_2)_2$-(indole), $R_2$ is O-β-fluorobenzyl, $R_3$ is O-(benzyl), $R_4$ is O-(benzyl), $R_5$ is O—$(CH_2)_5$—$NHC(O)CH_3$;

(q) $R_1$ is $(O)(CH_2)_2$-(indole), $R_2$ is O-β-fluorobenzyl, $R_3$ is O-(benzyl), $R_4$ is O-(benzyl), $R_5$ is O—$(CH_2)_6$—$NHC(O)CH_3$;

(r) $R_1$ is (O)—$(CH_2)_2$-(indole), $R_2$ is O—$CH_2$-β-naphthyl, $R_3$ is O-(benzyl), $R_4$ is O-(benzyl), $R_5$ is O—$(CH_2)_5NHC(O)CH_3$;

(s) $R_1$ is (O)—$(CH_2)_2$-(indole), $R_2$ is O—$CH_2$-β-naphthyl, $R_3$ is O-(benzyl), $R_4$ is O-(benzyl), $R_5$ is O—$(CH_2)_6NHC(O)CH_3$;

(t) $R_1$ is (O)—$(CH_2)_2$-(indole), $R_2$ is O-β-fluorobenzyl, $R_3$ is O-(benzyl), $R_4$ is O-(benzyl), $R_5$ is O—$(CH_2$-β-naphthyl);

(u) $R_1$ is $(CH_2)_2$-(indole), $R_2$ is O-(benzyl), $R_3$ is O-(benzyl), $R_4$ is O-(benzyl), $R_5$ is O—$(CH_2)$—$NHC(O)CH_3$;

(v) $R_1$ is methoxy, $R_2$ is O—$CH_2$-(imidazole), $R_3$ is O-(benzyl), $R_4$ is O-(benzyl), $R_5$ is O—$(CH_2)_5NH_2$;

(w) $R_1$ is methoxy, $R_2$ is O-(benzyl), $R_3$ is O—$CH_2$-(imidazole), $R_4$ is O-(benzyl), $R_5$ is O—$(CH_2)_5NH_2$;

(x) $R_1$ is methoxy, $R_2$ is O-(benzyl), $R_3$ is O—$CH_2$-(imidazole), $R_4$ is O-(benzyl), $R_5$ is O—$(CH_2)_6NH_2$;

(y) $R_1$ is O—(CH2)2-indole, $R_2$ is O—$CH_2$-(imidazole), $R_3$ is O-(benzyl), $R_4$ is O-(benzyl), $R_5$ is O—$(CH_2)_5NH_2$;

(z) $R_1$ is methoxy, $R_2$ is O-(benzyl), $R_3$ is O-(benzyl), $R_4$ is O-(benzyl), $R_5$ is O—$(CH_2)_5NH_2$;

(aa) $R_1$ is $(CH_2)_2$-indole, $R_2$ is O-(benzyl), $R_3$ is O-(benzyl), $R_4$ is O-(benzyl), $R_5$ is O—$(CH_2)_5NH_2$.

In certain other preferred embodiments, wherein the core structure is (11):

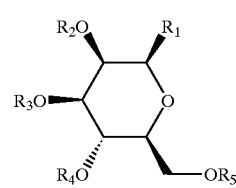

(11)

the compounds of the invention comprise those wherein $R_1$, $R_2$, $R_3$, $R_4$, and $R_5$ are H, OH, $OCH_3$, O—$(CH_2)_nNH_2$, O—$(CH_2)_nOH$, O—$(CH_2)_nNHC(O)CH_3$, O—$(CH_2)$-indole, O-(benzyl), pyridine, p-fluoro-benzyl, $CH_2$-β-naphthyl, $CH_2$-α-naphthyl, —$(CH_2)_n$-indole, —$CH_2$ Php-OH, —$CH_2$-picolyl, —$NH(CH_2)_5NH_2$, —$NH(CH_2)_3NH(CO)CH_3$, or —$NH(CH_2)_5OH$, —$NH(CH_2)_6OH$, wherein n is 1, 2, 3, 4, 5, or 6.

In certain other more preferred embodiments where the core structure is (11), the compounds of the invention comprise those wherein:

(a) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_6$—$NH_2$;

(b) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_5$—$NH_2$;

(c) $R_1$ is methoxy, $R_2$ is O—$(CH_2)$-(imidazole), $R_3$ is O-(benzyl) $R_4$ is O-(benzyl), $R_5$ is O—$(CH_2)_5$—$NH_2$;

(d) $R_1$ is methoxy, $R_2$ is O—$(CH_2)$-(imidazole), $R_3$ is O-(benzyl) $R_4$ is O-(benzyl), $R_5$ is O—$(CH_2)_6$—$NH_2$;

(e) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_6$—$NH_2$;

(f) $R_1$ is O—$(CH_2)_2$-(indole), $R_2$ is O—$(CH_2)$-(imidazole), $R_3$ is H, $R_4$ is O-(benzyl), $R_5$ is O—$(CH_2)_5$—$NH_2$;

(g) $R_1$ is methoxy, $R_2$ is O—$(CH_2)$-(imidazole), $R_3$ is O-(benzyl) $R_4$ is O-(benzyl), $R_5$ is O—$(CH_2)_5$—$NH_2$;

(h) $R_1$ is methoxy, $R_2$ is O—$(CH_2)$-(imidazole), $R_3$ is O-(benzyl) $R_4$ is O-(benzyl), $R_5$ is O—$(CH_2)_6$—$NH_2$;

(i) $R_1$ is methoxy, $R_2$ is O-(benzyl), $R_3$ is (O)—$(CH_2)$-(imidazole), $R_4$ is O-(benzyl), $R_5$ is O—$(CH_2)_5$—$NH_2$;

(j) $R_1$ is methoxy, $R_2$ is O-(benzyl), $R_3$ is (O)—$(CH_2)$-(imidazole), $R_4$ is O-(benzyl), $R_5$ is O—$(CH_2)_6$—$NH_2$;

(k) $R_1$ is (O)—$(CH_2)_2$-(indole), $R_2$ is O-(benzyl), $R_3$ is O-(benzyl), $R_4$ is O-(benzyl), $R_5$ is $NH(CH_2)_5OH$;

(l) $R_1$ is $(O)(CH_2)_2$-(indole), $R_2$ is O-(benzyl), $R_3$ is O-(benzyl), $R_4$ is O-(benzyl), $R_5$ is $NH(CH_2)_6OH$;

(m) $R_1$ is $(O)(CH_2)_2$-(indole), $R_2$ is O-(benzyl), $R_3$ is O-(benzyl), $R_4$ is O-(benzyl), $R_5$ is NH—$(CH_2)_5NH_2$;

(n) $R_1$ is $(O)(CH_2)_2$-(indole), $R_2$ is O-(benzyl), $R_3$ is O-(benzyl), $R_4$ is O-(benzyl), $R_5$ is NH—$(CH_2)_6NH_2$;

(o) $R_1$ is $(O)(CH_2)_2$-(indole), O—$CH_2$-β-naphthyl, $R_3$ is O-(benzyl), $R_4$ is O-(benzyl), $R_5$ is O-(p-fluorobenzyl);

(p) $R_1$ is $(O)(CH_2)_2$-(indole), $R_2$ is O-β-fluorobenzyl, $R_3$ is O-(benzyl), $R_4$ is O-(benzyl), $R_5$ is O—$(CH_2)_5$—$NHC(O)CH_3$;

(q) $R_1$ is $(O)(CH_2)_2$-(indole), $R_2$ is O-β-fluorobenzyl, $R_3$ is O-(benzyl), $R_4$ is O-(benzyl), $R_5$ is O—$(CH_2)_6$—$NHC(O)CH_3$;

(r) $R_1$ is (O)—$(CH_2)_2$-(indole), $R_2$ is O—$CH_2$-β-naphthyl, $R_3$ is O-(benzyl), $R_4$ is O-(benzyl), $R_5$ is O—$(CH_2)_5NHC(O)CH_3$;

(s) $R_1$ is (O)—$(CH_2)_2$-(indole), $R_2$ is O—$CH_2$-β-naphthyl, $R_3$ is O-(benzyl), $R_4$ is O-(benzyl), $R_5$ is O—$(CH_2)_6NHC(O)CH_3$;

(t) $R_1$ is (O)—$(CH_2)_2$-(indole), $R_2$ is O-β-fluorobenzyl, $R_3$ is O-(benzyl), $R_4$ is O-(benzyl), $R_5$ is O—$(CH_2$-β-naphthyl);

(u) $R_1$ is $(CH_2)_2$-(indole), $R_2$ is O-(benzyl), $R_3$ is O-(benzyl), $R_4$ is O-(benzyl), $R_5$ is O—$(CH_2)$—NHC(O)$CH_3$;

(v) $R_1$ is methoxy, $R_2$ is O—$CH_2$-(imidazole), $R_3$ is O-(benzyl), $R_4$ is O-(benzyl), $R_5$ is O—$(CH_2)_5NH_2$;

(w) $R_1$ is methoxy, $R_2$ is O-(benzyl), $R_3$ is O—$CH_2$-(imidazole), $R_4$ is O-(benzyl), $R_5$ is O—$(CH_2)_5NH_2$;

(x) $R_1$ is methoxy, $R_2$ is O-(benzyl), $R_3$ is O—$CH_2$-(imidazole), $R_4$ is O-(benzyl), $R_5$ is O—$(CH_2)_6NH_2$;

(y) $R_1$ is O—(CH2)2-indole, $R_2$ is O—$CH_2$-(imidazole), $R_3$ is O-(benzyl), $R_4$ is O-(benzyl), $R_5$ is O—$(CH_2)_5NH_2$;

(z) $R_1$ is methoxy, $R_2$ is O-(benzyl), $R_3$ is O-(benzyl), $R_4$ is O-(benzyl), $R_5$ is O—$(CH_2)_5NH_2$;

(aa) $R_1$ is $(CH_2)_2$-indole, $R_2$ is O-(benzyl), $R_3$ is O-(benzyl), $R_4$ is O-(benzyl), $R_5$ is O—$(CH_2)_5NH_2$.

As can be seen, the present invention provides a wide variety of peptide analogs which effectively and selectively are bound by individual G-protein-linked receptors. The peptide analogs which bear amino groups are capable of forming salts with various inorganic and organic acids and such salts are also within the scope of this invention. Examples of such acid addition salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-napthalenesulfonate, nitrate, oxalate, pamoate, persulfate, picrate, pivalate, propionate, succinate, sulfate, tartrate, tosylate, and undecanoate. The salts may be formed by conventional means, such as by reacting the free base form of the product with one or more equivalents of the appropriate acid in a solvent or medium in which the salt is insoluble, or in a solvent such as water which is later removed in vacuo or by freeze drying. The salts also may be formed by exchanging the anions of an existing salt for another anion on a suitable ion exchange resin.

The present invention also provides compositions which comprise one or more peptide analogs. To the extent that the compositions comprise individual peptide analogs which are bound by certain receptors, the compositions will likely also be bound by the same receptors. The analogs themselves may be present in the compositions in any of a wide variety of forms. For example, two or more peptide analogs may be merely mixed together or may be more closely associated through complexation, crystallization, or ionic or covalent bonding.

Those skilled in the art will appreciate that a wide variety of prophylactic, diagnostic, and therapeutic treatments may be prepared from the synthetic compounds and compositions of the invention, due in large part to the crossreactivity—that is, agonism or antagonism—of these moieties with one or more naturally-occurring peptides. For example, by administering an effective amount of a peptide analog, prophylactic or therapeutic responses can be produced in a human or some other type of mammal. Preferred responses are produced by modulating—that is, increasing, decreasing or otherwise modifying—the activity of at least one G-protein-linked receptor. It will be appreciated that the production of prophylactic or therapeutic responses includes the initiation or enhancement of desirable responses, as well as the cessation or suppression of undesirable responses.

Certain preferred peptide analogs of the present invention exhibit significant substance P receptor-binding activity and therefore, are of value in the treatment of a wide variety of clinical conditions which are characterized by the presence of an excess of tachykinin, in particular substance P, activity. These include disorders of the central nervous system such as anxiety, psychosis and schizophrenia; neurodegenerative disorders such as senile dementia of the Alzheimer type, Alzheimer's disease and Down's syndrome; respiratory diseases such as bronchospasm and asthma; inflammatory diseases such as inflammatory bowel disease, osteoarthritis and rheumatoid arthritis; adverse immunological reactions such as rejection of transplanted tissues; gastrointestinal (GI) disorders and diseases of the GI tract such as disorders associated with the neuronal control of viscera such as ulcerative colitis, Crohn's disease and incontinence; disorders of blood flow caused by vasodilation; pain or nociception, for example, that attributable to or associated with any of the foregoing conditions or the transmission of pain in migraine; and diabetes. Hence, these compounds are readily adapted to therapeutic use as substance P antagonists for the control and/or treatment of any of the aforesaid clinical conditions in mammals, including humans.

Compositions for use in the methods of this invention can be in the form of a solid, semisolid or liquid form and can include one or more of peptide analogs as an active ingredient in a mixture with an organic or inorganic carrier or excipient suitble for external, enteral or parenteral applications. The active ingredient may be compounded, for example, with the usual non-toxic, pharmaceutically acceptale carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manuacturing preparations, in solid, semisolid, or liquid form, and in addition auxiliary, stabilizing, thickening and coloring agents and perfumes may be used. The active ingredient is included in the pharmaceutical composition in an amount sufficient to produce the desired effect upon the process or condition of diseases.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water ethanol, propylene glycol, glycerin and various like combinations thereof.

For parenteral administration, solutions of said compounds in either sesame or peanut oil in aqueous proplyene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

A compound of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Dosage levels of the compounds within the present invention on the order from about 0.01 mg to about 50 mg per kilogram of body weight per day, preferably from about 0.1 mg to about 10 mg per kilogram body weight per day, are believed to be useful in the treatment of the above-indicated conditions (i.e., from about 0.7 mg to about 3.5 g per patient per day, assuming a 70 kg patient). In addition, the compounds of the present invention may be administered on an intermittent basis; i.e. at semi-weekly, weekly, semi-monthly or monthly intervals.

The amount of active ingredient that may be combined with the carrier materials to produce a single dosage form will vary depending upon the host treated and the particular mode of administration. For example, a formulation intended anisaldehyde solution (sugars), ninhydrin (primary amines), phosphomolybdic acid (secondary amines), or Erlich's reagent (incoles). Flash column chromatography was performed using Merck 60–200 mesh silica gel. All yields reflect purified isolated product after flash column chromatography or recrystallization unless otherwise noted.

EXAMPLE 1

Preparation of Analog Having Structure (1), 2-(1H-Indol-3yl)ethyl-6-O-(5-aminopentyl)-2,3,4-tri-O-benzyl-β-D-glucopyranoside A. 1-Bromo α-D glucose tetraacetate Hydrobromic acid (30% in acetic acid, 11.85 ml, 55.4 mmol) was added to β-D-glucose pentaacetate (12.01 g, 30.8 mmol) at 0° C. After 10 minutes, the resulting solution was warmed to room temperature and stirred for 4 hours. The reaction mixture was slowly poured, with stirring, into ice water (250 ml) and was stirred until the product solidified. The product was collected by vacuum filtration and washed with cold water. The white solid was dissolved in carbon tetrachloride (60 ml) and washed with $H_2O$ (1×20 ml), saturated aqueous $NaHCO_3$ (3×20 ml, until pH=7), $H_2O$ (1×20 ml), dried with $CaCl_2$, and poured into cold petroleum ether (250 ml). After 30 min, the crystalline product was collected by vacuum filtration to give the target compound as a white solid (10.0 g, 80%).

B. N-phenylsulfonyl tryptophol (a) 1-O-tert-butyldimethylsilyl-2-3-indolyl)ethanol To a solution of tryptophol (5.0 g, 31 mmol) in dimethylformamide (DMF, 30 ml) was added imidazole (4.64 g, 68 mmol) and the reaction cooled to 0° C. To the cooled solution was added tert-butyldimethylsilyl chloride (5.14 g, 34.1 mmol) and the reaction was stirred at room temperature overnight. The reaction was diluted with ethyl acetate (100 ml) and extracted with water (2×100 ml). The aqueous layer was extracted with ethyl acetate (1×200 ml.) The organic layers were combined and dried over anhydrous sodium sulfate. The solvents were removed under reduced pressure to yield a pale orange oil. Purification by flash column chromatography using 30% ether in petroleum ether yielded the target compound as a colorless oil (8.43 g, 99%).

(b) 1-O-tert-butyldimethylsilyl-2-[3-(1-N-phenylsulfonyl)indolyl]ethanol

Sodium hydride (1.91 g, 60% oil dispersion) was placed in a flame dried flask under argon. Dry DMF (64 ml) was added and the suspension cooled to 0° C. A solution of 1-O-tert-butyldimethylsilyl-2-3-indolyl)ethanol (8.43 g, 30.6 mmol) in dry DMF (30 ml) was added to the suspension and the reaction stirred to room temperature for 30 minutes. After cooling to 0° C., benzenesulfonyl chloride (5.30 ml, 39.7 mmol) was added dropwise. The reaction was stirred at room temperature overnight. A solution of ammonium chloride (100 ml) was added and the reaction was extracted with ether (3×200 ml). The organic layers were combined, extracted with saturated sodium chloride, and dried over anhydrous sodium sulfate. Removal of the solvents under reduced pressure yield a pale yellow oil. Purification by flash column chromatography using 30% ether in petroleum ether yielded the target compound as a colorless oil (7.37 g, 79%).

(c) N-phenylsulfonyl tryptophol

To a solution of 1-O-tert-butyldimethylsilyl-2-[3-(1-N-phenylsulfonyl)indolyl]ethanol (6.6 g, 21.9 mmol) in tetrahydrofuran (THF, 100 ml) was added tetrabutylammonium fluoride (21 ml, 1 M in THF) and the solution stirred at room temperature overnight. The reaction was diluted with ethyl acetate (100 ml) and extracted with water (2×100 ml). The organic layer was re-extracted with saturated sodium chloride solution, dried over anhydrous sodium sulfate and the solvents removed under reduced pressure to yield a pale yellow oil. Purification by flash column chromatography using 40% ethyl acetate in petroleum ether yielded the target compound as a pale yellow oil which crystallized upon standing (4.00 g, 84%).

C. 2-(1-Phenylsulfonyl-3-yl)ethyl-2,3,4,6-tetra-O-acetyl-β-D-glucopyranoside

To a suspension of crushed, flame dried 4 Å sieves (0.89 g) and silver (I) oxide (412 mg. 17.8 mmol) in 9 ml of dry hexane at room temperature, was added a solution of the above N-phenyl sulfonyl tryptophol (537 mg, 1.78 mmol) in 3 ml of dry benzene followed by a solution of 1-bromo α-D glucose tetraacetate (804 mg, 1.95 mmol) in 3 ml of dry benzene. The reaction vessel was covered with aluminum foil and allowed to stir for 2 days at room temperature. Thin layer chromatography (TLC, 5% ether in methylene chloride) revealed product and some unchanged starting material. Silver (I) oxide (206 mg, 8.9 mmol) was added followed by 1 ml of dry benzene to loosen the suspension. The reaction as allowed to stir at room temperature an additional 2 days. The reaction suspension was filtered through celite. Concentration and crystallization from ethyl acetate/petroleum ether afforded 580 mg of the β-isomer of the target compound as a white solid. Concentration of the filtrate and flash chromatography (silica, 5% ether in methylene chloride) afforded a mixture of the β-isomer along with the α-isomer and the corresponding ortho ester. Flash chromatography (silica, 70% ether in petroleum ether) on the mixture afforded an additional 134 mg of the β-isomer, bringing the yield to 64% (716 mg).

D. 2-(1-Phenylsulfonyl-indol-3-yl)ethyl-β-D-glucopyranoside

Sodium methoxide (221 mg, 4.09 mmol) was added to a suspension of 2-(1-phenylsulfonyl-3-yl)ethyl-2,3,4,6-tetra-O-acetyl-β-D-glucopyranoside (3.22 g, 5.12 mmol) in 26 ml of methanol at room temperature. After 20 minutes, the resulting solution was diluted with 26 ml of methanol and neutralized by addition of amberlyst H+ resin. The resin was quickly removed by filtration to avoid formation of the methyl glucoside. Concentration of the filtrate and flash chromatography (silica, 5:1:1 methylene chloride, methanol, acetone) afforded the target compound (2.09 g, 88%) as a white foam.

E. 2-(1-Phenylsulfonyl-indol-3-yl) ethyl-6-O-tert-butyldiphenylsilyl-β-D-glucopyranoside To a stirred solution of 2-(1-Phenylsulfonyl-indol-3-yl)ethyl-β-D-glucopyranoside (7.11 g, 15.4 mmol) in 51 ml of dry DMF was added at room temperature, imidazole (2.93 g, 43.1 mmol) followed by tert-butyldiphenylsilyl chloride (5.58 g, 21.6 mmol). The solution was maintained at 50° C. for 24 hours. After removal of the DMF under reduced pressure, the reaction mixture was diluted with 250 ml of ethyl acetate and washed with $H_2O$ (1×100 ml), saturated aqueous NaCl (1×100 ml), and dried over magnesium sulfate. Concentration and flash chromatography (silica, 5% methanol in dichloromethane) provided pure target compound (9.15 g, 85%) as a white foam.

F. 2-(1-Phenylsulfonyl-indol-3-yl)ethyl-2,3,4-tri-O-benzyl-6-O-tert-butyldiphenyl-silyl-β-D-glucopyranoside To a stirred suspension of sodium hydride (323 mg, 60% oil dispersion, 808 mmol) in 5 ml of dry THF at 0° C. was added a solution of 2-(1-phenylsulfonyl-indol-3-yl ethyl-6-O-tert-butyldiphenylsilyl-β-D-glucopyranoside (1.62 g, 2.31 mmol) in 7 ml dry THF. After stirring 1 hour at room temperature, benzyl bromide (1.09 ml, 9.24 mmol) was added dropwise to the reaction mixture at 0° C. followed by tetrabutylammonium iodide (85 mg, 0.23 mmol). After stirring 3 days at room temperature, the suspension was treated with 3 ml of saturated aqueous ammonium chloride at 0° C. The resulting solution was diluted with 80 ml of ether and washed with saturated aqueous $NH_4Cl$ (1×30 ml), saturated aqueous NaCl (1×30 ml) and dried over magnesium sulfate. Concentration and flash chromatography (silica, 20% ether in petroleum ether) afforded the target compound (1.66 g, 74%) as a white foam.

G. 2-(1-Phenylsulfonyl-indol-3-yl)ethyl-2,3,4 tri-O-benzyl-β-D-glucopyranoside

To a stirred solution of 2-(1-phenylsulfonyl-indol-3-yl)ethyl-2,3,4-tri-O-benzyl-6-O-tert-butyldiphenyl-silyl-β-D-glucopyranoside (1.55 g, 1.60 mmol) in 8 ml of dry THF at room temperature was added tetrabutylammonium fluoride (1 M in THF, 2.4 ml, 2.4 mmol). After stirring 7 hours, the solution was diluted with 70 ml of ethyl acetate and washed with $H_2O$ (1×30 ml) and saturated aqueous NaCl (1×30 ml) and dried over magnesium sulfate. Concentration and flash chromatography (silica, 30% ethyl acetate in petroleum ether) afforded the target compound (1.10 g, 94%) as a clear oil: $R_f$ 0.50 (40% ethyl acetate in petroleum ether); $^1$H NMR (500 MHz, CDCl$_3$) δ 7.84 (d, J=8.3 Hz, 1H), 7.82 (d, J=7.9 Hz, 2H), 7.53 (s, 1H), 7.48–7.17 (m, 21H), 4.92 (d, J=11.0 Hz, 1H), 4.86 (d, J=10.9 Hz, 1H), 481 (d, J=11.0 Hz, 1H), 4.74 (d, J=11.0 Hz, 1H), 4.62 (d, J=11.0 Hz, 1H), 4.48 (d, J=7.8 Hz, 1H), 4.20 (ddd, J=9.4, 7.0, 7.0 Hz, 1H), 3.91–3.86 (m, 2H), 3.73 (dd, J=3.5, 11.9 Hz, 1H), 3.63 (ddd, J=9.0, 9.0, 18.0 Hz, 2H), 3.40 (ap. t, J=8.0 Hz, 1H), 3.35 (ddd, J=9.4, 4.2, 2.6 Hz, 1H), 3.04–2.93 (m, 2H), 2.06 (s, 1H); $^{13}$C NMR (500 MHz, CDCl$_3$) δ 138.48, 138.21, 138.13, 137.95, 135.09, 133.60, 130.92, 129.10, 128.40, 128.30, 128.25, 128.22, 127.98, 127.90, 127.82, 127.76, 127.55, 126.58, 124.72, 123.57, 123.12, 119.61, 119.31, 113.66, 103.59, 84.39, 82.25, 77.37, 75.56, 75.16, 74.99, 74.75, 68.60, 61.77, 25.57; IR (thin film) 3480 (w), 3065 (w), 3035 (w), 2920 (m), 2878 (m), 1498 (w), 1450 (s), 1365 (s), 1280 (w), 1220 (m), 1176 (s), 1123 (s), 1090 (s), 1073 (s), 1030 (s), 750 (s), 700 (s) cm$^{-1}$; UV-Vis (c=9.21×10$^{-6}$, acetonitrile) $\lambda_{max}$ 254.0 ($\epsilon$=2.81×10$_3$), 211.6 ($\epsilon$=3.19×10$^4$) nm; HRMS m/e calculated for $C_{43}H_{43}NO_8S$ (M+H): 734.2774, found 734.2743; $[\alpha]D^{20}$ –13.3° (c=0.135, acetonitrile); Analysis calculated for $C_{43}H_{43}NO_8S$: C, 70.37; H, 5.91; found: C, 70.30; H, 6.08.

H. 2-(1Phenylsulfonyl-indol-3yl)ethyl-2,3,4-tri-O-benzyl-6-O-trifluoromethylsulfonyl-β-D-glucopyranoside To a stirred solution of 2-(1-phenylsulfonyl-indol-3yl) ethyl-2,3,4-tri-O-benzyl-β-D-glucopyranoside (196 mg, 0.27 mmol) in 2.7 mL of dry dichloromethane at –78° C. was added 2,6-di-tert-butyl-4-methyl pyridine (880 mg, 0.427 mmol) followed by triflic anhydride (58 μl, 0.347 mmol). After stirring 15 minutes at –78° C., the mixture was warmed to room temperature over 20 minutes, and then poured into saturated aqueous NaHCO$_3$ (20 mL) and extracted with ethyl acetate (60 mL). The organic layer was washed with saturated aqueous NaHCO$_3$ (3×20 mL), saturated aqueous NaCl (1×20 mL) and dried over magnesium sulfate. Concentration provided the crude triflate target compound, which used in the next step without purification.

I. N-trifluoroacetyl-5-amino pentanol

To a solution of 5-amino pentanol (1 g, 9.69 mmol) in methanol (25 ml, 0.4 M) at 0° C. was added triethylamine (2 ml, 1.5 equiv, 10 mmol) followed by very slow dropwise addition of trifluoroacetic anhydride (1.8 ml, 1.3 equiv, 12.5 mmol). The reaction mixture was warmed to room temperature and stirred overnight. TLC (5% $CH_3OH/CH_2Cl_2$) stained with ninhydrin revealed starting material; TLC stained with PMA revealed product. The reaction mixture was cooled to 0° C. and triethylamine (1.3 ml, 1 equiv. 9.69 mmol) was added followed by trifluoroacetic anhydride (1 ml, 0.8 equiv.). The reaction mixture was warmed to room temperature and stirred an additional night. Concentration and flash chromatography (silica, 60% EtOAc/petroleum ether) afforded the target compound (1.7 g, 85%).

J. 2-(1-Phenylsulfonyl-indol-3yl)ethyl-2,3,4 tri-O-benzyl-6-O-(N-trifluoroacetyl-5-aminopentyl)-β-D-glucopyranoside To a stirred suspension of sodium hydride (123 mg, 0.307 mmol, 60% oil dispersion) in 17 mL of dry THF at 0° C. was added a solution of N-trifluoroacetyl-5-amino pentanol (265 mg, 1.3 mmol) in 10 mL of dry THF. After stirring 10 minutes at 0° C., the suspension was warmed to room temperature, stirred for 1 hours, and cooled to 0° C. A solution of the above 2-(1-phenylsulfonyl-indol-3yl)ethyl-2,3,4-tri-O-benzyl-6-O-trifluoromethylsulfonyl-β-D-glucopyranoside (theoretically 0.27 mmol) in 16 ml of dry dichloromethane was added slowly dropwise. The reaction mixture was stirred at 0° C. for 30 minutes and then warmed to room temperature. After stirring 24 hours, TLC (2% methanol in dichloromethane) revealed diprotected target compound and a minor amount of monoprotected product. The reaction mixture was cooled to 0° C. and quenched with 10 mL of saturated aqueous ammonium chloride. The resulting mixture was diluted with ethyl acetate (150 mL) and washed with H$_2$O (1×50 mL), saturated aqueous NaCl (1×50 mL) and dried over magnesium sulfate. Concentration and flash chromatography (silica, 2% methanol in dichloromethane) yielded a mixture of diprotected target compound and monoprotected product which was used as a mixture in the next step.

K. Structure (1), 2-(1-Phenylsulfonyl-indol-3yl)ethyl-6-O-(5-aminopentyl)-2,3,4-tri-O-benzyl-β-D-glucopyranoside To a stirred solution of the mixture of step J, above, (theoretically 0.27 mmol) in 6 mL of ethanol at room temperature was added a solution of 5M NaOH (2 mL, 10 mmol). The solution was heated to reflux for 2 hours. The solvents were removed under reduced pressure. The reaction mixture was diluted with ethyl acetate (40 mL) and washed with H$_2$O (1×15 mL), saturated aqueous NaCl (1×15 mL) and dried over magnesium sulfate. Concentration and flash chromatography (silica, 5% methanol in dichloromethane provided structure (1) (150 mg, 83% for 3 steps) as an oil: R$_f$ 0.26 (7% methanol in dichloromethane); $^1$H NMR (500 MHz, CDCl$_3$) d 7.98 (s, 1H), 7.59 (d, J=7.9 Hz, 1H), 7.33–7.04 (m, 19H), 4.90 (d, J=10.9 Hz, 1H), 4.85 (d, J=11.1 Hz, 1H), 4.80 (d, J=11.0 Hz, 1H), 4.77 (d, J=10.9 Hz, 1H), 4.64 (d, J=11.0 Hz, 1H), 4.60 (d, J=11.1 Hz, 1H), 4.48 (d, J=7.8 Hz, 1H), 4.21 (ddd, J=9.4, 6.7, 6.7 Hz, 1H), 3.89 (ddd, J=9.4, 7.3, 7.3 Hz, 1H), 3.64 (dd, J=9.0, 9.0 Hz, 1H), 3.56 (t, J=6.4 Hz, 2H), 3.51–3.47 (m, 1H), 3.4 (t, J=9.2 Hz, 2H), 3.11 (t, 7.0 Hz, 2H), 2.96 (dd, J=12.3, 2.6 Hz 1H), 2.66 (dd, J=12.3, 7.8 Hz, 1H), 2.62–2.54 (m, 2H), 1.93 (s, 2H), 1.54–1.44 (m, 4H), 1.38–1.32 (m, 2H); $^{13}$C NMR (500 MHz, CDCl$_3$) d 138.57, 138.49, 138.14, 136.17, 128.43, 128.36, 128.29, 128.02, 127.88, 127.82, 127.60, 127.56, 127.50, 122.14, 121.96, 119.30, 118.68, 112.60, 111.13, 103.67, 84.61, 82.45, 79.70, 77.20, 75.68, 74.99, 74.73, 73.82, 70.25, 62.63, 50.52, 49.59, 32.36, 29.28, 25.86, 23.31; IR (thin film) 3420(w), 3300(w, 3063(w), 3033(w), 2938(m), 2860(m), 1495(w), 1455(m), 1360(m), 1210(w), 1072(s), 1026(m), 910(w), 538(s), 495(s) cm$^{-1}$; UV-Vis (c=1.14×10$^{-4}$, acetonitrile) I$_{max}$ 289.6 (e=4.17×10$^3$), 280.8 (e=4.97×10$^3$), 220.0 (e=2.4×10$^4$) nm; HRMS m/e calc'd C$_{42}$H$_{50}$N$_2$O$_6$(M+H): 679.373, found 679.370; [α]D$^{20}$+3.2° (c=0.31, acetonitrile).

EXAMPLE 2

Preparation of Analog Having Structure (7), 2-(1-Phenylsulfonyl-indol-3yl)ethyl-6-O-(5-acetamidopentyl)-2,3,4-tri-O-benzyl-β-D-glucopyranoside To a solution of 5-amino pentanol (0.75 g, 7.27 mmol) in methanol (15 ml, 0.5 M) at 0° C. was added triethylamine (1.62 ml, 1.6 equiv, 11.6 mmol) followed by acetic anhydride (0.891 ml, 1.3 equiv, 9.45 mmol). The reaction mixture was warmed to room temperature and stirred overnight. TLC (8% CH$_3$OH/CH$_2$Cl$_2$) stained with ninhydrin revealed starting material. Triethylamine (1.6 ml, 1.6 equiv, 11.6 mmol) was added to room temperature followed by acetic anhydride (0.9 ml, 1.3 equiv, 9.45 mmol) and the reaction mixture was stirred an additional night. Concentration and flash chromatography (silica, 7% CH$_3$OH/EtOAc) afforded N—CH$_3$CO-5-amino-pentanol (1 g, 100%).

Sodium hydride (0.108 g, 60% suspension in oil, 0.307 mmol, 2.2 equiv. compared to N—CH$_3$CO-5-amino-pentanol) was quickly weigh into a flame dried flask under argon. THF (20 ml, 0.01 M compared to moles of the triflate was added and the resulting suspension was cooled to 0° C.

A solution of N—CH$_3$CO-5-amino-pentanol (0.108 g, 0.22 moles, 5 equiv) in 5 ml of THF was added dropwise and then warmed to room temperature for 1 hour. The resulting suspension was cooled to 0° C. and a solution of the 2-(1-phenylsulfonyl-indol-3-yl)ethyl-2,3,4 tri-O-benzyl-β-D-glucopyranoside triflate prepared in Example 1H (assumed 0.245 mmol) in CH$_2$Cl$_2$ (15 ml, CH$_2$Cl$_2$:THF= 3:5) was added slowly dropwise and stirred for 1 hour. The reaction mixture was warmed to room temperature and stirred overnight. TLC (3% CH$_3$OH/CH$_2$Cl$_2$) revealed no starting material and a major and minor product very close in R$_f$. Both were collected since the minor product is deprotected indole and the mixture is transformed to the same product in the next step. The reaction mixture was cooled to 0° C. and quenched with aqueous saturated ammonium chloride. The reaction mixture was poured into EtOAc and washed 1×H$_2$O and 1×aqueous saturated NaCl. The organic layer was dried with MgSO$_4$ and filtered. Concentration and flash chromatography (silica, 3% CH$_3$OH/ CH$_2$Cl$_2$) yielded the major and minor product which was used as a mixture in the next step.

To a solution of the above mixture (assumed 0.245 mmol) in ethanol (4 ml, 0.05 M) at room temperature was added 2 ml of 5 M NaOH and the cloudy reaction mixture was heated to reflux for 2 hours. The reaction solvent was concentrated, diluted with EtOAc, and washed 1×H$_2$O and 1×aqueous saturated NaCl. The organic layer was dried with MgSO$_4$ and filtered. Concentration and flash chromatography (silica, 4% CH$_3$OH/CH$_2$Cl$_2$) yielded structure (8), 2-(1-Phenylsulfonyl-indol-3yl)ethyl-6-O-(5-acetamidopentyl)-2,3,4-tri-O-benzyl-β-D-glucopyranoside.

EXAMPLE 3

Preparation of Analog Having Structure (2), 2-(1H-indol-3-yl)ethyl-6-O-(5-aminopentyl)-2,4-di-O-deoxy-β-D-glucopyranoside A. Methyl 2-O-benzoyl-4,6-O-isopropylidene-α-D-glucopyranoside To a stirred solution of methyl 2-4,6-O-isopropylidene-α-D-glucopyranoside (28.8 g, 123 mmol) in 410 mL of dichloromethane at 0° C. was added triethylamine (25.7 mL, 185 mmol) followed by benzoic anhydride (30.73 g, 135 mmol). The solution was warmed to room temperature and stirred for 24 hours. The solvent was removed under reduced pressure and the residue was extracted with ethyl acetate (500 mL) and washed with H$_2$O (1×200 mL), a saturated salt solution (1×200 mL), and dried over magnesium sulfate. Concentration and flash chromatography (silica, 25% ethyl acetate in petroleum ether) provided the target compound (33.4 g, 80%) as a white form.

B. Methyl 2-O-benzoyl-3-O-(methylthio)thiocarbonyl-4,6-O-isopropylidene-α-D glucopyranoside To a stirred solution of methyl 2-O-benzoyl-4,6-O-isopropylidene-α-D-glucopyranoside (1 g, 2.95 mmol) in 10 mL of dry THF at −78° was added sodium bis(trimethyl silyl)amide (1 M solution in THF, 3.54 mL, 3.4 mmol) followed immediately by carbon disulfide (248 μl, 4.13 mmol). After stirring the solution for 15 minutes at −78° C., methyl iodide (550 μl, 11.8 mmol) was added. The solution was stirred at −78° C. an additional 10 minutes and then brought to room temperature. After stirring 30 minutes, the reaction was quenched with 2 mL of H$_2$O, diluted with 60 mL of ether, washed with H$_2$O (1×30 mL), a saturated solution of NaCl (1×30 mL) and dried over magnesium sulfate. Removal of the solvent yielded a crude xanthate (1.52 g crude). A 1.28 g aliquot of the crude xanthate was used in the next step without further purification. The remaining 0.24 g of target compound was purified by flash chromatography (silica, 20% either in petroleum ether) to yield a white solid.

C. Methyl 2-O-benzoyl-3-deoxy-4,6-O-isopropylidene-α-D-glucopyranoside

To a solution of crude methyl 2-O-benzoyl-3-O-(methylthio)thiocarbonyl-4,6-O-isopropylidene-α-D glucopyranoside (1.28 9, 2.48 mmol theoretically) in 10 mL of dry toluene at room temperature was added 2,2'-azobisisobutyro-nitrile (AIBN, 40 mg) followed by tributyl tin hydride (2 mL, 7.48 mmol). The reaction was heated to reflux for 2 hours. The toluene was removed under reduced pressure. The resulting oil was dissolved in 60 mL of acetonitrile and washed with petroleum ether (3×20 mL). Concentration of the acetonitrile and flash chromatography (silica, 10% ethyl acetate in petroleum ether) yielded pure target compound (585 mg, 73% from 3b) as a clear oil.

D. Methyl 3-deoxy-α-D-glucopyranoside

To a stirred suspension of methyl 2-O-benzoyl-3-deoxy-4,6-O-isopropylidene-α-D-glucopyranoside (520 mg, 1.61 mmol) in 8 mL of methanol at room temperature was added sodium methoxide (70 mg, 1.29 mmol). After stirring 2 h, the benzoyl group had been completely removed as evidenced by TLC. Amberlyst H$^+$ resin was added and the mixture stirred for 1 hours until the generation of the free triol was completed as evidenced by TLC. After filtration, the solvents were removed under reduced pressure. Flash chromatography (silica, 10% methanol in methylene chloride) yielded pure target compound (286 mg. 100%) as an oil.

E. Methyl 2,4,6-tri-O-acetyl-3-deoxy-α-D-glucopyranoside

To a stirred solution of methyl 3-deoxy-α-D-glucopyranoside (535 mg, 3.0 mmol) in mL of methylene chloride at 0° C. was added triethylamine (2.92 mL, 21.0 mmol), acetic anhydride (1.41 mL, 15.0 mmol) and dimethyl amino pyridine, one at a time (37 mg, 0.30 mmol). The solution was warmed to room temperature. After stirring 7 hours, the solution was diluted with mL of ethyl acetate and washed with H$_2$O (1×30 mL), a saturated solution of NaCl (1×30 mL), and dried over magnesium sulfate. Concentration and flash chromatography (silica, 40% ether in petroleum ether) provided pure target compound (820 mg. 90%) as a clear oil.

F. 1,2,4,6-tetra-O-acetyl-3-deoxy-α-D-glucopyranoside

To a stirred solution of methyl 2,4,6-tri-O-acetyl-3-deoxy-α-D-glucopyranoside (127 mg, 0.41 mmol) in 3 mL of acetic anhydride at 0° C. was added boron trifluoride etherate (15 µl, 0.12 mmol). The solution was warmed to room temperature, stirred for 1.25 hours, and poured into 30 mL of an ice cold saturated solution of NaHCO$_3$ and extracted with ethyl acetate (2×50 mL). The combined organic layers were washed with saturated aqueous NaHCO$_3$ and extracted with ethyl acetate (2×50 mL). The combined organic layers were washed with saturated aqueous NaHCO$_3$(2×40 mL), saturated aqueous NaCl (1×40 mL), and dried over magnesium sulfate. Concentration and flash chromatography (silica, 30% ethyl acetate in petroleum ether) provided the target compound (133 mg, 96%) as an oil.

G. Bromo 2,4,6-tri-O-acetyl-3-deoxy-α-D-glucopyranoside

Hydrobromic acid (30% in acetic acid solution, 3 mL, 14.0 mmol) was added to 1,2,4,6-tetra-O-acetyl-3-deoxy-α-D-glucopyranoside (750 mg, 2.26 mmol) at 0° C. After 10 minutes, the resulting solution was warmed to room temperature for 30 minutes The solution was then diluted with ether (20 mL) and poured into a mixture of ice and a saturated solution of NaHCO$_3$ (25 mL). An additional 30 ML of ether was added and the layers were separated. The organic layer was washed with saturated aqueous NaHCO$_3$ (3×25 mL), H$_2$O (1×25 mL, saturated aqueous NaCl (1×25 mL), and dried over magnesium sulfate. Removal of the solvent provided crude target compound, which was used in the next step without further purification.

H. 2-(1-Phenylsulfonyl-indol-3-yl)ethyl-2,4,6-tri-O-acetyl-3-deoxy-β-D-glucopyranoside To a stirred suspension of flame dried 4A sieves (1.33 g) in 11 mL of dry hexane at room temperature was added a solution of N-benzenesulfonyltryptophol (1.20 g, 4.0 mmol) in 4 mL of dry benzene. Next, a solution of the above bromo 2,4,6-tri-O-acetyl-3-deoxy-α-D-glucopyranoside (theoretically 2.26 mmol) in 4 mL of dry benzene was added, followed by silver(I)oxide (523 mg, 2.26 mmol). The reaction vessel was covered with aluminum foil and the suspension stirred for 3 days. After filtration through celite, concentration of the filtrate under reduced pressure and flash chromatography (silica, 10:1 methylene chloride:ether) provided pure target compound (781 mg, 60%) as a white foam.

I. 2-(1-Phenylsulfonyl-indol-3-yl)ethyl-3-deoxy-β-D-glucopyranoside

To a stirred suspension of 2-(1-phenylsulfonyl-indol-3-yl)ethyl-2,4,6-tri-O-acetyl-3-deoxy-β-D-glucopyranoside (735 mg, 1.28 mmol) in 6.4 mL of methanol was added sodium methoxide (55.2 mg, 1.02 mmol) at room temperature. After 90 minutes, the resulting solution was diluted with 6.4 mL of methanol (6.4 mL) and neutralized by addition of amberlyst H$^+$ resin. The resin was quickly removed by filtration to avoid formation of the methyl glucoside. Concentration of the filtrate and flash chromatography (silica, 12:1:1 methylene chloride, acetone, methanol) afforded pure target compound (498 mg, 87%) as a white solid.

J. 2-(1-Phenylsulfonyl-indol-3yl)ethyl-3-deoxy-6-O-tert-butyidiphenylsilyl-β-D-glucopyranoside To a stirred solution of 2-(1-phenylsulfonyl-indol-3-yl)ethyl-3-deoxy-β-D-glucopyranoside (779 mg, 1.74 mmol) in 17 mL of dry DMF was added imidazole (260 mg, 3.83 mmol) followed by tert-butyldiphenylsilyl chloride (541 µl, 2.09 mmol) at room temperature. The solution was stirred at 50° C. for 24 hours. The reaction mixture was diluted with 250 mL of ethyl acetate and washed with H$_2$O (2×100 mL), saturated aqueous NaCl (1×100 mL), and dried over magnesium sulfate. Concentration and flash chromatography (silica, 3% methanol in methylene chloride) provided pure target compound (1.04 g, 87%) as a white foam.

K. 2-(1-Phenylsulfonyl-indol-3yl)ethyl-3-deoxy-2,4-di-O-benzyl-6-O-tert-butyldiphenylsilyi-β-D-glucopyranoside To a stirred suspension of sodium hydride (4.63 mmol, 185 mg, 60% oil dispersion) in 5 mL of dry THF at 0° C. was added a solution of 2-(1-phenylsulfonyl-indol-3yl)ethyl-3-deoxy-6-O-tert-butyldiphenylsilyl-β-D-glucopyranoside (1.27 g, 1.85 mmol) in 10 mL of dry THF. After 10 minutes, the mixture was warmed to room temperature. After stirring 1 hours, the suspension was cooled to 0° C. and benzyl bromide (5.55 mmol. 660 µl) was added followed by tetrabutylammonium iodide (68 mg, 0.185 mmol). The mixture was warmed to room temperature and stirred for 3 days. The reaction was then quenched with 3 mL of aqueous saturated ammonium chloride at 0° C. The resulting solution was diluted with 80 mL of ether and washed with H$_2$O (2×30 mL), saturated aqueous NaCl (1×30 mL), and dried over magnesium sulfate. Concentration under reduced pressure and flash chromatography (silica, 25% ether in petroleum ether) provided pure target compound (760 mg, 47%) as a white foam.

L. 2-(1-phenylsulfonyl-indol-3yl)ethyl-3-deoxy-2,4-di-O-benzyl-β-D-glucopyranoside To a stirred solution of 2-(1-phenylsulfonyl-indol-3yl) ethyl-3-deoxy-2,4-di-O-benzyl-6-O-tert-butyldiphenylsilyl-β-D-glucopyranoside (675 mg, 0.780 mmol) in 10 mL of dry THF was added tetrabutylammonium fluoride (1 M solution in THF, 1.17 mmol, 1.17 mL) at room temperature. After stirring 2 hours, the solution was diluted with 80 mL of ethyl acetate and washed with H$_2$O (1×30 mL), saturated aqueous NaCl (1×30 mL), and dried over magnesium sulfate. Concentration and flash chromatography (silica, 60% ether in petroleum ether) afforded pure target compound (445 mg, 91%) as an oil.

M. 2-(1-Phenylsulfonyl-indol-3yl)ethyl-3-deoxy-2,4-di-O-benzyl-6-O-trifluoromethylsulfonyl-β-D-glucopyranoside To a stirred solution of 2-(1-phenylsulfonyl-indol-3yl) ethyl-3-deoxy-2,4-di-O-benzyl-β-D-glucopyranoside (360 mg, 0.575 mmol) in 3 mL of dichloromethane at −78° C. was added, 2.6 di-tert-butyl-4-methylpyridine (189 mg, 0.92 mmol) followed by triflic anhydride (126 μl, 0.748 mmol). After stirring 20 minutes at −78° C., the mixture was allowed to warm to room temperature for 20 minutes. The suspension was poured into aqueous saturated NaHCO$_3$(15 mL) and extracted with ethyl acetate (1×35 mL). The organic layer was washed with saturated aqueous NaHCO$_3$ (3×15 mL), saturated aqueous NaCl (1×15 mL) and dried over magnesium sulfate. Concentration afforded crude target compound as an oil which was used in the next step without further purification.

N. 2-(1-Phenylsulfonyl-3-yl)ethyl-2,4-di-O-benzyl-3-deoxy-6-O-(N-trifluoroacetyl-5-aminopentyl)-β-D-glucopyranoside To a stirred suspension of sodium hydride (8.63 mmol, 345 mg, 60% dispersion in oil) in 20 mL of dry THF at 0° C. was added a solution of N-trifluoro acetyl 5-amino pentanol (687 mg, 3.45 mmol) in 16 mL of dry THF. After stirring 10 minutes at 0° C., the suspension was allowed to warm to room temperature and stir for 90 minutes. The reaction mixture was then cooled to 0° C. and a solution of crude triflate of step M (theoretically 0.575 mmol) in 22 mL of dry dichloromethane was added. The suspension was stirred for 30 minutes at 0° C. and then warmed to room temperature. After stirring for an additional 24 hours, the reaction was quenched at 0° C. with 10 mL of saturated aqueous ammonium chloride. The resulting mixture was diluted with ethyl acetate (200 mL) and washed with H$_2$O (1×75 mL), saturated aqueous NaCl (1×75 mL) and dried over magnesium sulfate. Concentration and flash chromatography (silica, eluted column 5 times with 1% methanol in methylene chloride to 2% methanol in methylene chloride) afforded the target compound (392 mg) as a white foam which was used without further purification in the next step.

O. Structure (2), 2-(1H-indol-3-yl)ethyl-6-O-(5-aminopentyl)-2,4-di-O-deoxy-β-D-glucopyranoside To a stirred solution of 2-(1-phenylsulfonyl-indol-3yl) ethyl-3-deoxy-2,4-di-O-benzyl-6-O-trifluoromethylsulfonyl-β-D-glucopyranoside (392 mg, theoretically 0.575 mmol) in 6 mL of ethanol at room temperature was added a solution of 5 M NaOH (1 mL, 5 mmol). The solution was allowed to reflux for 2 hours. The solvents were removed under reduced pressure, and the reaction mixture was diluted with dichloromethane (75 mL) and washed with aqueous HCl (25 mL, 5 mmol). The water layer was re-extracted with dichloromethane (2×75 mL). The combined organic layers were washed with saturated aqueous NaCl (2×25 ML) and dried over magnesium sulfate. Concentration and flash chromatography (silica, 8% methanol in dichloromethane) afforded the pure product, structure (8) (172 mg, 52% for 3 steps) as an oil. R$_f$0.22 (8% methanol in dichloromethane); $^1$H NMR (500 MHz, CDCl$_3$) δ 8.44 (s, 1H), 7.57 (d, J=7.7 Hz, 1H), 7.31–7.23 (m, 10H), 7.17–7.14 (m, 1H), 7.11–7.07(m, 1H), 7.04(d, J=2.0 Hz, 1H), 4.71 (d, J=11.8 Hz, 1h), 4.57 (d, J=11.7 Hz, 1H), 4.56 (d, J=11.9 Hz, 1H), 4.46(d, J=7.5 Hz, 1H), d, J=11.5 Hz, 1H, 4.20 (ddd, J=13.8, 9.4, 6.8 Hz, 1H), 3.87 (ddd, J=14.9, 9.3., 7.4 Hz, 1H), 3.55–3.50 (m, 3H), 3.32–3.26 (M, 2H0, 3.11 (t, J=7.2 Hz 2H), 3.02 (dd, J=12.4, 2.9 Hz, 1H), 2.68 (dd, J=12.4, 8.1 Hz, 1H), 2.67–2.57 (m, 2H), 2.50 (ddd, J=12.3, 4.8, 4.8 Hz, 1H), 2.20 (s, 3h), 1.57–2.44(m, 5H), 1.36–1.30 (m, 2H); $^{13}$C NMR (500 MHz, CDCl$_3$) δ 138.61, 137.92, 136.14, 128.41, 128.27, 127.79, 127.70, 127.53, 127.49, 122.18, 121.84, 119.18, 118.67, 112.56, 111.12, 105.22, 105.18, 76.53, 75.14, 74.28, 72.69, 70.99, 69.91, 62.45, 50.69, 49.49, 34.86, 32.28, 29.16, 25.80, 23.27; IR (thin film) 3325(m, 3065(w), 3035(w), 3015(w), 2940(s), 2870 (s), 1500(w), 1458(m), 1354(w), 1220(w), 1076(s), 1030 (m), 745(s), 700(s), cm$^{-1'}$ UV-Vis (c=6.5×1-$^{-5}$. acetonitrile) λ$_{max}$ 281.2(ξ=6.2×10$^3$), 218.8 (ξ=3.62×10$^4$) nm; HRMS m/e calc'd for C$_{35}$H$_{44}$N$_2$O$_5$(M+H): 573.3315, found 573.3314; [α]D$^{20}$+16.7° (c=0.15, acetonitrile).

EXAMPLE 4

Preparation of Analog Having Structure (13), Methyl 2,3,4-tri-O-benzyl-6-O-(N-trifluoroacetyl-5-aminopentyl)-β-D-glucopyranoside A. Methyl 6-O-tert-butyldiphenylsilyl-β-D-glucopyranoside To a stirred solution of methyl β-D-glucopyranoside (5 g, 25.7 mmol) in 51 mL of dry DMF was added at room temperature imidazole (5.46 g, 80.2 mmol) followed by tert-butyldiphenyl-silyl chloride (11.3 mL, 43.4 mmol). The solution was heated to 50° C. for 24 hours and the DMF was removed under reduced pressure. The reaction mixture was diluted with 200 mL of ethyl acetate and washed with H$_2$O (1×100 mL), saturated aqueous NaCl (1×100 mL), and dried over magnesium sulfate. Concentration and flash chromatography (silica, 4% methanol in dichloromethane) provided pure target compound (9.82 g, 88%) as a white foam.

B. Methyl 6-O-tert-butyldiphenylsilyl-2,3,4-tri-O-benzyl-β-D-glucopyranoside

To a stirred suspension of sodium hydride (1.67 g, 41.6 mmol) in 100 mL of dry THF was added at 0° C. a solution of methyl 6-O-tert-butyldiphenylsilyl-β-D-glucopyranoside (4.0 g, 9.25 mmol) in 50 mL of dry THF. After 5 minutes, the suspension was warmed to room temperature and stirred for 1 hour. Benzyl bromide (5.50 mL, 46.2 mmol) was added at room temperature followed by tetrabutylammonium iodide (341 mg, 0.93 mmol). The suspension was warmed to 50° C. and stirred for 4 days. After quenching with 40 mL of saturated aqueous ammonium chloride, the resulting mixture was diluted with ether (600 mL) and washed with H$_2$O (2×200 mL), saturated aqueous NaCl (1×200 mL), and dried over magnesium sulfate. Concentration and flash chromatography (silica, 10% ether in petroleum ether) provided pure target compound (4.48 g, 69%) as a clear oil.

C. Methyl 2,3,4-tri-O-benzyl-β-D-glucopyranoside

To a stirred solution of methyl 6-O-tert-butyldiphenylsilyl-2,3,4-tri-O-benzyl-β-D-glucopyranoside (2.81 g, 3.98 mmol) in dry THF (40 ml, 0.1 M) at room temperature was added tetrabutyl ammonium fluoride (4.37 ml, 4.37 mmol, 1 M solution in THF). After stirring for 3 hours, the reaction solution was diluted with ethyl acetate (300 ml) and washed with water (1×100 ml) and saturated aqueous NaCl (1×100 ml), and dried with magnesium sulfate. Concentration and flash chromatography (silica, 50% ether in petroleum ether) provided pure target compound (1.62 g, 88%) as a white solid.

D. Methyl 2,3,4-tri-O-benzyl-6-O-trifluoromethylsulfonyl-β-D-glucopyranoside

To a stirred solution of methyl 6-O-tert-butyldiphenylsilyl-2,3,4-tri-O-benzyl-β-D-glucopyranoside (800 mg, 1.71 mmol) in 8.55 mL of dry dichloromethane at −78° C. was added 2,6-di-tert-butyl-4-methyl pyridine (632 mg, 3.08 mmol) followed by triflic anhydride (345 µl, 2.05 mmol). After stirring 15 minutes at −78° C., the mixture was warmed to room temperature over 20 minutes, and then poured into a solution of saturated aqueous NaHCO, (20 mL) and extracted with ethyl acetate (50 mL). The organic layer was washed with saturated NaHCO$_3$ (3×20 mL), saturated aqueous NaCl (1×20 mL), and dried over magnesium sulfate. Concentration provided crude target compound, which was used in the next step without further purification.

E. Structure (14), Methyl 2,3,4-tri-O-benzyl-6-O-(N-trifluoroacetyl-5-aminopentyl)-β-D-glucopyranoside To a stirred suspension of sodium hydride (855 mg, 21.4 mmol, 60% oil dispersion) in 60 mL of dry THF at 0° C. was added a solution of N-trifluoroacetyl-5-aminopentanol (1.7 g, 8.6 mmol) in 35 mL of dry THF. After stirring 10 minutes at 0° C., the suspension was warmed to room temperature, stirred for 1 hour, and cooled to 0° C. A solution of the above crude methyl 2,3,4-tri-O-benzyl-6-O-trifluoromethylsulfonyl-β-D-glucopyranoside (theoretically 1.71 mmol) in 57 mL of dry dichloromethane was added. The reaction mixture was stirred at 0° C. for 30 minutes and then warmed to room temperature. After stirring 24 hours, the reaction was cooled to 0° C. and quenched with 40 mL of saturated aqueous ammonium chloride. The resulting solution was diluted with ethyl acetate (400 mL) and washed with H$_2$O (1×150 mL), saturated aqueous NaCl (1×150 mL) and dried over magnesium sulfate. Concentration and flash chromatography (silica, 30% ethyl acetate in petroleum ether) provided the analog having structure (13), methyl 2,3,4-tri-O-benzyl-6-O-(N-trifluoroacetyl-5-aminopentyl)-β-D-glucopyranoside, (799 mg) as a white solid which was used without further purification.

EXAMPLE 5

Preparation of Analog Having Structure (8), Methyl 6-O-(5-aminopentyl)-2,3,4-tri-O-benzyl-β-D-glucopyranoside To a stirred solution of methyl 2,3,4-tri-O-benzyl-6-O-(N-trifluoroacetyl-5-aminopentyl)-β-D-glucopyranoside (799 mg, theoretically 1.71 mmol, structure (13) from Example 4) in 10 mL of ethanol at room temperature was added a solution of 5M (3 mL, 15 mmol). The solution was heated to reflux for 2 hours. The solvents were removed under reduced pressure. The reaction mixture was diluted with dichloromethane (70 mL) and washed with aqueous HCl (25 mL, 15 mmol). The water layer was re-extracted with dichloromethane (3×50 mL), and the combined organic layers were washed with saturated aqueous NaCl (1×75 mL) and dried over magnesium sulfate. Concentration and crystallization from ethyl acetate/petroleum ether provided pure analog having structure (9), methyl 6-O-(5-aminopentyl)-2,3,4-tri-O-benzyl-β-D-glucopyranoside, (675 mg, 72% from methyl 2,3,4-tri-O-benzyl-6-O-trifluoromethylsulfonyl-β-D-glucopyranoside) as a white solid: m.p. 95–95.5° C.; R$_F$ 0.19 (6% methanol in dichloromethane); $^1$H NMR (500 MHz, CDCl$_3$) δ 7.35–7.24 (m, 15H), 4.92 (d, J=7.5 Hz 1H), 4.90 (d, J=7.6 Hz, 1H), 4.85 (d,J=11.0 Hz, 1H), 4.78 (d, J=11.0 Hz, 1H), 4.70 (d, J=11.0 Hz, 1H), 4.60 (d, J=11.0 Hz, 1H), 4.32 (7.8, 1H), 3.66–3.59 (m, 3H), 3.56 (s, 3H), 3.48–3.36 (m, 3H), 2.94 (dd, J=12.5, 2.1 Hz, 1H), 2.68 (dd, J=12.0, 6.8 Hz, 1H), 2.64–2.53 (m, 2H), 1.71 (s, 2H), 1.59–1.53 (m, 2H), 1.51–1.45 (m, 2H), 1.42– 1.36 (m, 2H), $^{13}$C NMR (500 MHz, CDCl$_3$) δ 138.55, 138.47, 138.17, 128.39, 128.33, 128.03, 127.95, 127.85, 127.77, 127.60, 127.57, 104.72, 84.56, 82.45, 79.74, 75.66, 75.02, 74.74, 74.16, 62.62, 57.20, 50.69, 49.72, 32.49, 29.65, 23.37; IR (thin film) 3280(m), 3095(w), 3065(w), 3035(w), 2935(s), 2915(s), 2860(s), 1496(w), 1454(m), 1404(w), 1393(w), 1358(m), 1214(m), 1115(s), 1072(s), 1037(m), 1027(m), 1009(m), 911(w), 826(s), 747(s), 696(s) cm$^{-1}$; HRMS m/e calc'd for C$_{33}$H$_{43}$O$_6$N (M+H): 550.3168, found 550.3179; [α]$_D^{20}$+9.3° (c=0.15, acetonitrile).

EXAMPLE 6

Preparation of Analog Having Structure (12), 2-(1H-Indol-3yl)ethyl-2,3,4-tri-O-benzyl-β-glucopyranoside To a stirred solution of 2-(1-phenylsulfonyl-indol-3-yl)ethyl-2,3,4- tri-O-benzyl-β-D-glucopyranoside (100 mg, 0.136 mmol, prepared in Example 1, step G) in 3 ml of ethanol at room temperature was added a solution of 5M NaOH (1 mL, 5 mmol). The reaction mixture was refluxed for 2 h and the solvents were removed under reduced pressure. The resulting residue was diluted with dichloromethane (70 mL) and washed with aqueous HCl (24 mL, 5 mmol). The water layer was reextracted with dichloromethane (2×70 mL). The organic layers were combined and washed with saturated aqueous NaCl (1×50 mL) and dried over magnesium sulfate. Concentration and flash chromatography (silica, 25% ethyl acetate in petroleum ether) provided structure (13) (68 mg, 85%) as an oil: R$_F$ 0.42 (40% ethyl acetate in petroleum ether); $^1$H NMR (500 MHz, CDCl$_3$) d 7.83 (s, 1H), 7.59 (d, J=7.8 Hz, 1H), 7.33–7.24 (m, 15H), 7.20–7.17 (m, 2H), 7.11 (t, J=7.8 Hz, 1H), 7.01 (d, J=1.8 Hz, 1H), 4.91 (d, J=10.9 Hz, 1H), 4.85 (d, J=10.9, 1H), 4.80 (d, J=10.9 Hz, 1H), 4.79 (d, J=11.0 Hz, 1H), 4.64 (d, J=11.0 Hz, 1H), 4.63 (d, J=11.0 Hz, 1H), 4.49 (d, J=7.8 Hz, 1H), 4.22 (ddd, J=9.4, 6.7, 6.7 Hz, 1H), 3.90–3.82 (m, 2H), 3.72–3.67 (m, 1H), 3.65 9 ap. t, J=9.1 Hz, 1H), 3.56 (ap. t, J=9.3 Hz, 1H), 3.42 (ap. t, J=8.1 Hz, 1H), 3.35 (ddd, J=9.5, 4.3, 2.8 Hz, 1H), 3.11 (t, J=7.0 Hz, 2H), 1.87 (dd, J=7.6, 5.9 Hz, 1H); $^{13}$C NMR (500 MHz, CDCl$_3$) d 138.52, 138.44, 137.98, 136.17, 128.46, 128.36, 128.29, 128.05, 128.00, 127.89, 127.86, 127.60, 127.57, 127.45, 122.09, 122.01, 119.34, 118.68, 112.60, 111.13, 103.69, 84.49, 77.57, 75.64, 75.04, 75.01, 74.75, 70.25, 62.04, 25.86; IR (thin film) 3575(sh), 3435(m), 3085(sh), 3065(w), 3035(w), 2925(m), 2880(m), 1500(w), 1455(m), 1360(w), 1310(w), 1150(sh), 1085(s), 1030(s), 920(w), 810(w), 740(s), 700(s) xm$^{-1}$; UV-Vis (c=2.89×10$^{-4}$, acetonitrile)l$_{max}$ 289.6 (e=3.56×10$^3$), 281.2 (e=4.24×10$^3$), 222.4 (e=1.01×10$^4$) nm; HR MS m/e calc'd for C$_{37}$H$_{39}$O$_6$N(M+NH$_4$): 6.11.3121, found 611.3043; [α]$_D^{20}$ −2.5° (c=1.37, acetonitrile).

EXAMPLE 7

Preparation of Analog Having Structure (10), 2-(1H-Indol-3-yl)ethyl-6-O-aminopentyl)-2,3-di-O-benzyl-4-deoxy-β-D-glucopyranoside A. Methyl 2,3,6-tri-O-benzoyl-4-(methylthio)thiocarbonyl-α-D-glucopyranoside To a solution of the methyl 2,3,6-tri-O-benzoyl-4-O-α-D-glucopyranoside (5.00 g, 9.87 mmol) in 100 mL of dry THF at −78° C. was added carbon disulfide (0.45 mL, 7.48 mmol) followed by sodium bis(trimethylsilyl)amide (10.5 mL, 51.8 mmol). The solution was stirred at −78° C. for 20 minutes. Methyl iodide (2.10 mL, 33.7 mmol) was added, the solution was stirred for 5 minutes at −78° C. and then at room temperature for 45 minutes. The reaction was quenched by the addition of water (5 mL) and the mixture was by extracted with ethyl acetate (2×100 mL). The organic layer was washed with a saturated solution of sodium chloride, and dried over anhydrous sodium sulfate. The solvent was removed under reduced pressure to yield a pale yellow oil (5.70 g, 97%). The crude xanthate was used without purification in the next step. An analytical sample was purified by flash column chromatography using 20% ethyl acetate in petroleum ether to yield the target compound as white crystals.

B. Methyl 2,3,6-tri-O-benzoyl-4-deoxy-α-D-glucopyranoside

To a solution of the crude methyl 2,3,6-tri-O-benzoyl-4-(methylthio)thiocarbonyl-α-D-glucopyranoside (5.70 g, 9.55 mmol) in 120 mL of dry toluene was added AIBN (50 mg). Tributyl tin hydride (6.68 mL, 24.8 mmol) was added and the reaction was heated to reflux for 4 hours. The toluene was removed under reduced pressure. Acetonitrile (200 mL) was added and the mixture extracted with petroleum ether (5×100 mL) to remove all tin salts. After drying over anhydrous sodium sulfate, the solvent was removed under reduced pressure to yield a clear colorless oil which solidified on standing. Purification by flash column chromatography using 20% ethyl acetate in petroleum ether as the eluant gave the target compound as a white solid.

C. 1-O-Acetyl-2,3,6-tri-O-benzoyl-4-deoxy-α-D-glucopyranose

To a solution of methyl glycoside methyl 2,3,6-tri-O-benzoyl-4-deoxy-α-D-glucopyranoside (0.50 g, 1.1 mmol) in acetic anhydride (3.0 mL, 32 mmol) at 0° C. was added boron trifluoride etherate (0.1 mL). The solution was stirred at room temperature for 4 hours, diluted with ethyl acetate and poured in an ice-cold solution of saturated sodium bicarbonate. Extraction with ethyl acetate (2×100 mL) was followed by washing with a saturated solution of sodium chloride. The organic layer was dried over anhydrous sodium sulfate and evaporated under reduced pressure to yield the product as a colorless oil which crystallized upon standing to give the target compound as white needles (0.45 g, 85%).

D. 1-Bromo-2,3,6,-tri-O-benzoyl-4-deoxy-α-D-glucopyranose

To a stirred solution of 1-O-acetyl-2,3,6-tri-O-benzoyl-4-deoxy-α-D-glucopyranose (0.137 g, 0.29 mmol) in 3.0 mL of dry dichloromethane at 0° C. was added 30% hydrogen bromide in acetic acid (0.07 mL, 0.33 mmol). The solution was stirred under argon at room temperature for 4 hours, diluted with ethyl acetate (100 mL) and extracted with a saturated solution of sodium bicarbonate. The organic layer was washed with a saturated solution of sodium chloride, dried over anhydrous sodium sulfate and evaporated under reduced pressure to yield the target compound as a colorless oil which solidified upon standing. Crystallization from ether and petroleum ether gave the target compound as white crystals (0.15 g, 100%).

E. 2-(1-Phenylsulfonyl)-indol-3-yl-ethyl-2,3,6-tri-O-benzoyl-4-deoxy-β-D-glucopyranoside To a mixture of activated powdered 4 Å molecular sieves (0.83 g), the protected tryptophol prepared in Example 1, step B (0.37 g, 1.23 mmol) and silver (I) oxide (0.83 g, 3.58 mmol) in a flask wrapped with aluminum foil was added a solution of 1-bromo-2,3,6,-tri-O-benzoyl-4-deoxy-α-D-glucopyranose (0.40 g, 0.814 mmol) in 16.7 mL of 40% hexane in benzene. The mixture was stirred under argon for two days, filtered through celite, washed with ethyl acetate and the solvent was removed to yield a colorless oil. Purification by flash column chromatography using 50% ether in petroleum ether gave the target compound as a colorless solid (0.50 g, 81%).

F. 2-(1-Phenylsulfonyl)-indol-3-yl-ethyl-4-deoxy-β-D-glucopyranoside

To a solution of 2-(1-phenylsulfonyl)-indol-3-yl-ethyl-2,3,6-tri-O-benzoyl-4-deoxy-β-D-glucopyranoside (120 mg, 0.158 mmol) in 20 mL of methanol was added sodium methoxide (0.027 g, 0.507 mmol). The solution was stirred under argon overnight. Amberlyst H+ resin was added and the reaction stirred until neutral to wet pH paper. The resin was removed by filtration and washed with methanol. The filtrate was concentrated under reduced pressure to yield a tan solid. Purification by flash column chromatography using 10% methanol in dichloromethane gave the target compound as a white solid (65 mg, 91%).

G. 2-(1-Phenylsulfonyl)-indol-3-yl-ethyl-6-O-tert-butyidiphenylsilyl-4-deoxy-β-D-glucopyranoside To a solution of diol 2-(1-phenylsulfonyl)-indol-3-yl-ethyl-4-deoxy-β-D-glucopyranoside (0.24 g, 05.536 mmol) in 6 mL of dry DMF was added imidazole (73 mg, 1.07 mmol) followed by tert-butyldiphenylsilyl chloride (0.17 mL, 0.643 mmol). The solution was heated under argon in an oil bath at 70° C. for 48 hours. The reaction was quenched by addition of methanol (5 mL). The solvents were removed under reduced pressure. The residue was extracted with ethyl acetate (2×200 mL), washed with a saturated solution of sodium chloride and dried over anhydrous sodium sulfate. Removal of the solvent under reduced pressure gave a pale yellow oil. Purification by flash column chromatography using 3% methanol in dichloromethane gave the target compound as a colorless oil (0.36 g, 97%).

H. 2-(1-Phenylsulfonyl)-indol-3-yl-ethyl-2,3,-di-O-tert-butyidiphenyisily-4-deoxy-β-D-glucopyranoside To a stirred suspension of sodium hydride (73.0 mg. 3.04 mmol, 60% oil dispersion) in 2.7 mL of dry THF at 0° C. was added a solution of diol 2-(1-phenylsulfonyl)-indol-3-yl-ethyl-6-O-tert-butyldiphenylsilyl-4-deoxy-β-D-glucopyranoside (0.50 g, 0.729 mmol) in dry THF (6.8 mL). The reaction mixture was stirred at room temperature for 30 minutes. The mixture was cooled to 0° C. and benzyl bromide (0.26 mL, 2.18 mmol) was added dropwise. After stirring at room temperature for 3 days, the reaction was quenched by addition of ammonium chloride (10 mL) followed by extraction with ether (2×100 mL). The organic layer was washed with a saturated solution of sodium chloride, dried over anhydrous sodium sulfate and evaporated under reduced pressure to yield a pale yellow oil. Purification by flash column chromatography using 33% ether in petroleum ether afforded the target compound as a colorless oil (0.73 g, 76%).

I. 2-(1-Phenylsulfonyl)-indol-3-yl-ethyl-2,3,-di-O-benzyl-4-deoxy-β-D-glucopyranoside To a solution of the 2-(1-phenylsulfonyl)-indol-3-yl-ethyl-2,3,-di-O-benzyl-6-O-tert-butyldiphenylsilyl-4-deoxy-β-D-glucopyranoside (0.37 g, 0.427 mmol) in 10.5 mL of dry THF was added tetrabutylammonium fluoride (1.33 mL, 1M in THF, 1.33 mmol). The solution was stirred under argon for 3 hours, diluted with ethyl acetate (100 mL) and washed with water (100 mL). The organic layer was washed with a saturated solution of sodium chloride and dried over anhydrous sodium sulfate. Removal of the solvents under reduced pressure yielded a pale yellow oil. Purification by flash column chromatography using 33% petroleum ether in ethyl acetate yielded the target compound as a colorless oil (0.43 g, 85%).

J. 2-indol-3-yl-ethyl-2,3,-di-O-benzyl-4-deoxy-β-D-glucopyranoside

To a solution of the 2-(1-phenylsulfonyl)-indol-3-yl-ethyl-2,3,-di-O-benzyl-4-deoxy-β-D-glucopyranoside (140 mg, 0.223 mmol) in 6.0 mL of ethanol was added 5 M NaOH (2 mL) and the solution heated to reflux for hours. The solvents were removed under reduced pressure and the residue taken up in water (100 mL) and extracted with ethyl acetate (3×100 mL). The organic phase was washed with a saturated solution of sodium chloride, dried with anhydrous sodium sulfate and concentrated to yield a colorless oil. Purification by flash column chromatography using 3% methanol in dichloromethane yielded the target compound as a colorless oil (100 mg, 92%).

K. 5-Phthalimido-1-pentanol

To a solution of 5-amino-1-pentanol (5.00 g, 48.5 mmol) in benzene (150 mL) was added N-carboethoxyphthalimide (11.0 g, 50.2 mmol) and the solution was stirred at room temperature for 5 h). The solvents were removed under reduced pressure to yield a yellow oil. Purification by flash column chromatography using 25% ethyl acetate in petroleum ether yielded the target compound as a clear colorless oil (9.6 mg, 84%).

L. 5-Phthalimido-1-O-trifluoromethanesulfonylpentanol

To a solution of 5-phthalimido-1-pentanol (39.1 mg, 0.168 mmol) in dry dichloromethane (1.5 mL) was added 2,6-di-tert-butyl-4-methylpyridine (34.5 mg, 0.168 mmol) followed by triflic anhydride (28.3 μg, 0.168 mmol). The solution was stirred at room temperature for 10 minutes. The reaction was poured into water (25 mL) and extracted with dichloromethane (2×50 mL). The organic layer was washed with a saturated sodium chloride solution and dried with anhydrous sodium sulfate. The solvents were removed under reduced pressure to yield a pale yellow solid which was used immediately without further purification.

M. 2-(1-Phenylsulfonyl-3-yl)ethyl-2,3-di-O-benzyl-4-deoxy-6-O(phthalimidopentyl)-β-D-glucopyranoside To a solution of 5-phthalimido-1-O-trifluoromethanesulfonylpentanol (theoretically 0.168 mmol) in dry dichloromethane (1.5 mL) was 2,6-di-tert-butyl-4-methylpyridine (34.5 mg, 0.168 mmol). The solution was cooled to 0° C. and to it was added a solution of 2-indol-3-yl-ethyl-2,3,-di-O-benzyl-4-deoxy-β-D-glucopyranoside (18.4 mg, 0.029 mmol, from step J, above) in dry dichloromethane (1.5 mL). The solution was stirred for 30 minutes at 0° C. and then sodium hydride (7.0 mg, 0.29 mmol, 60% dispersion in oil) was added. Stirring was continued at 0° C. for 1 hour and then at room temperature for 24 hours. The reaction was poured into water (50 mL) and extracted with dichloromethane (2×100 mL). The organic layers were combined and washed with a saturated sodium chloride solution followed by drying with anhydrous sodium sulfate. The solvents were removed under reduced pressure to yield a pale yellow oil. Purification by flash column chromatography using 20% ethyl acetate in petroleum ether yielded the target compound as a clear colorless oil (19.4 mg, 80%).

N. Structure (11), 2-(1H-Indol-3-yl)ethyl-6-O-aminopentyl)-2,3-di-O-benzyl-4-deoxy-β-D-glucopyranoside To a solution of 2-(1-phenylsulfonyl-3-yl)ethyl-2,3-di-O-benzyl-4-deoxy-6-O(phthalimidopentyl)-β-D-glucopyranoside (150 mg, 0.178 mmol) in methanol (8 mL) was added sodium methoxide (40 mg, 0.740 mmol). The solution was heated to reflux for 24 hours. The reaction was poured into water (100 mL) and extracted with dichloromethane (2×100 mL). The organic layers were combined and washed with a saturated solution of sodium chloride and dried with anhydrous sodium sulfate. Concentration of the solvents under reduced pressure yielded a pale yellow oil. Purification by flash column chromatography using 10% methanol in dichloromethane yielded structure (11) as a colorless oil (72.0 mg, 71%) $R_f$ 0.32 (10% methanol in dichloromethane); $^1$H NMR (500 MHz, CDCl$_3$) δ 7.74 (brm, 1H), 7.48 (d, J=7.8 Hz, 1H), 7.36–6.93 (m, 15H), 4.62–4.49 (m, 4H), 4.32 (d, J=7.7 Hz, 1H, 4.11 (dt, J=9.4, 6.7 Hz, 1H), 3.78 (dt, 9.2, 7.4 Hz, 1H), 3.52 (m, 4H), 3.26 (m, 2H), 3.22 (t, J=7.2 Hz, 1H), 3.13 (t, J=7.8 Hz, 1H), 3.00 (t, J=7.0 Hz, 2H), 2.00 (ddd, J=6.7, 5.2, 1.4 1H), 1.29 (m, 9H); $^{13}$C NMR (500 MHz, CDCl$_3$) δ 140.11, 138.10, 130.75, 130.59, 129.31, 128.92, 128.84, 128.57, 128.44, 122.24, 119.40, 112.82, 112.31, 105.01, 84.13, 79.55, 75.76, 74.12, 73.12, 72.53, 72.18, 71.29, 41.05, 34.54, 30.38, 29.90, 27.07, 24.72, IR (CHCl$_3$) 3350, 3060, 2930, 2860, 1630, 1520, 1450, 1400, 1270, 1100, 740, 700; UV (c=1.57×10$^{-4}$M, acetonitrile) $\lambda_{max}$ 280.0 (ε=1.41×10$^3$), 224.8 (ε=1.66×10$^3$) nm; HRMS m/e calc'd for C$_{35}$H$_{45}$N$_2$O$_5$ (M+H): 573.3328, found 573.3301; [α]D$^{20}$+3.89° (c=1.8, acetonitrile).

EXAMPLE 8

Preparation of Analog Having Structure (11), 2-Indol-3-yl-ethyl-2,3,-di-O-benzyl-4-deoxy-β-D-glucopyranoside To a solution of 2-(1-phenylsulfonyl)-indol-3ylethyl-2,3,-di-O-benzyl-4-deoxy-β-D-glucopyranoside (140 mg, 0.223 mmol, from Example 7, step I, above) in 6.0 mL of ethanol was added 5M NaOH (2 mL) and the solution heated to reflux for 2 hours. The solvents were removed under reduced pressure and the residue taken up in water (100 mL) and extracted with ethyl acetate (3×100 mL). The organic phase was washed with a saturated solution of sodium chloride, dried with anhydrous sodium sulfate and concentrated to yield a colorless oil. Purification by flash column chromatography using 3% methanol in dichloromethane yielded the analog having structure (12) (2-indol-3-yl-ethyl-2,3,-di-O-benzyl-4-deoxy-β-D-glucopyranoside) as a colorless oil (100 mg, 92%). $R_f$ 0.59 (10% methanol in dichloromethane); $^1$H NMR (500 MHz, CDCl$_3$) δ 7.86 (br s, 1H), 7.59 (d, J=7.8 Hz, 1H), 7.31–6.99 (m, 14H), 4.78–4.66 (m, 4H), 4.41 (d, J=7.7 Hz, 1H), 4.22 (dt, J=9.4, 7.4 Hz, 1H), 3.61–3.56 (m, 3H), 3.49–3.45 (m, 1H), 3.32 (t, J=7.9 Hz, 1H), 3.11 (t, J=6.9 Hz, 2H), 2.03 (br s, 1H), 1.95 (ddd, J=12.8, 5.3, 1.8 Hz, 1H), 1.49 (q, J=11.7 Hz, 1H); $^{13}$C NMR (500 MHz, CDCl$_3$) δ 138.72, 138.48, 136.12, 128.33, 128.20, 127.97, 127.60, 127.56, 127.46, 122.15, 121.92, 119.27, 118.66, 112.57, 111.10, 103.87, 82.81, 78.10, 74.86, 72.23, 72.13, 70.18, 65.17, 32.69, 25.84; UV-Vis (c=1.85×10$^{-4}$, acetonitrile) $\lambda_{max}$281.2 (ξ=614.13), 220.0 (ξ=864.86) mn; HRMS m/e calculated for $C_{30}H_{34}NO_5$ (M+H): 488.2436, found 488.2483; $[\alpha]_D^{20}$ +5.55° (c=1.8, acetonitrile).

EXAMPLE 9

Preparation of Imidazol Compounds

To distinguish the compounds described in this example an "I" preceeds each compound number. The chemical structures and synthetic schemes for the compounds in this example are presented in FIG. 1.

A. Phthalimido-protected amine (−)-I-21

5-Phthalimidopentyl triflate I-20 was prepared as follows: A stirred solution of 5-phthalimido-1-pentanol (1.32 g, 4.67 mmol) and 2,6-di-tert-butyl-4-methylpyridine (0.960 g, 4.67 mmol) in dry dichloromethane (10 ml) was treated with triflic anhydride (0.784 ml, 4.67 mmol). After 10 min at room temperature, the mixture was diluted with water (100 ml) and extracted with dichloromethane (2×200 ml). The combined extracts were washed with brine, dried over sodium sulfate, filtered, and concentrated in vacuo, affording a yellow solid which was used without purification in the next reaction. Sodium hydride (60% dispersion in oil, 0.20 g, 5.06 mmol) was added to a solution of alcohol I-19 (1.27 g, 3.89 mmol), 5-phthalimidopentyl triflate I-20 (4.67 mmol), and 15-crown-5 (20 mg, 2.3 mol %), in methylene chloride (100 ml) at 0° C. After stirring for 24 h at room temperature, the mixture was poured into water. The aqueous layer was extracted with methylene chloride (3×50 ml) and the combined extracts were washed with water, dried over magnesium sulfate and concentrated in vacuo. Flash chromatography (3% ether/methylene chloride) provided I-21 (1.82 g, 86% yield) as a colorless oil; $[\alpha]D^{25}$ −8.2° (c 0.70, CHCl$_3$); $^1$H NMR (500 MHz, CDCl$_3$) δ 7.80 (m, 2H), 7.68 (m, 2H), 7.25–7.34 (m, 10H), 6.38, (dd, J=6.1, 1.2 Hz, 1H), 4.84 (m, 2H), 4.66 (d, J=11.4 Hz, 1H), 4.63 (d, J=11.7 Hz, 1H), 4.55 (d, J=11.7 Hz, 1H), 4.19 (m, 1H), 4.00 (m, 1H), 3.81 (dd, J=8.7, 6.2 Hz, 1H), 3.64–3.74 (m, 4H), 3.40–3.50 (m, 2H), 1.60–1.70 (m, 4H), 1.40 (m, 2H); $^{13}$C NMR (62.9 MHz, CDCl$_3$) δ 168.4, 144.8, 138.4, 138.3, 133.9, 132.2, 128.4, 127.9, 127.8, 127.6, 123.2, 99.9, 76.8, 75.8, 74.5, 73.8, 71.4, 70.5, 69.2, 37.9, 29.2, 28.5, 23.5; high resolution mass spectrum (Cl, NH$_3$) m/z 541.2483 (M$^+$; calcd for $C_{33}H_{35}NO_6$: 541.2464).

B. Alcohol (−)-I-23

A solution of dimethyldioxirane in acetone (1.2 equiv, ca. 0.05 M) was added dropwise to glycal I-21 (1.53 g, 2.80 mmol) in dichloromethane (26 ml) at 0° C. The mixture was stirred at 0° C. for 1 h and concentrated in vacuo.

To a solution of the crude epoxide and I-22 (1.15 g, 3.82 mmol) in THF (12 ml) at −78° C. was added ZnCl$_2$ (1.0 M in ether, 5.6 ml, 5.6 mmol) and the mixture was stirred at −78° C. for 1 h. The solution was then slowly warmed to room temperature and stirred for 18 h. The mixture was poured into saturated aqueous sodium bicarbonate (50 ml) and extracted with ethyl acetate (3×50 ml) and the combined extracts were washed with water, dried over magnesium sulfate, and concentrated in vacuo. Flash chromatography (45% ethyl acetate/hexane) yielded I-23 (1.05 g, 44% yield) as a colorless oil; $[\alpha]D^{25}$ −8.1° (c 1.8 CHCl$_3$); $^1$H NMR (500 MHz, CDCl$_3$) δ 7.96 (dd, J=8.1, 0.6 Hz, 1H), 7.85 (dd, J=8.2, 0.9 Hz, 2H), 7.78 (m, 2H), 7.66 (m, 2H), 7.20–7.50 (m, 17H), 4.89 (d, J=11.3 Hz, 1H), 4.86 (d, J=11.0 Hz, 1H), 4.83 (d, J=11.4 Hz, 1H), 4.60 (d, J=10.9 Hz, 1H), 4.24 (d, J=7.6 Hz, 1H), 4.20 (dt, J=9.5, 6.4 Hz, 1H), 3.76 (dt, J=9.5, 7.2 Hz, 1H), 3.37–3.68 (m, 10H), 2.98 (m, 2H), 2.13 (br s, 1H), 1.57–1.68 (m, 4H), 1.38 (m, 2H); $^{13}$C NMR (62.9 MHz, CDCl$_3$) δ 168.4, 138.6, 138.2, 135.1, 133.8, 133.7, 132.1, 131.0, 129.1, 128.4, 127.9, 127.8, 127.7, 126.7, 124.7, 123.5, 123.1, 119.7, 119.4, 113.7, 102.8, 84.4, 76.5, 75.1, 71.5, 69.6, 68.7, 37.8, 29.2, 28.4, 25.4, 23.5; high resolution mass spectrum (Cl, NH3) m/z 662.2774 (M$^+$; calcd for $C_{35}H_{42}SO_7$: 662.2775).

C. Dibenzyl ether (−)-I-24

A solution of I-23 (0.455 g, 0.530 mmol) in THF (10 ml) was cooled to −78° C. and treated with carbon disulfide (27 ml, 0.583 mmol) followed by sodium bis(trimethylsilyl) amide (0.6 M in toluene, 0.953 ml, 0.572 mmol). After 20 min, methyl iodide (59 ml, 0.640 mmol) was added and the solution was stirred for 5 min at −78° C. and then at room temperature for 45 min. The reaction mixture was quenched with water (50 ml) and extracted with ethyl acetate (3×50 ml). The organic layer was washed with brine, dried over sodium sulfate, filtered, and concentrated in vacuo, affording the crude xanthate as a pale yellow oil (0.462 g, 92% yield) which was used without purification in the next step.

To a solution of the crude xanthate (0.462 g, 0.487 mmol) and AIBN (10 mg) in toluene (8 ml) was added tributyltin hydride (0.214 ml, 0.795 mmol) and the reaction mixture heated at reflux for 4 h, cooled, and concentrated in vacuo. The residue was taken up in acetonitrile (30 ml) and washed with petroleum ether (5×10 ml), dried over sodium sulfate, filtered, and concentrated in vacuo to an oil. Flash chromatography (20% ethyl acetate/petroleum ether) yielded I-24 (0.296 g, 72% yield) as a colorless oil; $[\alpha]D^{25}$ −10° (c 1.1 CHCl$_3$); $^1$H NMR (500 MHz, CDCl$_3$) δ 7.96 (d, J=7.5 Hz, 1H), 7.84 (m, 2H), 7.79 (m, 2H), 7.66 (m, 2H), 7.20–7.41 (m, 15H), 4.91 (d, J=11.0 Hz, 1H), 4.60 (m, 2H), 4.66 (d, J=11.7 Hz, 1H), 4.41 (dd, J=9.7, 1.8 Hz, 1H), 4.15 (dt, J=9.5, 6.6 Hz, 1H), 3.59–3.71 (m, 6H), 3.47 (m, 2H), 3.40 (m, 1H), 2.94 (t, J=6.6 Hz, 2H), 2.57 (ddd, J=14.2, 5.0, 3.2 Hz, 1H), 1.57–1.68 (m, 5H), 1.38 (m, 2H); $^{13}$C NMR (62.9 MHz, CDCl$_3$) δ 23.5, 25.5, 28.4, 29.2, 36.7, 37.9, 68.1, 70.0, 71.4, 75.0, 75.2, 78.2, 79.3, 99.9, 113.6, 119.6, 123.1, 123.5, 124.7, 126.7, 127.7, 128.0, 128.4, 129.2, 131.1, 132.1, 133.6, 133.8, 135.1, 138.3, 138.5, 168.4; high resolution mass spectrum (Cl, NH3) m/z 814.3287 (M$^+$; calcd for $C_{44}H_{50}SO_8N_2$: 814.3289).

D. Amine (−)-I-15

A solution of hydrazine (0.2 M in MeOH, 6 ml) was added to I-24 (0.034 g, 0.043 mmol). After stirring for 16 h, the reaction mixture was concentrated in vacuo, the residue was dissolved in ethanol (4 ml), and 5N NaOH (0.90 ml) added. The mixture was heated at reflux for 4 h, cooled, and extracted with methylene chloride (3×10 ml). The combined extracts were washed with brine, dried over magnesium sulfate, and concentrated in vacuo to an oil. Flash chromatography (11% methanol/methylene chloride) afforded I-15 (11 mg, 44%) as a pale yellow oil; $[\alpha]D^{25}$ −15° (c 0.62, CHCl$_3$); IR (CHCl$_3$) 3490 (m), 3345 (br, m), 3020 (m), 2945 (s), 2882 (s), 1625 (w), 1500 (w), 1459 (m), 1370 (m), 1230 (w), 1100 (s), 695 (w) cm$^{-1}$; $^1$H NMR (500 MHz, CDCl$_3$) δ 8.80 (br s, 1H), 7.49 (d, J=7.9 Hz, 1H), 7.19–7.31 (m, 11H), 7.10 (t, J=7.1 Hz, 1H), 7.00 (t, J=8.0 Hz, 1H), 6.97 (s, 1H), 4.83 (d, J=11.1 Hz, 1H), 4.59 (d, J=11.7 Hz, 1H), 4.51 (d, J=11.0 Hz), 4.50 (d, J=11.7, 1H), 4.39 (d, J=9.7 Hz, 1H), 4.00 (apparent q, J=7.3 Hz, 1H), 3.67 (apparent q, J=7.3 Hz, 1H), 3.60 (d, J=9.0 Hz, 1H), 3.56 (m, 1H), 3.46 (dd, J=10.8, 5.3 Hz), 3.31 (m, 4H), 2.98 (t, J=7.2 Hz, 2H), 2.50 (t, J=7.3 Hz, 2H), 2.28 (m, 2H), 1.57 (q, J=10 Hz, 1H), 1.42 (m, 4H), 1.19 (m, 2H); $^{13}$C NMR (62.9 MHz, CDCl$_3$) δ 138.3, 138.2, 136.2, 128.4, 128.0, 127.7, 127.5, 122.3, 121.8, 119.1, 118.7, 112.0, 111.4, 99.9, 79.3, 78.2, 74.9, 71.4, 71.0, 69.9, 69.8, 39.7, 36.7, 28.8, 27.6, 25.7, 23.1; high resolution mass spectrum (FAB, m-nitrobenzyl alcohol) m/z 573.3371 [(M+H)$^+$; calcd for $C_{35}H_{44}N_2O_5$: 573.3328].

E. Azide (−)-I-27

5-Azidopentyl triflate I-26 was prepared as follows: A stirred solution of 5-azido-1-pentanol (0.149, 1.08 mmol) and 2,6-di-tert-butyl-4-methylpyridine (0.22 g, 1.08 5-azido-1-pentanol (0.149, 1.08 mmol) and 2,6-di-tert-butyl-4-methylpyridine (0.22 g, 1.08 mmol in dry dichloromethane (5 ml) was treated with triflic anhydride (0.19 ml, 1.08 mmol). After 10 min at room temperature, the mixture was diluted with water (100 ml) and extracted with dichloromethane (2×200 ml). The combined extracts were washed with brine, dried over sodium sulfate, filtered, and concentrated in vacuo, affording a yellow solid which was used without purification in the next reaction.

Sodium hydride (60% dispersion in oil, 0.053 g, 2.30 mmol) was added to a solution of alcohol I-25 (0.353 g, 1.08 mmol), 5-azidodopentyl triflate 26 (1.08 mmol), and 15-crown-5 (10 mg), in methylene chloride (10 ml) at 0° C. After stirring for 24 h at room temperature, the mixture was poured into water. The aqueous layer was extracted with methylene chloride (3×50 ml) and the combined extracts were washed with water, dried over magnesium sulfate and concentrated in vacuo. Flash chromatography (20% ethyl acetate/petroleum ether) provided I-27 (260 mg, 60%) as a colorless oil; $[\alpha]D^{25}$ −8.5° (c 0.89, CHCl); IR (CHCl$_3$) 3090 (w), 3062 (w), 1235 (m), 1210 (m), 1100 (br, s), 1070(s), 1028 (s), 705(w), 691 (m), cm$^{-1}$; $^1$H NMR (500 (w), 1235 (m), 1210 (m), 1100 (br, s), 1070 (s), 1028 (s), 705 (w), 691 (m), cm$^{-1}$; $^1$H NMR (500 MHz, CDCl$_3$) δ 1.42 (m, 2H), 1.61 (m, 4H), 3.24 (t, J=6.9 Hz, 2H), 3.47 (m, 4H), 3.70 (dd, J=10.8, 2.7 Hz, 1H), 3.76 (dd, J=10.8, 5.1 Hz, 1H), 3.84 (dd, J=8.7, 6.2 Hz, 1H), 4.03 (m, 1H), 4.21 (ddd, J=6.2, 2.5, 1.5 Hz, 1H), 4.56 (d, J=11.6 Hz, 1H), 4.64 (d, J=11.6 Hz, 1H), (m, 10H); $^{13}$C NMR (62.9 MHz, CDCl$_3$) δ 23.4, 28.7, 29.2, 51.3, 69.2, 70.5, 71.3, 73.8, 74.5, 2H), 7.27–7.38 (m, 10H); $^{13}$C NMR (62.9 MHz, CDCl$_3$) δ 23.4, 28.7, 29.2, 51.3, 69.2, 70.5, 71.3, 73.8, 74.5, 76.8, 99.9, 127.6, 127.8, 128.4, 138.3, 144.7; high resolution mass spectrum (FAB, m-nitrobenzyl alcohol) m/z 472.2031 [(M+Cl)$^+$; calcd for $C_{25}H_{31}O_4N_3Cl$ :8471.2003].

F. Amide (−)-I-28

To a solution of sugar I-27 (0.117 g, 0.268 mmol) in THF (5 ml) was added H$_2$O (0.217 ml, 12.1 mmol) and PPh$_3$ (0.176 g, 0.671 mmol) and the reaction mixture was heated to 55° C. for 10 h, cooled, and concentrated in vacuo. Flash chromatography (15% methanol/methylene chloride) provided the amine as a colorless oil (82 mg, 77%); $[\alpha]D^{25}$ −7.2° (c 0.25, CHCl$_3$); IR (CHCl$_3$) 3500–2600 (br, w), 3090 (w), 3060 (w), 3003 (m), 2933 (s), 2864 (s), 1650 (m), 1495 (w), 1452 (m), 1355 (w), 1235 (m), 1220 (m), 1100 (br, s), 1025 (m), 850 (br, w), 690 (m) cm$^{-1}$; $^1$H NMR (500 MHz, CDCl$_3$) δ 1.36 (m, 2H), 1.43 (quin., J=7.4 Hz, 1H), 1.59 (quin., J=6.7 Hz, 1H), 2.65 (t, J=6.9 Hz, 2H), 3.46 (m, 2H), 3.69 (dd, J=10.8, 2.7 Hz, 1H), 3.73 (dd, J=10.8, 5.1 Hz, 1H), 3.82 (dd, J=8.7, 6.3 Hz, 1H), 4.01 (m, 1H), 4.22 (m, 1H), 4.55 (d, J=11.7 Hz, 1H), 4.63 (d, J=11.7 Hz, 1H), 4.67 (d, J=11.4 Hz, 1H), 4.85 (m, 2H), 6.40 (d, J=6.2 Hz, 1H), 7.26–7.36 (m, 10H); $^{13}$C NMR (125.8 MHz, CDCl$_3$) δ 22.4, 28.4, 32.5, 41.0, 68.1, 69.4, 70.5, 72.7, 73.5, 74.8, 75.7, 98.9, 126.6, 126.7, 127.3, 127.3, 137.2, 137.3, 143.7.

To a solution of the amine (0.077 g, 0.19 mmol) in CH$_2$Cl$_2$ (2.5 ml) at 0° C. was added Et$_3$N (0.040 ml, 0.29 mmol) and Ac$_2$O (0.020 ml, 0.21 mmol). After stirring for one minute, the mixture was poured into water. The aqueous layer was extracted with methylene chloride (3 ×20 ml) and the combined extracts were washed with water, dried over magnesium sulfate and concentrated in vacuo. Flash chromatography (8% methanol/methylene chloride) provided I-28 (80 mg, 94%) as a colorless oil; $[\alpha]D^{25}$ −8.2° (c 0.38, CHCl$_3$); IR (CHCl$_3$) 3450 (w), 3090 (w), 3062 (w), 3004 (m), 2940 (m), 2865 (m), 1665 (s), 1520 (br, m), 1455 (m), 1367 (br, m), 1237 (m), 1208 (m), 1102 (br, s), 1025 (m), 690 (m) cm$^{-1}$; $^1$H NMR (500 MHz, CDCl$_3$) δ 1.37 (m, 2H), 1.48 (quin., J=7.5 Hz, 2H), 1.59 (m, 2H), 1.92 (s, 3H), 3.20 (m, 2H), 3.45 (m, 2H), 3.68 (dd, J=10.9, 2.6 Hz, 1H), 3.73 (dd, J=10.9, 5.1 Hz, 1H), 3.81 (dd, J=8.7, 6.3 Hz, 1H), 4.00 (m, 1H), 4.20 (m, 1H), 4.55 (d, J=11.6 Hz, 1H), 4.63 (d, J=11.6 Hz, 1H), 4.67 (d, J=11.3 Hz, 1H), 4.87 (m, 2H), 5.45 (br s, 1H), 6.39 (dd, J=6.2, 1.3 Hz, 1H), 7.27–7.35 (m, 10H); $^{13}$C NMR (125.8 MHz, CDCl$_3$) δ 23.3, 23.6, 29.3, 29.3, 39.5, 69.2, 70.6, 71.4, 73.8, 74.6, 75.9, 77.6, 100.0, 127.7, 127.8, 127.8, 128.5, 138.3, 144.7, 170.0; high resolution mass spectrum (FAB, m-nitrobenzyl alcohol) m/z 488.2537 [(M+Cl)$^+$; calcd for $C_{27}H_{35}O_5NCl$:488.2515].

G. α-Amide (+)-I-29

To a solution of amide I-28 (0.022 g, 0.051 mmol) and tryptophol (0.041 g. 0.26 mmol) in acetonitrile (1 ml) was added CSA (1 mg). After stirring for 24 h at room temperature the mixture was added to saturated sodium bicarbonate and extracted with methylene chloride (3×20 ml ). The combined extracts were washed with water, dried over magnesium sulfate and concentrated in vacuo. Flash chromatography (ethyl acetate) provided I-29α (4.2 mg, 14%) as a colorless oil; $[\alpha]D^{25}$ +55.0° (c 0.40, CHCl$_3$); IR (CHCl$_3$) 3485 (m), 3460 (m), 3300 (br, w), 3015 (m), 2950 (m), 2875 (m), 1670 (s), 1525 (w), 1460 (m), 1370 (w), 1130 (m), 1105 (br, s), 1030 (m), 980 (w), 695 (w) cm$^{-1}$; $^1$H NMR (500 MHz, CDCl$_3$) δ 1.31 (m, 2H), 1.43 (quin., J=7.4 Hz, 2H), 1.54 (m, 2H), 1.67 (dt, J=12.4,3.3 Hz, 1H), 1.91 (s, 3H), 2.29 (dd, J=12.7, 5.0 Hz, 1H), 3.02 (m, 2H), 3.14 (m, 2H), 3.35 (m, 1H), 3.40–3.59 (m, 4H), 3.65 (m, 2H), 3.89 (q, J=7.5 Hz, 1H), 4.21 (m, 1H), 4.58 (d, J=11.1 Hz, 1H), 4.63 (d, J=11.5 Hz, 1H), 4.67 (d, J=11.5 Hz, 1H), 4.90 (d, J=11.1 Hz, 1H), 4.97 (d, J=11.7 Hz, 1H), 5.37 (br s, 1H), 6.98 (s, 1H), 7.09 (t, J=7.1 Hz, 1H), 7.17 (t, J=7.1 Hz, 1H), 7.27–7.37 (m, 11H), 7.59 (d, J=7.9 Hz, 1H), 8.30 (br s, 1H); $^{13}$C NMR (62.9 MHz, CDCl$_3$) δ 23.2, 23.6, 25.6, 29.3, 35.5, 127.6, 127.8, 128.4, 136.2, 138.7, 170.1; high resolution mass spectrum (FAB, m-nitrobenzyl alcohol) m/z 615.3407 [(M+H)$^+$; calcd for C37H47O6N2:615.3434].

H. β-Amide (−)-I-29

(1.7 mg, 6%) as a colorless oil; $[\alpha]D^{25}$ −13.0° (c 0.16, CHCl$_3$); IR (CHCl$_3$) 3480 (w), 3010 (m), 2940 (m), 2877 (m), 1670 (s), 1532 (w), 1458 (m), 1369 (m), 1270 (w), 1100 (br s), 1011 (w), 695 (w) cm$^{-1}$; $^1$H NMR (500 MHz, CDCl$_3$) δ 1.22 (m, 2H), 1.45 (m, 2H), 1.53–169 3.38 (m, 1H), 3.40–3.51 (m, 3H), 3.57–3.67 (m, 2H), 3.69 (dd, J=10.8, 1.8 Hz, 1H), 3.75 (m, 1H), 4.13 (dt, J=9.6, 2.0 Hz, 1H), 4.46 (dd, J=9.7, 1.8 Hz, 1H), 4.58 (d, J=11.7 Hz, 1H), 4.61 (d, J=11.1 7.09 (m, 1H), 7.17 (m, 1H), 7.26–7.36 (m, 11H), 7.59 (d, J=7.8 Hz, 1H), 7.05 (s, 1H), 7.09 (m, 1H), 7.17 (m, 1H), 7.26–7.36 (m, 11H), 7.59 (d, J=7.8 Hz, 1H), 8.37 (br s, 1H); $^{13}$C NMR (125.8 MHz, CDCl$_3$) δ 23.6, 23.7, 25.7, 29.3, 36.8, 39.7, 69.6, 70.1, 71.4, 74.9, 75.2, 76.8, 78.4, 79.4, 99.9, 111.2, 112.5, 118.7, 119.1, 121.9, 122.1, 127.7, 127.7, 127.9, 128.4, 138.3, 170.2; high resolution mass spectrum (FAB, m-nitrobenzyl alcohol) m/z 615.3410 [(M+H)$^+$; calcd for $C_{37}H_{47}O_6N_2$ :615.3434].

I. Acetal (−)-I-31

To a solution of the triol I-30 (9.43 g, 21.1 mmol) dissolved in DMF (35 ml) was added α,α-dimethoxytoluene (3.42 ml, 22.8 mmol) and pTsOH (100 mg) and the mixture was heated to 45° C. under aspirator pressure for 5 h. After cooling, the mixture was added to $H_2O$ (300 ml) and saturated sodium bicarbonate (10 ml) and extracted with ethyl acetate (3×150 ml). The combined extracts were washed with water, dried over magnesium sulfate and concentrated in vacuo. Flash chromatography (40% ethyl acetate/ptroleum ether) provided I-31 (10.0 g, 89% yield) as a colorless oil: $[\alpha]D^{25}$ −8.2° (c 0.70, $CHCl_3$); 3590 br w), 3080 (w), 3010 (w), 2920 (w), 2880 (w), 1450 (m), 1375 (m), 1330 (w), 1280 (w), 1182 (m), 1175 (s), 1130 (m), 1120 (m), 1100 (s), 1085 (s), 1070 (s), 1018 (m), 1000 (m), 905 (w), 680 (w), 595 (m), 565 (m) $cm^{-1}$; $^1H$ NMR (500 MHz, $CDCl_3$) δ 1.70 (q, J=11.7 Hz, 1H), 2.05 (br s, 1H), 2.43 (dt, J=9.2, 4.6 Hz, 1H), 3.00 (m, 2H), 3.44 (m, 1H), 3.59 (m, 2H), 3.79 (m, 2H), 4.24 (dt, J=9.5, 6.4 Hz, 1H), 4.31 (m, 2H), 5.52 (s, 1H), 7.25 (m, 2H), 7.36 (m, 4H), 7.40–7.54 (m, 6H), 7.87 (m, 2H), 7.99 (d, J=8.1 Hz, 1H); $^{13}C$ NMR (125.8 MHz, $CDCl_3$) δ 25.5, 34.9, 68.7, 68.8, 68.9, 70.5, 76.0, 101.7, 105.2, 113.6, 119.2, 119.5, 123.0, 123.3, 124.6, 126.5, 128.3, 128.8, 129.0, 131.0, 133.6, 135.0, 137.1; high resolution mass spectrum (Cl, $CH_4$) m/z 536.1722 $[(M+H)^+]$; calcd for $C_{29}H_{30}SO_7$ N: 536.1743].

J. Acetal (−)-I-32

To a solution of the acetal I-31 (1.84 g, 3.44 mmol) dissolved in DMF (4 ml) was added imidazole (0.52 g, 7.57 mmol) followed by TIPSCI (0.81 ml, 3.78 mmol). After stirring for 24 h, the mixture was added to $H_2O$ (200 ml) and extracted with ether (3×100 ml). The combined extracts were washed with water, dried over magnesium sulfate and concentrated in vacuo. Flash chromatography (15% ethyl acetate/ptroleum ether) provided I-32 (2.12 g, 90% yield) as a colorless oil: $[\alpha]D^{25}$ −27.8° (c 0.95, $CHCl_3$); IR ($CHCl_3$) 3080 (w), 3040 (w), 3020 (w), 2960(s), 2905 (s), 2880 (s), 1467 (m), 1453(m), 1335(w), 1285 (w), 1190(m), 1179(s), 1135 (s), 1130 (s), 1095 (s), 1000 (br m), 885 (m), 810 (m), 720 (w), 670 (br, m), 600 (m), 572 (m) $cm^{-1}$; $^1H$ NMR (500 MHz, $CDCl_3$) δ 1.05 (m, 21H), 1.77 (q, J=11.2 Hz, 1H), 2.44 (m, 1H), 3.00 (t, J=7.7 Hz, 2H), 3.42 (m, 1H), 3.56 (m, 1H), 3.73–3.85 (m, 3H), 4.12 (m, 1H), 4.29 (dd, J=10.5, 4.9 Hz, 1H), 4.38 (d, J=7.3 Hz, 1H), 5.50 (s, 1H), 7.23 (m, 1H), 7.25 (s, 1H), 7.28–7.38 (m, 3H), 7.43 (m, 3H), 7.46–7.54 (m, 4H), 7.86 (m, 2H), 7.97 (dt, J=8.3, 0.8 Hz); $^{13}C$ NMR (62.9 MHz, $CDCl_3$) δ 12.4, 17.7, 18.0, 25.6, 38.0, 68.9, 69.2, 70.0, 70.2, 75.9, 101.7, 106.0, 113.7, 119.4, 123.1, 123.5, 124.8, 126.2, 126.7, 128.4, 129.1, 129.2, 131.0, 133.7, 135.2, 137.4, 138.4; high resolution mass spectrum (Cl, CH4) m/z 691.3041 $(M^+$; calcd for $C_{36}H_{49}SiSO_7$ N: 691.2998).

K. Alcohol (−)-I-33

To a solution of the acetal I-32 (1.45 g, 2.10 mmol) dissolved in $CH_2Cl_2$ (30 ml) was added DIBAL (1.0 M toluene; 21.0 ml, 21.0 mmol) at 0° C. After stirring for 4 h the mixture was quenched with Rochelle's salt (100 ml) and water (100 ml) and extracted with ethyl acetate (3×100 ml). The combined extracts were washed with water, dried over magnesium sulfate and concentrated in vacuo. Flash chromatography (20% ethyl acetate/ptroleum ether) provided I-33 (1.31 g, 90% yield) as a colorless oil: $[\alpha]D^{25}$ −11.6° (c 1.12, $CHCl_3$); IR ($CHCl_3$) 3080 (w), 3040 (w), 3018 (w), 2960 (s), 2880 (s), 1455 (s), 1375 (s), 1285 (w), 1185 (m), 1179 (s), 1138 (s), 1135 (s), 1090 (s), 1040 (m), 1030 (m), 1020 (m), 885 (m), 810 (w), 680 (m), 600 (m), 570 (m) $cm^{-1}$; $^1H$ NMR (500 MHz, $CDCl_3$) δ 1.07 (m, 21H), 1.58 (q, J=11.4 Hz, 1H), 2.10 (br s, 1H), 2.45 (dt, J=12.3, 4.8 Hz, 1H), 2.98 (m, 2H), 3.42 (m, 1H), 3.52 (m, 1H), 3.59 (m, 1H), 3.86 (m, 2H), 4.13 (dt, J=9.2, 7.7 Hz, 1H), 4.32 (d, J=7.3 Hz, 1H), 4.54 (d, J=1.5 Hz, 1H), 4.64 (d, J=11.5 Hz, 1H), 7.24 (m, 1H), 7.28 (s, 1H), 7.24–7.39 (m, 5H), 7.43 (m, 2H), 7.48 (d, J=7.8 Hz, 1H), 7.51 (m, 2H), 7.87 (m, 2H), 8.00 (d, J=8.3 Hz, 1H); $^{13}C$ NMR (62.9 MHz, $CDCl_3$) δ 12.6, 18.2, 25.8, 38.2, 62.6, 68.5, 69.5, 71.8, 72.2, 78.2, 104.8, 113.9, 19.3, 119.6, 123.5, 123.9, 124.8, 127.0, 128.0, 128.5, 129.8, 131.2, 133.9, 135.4, 138.1, 138.5; high resolution mass spectrum (Cl, $NH_3$) m/z 693.31 67($M^+$; calcd for $C_{38}H_{51}SiSO_7$ N: 693.3155).

L. Azide (−)-I-35

6-Azidohexyl triflate I-34 was prepared as follows: A stirred solution of 6-azido-1-hexanol (0.17 g, 1.17 mmol) and 2,6-di-tert-butyl-4-methylpyridine (0.24 g, 1.17 mmol) in dry dichloromethane (10 ml) was treated with triflic anhydride (0.19 ml, 1.17 mmol). After 10 min at room temperature, the mixture was diluted with water (50 ml) and extracted with dichloromethane (3×25 ml). The combined extracts were washed with brine, dried over sodium sulfate, filtered, and concentrated in vacuo, affording a yellow solid which was used without purification in the next reaction. To a solution of alcohol I-33 (0.54 g, 0.78 mmol) in dry $CH_2Cl_2$ (30 ml) at 0° C. was added NaH (60%, 0.050 g, 1.17 mmol) and 15-crown-5 (5 mg) After stirring for 20 minutes, triflate 34 (0.32 g, 1.17 mmol) as a solution in $CH_2Cl_2$ (2 ml) was added via cannula. The mixture was stirred for an additional 24 h, quenched with water (30 ml) and the layers were separated. The aqueous layer was further extracted with $CH_2Cl_2$ (3×20 ml) and the combined extracts were washed with water, dried over magnesium sulfate and concentrated in vacuo. Flash chromatography (12% ethyl acetate/ptroleum ether) provided I-35 (0.57 g, 89% yield) as a colorless oil: $[\alpha]D^{25}$ −14.6° (c 1.22, $CHCl_3$); IR ($CHCl_3$) 3075 (w), 3017 (w), 2955 (s), 2880 (s), 2105 (s), 1450 (m), 1375 (m), 1275 (br, w), 1180 (s), 1125 (s), 1097 (s), 1070 (s), 975 (w), 885 (w), 810 (w), 670 (br, w), 600 (m), 570 (m) $cm^{-1}$; $^1H$ NMR (500 MHz, $CDCl_3$) δ 1.03 (s, 21H), 1.31 (m, 4H), 1.51 (m, 5H), 2.40 (dt, J=12.3, 4.7 Hz, 1H), 2.98 (t, J=7.2 Hz, 2H), 3.15 (t, J=6.9 Hz, 2H), 3.40 (m, 4H), 3.56 (m, 2H), 3.77 (m, 2H), 4.09 (m, 1H), 4.24 (d, J=7.3 Hz, 1H), 4.48 (d, J=11.6 Hz, 1H), 4.59 (d, J=11.6 Hz, 1H), 7.22 (t, J=7.6 Hz, 1H), 7.25 (s, 1H), 7.30 (m, 5H), 7.40 (m, 3H), 7.47 (m, 2H), 7.84 (d, J=7.9 Hz, 2H), 7.96 (d, J=8.4 Hz, 1H); $^{13}C$ NMR (62.9 MHz, $CDCl_3$) δ 12.4, 18.0, 25.6, 25.7, 26.6, 28.8, 29.5, 38.3, 51.4, 68.5, 69.4, 70.1, 71.4, 71.5, 72.3, 78.1, 105.6, 113.7, 119.4, 119.7, 123.1, 123.4, 124.7, 126.8, 127.8, 128.4, 129.3, 131.1, 133.6, 135.2, 138.2, 138.3; high resolution mass spectrum (FAB, m-nitrobenzyl alcohol) m/z 853.3835$[(M+Cl)^+]$; calcd for $C_{44}H_{62}SiSO_7$ $N_4Cl$: 853.3797).

M. Alcohol (−)-I-36

A solution of azide I-35 (0.18 g 0.22 mmol) in THF (3 ml) was cooled to 0° C. and TBAF (0.26 ml, 1.00 M, 0.26 mmol) was added dropwise. The mixture was stirred for 2 h, added to water and extracted with EtOAc (3×20 ml). The combined extracts were washed with water, dried over magnesium sulfate and concentrated in vacuo. Flash chromatography (12% ethyl acetate/petroleum ether) yielded the alcohol as a colorless oil (0.14 g, 99%); $[\alpha]D^{25}$ −8.8° (c 1.1, $CHCl_3$); IR ($CHCl_3$) 3002 (w), 2940 (m), 2870 (m), 2100 (s), 1450 (s), 1370 (s), 1280 (w), 1172 (s), 1130 (s), 1120 (s), 1100 (s), 1088 (s), 1070 (s), 970 (w), 600 (m), 570 (m) $cm^{-1}$; $^1H$ NMR (500 MHz, $CDCl_3$) δ 1.38 (m, 4H), 1.59 (m, 5H), 2.10 (br s, 1H), 2.47 (dt, J=12.5, 4.5 Hz, 1H), 3.01 (m, 2H), 3.23 (t, J=6.9 Hz, 2H), 3.45 (m, 3H), 3.59 (m, 5H), 3.70 (dd, J=12.3, 4.3 Hz, 1H), 3.77 (dt, J=9.5, 7.0 Hz, 1H), 4.21 (dt, J=9.6, 6.5 Hz, 1H), 4.29 (d, J=6.9 Hz, 1H), 4.51, (d, J=11.5 Hz, 1H), 4.63 (d, J=11.6 Hz, 1H), 7.26 (t, J=7.7 Hz, 1H), 7.28 (s, 1H), 7.35 (m, 5H), 7.45 (m, 3H), 7.53 (m, 2H), 7.89 (m, 2H), 8.00

(d, J=7.9 Hz, 1H); $^{13}$C NMR (62.9 MHz, CDCl$_3$) δ 25.5, 25.7, 26.5, 28.7, 29.4, 33.8, 51.3, 68.3, 68.6, 70.0, 71.3, 71.4, 72.1, 77.7, 104.5, 113.8, 119.4, 119.9, 123.1, 123.5, 124.8, 126.7, 127.7, 127.8, 128.4, 129.2, 131.0, 133.7, 135.2, 137.9, 138.3; high resolution mass spectrum (FAB, m-nitrobenzyl alcohol) m/z 662.2811 (M$^+$; calcd for C$_{35}$H$_{42}$SO$_7$ N$_4$: 662.2774).

N. Mmt-Chloromethylimidazole (I-37)

To a solution of the chloromethylimidazole (0.20 g, 1.30 mmol) and MmtCl (0.82 g, 2.65 mmol) in dichloromethane at 0° C. was rapidly added Hunig's base (0.51 ml, 2.91 mmol). After stirring for 0.5 h the mixture was added to water and the layers were separated. The aqueous layer was further extracted with dichloromethane (2×20 ml). The combined extracts were washed with water, dried over magnesium sulfate and concentrated in vacuo. Flash chromatography (30% ethyl acetate/petroleum ether) yielded I-37 as a colorless oil (0.24 g, 47%) which was used immediately in the next reaction; IR (CHCl$_3$) 3095 (w), 3060 (w), 3005 (m), 2960 (m), 2840 (w), 1610 (m), 1586 (w), 1510 (s), 1487 (m), 1463 (m), 1445 (m), 1300 (w), 1255 (s), 1180 (m), 1155 (m), 1120 (m), 1085 (w), 1031 (m), 990 (w), 905 (w), 825 (m), 695 (m); $^1$H NMR (500 MHz, CDCl$_3$) δ 3.79 (s, 3H), 4.56 (s, 2H), 6.84 (m, 3H), 7.05 (d, J=8.8 Hz, 2H), 7.10 (m, 4H), 7.32 (m, 6H), 7.39 (br s, 1H); $^{13}$C NMR (62.9 MHz, CDCl$_3$) δ 39.9, 55.2, 75.1, 113.3, 120.2, 128.0, 129.6, 131.1, 134.1, 137.4, 139.2, 147.4, 159.1.

O. Imidazole-Azide (+)-I-38

To a solution of alcohol I-36 (0.20 g, 0.31 mmol) in dry THF (4 ml) at 0° C. was added NaHMDS (0.6 M toluene, 0.56 ml, 0.34 mmol). After 10 minutes, chloro-imidazole I-37 (0.24 g, 0.62 mmol) as a solution in THF (5 ml) was added via cannula. After stirring for 48 h at room temperature, the mixture was added to water and extracted with CH$_2$Cl$_2$ (3×20 ml). The combined extracts were washed with water, dried over magnesium sulfate and concentrated in vacuo. Flash chromatography (toluene/ethyl acetate/methanol, 7.7:2.0:0.3) provided I-38 (0.071 g, 23% yield) as a colorless oil: [α]D$^{25}$ +1.4° (c 0.86, CHCl$_3$); IR (CHCL$_3$) 3009, (m), 2965 (m), 2880 (m), 2110 (s), 1610 (w), 1510 (m), 1455 (m), 1375 (m), 1260 (m), 1180 (s), 1135(s), 1125 (s), 1090 (s), 1075(s) 1040 (m), 830 (w), 700(w), 600 (m), 570 (m), cm$^{-1}$; $^1$H NMR (500 MHz, CDCl$_3$) δ 1.32 (m, 4H), 1.55 (m, 5H), 2.58 (m, 1H), 2.92 (t, J=7.2 Hz, 2H), 3.17 (t, J=6.9 Hz, 2H), 3.35 (m, 1H), 3.42 (m, 3H), 3.46 (dt, J=9.5, 6.5 Hz, 1H), 3.55 (dd, J=10.7, 5.1 Hz, 1H), 3.75 (m, 2H), 3.76 (s superimposed on a m, 3H), 4.11 (dt, J=9.6, 7.1 Hz, 1H), 4.37 (d, J=7.6 Hz, 1H), 4.40 (d, J=11.4 Hz, 1H), 4.46 (d, J=12.1 Hz, 1H), 4.58 (d, J=11.4 Hz, 1H), 4.65 (d, J=12.2 Hz, 1H), 6.76 (s, 1H), 6.80 (m, 2H), 7.04 (m, 2H), 7.11 (m, 4H), 7.15 (m, 1H), 7.21–7.37 (m, 15H), 7.45 (m, 3H), 7.81 (m, 2H), 7.93 (d, J=8.3 Hz, 1H); $^{13}$C NMR (125.8 MHz, CDCl$_3$) δ 25.6, 25.7, 26.5, 28.7, 29.5, 34.9, 51.3, 55.2, 66.9, 68.3, 70.0, 71.1, 71.5, 72.4, 74.9, 75.2, 78.0, 105.1, 113.2, 113.6, 119.5, 120.0, 123.0, 123.6, 126.7, 127.7, 127.9, 128.0, 128.3, 129.0, 129.6, 131.0, 131.1, 133.6, 134.5, 135.1, 138.1, 138.5, 139.0, 142.3, 159.0; high resolution mass spectrum (FAB, m-nitrobenzyl alcohol) m/z 1015.4496[(M+H)$^+$; calcd for C$_{59}$H$_{63}$SO$_8$ N$_6$: 1015.4496].

P. Amine (+)-I-39

To a solution of azide I-38 (0.071 g, 0.070 mmol) in THF (5 ml) was added H$_2$O (0.059 ml, 3.30 mmol) and PPh$_3$ (0.046 g, 0.17 mmol) and the reaction mixture heated to 55° C. for 10 h, cooled, and concentrated in vacuo. Flash chromatography (15% methanol/methylene chloride) provided I-39 as a colorless oil (62 mg, 90%); [α]D$^{25}$ +1.8° (c 1.24, CHCl$_3$); IR (CHCl$_3$) 3300 (br, w), 3080 (w), 3005 (w), 2940 (m), 2880 (m), 1605 (w), 1510 (w), 1450 (m), 1375 (m), 1290 (w), 1255 (w), 1175 (s), 1130 (s), 1120 (s), 1095 (s), 1085 (s), 830 (w), 595 (m), 565 (m) cm$^{-1}$; $^1$H NMR (500 MHz, CDCl$_3$) δ 1.29 (m, 4H), 1.42 (m, 2H), 1.54 (m, 3H), 2.56 (m, 1H), 2.67 (t, J=7.1 Hz, 2H), 2.92 (t, J=7.1 Hz, 2H), 3.23 (brs, 2H), 3.33 (m, 1H), 3.42 (, 4H), 3.56 (dd, J=10.7, 4.5 Hz, 1H), 3.70 (d, J 10.6 Hz, 1H), 3.76 (m, 1H), 3.76 (s superimposed on a m, 3H), 4.13 (dt, J=9.5, 7.1 Hz, 1H), 4.37 (d, J=7.5 Hz, 1H), 4.40 (d, J=11.1 Hz, 1H), 4.46 (d, J=12.1 Hz, 1H), 4.57 (d, J=11.4 Hz, 1H), 4.64 (d, J=12.1 Hz, 1H), 6.76 (s, 1H), 6.80 (m, 2H), 7.04 (m, 2H), 7.15 (t, J=7.8 Hz, 1H), 7.20–7.46 (m, 18H), 7.81 (dd, J=8.2, 0.9 Hz, 2H), 7.91 (d, J=8.3 Hz, 1H); $^{13}$C NMR (125.8 MHz, CDCl$_3$), δ 25.5, 25.9, 26.5, 29.5, 29.7, 34.9, 55.2, 66.8, 58.3, 70.0, 71.1, 71.6, 72.3, 74.9, 75.2, 78.0, 105.1, 113.2, 113.6, 119.5, 119.9, 120.1, 123.1, 124.6, 126.7, 127.7, 127.7, 127.9, 128.0, 128.4, 129.1, 129.7, 131.1, 131.1, 133.6, 134.4, 135.0, 138.1, 138.3, 138.4, 139.0, 142.7, 159.1; high resolution mass spectrum (FAB, m-nitrobenzyl alcohol) m/z 989.4483 [(M+H)$^+$; calcd for C$_{59}$H$_{65}$SO$_8$N$_4$: 989.4522].

Q. Free imidazole (+)-I-16

To a solution of amine I-39 (0.020 g, 0.020 mmol) in EtOH (3 ml) was added 5M NaOH (0.50 ml) and the mixture was heated at reflux for 4 h. After cooling, the mixture was diluted with water and extracted with methylene chloride (3×10 ml). The combined extracts were washed with brine, dried over magnesium sulfate, and concentrated in vacuo to an oil. Flash chromatography (15% methanol/methylene chloride) afforded the amine (11 mg, 63%) as a pale yellow oil; [α]D$^{25}$ +10.1° (c 0.54, CHCl$_3$); IR (CHCl$_3$) 3480 (w), 3500–2700 (br, w), 3060 (w), 3005 (m), 2955 (s), 2860 (m), 1605 (w), 1505 (m), 1450 (m), 1290 (w), 1255 (m), 1180 (w), 1155 (w), 1128 (s), 1075 (br, s), 1030 (s), 820 (w), 690 (w) cm$^{-1}$; $^1$H NMR (500 MHz, CDCl$_3$) δ 1.25–1.45 (m, 6H), 1.55 (m, 3H), 2.33 (br s, 2H), 2.59 (m, 1H), 2.65 (t, J=7.1 Hz, 2H), 3.08 (m, 2H), 3.38 (m, 1H), 3.40–3.56 (m, 6H), 3.58 (dd, J=10.8, 5.2 Hz, 1H), 3.75 (d, J=9.6 Hz, 1H), 3.81 (s superimposed on a m, 3H), 3.81 (m, 1H), 4.24 (m, 2H), 4.45 (m, 2H), 4.49 (d, J=11.9 Hz, 1H), 4.60 (d, J=11.4 Hz, 1H), 4.66 (d, J=12.0 Hz, 1H), 6.75 (s, 1H), 6.85 (m, 2H), 7.05–7.18 (m, 8H), 7.25 (d, J=8.2 Hz, 1H), 7.27–7.38 (m, 12H), 7.42 (s, 1H), 7.57 (d, J=7.9 Hz, 1H), 8.41 (br s, 1H); $^{13}$C NMR (125.8 MHz, CDCl$_3$) δ 24.6, 24.9, 25.6, 28.6, 31.8, 33.9, 40.6, 54.2, 65.8, 68.5, 69.0, 70.5, 71.4, 74.1, 76.9, 104.0, 110.0, 111.6, 112.2, 117.6, 119.0, 120.6, 121.3, 126.6, 126.9, 126.9, 127.3, 128.6, 130.1, 133.4, 135.0, 137.0, 137.5, 137.9, 141.7, 158.0; high resolution mass spectrum (FAB, m-nitrobenzyl alcohol) m/z 849.4672[(M+H)$^+$; calcd for C$_{53}$H$_{61}$O$_6$N$_4$: 849.4591].

To a solution of the amine (0.023 g, 0.027 mmol) in dry CH$_2$Cl$_2$ (2 ml) was added TFA (3.5 ml, 0.045 mmol). After stirring for 5 minutes, the mixture was added to brine (20 ml) that had been adjusted to pH 8.0 with aqueous sodium bicarbonate and extracted with methylene chloride (3×15 ml). The combined extracts were washed with brine, dried over magnesium sulfate, and concentrated in vacuo to an oil. Purification by RP HPLC (water/acetonitrile) afforded I-16 (9.7 mg, 63%) as a pale yellow oil; [α]D$^{25}$ +11.2° (c 0.42, CH$_3$OH); $^1$H NMR (500 MHz, CD$_3$OD) δ 1.26–1.42 (m, 5H), 1.52 (m, 4H), 2.44 (m, 1H), 2.78 (t, J=6.6 Hz, 2H), 3.16 (m, 1H), 3.36–3.48 (m, 4H), 3.52 (dd, J=10.9, 4.8 Hz, 1H), 3.64 (dd, J=11.1, 1.5 Hz, 1H), 3.79 (dt, J=9.4, 7.3 Hz, 1H), 4.15 (dt, J=9.4, 6.1 Hz, 1H), 4.35 (m, 2H), 4.39 (d, J=11.7 Hz, 1H), 4.42 (d, J=13.0 Hz, 1H), 4.53 (d, J=11.6 Hz, 1H), 6.92 (m, 2H), 6.99 (m, 1H), 7.02 (s, 1H), 7.25 (m, 6H), 7.49 (d, J=7.9 Hz, 1H), 8.64 (s, 1H); $^{13}$C NMR (62.9 MHz, CD$_3$OD) δ 26.8, 26.9, 27.2, 28.5, 30.5, 35.8, 40.6, 62.8, 71.0, 72.3, 72.5, 73.2, 76.8, 79.1, 106.2, 112.2, 113.0, 117.9, 119.5, 119.6, 122.3, 123.8, 128.8, 128.9, 129.4, 132.5, 135.3, 138.0, 139.6; high resolution mass spectrum (FAB, m-nitrobenzyl alcohol) m/z 577.3421[(M+H)$^+$; calcd for C$_{33}$H$_{45}$O$_5$N$_4$: 577.3390].

R. Amide (+)-I-40

To a solution of amine I-39 (0.043 g, 0.043 mmol) in methylene chloride (1 ml) and methanol (2 ml) was added acetic anhydride (4.4 ml, 0.043 mmol). After 2 h, two additional equivalents of acetic anhydride (8.8 ml) were added and stirring was continued for a total of 24 h. The mixture was diluted with methylene chloride (15 ml) and washed sequentially with saturated sodium bicarbonate and water. The organic layer was dried over magnesium sulfate, and concentrated in vacuo to an oil. Flash chromatography (15% methanol/methylene chloride) afforded two inseperable components which were used uncharacterized in the following reaction.

To a solution of the above sugars in ethanol (4 ml) was added 5N NaOH (0.200 ml) and mixture was heated at reflux for 2 h. After cooling, the mixture was diluted with water, adjusted to pH 8.0 with HCl, and extracted with methylene chloride (3×10 ml). The combined extracts were washed with brine, dried over magnesium sulfate, and concentrated in vacuo to an oil. Purification by RP HPLC (water/acetonitrile) afforded I-40 (10 mg, 38%) as a colorless oil; [α]D$^{25}$ +13.4° (c 0.62, C$_2$H$_5$OH); $^1$H NMR (500 MHz, CD$_3$OD) δ 1.21–1.35 (m, 4H), 1.36 (m, 3H), 1.48 (m, 2H), 1.83 (s, 3H), 2.40 (dt, J=12.2, 4.7 Hz, 1H), 2.99 (t, J=6.7 Hz, 2H), 3.03 (t, J=7.1 Hz, 2H), 3.15 (m, 1H), 3.35–3.46 (m, 4H), 3.51 (dd, J=10.9, 4.9 Hz, 1H), 3.63 (dd, J=11.0, 1.7 Hz, 1H), 3.79 (dt, J=9.4, 7.3 Hz, 1H), 4.13 (dt, J=9.3, 6.1 Hz, 1H), 4.33 (d, J=7.5 Hz, 1H), 4.37 (d, J=13.0 Hz, 1H), 4.39 (d, J=11.7 Hz, 1H), 4.42 (d, J=13.0 Hz, 1H), 4.52 (d, J=11.6 Hz, 1H), 6.92 (m, 2H), 6.99(dt, J=7.1, 1.0 Hz, 1H), 7.02 (s, 1H), 7.22 (m, 6H), 7.48 (d, J=7.9 Hz, 1H), 8.63 (s, 1H); $^{13}$C NMR (125.8 MHz, CD$_3$OD) δ 22.5, 26.9, 27.0, 30.3, 30.6, 35.8, 40.5, 62.7, 70.8, 70.9, 72.4, 72.6, 73.3, 76.8, 79.2, 106.2, 112.2, 113.1, 118.0, 119.5, 119.6, 122.3, 123.8, 128.8, 128.9, 129.4, 132.5, 135.3, 138.0, 139.7, 173.2; high resolution mass spectrum (FAB, m-nitrobenzyl alcohol) m/z 619.3521[(M+H)$_+$; calcd for C$_{35}$H$_{47}$O$_6$N$_4$: 619.3495].

S. Azide (−)-44

1-Iodo-6-azido-2-hexyne I-43 was prepared as follows: To a stirred solution of 6-azido-2-hexyn-1-ol (0.10 g, 0.72 mmol), imidazole (0.059 g, 0.86 mmol), and triphenylphosphine (0.23 g, 0.86 mmol) in Et$_2$O/CH$_3$CN (2 ml; 5:3) at 0° C., was added iodine (0.23 g, 0.86 mmol). After 5 min at room temperature, the mixture was diluted with ether (10 ml) and washed successively with saturated Na$_2$S$_2$O$_3$ and CuSO$_4$. The ether layer was dried over magnesium sulfate, filtered, and concentrated in vacuo, affording a yellow solid which was used without purification in the next reaction.

To a solution of alcohol I-33 (0.13 g, 0.19 mmol) and iodide I-43 (0.13 g, 0.52 mmol) in dry THF (2 ml) at 0° C. was added NaH (60%, 0.012 g, 0.30 mmol). After stirring for 6 h the mixture was poured into water (30 ml) and extracted with Et$_2$O (3×15 ml). The combined extracts were washed with water, dried over magnesium sulfate and concentrated in vacuo. Flash chromatography (15% ethyl acetate/petroleum ether) provided I-44 (107 mg, 70% yield) as a colorless oil: [α]D$^{25}$ −15.1° (c 0.72, CHCl$_3$); IR (CHCl$_3$) 3075 (w), 3039 (w), 3018 (w), 2958 (s), 2876 (s), 2108 (s), 1452 (m), 1371 (br, m), 1175 (s), 1135 (s), 1122 (s), 1100 (s), 1060 (m), 1020 (w), 882 (w), 810 (w), 670 (br, w), 595 (m) cm$^{-1}$; $^1$H NMR (500 MHz, CDCl$_3$) δ 1.03 (s, 21H), 1.53 (m, 1H), 1,69 (m, 2H), 2.24 (tt, J=7.0, 1.9 Hz, 2H), 2.40 (m, 1H), 2.98 (t, J=7.0 Hz, 2H), 3.30 (t, J=6.6 Hz, 2H), 3.46 (m, 2H), 3.58 (m, 1H), 3.72–3.80 (m, 3H), 4.11 (m, 1H), 4.14–4.22 (m, 2H), 4.24 (d, J=7,3 Hz, 1H), 4.53 (d, J=11.5 Hz, 1H), 4.60 (d, J=11.6 Hz, 1H), 7.21 (t, J=7.4 Hz, 1H), 7.25 (s, 1H), 7.26–7.33 (m, 5H), 7.39 (m, 3H), 7.48 (m, 2 H), 7.85 (d, J=7.5 Hz, 2H), 7.96 (d, J=7.9 Hz, 1H); $^{13}$C NMR (62.9 MHz, CDCl$_3$) δ 12.4 16.1, 18.0, 25.6, 27.7, 38.3, 50.2, 59.1, 68.5, 68.7, 69.4, 71.5, 71.9, 77.9, 85.1, 105.6, 113.7, 119.4, 119.7, 123.1, 123.4, 124.7, 126.8, 127.8, 128.4, 129.2, 131.1, 133.6, 135.2, 138.2, 138.4.

T. Alcohol (−)-I-45

A solution of azide I-44 (0.20 g 0.24 mmol) in THF (5 ml) was cooled to 0° C. and TBAF (0.29 ml, 1.0 M, 0.29 mmol) was added dropwise. The mixture was stirred for 2 h, added to water and extracted with Et$_2$O (3×20 ml). The combined extracts were washed with water, dried over magnesium sulfate and concentrated in vacuo. Flash chromatography (40% ethyl acetate/petroleum ether) yielded the alcohol as a colorless oil (0.16 g, 100%); [α]D$^{25}$−12.8° (c 0.39, CHCl$_3$); IR (CHCl$_3$) 3050 (w), 3039 (w), 3020 (w), 2945 (m), 2888 (m), 2117 (s), 1455 (s), 1375 (s), 1280 (br, m), 1185 (s), 1140 (s), 1130 (s), 1105 (s), 1093 (s), 1075 (s), 1056 (s), 600 (m), 575 (m) cm$^{-1}$; $^1$H NMR (500 MHz, CDCl$_3$) δ 1.52 (m, 1H), 1.60 (quin., J=6.8 Hz, 2H), 2.19 (d, J=3.1 Hz, 1H), 2.26 (tt, J=7.0, 2.0 Hz, 2H), 2.45 (m, 1H), 2.98 (m, 2H), 3.22 (t, J=6.6 Hz, 2H), 3.43 (m, 1H), 3.75 (m, 3H), 4.11–4.23 (m, 3H), 4.25 (d, J=7.1 Hz, 1H), 4.52 (d, J=11.5 Hz, 1H), 4.61 (d, J=11.5 Hz, 1H), 7.23 (m, 1H), 7.27–7.36 (m, 2H), 7.43 (m, 3H), 7.50 (m, 2H), 7.86 (m, 2H), 7.98 (m, 1H); $^{13}$C NMR (125.8 MHz, CDCl$_3$)δ 16.1, 25.5, 27.7, 34.2, 50.1, 59.1, 68.3, 68.6, 68.6, 71.4, 71.8, 77.7, 85.2, 104.7, 113.8, 119.4, 123.2, 123.5, 124.8, 126.7, 127.7, 127.8, 128.4, 129.2, 131.1, 133.7, 135.2, 138.0, 139.0, 139.2; high resolution mass spectrum (FAB, m-nitrobenzyl alcohol) m/z 658.2482 (M$^+$; calcd for C$_{35}$H$_{38}$SO$_7$ N$_4$: 658.2461].

U. Imidazole-Azide (−)-I-46

To a solution of alcohol I-45 (0.16 g, 0.24 mmol) and chloro-imidazole I-37 (0.27 g, 0.69 mmol) at 0° C. in dry THF (4 ml) was added NaH (60%, 0.015 g, 0.36 mmol). After stirring for 12 h at room temperature, the mixture was added to water and extracted with Et$_2$O (3×20 ml). The combined extracts were washed with water, dried over magnesium sulfate and concentrated in vacuo. Flash chromatography (60% ethyl acetate/petroleum ether) yielded I-46 as a colorless oil (0.13 g, 54%); [α]D$^{25}$ −0.4° (c 1.14, CHCl$_3$); IR (CHCl$_3$) 3025 (w), 3017 (w), 3010 (m), 2980 (m), 2959 (m), 2880 (m), 2108 (s), 1613 (w), 1590 (w), 1516 (m), 1452 (s), 1385 (s), 1360 (s), 1290 (s), 1280 (s), 1238 (s), 1225 (s), 1100 (s), 1075 (s), 1050 (s), 830 (m), 700 (m), 600 (m), 572 (m) cm$^{-1}$; $^1$H NMR (500 MHz, CDCl$_3$) δ 1.51 (m, 1H), 1.70 (quin., J=6.8 Hz, 2H), 2.25 (tt, J=7.0, 2.1 Hz, 2H), 2.59 (m, 1H), 2.92 (t, J=7.0 Hz, 2H), 3.29–3.39 (m, 3H), 3.45 (m, 2H), 3.69–3.80 (m, 3H), 3.28 (s superimposed on a m, 3H), 4.10–4.20 (m, 3H), 4.37 (d, J=7.6 Hz, 1H), 4.44 (d, J=11.4 Hz, 1H), 4.46 (d, J=12.2 Hz, 1H), 4.59 (d, J=11.5 Hz, 1H), 4.64 (d, J=12.2 Hz, 1H), 6.79 (m, 3H), 7.04 (m, 2H), 7.10 (m, 4H), 7.15 (m, 1H), 7.20–7.49 (m, 18H), 7.82 (m, 2H), 7.91 (d, J=8.2 Hz, 1H); $^{13}$C NMR (125.8 MHz, CDCl$_3$) δ 13.1, 15.0, 24.5, 26.7, 33.9, 49.1, 54.2, 58.1, 65.9, 67.3, 67.6, 70.1, 71.0, 73.8, 74.0, 76.2, 76.7, 84.0, 104.1, 112.2, 112.6, 118.4, 118.8, 122.0, 122.5, 125.5, 125.6, 126.6, 126.8, 126.9, 127.3, 128.1, 128.6, 130.0, 130.1, 132.5, 133.4, 134.1, 137.0, 137.2, 137.4, 137.9, 141.7, 158.0; high resolution mass spectrum (FAB, m-nitrobenzyl alcohol) m/z 1011.4100 [(M+H)$^+$; calcd for C$_{59}$H$_{59}$SO$_8$ N$_6$: 1011.4115].

V. Free imidazole (+)-42

To a solution of azide I-45 (0.11 g, 0.11 mmol) in THF (5 ml) was added H$_2$O (0.095 ml, 5.27 mmol) and PPh$_3$ (0.073 g, 0.28 mmol) and the reaction mixture heated to 55° C. for 6 h, cooled, and concentrated in vacuo. Flash chromatography (10% methanol/methylene chloride) provided the amine as a colorless oil (103 mg, 93%); [α]D$^{25}$ +2.2° (c 0.87, CHCl$_3$); IR (CHCl$_3$) 3070 (w), 3010 (m), 2960 (m), 2942 (m), 2878 (m), 1612 (m), 1590 (w), 1515 (m), 1452 (m), 1374 (m), 1259 (m), 1179 (s), 1145 (s), 1120 (s), 1090 (s), 1070 (m), 1050 (m), 827 (w), 700 (w), 597 (w), 569 (w) cm$^{-1}$; $^1$H NMR (500 MHz, CDCl$_3$) δ 1.52 (m, 1H), 1.76 (m, 2H), 2.23 (m, 2H), 2.55 (m, 1H), 2.91 (m, 4H), 3.38 (m, 1H), 3.47 (m, 2H), 3.69 (dd, J=10.5, 4.8 Hz, 1H), 3.77 (m, 5H), 4.11 (m, 3H), 4.40 (d, J=7.7 Hz, 1H), 4.43 (d, J=11.4 Hz, 1H), 4.44 (d, J=12.2 Hz, 1H), 4.59 (d, J=11.2 Hz, 1H), 4.60 (d, J=12.2 Hz, 1H), 5.60 (br s, 1H), 6.71 (s, 1H), 6.78 (m, 2H), 7.00 (m, 2H), 7.08 (m, 4H), 7.12 (m, 1H), 7.20 (m, 1H), 7.22–7.38 (m, 14H), 7.45 (m, 3H), 7.81 (dd, J=8.4, 1.0 Hz, 2H), 7.91 (d, J=7.6 Hz, 1H); $^{13}$C NMR (62.9 MHz, CDCl$_3$) δ 16.2, 25.6, 28.0, 34.8, 39.7, 55.3, 59.1, 66.7, 68.4, 68.7, 71.2, 72.2, 75.0, 75.2, 77.4, 77.5, 77.7, 85.1, 105.0, 113.3, 113.6, 119.6, 119.9, 120.1, 123.1, 123.7, 124.6, 126.7, 127.8, 128.0, 128.4, 129.2, 129.7, 131.2, 133.6, 134.4, 135.1, 138.1, 138.3, 138.3, 139.0, 142.6, 159.1; high resolution mass spectrum (FAB, m-nitrobenzyl alcohol) m/z 985.4254 [(M+H)$^+$; calcd for C$_{59}$H$_{61}$SO$_8$ N$_4$: 985.4210].

To a solution of the amine (0.085 g, 0.087 mmol) in EtOH (3 ml) was added 5M NaOH (0.50 ml) and mixture was heated at reflux for 4 h. After cooling, the mixture was diluted with water and extracted with methylene chloride (3×10 ml). The combined extracts were washed with brine, dried over magnesium sulfate, and concentrated in vacuo to an oil. Flash chromatography (15% methanol/methylene chloride) afforded the amine (39 mg, 56%) as a colorless oil; [α]D$^{25}$ +3.1° (c 1.95, CHCl$_3$); IR (CHCl$_3$) 3480 (w), 3520–2500 (br, w), 3020 (s), 2960 (s), 2940 (s), 2880 (s), 1609 (m), 1590 (w), 1513 (s), 1493 (m), 1459 (m), 1447 (m), 1355 (m), 1340 (m), 1302 (m), 1257 (s), 1185 (m), 1156 (m), 1130 (s), 1090 (s), 1037 (s), 1010 (m), 910 (w), 825 (m0, 695 (m), 660 (w), 582 (w) cm$^{-1}$; $^1$H NMR (500 MHz, CDCl$_3$) δ 1.50 (q, J=11.4 Hz, 1H), 1.61 (m, 1H), 1.69 (m, 1H), 2.11 (m, 2H), 2.52 (m, 1H), 2.79 (m, 2H), 3.01 (m, 2H), 3.36–3.49 (m, 3H), 3.65 (dd, J=10.8., 5.0 Hz, 1H), 3.77 (m, 5H), 4.05–4.17 (m, 3H), 4.40 (m, 2H), 4.47 (d, J=11.9 Hz, 1H), 4.54 (d, J=11.4 Hz, 1H), 4.60 (d, J=12.0 Hz, 1H), 6.72 (br s, 1H), 6.80 (apparent d, J=9.0 Hz, 2H), 6.98–7.13 (m, 9H), 7.23–7.33 (m, 12H), 7.40 (br s, 1H), 7.50 (d, J=7.1 Hz, 1H), 8.75 (br s, 1H); $^{13}$C NMR (62.9 MHz, CDCl$_3$) δ 16.1, 25.8, 26.0, 34.8, 38.9, 55.3, 59.1, 66.3, 68.7, 70.0, 71.2, 72.2, 75.1, 77.7, 84.7, 105.1, 111.5, 112.2, 113.3, 118.6, 119.0, 120.2, 121.7, 122.8, 128.1, 128.4, 129.7, 131.2, 134.2, 136.2, 138.0, 138.8, 142.5, 159.2; high resolution mass spectrum (FAB, m-nitrobenzyl alcohol) m/z 845.4261 [(M+H)$^+$; calcd for C$_{53}$H$_{57}$SO$_6$ N$_4$: 845.4278].

To a solution of the amine (0.040 g, 0.047 mmol) in dry CH$_2$Cl$_2$ (2 ml) was added TFA (24 ml, 0.31 mmol). After stirring for 5 minutes, the mixture was added to brine (20 ml) that had been adjusted to pH 8.0 with aqueous sodium bicarbonate and extracted with methylene chloride (3×15 ml). The combined extracts were washed with brine, dried over magnesium sulfate, and concentrated in vacuo to an oil. Purification by RP HPLC (water/acetonitrile) afforded I-42 (12.3 mg, 45%) as a pale yellow oil; [α]D$^{25}$ +0.9° (c 0.56, CH$_3$OH); $^1$H NMR (500 MHz, CD$_3$OD) δ 1.42 (m, 1H), 1.78 (apparent quin., J=7.0 Hz, 2H), 2.30 (tt, J=7.0, 2.1 Hz, 2H), 2.47 (m, 1H), 2.95 (t, J=7.6 Hz, 2H), 3.06 (t, J=6.7 Hz, 2H), 3.20 (m, 2H), 3.47 (m, 2H), 3.69 (dd, J=10.7, 4.4 Hz, 1H), 3.76 (dd, J=11.0, 1.4 Hz, 1H), 3.86 (dt, J=9.4, 7.3 Hz, 1H), 4.18 (m, 3H), 4.40 (m, 2H), 4.49 (m, 2H), 4.60 (d, J=11.6 Hz, 1H), 6.98 (m, 2H), 7.06 (m, 1H), 7.09 (s, 1H), 7.26–7.34 (m, 7H), 7.55 (d, 7.8 Hz, 1H), 8.70 (br s, 1H); $^{13}$C NMR (62.9 MHz, CD$_3$OD) δ 16.6, 26.9, 27.5, 35.8, 39.8, 59.7, 62.7, 69.6, 71.0, 72.3, 73.1, 76.8, 78.4, 79.0, 85.6, 106.2, 112.2, 113.1, 117.9, 119.5, 119.6, 122.3, 124.0, 128.8, 128.9, 129.4, 132.5, 135.4, 139.7, 142.2; high resolution mass spectrum (FAB, m-nitrobenzyl alcohol) m/z 573.3062 [(M+H)$^+$; calcd for C$_{33}$H$_{41}$SO$_5$ N$_4$: 845.4278].

W. Saturated amine I-16 from Pd/CaCO3 reduction of acetylene-azide I-46

To a solution of azide I-46 (8 mg) in ethanol (1.7 ml) was added Pd/CaCO$_3$ (1 mg). The system was evacuated and back flushed with H$_2$ gas four times and then allowed to stir under an atmosphere of H$_2$ gas for 2.5 h. The mixture was filtered through celite, the celite was washed with Et$_2$O (20 ml), and the filtrate was concentrated in vacuo. Flash chromatography (20% methanol/methylene chloride) afforded I-16 (5.1 mg, 64%) as a pale yellow oil which was identical in all respects with material obtained by other methods.

X. Benzyl ether (−)-I-50

To a solution of the alcohol I-33 (0.044 g, 0.063 mmol) and benzyl bromide (8.3 ml, 0.070) in dichloromethane (2 ml) at 0° C. was added NaH (60%, 3.0 mg, 0.070 mmol) and 15-crown-5 (1 ml). After stirring for 5 h, the mixture was added to H$_2$O (200 ml) and extracted with dichloromethane (3×10 ml). The combined extracts were washed with water, dried over magnesium sulfate and concentrated in vacuo. Flash chromatography (10% ethyl acetate/petroleum ether) provided I-50 (0.035 g, 70% yield) as a colorless oil: [α]D$^{25}$ −10.2° (c 3.0, CHCl$_3$); IR (CHCl$_3$) 3065 (w), 3010 (m), 2950 (s), 2877 (s), 1610 (w), 1496 (w), 1465 (m), 1452 (s), 1370 (s), 1270 (w), 1205 (m), 1175 (s), 1125 (s), 1098 (s), 1070 (s), 880 (m), 725 (br, s), 665 (s), 595 (m), 569 (m) cm$^{-1}$; $^1$H NMR (500 MHz, CDCl$_3$) δ 1.04 (s, 21H), 1.51 (apparent q. J=11.1 Hz, 1H), 2.41 (dt, J=12.3, 4,8 Hz, 1H), 3.00 (t, J=7.9 Hz, 3H), 3.43–3.52 (m, 2H), 3.60 (m, 1H), 3.66 (dd, 10.7, 5.1 Hz, 1H), 3.78 (m, 2H), 4.12 (m, 1H), 4.26 (d, J=7.3 Hz, 1H), 4.43 (d, J=11.5 Hz, 1H), 4.53 (d, J=7.0 Hz, 1H), 4.57 (d, J=6.2 Hz, 1H), 4.59 (d, J=12.3 Hz, 1H), 7.18–7.32 (m, 12H), 7.36–7.41 (m, 3H), 7.47 (m, 2H), 7.83 (m, 2H), 7.97 (apparent d, J=8.4 Hz, 1H); $^{13}$C NMR (62.9 MHz, CDCl$_3$) δ 12.4, 18.0, 25.7, 38.3, 68.5, 69.4, 71.4, 72.2, 73.5, 78.1, 105.6, 113.7, 119.4, 119.7, 123.1, 123.4, 124.7, 126.7, 127.5, 127.7, 128.3, 128.4, 129.2, 131.1, 133.6, 135.2, 138.1, 138.4; high resolution mass spectrum (FAB, m-nitrobenzyl alcohol) m/z 783.3662(M$^+$; calcd for C$_{45}$H$_{57}$SiSO$_7$ N: 783.3625).

Y. Alcohol (−)-I-51

A solution of benzyl ether I-50 (0.080 g 0.10 mmol) in THF (2 ml) was cooled to 0° C. and TBAF (0.11 ml, 1.0 M, 0.11 mmol) was added dropwise. The mixture was stirred for 2 h, added to water and extracted with EtOAc (3×20 ml). The combined extracts were washed with water, dried over magnesium sulfate and concentrated in vacuo. Flash chromatography (40% ethyl acetate/petroleum ether) yielded alcohol I-51 as a colorless oil (0.070 g, 100%); [α]D$^{25}$ −7.7° (c 0.27, CHCl$_3$); IR (CHCl$_3$) 3080 (w), 3040 (w), 3010 (m), 2955 (m), 2880 (m), 1450 (m), 1370 (m), 1280(w), 1173(s), 1120 (s), 1100 (s), 1060 (s), 690 (w), 680 (w) cm$^{-1}$; $^1$H NMR (500 MHz, CDCl$_3$) δ1.53 (apparent q, J=10.2 Hz, 1H), 2.30 (br s, 1H), 2.45 (dt, J=12.4, 4.6 Hz, 1H), 2.99 (m, 2H), 3.46 (m, 1H), 3.55 (m, 1H), 3.59 (m, 1H), 3.65 (dd, J=10.5, 5.0 Hz, 1H), 3.74 (m, 2H), 4.20 (dt, J=9.5, 6.5 Hz, 1H), 4.27 (d, J=6.9 Hz, 1H), 4.43 (d, J=11.5 Hz, 1H), 4.49–4.58 (m, 3H), 7.21–7.33 (m, 12H), 7.39 (m, 2H), 7.43 (s, 1H), 7.49 (d, 2H), 7.85 (m, 2H), 7.99 (d, J=8.4 Hz, 1H); $^{13}$C NMR (62.9 MHz, CDCl$_3$) δ 24.5, 32.8 67.2, 67.5, 68.3, 70.2, 71.0, 72.3, 76.7, 103.5, 112.7, 118.4, 118.8, 122.1, 122.4, 123.7, 125.6, 126.5, 126.6, 126.7, 126.7, 127.3, 127.4, 128.1, 130.0, 132.6, 134.1, 136.8, 137.2; high resolution mass spectrum (FAB, m-nitrobenzyl alcohol) m/z 628.2335 [(M+H)$^+$; calcd for C$_{36}$H$_{38}$SO$_7$ N: 628.2368].

Z. Azide (−)-I-53

1-Iodo-5-azido-2-pentyne I-52 was prepared as follows: To a stirred solution of 5-azido-2-pentyn-1-ol (0.13 g, 1.00 mmol), imidazole (0.085 g, 1.25 mmol), and triphenylphosphine (0.32 g, 1.25 mmol) in Et$_2$O/CH$_3$CN (2 ml; 5:3) at 0° C., was added iodine (0.32 g, 1.25 mmol). After 5 min at room temperature, the mixture was diluted with ether (10 ml) and washed successively with saturated Na$_2$S$_2$O$_3$ and CuSO$_4$. The ether layer was dried over magnesium sulfate, filtered, and concentrated in vacuo, affording a yellow solid which was used without purification in the next reaction.

To a solution of alcohol I-51 (0.073 g, 0.12 mmol) and iodide I-52 (0.24 g, 1.00 mmol) in dry dichloromethane (2 ml) at 0° C. was added NaH (60%, 6.0 mg, 0.15 mmol). After stirring for 6 h the mixture was poured into water (30 ml) and extracted with CH$_2$Cl$_2$ (3×15 ml). The combined extracts were washed with water, dried over magnesium sulfate and concentrated in vacuo. Flash chromatography (30% ethyl acetate/petroleum ether) provided I- 53 (64 mg, 75% yield) as a colorless oil: [α]D$^{25}$ −8.9° (c 0.63, CHCl$_3$); IR (CHCl$_3$) 3070 (w), 3028 (w), 3010(m), 2940 (m), 2870 (m), 2110(s), 1450 (s), 1378 (s), 1270 (m), 1250 (s), 1178 (s), 1133 (s), 1120 (s), 1090 (s), 1072 (s), 1045 (s), 690 (w), 595 (m) cm$^{-1}$; $^1$H NMR (500 MHz, CDCl$_3$) δ 1.48 (q, J=12.0 Hz, 1H), 2.50 (tt, J=6.9, 2.1 Hz, 2H), 2.55 (dt, J=12.2, 4.7 Hz, 1H), 3.00 (t, J=6.9 Hz, 2H), 3.39 (m, 3H), 3.50 (m, 2H), 3.66 (dd, J=10.7, 5.0 Hz, 1H), 3.78 (m, 2H), 4.19 (m, 1H), 4.24 (tq, J=15.2, 2.2 Hz, 2H), 4.34 (d, J=7.6 Hz, 1H), 4.40 (d, J=11.4 Hz, 1H), 4.58 (m, 3H), 7.19–7.31 (m, 12H), 7.39 (m, 2H), 7.48 (m, 4H), 7.85 (m, 2H), 7.98 (d, J=8.3 Hz, 1H); $^{13}$C NMR (62.9 MHz, CDCl$_3$) δ 19.9, 25.6, 34.8, 49.7, 58.3, 68.3, 69.2, 71.3, 72.1, 73.4, 74.3, 78.0, 78.5, 82.4, 104.9, 113.7, 123.1, 123.6, 124.7, 126.7, 127.5, 127.7, 128.3, 128.4, 129.2, 131.0, 133.6, 135.1, 137.9, 138.3; high resolution mass spectrum (FAB, m-nitrobenzyl alcohol) m/z 735.2827 [(M+H)$^+$; calcd for C$_{41}$H$_{43}$SO$_7$ N$_4$: 735.2852].

AA. Amine (−)-I-54

To a solution of azide I-53 (0.021 g, 0.027 mmol) in THF (1.5 ml) was added H$_2$O (0.012 ml, 0.69 mmol) and PPh$_3$ (0.014 g, 0.055 mmol) and the reaction mixture was heated to 55° C. for 4 h, cooled, and concentrated in vacuo. Flash chromatography (6% methanol/methylene chloride) provided I-54 as a colorless oil (16.2 mg, 83%); [α]D$^{25}$ −9.0° (c 0.81, CHCl$_3$); IR (CHCl$_3$) 3070(w), 3038(w), 3017 (w), 2940 (m), 2878 (w), 1451 (m), 1370 (br, m), 1210 (s), 1187 (m), 1179 (m), 1122 (m), 1090 (m), 1072 (m), 930 (w), 750 (br, s), 665 (s), 595 (m), 569 (m) cm$^{-1}$; $^1$H NMR (500 MHz, CDCl$_3$) δ 1.48 (q, J=12.0 Hz, 1H), 2.00 (br s, 2H), 2.36 (br s, 2H), 2.55 (dt, J=12.3, 4.7 Hz, 1H), 2.83 (br s, 2H), 3.00 (t, J=6.7 Hz, 2H), 3.39 (m, 1H), 3.50 (m, 2H), 3.66 (dd, J=10.8, 5.0 Hz, 1H), 4.19 (m, 1H), 4.25 (tq, J=15.3, 2.1 Hz, 2H), 4.35 (d, J=7.6 Hz, 1H), 4.40 (d, J=11.4 Hz, 1H), 4.56 (m, 3H), 7.20–7.33 (m, 12H), 7.38 (m, 3H), 7.48 (m, 4H), 7.85 (m, 2H), 7.97 (d, J=8.4 Hz, 1H); $^{13}$C NMR (125.8 MHz, CDCl$_3$) δ 25.6, 34.8, 58.4, 68.3, 69.2, 71.3, 72.1, 73.4, 74.3, 77.9, 80.0, 84.2, 104.9, 113.7, 119.4, 119.8, 123.7, 124.7, 126.7, 127.5, 127.7, 127.7, 127.8, 128.3, 128.4, 129.1, 131.0, 133.6, 135.1, 137.9, 138.3, 138.3; high resolution mass spectrum (FAB, m-nitrobenzyl alcohol) m/z 709.2980 [(M+H)$^+$; calcd for C$_{41}$H$_{45}$SO$_7$N$_2$: 709.2947].

AB. Amine (+)-I-48

To a solution of amine I-54 (0.012 g, 0.017 mmol) in MeOH (1.5 ml) was added 5M KOH (0.30 ml) and the mixture was heated at reflux for 8 h. After cooling, the mixture was diluted with water and extracted with methylene chloride (3×10 ml). The combined extracts were washed with brine, dried over magnesium sulfate, and concentrated in vacuo to an oil. Flash chromatography (8% methanol/ methylene chloride) afforded I-48 (7.1 mg, 73%) as a pale yellow oil; [α]D$^{25}$ +13.5° (c 0.31, CHCl$_3$); IR (CHCl$_3$) 3480 (m), 3010 (s), 2930 (s), 2879 (s), 2861 (s), 1460 (m), 1270 (w), 1140 (w), 1105 (m), 1079 (s), 861 (w), 690 (m) cm$^{-1}$; $^1$H NMR (500 MHz, CDCl$_3$) δ 1.49 (q, J=11.9 Hz, 1H), 2.38 (br s, 2H), 2.51 (dt, J=12.3, 4.6 Hz, 2H), 2.66 (br s, 2H), 2.84 (br s, 2H), 3.09 (t, J=6.7 Hz, 2H), 3.33 (m, 1H), 3.45–3.55 (m, 2H), 3.66 (dd, J=10.7, 4.9 Hz, 1H), 3.76 (dd, J=10.9, 1.8 Hz, 1H), 3.83 (dt, J=9.4, 7.2 Hz, 1H), 4.17 (dt, J=15.0, 2.0 Hz, 1H), 4.24 (dt, J=9.5, 6.3 Hz, 1H), 4.29 (dt, J=15.0, 2.1 Hz, 1H), 4.39 (m, 2H), 4.56 (m, 3H), 7.08 (t, J=7.9 Hz, 1H), 7.12 (s, 1H), 7.16 (t, J=7.3 Hz, 1H), 7.20–7.35 (m, 11H), 7.58 (d, J=7.8 Hz, 1H), 8.63 (br s, 1H); $^{13}$C NMR (62.9 MHz, CDCl$_3$) δ 22.7, 29.7, 34.9, 58.6, 69.1, 69.5, 71.3, 72.2, 73.5, 74.4, 77.9, 78.4, 83.6, 104.9, 111.1, 112.7, 118.7, 119.1, 121.7, 122.5, 127.6, 127.8, 128.3, 128.4, 136.2, 138.0, 138.3; high resolution mass spectrum (FAB, m-nitrobenzyl alcohol) m/z 569.3029 [(M+H)$^+$; calcd for C$_{35}$H$_{41}$O$_5$ N$_2$: 569.3015].

AC. Amide (+)-I-56

To a solution of amine I-54 (8.4 mg, 0.012 mmol) in CH$_2$Cl$_2$ (1 ml) at 0° C. was added Et$_3$N (1.8 ml, 0.013 mmol) and Ac$_2$O (1.2 ml, 0.013 mmol). After stirring for one minute, the mixture was poured into water. The aqueous layer was extracted with methylene chloride (3×20 ml) and the combined extracts were washed with water, dried over magnesium sulfate and concentrated in vacuo. $^1$H NMR (500 MHz, CDCl$_3$, Crude) δ 1.47 (q, J=11.9 Hz, 1H), 1.95 (s, 3H), 2.40 (m, 2H), 2.53 (dt, J=12.2, 4.8 Hz, 1H), 2.99 (m, 2H), 3.28 (m, 1H), 3.39 (m, 2H), 3.49 (m, 2H), 3.65 (dd, J=10.7, 5.0 Hz, 1H), 3.78 (m, 2H), 4.22 (m, 3H), 4.34 (d, J=7.6 Hz, 1H), 4.40 (d, J=11.4 Hz, 1H), 4.56 (m, 3H), 6.05 (br s, 1H), 7.20–7.33 (m, 12H), 7.39 (apparent t, J=8.2 Hz, 2H), 7.48 (m, 3H), 7.85 (m, 2H), 7.95 (d, J=8.2 Hz, 1H).

To a solution of the crude amide in MeOH (1 ml) was added 5M KOH (0.20 ml) and mixture was heated at reflux for 6 h. After cooling, the mixture was diluted with water and extracted with methylene chloride (3×10 ml). The combined extracts were washed with brine, dried over magnesium sulfate, and concentrated in vacuo to an oil. Flash chromatography (2% methanol/methylene chloride) afforded I-56 (4.9 mg, 68% from I-54) as a pale yellow oil; [α]D$^{25}$ +18.4° (c 0.25, CHCl$_3$); IR (CHCl$_3$) 3480 (w), 3010 (m), 2940 (m), 2870 (m), 1675 (s), 1520 (w), 1456 (m), 1367 (w), 1250 (br, w), 1285 (br, s0, 695 cm$^{-1}$; $^1$H NMR (500 MHz, CDCl$_3$) δ 1.50 (q, J=11.9 Hz, 1H), 1.95 (s, 3H), 2.41 (m, 2H), 2.51 (dt, J=12.2, 4.7 Hz, 1H), 3.10 (t, J=7.0 Hz, 2H), 3.27 (m, 1H), 3.40 (m, 2H), 3.45–3.55 (m, 2H), 3.66 (dd, J=10.8, 4.9 Hz, 1H), 3.76 (dd, J=10.8, 1.8 Hz, 1H), 3.85 (dt, J=9.5, 7.3 Hz, 1H), 4.19–4.29 (m, 3H), 4.37 (d, J=7.6 Hz, 1H), 4.41 (d, J=11.4 Hz, 1H), 4.53–4.61 (m, 3H), 7.09 (m, 2H), 7.16 (m, 1H), 7.20–7.36 (m, 11H), 7.59 (d, J=8.2 Hz, 1H), 8.15 (br s, 1H); $^{13}$C NMR (125.8 MHz, CDCl$_3$) δ 19.9, 23.9, 25.8, 34.8, 38.2, 58.3, 69.1, 69.6, 71.3, 72.2, 73.4, 74.1, 78.0, 78.1, 83.7, 104.8, 11.1, 112.7, 118.7, 119.2, 121.9, 122.2, 127.5, 127.7, 128.3, 128.4, 136.2, 138.0, 170.3; high resolution mass spectrum (FAB, m-nitrobenzyl alcohol) m/z 633.2923 [(M+Na)$^+$; calcd for $C_{37}H_{42}O_6N_2Na$: 633.2940].

AD. Alkane (+)-I-47

To a solution of azide I-53 (0.020 g, 0.027 mmol) in EtOH (1 ml) was added 5% Pd/CaCO$_3$ (6 mg, 33 wgt. %). The system was evacuated and back flushed with H$_2$ gas four times and then allowed to stir under an atmosphere of H$_2$ gas for 4 h. The mixture was filtered through celite, the celite was washed with Et$_2$O (20 ml), and the filtrate was concentrated in vacuo. Flash chromatography (20% methanol/methylene chloride) afforded the amine (12 mg, 62%) as a pale yellow oil; $[\alpha]D^{25}$ +6.0° (c 0.57, CHCl$_3$); IR (CHCl$_3$) 3059 (w), 3020 (w), 3017 (m), 2845 (m), 2878 (m), 1455 (m), 1372 (br, m), 1209 (w), 1179 (s), 1122 (s), 1095 (s), 720 (br, m), 600 (m), 570 (m) cm$^{-1}$; $^1$H NMR (500 MHz, CD$_3$OD) δ 1.35 (m, 2H), 1.42–1.54 (m, 4H), 2.45 (m, 1H), 2.59 (t, J=7.4 Hz, 1H), 2.90 (t, J=5.9 Hz, 2H), 3.04 (m, 1H), 3.32 (dt, J=9.4, 6.4 Hz, 1H), 3.38–3.46 (m, 3H), 3.58 (dd, J=10.8, 4.9 Hz, 1H), 3.69 (dd, J=11.0, 1.5 Hz, 1H), 3.76 (dt, J=9.7, 6.5 Hz, 1H), 4.11 (dt, J=9.7, 5.9 Hz, 1H), 4.25 (d, J=7.5 Hz, 1H), 4.36 (d, J=11.6 Hz, 1H), 4.44 (d, J=12.0 Hz, 1H), 4.48 (d, J=12.0 Hz, 1H), 4.52 (d, J=11.5 Hz, 1H), 7.11–7.26 (m, 12H), 7.37 (m, 3H), 7.47 (m, 3H), 7.80 (m, 2H), 7.88 (d, J=8.3 Hz, 1H); $^{13}$C NMR (62.9 MHz, CD$_3$OD) δ 24.3, 26.4, 30.8, 32.0, 35.9, 41.9, 69.3, 70.4, 71.7, 72.3, 73.4, 74.4, 77.0, 79.1, 106.2, 114.7, 120.8, 122.0, 124.4, 125.3, 125.7, 127.9, 128.7, 128.8, 129.0, 129.4, 130.4, 132.6, 135.1, 136.6, 139.4, 139.6; high resolution mass spectrum (FAB, m-nitrobenzyl alcohol) m/z 713.3251 [(M+H)$^+$; calcd for $C_{41}H_{49}SO_7N_2$: 713.3260].

To a solution of the amine (0.011 g, 0.016 mmol) in MeOH (1.5 ml) was added 5M KOH (0.30 ml) and mixture was heated at reflux for 6 h. After cooling, the mixture was diluted with water and extracted with methylene chloride (3×10 ml). The combined extracts were washed with brine, dried over magnesium sulfate, and concentrated in vacuo. Flash chromatography (20% methanol/methylene chloride) afforded I-47 (5.2 mg, 58%) as a pale yellow oil; $[\alpha]D^{25}$ +3.8° (c 0.16, CHCl$_3$); IR (CHCl$_3$) 3492 (m), 3018 (m), 2960 (m), 2872 (m), 1455 (m), 1370 (w), 1208 (s), 1090 (br, s), 720 (br, s) cm$^{-1}$; $^1$H NMR (500 MHz, CDCl$_3$) δ 1.35 (m, 2H), 1.48 (m, 2H), 1.80 (br s, 2H), 2.54 (m, 1H), 2.73 (t, J=4.0 Hz, 2H), 3.12 (t, J=6.7 Hz, 2H), 3.21 (m, 3H), 3.50 (m, 3H), 3.67 (m, 2H), 3.81 (d, J=10.1 Hz, 1H), 3.85 (dt, 9.5, 7.3 Hz, 1H), 4.28 (dt, J=9.3, 6.2 Hz, 1H), 4.38 (d, J=5.6 Hz, 1H), 4.42 (d, J=11.3 Hz, 1H), 4.61 (m, 3H), 7.11 (t, J=7.1 Hz, 1H), 7.15 (br s, 1H), 7.19 (t, J=7.1 Hz, 1H), 7.25–7.37 (m, 11H), 7.62 (d, J=7.8 Hz, 1H), 8.87 (br s, 1H); $^{13}$C NMR (125.8 MHz, CDCl$_3$) δ 23.2, 25.6, 30.0, 32.8, 34.9, 41.7, 69.3, 69.5, 70.8, 71.2, 72.4, 73.4, 75.8, 78.0, 105.0, 111.0, 112.9, 118.7, 119.0, 121.6, 122.4, 127.5, 127.6, 127.7, 128.1, 128.3, 128.4, 136.2, 138.1, 138.4; high resolution mass spectrum (Cl, NH3) m/z 573.3301 [(M+H)$^+$; calcd for $C_{35}H_{45}O_5N_2$: 573.3328].

AE. Alkene (I-49)

To a solution of amine I-54 (0.018 g, 0.026 mmol) and quinoline (6 ml) in benzene (1.5 ml) was added Linlar's catalyst (6 mg, 30 wgt. %). The system was evacuated and back flushed with H$_2$ gas four times and then allowed to stir under an atmosphere of H$_2$ gas for 4 h. The mixture was filtered through celite, the celite was washed with Et$_2$O (20 ml), and the filtrate was concentrated in vacuo. The residue was used without purification in the next reaction.

To a solution of the crude amine in MeOH (1.5 ml) was added 5M KOH (0.30 ml) and mixture was heated at reflux for 6 h. After cooling, the mixture was diluted with water and extracted with methylene chloride (3×10 ml). The combined extracts were washed with brine, dried over magnesium sulfate, and concentrated in vacuo to an oil. Flash chromatography (methylene chloride/toluene/methanol; 9:8:3) afforded I-49 (1.5 mg, 10% from I-54) as a pale yellow oil; $^1$H NMR (500 MHz, CDCl$_3$) δ 1.49 (m, 1H), 2.06 (m, 2H), 2.49 (m, 2H), 2.57 (m, 1H), 3.09 (t, J=5.8 Hz, 2H), 3.28 (m, 1H), 3.51 (m, 2H), 3.67 (m, 1H), 3.75 (d, J=10.8 Hz, 1 H), 3.87 (dt, 9.3, 7.4 Hz, 1H), 3.94–4.08 (m, 2H), 4.25 (dt, J=9.3, 7.0 Hz, 1H), 4.40 (m, 2H), 4.56 (m, 3H), 5.35 (m, 1H), 5.60 (m, 1H), 7.08 (t, J=7.0 Hz, 1H), 7.08 (s, 1H), 7.14 (t, J=7.1 Hz, 1H), 7.21–7.35 (m, 11H), 7.59 (d, 7.7 Hz, 1H), 8.90 (br s, 1H); high resolution mass spectrum (Cl, NH$_3$) m/z 571.3182 [(M+H)$^+$; calcd for $C_{35}H_{43}O_5N_2$: 571.3171].

AF. Benzoylamide (+)-I-59

Triflate I-62 was generated in the following way: A stirred solution of alcohol I-61 (0.20 g, 0.27 mmol) and 2,6-di-tert-butyl-4-methylpyridine (0.089 g, 0.44 mmol) in dry dichloromethane (3 ml) at −11° C. was treated with triflic anhydride (0.060 ml, 0.35 mmol). After 10 min, the mixture was diluted with water (100 ml), saturated sodium bicarbonate (2 ml) and extracted with dichloromethane (2×200 ml). The combined extracts were washed with brine, dried over magnesium sulfate, filtered, and concentrated in vacuo, affording a yellow oil which was used without purification in the next reaction.

To a stirred solution of N-benzoyl-5-amino-1-pentanol (0.28 g, 1.36 mmol) in THF (6 ml) was added sodium hydride (60% dispersion in oil, 0.11 g, 2.80 mmol). The mixture was allowed to stir for 1.5 h, then cooled to 0° C. before triflate I-62 was added via cannula (4 ml THF). After stirring an additional 18 h, the mixture was added to water (100 ml) and extracted with ether (3×20 ml). The combined extracts were washed with water, dried over magnesium sulfate, and concentrated in vacuo. Flash chromatography (40% ethyl acetate/hexanes) afforded the amide (90 mg, 36%) as a pale yellow oil which was used immediately in the next reaction.

To a solution of the amine (0.055 g, 0.060 mmol) in MeOH (3 ml) was added 5M KOH (0.30 ml) and the mixture was heated at reflux for 3 h. After cooling, the mixture was diluted with water and extracted with methylene chloride (4×10 ml). The combined extracts were washed with brine, dried over magnesium sulfate, and concentrated in vacuo to an oil. Flash chromatography (40% ethyl acetate/hexanes) afforded I-59 (42 mg, 90%) as a clear yellow oil; $[\alpha]D^{25}$ +12.3° (c 0.31, CHCl$_3$); IR (CHCl$_3$) 3480 (m), 3097 (w), 3069 (w), 3035 (w), 3010 (m), 2960 (m), 2875 (m), 1660 (br, m), 1582 (w), 1520 (br, m), 1489 (m), 1455 (m), 1360 (br, m), 1305 (br, w), 1285 (br, w), 1070 (br, s), 695 (m) cm$^{-1}$; $^1$H NMR (500 MHz, CDCl$_3$) δ 1.43 (m, 2H), 1.59 (m, 4H), 3.11 (t, J=7.0 Hz, 2H), 3.36 (m, 2H), 3.44 (m, 4H), 3.49–3.56 (m, 2H), 3.60 (dd, J=10.8, 5.5 Hz, 1H), 3.64 (t, J=9.0 Hz, 1H), 3.69 (dd, J=10.8, 1.6 Hz, 1 H), 3.85 (dt, J=9.3, 7.4 Hz, 1H), 4.22 (dt, J=9.4, 6.8 Hz, 1H), 4.45 (d, J=7.8 Hz, 1H), 4.60 (d, J=11.0 Hz, 1H), 4.65 (d, J=11.0 Hz, 1H), 4.76 (d, J=10.9 Hz, 1H), 4.85 (m, 2H), 4.91 (d, J=10.9 Hz, 1H), 6.09 (br s, 1H), 7.03 (m, 1H), 7.09 (m, 1H), 7.16 (m, 1H), 7.21 (m, 2H), 7.25–7.33 (m, 14H), 7.40 (m, 2H), 7.47 (m, 1H), 7.59 (d, J=7.8 Hz, 1H), 7.73 (m, 2H), 8.22 (br s, 1H); $^{13}$C NMR (125.8 MHz, CDCl$_3$) δ 23.7, 25.7, 29.3, 29.4, 40.0, 69.7, 70.1, 71.5, 74.7, 74.8, 74.9, 75.7, 78.1, 82.3, 84.7, 103.7, 11.2, 112.5, 118.6, 119.2, 122.2, 126.8, 127.5, 127.5, 127.6, 127.8, 127.9, 128.0, 128.3, 128.3, 128.4, 128.5, 131.3, 134.7, 136.2, 138.2, 138.5, 138.6, 167.6; high resolution mass spectrum (FAB, m-nitrobenzyl alcohol) m/z 782.3900 (M+; calcd for $C_{49}H_{54}O_7 N_2$: 782.3931).

AG. Trifluoroacetamide (+)-I-58

To a stirred solution of N-trifluoracetyl-5-amino-1-pentanol (0.27 g, 1.36 mmol) in THF (4 ml) was added sodium hydride (60% dispersion in oil, 0.12 g, 3.00 mmol). The mixture was allowed to stir for 1.5 h, then cooled to 0° C. before triflate I-62 was added via cannula (8 ml dichloromethane). After stirring an additional 18 h, the mixture was added to water (100 ml) and extracted with dichloromethane (2×50 ml). The combined extracts were washed with water, dried over magnesium sulfate, and concentrated in vacuo. Flash chromatography (40% ethyl acetate/hexanes) afforded the amide (178 mg, 84%) as a pale yellow oil which was used immediately in the next reaction.

A solution of the amide (0.010 g, 0.011 mmol), 1,5-dimethoxynaphthalene (0.0062 g, 0.033 mmol) and NaC-NBH$_3$ (0.0021 g, 0.011 mmol) in EtOH (4.8 ml) and water (0.16 ml) was purged with argon then irradiated with a Hanovia apparatus through pyrex for 4 h. The solvent was removed in vacuo and the remaining oil was diluted with water and extracted with dichloromethane (3×10 ml). The combined extracts were washed with water, dried over magnesium sulfate, and concentrated in vacuo. Preparative TLC (0.5 mm, 3% MeOH/CH$_2$Cl$_2$, 2×) afforded the amide (5 mg, 59%) as a pale yellow oil; $[\alpha]D^{25}$ +17.6®(c 0.46, CH$_2$Cl$_2$); IR (CHCl$_3$) 3490 (m), 3100 (w), 3075 (w), 3034 (w), 3014 (w), 2945 (m), 2880 (m), 1692 (s), 1610 (w), 1460 (m), 1362 (w), 1230 (w), 1200 (m), 1152 (s), 1090 (s), 1070 (s), 1040 (m), 910 (w), 697 (w) cm$^{-1}$; $^1$H NMR (500 MHz, d6-DMSO, 380 K) δ 1.26 (m, 2H), 1.42 (m, 2H), 1.56 (m, 2H), 3.00 (t superimposed on a br s, J=7.2 Hz, 2H), 3.00 (br s, 2H), 3.35–3.42 (m, 3H), 3.45 (m 2H), 3.68 (t, J=8.8 Hz, 2H), 3.81 (dt superimposed on a br s, J=9.6, 7.2 Hz, 1H), 3.81 (brs, 1H), 4.10 (dt, J=9.7, 6.9 Hz, 1H), 4.56 (br d, J=7.2 Hz, 1H), 4.61 (d, J=11.6 Hz, 1H), 4.63 (d, J=11.3 Hz, 1H), 4.71 (d, J=11.5 Hz, 1H), 4.77 (d, J=11.5 Hz, 1H), 4.79 (d, J=11.4 Hz, 1H), 4.83 (d, J=11.5 Hz, 1H), 6.96 (m, 1H), 7.05 (m, 1H), 7.08 (br s, 1H), 7.20–7.34 (m, 16H), 7.49 (d, J=7.7 Hz, 1H); $^{13}$C NMR (125.8 MHz, CDCl$_3$) δ 22.9, 25.8, 26.2, 28.2, 32.1, 32.2, 47.9, 48.4, 48.5, 48.7, 62.5, 62.6, 70.0, 70.2, 72.5, 74.5, 74.7, 74.7, 74.8, 75.0, 75.7, 75.8, 78.9, 79.5, 82.1, 82.2, 84.3, 84.5, 103.5, 103.5, 111.1, 111.2, 115.2, 115.4, 117.5, 117.7, 118.6, 119.3, 119.3, 122.0, 122.0, 122.0, 122.1, 127.6, 27.6, 27.7, 127.7, 127.9, 127.9, 127.9, 128.0, 128.1, 128.1, 128.2, 128.3, 128.3, 128.4, 128.4, 128.4, 128.5, 136.2, 136.2, 137.5, 137.9, 138.2, 138.3, 138.3, 138.4, 156.4, 156.7, 157.0, 157.3; high resolution mass spectrum (FAB, m-nitrobenzyl alcohol) m/z 775.3543 [(M+H)+; calcd for $C_{44}H_{50}O_7 N_2F_3$: 782.3931).

EXAMPLE 10

Preparation of Ester Compounds

In order to distinguish these compounds from those previously described, each compound number is preceeded by "-II". The chemical structures and the synthesis schemes for the compounds of Example 10 are presented in FIG. 2.

A. 1,2,4,6-Tetra-O-acetyl-β-D-glucopyranoside (II-4)

A solution of 3-deoxy-diacetone-D-glucose I-3 in 60% aqueous acetic acid (200 ml) was heated at 90° C. for 1 h, evaporated and azeotroped with dry benzene (4×20 ml). The residue was taken up in dry pyridine (250 ml), acetic anhydride (107 ml, 1.13 mol), DMAP (2 mol %, 275 mg) was added, and the solution was stirred at room temperature for 30 minutes. The mixture was evaporated, diluted with water (40 ml) and extracted with methylene chloride (3×40 ml). The combined extracts were washed with brine (40 ml), dried over sodium sulphate and evaporated. The residue was recrystallised from ether to afford the pure β-anomer as a fine white powder (11.3 g). The supernatent was evaporated and purified by flash chromatography eluting with 45% ethyl acetate in hexane to give a mixture of α- and β-anomers II-4 as a colorless gum (23.0 g, total yield 91.7%). β-Anomer II-4: m.p. 127–128° (ether) (lit. 129–130°); $[\alpha]D^{25}$–17.14° (c 1.05, CH$_3$OH); IR (CHCl$_3$) 3010 (m), 2940 (w), 2870 (w), 1745 (s), 1510 (w), 1365 (m), 1230 (s), 1210 (s), 1030 (s) cm$^{-1}$; $^1$H NMR (500 MHz, CDCl$_3$) δ 5.67 (d, J=7.9 Hz, 1H), 4.89–4.81 (m, 2H), 4.21 (dd, J=5.1, 12.3 Hz, 1H), 4.12 (dd, J=2.5, 12.2 Hz, 1H), 3.81–3.79 (m, 1H), 2.60 (ddd, J=5.0, 5.0, 12.3 Hz, 1H), 2.10 (s, 3H), 2.06 (s, 3H), 2.03 (s, 3H), 2.02 (s, 3H), 1.64 (dd, J=11.0, 23.2 Hz, 1H); $^{13}$C NMR (62.9 M Hz, CDCl$_3$) δ 170.69, 169.43, 169.31, 169.19, 93.06, 75.68, 67.33, 65.00, 62.07, 32.69, 20.92, 20.77; high resolution mass spectrum (Cl) m/z 367.0773 [(M+Cl+); calcd for $C_{14}H_{20}O_9Cl$: 367.0796].

Anal. calcd for $C_{14}H_{20}O_9$: C, 50.60; H, 6.07; found: C, 50.65; H, 6.16.

B. 2-(1H-Indol-3-yl)ethyl 2,4,6-Tri-O-acetyl-3-deoxy-β-D-glucopyranoside (II-5)

Hydrogen bromide (30% in acetic acid) was added dropwise to a solution of the tetraacetate II-4 (9.97 g, 30.0 mmol) in methylene chloride at 0° C. Stirring was continued at room temperature for 3 h, the mixture was poured into saturated aqueous sodium bicarbonate (500 ml) and extracted with ether (3×100 ml). The combined extracts were washed with saturated aqueous sodium bicarbonate (200 ml) and brine (200 ml), dried over sodium sulphate and evaporated. The pale yellow oil was azeotroped with benzene (4×20 ml) and dried under vacuum. A solution of the crude bromide in benzene (200 ml) was introduced into a flask containing activated powdered 4 Angstrom molecular sieves (10 g) and tryptophol (4.84 g, 30.0 mmol). Hexane (50 ml) and silver oxide (21 g, 90 mmol) were added, and the mixture was stirred vigorously in the dark for 18 h. The solution was filtered through celite, evaporated, and purified by flash chromatography eluting with 10% ether in methylene chloride to afford the triacetate II-5 as a pale pinkish oil.(8.37 g, 64.4%): $[\alpha]D^{25}$+22.04° (c 1.08, CHCl$_3$); IR (CHCl$_3$) cm$^{-1}$ 3020 (w), 2965 (w), 1745 (s), 1370 (m), 1230 (s), 1220 (s), 1205 (s), 1050 (s), 1035 (m), 740 (m) cm$^{-1}$; $^1$H NMR (500 MHz, CDCl$_3$) δ 8.06 (br s, 1H), 7.57 (d, J=16.9 Hz, 1H), 7.32 (d, J=17.8 Hz, 1H), 7.16 (ddd, J=1.0, 8.8 Hz, 1H), 7.09 (ddm, J=8, 8 Hz, 1H), 7.02 (d, J=2.2, 1H), 4.84–4.77 (m, 1H), 4.49 (d, J=7.5 Hz, 1H), 3.84–3.77 (m, 3H), 3.77 (dd, J=7.3, 16.9 Hz, 1H), 3.69–3.65 (m, 1H), 3.04 (t, J=7.1 Hz, 2H), 2.52 (ddd, J=5.1, 5.1, 12.3 Hz, 1H), 2.04 (s, 1H), 2.02 (s, 1H), 1.89 (s, 1H), 1.57 (dd, J=9.0, 22 Hz, 1H); $^{13}$C NMR (62.9 MHz, CDCl$_3$) δ 170.83, 169.52, 136.06, 127.43, 122.26, 121.82, 119.19, 118.64, 112.41, 111.05, 102.08, 74.82, 69.80, 68.39, 65.83, 62.66, 32.71, 25.53, 20.83, 20.75; high resolution mass spectrum (Cl) m/z 434.1782 [(M+H+); calcd for $C_{22}H_{28}O_8$: 434.1815].

C. 2-(1H-Indol-3-yl)ethyl 3-Deoxy-β-D-glucopyranoside (II-6)

Sodium methoxide (9.42 mmol) was added in aliquots to a stirred solution of the triacetate II-5 (1.17 g, 2.69 mmol) in methanol (50 ml) at 0° C., and the solution stirred at room temperature for 15 h. Amberlyst® 15 ion-exchange resin was added to pH 7, and the mixture was filtered, evaporated and purified by flash chromatography eluting with 15% methanol in methylene chloride to afford the title compound II-6 as a colorless oil (752 mg, 90.9%): [α]D$^{25}$ +76.19° (c1.05, CH$_3$OH); IR (CHCl$_3$) 3600–3200 (br), 2900 (s) cm$^{-1}$; $^1$H NMR (500 MHz, CDCl$_3$) δ 7.55 (d, J=8.8 Hz, 1H), 7.30 (d, J=9 Hz, 1H), 7.10–6.96 (m, 3H), 4.27 (d, J=7.6 Hz, 1H), 4.18–4.13 (m, 1H), 3.85–3.80 (m, 2H), 3.64 (dd, J=5.9, 11.8 Hz, 1H), 3.53–3.48 (m, 1H), 3.42–3.37 (m, 1H), 3.34–3.29 (m, 1H), 3.25–3.21 (m, 1H), 3.09–3.03 (m, 2H), 2.28 (ddd, J=4.9, 4.9, 21.1 Hz, 1H), 1.47 (dd, J=11.5, 23.4 Hz, 1H); $^{13}$C NMR (62.9 MHz, CDCl$_3$) δ 137.98, 128.87, 123.63, 122.21, 119.5, 119.28, 112.55, 112.16, 106.49, 81.68, 71.11, 69.38, 66.14, 62.79, 40.56, 26.78; high resolution mass spectrum (Cl) m/z [(M+H$^+$]; calcd for C$_{16}$H$_{21}$O$_5$N:].

D. 2-(1H-Indol-3-yl)ethyl 6-(p-Toluenesulphonyl)-2,4-di-O-(tert-butyldimethyl)silyl-3-deoxy-β-D-glucopyranoside (II-11)

p-Toluenesulphonyl chloride (0.559 mmol, 106 mg) and DMAP (10 mg) were added to a stirred solution of triol II-6 (56 mg, 0.508 mmol) and triethylamine (4.06 mmol, 0.76 ml) in methylene chloride (10 ml) at 0° C. and the solution was stirred at room temperature for 30 min. More p-toluenesulphonyl chloride (5 mg) was added and the solution was stirred for a further 1 h, poured into saturated aqueous sodium bicarbonate (40 ml), extracted with methylene chloride (2×20 ml) and the combined extracts were washed with brine (20 ml), dried over sodium suphate and evaporated. The resulting yellow oil was dissolved in methylene chloride (12 ml) and 2,6-lutidine (0.36 ml, 3.05 mmol) was added, followed by dropwise addition of tributyldimethylsilyl triflate (2.03 mmol, 0.47 ml) at 0° C. The solution was stirred at room temperature for 16 h, diluted with saturated aqueous sodium bicarbonate (25 ml), extracted with methylene chloride (3×20 ml) and the combined organic extracts were washed with brine (50 ml), dried over sodium sulphate and evaporated. The residue was purified by flash chromatography eluting with 30% ethyl acetate in hexane to give the title compound II-11 as a colorless oil (201 mg, 57.4%): [α]D$^{25}$ +2.25° (c 0.71, CHCl$_3$); IR (CHCl$_3$) 2960 (s), 2950 (s), 2900 (s), 2860 (s), 1800 (w), 1605 (w), 1460 (s), 1365 (s), 1260 (s), 1100 (s), 980 (s) 920–890 (br), 840 (s), 695 (s), 550 (s) cm$^{-1}$; $^1$H NMR (500 MHz, CDCl$_3$) δ 8.01 (br s, 1H), 7.72 (d, J=8.3 Hz, 2H), 7.56 (d, J=7.8 Hz, 1H), 7.34 (d, J=8.1 Hz, 1H), 7.19–7.09 (m, 5H), 4.21 (dd, J=2.0, 10.3 Hz, 1H), 4.18 (d, J=7.6 Hz, 1H), 4.07–3.99 (m, 2H), 3.79–3.74 (m, 1H), 3.51–3.34 (m, 3H), 3.06–3.03 (m, 2H), 2.29 (s, 3H), 2.14–2.10 (m, 1H), 1.52 (app. q, J=11.4 Hz, 1H), 0.86 (s, 9H), 0.81 (s, 9H), 0.03 (s, 6H), 0.00 (s, 6H); $^{13}$C NMR (62.9 MHz, CDCl$_3$) δ 144.61, 136.10, 132.75, 129.67, 127.87, 127.52, 122.14, 121.79, 119.16, 118.56, 112.40, 111.08, 105.09, 77.26, 69.88, 69.29, 69.00, 65.7, 41.50, 25.71, 25.58, 21.42, 18.11, 17.72.

E. 2-(1H-Indol-3-yl)ethyl 6-Iodo-2,4-di-O-(tert-butyldimethyl)silyl-3-deoxy-β-D-glucopyranoside (II-12)

A solution of tosylate II-11 (147 mg, 0.213 mmol) and sodium iodide (4.26 mmol, 639 mg) in dry acetone (8.0 ml) was heated to reflux for 16 h, diluted with saturated aqueous sodium thiosulphate (15 ml) and extracted with methylene chloride (3×15 ml). The combined extracts were washed with brine (10 ml), dried over sodium sulphate and evaporated. The residue was purified by flash chromatography eluting with 10% ethyl acetate in hexane to give the title compound II-12 (r$_f$ 0.40) (91.3 mg, 66.3%) and starting material II-11 (r$_f$ 0.20) (3.71 mg, 25.2%). 2-(1H-Indol-3-yl)ethyl6-(p-Toluenesulphonyl)-2,4-di-O-(tert-butyldimethyl)silyl-3-deoxy-β-D-glucopyranoside II-12: [α]D$^{25}$−4.63° (c 0.67, CHCl$_3$); IR (CHCl$_3$) 3490 (w), 3010 (w), 2960 (m), 2930 (m), 2895 (w), 2860 (m), 1350 (w), 1090 (s), 835 (s) cm$^{-1}$; $^1$H NMR (500 MHz, CDCl$_3$) δ 7.93 (br s, 1H), 7.61 (d, J=6.8 Hz, 1H), 7.33 (d, J=8.1 Hz, 1H), 7.18–7.15 (m, 1H), 7.11–7.08 (m, 2H), 4.28 (d, J=7.4 Hz, 1H), 4.19 (dt, J=6.4, 9.3 Hz), 3.84 (dt, J=6.4, 9.3 Hz, 1H), 3.53–3.39 (m, 3H), 3.18–3.07 (m, 3H), 2.15–2.10 (m, 1H), 1.57 (app. q, J=11.3 Hz, 1H), 0.87 (s, 9H), 0.86 (s, 9H), 0.07 (s, 6H), 0.06 (s, 6H); $^{13}$C NMR (62.9 MHz, CDCl$_3$) δ 136.11, 127.56, 122.06, 121.87, 119.23, 118.82, 112.58, 111.03, 105.35, 78.82, 70.00, 69.92, 69.50, 41.50, 25.82, 25.76, 25.70, 18.18, 17.83, 6.78, −4.08, −4.43, −4.63, −4.90.

F. 2-(1H-Indol-3-yl)ethyl 6-(Trimethyl)acetyl-2,4-di-O-(tert-butyldimethyl)silyl-3-deoxy-β-D-glucopyranoside (II-13)

Pivaloyl chloride (18.6 mmol, 2.31 ml) was added dropwise at 0° C. to a solution of the triol II-6 (5.18 g, 16.9 mmol) and DMAP (20 mg) in methylene chloride (150 ml) and triethylamine (135 mmol, 25.6 ml). The solution was stirred for 20 minutes at room temperature, an extra 0.32 ml (0.15 mmol) of pivaloyl chloride was added, and stirring was continued for 15 minutes. The solution was poured into ice-cold 1N HCl (200 ml), extracted with methylene chloride (3×50 ml) and the extracts were washed with saturated aqueous sodium bicarbonate (150 ml) and back-extracted with methylene choride (50 ml). The combined organic extracts were washed with brine (100 ml), dried (sodium sulphate) and evaporated. The resulting yellow oil was dissolved in methylene chloride and 2,6-lutidine (12.0 ml, 135 mmol) was added, followed by tributyldimethylsilyl triflate (50.7 mmol, 11.6 ml) added dropwise at 0° C. The solution was stirred at room temperature for 15 h, diluted with saturated aqueous sodium bicarbonate (100 ml), extracted with methylene chloride (3×50 ml) and the combined organic extracts were washed with brine (100 ml), dried over sodium sulphate and evaporated. The residue was purified by flash chromatography eluting with 15% ethyl acetate in hexane to give the title compound II-13 as a colorless oil (8.23 g, 78.7%): [α]D$^{25}$−1.31° (c 3.29, CHCl$_3$); IR (CHCl$_3$) 3480 (m), 3020 (m), 2960 (s), 2920 (s), 2890 (m), 2860 (s), 1730 (s), 1470 (m), 1420 (m), 1390 (m), 1250 (s), 1230 (s), 1155 (s), 1080 (s), 1045 (s), 920 (m), 835 (s), 780–725 (s), 660 (s) cm$^{-1}$; $^1$H NMR (500 MHz, CDCl$_3$) δ 7.97 (br s, 1H), 7.56 (d, J=7.8, 1H), 7.33 (d, J=8.1 Hz, 1H), 7.16 (dd, J=7, 9 Hz, 1H), 7.09 (dd, J=7, 8 Hz, 1H), 7.04 (dd, J=1.1, 1.1 Hz, 1H), 4.38 (d, J=11.6, 1H), 4.23 (d, J=7.4 Hz, 1H), 4.13–4.03 (m, 2H), 3.79 (m, 1H), 3.57–3.41 (m, 3H), 3.09 (dd, J=7.2, 7.3 Hz, 1H), 2.14 (dt, J=4.9, 12.4 Hz, 1H), 1.56 (dd, J=11.4, 23.8 Hz, 1H), 1.22 (s, 9H), 0.89 (s, 9H), 0.86 (s, 9H), 0.08 (s, 3H), 0.08 (s. 3H), 0.06 (s, 3H), 0.05 (s, 3H); $^{13}$C NMR (62.9 MHz, CDCl$_3$) δ 178.33, 136.12, 127.52, 121.98, 118.64, 112.49, 111.02, 105.23, 77.73, 69.83, 69.22, 66.58, 63.65, 41.78, 38.76, 27.16, 27.01, 25.74, 25.65, 18.16, 17.83, −3.60, −4.16, −4.45, −4.95; high resolution mass spectrum (+ve FAB) m/z 619.3705 (M$^+$; calcd for C$_{33}$H$_{37}$O$_6$NSi$_2$: 619.3724).

G. 2-(1H-Indol-3-yl)ethyl 2,4-Di-O-(tert-butyldimethyl)silyl-3-deoxy-β-D-glucopyranoside (II-14)

Sodium methoxide (6.0 mmol, 1.32 ml) was added in aliquots with stirring to pivaloate II-13 (740 mg, 1.20 mmol) in methanol (50 ml) and stirring was continued for 15 h. The solution was neutralised with Amberlyst® 15 ion-exchange resin, filtered and evaporated. The residue was purified by flash chromatography eluting with 30% ethyl acetate in hexane to afford the title compound II-14 as a colorless oil (468 mg, 73.2%): [α]D$^{25}$ +15.67° (c 5.68, CHCl$_3$); IR (CHCl$_3$) 3480 (m), 3000 (s), 2960 (s), 2925 (s),m 2880 (s), 2845 (s), 1710 (s), 1415 (m), 1360 (s), 1250 (s), 1220 (s), 1085 (s), 1030 (s), 1000 (m), 905 (m), 875 (s), 830 (s), 520

(m) cm$^{-1}$; $^1$H NMR (500 MHz, CDCl$_3$) δ 7.97 (br s, 1H), 7.57 (d, J=7.8 Hz, 1H), 7.33 (d, J=7.8 Hz, 1H), 7.17 (ddd, J=1.1, 7.7, 7.5), 7.10 (ddd, J=0.9, 8, 8 Hz), 7.03 (s, 1H), 4.28 (d, J=7.4 Hz, 1H), 4.10 (dd, J=8.5, 16.3 Hz, 1H), 3.83–3.77 (m, 2H), 3.63–3.56 (m, 2H), 3.50–3.45 (m, 1H), 3.28–3.24 (m, 1H), 3.09 (t, J=7 Hz, 2H), 2.26–2.22 (m, 1H), 1.58 (dd, J=11.3, 22.1 Hz, 1H), 0.88 (s, 9H), 0.84 (s, 9H), 0.09 (s, 6H), 0.08 (s, 6H); $^{13}$C NMR (62.9 MHz, CDCl$_3$) δ 136.14, 127.45, 121.96, 119.27, 118.64, 112.35, 111.09, 105.35, 79.65, 70.16, 69.39, 66.09, 62.42, 41.62, 25.75, 25.67, 18.17, 17.84, −4.28, −4.46, −4.87, −5.01; high resolution mass spectrum (Cl) m/z 535.3172 [(M+H$^+$); calcd for C$_{28}$H$_{49}$O$_5$NSi$_2$: 535.3149].

H. 2-(1H-Indol-3-yl)ethyl 2,4-Di-O-(tert-butyldimethyl)silyl-3-deoxy-O-(6-azidohexyl)-β-D-glucopyranoside (II-15a)

Triflic anhydride (2.15 mmol, 0.36 ml) was added dropwise at −78° C. to a solution of the alcohol II-14 (764 mg, 1.43 mmol) and 2,2-di-tert-butyl-4-methylpyridine (2.57 mmol, 528 mg) in methylene chloride (45 ml). The solution was stirred for 20 minutes, warmed to room temperature for 20 minutes, poured into saturated aqueous sodium bicarbonate (80 ml) and extracted with methylene chloride (2×40 ml). The extracts were combined, washed with brine (40 ml), dried over sodium sulphate, evaporated and dried under vacuum. Sodium hexamethyldisilylazide (0.6 M in toluene, 1.86 mmol, 3.10 ml) was added dropwise to a solution of 6-azidohexanol (494 mg, 3.45 mmol) in methylene chloride (40 ml) at 0° C. The colorless triflate (purified by thin layer chromatography) was dissolved in methylene chloride and then added to the above solution at 0° C. via cannula. Stirring was continued at room temperature for 38 h, the solution diluted with saturated aqueous sodium bicarbonate (50 ml) and extracted with methylene chloride (3×25 ml). The combined organic extracts were washed with brine (40 ml), dried over sodium sulphate and evaporated. Purification by flash chromatography (eluting with methylene chloride) furnished the title compound II-15a as a colorless viscous oil (257 mg, 27.3%): [α]D$^{25}$ +10.05° (c 2.13, CHCl$_3$); IR (CHCl$_3$) 3480 (w), 3000 (w), 2950 (m), 2930 (m), 2855 (m), 2090 (m), 1360 (m), 1250 (w), 1080 (s), 830 (s) cm$^{-1}$; $^1$H NMR (500 MHz, CDCl$_3$) δ 8.00 (br s, 1H), 7.58 (d, J=7.7 Hz, 1H), 7.33 (d, J=8.2 Hz, 1H), 7.16 (dd, J=7.1, 7.1, 1H), 7.09 (dd, J=7.0, 7.0 Hz, 1H), 7.02 (s, 1H), 4.23 (d, J=6.4 Hz, 1H), 4.15–4.09 (m, 1H), 3.80–3.75 (m, 1H), 3.66 (dd, J=1.9, 10.8 Hz, 1H), 3.58–3.41(m, 4H), 3.35–3.31 (m, 1H), 3.14 (t, J=7.0 Hz, 2H), 3.09 (t, J=7.5 Hz, 2H), 2.17–2.12 (m, 1H), 1.60–1.45 (m, 5H), 1.35–1.24 (m, 4H)), 0.87 (s, 9H), 0.86 (s, 9H), 0.08 (s, 3H), 0.07 (s, 3H), 0.06 (s, 3H), 0.04 (s, 3H); $^{13}$C NMR (62.9 MHz, CDCl$_3$) δ 136.11, 127.54, 121.96, 121.84, 119.17, 117.70, 112.52, 111.03, 105.35, 79.65, 51.31, 41.83, 29.50, 28.67, 26.51, 25.77, 25.69, 18.19, 17.86, −4.19, −4.43, −4.90, −4.96; high resolution mass spectrum (+ve FAB) m/z 661.4213 [(M+H$^+$); calcd for C$_{34}$H$_{61}$N$_4$O$_6$Si$_2$: 661.4180].

I. 2-(1H-Indol-3-yl)ethyl 2,4-Di-O-(tert-butyldimethyl)silyl-3-deoxy-O-(5-azidopentyl)-β-D-glucopyranoside (II-15b)

The same procedure as detailed above, using 5-azido-1-pentanol (2.4 eq., 4.08 mmol, 461 mg) furnished the title compound II-15b as a colorless oil (284 mg, 25.9%): [α]D$^{25}$ +7.31° (c 1.67, CHCl$_3$); IR (CHCl$_3$) 3460 (m), 3000 (m), 2940 (s), 2920 (s), 2850 (s), 2080 (s), 1450 (w), 1250 (m), 1110 (s), 1080 (s), 830 (s) cm$^{-1}$; $^1$H NMR (500 MHz, CDCl$_3$) δ 8.00 (br s, 1H), 7.57 (d, J=7.7 Hz, 1H), 7.33 (d, J=8.2 Hz, 1H), 7.17 (dt, J=8.1, 1, 1H), 7.09 (t, J=7.0 Hz, 1H), 7.03 (d, J=2.2, 1H), 4.23 (d, J=7.4 Hz, 1H), 4.11 (app. dd, J=8.5, 16.6 Hz, 1H), 3.77 (app. dd, J=8.6, 16.8 Hz, 1H), 3.58–3.43 (m, 5H), 3.34–3.31 (m, 1H), 3.12–3.07 (m, 4H), 2.17–2.12 (m, 2H), 1.58–1.48 (m, 5H), 1.38–1.33 (m, 2H)), 0.88 (s, 9H), 0.86 (s, 9H), 0.08 (s, 3H), 0.07 (s, 3H), 0.05 (s, 3H), 0.04 (s, 3H); $^{13}$C NMR (62.9 MHz, CDCl$_3$) δ 136.12, 127.50, 121.99, 119.11, 118.64, 112.39, 111.055, 105.35, 79.62, 71.33, 70.13, 69.99, 69.30, 66.10, 51.21, 41.80, 29.15, 28.58, 25.74, 25.67, 23.32, 18.16, 17.83, −4.20, −4.45, −4.92, −4.98; high resolution mass spectrum (+ve Cl) m/z 646.3887 (M$^+$; calcd for C$_{33}$H$_{58}$N$_4$O$_5$Si: 646.3946).

J. 2-(1H-Indol-3-yl)ethyl 3-Deoxy-O-(6-azidohexyl)-β-D-glucopyranoside (II-16a)

Tetrabutylammoniumflouride (1.0 M in THF (1.74 mmol, 1.74 ml) was added to a solution of the azide II-15a (230 mg, 0.348 mmol) in THF (10 ml) and stirred for 1 h. The solution was evaporated and the residue was purified by flash chromatography eluting with 10% methanol in methylene chloride to afford the title compound II-16a as a colorless oil (150 mg, 100%): [α]D$^{25}$ +38.24° (c 1.53, CHCl$_3$); IR (CHCl$_3$) 3600 (w), 3470 (m), 3000 (w), 2930 (m), 2860 (m), 2090 (s), 1200 (m), 1080 (s), 1060 (s), 710 (s), 655 (s) cm$^{-1}$; $^1$H NMR (500 MHz, CDCl$_3$) δ 8.08 (br s, 1H), 7.60 (d, J=7.8 Hz, 1H), 7.34 (d, J=8.1 Hz, 1H), 7.17 (dd, J=7.7 Hz, 1H), 7.10 (dd, J=7.7 Hz, 1H), 7.03 (s, 1H), 4.22–4.16 (m, 2H), 3.85–3.38 (m, 10H), 3.25–2.99 (m, 4H), 2.35–2.27 (m, 1H), 2.14 (br s, 1H), 1.72–1.24 (m, 9H); $^{13}$C NMR (62.9 MHz, CDCl$_3$) δ 136.2, 122.12, 121.90, 119.43, 118.70, 111.25, 105.14, 76.06, 72.78, 71.85, 70.42, 69.17, 68.29, 51.32, 37.28, 29.33, 28.72, 26.46, 25.74, 25.61; high resolution mass spectrum (+ve FAB) m/z 432.2411 (M+; calcd for C$_{22}$H$_{32}$N$_4$O$_5$: 432.2373).

K. 2-(1H-Indol-3-yl)ethyl 3-Deoxy-O-(5-azidopentyl)-β-D-glucopyranoside (II-16b)

The same procedure as detailed above afforded the title compound II-16b as a colorless oil (173 mg, 100%): [α]D$^{25}$ +31.01° (c 0.79, CHCl$_3$); IR (CHCl$_3$) 3480 (m), 3005 (w), 2950 (m), 2880 (m), 2100 (s), 1455 (w), 1280 (w), 1090 (w), 1070 (s), 1060 (s), 1020 (w), 1010 (w) cm$^{-1}$; $^1$H NMR (500 MHz, CDCl$_3$) δ 8.02 (br s, 1H), 7.61 (d, J=7 Hz, 1H), 7.33 (dd, J=0.7, 8.0 Hz, 1H), 7.18 (app. t, J=8 Hz, 1H), 7.11 (app. t, J=8 Hz, 1H), 7.03 (d, J=2.3, 1H), 4.22–4.18 (m, 2H), 3.75–3.65 (m, 3H), 3.61 (dd, J=7.2, 9.6 Hz, 1H), 3.52–3.38 (m, 4H), 3.23 (t, J=6.9 Hz, 2H); 3.13–3.00 (m, 4H), 2.35–2.31 (m, 1H), 2.11 (br s, 1H), 1.75–1.68 (m, 1H), 1.61–1.35 (m, 7H); $^{13}$C NMR (62.9 MHz, CDCl$_3$) δ 1136.10, 127.45, 122.03, 121.84, 119.16, 118.52, 112.43, 111.23, 104.95, 76.53, 72.15, 71.54, 70.16, 68.27, 68.15, 52.83, 51.15, 37.37, 28.89, 28.45, 25.60, 25.19, 23.15, 19.74, 13.39; high resolution mass spectrum (+ve Cl) m/z 436.2537 [(M+NH4$^+$); calcd for C$_{21}$H$_{34}$N$_5$O$_5$: 436.2560].

L. 2-(1H-Indol-3-yl)ethyl 2,4-Di-O-(2,2-dimethyl-3-phenylpropanoyl)-3-deoxy-O-(6-azidohexyl)-β-D-glucopyranoside (II-17a) and 2-(1H-Indol-3-yl)ethyl 2-O-(2,2-Dimethyl-3-phenylpropanoyl)-3-deoxy-O-(6-azidohexyl)-β-D-glucopyranoside (II-18a)

2,2-Dimethyl-4-aminopyridine (40 mol %, 11 mg) was added to a vigorously stirred solution of diol II-16a (91.4 mg, 0.212 mmol), 2,2-dimethyl-3-phenylpropanoic acid (242 mg, 1.27 mmol) and dicyclohexylcarbodiimide (703 mg, 3.39 mmol) in chloroform (5 ml) and the mixture was refluxed for 40 h. The cooled solution was evaporated, taken up in ether, filtered and evaporated again. The residue was purified by flash chromatography eluting with 25% ethyl acetate in hexane to afford an impure component (RF 0.28). The gradient was increased to 40% ethyl acetate in hexane affording an impure component (RF 0.23). The higherrunning compound was recolumned in 50% methylene chloride in hexane increasing to 10% ether in methylene chloride to afford the pure bis-ester II-17a as a colorless oil (97.2 mg, 61.1%). The lower-running compound was recolumned in 10% ether in methylene chloride to give the pure mono-ester II-18a as a colorless oil (39.5 mg, 31.3%).

2-(1H-Indol-3-yl)ethyl 2,4-Di-O-(2,2-dimethyl-3-phenylpropanoyl)-3-deoxy-O-(6-azidohexyl)-β-D-glucopyranoside (II-17a) (bis-ester): $[\alpha]D^{25}$ +36.18° (c 0.34, CHCl$_3$); IR (CHCl$_3$) 3480 (w), 3020 (w), 2935 (m), 2860 (m), 1730 (s), 1725 (s), 1455 (w), 1120 (s), 1005 (w), 690 (m) cm$^{-1}$; $^1$H NMR (500 MHz, CDCl$_3$) d7.84 (br s, 1H), 7.53 (d, J=7.8 Hz, 1H), 7.32 (d, J=8.0 Hz, 1H), 7.26–7.03 (m, 12H), 6.99 (s, 1H), 4.83–4.75 (m, 2H), 4.54 (d, J=7.8 Hz, 1H), 4.09 (ddm, J=8, 17 Hz, 1H), 3.79 (ddm, J=8.16 Hz, 1H), 3.67–3.64 (m, 1H), 3.54 (d, J=11.2 Hz, 1H), 3.48–3.35 (m, 3H), 3.18 (br s, 2H), 3.05–3.02 (m, 2H), 2.88 (d, J=13.4 Hz, 1H), 2.74 (d, J=13.4 Hz, 1H), 2.53–2.47 (m, 2H), 1.80 (t, J=8.4 Hz, 2H), 1.52–11.4(m, 9H), 1.21 (s, 6H), 1.14 (s, 3H), 1.08 (s, 3H); $^{13}$C NMR (62.9 MHz, CDCl$_3$) δ 176.13, 175.99, 141.93, 137.67, 136.25, 130.23, 128.43, 128.22, 127.95, 127.46, 126.43, 125.93, 122.29, 121.70, 119.02, 118.57, 111.78, 111.21, 102.34, 77.20, 71.75, 70.00, 69.89. 68.73, 66.33, 45.94, 43.48, 42.43, 42.36, 33.88, 33.35, 31.42, 29.68, 29.59, 29.33, 26.52, 25.70, 25.36, 25.18, 24.92, 24.31; high resolution mass spectrum (+ve FAB) m/z 753.4263 [(M+H$^+$); calcd for C$_{44}$H$_{57}$N$_4$O$_7$: 753.4227].

2-(1H-Indol-3-yl)ethyl 2-O-(2,2-Dimethyl-3-phenylpropanoyl)-3-deoxy-O-(6-azidohexyl)-β-D-glucopyranoside (II-18a) (mono-ester): $[\alpha]D^{25}$ +31.15° (c 1.11, CHCl$_3$); IR (CHCl$_3$) 3680 (w), 3620 (w), 3480 (s), 3020 (s), 2975 (m), 2935 (m), 2875 (m), 2090 (m), 1725 (m), 1520 (m), 1470 (m), 1420 (m), 1220 (s), 1070 (m), 925 (m), 760 (s), 660 (s), 615 (m) cm$^{-1}$; $^1$H NMR (500 MHz, CDCl$_3$) d7.87 (br s, 1H), 7.53 (d, J=8.0 Hz, 1H), 7.31 (d, J=8.1 Hz, 1H), 7.23–7.06 (m, 7H), 6.98 (s, 1H), 4.77–4.72 (m, 1H), 4.50 (d, J=7.7 Hz, 1H), 4.07 (dd, J=8.2, 16.0 Hz, 1H), 3.78–3.70 (m, 2H), 3.61 (app. t, J=7.6 Hz, 1H), 3.51–3.43 (m, 2H), 3.23(t, J=6.9 Hz, 1H), 3.01 (dt, J=3, 7 Hz, 2H), 2.84 (d, J=13.3, 1H), 2.76 (d, J=13.3 Hz, 1H), 2.42 (app. dt, J=12.2, 5.0 Hz, 1H), 1.58–1.47 (m, 5H), 1.36–1.34 (m, 4H), 1.12 (s, 3H); $^{13}$C NMR (62.9 MHz, CDCl$_3$) δ 176.15, 137.73, 136.07, 130.22, 127.96, 127.41, 126.43, 122.11, 121.88, 119.22, 118.60, 112.29, 111.06, 102.26, 76.02, 72.70, 69.71, 69.18, 68.71, 51.30, 45.87, 43.47, 35.80, 29.31, 28.69, 26.44, 25.68, 25.59, 25.13, 24.49; high resolution mass spectrum (+ve FAB) m/z 592.3228 [(M+H$^+$); calcd for C$_{33}$H$_{44}$N$_4$O$_6$: 592.3261].

M. 2-(1H-Indol-3-yl)ethyl 2-O-(2,2-Dimethyl-3-phenylpropanoyl)-4-O-(2,2-dimethyl-3-phenylbutanoyl)-3-deoxy-O-(6-azidohexyl)-β-D-glucopyranoside (II-19a)

2,2-Dimethyl-4-aminopyridine (2 mg) was added to a vigorously stirred solution of mono-ester II-18a (25.6 mg, 0.0430 mmol), 2,2-dimethyl-4-phenylbutanoic acid (49.5 mg, 0.258 mmol) and dicyclohexylcarbodiimide (88.7 mg, 0.430 mmol) in methylene chloride (2 ml) and the mixture refluxed for 18 h. The cooled solution was evaporated, taken up in ether, filtered and evaporated. The residue was purified by flash chromatography eluting with 20% ethyl acetate in hexane to furnish the title compound II-19a as a colorless oil (29.0 mg, 87.7%): $[\alpha]D^{25}$ +8.33° (c 0.60, CHCl$_3$); IR (CHCl$_3$) 3480 (w), 3020 (w), 2940 (m), 2860 (m), 2100 (m), 1735 (s), 1455 (m), 1120 (s), 895 (w) cm$^{-1}$; $^1$H NMR (500 MHz, CDCl$_3$) d7.94 (br s, 1H), 7.54 (d, J=7.9 Hz, 1H), 7.31 (d, J=8.1 Hz, 1H), 7.28–7.07 (m, 12H), 6.99 (d, J=1.2 Hz, 1H), 4.86–4.78 (m, 2H), 4.55 (d, J=7.8 Hz, 1H), 4.13 (ddm, J=8.5, 15.9 Hz, 1H), 3.80 (ddm, J=8.5, 16.4 Hz, 1H), 3.69–3.65 (m, 1H), 3.56 (dd, J=2.1, 11.0 Hz, 1H), 3.51–3.36 (m, 3H), 3.15 (t, J=7.0 Hz, 2H), 3.08–3.01 (m, 1H), 2.87 (d, J=13.3 Hz, 1H), 2.74 (d, J=13.3 Hz, 1H), 2.56–2.47 (m, 3H), 1.82 (t, J=8.8 Hz, 2H), 1.54–1.45 (m, 4H), 1.36–1.25 (m, 6H), 1.23 (s, 6H), 1.13 (s, 3H), 1.07 (s, 3H); $^{13}$C NMR (62.9 MHz, CDCl$_3$) δ 176.07, 175.90, 141.93, 137.69, 136.07, 130.23, 128.41, 128.20, 127.93, 127.43, 126.41, 125.92, 122.17, 121.87, 119.20, 118.61, 112.29, 111.06, 102.34, 77.17, 71.75, 70.03, 69.73, 68.77, 66.28, 51.30, 45.90, 43.44, 42.44, 42.33, 33.22, 31.41, 29.44, 28.68, 26.47, 25.63, 25.27, 25.16, 24.95, 24.28; high resolution mass spectrum (+ve FAB) m/z 767.4361 [(M+H$^+$); calcd for C$_{45}$H$_{59}$N$_4$O$_7$: 767.4384].

N. 2-(1H-Indol-3-yl)ethyl 2-O-(2,2-Dimethyl-3-phenylpropanoyl)-4-O-(2,2-dimethyl-3-phenylbutanoyl)-3-deoxy-O-(6-aminohexyl)-β-D-glucopyranoside (II-1a)

A solution of bis-ester II-19a (11.7 mg, 0.0152 mmol) and triphenylphosphine (9.97 mg, 0.0380 mmol) in THF (0.8 ml) and water (12 ml) was heated at 55° C. for 15 h. The cooled solution was evaporated and purified by flash chromatography eluting with methanol/methylene chloride/acetic acid (10:90:1) increasing the gradient to (30:70:1). Fractions containing the title compound were treated with solid sodium bicarbonate, filtered, evaporated, redissolved in methylene chloride, filtered and evaporated, to afford the title compound II-1a as a colorless oil (10.6 mg, 93.8%): $[\alpha]D^{25}$ +36.18° (c 0.34, CHCl$_3$); IR (CHCl$_3$) 3480 (w), 3020 (w), 2935(m), 2860 (m), 1730 (s), 1725(s), 1455(w), 1120 (s), 1005 (w), 690 (m) cm$^{-1}$; $^1$H NMR (500 MHz, CDCl$_3$) d8.84(br s, 1H), 7.53 (d, J=7.8 Hz, 1H), 7.32 (d, J=8.0 Hz, 1H), 7.26–7.03 (m, 12H), 6.99 (s, 1H), 4.83–4.75 (m, 2H), 4.54 (d, J=7.8 Hz, 1H), 4.09 (ddm, J=8, 17 Hz, 1H), 3.79 (ddm, J=8, 16 Hz, 1H), 3.67–3.64 (m, 1H), 3.54 (d, J=11.2 Hz, 1H), 3.48–3.35 (m, 3H), 3.18 (br s, 2H), 3.05–3.02 (m, 2H), 2.88 (d, J=13.4 Hz, 1H), 2.74 (d, J=13.4 Hz, 1H), 2.53–2.47 (m, 2H), 1.80 (t, J=8.4 Hz, 2H), 1.52–1.114 (m, 9H), 1.21 (s, 6H), 1.14 (s, 3H), 1.08 (s, 3H); $^{13}$C NMR (62.9 MHz, CDCl$_3$) δ176.13, 175.99, 141.93, 127.67, 136.25, 130.23, 128.43, 128.22, 127.95, 127.46, 126.43, 125.93, 122.29, 121.70, 119.02, 118.57, 111.78, 111.21, 102.34, 77.20, 71.75, 70.00, 69.89, 68.73, 66.33, 45.94, 43.48, 42.43, 42.36, 33.88, 33.35, 31.42, 29.68, 29.59, 29.33, 26.52, 25.70, 25.36, 25.18, 24.92, 24.31; high resolution mass spectrum (+ve FAB) m/z 741.4430 [(M+H$^+$); calcd for C$_{45}$H$_{61}$N$_2$O$_7$: 741.4478].

O. 2-(1H-Indol-3-yl)ethyl 2,4-Di-O-(2,2-dimethyl-3-phenylpropanoyl)-3-deoxy-O-(6-aminohexyl)-β-D-glucopyranoside (II-1c)

The same procedure as detailed above afforded the title compound II-1c as a colorless oil (27.5 mg, 81.6%): $[\alpha]D^{25}$ +2.86° (c 0.28, CHCl$_3$); IR (CHCl$_3$) 3680 (w), 3480 (w), 3025 (w), 3005 (w), 2965 (w), 2930 (m), 2860 (w)m 1730 (s), 1600 (w), 1450 (w), 1115 (s), 895 (w) cm$^{-1}$; $^1$H NMR (500 MHz, CDCl$_3$) δ 8.55 (br s, 1H), 7.51 (d, J=7.9 Hz, 1H), 7.32 (d, J=9.4 Hz, 1H), 7.28–7.03 (m, 12H), 6.99 (s, 1H), 4.81–4.76 (m, 1H), 4.74–4.69 (m, 1H), 4.51 (d, J=7.8 Hz, 1H), 4.09 (ddm, J=8, 14 Hz, 1H), 3.78 (ddm, J2 =8, 17 Hz, 1H), 3.62–3.58 (m, 1H), 3.38–3.33 (m, 3H), 3.06–3.00 (m, 2H), 2.88 (d, J=13.3 Hz, 1H), 2.81 (s, 2H), 2.75 (d, J=13.3 Hz, 1H), 2.47–2.42 (m, 1H), 2.3 (brs, 2H), 1.49–1.16 (m, 9H), 1.14 (s, 6H), 1.14 (s, 3H), 1.08 (s, 3H); $^{13}$C NMR (62.9 MHz, CDCl$_3$) δ 176.04, 175.92, 137.69, 137.43, 136.14, 130.22, 127.98, 127.43, 126.53, 126.41, 122.23, 121.73, 119.07, 118.55, 112.01, 111.14, 102.24, 77.12, 71.74, 69.91, 69.73, 68.74, 66.56, 45.98, 45.88, 43.45, 33.18, 29.56, 26.55, 25.85, 25.60, 25.28, 24.83, 24.31; high resolution mass spectrum (+ve FAB) m/z 727.4341 (M+H$^+$; calcd for C$_{44}$2H$_{59}$N$_2$O$_7$: 727.4322).

P. 2-(1H-Indol-3-yl)ethyl 2-O-(2,2-dimethyl-3-phenylpropanoyl)-3-deoxy-O-(5-azidopentyl)-β-D-glucopyranoside (II-14b)

2,2-Dimethyl-4-aminopyridine (40 mol %, 18 mg) was added to a vigorously stirred solution of diol II-16b (146 mg, 0.349 mmol), 2,2-dimethyl-3-phenylpropanoic acid (333 mg, 1.75 mmol) and dicyclohexylcarbodiimide (1.09 g, 5.24 mmol) in chloroform (10 ml) and the mixture refluxed for 18 h. The cooled solution was evaporated, taken up in ether, filtered and evaporated. The residue was purified by flash chromatography eluting with 40% ethyl acetate in hexane to afford the somewhat impure mono-ester (RF 0.20). The eluant was changed to 10% methanol/dichloromethane to afford recovered starting material (61.2 mg, 41.9%). The mono-ester was further purified by flash chromatography eluting with 10% ether/dichloromethane to give the title compound II-18b as a colorless oil (65.3 mg, 32.1%): $[\alpha]D^{25}$ +36.61° (c 1.21, CHCl$_3$); IR (CHCl$_3$) 3500 (m), 3010 (w), 2940 (m), 2880 (m), 2100 (s), 1460 (m), 1120 (s), 1070 (s) cm$^{-1}$; $^1$H NMR (500 MHz, CDCl$_3$) d7.92 (br s, 1H), 7.54 (d, J=7.9 Hz 1H), 7.32 (d, J=8.1 Hz, 1H), 7.26–7.07 (m, 7H), 7.08 (d, J=7, 1H), 4.79–4.74 (m, 1H), 4.52 (d, J=7.6 Hz, 1H), 4.10 (m, 1H), 3.80–3.71 (m, 3H), 3.62 (dd, J=7.3, 9.6 Hz, 1H), 3.54–3.45 (m, 3H), 3.24 (t, J=6.9 Hz, 2H), 3.12 (br s, 1H), 3.06–3.00 (m, 2H), 2.86 (d, J=13.4 Hz, 1H), 2.77 (d, J=13.4 Hz, 1H), 2.46–2.41 (m, 1H), 1.63–1.38 (m, 7H), 1.14 (s, 3H), 1.09 (s, 3H); $^{13}$C NMR (62.9 MHz, CDCl$_3$) δ 176.16, 137.67, 136.05, 130.17, 127.93, 127.37, 126.40, 122.12, 121.80, 119.13, 118.53, 112.12, 111.06, 102.20, 76.27, 72.43, 71.64, 69.70, 69.18, 68.30, 51.18, 45.83, 43.44, 35.82, 28.95, 28.51, 25.65, 25.10, 24.45, 23.20; high resolution mass spectrum (+ve Cl) m/z 578.3107 (M$^+$; calcd for C$_{32}$H$_{42}$N$_4$O$_6$: 578.3104).

Q. 2-(1H-Indol-3-yl)ethyl 2-O-(2,2-Dimethyl-3-phenylpropanoyl)-4-O-(2,2-dimethyl-3-phenylbutanoyl)-3-deoxy-O-(5-azidopentyl)-β-D-glucopyranoside (II-19b)

2,2-Dimethyl-4-aminopyridine (2 mg) was added to a vigorously stirred solution of mono-ester II-18b (34.8 mg, 0.0598 mmol), 2,2-dimethyl-4-phenylbutanoic acid (68.9 mg, 0.359 mmol) and dicyclohexylcarbodiimide (123 mg, 0.598 mmol) in methylene chloride (2.5 ml) and the mixture was refluxed for 20 h. The cooled solution was evaporated, taken up in ether, filtered and evaporated. The residue was purified by flash chromatography eluting with 20% ethyl acetate in hexane to furnish the title compound II-19b as a colorless oil (39.4 mg, 87.2%): $[\alpha]D^{25}$ +6.03° (c 0.58, CHCl$_3$); IR (CHCl$_3$) 33490 (w), 2940 (m), 2930 (m), 2100 (m), 1735 (s), 1730 (s), 1140 (s) cm$^{-1}$; $^1$H NMR (500 MHz, CDCl$_3$) d7.89 (br s, 1H), 7.53 (d, J=7.9 Hz, 1H), 7.31 (dd, J=0.5, 8.1 Hz, 1H), 7.27–7.06 (m, 12H), 7.00 (d, J=2.0 Hz, 1H), 4.84–4.78 (m, 2H), 4.53 (d, J=7.8 Hz, 1H), 4.12 (dt, J=6.7, 8.6 Hz, 1H), 3.80–3.76 (m, 1H), 3.54 (dd, J=2.0, 11.0 Hz), 3.49–3.35 (m, 3H), 3.12 (t, J=6.9 Hz, 2H), 3.07–3.00 (m, 1H), 2.85 (d, J=13.3 Hz, 1H), 2.73 (d, J=13.3 Hz, 1H), 2.55–2.48 (m, 2H), 1.81 (t, J=8.8 Hz, 2H), 1.54–1.44 (m, 7H), 1.36–1.29 (m, 2H), 1.22 (s, 6H), 1.12 (s, 3H), 1.06 (s, 3H); $^{13}$C NMR (62.9 MHz, CDCl$_3$) δ 176.06, 175.89, 141.90, 137.66, 136.06, 130.21, 128.40, 128.17, 127.90, 127.41, 126.39, 125.90, 122.16, 121.85, 119.17, 118.57, 112.25, 111.06, 102.32, 77.12, 71.56, 70.03, 69.71, 68.74, 66.24, 51.21, 45.89, 43.42, 42.39, 42.33, 33.29, 31.37, 29.07, 28.54, 25.63, 25.25, 25.12, 24.92, 24.27, 23.27; high resolution mass spectrum (+ve Cl) m/z 753.4261 [(M+H$^+$); calcd for C$_{44}$H$_{57}$N$_4$O$_7$: 753.4228].

R. 2-(1H-Indol-3-yl)ethyl 2-O-(2,2-Dimethyl-3-phenylpropanoyl)-4-O-(2,2-dimethyl-3-phenylbutanoyl)-3-deoxy-O-(5-aminopentyl)-β-D-glucopyranoside (II-1b)

A solution of bis-ester II-19b (26.7 mg, 0.0353 mmol) and triphenylphosphine (23.2 mg, 0.0833 mmol) in THF (1.5 ml) and water (20 ml) was heated at 55° C. for 15 h. The cooled solution was evaporated and purified by flash chromatography eluting with methanol/methylene chloride/acetic acid (10:90:1) increasing the gradient to (30:70:1). Fractions containing the title compound were treated with solid sodium bicarbonate, filtered, evaporated, redissolved in methylene chloride, refiltered and evaporated to afford the title compound II-1b as a colorless oil (18.7 mg, 72.5%): $[\alpha]D^{25}$ +25.00° (c 0.32, CHCl$_3$); IR (CHCl$_3$) 3480 (w), 3010 (s), 2920 (m), 2860 (w), 2390 (m), 1730 (m), 1520 (m), 1470 (m), 1420 (m), 1210 (s), 1120 (m), 920 (m), 840 (m), 750 (s), 660 (s), 615 (m) cm$^{-1}$; $^1$H NMR (500 MHz, CDCl$_3$) δ 9.13(br s, 1H), 7.52 (d, J=7.9 Hz, 1H), 7.32–7.11 (m, 12H), 7.05 (t, J=5.7 Hz, 1H), 6.98 9s, 1H), 4.83–4.75 (m, 2H), 4.68 (br s, 2H), 4.53 (d, J=7.8 Hz, 1H), 4.10–4.05 (m, 1H), 3.81–3.76 (m, 1H), 3.66–3.63 (m, 1H), 3.51 (dd, J=1.8, 11.1 Hz, 1H), 3.45–3.31 (m, 3H), 3.06–3.00 (m, 2H), 2.89 (d, J=13.3 Hz, 1H), 2.74 (d, J=13.3 Hz, 1H), 2.55–2.45 (m, 4H), 1.80 (t, J=8.8 Hz, 2H), 1.52–1.34 (m, 5H), 1.30–1.21 (m, 3H), 1.21 (s, 6H), 1.15 (s, 3H), 1.09 (s, 3H); $^{13}$C NMR (62.9 MHz, CDCl$_3$) δ 176.17, 175.99, 141.90, 137.67, 136.24, 130.23, 128.43, 128.21, 127.96, 126.45, 125.95, 122.31, 121.70, 119.01, 118.55, 11.82, 111.26, 102.28, 71.48, 69.83, 68.72, 66.27, 45.95, 43.51, 42.36, 33.32, 31.42, 29.70, 29.22, 25.61, 25.39, 25.17, 24.95, 24.32, 23.28; high resolution mass spectrum (–ve Cl) m/z 761.3902 [(M+Cl$^+$); calcd for C$_{44}$H$_{58}$N$_2$O$_7$Cl: 761.3932].

S. 2-(1H-Indol-3-yl)ethyl 2-O-(3-phenylpropanoyl)-3-deoxy-O-(6-azidohexyl)-β-D-glucopyranoside (II-23)

A solution of diol II-16a (143 mg, 0.331 mmol) in methylene chloride (10 ml) was added dropwise to a stirred solution of hydrocinnamic acid (0.331 mmol, 49.7 mg), dicyclohexylcarbodiimide (0.331 mmol, 68.2 mg) and 2,2'-dimethyl-4-aminopyridine (1 mg) in methylene chloride at 0° C. The solution was warmed to room temperature and stirred for 16 h, evaporated, taken up in ether, filtered and evaporated. The residue was purified by flash chromatography eluting with 45% ethyl acetate/hexane to give a higher component (C-4 monoester II-24) (Rf 0.25), mixed fractions and a lower component (C-2 monoester II-23) (Rf 0.23). The mixed fractions were combined and the process was repeated twice. This produced a pure sample of the lower, C-2 monoester II-23 as a colorless oil (35.0 mg, 18.7%): $[\alpha]D^{25}$ +25.00° (c 0.32, CHCl$_3$); IR (CHCl$_3$) 3480 (w), 3010 (s), 2920 (m), 2860 (w), 2390 (m), 1730 (m), 1520 (m), 1470 (m), 1420 (m), 1210 (s), 1120 (m), 920 (m), 840 (m), 750 (s), 660 (s), 615 (m) cm$^{-1}$; $^1$H NMR (500 MHz, CDCl$_3$) δ 9.13 (br s, 1H), 7.52 (d, J=7.9 Hz, 1H), 7.32–7.11 (m, 12H), 7.05 (t, J=5.7 Hz, 1H), 6.98(s, 1H), 4.83–4.75 (m, 2H), 4.68 (br s, 2H), 4.53 (d, J=7.8 Hz, 1H), 4.10–4.05 (m, 1H), 3.81–3.76 (m, 1H), 3.66–3.63 (m, 1H), 3.51 (dd, J=1.8, 11.1 Hz, 1H), 3.45–3.31 (m, 3H), 3.06–3.00 (m, 2H), 2.89 (d, J=13.3 Hz, 1H), 2.74 (d, J=13.3 Hz, 1H), 2.55–2.45 (m, 4H), 1.80 (t, J=8.8 Hz, 2H), 1.52–1.34 (m, 5H), 1.30–1.21 (m, 3H), 1.21 (s, 6H), 1.15 (s, 3H), 1.09 (s, 3H); $^{13}$C NMR (62.9 MHz, CDCl$_3$) δ 176.17, 175.99, 141.90, 137.67, 136.24, 130.23, 128.43, 128.21, 127.96, 126.45, 125.95, 122.31, 121.70, 119.01, 118.55, 11.82, 111.26, 102.28, 71.48, 69.83, 68.72, 66.27, 45.95, 43.51, 42.36, 33.32, 31.42, 29.70, 29.22, 25.61, 25.39, 25.17, 24.95, 24.32, 23.28; high resolution mass spectrum (–ve Cl) m/z 761.3902 [(M+Cl$^+$); calcd for C$_{44}$H$_{58}$N$_2$O$_7$Cl: 761.3932].

T. 2-(1H-Indol-3-yl)ethyl 2-O-(3-phenylpropanoyl)-4-O-(4-phenylbutanoyl)-3-deoxy-O-(6-azidohexyl)-β-D-glucopyranoside (II-25)

2,2-Dimethyl-4-aminopyridine (1 mg) was added to a vigorously stirred solution of mono-ester II-23 (13.8 mg, 0.0245 mmol), 4-phenylbutyriic acid (8.0 mg, 0.0490 mmol) and dicyclohexylcarbodiimide (20.2 mg, 0.0980 mmol) in methylene chloride (1.5 ml) and the mixture was stirred at room temperature for 20 h, evaporated, taken up in ether, refiltered and evaporated. The residue was purified by flash chromatography eluting with 25% ethyl acetate/hexane to furnish the title compound II-25 as a colorless oil (17.0 mg, 97.9%): $[\alpha]D^{25}$ +9.15° (c 0.59, $CHCl_3$); IR ($CHCl_3$) 3490 (m), 3020 (w), 2950 (m), 2870 (m), 2100 (s), 1745 (s), 1460 (m), 1160 (m), 1135 (m), 1080 (m) $cm^{-1}$; $^1H$ NMR (500 MHz, $CDCl_3$) δ 7.86 (br s, 1H), 7.56 (d, J=7.3 Hz, 1H), 7.33–7.07 (m, 13H), 6.99 (d, J=2.3 Hz, 1H), 4.82–4.77 (m, 2H), 4.46 (d, J=7.5 Hz, 1H), 4.14–4.10 (m, 1H), 3.76–3.72 (m, 1H), 3.62–3.58 (m, 1H), 3.54–3.50 (m, 1H), 3.47–3.35 (m, 3H), 3.17 (t, J=7.0 Hz, 2H), 3.03–3.00 (m, 2H), 2.92–2.83 (m, 3H), 2.63–2.57 (m, 3H), 2.49–2.41 (m, 3H), 2.27 (t, J=7.4 Hz, 2H), 2.27–2.15 (obs m, 1H), 1.95–1.87 (m, 3H), 1.57–1.24 (m, 11H); $^{13}C$ NMR (125 MHz, $CDCl_3$) δ 172.00, 171.44, 141.14, 140.44, 136.07, 128.47, 128.43, 128.29, 127.53, 126.26, 126.07, 122.17, 121.91, 119.26, 118.75, 112.71, 111.04, 101.94, 76.82, 71.69, 70.17, 69.61, 68.69, 66.44, 51.35, 35.63, 35.05, 33.59, 32.87, 30.74, 29.47, 28.73, 26.50, 26.45, 25.63, 25.58; high resolution mass spectrum (+ve FAB) m/z 710.3717 ($M^+$; calcd for $C_{41}H_{50}N_4O_7$: 710.3680).

U. 2-(1H-Indol-3-yl)ethyl 2-O-(3-phenylpropanoyl)-4-O-(4-phenylbutanoyl)-3-deoxy-O-(6-aminohexyl)-β-D-glucopyranoside (II-20)

A solution of bis-ester 25 (17.0 mg, 0.0239 mmol) and triphenylphosphine (15.6 mg, 0.0599 mmol) in THF (2.0 ml) and water (20 ml) was heated at 55° C. for 16 h. The cooled solution was evaporated and purified by flash chromatography eluting with methanol/methylene chloride/acetic acid (10:90:1) increasing the gradient to (30:70:1). Fractions containing the title compound were treated with solid sodium bicarbonate, filtered, evaporated, redissolved in methylene chloride, filtered and evaporated, to afford the title compound II-20 as a colorless oil (16.0 mg, 97.8%) $[\alpha]D^{25}$ +6.25° (c 0.24, $CHCl_3$); IR ($CHCl_3$) 3480 (w), 3020 (w), 2930 (s), 2860 (m), 1740 (s), 1450 (w), 1155 (m), 1140 (m), 690 (w) $cm^{-1}$; $^1H$ NMR (500 MHz, $CDCl_3$) δ 8.87 (br s, 1H), 7.55 (d, J=8.0 Hz, 1H), 7.30–7.04 (m, 13H), 6.98 (s, 1H), 4.82–4.73 (m, 2H), 5.0–4.7 (br s, 2H), 4.47 (d, J=7.4 Hz, 1H), 4.10–4.05 (m, 1H), 3.78–3.74 (m, 1H), 3.62–3.58 (m, 1H), 3.49 (dd, J=2.6, 11.1 Hz, 1H), 3.44–3.33 (m, 3H), 3.02 (t, J=7.3 Hz, 2H), 2.87 (t, J=7.8 Hz, 2H), 2.63–2.56 (m, 3H), 2.50 (t, J=8 Hz, 2H), 1.96–1.88 (m, 4H), 1.53–1.22 (m, 11H); $^{13}C$ NMR (125 MHz, $CDCl_3$) δ 172.03, 171.50, 141.11, 140.38, 136.20, 128.46, 128.43, 128.28, 127.53, 126.26, 126.07, 122.26, 121.72, 119.05, 118.68, 112.19, 111.13, 101.88, 71.71, 70.09, 69.69, 68.69, 66.41, 40.46, 35.69, 35.03, 33.56, 32.86, 30.77, 29.69, 29.59, 26.51, 26.43, 25.76, 25.61.

V. 2-(1H-Indol-3-yl)ethyl 2,4-Di-O-(3-phenylpropanoyl-3-deoxy-O-(6-azidohexyl)-β-D-glucopyranoside (II-22)

2,2'-dimethyl-4-aminopyridine (1 mg) was added to a stirred solution of diol II-16a (18.0 mg, 0.0417 mmol), hydrocinnamic acid (0.104 mmol, 15.7 mg) and dicyclohexylcarbodiimide (0.209 mmol, 42.9 mg) in methylene chloride (2.0 ml). The solution was stirred for 1 h, evaporated, taken up in ether, filtered and evaporated. The residue was purified by flash chromatography eluting with 30% ethyl acetate/hexane to give the title compound II-22 as a colorless oil (27.8 mg, 95.9%): $[\alpha]D^{25}$ +5.96° (c 0.94, $CHCl_3$); IR ($CHCl_3$) 3480 (m), 3010 (w), 2950 (m), 2860 (m), 2100 (s), 1745 (m), 1300 (w), 1290 (m), 1260 (w), 1160 (m), 1140 (m), 1080 (m), 690 (w) $cm^{-1}$; $^1H$ NMR (500 MHz, $CDCl_3$) δ 7.86 (br s, 1H), 7.57 (d, J=6.9 Hz, 1H), 7.34–7.02 (m, 13H), 6.99 (d, J=2.4 Hz, 1H), 4.81–4.75 (m, 2H), 4.44 (d, J=7.4 Hz, 1H), 4.14–4.09 (m, 1H), 3.80–3.70 (m, 1H), 3.59–3.55 (m, 1H), 3.50–3.31 (m, 4H), 3.18 (t, J=6.9 Hz, 2H), 3.01 (t, J=6.3 Hz, 2H), 2.91 (t, J=7.5 Hz, 2H), 2.85 (t, J=7.9 Hz, 2H), 2.63–2.37 (m, 5H), 1.57–1.24 (m, 9H); $^{13}C$ NMR (62.9 MHz, $CDCl_3$) δ 171.42, 140.09, 140.08, 128.48, 128.25, 128.20, 126.33, 126.23, 122.17, 121.84, 119.18, 118.70, 112.55, 111.02, 101.88, 76.67, 71.58, 70.02, 69.59, 68.63, 66.52, 51.29, 35.72, 35.59, 32.75, 30.79, 30.69, 29.42, 28.68, 26.45, 25.56; high resolution mass spectrum (−ve CI) m/z 731.3245 [(M+$Cl^+$; calcd for $C_{40}H_{48}N_4O_7Cl$: 731.3211].

W. 2-(1H-Indol-3-yl)ethyl 2,4-Di-O-(3-phenylpropanoyl)-3-deoxy-O-(6-aminohexyl)-β-D-glucopyranoside (II-21)

The same procedure as that detailed above for the preparation of compound II-20 yielded the title compound II-21 as a clear colorless oil (20.1 mg, 83.9%): $[\alpha]D^{25}$ +23.10° (c 0.58, $CHCl_3$); IR ($CHCl_3$) 3480 (w), 3020 (w), 2920 (m), 2850 (w), 1745 (s), 1455 (w), 1155 (m), 690 (w) $cm^{-1}$; $^1H$ NMR (500 MHz, $CDCl_3$) δ 9.08 (br s, 1H), 7.54 (d, J=7.9 Hz, 1H), 7.32–7.00 (m, 13H), 6.96 (s, 1H), 6.65 (br s, 1H), 4.80–4.70 (m, 2H), 4.46 (d, J=7.4 Hz, 1H), 4.08–4.03 (m, 1H), 3.77–3.72 (m, 1H), 3.59–3.55 (m, 1H), 3.51–3.28 (m, 4H), 3.02 (t, J=7.5 Hz, 2H), 2.97–2.86 (m, 4H), 2.64–2.50 (m, 5H), 2.42–2.37 (m, 1H); $^{13}C$ NMR (125 MHz, $CDCl_3$) δ 171.47, 140.06, 136.23, 128.51, 128.46, 128.26, 128.21, 127.51, 126.35, 126.25, 122.25, 121.66, 119.00, 118.66, 112.04, 111.14, 101.84, 76.90, 71.56, 69.98, 69.73, 68.67, 66.51, 35.75, 35.69, 32.77, 30.82, 30.77, 29.69, 29.57, 26.45, 25.68, 25.62.

X. 4-Azido-1-butyne (II-32)

p-Toluenesulphonyl chloride (127 mmol, 24.3 g) was added in aliquots to a solution of 3-butyn-1-ol (84.9 mmol, 5.86 g) in pyridine (20 ml) at 0° C. and DMAP was added (10 mg). The mixture was allowed to stand for 15 h, then poured into water (100 ml) and extracted with ether (100 ml). The ether extract was washed with 1 N HCl (100 ml), water (100 ml) and brine (50 ml), dried over sodium suphate and evaporated to afford a yellow oil. To a stirred solution of this tosylate in DMSO (100 ml) at 35° C. was added sodium azide (170 mmol, 11.0 g). After stirring for 3 h, the mixture was poured into ether (50 ml), washed with water (3×100 ml), dried over sodium sulphate and evaporated at 0° C. (water aspirator). Cautious distillation into a flask cooled to −78° C. yielded the pure azide II-32 as a colorless, volatile liquid (b.p. 30–32° C. at 12 mmHg) (3.90 g, 48.3%): IR ($CHCl_3$) 3300 (s), 3000 (m), 2950 (m), 2880 (w), 2120 (s), 1450 (m), 1420 (m), 1350 (m), 1320 (m), 1290–1210 (br), 1050 (w), 950 (w), 910 (w), 630 (s) $cm^{-1}$; $^1H$ NMR (500 MHz, $CDCl_3$) δ 3.40 (t, J=6.9 Hz, 2H), 2.48–2.44 (m, 2H), 2.04 (t, J=2.8 Hz, 1H); $^{13}C$ NMR (62.9 MHz, $CDCl_3$) δ 80.29, 70.44, 49.62, 19.39.

Y. 5-Azido-2-pentyn-1-ol (II-33)

n-Butyl lithium (1.6 M in hexane, 18.8 mmol, 11.7 ml) was added dropwise at −78° C. to a solution of 4-azido-1-butyne II-32 (1.28 g, 17.3 mmol) in THF (35 ml). After stirring the resulting green solution for 1 h, paraformaldehyde was added in one portion, the solution was stirred for 5 min, and then warmed to room temperature for 2 h (an orange suspension gradually formed). The reaction mixture was poured into saturated aqueous ammonium chloride (100 ml) and extracted with ether (3×50 ml). The combined extracts were washed with brine (50 ml), dried over sodium sulphate and evaporated to give a yellow oil. This was purified by flash chromatography eluting with pentane/ether 1:1 to afford the title compound II-33 as a pale yellow oil (930 mg, 70.7%): IR (CHCl$_3$) 3600 (m), 3000 (m), 2940 (m), 2880 (m), 2100 (s), 1550 (w), 1380 (m), 1270 (m), 1220 (br), 1140 (m), 1000 (s) cm$^{-1}$; $^1$H NMR (500 MHz, CDCl$_3$) δ 4.24–4.22 (m, 2H), 3.37 (t, J=6.8 Hz, 2H), 2.51–2.48 (m, 2H), 1.84 (t, J=6.0 Hz, 1H); $^{13}$C NMR (62.9 MHz, CDCl$_3$) δ 77.42, 70.47, 49.68, 19.45.

Z. 5-Azido-1-iodo-2-pentyne (II-31)

Iodine (2.94 g, 11.6 mmol) was added to a stirred solution of triphenylphosphine (12.2 mmol, 3.20 g) and imidazole (14.5 mmol, 987 mg) in THF (25 ml) at 0° C. To the resulting brown solution was added 5-azido-2-pentyn-1-ol 33 (725 mg, 5.80 mmol) in THF (10 ml). The mixture was warmed to room temperature, stirred for 10 min and evaporated (water aspirator). Pentane was added and the solid was filtered off. Evaporation yielded the iodide II-31 (contaminated with a small amount of triphenylphosphine) (905 mg, 66.4%).

AA. 2-[(N-Benzenesulphonyl)indol-3-yl]ethyl 4,6-Di-O-isopropylidene-3-deoxy-β-D-glucopyranoside (II-29)

Triol II-28 (25.0 mg, 0.0534 mmol) was stirred with di-camphorsulphonic acid (1 mg) in 2,2-dimethoxypropane (2.0 ml) for 15 h, triethylamine (0.05 ml) was added and the solution was evaporated. The residue was purified by flash chromatography (50% ethyl acetate/hexane) to yield the title compound II-29 as a colorless foam (26.9 mg, 99.1%): [α]D$^{25}$ +38.9° (c 0.99, CHCl$_3$); IR (CHCl$_3$) 3600 (w), 3010 (w), 2890 (w), 1730 (w), 1520 (w), 1450 (m), 1380 (m), 1220 (s), 1210 (s), 1180 (m), 1100 (m), 1055 (m), 930 (m), 780–720 (br), 660 (s) cm$^{-1}$; $^1$H NMR (500 MHz, CDCl$_3$) δ 7.96 (br s, 1H), 7.84 (d, J=7.8 Hz, 2H), 7.52–7.39 (m, 4H), 7.30 (app. t, J=8.1 Hz, 1H), 7.22 (app. t, J=8.3 Hz, 2H), 4.23 (d, J=7.5 Hz, 1H), 4.18 (dt, J=6.6,9.5 Hz, 1H), 3.87 (dd, J=5.3, 10.9 Hz, 1H), 3.77–3.73 (m, 2H), 3.64–3.59 (m, 1H), 3.54–3.49 (m, 1H), 3.23–3.19 (m, 1H), 3.02–2.92 (m, 2H), 2.27–2.11 (m, 1H), 1.56 (app. q, J=18.5 Hz, 1H), 1.47 (s, 3H), 1.39 (s, 3H); $^{13}$C NMR (125 MHz, CDCl$_3$) δ 138.25, 135.16, 133.73, 130.99, 129.23, 126.69, 124.87, 123.49, 123.20, 119.63, 119.34, 113.79, 105.43, 99.34, 71.68, 69.22, 69.03, 68.40, 62.44, 35.38, 29.11, 25.48, 19.01.

AB. 2-[(N-Benzenesulphonyl)indol-3-yl]ethyl 2-O-(5-azido-2-pentynyl)-4,6-di-O-isopropylidene-3-deoxy-β-D-glucopyranoside (II-34)

Sodium hydride (60% dispersion in mineral oil, 0.276 mmol, 11.0 mg) was added to a solution of acetonide II-29 (100 mg, 0.197 mmol) and 5-azido-1-iodo-2-pentyne II-31 (93 mg, 0.39 mmol) in dry acetonitrile (3.0 ml) at 0° C. followed by the addition of 15-crown-5 ether (0.001 ml). The solution was warmed to room temperature and stirred for 36 h (a brown color gradually appeared), then poured into saturated aqueous sodium bicarbonate (10 ml) and extracted with methylene chloride (3×5 ml). The combined extracts were washed with brine (10 ml), dried over sodium sulphate and evaporated. The residue was purified by flash chromatography eluting with 30% ethyl acetate/hexane to afford the title compound II-34 as a colorless oil (30.7 mg, 25.4%). The gradient was increased to 50% ethyl acetate/hexane to yield the starting material II-29 as a colorless oil (65 mg, 65%).

2-[(N-Benzenesulphonyl)indol-3-yl]ethyl 2-O-(5-azido-2-pentynyl)-4,6-di-O-isopropylidene-3-deoxy-β-D-glucopyranoside: [α]D$^{25}$ +11.59° (c 0.63, CHC$_3$3); IR (CHCl$_3$) 3020 (m), 2950 (w), 2890(w), 2890(w), 2110(s), 1450 (m), 1370(m), 1260 (m), 1175 (s), 1090 (s), 1080 (s), 850 (w), 600 (m), 570 (m) cm$^{-1}$; $^1$H NMR (500 MHz, CDCl$_3$) δ 7.95 (d, J=7.6 Hz, 1H), 7.84 (d, J=8 Hz, 2H), 7.52–7.39 (m, 5H), 7.29 (dt, J=1.2, 7.4 Hz, 1H), 7.23–7.20 (m, 1H), 4.37 (d, J=7.5 Hz, 1H), 4.24–4.20 (m, 2H), 4.17–4.12 (m, 1H), 3.86 (dd, J=10.8, 5.3 Hz, 1H), 3.81–3.72 (m, 2H), 3.62–3.57 (m, 1H), 3.49–3.42 (m, 1H), 3.35 (t, J=6.8 Hz, 2H), 3.20–3.15 (m, 1H), 2.96 (t, J=6.2 Hz, 2H), 2.50–2.46 (m, 2H), 2.32–2.28 (m, 1H), 1.52 (app. q, J=11.7 Hz, 1H), 1.47 (s, 3H), 1.39 (s, 3H); $^{13}$C NMR (62.9 MHz, CDCl$_3$) δ 138.50, 135.09, 133.65, 130.95, 129.17, 126.70, 124.73, 123.11, 119.61, 119.35, 113.67, 105.00, 99.26, 82.59, 78.29, 74.96, 71.15, 68.59, 68.32, 62.46, 58.32, 49.74, 35.02, 29.11, 25.49, 19.84, 19.01.

EXAMPLE 11

Preparation of Other Compounds

To distinguish the compounds described in this example from those described in other examples, a "III" preceeds each compound number. The chemical structures and synthetic schemes of Example 11 are presented in FIG. 10.

A. N-(Phenylsulfonyl)tryptophol (III-12)

(a). 1-O-tert-Butyldimethylsilyl-2-(3-indolyl)ethanol

A solution of tryptophol (5.0 g, 31 mmol) in DMF (30 ml) was treated with imidazole (4.64 g, 68 mmol) and cooled to 0° C. tert-Butyldimethylsilyl chloride (5.14 g, 34.1 mmol) was added and the mixture was stirred at room temperature for 16 h. The mixture was then diluted with ethyl acetate (100 ml) and washed with water (2×100 ml) and the aqueous solutions were extracted with ethyl acetate (200 ml). The combined organic layers were dried over sodium sulfate, filtered, and concentrated in vacuo. Flash chromatogaphy (30% ether/petroleum ether) yielded the title compound (8.43 g, 99% yield) as a colorless oil: IR (CCl$_4$) 3910 (s), 3060 (w), 2960 (s), 2930 (s), 2850 (s), 1450 (m), 1370 (w), 1260 (s), 1100 (s), 900 (m), 840 (s), 780 (s), 750 (s) cm$^{-1}$; $^1$H NMR (500 MHz, CDCl$_3$) δ 8.26 (br s, 1H), 7.99 (d, J=7.8 Hz, 1H), 7.64–7.50 (m, 4H), 4.28 (t, J=7.3 Hz, 2H), 3.38 (t, J=7.3 Hz, 2H), 1.29 (s, 2H), -0.43 (s, 6H); $^{13}$C NMR (125 MHz, CDCl$_3$) δ 136.08, 127.62, 122.08, 121.75, 119.12, 118.79, 112.84, 111.04, 63.89, 28.98, 25.98, 18.34, -5.29; high resolution mass spectrum (Cl, NH$_3$) m/z 276.1750 [(M+H)$^+$; calcd for C$_{16}$H$_{25}$NOSi: 276.1783].

(b). 1-O-tert-Butyldimethylsilyl-2-[3-(1-N-phenylsulfonyl)indolyl]ethanol

A suspension of sodium hydride (1.91 g, 60% oil dispersion) in dry DMF (64 ml) was cooled to 0° C. and a solution of 1-O-tert-butyldimethylsilyl-2-(3-indolyl)ethanol (8.43 g, 30.6 mmol) in DMF (30 ml) was added. The mixture was stirred at room temperature for 30 min, recooled to 0° C., and treated dropwise with benzenesulfonyl chloride (5.30 ml, 39.7 mmol). The reaction was then stirred at room temperature for 16 h, quenched with saturated aqueous ammonium chloride (100 ml), and extracted with ether (3×200 ml). The combined extracts were washed with brine, dried over sodium sulfate, filtered, and concentrated in vacuo. Flash chromatography (30% ether/petroleum ether) afforded the title compound (7.37 g, 79% yield) as a colorless oil: $^1$H NMR (500 MHz, CDCl$_3$) δ 7.77 (d, J=8.4 Hz, 1H), 7.62 (d, J=7.5 Hz, 2H), 7.26–6.98 (m, 7H), 3.64 (t, J=6.7 Hz, 2H), 2.64 (t, J=6.7 Hz, 2H), 0.64 (s, 9H), -0.24 (s, 6H); $^{13}$C NMR (125 MHz, CDCl$_3$) δ 135.10, 133.55, 131.21, 129.12, 126.65, 124.56, 123.42, 122.00, 120.31, 119.57, 113.59, 62.51, 28.51, 25.87, 18.22, -5.44; high resolution mass spectrum (FAB, m-nitrobenzyl alcohol) m/z 433.1920 [(M+NH$_4$)$^+$; calcd for C$_{22}$H$_{29}$NSO$_3$Si: 433.1971].

(c). N-Phenylsulfonyltryptophol (III-12)

Tetrabutylammonium fluoride (21 ml, 1 M in THF) was added to a solution of 1-O-tert-butyldimethylsilyl-2-[3-(1-N-phenylsulfonyl)indolyl]ethanol (6.6 g, 22 mmol) in THF (100 ml) and the reaction was stirred at room temperature for 16 h. The mixture was then diluted with ethyl acetate (100 ml) and extracted with water (2×100 ml). The organic layer was washed with brine, dried over sodium sulfate, filtered, and concentrated in vacuo. Flash chromatography (40% ethyl acetate/petroleum ether) furnished III-11 (4.00 g, 84% yield) as a pale yellow oil which crystallized upon standing: mp 63–64° C.; IR (CCl$_4$) 3580 (m), 3400 (m), 3100 (w), 3080 (w), 2950 (m), 2890 (m), 1460 (s), 1360 (s), 1280 (m), 1160 (s), 1120 (s), 1100 (m), 1080 (w), 1060 (w), 1020 (w), 980 (w), 750 (s), 720 (s), 690 (s) cm$^{-1}$; $^1$H NMR (500 MHz, CDCl$_3$) δ 7.86 (d, J=7.6 Hz, 1H), 7.70 (d, J=7.6 Hz, 2H), 7.32–7.04 (m, 7H), 3.68 (t, J=6.2 Hz, 2H), 2.72 (t, J=6.2 Hz, 2H), 2.36 (br s, 1H); $^{13}$C NMR (125 MHz, CDCl$_3$) δ 137.79, 134.99, 133.55, 130.78, 129.00, 126.43, 124.63, 123.39, 123.05, 119.67, 119.38, 61.40, 28.07; high resolution mass spectrum (Cl, NH$_3$) m/z 301.0748 (M$^+$; calcd for C$_{16}$H$_{15}$NO$_3$S: 301.0772).

B. 2-(N-Phenylsulfonylindol-3-yl)ethyl 2,3,4,6-Tetra-O-acetyl-b-D-glucopyranoside (III-13)

A solution of III-12 (537 mg, 1.78 mmol) in dry benzene (3 ml) was added to a suspension of powdered, activated 4 Angstrom molecular sieves (0.89 g) and silver(I) oxide (412 mg, 17.8 mmol) in dry hexane (9 ml) at room temperature. A solution of bromide III-11 (804 mg, 1.95 mmol) in dry benzene (3 ml) was then added, the flask was covered with aluminum foil and the mixture allowed to stir for 2 days at room temperature. More silver(I) oxide (206 mg, 8.9 mmol) and benzene (1 ml) were added and the reaction was stirred at room temperature for an additional 2 days. After filtration through Celite, concentration in vacuo and recrystallization (ethyl acetate/petroleum ether) afforded pure II-13 (580 mg) as a white solid. Concentration of the filtrate in vacuo and flash chromatography (5% ether/dichloromethane) afforded III-13 admixed with the a anomer and the corresponding ortho ester. Further flash chromatography (70% ether/petroleum ether) then gave an additional 134 mg of pure III-13 (64% total yield): mp 145–146° C.; [α]D$^{25}$ –16° (c 0.14, acetonitrile); UV (1.05×10$^{-4}$ M, acetonitrile) λmax 253.6 (ε 1.19×10$^4$), 214.0 (2.50×10$^4$) nm; IR (thin film) 3028 (w), 2950 (w), 2880 (w), 1758 (s), 1450 (m), 1377 (s), 1225 (s), 1178 (s), 1122 (m), 1040 (s), 910 (w), 754 (s), 688 (w) cm$^{-1}$; $^1$H NMR (500 MHz, CDCl$_3$) δ 7.96 (d, J=8.3 Hz, 1H), 7.87–7.21 (m, 9H), 5.18 (dd, J=9.5, 9.5 Hz, 1H), 5.09 (dd, J=9.6, 9.6 Hz, 1H), 5.00 (dd, J=9.5, 8.0 Hz, 1H), 4.53 (d, J=8.0 Hz, 1H), 4.26 (dd, J=12.3, 4.7 Hz, 1H), 4.18–4.12 (m, 2H), 3.76 (ddd, J=9.3, 6.9, 6.9 Hz, 1H), 3.69 (ddd, J=9.8, 4.6, 2.4 Hz, 1H), 2.94 (t, J=6.6 Hz, 2H), 2.07 (s, 3H), 2.02 (s, 3H), 2.00 (s, 3H), 1.89 (s, 3H); $^{13}$C NMR (125 MHz, CDCl$_3$) δ 170.66, 170.24, 169.34, 138.24, 135.08, 133.70, 130.94, 129.22, 126.73, 124.75, 123.56, 123.21, 119.57, 119.42, 113.65, 106.61, 100.70, 72.87, 71.16, 68.75, 68.39, 61.91, 25.31, 20.72, 20.57, 20.43; high resolution mass spectrum (Cl, NH$_3$) m/z 649.2021 [(M+NH$_4$)$^+$; calcd for C$_{30}$H$_{33}$NO$_{12}$S: 649.2054]. Anal. Calcd for C$_{30}$H$_{33}$NO$_{12}$S: C, 57.04; H, 5.27. Found: C, 56.75; H, 5.30.

C. 2-(N-Phenylsulfonylindol-3-yl)ethyl β-D-glucopyranoside (III-14)

Sodium methoxide (221 mg, 4.09 mmol) was added to a suspension of III-13 (3.22 g, 5.12 mmol) in methanol (26 ml) at room temperature. After 20 min, the resultant solution was diluted with methanol (26 ml) and neutralized with Amberlyst® 15 ion exchange resin. The resin was quickly removed by filtration to avoid formation of the methyl glucoside. Concentration and flash chromatography (5:1:1 dichloromethane/methanol/acetone) afforded III-13 (2.09, 88% yield) as a white foam: [α]D$^{25}$ –23° (c 0.09, acetonitrile); UV (1.62×10$^{-4}$ M, acetonitrile) λmax 253.6 (ε 1.17×10$^4$), 214.0 (1.93×10$^4$) nm; IR (film) 3390 (s), 3065 (w), 3015 (w), 2920 (m), 2880 (m), 1450 (s), 1363 (s), 1282 (m), 1175 (s), 1123 (s), 1085 (s), 1021 (s), 748 (s), 725 (m), 686 (m), cm$^{-1}$; $^1$H NMR (500 MHz, acetone-d$_6$) δ 8.00–7.97 (m, 3H), 7.71 (s, 1H), 7.64–7.53 (m, 4H), 7.35–7.31 (m, 1H), 7.26–7.23 (m, 1H), 4.40 (d, J=7.7 Hz, 1H), 4.30 (d, J=3.7 Hz, 1H), 4.25 (d, J=3.7 Hz, 1H), 4.22 (d, J=4.0 Hz, 1H), 4.16 (ddd, J=9.7, 6.7, 6.7 Hz, 1H), 3.89–3.82 (m, 2H), 3.70 (ddd, J=11.8, 5.9, 5.9 Hz, 1H), 3.58 (t, J=6.4 Hz, 1H), 3.45 (ddd, J=8.8, 8.8, 3.8 Hz, 1H), 3.39 (ddd, J=8.5, 8.5, 4.0 Hz, 1H), 3.34 (ddd, J=9.3, 5.5, 2.7 Hz, 1H), 3.25 (ddd, J=8.6, 7.8, 3.8 Hz, 1H), 2.98 (t, J=6.6 Hz, 2H); $^{13}$C NMR (125 MHz, acetone-d$_6$) δ 139.40, 136.57, 134.87, 132.21, 130.31, 127.67, 125.41, 125.30, 124.07, 121.33, 120.56, 114.35, 104.07, 78.07, 77.53, 74.93, 71.73, 68.76, 63.00, 49.72, 25.92; high resolution mass spectrum (Cl, NH$_3$) m/z 481.1656 [(M+NH$_4$)$^+$; calcd for C$_{22}$H$_{25}$NO$_8$S: 481.1634].

D. 2-(N-Phenylsulfonylindol-3-yl)ethyl 6-O-tert-Butyldiphenylsilyl-β-D-glucopyranoside (III-15)

At room temperature a stirred solution of III-14 (7.11 g, 15.4 mmol) in dry DMF (51 ml) was treated with imidazole (2.93 g, 43.1 mmol) followed by tert-butyldiphenylsilyl chloride (5.58 g, 21.6 mmol). The solution was heated at 50° C. for 24 h. After concentration in vacuo, the mixture was diluted with ethyl acetate (250 ml) and washed with water (100 ml). The organic phase was then washed with brine (100 ml), dried over magnesium sulfate, filtered, and concentrated in vacuo. Flash chromatography (5% methanol/dichloromethane) provided pure III-15 (9.15 g, 85% yield) as a white foam: [α]D$^{25}$ –26° (c 0.14, acetonitrile); UV (5×10$^{-5}$ M, acetonitrile) λmax 280.0 (ε 7.1×10$^3$), 220.8 (5.17×10$^4$) nm; IR (film) 3410 (s), 3070 (w), 3045 (w), 3010 (w), 2925 (m), 2885 (m), 2855 (m), 1474 (w), 1458 (w), 1430 (m), 1363 (w), 1220 (w), 1113 (s), 1047 (s), 1010 (s), 823 (m), 805 (w), 742 (s), 704 (s) cm$^{-1}$; $^1$H NMR (500 MHz, acetone-d$_6$) δ 8.02 (d, J=8.3 Hz, 1H), 7.96–7.95 (m, 2H), 7.78–7.74 (m, 4H), 7.70 (s, 1H), 7.57 (d, J=7.8 Hz, 1H), 7.54–7.50 (m, 1H), 7.47–7.43 (m, 2H), 7.39–7.30 (m, 7H), 7.21–7.18 (m, 1H), 4.49 (m, 2H), 4.46 (d, J=7.7 Hz, 1H), 4.20 (ddd, J=9.7, 6.7, 6.7 Hz, 1 H), 4.11 (dd, J=11.2, 0.9 Hz, 1H), 3.96 (dd, J=11.0, 4.9 Hz, 1H), 3.85 (ddd, J=9.7, 6.9, 6.9 Hz, 1H), 3.52 (m, 2H), 3.38–3.34 (m, 1H), 3.05 (t, J=6.6 Hz, 2H), 2.86 (s, 1H), 2.75 (s, 1H), 1.02 (s, 9H); $^{13}$C NMR (125 MHz, acetone-d$_6$) δ 206.17, 138.97, 136.39, 136.30, 135.95, 134.83, 134.60, 134.47, 132.13, 130.45, 130.41, 130.26, 128.47, 127.59, 125.40, 125.01, 124.04, 121.24, 120.60, 114.31, 104.11, 78.17, 77.76, 74.94, 71.14, 68.93, 64.72, 27.12, 26.10, 19.82; high resolution mass spectrum (Cl, NH$_3$) m/z 684.2532 [(M–OH)$^+$; calcd for C$_{38}$H$_{43}$NO$_8$SSi: 684.2449]. Anal. Calcd for C$_{38}$H$_{43}$NO$_8$SSi: C, 65.03; H, 6.18. Found: C, 64.96; H, 6.28.

E. 2-(N-Phenylsulfonylindol-3-yl)ethyl 2,3,4-Tri-O-benzyl-6-O-tert-butyidiphenylsilyl-β-D-glucopyranoside (III-16)

A solution of III-15 (1.62 g, 2.31 mmol) in THF (7 ml) was added to a stirred suspension of sodium hydride (323 mg, 60% oil dispersion, 8.08 mmol) in THF (5 ml) at 0° C. After the mixture was stirred for 1 h at room temperature and recooled to 0° C., benzyl bromide (1.09 ml, 9.24 mmol) was added dropwise followed by tetrabutylammonium iodide (85 mg, 0.23 mmol). The reaction was then allowed to stir for 3 days at room temperature. The resultant suspension was diluted with saturated aqueous ammonium chloride (3 ml) at 0° C. and extracted with ether (2×80 ml). The combined extracts were washed with saturated aqueous ammonium chloride (30 ml) and brine (30 ml), dried over magnesium sulfate, filtered, and concentrated in vacuo. Flash chromatography (20% ether/petroleum ether) afforded III-16 (1.66 g, 74% yield) as a white foam: $[\alpha]D^{25}$ −7.0° (c 0.12, acetonitrile); UV ($5.90\times10^{-5}$ M, acetonitrile) λmax 253.6 (ε $2.90\times10^3$), 213.6 ($5.11\times10^4$) nm; IR (film) 3065 (m), 3030 (m), 2930 (s), 2855 (s), 1608 (w), 1590 (w), 1496 (w), 1472 (w), 1464 (w), 1449 (s), 1429 (m), 1377 (s), 1338 (w), 1312 (m), 1280 (m), 1215 (m), 1176 (s), 1113 (s), 1088 (s), 1072 (s), 1029 (s), 952 (w), 920 (w), 825 (m), 805 (w), 746 (s), 700 (s) cm$^{-1}$; $^1$H NMR (500 MHz, CDCl$_3$) δ 7.99 (d, J=8.3 Hz, 1H), 7.82 (d, J=7.5 Hz, 2H), 7.73 (d, J=6.7 Hz, 2H), 7.68 (d, J=6.7 Hz, 2H), 7.50 (d, J=7.8 Hz, 1H), 7.44–7.17 (m, 27H), 4.91 (d, J=10.9 Hz, 1H), 4.88 (d, J=11.2 Hz, 1H), 4.80 (d, J=10.7 Hz, 1H), 4.77 (d, J=11.2 Hz, 1H), 4.68 (d, J=10.8 Hz, 1H), 4.63 (d, J=10.8 Hz, 1H), 4.44 (d, J=7.7 Hz, 1H), 4.19 (dd, J=14.6, 7.1 Hz, 1H), 3.92 (d, J=2.9 Hz, 2H), 3.81 (dd, J=15.4, 7.6 Hz, 1H), 3.74 (dd, J=8.8, 8.8 Hz, 1H), 3.64 (dd, J=9.1, 9.1 Hz, 1H), 3.46 (dd, J=8.1, 8.1 Hz, 1H), 3.35 (apparent d, J=7.6 Hz, 1H), 3.05 (t, J=7.0 Hz, 2 H), 1.04 (s, 9H); $^{13}$C NMR (125 MHz, CDCl$_3$) δ 138.58, 138.47, 138.32, 138.19, 135.83, 135.35, 135.23, 133.64, 133.58, 133.18, 130.96, 129.60, 129.13, 128.39, 128.30, 127.97, 127.90, 127.72, 127.66, 127.55, 127.51, 126.63, 124.77, 123.38, 123.16, 119.74, 119.57, 113.71, 103.62, 84.71, 82.55, 77.66, 75.81, 75.79, 75.10, 74.80, 68.53, 62.80, 26.78, 25.90, 19.29; high resolution mass spectrum (FAB, m-nitrobenzyl alcohol) m/z 972.4071 [(M+H)$^+$; calcd for C$_{59}$H$_{61}$NO$_8$SSi: 972.3970].

F. 2-(N-Phenylsulfonylindol-3-yl)ethyl 2,3,4-Tri-O-benzyl-β-D-glucopyranoside (III-17)

Tetrabutylammonium fluoride (1 M in THF, 2.4 ml, 2.4 mmol) was added to a stirred solution of III-16 (1.55 g, 1.60 mmol) in THF (8 ml) at room temperature. After 7 h the reaction mixture was diluted with ethyl acetate (70 ml), washed with water (30 ml) and brine (30 ml), dried over magnesium sulfate, filtered, and concentrated in vacuo. Flash chromatography (30% ethyl acetate/petroleum ether) afforded III-17 (1.10 g, 94% yield) as a clear oil: $[\alpha]D^{25}$ −13° (c 0.14, acetonitrile); UV ($9.21\times10^{-5}$ M, acetonitrile) λmax 254.0 (ε $2.81\times10^3$), 211.6 ($3.19\times10^4$) nm; IR (film) 3480 (w), 3065 (w), 3035 (w), 2920 (m), 2878 (m), 1498 (w), 1450 (s), 1365 (s), 1280 (w), 1220 (m), 1176 (s), 1123 (s), 1090 (s), 1073 (s), 1030 (s), 750 (s), 700 (s), cm$^{-1}$; $^1$H NMR (500 MHz, CDCl$_3$) δ 7.84 (d, J=8.3 Hz, 1H), 7.82 (d, J=7.9 Hz, 2H), 7.53 (s, 1H), 7.48–7.17 (m, 21H), 4.92 (d, J=11.0 Hz, 1H), 4.86 (d, J=10.9 Hz, 1H), 4.81 (d, J=11.0 Hz, 1H), 4.74 (d, J=11.0 Hz, 1H), 4.65 (d, J=10.9 Hz, 1H), 4.62 (d, J=11.0 Hz, 1H), 4.48 (d, J=7.8 Hz, 1H), 4.20 (ddd, J=9.4, 7.0, 7.0 Hz, 1H), 3.91–3.86 (m, 2H), 3.73 (dd, J=3.5, 11.9 Hz, 1H), 3.63 (ddd, J=9.0, 9.0, 18.0 Hz, 2H), 3.40 (apparent t, J=8.0 Hz, 1H), 3.35 (ddd, J=9.4, 4.2, 2.6 Hz, 1H), 3.04–2.93 (m, 2H), 2.06 (s, 1H); $^{13}$C NMR (125 MHz, CDCl$_3$) δ 138.48, 138.21, 138.13, 137.95, 135.09, 133.60, 130.92, 129.10, 128.40, 128.30, 128.25, 128.22, 127.98, 127.90, 127.82, 127.76, 127.55, 126.58, 124.72, 123.57, 123.12, 119.61, 119.31, 113.66, 103.59, 84.39, 82.25, 77.37, 75.56, 75.16, 74.99, 74.75, 68.60, 61.77, 25.57; high resolution mass spectrum (Cl, NH$_3$) m/z 734.2743 [(M+H)$^+$; calcd for C$_{43}$H$_{43}$NO$_8$S: 734.2774]. Anal. Calcd for C$_{43}$H$_{43}$NO$_8$S: C, 70.37; H, 5.91. Found: C, 70.30; H, 6.08.

G. 2-(N-Phenylsulfonylindol-3-yl)ethyl 2,3,4-Tri-O-benzyl-6-O-(5-azidopentyl)-β-D-glucopyranoside (III-19a)

Sodium azide (1.83 g, 28.2 mmol) was added to a stirred solution of 5-bromo-1-pentanol (0.79 g, 4.7 mmol) in DMSO (15 ml). The resultant mixture was stirred at room temperature for 2.5 h, diluted with water, and extracted with diethyl ether. The combined organic solutions were washed with saturated aqueous sodium bicarbonate and brine, dried over magnesium sulfate, filtered, and concentrated in vacuo. The azide was used without purification in the next step.

A stirred solution of crude 5-azido-1-pentanol (280 mg, equivalent to 2.17 mmol) and 2,6-di-tert-butyl-4-methylpyridine (441 mg, 2.17 mmol) in dichloromethane (9 ml) was treated dropwise with triflic anhydride (0.36 ml, 2.17 mmol). After 10 min the mixture was poured into brine (40 ml) and extracted with dichloromethane (2×40 ml). The combined organic layers were dried over magnesium sulfate, filtered, and concentrated in vacuo. The resultant triflate was used without purification in the next step. Sodium hydride (12.4 mg, 0.31 mmol, 60% dispersion in oil) was added to a solution of alcohol 17 (225 mg, 0.309 mmol) and crude azidotriflate (161 mg, equivalent to 0.62 mmol) in dichloromethane (4 ml) at room temperature. The mixture was stirred for 24 h, diluted with dichloromethane (40 ml), and poured into saturated aqueous ammonium chloride (40 ml). The aqueous phase was extracted with dichloromethane and the combined organic layers were washed with brine, dried over magnesium sulfate, filtered, and concentrated in vacuo. Flash chromatography (15% ethyl acetate/hexane) furnished III-19a (248 mg, 95% yield) as a colorless oil: $[\alpha]D^{25}$ +1.3° (c 0.48, CHCl$_3$); IR (CHCl$_3$) 3070 (w), 3015 (m), 2935 (s), 2875 (s), 2100 (s), 1450 (s), 1370 (s), 1280 (w), 1178 (m), 1122 (m), 1070 (s), 695 (m), 597 (m) cm$^{-1}$; $^1$H NMR (500 MHz, CDCl$_3$) δ 7.93 (d, J=8.4 Hz, 1H), 7.78 (apparent d, J=8.4 Hz, 2H), 7.44–7.41 (m, 3H), 7.39–7.10 (m, 19H), 4.86 (d, J=10.9 Hz, 1H), 4.81 (d, J=10.9 Hz, 1H), 4.73 (d, J=11.0 Hz, 1H), 4.67 (d, J=11.0 Hz, 1H), 4.56 (d, J=10.9 Hz, 1H), 4.54 (d, J=11.0 Hz, 1H), 4.36 (dd, J=7.8, 1.0 Hz, 1H), 4.15 (dt, J=9.5, 7.1 Hz, 1H), 3.79 (dt, J=9.5, 7.3 Hz, 1H), 3.64–3.44 (m, 5H), 3.36 (m, 3H), 3.13 (t, J=7.0 Hz, 2H), 2.96 (t, J=7.0 Hz, 2H), 1.56–1.48 (m, 4H), 1.39–1.31 (m, 2H); $^{13}$C NMR (125 MHz, CDCl$_3$) δ 138.56, 138.31, 138.28, 138.22, 135.18, 133.60, 130.96, 129.13, 128.42, 128.35, 128.28, 128.00, 127.85, 127.82, 127.77, 127.57, 127.51, 126.67, 124.74, 123.47, 123.11, 119.65, 119.44, 113.72, 103.74, 84.64, 82.25, 77.93, 75.66, 74.97, 74.90, 74.75, 71.40, 69.70, 68.76, 29.67, 29.18, 28.66, 25.71, 23.41; high resolution mass spectrum (FAB, m-nitrobenzyl alcohol) m/z 867.3532 (M$^+$; calcd for C$_{48}$H$_{52}$N$_4$O$_8$S: 867.3494).

H. 2-(1H-Indol-3-yl)ethyl 2,3,4-Tri-O-benzyl-6-O-(5-aminopentyl)-β-D-glucopyranoside (III-4a)

A stirred solution of azide III-19a (31 mg, 0.037 mmol) in THF (2 ml) and water (0.032 ml) was treated with triphenylphosphine (25 mg, 0.095 mmol). The mixture was heated at reflux for 2.5 h, cooled, and concentrated in vacuo. Flash chromatography (10% methanol/dichloromethane) furnished the corresponding amine (26 mg, 86% yield) as a colorless oil: ($[\alpha]D^{25}$) 1.5° (c 0.1.12, CHCl$_3$); IR (CHCl$_3$) 3010(m), 2920(s), 2870(s), 1505(w), 1455(s), 1370(s), 1180 (s), 1125(s), 1075(s), 910(w), 695(m), 595(m), 570(m) cm$^{-1}$; $^1$H NMR (500 MHz, CDCl$_3$) δ 8.03 (d, J=8.2 Hz, 1H), 7.89 (dd, J=8.5, 0.9 Hz, 2H), 7.39–7.21 (m, 22H), 4.96 (d, J=10.9 Hz, 1H), 4.91 (d, J=10.9 Hz, 1H), 4.84 (d, J=10.9 Hz, 1H), 4.78 (d, J=11.3 Hz, 1H), 4.67 (d, J=10.8 Hz, 1H), 4.65 (d, J=11.0 Hz, 1H), 4.47 (d, J=7.8 Hz, 1H), 4.26 (dt, J=9.5, 6.9 Hz, 1H), 3.90 (dt, J=9.5, 7.1 Hz, 1H), 3.75–3.62 (m, 4H), 3.56 (dt, J=9.4, 6.5 Hz, 1H), 3.49–3.44 (m, 3H), 3.06 (t, J=6.9 Hz, 2H), 2.68 (t, J=6.9 Hz, 2H), 1.91 (br s, 2H), 1.66–1.58 (m, 2H), 1.50–1.34 (m, 4H); $^{13}$C NMR (62.5 MHz, CDCl$_3$) δ 138.49, 138.23, 138.14, 135.25, 133.56, 133.20, 132.08, 131.56, 131.90, 130.09, 129.08, 128.52, 128.32, 128.23, 127.93, 127.79, 127.52, 126.59, 124.67, 123.39, 123.06, 119.60, 119.40, 113.62, 103.65, 84.56, 82.17, 77.85, 75.60, 74.91, 74.80, 74.68, 71.56, 69.56, 68.68, 41.88, 33.18, 29.37, 25.63, 23.36; high resolution mass spectrum (FAB, m-nitrobenzyl alcohol) m/z 819.3687 (M$^+$; calcd for C$_{48}$H$_{54}$N$_2$O$_8$S: 819.3679).

The above amine (26 mg, 0.032 mmol) was dissolved in ethanol (4 ml) and treated with 5 M aqueous sodium hydroxide (0.65 ml). The resultant mixture was heated at reflux for 3 h, cooled, diluted with brine, and poured into dichloromethane. The aqueous layer was extracted with dichloromethane (2×40 ml) and the combined organic solutions were dried over sodium sulfate, filtered, and concentrated in vacuo. Flash chromatography (10% methanol/dichloromethane) afforded III-4a (19.7 mg, 91% yield) as a colorless oil: [α]D$^{25}$ +13° (c 0.03, CHCl$_3$); IR (CHCl$_3$) 3009 (s), 2930 (m), 2860 (m), 1450 (w), 1360 (w), 1200 (s), 1062 (s), 920 (w), 690 (m) cm$^{-1}$; $^1$H NMR (500 MHz, CDCl$_3$) δ 8.75 (br s, 1H), 7.59 (d, J=7.9 Hz, 1 H), 7.38–7.24 (m, 16H), 7.17 (t, J=7.2 Hz, 1H), 7.10 (t, J=7.2 Hz, 1H), 7.07 (s, 1H), 4.93 (d, J=10.9 Hz, 1H), 4.89 (d, J=11.0 Hz, 1H), 4.85 (d, J=11.0 Hz, 1H), 4.80 (d, J=10.9 Hz, 1H), 4.71 (d, J=11.0 Hz, 1H), 4.57 (d, J=11.0 Hz, 1H), 4.48 (d, J=7.8 Hz, 1H), 4.18 (dt, J=9.4, 7.1 Hz, 1H), 3.88 (dt, J=9.4, 7.1 Hz, 1H), 3.68–3.64 (m, 2H), 3.55–3.35 (m, 6H), 3.12 (t, J=7.1 Hz, 2H), 2.43 (brt, J=7.1 Hz, 2H), 1.59–1.54 (m, 2H), 1.52–1.54 (m, 2H), 1.37–1.28 (m, 4H); $^{13}$C NMR (62.5 MHz, CDCl$_3$) δ 138.48, 138.20, 138.05, 136.14, 130.90, 128.97, 128.45, 128.37, 128.07, 127.88, 127.61, 127.40, 122.47, 121.87, 119.17, 118.64, 112.15, 111.44, 103.70, 84.62, 82.29, 77.88, 77.21, 75.68, 74.97, 74.79, 74.56, 71.03, 70.46, 69.51, 66.80, 29.69, 28.89, 28.64, 25.77, 22.95; high resolution mass spectrum (FAB, m-nitrobenzyl alcohol) calcd for C$_{42}$H$_{50}$N$_2$O$_6$).

I. 2-(1H-Indol-3-yl)ethyl 2,3,4-Tri-O-benzyl-6-O-(4-azidobutyl)-β-D-glucopyranoside (III-19b)

Alcohol 17 (0.164 g, 0.223 mmol) and 2,6-di-tert-butyl-4-methyl-pyridine (0.06 g, 0.29 mmol) were dissolved in dichloromethane (5 ml) and triflic anhydride (0.041 ml, 0.246 mmol) was added dropwise. The mixture was stirred at room temperature for 10 min, diluted with dichloromethane (40 ml), and poured into brine (40 ml). The organic phase was dried over magnesium sulfate, filtered, and concentrated. The resultant white solid was redissolved in dichloromethane (3 ml) and treated sequentially with 4-azido-1-butanol (0.13 g, 1.21 mmol), prepared in a similar manner to 5-azido-1-pentanol above, and sodium hydride (0.045 g, 1.13 mmol, 60% dispersion in oil). The mixture was then stirred for 24 h, diluted with dichloromethane (40 ml), and poured into saturated aqueous ammonium chloride (40 ml). The aqueous phase was extracted with dichloromethane (2×20 ml) and the combined organic solutions were washed with brine (40 ml), dried over magnesium sulfate, filtered, and concentrated in vacuo. Flash chromatography (15% ethyl acetate/hexane) yielded III-19b (85.2 mg, 56% yield) as a colorless oil: [α]D$^{25}$ +10.2° (c 0.3, CH$_2$Cl$_2$); IR (CH$_2$Cl$_2$) 3485 (m), 3044 (w), 2910 (m), 2885 (m), 2090 (s), 1735 (m), 1610 (w), 1460 (m), 1420 (m), 1360 (m), 1250 (m), 1060 (s) cm$^{-1}$; $^1$H NMR (500 MHz, CDCl$_3$) δ 7.84 (br s, 1H), 7.60 (d, J=7.8 Hz, 1H), 7.16–7.33 (m, 17H), 7.11 (apparent t, J=7.2 Hz, 1H), 7.03 (br s, 1H), 4.91 (d, J=10.9 Hz, 1H), 4.86 (d, J=11.0 Hz, 1H), 4.80 (d, J=11.0 Hz, 1H), 4.78 (d, J=10.9 Hz, 1H), 4.64 (d, J=11.0 Hz, 1H), 4.59 (d, J=7.8 Hz, 1H), 4.43 (d, J=7.8 Hz, 1H), 4.24 (dt, J=9.3, 6.8 Hz, 1H), 3.86 (dt, J=9.3, 7.4 Hz, 1H), 3.68–3.60 (m, 3H), 3.57–3.51 (m, 2H), 3.44 (t, J=5.9 Hz, 2H), 3.46–3.40 (m, 1H), 3.24 (br t, J=6.5 Hz, 2H), 3.12 (t, J=6.9 Hz, 2H), 1.65–1.62 (m, 4H); $^{13}$C NMR (125 MHz, CDCl$_3$) δ 138.60, 138.56, 138.24, 136.17, 128.43, 128.28, 128.04, 127.90, 127.86, 127.78, 127.60, 127.53, 122.12, 121.96, 119.29, 118.73, 112.81, 111.10, 103.71, 84.70, 82.33, 77.99, 75.69, 74.97, 74.84, 74.69, 70.97, 70.05, 69.76, 51.29, 26.88, 25.84, 25.81.

J. 2-(1H-Indol-3-yl)ethyl 2,3,4-Tri-O-benzyl-6-O-(4-aminobutyl)-β-D-glucopyranoside (III-4b)

A solution of azide III-19b (0.037 g, 0.056 mmol) in THF (3 ml) was treated sequentially with water (0.025 ml, 1.39 mmol) and triphenylphosphine (0.29 g, 0.11 mmol). The mixture was then heated at 60° C. for 6 h, cooled, and concentrated in vacuo. Flash chromatography (10% methanol/dichloromethane) yielded III-4b (26.6 mg, 72% yield) as a colorless oil: [α]D$^{25}$ (CH$_2$Cl$_2$); IR (CH$_2$Cl$_2$) 3700 (w), 3487 (m), 3028 (m), 3020 (m,), 2918 (s), 2878 (s), 1608 (w), 1498 (w), 1277 (m), 1212 (m), 1072 (s), 1465 (s), 1371 (s) cm$^{-1}$; $^1$H NMR (500 MHz, CDCl$_3$) δ 8.29 (br s, 1H), 7.60 (d, J=7.8 Hz, 1H), 7.34–7.60 (m, 18H), 7.09 (br s, 1H), 4.92 (d, J=10.9 Hz, 1H), 4.86 (d, J=10.9 Hz, 1H), 4.83 (d, J=11.0 Hz, 1H), 4.79 (d, J=10.9 Hz, 1H), 4.66 (d, J=11.0 Hz, 1H), 4.61 (d, J=10.9 Hz, 1H), 4.45 (d, J=7.8 Hz, 1H), 4.24 (dt, J=9.3, 6.9 Hz, 1H), 3.89 (dt, J=9.3, 7.1 Hz, 1H), 3.12 (t, J=6.9 Hz, 2H), 2.66 (t, J=6.8 Hz, 2H), 1.62–1.47 (m, 6H); $^{13}$C NMR (125 MHz, CDCl$_3$) δ 137.55, 137.49, 137.21, 135.11, 127.34, 127.27, 127.20, 126.96, 126.80, 126.67, 126.49, 126.45, 121.18, 120.75, 118.09, 117.59, 111.69, 110.04, 102.60, 83.61, 81.28, 76.09, 74.59, 73.90, 73.73, 73.63, 70.42, 68.88, 68.51, 40.90, 29.29, 26.00, 24.69.

K. 2-(N-Phenylsulfonylindol-3-yl)ethyl 2,3,4-Tri-O-benzyl-6-O-(6-azidohexyl)-β-D-glucopyranoside (III-19c)

A stirred solution of 6-azido-1-hexanol (0.087 g, 0.61 mmol), prepared in a manner similar to 5-azido-1-pentanol above, and 2,6-di-tert-butyl-4-methylpyridine (0.125 g, 0.061 mmol) in dichloromethane (5 ml) was treated with triflic anhydride (0.1 ml, 0.61 mmol) at room temperature. After 15 min the solution was diluted with dichloromethane (20 ml) and poured into saturated aqueous sodium bicarbonate (20 ml). The organic phase was washed with brine, dried over magnesium sulfate, filtered, and concentrated, to afford a white semisolid which was used without purification. A solution of the alcohol III-17 (0.3 g, 0.41 mmol) and the crude triflate in dichloromethane (3 ml) was treated with sodium hydride (0.024 g, 0.6 mmol, 66% dispersion in oil) followed by 15-crown-5 (10 mg). The mixture was then stirred at ambient temperature for 48 h, diluted with dichloromethane (25 ml), and poured into saturated aqueous ammonium chloride (20 ml). The aqueous phase was extracted with dichloromethane (2×20 ml) and the combined organic solutions were washed with brine (25 ml), dried over magnesium sulfate, filtered, and concentrated in vacuo. Flash chromatography (15% ethyl acetate/hexane) furnished III-19c (302 mg, 86% yield) as a colorless oil: [α]D$^{25}$ −4.8° (c 1.06, CH$_2$Cl$_2$); IR (solvent?) 3030 (m), 2991 (w), 2920 (m), 2832 (m), 2110 (s), 1720 (w), 1609 (w), 1450 (s), 1372 (s), 1252 (s), 1212 (w), 1180 (s), 1122 (s), 1091 (s), 1071 (s), 892 (w), 692 (br), 600 (s), 573 (s) cm$^{-1}$; $^1$H NMR (500 MHz, CDCl$_3$) δ 7.97 (d, J=7.8 Hz, 1H), 7.83 (dd, J=8.5, 1.1 Hz, 2H), 7.50–7.16 (m, 22H), 4.91 (d, J=10.9 Hz, 1H), 4.85 (d, J=10.9 Hz, 1H), 4.78 (d, J=10.9 Hz, 1H), 4.73 (d, J=11.0 Hz, 1H), 4.61 (d, J=10.9 Hz, 1H), 4.41 (d, J=7.7 Hz, 1H), 4.20 (dt, J=9.4, 7.1 Hz, 1H), 3.83 (dt, J=9.4, 7.5 Hz, 1H), 3.69–3.56 (m, 4H), 3.53–3.48 (m, 1H), 3.43–3.40 (m, 3H), 3.19 (t, J=6.9 Hz, 2H), 3.01 (t, J=7.0 Hz, 2H), 1.63–1.20 (m, 8H); $^{13}$C NMR (125 MHz, CDCl$_3$) δ 138.56, 138.37, 138.27, 138.23, 135.17, 133.59, 130.96, 129.12, 128.41, 128.33, 128.27, 127.99, 127.84, 127.75, 127.57, 127.56, 126.66, 124.72, 123.46, 123.11, 119.64, 119.44, 113.70, 103.74, 84.64, 82.24, 77.93, 75.66, 74.96, 74.89, 74.73, 71.52, 69.65, 68.75, 51.33, 29.48, 28.72, 26.52, 25.73, 25.71; high resolution mass spectrum (FAB, m-nitrobenzyl alcohol) m/z 881.3538 [(M+Na)$^+$; calcd for C$_{49}$H$_{54}$N$_4$O$_8$S: 881.3560].

L. 2-(1H-Indol-3-yl)ethyl 2,3,4-Tri-O-benzyl-6-O-(6-aminohexyl)-β-D-glucopyranoside (III-4c)

A solution of azide III-19c (0.234 g, 0.272 mmol) in THF (15 ml) was treated sequentially with water (0.12 ml, 6.67 mmol) and triphenylphosphine (0.142 g) and then heated to 60° C. for 4 h. The mixture was then cooled and concentrated to a gum. Flash chromatography (10% methanol/dichloromethane) yielded the requisite amine (190 mg, 84% yield) as a colorless oil: [α]$_D^{25}$ −1.7° (c 0.52, CHCl$_3$); IR (CH$_2$Cl$_2$) 3730 (w), 3045 (m), 2940 (m), 1610 (w), 1450 (m), 1426 (s), 1372 (m), 1271 (s), 1183 (s), 1180 (s), 1115 (s), 1091 (s), 1076 (s), 900 (s), 730 (br s) cm$^{-1}$; $^1$H NMR (500 MHz, CDCl$_3$) δ 7.97 (d, J=8.3 Hz, 1H), 7.83 (apparent d, J=7.4 Hz, 2H), 7.49–7.44 (m, 3H), 7.37–7.14 (m, 17H), 4.90 (d, J=10.9 Hz, 1H), 4.85 (d, J=10.9 Hz, 1H), 4.78 (d, J=10.9 Hz, 1H), 4.72 (d, J=11.0 Hz, 1H), 4.61 (d, J=10.9 Hz, 1H), 4.59 (d, J=11.0 Hz, 1H), 4.41 (d, J=7.8 Hz, 1H), 4.20 (dt, J=9.6, 6.9 Hz, 1H), 3.83 (dt, J=9.6, 7.2 Hz, 1H), 3.67 (apparent t, J=9.0 Hz, 2H), 3.63–3.60 (m, 1H), 3.58 (apparent t, J=9.0 Hz, 2H), 3.49 (dt, J=9.4, 6.5 Hz, 1H), 3.41 (t, J=6.7 Hz, 2H), 3.39–3.37 (m, 1H), 3.00 (t, J=6.9 Hz, 2H), 2.99–2.97 (br, 2H), 1.57–1.25 (m, 8H); $^{13}$C NMR (125 MHz, CDCl$_3$) δ 138.24, 133.60, 129.13, 128.41, 128.34, 128.27, 128.00, 127.85, 127.84, 127.56, 126.67, 124.74, 123.47, 123.12, 119.68, 113.71, 103.73, 84.65, 82.25, 77.95, 75.65, 74.97, 74.90, 74.74, 71.64, 69.65, 68.76, 29.55, 26.60, 25.88, 25.71.

A solution of the above amine (0.248 g, 0.30 mmol) in ethanol (22.5 ml) was treated with 5 M aqueous potassium hydroxide (4.5 ml) and heated to reflux. After 5 h the mixture was cooled, diluted with saturated aqueous ammonium chloride (30 ml), and poured into dichloromethane (30 ml). The aqueous phase was extracted with dichloromethane and the combined organic solutions were washed with brine, dried over anhydrous sodium sulfate, and concentrated in vacuo. Flash chromatography (10% methanol/dichloromethane) furnished III-4c (179 mg, 87% yield) as a colorless oil: [α]$_D^{25}$ +9.4° (c 0.25, CHCl$_3$); IR (CH$_2$Cl$_2$) 3700 (br), 3026 (s), 2980 (s), 2925 (m), 2860 (m), 2085 (m), 1610 (w), 1440 (s), 1421 (s), 1365 (s), 1255 (s), 1175 (s), 1120 (s), 1085 (s), 1075 (s), 980 (w), 890 (s), 700 (br) cm$^{-1}$; $^1$H NMR (500 MHz, CDCl$_3$) δ 8.49 (br s, 1H), 7.49 (d, J=7.8 Hz, 1H), 7.26–7.15 (m, 16H) 7.07 (t, J=8.0 Hz, 1H), 7.00 (t, J=7.1 Hz, 1H), 6.92 (s, 1H), 4.84 (d, J=11.0 Hz, 1H), 4.77 (d, J=10.9 Hz, 1H), 4.76 (d, J=10.9 Hz, 1H), 4.70 (d, J=10.9 Hz, 1H), 4.59 (d, J=11.0 Hz, 1H), 4.49 (d, J=11.0 Hz, 1H), 4.38 (d, J=7.8 Hz, 1H), 4.08 (dt, J=9.3, 6.9 Hz, 1H), 3.77 (dt, J=9.3, 7.1 Hz, 1H), 3.62–3.28 (m, 8H), 3.03 (t, J=7.3 Hz, 2H), 2.67 (t, J=7.5 Hz, 2H), 1.48–1.37 (m, 4H), 1.17–1.13 (m, 4H); $^{13}$C NMR (125 MHz, CDCl$_3$) δ 138.54, 138.48, 136.15, 136.11, 128.39, 128.32, 128.27, 128.03, 127.84, 127.75, 127.54, 127.47, 122.20, 121.79, 119.12, 118.64, 112.16, 111.23, 103.68, 84.65, 82.29, 78.09, 75.62, 74.91, 74.83, 74.68, 71.37, 70.26, 69.77, 39.74, 29.35, 27.37, 26.13, 25.83, 25.42.

M. 5-Trifluoroacetamido-1-pentanol (III-18a)

A solution of 5-amino-1-pentanol (1.00 g, 9.69 mmol) in methanol (8 ml) was cooled to 0° C. and treated with triethylamine (3.28 ml, 23.5 mmol), followed by dropwise addition of trifluoroacetic anhydride (1.88 ml, 13.4 mmol). The reaction mixture was stirred at room temperature for 16 h. Concentration and flash chromatography (60% ethyl acetate/petroleum ether) then furnished III-18a (1.7 g, 89% yield) as an oil: IR (film) 3300 (s), 3100 (m), 2950 (s), 2875 (m), 1705 (s), 1563 (m), 1450 (w), 1375 (w), 1345 (w), 1210 (s), 1185 (s), 1160 (s), 1075 (w), 1055 (m), 1028 (w), 1003 (w), 970 (w), 875 (w), 720 (m) cm$^{-1}$; $^1$H NMR (500 MHz, CDCl$_3$) δ 6.72 (s, 1H), 3.66 (m, 2H), 3.37 (dd, J=13.3, 6.8 Hz, 2H), 1.77 (s, 1H), 1.66–1.58 (m, 4H), 1.47–1.41 (m, 2H); high resolution mass spectrum (Cl, CH$_4$) m/z 200.0901 [(M+H)$^+$; calcd for C$_7$H$_{13}$F$_3$NO$_2$: 200.0696].

N. 2-(1H-Indol-3-yl)ethyl 2,3,4-Tri-O-benzyl-6-amino-6-deoxy-6-N-(5-hydroxypentyl)-β-D-glucopyranoside (III-4e)

A stirred solution of III-17 (196 mg, 0.27 m mol) in dry dichloromethane (2.7 ml) was cooled to −78° C. and treated with 2,6-di-tert-butyl-4-methylpyridine (880 mg, 0.427 mmol) followed by triflic anhydride (58 ml, 0.347 mmol). The mixture was stirred for 15 min at −78° C., warmed to room temperature over 20 min, and then poured into saturated aqueous sodium bicarbonate (20 ml) and extracted with ethyl acetate (60 ml). The organic layer was washed with saturated aqueous sodium bicarbonate (3×20 ml) and brine (20 ml) and dried over magnesium sulfate. Filtration and concentration in vacuo provided crude triflate which was used without purification.

A solution of 5-trifluoroacetamido-1-pentanol (III-18a) (265 mg, 1.3 mmol) in THF (10 ml) was added to a stirred suspension of sodium hydride (123 mg, 3.07 mmol, 60% oil dispersion) in THF (17 ml) at 0° C. After 10 min the suspension was warmed to room temperature, stirred for 1 h, and recooled to 0° C. and a solution of the above triflate (0.574 mmol) in dichloromethane (25 ml) was added dropwise. The reaction was stirred at 0° C. for 30 min and then at room temperature for 24 h, cooled to 0° C., quenched with saturated aqueous ammonium chloride (10 ml), and extracted with ethyl acetate (2×150 ml). The combined extracts were washed with water (50 ml) and brine (50 ml), dried over magnesium sulfate, filtered, and concentrated in vacuo. Flash chromatography (2% methanol/dichloromethane) afforded an inseperable mixture of compounds, presumably III-19d and its benzenesulfonamide deprotected counterpart, which was used directly in the next step.

A stirred solution of the above mixture in ethanol (6 ml) was treated with 5 M aqueous NaOH (2 ml, 10 mmol) and the reaction mixture was heated to reflux for 2 h, cooled, and concentrated in vacuo. The residue was dissolved in ethyl acetate (40 ml) and the solution was washed with water (15 ml) and brine (15 ml), dried over magensium sulfate, filtered, and concentrated in vacuo. Flash chromatography (5% methanol/dichloromethane) afforded III-4e (150 mg, 83% yield for 3 steps) as a pale yellow oil: [α]$_D^{25}$ +3.2° (c 0.31, acetonitrile); UV (1.14×10$^{-4}$ M, acetonitrile) λmax 289.6 (ε 4.17×10$^3$), 280.8 (4.97×10$^3$), 220.0 (2.4×10$^4$) nm; IR (film) 3420 (w), 3300 (w), 3063 (w), 3033 (w), 2938 (m), 2860 (m), 1495 (w), 1455 (m), 1360 (m), 1210 (w), 1072 (s), 1026 (m), 910 (w), 538 (s), 495 (s) cm$^{-1}$; $^1$H NMR (500 MHz, CDCl$_3$) δ 7.98 (s, 1H), 7.59 (d, J=7.9 Hz, 1H), 7.33–7.04 (m, 19H), 4.90 (d, J=10.9 Hz, 1H), 4.85 (d, J=11.1 Hz, 1H), 4.80 (d, J=11.0 Hz, 1H), 4.77 (d, J=10.9 Hz, 1H), 4.64 (d, J=11.0 Hz, 1H), 4.60 (d, J=11.1 Hz, 1H), 4.48 (d, J=7.8 Hz, 1H), 4.21 (ddd, J=9.4, 6.7, 6.7 Hz, 1H), 3.89 (ddd, J=9.4, 7.3, 7.3 Hz, 1H), 3.64 (dd, J=9.0, 9.0 Hz, 1H), 3.56 (t, J=6.4 Hz, 2H), 3.51–3.47 (m, 1H), 3.42 (t, J=9.2 Hz, 2H), 3.11 (t, J=7.0 Hz, 2H), 2.96 (dd, J=12.3, 2.6 Hz, 1H), 2.66 (dd, J=12.3, 7.8 Hz, 1H), 2.62–2.54 (m, 2H), 1.93 (s, 2H), 1.54–1.44 (m, 4H), 1.38–1.32 (m, 2H); $^{13}$C NMR (125 MHz, CDCl$_3$) δ 138.57, 138.49, 138.14, 136.17, 128.43, 128.36, 128.29, 128.02, 127.88, 127.82, 127.60, 127.56, 127.50, 122.14, 121.96, 119.30, 118.68, 112.60, 111.13, 103.67, 84.61, 82.45, 79.70, 77.20, 75.68, 74.99, 74.73, 73.82, 70.25, 62.63, 50.52, 49.59, 32.36, 29.28, 25.86, 23.31; high resolution mass spectrum (FAB, m-nitrobenzyl alcohol) m/z 679.3700 [(M+H)$^+$; calcd for C$_{42}$H$_{50}$N$_2$O$_6$: 679.3747].

O. 4-Trifluoroacetamido-1-butanol (III-18b)

Trifluoroacetylation of 4-amino-1-butanol (0.700 g, 7.86 mmol) as described for III-18a followed by flash chromatography (55% ethyl acetate/hexane) afforded III-18b (1.32 g, 85% yield) as an oil: IR (film) 3310 (s), 3100 (m), 2950 (m), 2890 (m), 1710 (s), 1568 (m), 1450 (w), 1380 (w), 1348 (w), 1215 (s), 1186 (s), 1160 (s), 1073 (m), 1053 (m), 1028 (w), 900 (w), 880 (w), 857 (w), 723 (m) cm$^{-1}$; $^1$H NMR (500 MHz, CDCl$_3$) δ 7.28 (s, 1H), 3.72 (dd, J=10.2, 5.8 Hz, 2H), 3.40 (dd, J=12.6, 6.3 Hz, 2H), 1.99 (t, J=4.2 Hz, 1H), 1.78–1.70 (m, 2H), 1.68–1.62 (m, 2H); high resolution mass spectrum (Cl, CH$_4$) m/z 186.0732 [(M+H)$^+$; calcd for C$_6$H$_{11}$F$_3$NO$_2$: 186.0742].

P. 2-(1H-Indol-3-yl)ethyl 2,3,4-Tri-O-benzyl-6-amino-6-deoxy-6-N-(4-hydroxybutyl)-β-D-glucopyranoside (III-4f)

A solution of 4-trifluoroacetamido-1-butanol (III-18b) (425 mg, 2.29 mmol) in THF (10 ml) was added to a stirred suspension of sodium hydride (60% dispersion in oil, 210 mg, 5.27 mmol) in THF (28 ml) at 0° C. After 10 min the suspension was warmed to room temperature, stirred for 1 h, and recooled to 0° C. Crude triflate (0.27 mmol), prepared as described for III-4e, was dissolved in dichloromethane (16 ml) and added dropwise. The reaction was stirred at 0° C. for 1 h and then at room temperature for 24 h, cooled to 0° C., quenched with saturated aqueous ammonium chloride (10 ml), and extracted with ethyl acetate (2×150 ml). The combined extracts were washed with water (50 ml) and brine (50 ml), dried over magnesium sulfate, filtered, and concentrated in vacuo. Flash chromatography (3% methanol/dichloromethane) afforded an inseperable mixture of compounds, presumably III-19e and its benzenesulfonamide deprotected counterpart, which was used directly in the next step.

A stirred solution of the above mixture in ethanol (11 ml) was treated with 2.5 M aqueous NaOH (7.0 ml, 17.5 mmol) and the reaction mixture was heated to reflux for 2 h, cooled to room temperature, and concentrated in vacuo. The residue was taken up in dichloromethane (60 ml) and the solution was washed with brine (20 ml), dried over magnesium sulfate, filtered, and concentrated in vacuo. Flash chromatography (5% methanol/dichloromethane) provided III-4f (148 mg, 39%) as a pale yellow oil: IR (film) 3435 (w), 3310 (w), 2930 (m), 2870 (m), 1502 (w), 1460 (m), 1364 (m), 1215 (w), 1075 (s), 1032 (sh), 1012 (sh), 913 (m), 815 (w), 740 (s), 700 (s) cm$^{-1}$; $^1$H NMR (500 MHz, CDCl$_3$) δ 7.98 (s, 1H), 7.59 (d, J=7.9 Hz, 1H), 7.33–7.21 (m, 1 5H), 7.19–7.16 (m, 2H), 7.12–7.09 (m, 1H), 7.04 (d, J=2.1 Hz, 1H), 4.90 (d, J=10.9 Hz, 1H), 4.86 (d, J=11.1 Hz, 1H), 4.78 (d, J=11.1 Hz, 1H), 4.76 (d, J=10.9 Hz, 1H), 4.63 (d, J=11.0 Hz, 1H), 4.58 (d, J=11.1 Hz, 1H), 4.46 (d, J=7.8 Hz, 1H), 4.20 (ddd, J=9.5, 6.7, 6.7 Hz, 1H), 3.89 (ddd, J=9.5, 7.3, 7.3 Hz, 1H), 3.62 (apparent t, J=9.0 Hz, 1H), 3.53 (t, J=5.3 Hz, 2H), 3.46 (ddd, J=9.5, 4.4, 2.9 Hz, 1H), 3.41 (dd, J=9.1, 7.9 Hz, 1H), 3.36 (apparent t, J=9.2 Hz, 1H), 3.11 (t, J=6.9 Hz, 2H), 2.93 (dd, J=12.3, 2.9 Hz, 1H), 2.63 (dd, J=12.3, 7.9 Hz, 1H), 2.59 (t, J=5.7 Hz, 2H), 1.61 (m, 2H), 1.55 (m, 2H); $^{13}$C NMR (125 MHz, CDCl$_3$) δ 138.50, 138.46, 138.07, 136.15, 128.43, 128.35, 128.28, 127.98, 127.87, 127.82, 127.59, 127.53, 127.46, 122.15, 121.95, 119.29, 118.67, 112.60, 111.14, 103.61, 84.58, 82.38, 79.73, 75.66, 74.97, 74.69, 73.36, 70.20, 62.54, 50.32, 49.49, 32.11, 28.10, 25.85; high resolution mass spectrum (Cl, NH$_3$) m/z 665.3640 [(M+H)$^+$; calcd for C$_{41}$H$_{48}$N$_2$O$_6$: 665.3590].

Q. 2-(1H-Indol-3-yl)ethyl 2,3,4-Tri-O-benzyl-6-O-6-N-(6-hydroxyhexyl)-β-D-glucopyranoside (III-4g)

A solution of 6-trifluoroacetamido-1-hexanol (III-18c) (145.0 mg, 0.680 mmol) in THF (2 ml) was added to a suspension of sodium hydride (60.0 mg, 1.50 mmol, 60% dispersion in oil) in THF (2 ml) at 0° C. The mixture was stirred at room temperature for 1.5 h, cooled to 0° C., and treated with a solution of the triflate derived from III-17 (0.136 mmol), prepared as described for the synthesis of III-4e, in dichloromethane (4 ml). The reaction mixture was then stirred at room temperature for 48 h, cooled to 0° C., quenched with saturated aqueous ammonium chloride (10 ml), and extracted with ethyl acetate (3×10 ml). The combined organic layers were dried over sodium sulfate, filtered, and concentrated in vacuo. Flash chromatography (5% methanol/dichloromethane) afforded an inseperable mixture of compounds, presumably III-19f and its benzenesulfonamide deprotected counterpart, which was used directly in the next step.

A stirred solution of the above mixture in ethanol (6 ml) was treated with 5 N aqueous sodium hydroxide (2 ml) and heated to reflux for 2 h. Cooling followed by concentration in vacuo gave an oily residue which was taken up in water (5 ml) and extracted with dichloromethane (3×5 ml). The organic layer was dried over anhydrous sodium sulfate, filtered, and concentrated in vacuo. Flash chromatography (6% methanol/dichloromethane) furnished III-4g as a colorless oil (36.4 mg, 54% yield): [α]$_D^{25}$ −18° (c 0.18, acetonitrile); UV (1.72×10−4 M, acetonitrile) λmax 290.0 (ε 1.02×10$^3$), 281.2 (1.13×10$^3$), 228.4 (1.39×10$^3$) nm; IR (film) 3440 (m), 3310 (m), 3060 (m), 3030 (m), 2930 (s), 2860 (s), 2240 (w), 1497 (w), 1455 (s), 1360 (m), 1210 (w), 1070 (s), 910 (s), 740 (s), 700 (s) cm$^{-1}$; $^1$H NMR (500 MHz, CDCl$_3$) δ 8.17 (br s, 1H), 7.59 (d, J=7.9 Hz, 1H), 7.33–7.00 (m, 1 9H), 4.91 (d, J=10.9 Hz, 1H), 4.86 (d, J=11.1 Hz, 1H), 4.80 (d, J=11.3 Hz, 1H), 4.78 (d, J=11.1 Hz, 1H), 4.65 (d, J=11.0 Hz, 1H), 4.60 (d, J=11.1 Hz, 1H), 4.47 (d, J=7.8 Hz, 1H), 4.21 (dt, J=9.4, 6.8 Hz, 1H), 3.86 (dt, J=9.4, 7.6 Hz, 1H), 3.64 (t, J=9.0 Hz, 1H), 3.55 (t, J=6.6 Hz, 2H), 3.51–3.40 (m, 3H), 3.12 (t, J=7.2 Hz, 2H), 2.96–2.13 (dd, J=12.2, 2.6 Hz, 1H), 2.68–2.51 (m, 3H), 1.87 (br s, 2H), 1.51–1.41 (m, 4H), 1.33–1.25 (m, 4H); $^{13}$C NMR (125 MHz, CDCl$_3$) δ 138.47, 138.39, 138.05, 136.11, 128.39, 128.34, 128.27, 128.02, 127.96, 127.88, 127.80, 127.59, 127.55, 127.40, 122.10, 121.87, 119.21, 118.62, 112.32, 111.13, 103.61, 84.55, 82.38, 79.77, 75.69, 75.00, 74.72, 73.91, 70.25, 62.67, 50.64, 49.61, 32.55, 29.78, 26.97, 25.81, 25.55; high resolution mass spectrum (Cl, CH$_4$) m/z 693.3946 (M$^+$; calcd for C$_{43}$H$_{50}$N$_2$O$_6$: 693.3903).

R. 5-Acetamido-1-pentanol (III-20)

A solution of 5-amino-1-pentanol (0.650 g, 6.31 mmol) in methanol (15 ml) was cooled to 0° C. and treated with triethylamine (1.62 ml, 11.6 mmol) followed by acetic anhydride (0.891 ml, 9.45 mmol). The reaction mixture was stirred at room temperature overnight. TLC analysis (8% methanol/dichloromethane) then revealed some unreacted material, so additional triethylamine (1.6 ml, 11.6 mmol) and acetic anhydride (0.9 ml, 9.5 mmol) were added at room temperature and the solution was stirred 16 h further. Concentration in vacuo and flash chromatography (7% methanol/dichloromethane) afforded III-20 (1 g, 94% yield) as a pale yellow oil: IR (film) 3300 (s), 3100 (m), 2940 (s), 2870 (m), 1650 (s), 1560 (s), 1439 (m), 1372 (m), 1295 (m), 1220 (w), 1180 (w), 1050 (m), 1010 (w) cm$^{-1}$; $^1$H NMR (500 MHz, CDCl$_3$) δ 6.21 (s, 1H), 3.62 (t, J=6.4 Hz, 2H), 3.23 (dd, J=12.9, 7.0 Hz, 2H), 2.87 (s, 1H), 1.97 (s, 3H), 1.60–1.50 (m, 4H), 1.43–1.37 (m, 2H); high resolution mass spectrum (Cl, CH$_4$) m/z 146.1164 [(M+H)$^+$; calcd for C$_7$H$_{16}$NO$_2$: 146.1181].

S. 2-(N-Phenylsulfonylindol-3-yl)ethyl 2,3,4-Tri-O-benzyl-6-O-(5-acetamidopentyl)-β-D-glucopyranoside (III-4d)

A solution of 5-acetamido-1-pentanol (177 mg, 1.22 mmol) in THF (8 ml) was added to a stirred suspension of sodium hydride (60% dispersion in oil, 108 mg, 2.70 mmol) in THF (20 ml) at 0° C. After 10 min the mixture was stirred at room temperature for 1.5 h and cooled to 0° C. The triflate derived from III-17 (0.245 mmol), prepared as described for the synthesis of III-4a, was dissolved in dichloromethane (20 ml) and slowly added dropwise. The reaction was stirred at 0° C. for 1 h and at room temperature for 24 h, and then was cooled to 0° C., quenched with saturated aqueous ammonium chloride (10 ml) and diluted with ethyl acetate (150 ml). The organic layer was washed with water and brine, dried over magnesium sulfate, filtered, and concentrated in vacuo. Flash chromatography (3% methanol/dichloromethane) afforded an inseperable mixture of compounds, presumably III-21 and its benzenesulfonamide deprotected counterpart, which was used directly in the next step.

A stirred solution of the above mixture in ethanol (4 ml) was treated with 5 N aqueous NaOH (2 ml, 10 mmol) and then heated to reflux for 2 h, cooled, and concentrated in vacuo. The residue was dissolved in ethyl acetate (40 ml) and the resultant solution was washed with water and brine, dried over magnesium sulfate, filtered, and concentrated in vacuo. Flash chromatography (4% methanol/dichloromethane) provided III-4d (88 mg, 50% yield) as a colorless oil: [α]D$^{25}$ +14.5° (c 0.53, CHCl$_3$); IR (film) 3300 (s), 3090 (w), 3065 (m), 3035 (m), 2940 (s), 2870 (s), 1960 (w), 1885 (w), 1815 (w), 1662 (s), 1550 (m), 1500 (m), 1458 (s), 1369 (s), 1285 (m), 1213 (m), 1070 (s), 914 (w), 810 (w), 742 (s), 700 (s) cm$^{-1}$; $^1$H NMR (500 MHz, CDCl$_3$) δ 8.26 (s, 1H), 7.59 (d, J=8.1 Hz, 1H), 7.34–7.21 (m, 16H), 7.19–7.16 (m, 1H), 7.12–7.08 (m, 1H), 7.03 (d, J=2.2 Hz, 1H), 5.41 (s, 1H), 4.92 (d, J=10.9 Hz, 1H), 4.85 (d, J=11.0 Hz, 1H), 4.83 (d, J=11.0 Hz, 1H), 4.78 (d, J=11.0 Hz, 1H), 4.66 (d, J=11.0 Hz, 1H), 4.59 (d, J=11.0 Hz, 1H), 4.45 (d, J=7.8 Hz, 1H), 4.22 (ddd, J=9.4, 6.9, 6.9 Hz, 1H), 3.86 (ddd, J=9.4, 7.5, 7.5 Hz, 1H), 3.68 (dd, J=10.9, 1.8 Hz, 1H), 3.64 (apparent t, J=9.0 Hz, 1H), 3.59 (dd, J=10.9, 5.1 Hz, 1H), 3.55 (apparent t, J=9.0 Hz, 1H), 3.51–3.39 (m, 4H), 3.17–3.13 (m, 2H), 3.12 (t, J=7.2 Hz, 2H), 1.91 (s, 3H), 1.58–1.53 (m, 2H), 1.48–1.42 (m, 2H), 1.38–1.32 (m, 2H); $^{13}$C NMR (125 MHz, CDCl$_3$) δ 170.06, 138.57, 138.22, 136.21, 128.41, 128.35, 128.27, 128.03, 127.87, 127.84, 127.76, 127.59, 127.55, 127.49, 122.18, 121.81, 119.14, 118.61, 112.46, 111.19, 103.68, 84.68, 82.33, 78.04, 77.20, 75.67, 74.93, 74.83, 74.67, 71.42, 70.06, 69.71, 39.56, 29.29, 25.76, 23.61, 23.27; high resolution mass spectrum (Cl. NH$_3$) m/z 721.3790 [(M+H)$^+$; calcd for C$_{44}$H$_{53}$N$_2$O$_7$: 721.3852].

T. 1,2,4,6-Tetra-O-acetyl-3-deoxy-β-D-glucopyranoside (III-23)

A solution of 3-deoxydiacetone-D-glucose (III-22) (27.5 g, 113 mmol) in 60% aqueous acetic acid (200 ml) was heated at 90° C. for 1 h, cooled, and concentrated in vacuo, and the residue was azeotroped with dry benzene (4×20 ml). A solution of the concentrate in dry pyridine (250 ml) was treated with acetic anhydride (107 ml, 1.13 mol) and DMAP (2 mol %, 275 mg) and stirred at room temperature for 30 min. After concentration in vacuo the residue was diluted with water (40 ml) and extracted with dichloromethane (3×40 ml), and the combined extracts were then washed with brine (40 ml), dried over sodium sulfate, filtered, and concentrated in vacuo. Recrystallization from ether afforded the pure β-anomer (11.3 g) as a fine white powder. Concentration of the filtrate and flash chromatography (45% ethyl acetate/hexane) gave a mixture of α- and β-anomers as a colorless gum (23.0 g, total yield 91.7%). β-Anomer III-23: [α]D$^{25}$ 17.1° (c 1.05, CH$_3$OH); IR (CHCl$_3$) 3010 (m), 2940 (w), 2870 (w), 1745 (s), 1510 (w), 1365 (m), 1230 (s), 1210 (s), 1030 (s) cm$^{-1}$; $^1$H NMR (500 MHz, CDCl$_3$) δ 5.67 (d, J=7.9 Hz, 1H), 4.89–4.81 (m, 2H), 4.21 (dd, J=5.1, 12.3 Hz, 1H), 4.12 (dd, J=2.5, 12.2 Hz, 1H), 3.81–3.79 (m, 1H), 2.60 (ddd, J=5.0, 5.0, 12.3 Hz, 1H), 2.10 (s, 3H), 2.06 (s, 3H), 2.03 (s, 3H), 2.02 (s, 3H), 1.64 (apparent q, J=11.0, 1H); $^{13}$C NMR (62.9 MHz, CDCl$_3$) δ 170.69, 169.43, 169.31, 169.19, 93.06, 75.68, 67.33, 65.00, 62.07, 32.69, 20.92, 20.77; high resolution mass spectrum (Cl, NH$_3$) m/z 350.1412 [(M+NH$_4$)+; calcd for C$_{14}$H$_{20}$O$_9$Cl: 350.1450]. Anal. Calcd for C$_{14}$H$_{20}$O$_9$: C, 50.60; H, 6.07. Found: C, 50.65; H, 6.16.

U. 2-(N-Phenylsulfonylindol-3-yl)ethyl 2,3,4-Tri-O-benzyl-6-O-(6-aminohexyl) deoxy-β-D-glucopyranoside (III-24)

Hydrobromic acid (30% in acetic acid, 3 ml, 14.0 mmol) was added to III-23 (750 mg, 2.26 mmol) at 0° C. After 10 min, the solution was warmed to room temperature, stirred for 30 min, diluted with ether (20 ml), and poured into a mixture of ice and saturated aqueous sodium bicarbonate (25 ml). An additional 30 ml of ether was added and the layers were separated. The organic layer was washed with saturated aqueous sodium bicarbonate (3×25 ml), water, and brine, dried over magnesium sulfate, filtered, and concentrated in vacuo. The crude bromide was used without purification in the next step: high resolution mass spectrum (FAB, m-nitrobenzyl alcohol) m/z 370.0470 [(M+NH$_4$)$^+$; calcd for C$_{12}$H$_{17}$BrO$_7$: 370.0494].

A solution of N-(benzenesulfonyl)tryptophol (III-12) (1.20 g, 4.0 mmol) in dry benzene (4 ml) was added to a stirred suspension of activated, powdered 4 Angstrom molecular sieves (1.33 g) in dry hexane (11 ml) at room temperature. A solution of the bromide (2.26 mmol) in dry benzene (4 ml) was introduced, followed by silver(I) oxide (523 mg, 2.26 mmol). The reaction vessel was covered with aluminum foil, and the mixture was stirred for 3 days and then filtered through Celite. Concentration and flash chromatography (10:1 dichloromethane/ether) provided pure III-24 (781 mg, 60% yield) as a white foam: mp 49–51° C.; [α]D$^{25}$ −12° (c 0.21, acetonitrile); UV (8.3×10$^{-5}$ M, acetonitrile) λmax 253.6 (ε 1.12×10$^4$), 214.0 (2.43×10$^4$) nm; IR (film) 3045 (w), 2970 (w), 2895 (w), 1745 (s), 1449 (m), 1370 (s), 1230 (s), 1167 (m), 1120 (w), 1083 (w), 1035 (m), 908 (w), 853 (w), 748 (s), 720 (w), 682 (w) cm$^{-1}$; $^1$H NMR (500 MHz, CDCl$_3$) δ 7.97 (d, J=8.3 Hz, 1H), 7.86–7.84 (m, 2H), 7.53–7.41 (m, 5H), 7.32–7.29 (m, 1H), 7.25–7.22 (t, J=7.6 Hz, 1H), 4.84 (ddd, J=10.7, 9.6, 4.9 Hz, 1H), 4.77 (ddd, J=12.8, 7.6, 5.2 Hz, 1H), 4.49 (d, J=7.6 Hz, 1H), 4.24–4.14 (m, 3H), 3.76 (ddd, J=9.4, 6.9, 6.9 Hz, 1H), 3.68 (ddd, J=9.2, 5.0, 3.0 Hz, 1H), 2.96 (t, J=7.1 Hz, 2H), 2.55 (ddd, J=12.2, 5.0, 3.0 Hz, 1H), 2.06 (s, 3H), 2.04 (s, 3H), 1.93 (s, 3H), 1.56 (apparent q, J=11.5 Hz, 1H); $^{13}$C NMR (125 MHz, CDCl$_3$) δ 170.80, 169.47, 133.68, 131.06, 129.20, 126.72, 124.73, 123.56, 123.16, 119.84, 119.50, 113.66, 106.62, 102.09, 75.03, 68.46, 68.38, 65.83, 62.65, 32.92, 25.37, 20.87, 20.79; high resolution mass spectrum (FAB, m-nitrobenzyl alcohol) m/z 573.1623 (M$^+$; calcd for $C_{28}H_{31}NO_{10}S$: 573.1669).

V. 2-(N-Phenylsulfonylindol-3-yl)ethyl 3-Deoxy-β-D-glucopyranoside (III-25)

Sodium methoxide (55.2 mg, 1.02 mmol) was added to a suspension of III-24 (735 mg, 1.28 mmol) in methanol (6.4 ml). The mixture was stirred at room temperature for 90 min, diluted with methanol (6 ml), and neutralized with Amberlyst® 15 ion exchange resin. The resin was quickly filtered. Concentration in vacuo and flash chromatography (12:1:1 dichloromethane/acetone/methanol) afforded pure III-25 (498 mg, 87% yield) as a white solid: mp 55–57° C.; $[\alpha]D^{25}$ −26° (c 0.25, methanol); UV (1.39×10$^{-4}$ M, acetonitrile) λmax 254.0 (ε 1.24×10$^4$), 216.0 (2.02×10$^4$) nm; IR (film) 3415 (s), 3070 (w), 3025 (w), 2945 (m), 2890 (m), 1605 (w), 1449 (s), 1366 (s), 1279 (w), 1215 (w), 1173 (s), 1125 (m), 1078 (s), 1028 (s), 975 (w), 741 (s), 720 (m), 681 (m) cm$^{-1}$; $^1$H NMR (500 MHz, CD$_3$OD) δ 7.96–7.94 (m, 1H), 7.91–7.89 (m, 1H), 7.61 (s, 1H), 7.59–7.54 (m, 2H), 7.49–7.45 (m, 2H), 7.31–7.28 (m, 1H), 7.24–7.21 (m, 1H), 4.30 (d, J=7.6 Hz, 1H), 4.18 (ddd, J=9.6, 7.0, 7.0 Hz, 1H), 3.88–3.82 (m, 2H), 3.66 (dd, J=11.8, 6.2 Hz, 1H), 3.50 (ddd, J=11.2, 9.4, 4.8 Hz, 1H), 3.40 (ddd, J=12.4, 7.6, 5.0 Hz, 1H), 3.31 (s, 2H), 3.27 (ddd, J=9.2, 6.1, 2.5 Hz, 1H), 3.00 (t, J=6.8 Hz, 2H), 2.31 (ddd, J=12.2, 4.9, 4.9 Hz, 1H), 1.50 (apparent q, J=11.8 Hz, 1H); $^{13}$C NMR (500 MHz, CD$_3$OD) δ 139.40, 136.57, 135.02, 132.62, 130.38, 127.89, 125.65, 125.30, 124.36, 121.74, 120.63, 114.70, 106.49, 81.82, 69.41, 69.37, 66.27, 62.95, 40.72, 26.32; high resolution mass spectrum (Cl, NH$_3$) m/z 465.1627 [(M+NH$_4$)$^+$; calcd for $C_{22}H_{25}NO_7S$: 465.1685].

W. 2-(N-Phenylsulfonylindol-3-yl)ethyl 3-Deoxy-6-O-tert-butyldiphenylsilyl-β-D-glucopyranoside (III-26)

A stirred solution of III-25 (779 mg, 1.74 mmol) in dry DMF (17 ml, 0.1 M) was treated with imidazole (260 mg, 3.83 mmol) followed by tert-butyldiphenylsilyl chloride (0.541 ml, 2.09 mmol). The solution was heated at 50° C. for 24 h, cooled, diluted with ethyl acetate (250 ml), and washed with water and brine. The organic phase was dried over magensium sulfate, filtered, and concentrated in vacuo. Flash chromatography (3% methanol/dichloromethane) provided pure III-26 (1.04 g, 87% yield) as a white foam: $[\alpha]D^{25}$ −24° (c 0.46, acetonitrile); UV (1.68×10$^{-4}$ M, acetonitrile) λmax 254.0 (ε 1.11×10$^4$), 220.4 (1.90×10$^4$) nm; IR (film) 3430 (s), 3080 (w), 3060 (w), 3020 (w), 2940 (s), 2865 (s), 1668 (m), 1449 (s), 1428 (m), 1370 (s), 1275 (w), 1213 (w), 1112 (s), 1070 (s), 855 (w), 820 (w), 740 (s), 720 (w), 700 (m), 680 (w) cm$^{-1}$; $^1$H NMR (500 MHz, acetone-d$_6$) δ 7.98–7.96 (m, 1H), 7.84–7.82 (m, 2H), 7.68–7.65 (m, 4H), 7.51–7.36 (m, 11H), 7.31–7.28 (m, 1H), 7.21–7.18 (m, 1H), 4.19 (d, J=7.4 Hz, 1H), 4.09 (ddd, J=9.5, 6.2, 6.2 Hz, 1H), 3.92 (dd, J=10.3, 5.0 Hz, 1H), 3.84 (dd, J=10.4, 7.3 Hz, 1H), 3.82–3.77 (m, 1H), 3.68 (ddd, J=9.5, 7.1, 7.1 Hz, 1H), 3.48–3.40 (m, 2H), 3.29 (d, J=2.3 Hz, 1H), 2.97–2.89 (m, 2H), 2.37 (ddd, J=12.4, 4.8, 4.8 Hz, 1H), 2.10 (d, J=2.5 Hz, 1H), 1.53 (apparent q, J=11.5 Hz, 1H), 1.06 (s, 9H); $^{13}$C NMR (125 MHz, acetone-d$_6$) δ 138.24, 135.54, 135.51, 135.14, 133.65, 132.46, 132.38, 130.97, 130.00, 129.17, 128.30, 127.86, 126.65, 124.79, 123.42, 123.13, 119.67, 119.34, 113.73, 104.73, 77.34, 68.83, 68.58, 68.28, 66.11, 37.34, 26.77, 25.45, 19.09; high resolution mass spectrum (FAB, m-nitrobenzyl alcohol) m/z 686.2651 [(M+H)$^+$; calcd for $C_{38}H_{43}NO_7SSi$: 686.2607]. Anal. Calcd for $C_{38}H_{43}O_7NSSi$: C, 66.54; H, 6.32. Found: C, 66.18; H, 6.14.

X. 2-(N-Phenylsulfonylindol-3-yl)ethyl 3-Deoxy-2,4-di-O-benzyl-6-O-tert-butyldiphenylsilyl-β-D-glucopyranoside (III-27)

A stirred suspension of sodium hydride (4.63 mmol, 185 mg, 60% oil dispersion) in THF (5 ml) was cooled to 0° C. and a solution of III-26 (1.27 g, 1.85 mmol) in THF (10 ml) was added. After 10 min the reaction mixture was warmed to room temperature, stirred for 1 h, recooled to 0° C. and treated with benzyl bromide (5.55 mmol, 0.660 ml) followed by tetrabutylammonium iodide (68 mg, 0.185 mmol). The reaction was then warmed to room temperature, stirred for 3 days, and quenched with saturated aqueous ammonium chloride (3 ml) at 0° C. The mixture was diluted with ether (80 ml), washed with water (2×30 ml) and brine (30 ml), dried over magnesium sulfate, filtered, and concentrated in vacuo. Flash chromatography (25% ether/petroleum ether) furnished pure III-27 (760 mg, 47% yield) as a white foam: $[\alpha]D^{25}$ −2.7° (c 0.66, acetonitrile); UV (1.9×10$^{-4}$ M, acetonitrile) λmax 254.0 (ε 1.19×10$^4$), 220.8 (1.71×10$^4$) nm; IR (film) 3080 (m), 3040 (m), 2945 (s), 2870 (s), 1585 (w), 1494 (w), 1445 (s), 1425 (m), 1369 (s), 1330 (w), 1307 (w), 1275 (m), 1205 (m), 1171 (s), 1109 (s), 1100 (s), 1025 (s), 972 (m), 935 (w), 905 (w), 849(w), 817 (m), 739(s), 695(s) cm$^{-1}$; $^1$H NMR (500 MHz, CDCl$_3$) δ 7.99–7.97 (m, 1H), 7.83–7.80 (m, 2H), 7.71–7.67 (m, 4H), 7.51–7.18 (m, 23H), 4.70 (d, J=12.0 Hz, 1H), 4.59 (d, J=11.4 Hz, 1H), 4.56 (d, J=12.0 Hz, 1H), 4.44 (d, J=11.5 Hz, 1H), 4.42 (d, J=7.5 Hz, 1H), 4.19 (ddd, J=9.6, 6.7, 6.7 Hz, 1H), 3.95 (dd, J=11.2, 1.9 Hz, 1H), 3.88 (dd, J=11.2, 5.0 Hz, 1H), 3.80 (ddd, J=9.6, 7.3, 7.3 Hz, 1H), 3.55 (ddd, J=11.0, 9.4, 4.6 Hz, 1H), 3.41 (ddd, J=9.2, 4.9, 1.8 Hz, 1H), 3.32 (m, 1H), 3.04 (t, J=7.2 Hz, 2H), 2.52 (ddd, J=12.3, 4.9, 4.9 Hz, 1H), 1.55 (apparent q, J=11.6 Hz, 1H), 1.03 (s, 9H); $^{13}$C NMR (125 MHz, CDCl$_3$) δ 138.68, 138.32, 138.08, 135.72, 135.56, 135.18, 133.74, 133.54, 133.49, 131.06, 129.52, 129.10, 128.36, 128.30, 127.66, 127.63, 127.59, 127.51, 127.45, 126.63, 124.69, 123.47, 123.12, 119.94, 119.57, 113.67, 105.11, 79.10, 75.27, 72.68, 72.06, 71.37, 68.18, 63.23, 34.99, 26.77, 25.80, 19.29; high resolution mass spectrum (FAB, m-nitrobenzyl alcohol) m/z 865.3419 (M$^+$; calcd for $C_{52}H_{55}NO_7SSi$: 865.3468).

Y. 2-(N-Phenylsulfonylindol-3-yl)ethyl 3-Deoxy-2,4-di-O-benzyl-β-D-glucopyranoside (III-28)

Tetrabutylammonium fluoride (1.0 M in THF, 1.17 mmol, 1.17 ml) was added to a stirred solution of III-27 (675 mg, 0.780 mmol) in THF (10 ml). The solution was stirred for 2 h, diluted with ethyl acetate, washed with water and brine, and dried over magnesium sulfate, filtered, and concentrated in vacuo. Flash chromatography (60% ether/petroleum ether) afforded pure III-28 (445 mg, 91% yield) as a pale yellow oil: $[\alpha]D^{25}$ +2.5° (c 0.44, acetonitrile); UV (9.97×10$^{-5}$ M, acetonitrile) λmax 254.0 (ε 1.06×10$^4$), 210.0 (2.88×10$^4$) nm; IR (film) 3485 (m), 3080 (w), 3045 (w), 2945 (m), 2890 (m), 1603 (w), 1484(w), 1447 (s), 1369 (s), 1277 (w), 1206 (w), 1173 (s), 1118 (m), 1082 (s), 1039 (m), 1025 (m), 948 (w), 900(w), 745 (s), 717 (m), 693 (m), 678 (m) cm$^{-1}$; $^1$H NMR (500 MHz, CDCl$_3$) δ 7.97 (d, J=8.3 Hz, 1H), 7.84–7.82 (m, 2H), 7.53 (s, 1H), 7.49–7.44 (m, 2H), 7.37–7.21 (m, 1 4H), 4.67 (d, J=12.0 Hz, 1H), 4.60 (d, J=11.4 Hz, 1H), 4.54 (d, J=12.0 Hz, 1H), 4.47 (d, J=11.6 Hz, 1H), 4.45 (d, J=7.5 Hz, 1H), 4.19 (ddd, J=9.5, 6.8, 6.8 Hz, 1H), 3.89–3.84 (m, 2H), 3.73 (dd, J=11.9, 4.6 Hz, 1H), 3.47 (ddd, J=11.0, 9.3, 4.6 Hz, 1H), 3.39 (ddd, J=9.1, 4.5, 3.1 Hz, 1H), 3.26 (ddd, J=11.7, 9.2, 5.1 Hz, 1H), 2.99 (m, 2H), 2.51 (ddd, J=12.3, 4.8, 4.8 Hz, 1H), 1.89 (s, 1H), 1.55 (dd, J=23.4, 11.7 Hz, 1H); $^{13}$C NMR (125 MHz, CDCl$_3$) δ 138.44, 138.30, 137.82, 135.15, 133.63, 131.03, 129.15, 128.49, 128.35, 127.89, 127.79, 127.63, 127.58, 126.68, 124.75, 123.65, 123.15, 119.80, 119.38, 113.73, 105.19, 78.18, 75.02, 72.71, 72.23, 71.29, 68.38, 62.38, 34.83, 25.61; high resolution mass spectrum (FAB, m-nitrobenzyl alcohol) m/z 627.2370 ($M^+$; calcd for $C_{36}H_{37}NO_7S$: 627.2291).

Z. 2-(N-Phenylsulfonylindol-3-yl)ethyl 2,4-Di-O-benzyl-3-deoxy-6-O-(5-azidopentyl)-β-D-glucopyranoside (III-29a)

A stirred solution of 5-bromo-1-pentanol (0.79 g, 4.7 mmol) in DMSO (15 ml) was treated with sodium azide (1.83 g, 28.2 mmol). The resultant mixture was stirred at room temperature for 2.5 h, diluted with water, and extracted with diethyl ether. The combined organic layers were washed with saturated aqueous sodium bicarbonate and brine, dried over magnesium sulfate, filtered, and concentrated in vacuo. The azide was used without purification in the next step. Crude 5-azido-1-pentanol (280 mg, equivalent to 2.17 mmol) and 2,6-di-tert-butyl-4-methylpyridine (441 mg, 2.17 mmol) were dissolved in dichloromethane (9 ml) and triflic anhydride (0.36 ml, 2.17 mmol) was added dropwise. After 10 min the mixture was poured into brine (40 ml) and extracted with dichloromethane (2×40 ml). The combined organic layers were dried over magnesium sulfate, filtered, and concentrated in vacuo. The triflate was used without purification in the next step.

Sodium hydride (16 mg, 0.40 mmol, 60% dispersion in oil) was added to a solution of alcohol III-28 (120 mg, 0.198 mmol) and azido triflate (105 mg, equivalent to 0.40 mmol) in dichloromethane (3 ml) at room temperature. The mixture was stirred for 24 h, diluted with dichloromethane (40 ml) and poured into saturated ammonium chloride (40 ml). The aqueous phase was extracted with dichloromethane and the combined organic solutions were washed with brine, dried over magnesium sulfate, filtered, and concentrated in vacuo. Flash chromatography (15% ethyl acetate/hexane) afforded III-29a (121 mg, 83% yield) as a colorless oil: $[\alpha]D^{25}$ +4.0° (c 0.24, $CHCl_3$); IR ($CHCl_3$) 3022 (s), 2940 (s), 2880 (m), 2105 (s), 1455 (s), 1375 (s), 1270 (s), 1210 (m), 1180 (m), 1125 (m), 1090 (m), 725 (s), 599 (m) $cm^{-1}$; $^1H$ NMR (500 MHz, $CDCl_3$) δ 7.96 (d, J=8.1 Hz, 1H), 7.82 (dd, J=8.2, 0.9 Hz, 2H), 7.50–7.43 (m, 3H), 7.29–7.19 (m, 14H), 4.65 (d, J=12.0 Hz, 1H), 4.58 (d, J=11.4 Hz, 1H), 4.52 (d, J=12.0 Hz, 1H), 4.42 (d, J=11.5 Hz, 1H), 4.18 (dt, J=9.5, 6.7 Hz, 1H), 3.81 (dt, J=9.5, 7.1 Hz, 1H), 3.71 (d, J=10.6 Hz, 1H), 3.57 (dd, J=10.8, 4.7 Hz, 1H), 3.51–3.38 (m, 4H), 3.31–3.21 (m, 1H), 3.16 (t, J=6.9 Hz, 2H), 3.00 (t, J=6.9 Hz, 2H), 2.50–2.46 (dt, J=12.1, 4.5 Hz, 1H), 1.63–1.50 (m, 5H), 1.48–1.32 (m, 3H); $^{13}C$ NMR (62.5 MHz, $CDCl_3$) δ 138.52, 138.23, 137.00, 135.07, 133.59, 131.09, 129.14, 128.43, 128.31, 127.78, 127.68, 127.50, 126.70, 126.69, 124.70, 123.54, 123.09, 119.71, 119.48, 113.70, 105.26, 78.01, 74.92, 72.67, 72.25, 71.38, 71.24, 69.96, 68.41, 34.97, 29.62, 29.15, 28.66, 25.65, 23.39; high resolution mass spectrum (FAB, m-nitrobenzyl alcohol) m/z 761.2973 ($M^+$; calcd for $C_{41}H_{46}N_4O_7S$: 761.2985).

AA. 2-(1H-Indol-3-yl)ethyl 2,4-Di-O-benzyl-3-deoxy-6-O-(5-aminopentyl)-β-D-glucopyranoside (III-5a)

A stirred solution of azide III-29a (80 mg, 0.109 mmol) in THF (5.2 ml) and water (0.083 ml was treated with triphenylphosphine (65 mg, 0.248 mmol), heated at reflux for 2.5 h, cooled, and concentrated in vacuo. Flash chromatography (10% methanol/dichloromethane) furnished the corresponding amine (70 mg, 90% yield) as a colorless oil: IR ($CHCl_3$) 3028 (m), 2940 (s), 2875 (m), 1450 (s), 1370 (s), 1280 (w), 1178 (s), 1122 (m), 1070 (m), 695 (w), 597 (w) $cm^{-1}$; $^1H$ NMR (500 MHz, $CDCl_3$) δ 7.99(d, δ=7.9 Hz, 1H); 7.86 (d, δ=7.7 Hz, 2H); 7.53–7.45 (m, 3H); 7.40–7.23 (m, 14H), 4.68 (d, δ=12.0 Hz, 14); 4.61 (d, δ=11.5 Hz, 1H); 4.55 (d=δ=12.0 Hz, 1H); 4.43 (d, δ=11.5 Hz, 1H); 4.23 (dt, δ−9.5, 6.7 Hz); 3.85 (dt, δ=9.5, 7.1 Hz, 1H); 3.74 (d, δ=10.2 Hz, 1H); 3.60 (dd, δ−10.7, 4.7 Hz, 1H); 3.53–3.42 (m, 4H); 3.33–3.29 (m, 1H); 3.03 (t, δ=6.9 Hz, 2H); 2.86 (brs, 2H), 2.72 (br s, 2H), 2.52 (dt, δ=12.2, 4.1 Hz, 1H); 1.62–1.47 (m, 4H), 1.40–1.35 (m. 3H) $^{13}C$ NMR (125 MHz, $CDCl_3$) δ 138.51, 138.25, 138.00, 135.13, 133.58, 131.05, 129.11, 128.40, 128.27, 127.76, 127.69, 127.62, 127.46, 126.65, 124.68, 123.54, 123.09, 119.91, 119.48, 133.66, 105.21, 77.97, 74.96, 72.64, 72.18, 71.34, 71.21, 69.94, 68.39, 39.70, 34.94, 28.89, 25.59, 23.44, 23.26; high resolution mass spectrum (FAB, m-nitrobenzyl alcohol) m/z 713.3241 ($M^+$; calcd for $C_{41}H_{48}N_2O_7S$: 713.3260).

The above amine (14 mg, 0.020 mmol) was dissolved in ethanol (2.2 ml) and treated with 5 M aqueous sodium hydroxide (0.36 ml). The resultant mixture was heated at reflux for 3 h, cooled, diluted with brine, and poured into dichloromethane. The aqueous layer was extracted with dichloromethane (2×40 ml) and the combined organic solutions were dried over sodium sulfate, filtered, and concentrated in vacuo. Flash chromatography (10% methanol/dichloromethane) afforded III-5a (7 mg, 61% yield) as a colorless oil: $[\alpha]D^{25}$ −12° (c 0.11, $CHCl_3$); $^1H$ NMR (500 MHz, $CDCl_3$) δ 9.05 (br s, 1H), 7.58 (d, J=7.8 Hz, 1H), 7.34–7.25 (m, 11H), 7.14 (t, J=7.5 Hz, 1H), 7.07 (t, J=7.5 Hz, 1H), 7.04 (s, 1H), 4.77 (d, J=11.8 Hz, 1H), 4.60 (d, J=12.0 Hz, 1H), 4.57 (d, J=11.6 Hz, 1H), 4.44 (d, J=7.5 Hz, 1H), 4.39 (d, J=11.5 Hz, 1H), 4.16 (dt, J=9.3, 7.3 Hz, 1H), 3.85 (dt, J=9.3, 7.2 Hz, 1H), 3.70 (d, J=10.4 Hz 1H), 3.51 (dd, J=10.6, 5.8 Hz, 1H), 3.46–3.36 (m, 4H), 3.35–3.29 (m, 1H), 3.11 (t, J=7.2 Hz, 2H), 2.68 (br t, J=7.1 Hz, 2H), 2.53–2.49 (dt, J=12.3, 4.7 Hz, 1H), 1.56–1.42 (m, 5H), 1.36–1.25 (m, 4H); $^{13}C$ NMR (125 MHz, $CDCl_3$) δ 138.53, 137.86, 136.12, 128.45, 128.38, 127.86, 127.82, 127.72, 127.62, 127.12, 123.06, 122.02, 119.32, 118.62, 112.26, 111.63, 105.43, 77.49, 75.28, 72.79, 71.34, 71.19, 71.05, 70.39, 68.85, 39.21, 34.65, 27.54, 26.16, 25.72, 22.51; high resolution mass spectrum (FAB, m-nitrobenzyl alcohol) m/z 573.3313 ($M^+$; calcd for $C_{35}H_{44}N_2O_5$: 573.3328).

AB. 2-(N-Phenylsulfonylindol-3-yl)ethyl 2,4-Di-O-benzyl-3-deoxy-6-O-(6-azidohexyl)-β-D-glucopyranoside (III-29b)

A solution of alcohol III-28 (0.21 g, 0.317 mmol) and benzyl bromide (0.307 g, 1.79 mmol) in THF (4 ml) was sequentially treated with sodium hydride (0.016 g, 0.4 mmol, 60% dispersion in oil) and tetra-n-butylammonium iodide (0.01 g. The mixture was then stirred for 36 h, diluted with saturated aqueous ammonium chloride (10 ml), and poured into ethyl acetate (30 ml). The aqueous phase was extracted with ethyl acetate (3×20 ml) and the combined organic solutions were, washed with brine (20 ml), dried over magnesium sulfate, filtered, and concentrated in vacuo. Flash chromatography (15% ethyl acetate/hexane) furnished III-29b (192 mg, 81% yield) as a colorless oil: $[\alpha]D^{25}$ +6.2° (c 0.45, $CH_2Cl_2$); IR ($CH_2Cl_2$) 3041 (s), 2980 (m), 2940 (m), 2865 (m), 2100 (s), 1610 (m), 1450 (s), 1375 (s), 1262 (s), 1190 (s), 1178 (s), 680 (br) $cm^{-1}$; $^1H$ NMR (500 MHz, $CDCl_3$) δ 7.97 (dd, J=6.4, 0.5 Hz, 1H), 7.83 (apparent t, J=7.5 Hz, 2H), 7.51–7.45 (m, 3H), 7.38–7.20 (m, 14H), 4.66 (d, J=12.0 Hz, 1H), 4.59 (d, J=11.4 Hz, 1H), 4.53 (d, J=12.0 Hz, 1H), 4.43 (d, J=11.4 Hz, 1H), 4.41 (d, J=7.6 Hz, 1H), 4.19 (dt, J=9.5, 6.8 Hz, 1H), 3.82 (dt, J=9.5, 7.1 Hz, 1H), 3.72 (d, J=10.9 Hz, 1H), 3.59 (dd, J=10.9, 4.9 Hz, 1H), 3.51–3.39 (m, 4H), 3.30–3.25 (m, 1H), 3.18 (t, J=6.9 Hz, 2H), 3.01 (t, J=6.9 Hz, 2H), 2.49 (dt, J=12.2, 4.4 Hz, 1H), 1.56–1.49 (m, 5), 1.36–1.31 (m, 4H); $^{13}$C NMR (125 MHz, CDCl$_3$) δ 138.54, 138.32, 138.04, 135.16, 133.58, 131.06, 129.13, 128.41, 128.30, 127.78, 127.69, 127.66, 127.49, 126.69, 124.69, 123.54, 123.09, 119.87, 119.48, 113.69, 105.26, 78.03, 74.96, 72.67, 72.29, 71.52, 71.27, 69.94, 68.41, 51.35, 34.99, 29.48, 28.75, 26.53, 25.72, 25.66; high resolution mass spectrum (FAB, m-nitrobenzyl alcohol) m/z 775.3132 [(M+Na)$^+$; calcd for C$_{42}$H$_{48}$N$_4$O$_7$S: 775.3142].

AC. 2-(1H-Indol-3-yl)ethyl 2,4-Di-O-benzyl-3-deoxy-6-O-(6-aminohexyl)-β-D-glucopyranoside (III-5b)

A solution of azide III-29b (0.16 g, 0.21 mmol) in THF (13.3 ml) was treated sequentially with water (0.093 ml, 5.16 mmol) and triphenylphosphine (0.112 g, 0.43 mmol). The mixture was then heated at 60° C. for 5 h, cooled to room temperature, and concentrated in vacuo. Flash chromatography (10% methanol/dichloromethane) yielded the corresponding amine (142.3 mg, 92% yield) as a colorless oil: [α]D$^{25}$ +7.0° (c 1.7, CHCl$_3$); IR (CH$_2$Cl$_2$) 3680 (w), 3045 (m), 2938 (s), 2880 (s), 1606 (m), 1582 (m), 1450 (s), 1370 (s), 1260 (s), 1208 (m), 1180 (s), 1090 (s), 1075 (s), 590 (m), 570 (m) cm$^{-1}$; 1NMR (500 MHz, CDCl$_3$) δ 7.90 (d, J=8.4 Hz, 1H), 7.76 (d, J=7.9 Hz, 1H), 7.76 (d, J=8.4 Hz, 1H), 7.43–7.13 (m, 17H), 4.58 (d, J=12.0 Hz, 1H), 4.52 (d, J=11.5 Hz, 1H), 4.45 (d, J=12.0 Hz, 1H), 4.36 (d, J=11.5 Hz, 1H), 4.33 (d, J=7.5 Hz, 1H), 4.13 (dt, J=9.5, 6.8 Hz, 1H), 3.75 (dt, J=9.51, 7.2 Hz, 1H), 3.65 (d, J=10.4 Hz, 1H), 3.51 (dd, J=10.7, 4.7 Hz, 1H), 3.44–3.32 (m, 4H), 3.20 (m, 1H), 2.93 (t, J=6.9 Hz, 2H), 2.55 (t, J=7.0 Hz, 2H), 2.41 (dt, J=12.3, 4.2 Hz, 1H), 1.53–1.42 (m, 7H), 1.34–1.18 (m, 6H); $^{13}$C NMR (125 MHz, CDCl$_3$) δ 138.30, 138.06, 137.81, 134.93, 133.32, 130.82, 128.87, 128.15, 128.04, 127.51, 127.45, 127.40, 127.23, 126.43, 124.43, 123.29, 122.84, 119.63, 119.24, 113.43, 105.01, 76.49, 72.41, 72.05, 71.42, 71.03, 69.66, 68.14, 44.72, 41.80, 34.77, 33.26, 29.34, 26.45, 25.75, 25.37.

A solution of the above amine (0.119 g, 0.16 mmol) in ethanol (15 ml) was treated with 5 M aqueous potassium hydroxide (3 ml) and then heated to reflux. After 5 h the mixture was cooled, diluted with saturated aqueous ammonium chloride (25 ml), and poured into dichloromethane (30 ml). The aqueous phase was extracted with dichloromethane (4×10 ml) and the combined organic solutions were dried over sodium sulfate, filtered, and concentrated in vacuo. Flash chromatography (15% methanol/dichloromethane) furnished III-5b (80.9 mg, 73% yield) as a colorless oil: [α]D$^{25}$ +11.8° (c 0.43, CH$_2$Cl$_2$); IR, 3681 (w), 3436 (m), 3025 (m), 2918 (s), 2862 (s), 1729 (m), 1609 (m), 1458 (s), 1251 (m), 1098 (s), 1076 (s) cm$^{-1}$; $^1$H NMR (500 MHz, CDCl$_3$) δ 8.64 (br s, 1H), 7.49 (d, J=8.6 Hz, 1H), 7.27–7.16 (m, 11H), 7.05 (apparent t, J=7.1 Hz, 1H), 6.98 (apparent t, J=5.9 Hz, 1H), 6.93 (s, 1H), 4.67 (d, J=11.8 Hz, 1H), 4.51 (d, J=11.8 Hz, 1H), 4.49 (d, J=11.4 Hz, 1H), 4.36 (d, J=7.6 Hz, 1H), 4.31 (d, J=11.4 Hz, 1H), 4.07 (dt, J=9.5, 7.3 Hz, 1H), 3.75 (dt, J=9.5, 7.5 Hz, 1H), 3.44–3.21 (m, 6H), 3.02 (t, J=7.4 Hz, 2H), 2.63 (br t, J=6.9 Hz, 2H), 2.42 (dt, J=12.3, 4.7 Hz, 1H), 1.49–1.35 (m, 6H), 1.18–1.1 (m, 5H); $^{13}$C NMR (125 MHz, CDCl$_3$) δ 138.70, 138.04, 136.20, 128.42, 128.31, 127.75, 127.58, 127.50, 122.27, 121.78, 119.11, 118.71, 112.42, 111.22, 105.30, 77.92, 75.09, 72.70, 72.40, 71.31, 71.09, 70.00, 69.93, 39.76, 34.91, 29.29, 27.37, 26.09, 25.82, 25.42; high resolution mass spectrum (FAB m-nitrobenzyl alcohol) m/z 609.3332 [(M+Na)$^+$; calcd for C$_{36}$H$_{46}$N$_2$O$_5$: 609.3305].

AD. 2-(1H-Indol-3-yl)ethyl 2,4-Di-O-benzyl-3,6-dideoxy-6-amino-6-N-(5-hydroxypentyl)-β-D-glucopyranoside (III-5c)

Triflic anhydride (126 ml, 0.748 mmol) was added to a stirred solution of III-28 (360 mg, 0.575 mmol) and 2,6-di-tert-butyl-4-methylpyridine (189 mg, 0.92 mmol) in dichloromethane (3 ml) at −78° C. After 20 min at −78° C., the mixture was allowed to warm to room temperature over 20 min. The resultant suspension was poured into saturated aqueous sodium bicarbonate and extracted with ethyl acetate. The organic layer was washed with saturated aqueous sodium bicarbonate and brine, dried over magnesium sulfate, filtered, and concentrated in vacuo. The oily crude triflate was used without purification in the next step. A solution of 5-trifluoroacetamido-1-pentanol (III-18a) (687 mg, 3.45 mmol) in THF (16 ml) was added to a stirred suspension of sodium hydride (8.63 mmol, 345 mg, 60% dispersion in oil) in THF (20 ml) at 0° C. After 10 min the mixture was allowed to warm to room temperature, stirred for 90 min, recooled to 0° C., and treated with a solution of crude triflate (0.575 mmol) in dichloromethane (22 ml). The suspension was stirred for 30 min at 0° C. and then at room temperature for an additional 24 h. The reaction was quenched at 0° C. with saturated aqueous ammonium chloride (10 ml) and extracted with ethyl acetate, and the extracts were washed with water and brine, dried over magnesium sulfate, filtered, and concentrated in vacuo. Flash chromatography (gradient elution, 1% to 2% methanol/dichloromethane) afforded an inseperable mixture of compounds, presumably III-29c and its benzenesulfonamide deprotected counterpart, which was used directly in the next step.

A stirred solution of the above mixture in ethanol (6 ml) was treated with 5 N NaOH (1 ml, 5 mmol), heated at reflux for 2 h, cooled, and concentrated in vacuo. The residue was taken up in dichloromethane and the resultant solution washed with 2 N HCl. The aqueous layer was extracted with dichloromethane and the combined organic layers were washed with brine, dried over magnesium sulfate, filtered, and concentrated in vacuo. Flash chromatography (8% methanol/dichloromethane) yielded pure III-5c (172 mg, 52% yield for 3 steps) as a colorless oil: [α]D$^{25}$ +17° (c 0.15, acetonitrile); UV (6.5×10$^{-5}$ M, acetonitrile) λmax 281.2 (ε 6.2×10$^3$), 218.8 (3.62×10$^4$) nm; IR (film) 3325 (m), 3065 (w), 3035 (w), 3015 (w), 2940 (s), 2870 (s), 1500 (w), 1458 (m), 1354 (w), 1220 (w), 1076 (s), 1030 (m), 745 (s), 700 (s) cm$^{-1}$; $^1$H NMR (500 MHz, CDCl$_3$) δ 8.44 (s, 1H), 7.57 (d, J=7.7 Hz, 1H), 7.31–7.23 (m, 10H), 7.17–7.14 (m, 1H), 7.11–7.07 (m, 1H), 7.04 (d, J=2.0 Hz, 1H), 4.71 (d, J=11.8 Hz, 1H), 4.57 (d, J=11.7 Hz, 1H), 4.56 (d, J=11.9 Hz, 1H), 4.46 (d, J=7.5 Hz, 1H), 4.40 (d, J=11.5 Hz, 1H), 4.20 (ddd, J=13.8, 9.4, 6.8 Hz, 1H), 3.87 (ddd, J=14.9, 9.3, 7.4 Hz, 1H), 3.55–3.50 (m, 3H), 3.32–3.26 (m, 2H), 3.11 (t, J=7.2 Hz, 2H), 3.02 (dd, J=12.4, 2.9 Hz, 1H), 2.68 (dd, J=12.4, 8.1 Hz, 1H), 2.67–2.57 (m, 2H), 2.50 (ddd, J=12.3, 4.8, 4.8 Hz, 1H), 2.20 (s, 3H), 1.57–1.44 (m, 5H), 1.36–1.30 (m, 2H); $^{13}$C NMR (125 MHz, CDCl$_3$) δ 138.61, 137.92, 136.14, 128.41, 128.27, 127.79, 127.70, 127.53, 127.49, 122.18, 121.84, 119.18, 118.67, 112.56, 111.12, 105.22, 105.18, 76.53, 75.14, 74.28, 72.69, 70.99, 69.91, 62.45, 50.69, 49.49, 34.86, 32.28, 29.16, 25.80, 23.27; high resolution mass spectrum (FAB, m-nitrobenzyl alcohol) m/z 573.3314 [(M+H)$^+$; calcd for C$_{35}$H$_{44}$N$_2$O$_5$: 573.3328].

AE. 2-(1H-Indol-3-yl)ethyl 2,4-Di-O-benzyl-3,6-dideoxy-6-amino-6-N-(6-hydroxyhexyl)-β-D-glucopyranoside (III-5d)

A solution of 6-trifluoroacetamido-1-hexanol (III-18c) (147 mg, 0.690 mmol) in THF (1 ml) was added to a suspension of sodium hydride (60% oil dispersion, 69.0 mg, 1.73 mmol) in THF (3 ml) at 0° C. The mixture was stirred at room temperature for 1 h, recooled to 0° C., and treated with a solution of the crude triflate derived from 28 (0.115 mmol), prepared as described for the synthesis of III-5c, in dry dichloromethane (5 ml). The reaction mixture was then warmed to room temperature, stirred for 48 h, and quenched at 0° C. with saturated ammonium chloride solution. The mixture was extracted with ethyl acetate and the combined organic layers were dried over sodium sulfate, filtered, and concentrated in vacuo, affording an inseperable mixture of compounds, presumably III-29d and its benzenesulfonamide deprotected counterpart, which was used directly in the next step.

A stirred solution of the above mixture in ethanol (6 ml) was treated with 5 N sodium hydroxide (2 ml), heated to reflux for 2 h, cooled, and concentrated in vacuo. The oily residue was taken up in water and extracted with dichloromethane, and the organic layer was dried over sodium sulfate, filtered, and concentrated in vacuo. Flash chromatography (5% methanol/dichloromethane) yielded III-5d (56 mg, 64% yield for 2 steps) as a colorless oil: $[\alpha]D^{25}$ +13° (c 0.12, acetonitrile); UV ($1.23 \times 10^{-4}$ M, acetonitrile) $\lambda$max 289.6 ($\epsilon$ $1.78 \times 10^3$), 280.8 ($1.37 \times 10^3$), 228.0 ($2.63 \times 10^3$) nm; IR (film) 3300 (br), 3060 (w), 3030 (w), 2930 (s), 2860 (m), 1450 (m), 1350 (w), 1070 (s), 740 (s), 700 (s) cm$^{-1}$; $^1$H NMR (500 MHz, CDCl$_3$) $\delta$ 8.16 (br s, 1H), 7.60 (d, J=7.8 Hz, 1H), 7.35–7.04 (m, 14H), 4.71 (d, J=11.8 Hz, 1H), 4.60 (d, J=11.6 Hz, 1H), 4.57 (d, J=11.9, 1H), 4.47 (d, J=7.6 Hz, 1H), 4.41 (d, J=11.5 Hz, 1H), 4.20 (dt, J=9.4, 6.8 Hz, 1H), 3.87 (dt, J=9.3, 7.6 Hz, 1H), 3.56 (t, J=10.0 Hz, 1H), 3.52 (m, 1H), 3.12 (t, J=6.9 Hz, 2H), 3.04 (d, J=2.8 Hz, 1H), 3.02 (d, J=2.8 Hz, 1H), 2.70–2.48 (m, 4H), 2.05 (br s, 2H), 1.54 (q, J=11.6 Hz, 1H), 1.48–1.26 (m, 8H); $^{13}$C NMR (125 MHz, CDCl$_3$) $\delta$ 138.61, 137.95, 136.14, 128.40, 128.27, 127.77, 127.69, 127.53, 127.49, 122.12, 121.85, 119.19, 118.68, 112.54, 111.10, 105.24, 76.87, 76.74, 75.17, 74.37, 72.70, 71.00, 69.92, 62.71, 50.81, 49.58, 34.90, 32.53, 29.67, 26.94, 25.81, 25.53; high resolution mass spectrum (Cl, CH$_4$) m/z 587.3557 [(M+H)$^+$; calcd for C$_{36}$H$_{47}$N$_2$O$_5$: 587.3485].

AF. 5-Phthalimido-1-pentanol (III-33)

A solution of 5-amino-1-pentanol (5.00 g, 48.5 mmol) in benzene (150 ml) was treated with N-carboethoxyphthalimide (11.0 g, 50.2 mmol) and stirred at room temperature for 5 h. Concentration in vacuo and flash chromatography (25% ethyl acetate/petroleum ether) yielded III-33 (9.6 mg, 84% yield) as a clear, colorless oil: UV ($9.65 \times 10^{-4}$ M, acetonitrile) $\lambda$max 292.0 ($\epsilon$ 212), 242.4 (226) nm; IR (CHCl$_3$) 3460 (br), 2940 (s), 2860 (s), 1770 (s), 1710 (s), 1610 (s), 1470 (s), 1440 (s), 1400(s), 1370 (s), 1190 (m), 1170 (m), 1130 (m), 1050 (s), 960 (m), 890 (m), 875 (m), 790 (m), 720 (s) cm$^{-1}$; $^1$H NMR (500 MHz, CDCl$_3$) $\delta$ 7.72–7.70 (m, 2H), 3.69 (t, J=7.2 Hz, 1H), 3.64 (t, J=6.5 Hz, 1H), 2.17 (br s, 1H), 1.74–1.59 (m, 2H), 1.46–1.40 (m, 1H); $^{13}$C NMR (125 MHz, CDCl$_3$) $\delta$ 169.39, 133.78, 131.96, 123.05, 62.34, 37.74, 32.03, 28.22, 22.93; high resolution mass spectrum (Cl, NH$_3$) m/z 234.1108 [(M+H)$^+$; calcd for C$_{13}$H$_{15}$NO$_3$: 234.1129].

AG. 3,4-Di-O-Benzyl-6-O-(5-phthalimidopentyl)-D-glucal (III-34)

5-Phthalimidopentyl triflate was prepared as follows: A stirred solution of 5-phthalimido-1-pentanol (III-33) (1.32 g, 4.67 mmol) and 2,6-di-tert-butyl-4-methylpyridine (0.960 g, 4.67 mmol) in dry dichloromethane (10 ml) was treated with triflic anhydride (0.784 ml, 4.67 mmol). After 10 min at room temperature, the mixture was diluted with water (100 ml) and extracted with dichloromethane (2×200 ml). The combined extracts were washed with brine, dried over sodium sulfate, filtered, and concentrated in vacuo, affording a yellow solid which was used without purification in the next reaction. Sodium hydride (60% dispersion in oil, 0.20 g, 5.06 mmol) was added to a solution of alcohol III-32 (1.27 g, 3.89 mmol), 5-phthalimdopentyl triflate (4.67 mmol), and 15-crown-5 (20 mg, 2.3 mol %), in dichloromethane (100 ml) at 0° C. After stirring for 24 h at room temperature, the mixture was poured into water. The aqueous layer was extracted with dichloromethane (3×50 ml) and the combined extracts were washed with water, dried over magnesium sulfate and concentrated in vacuo. Flash chromatography (3% ether/dichloromethane) provided III-34 (1.82 g, 86% yield) as a colorless oil: $[\alpha]D^{25}$ –8.2° (c 0.70, CHCl$_3$); IR (CHCl$_3$) 3080 (w), 3020 (m), 3009 (m), 2959 (m), 2880 (m), 1780 (m), 1719 (s), 1652 (m), 1500 (w), 1470 (w), 1457 (m), 1440 (m), 1400 (s), 1365 (m), 1235 (m), 1110 (br, s), 1058 (br, s), 908 (w), 692 (m), cm$^{-1}$; $^1$H NMR (500 MHz, CDCl$_3$) $\delta$ 7.80 (m, 2H), 7.68 (m, 2H), 7.25–7.34 (m, 10H), 6.38 (dd, J=6.1, 1.2 Hz, 1H), 4.84 (m, 2H), 4.66 (d, J=11.4 Hz, 1H), 4.63 (d, J=11.7 Hz, 1H), 4.55 (d, J=11.7 Hz, 1H), 4.19 (m, 1H), 4.00 (m, 1H), 3.81 (dd, J=8.7, 6.2 Hz, 1H), 3.64–3.74 (m, 4H), 3.40–3.50 (m, 2H), 1.60–1.70 (m, 4H), 1.40 (m, 2H); $^{13}$C NMR (62.9 MHz, CDCl$_3$) $\delta$ 168.4, 144.8, 138.4, 138.3, 133.9, 132.2, 128.4, 127.9, 127.8, 127.6, 123.2, 99.9, 76.8, 75.8, 74.5, 73.8, 71.4, 70.5, 69.2, 37.9, 29.2, 28.5, 23.5; high resolution mass spectrum (Cl, NH$_3$) m/z 541.2483 (M$^+$; calcd for C$_{33}$H$_{35}$NO$_6$: 541.2464).

AH. 2-(N-Phenylsulfonylindol-3-yl)ethyl 3,4-Di-O-benzyl-6-O-(5-phthalimidopentyl)-$\beta$-D-glucopyranoside (III-35)

A solution of dimethyldioxirane in acetone (1.2 equiv, ca. 0.05 M) was added dropwise to glycal III-34 (1.53 g, 2.80 mmol) in dichloromethane (26 ml) at 0° C. The mixture was stirred at 0° C. for 1 h and concentrated in vacuo. To a solution of the crude epoxide and III-12 (1.15 g, 3.82 mmol) in THF (12 ml) at –78° C. was added ZnCl$_2$ (1.0 M in ether, 5.6 ml, 5.6 mmol) and the mixture was allowed to stir at –78° C. for 1 h. The solution was then slowly warmed to room temperature and stirred 18 h. The mixture was poured into saturated aqueous sodium bicarbonate (50 ml) and extracted with ethyl acetate (3×50 ml) and the combined extracts were washed with water, dried over magnesium sulfate, and concentrated in vacuo. Flash chromatography (45% ethyl acetate/hexane) yielded III-35 (1.05 g, 44% yield) as a colorless oil: $[\alpha]D^{25}$ –8.1° (c 1.8 CHCl$_3$); IR (CHCl$_3$) 3069 (w), 3039 (m), 3019 (m), 2955 (m), 2879 (m), 1780 (m), 1719 (s), 1612 (w), 1472 (w), 1451 (s), 1401 (s), 1370 (s), 1175 (s), 1121 (s), 1068 (s), 695 (w), 680 (w), 596 (m), 570 (m) cm$^{-1}$; $^1$H NMR (500 MHz, CDCl$_3$) $\delta$ 7.96 (dd, J=8.1, 0.6 Hz, 1H), 7.85 (dd, J=8.2, 0.9 Hz, 2H), 7.78 (m, 2H), 7.66 (m, 2H), 7.20–7.50 (m, 17H), 4.89 (d, J=11.3 Hz, 1H), 4.86 (d, J=11.0 Hz, 1H), 4.83 (d, J=11.4 Hz, 1H), 4.60 (d, J=10.9 Hz, 1H), 4.24 (d, J=7.6 Hz, 1H), 4.20 (dt, J=9.5, 6.4 Hz, 1H), 3.76 (dt, J=9.5, 7.2 Hz, 1H), 3.37–3.68 (m, 10H), 2.98 (m, 2H), 2.13 (br s, 1H), 1.57–1.68 (m, 4H), 1.38 (m, 2H); $^{13}$C NMR (62.9 MHz, CDCl$_3$) $\delta$ 168.4, 138.6, 138.2, 135.1, 133.8, 133.7, 132.1, 131.0, 129.1, 128.4, 127.9, 127.8, 127.7, 126.7, 124.7, 123.5, 123.1, 119.7, 119.4, 113.7, 102.8, 84.4, 76.5, 75.1, 71.5, 69.6, 68.7, 37.8, 29.2, 28.4, 25.4, 23.5; high resolution mass spectrum (Cl, NH$_3$) m/z 662.2774 (M$^+$; calcd for C$_{35}$H$_{42}$SO$_7$: 662.2775).

AI. 2-Deoxy-3,4-di-O-benzyl-6-O-(5-phthalimidopentyl)-$\beta$-D-glucopyranoside (III-36)

A solution of III-35 (0.455 g, 0.530 mmol) in THF (10 ml) was cooled to –78° C. and treated with carbon disulfide (27 ml, 0.583 mmol) followed by sodium bis(trimethylsilyl) amide (0.6 M in toluene, 0.953 ml, 0.572 mmol). After 20 min, methyl iodide (59 ml, 0.640 mmol) was added and the solution was stirred for 5 min at −78° C. and then at room temperature for 45 min. The reaction mixture was quenched with water (50 ml) and extracted with ethyl acetate (3×50 ml). The organic layer was washed with brine, dried over sodium sulfate, filtered, and concentrated in vacuo, affording the crude xanthate as a pale yellow oil (0.462 g, 92% yield) which was used without purification in the next step.

To a solution of the crude xanthate (0.462 g, 0.487 mmol) and AIBN (10 mg) in toluene (8 ml) was added tributyltin hydride (0.214 ml, 0.795 mmol) and the reaction mixture heated to reflux for 4 h, cooled, and concentrated in vacuo. The residue was taken up in acetonitrile (30 ml) and washed with petroleum ether (5×10 ml), dried over sodium sulfate, filtered, and concentrated in vacuo to an oil. Flash chromatography (20% ethyl acetate/petroleum ether) yielded III-36 (0.296 g, 72% yield) as a colorless oil: $[\alpha]D^{25}$ −10° (c 1.1 $CHCl_3$); IR ($CHCl_3$) 3062 (w), 3031 (w), 3009 (w), 2939 (m), 2864 (m), 1777 (w), 1712 (s), 1610 (w), 1469 (w), 1449 (m), 1396 (s), 1378 (s), 1181 (m), 1171 (s), 1120 (s), 1090 (s), 990 (w), 910 (s), 692 (w), 595 (m) $cm^{-1}$; $^1H$ NMR (500 MHz, $CDCl_3$) δ 7.96 (d, J=7.5 Hz, 1H), 7.84 (m, 2H), 7.79 (m, 2H), 7.66 (m, 2H), 7.20–7.41 (m, 15H), 4.91 (d, J=11.0 Hz, 1H), 4.60 (m, 2H), 4.66 (d, J=11.7 Hz, 1H), 4.41 (d, J=9.7, 1.8 Hz, 1H), 4.15 (dt, J=9.5, 6.6 Hz, 1H), 3.59–3.71 (m, 6H), 3.47 (m, 2H), 3.40 (m, 1H), 2.94 (t, J=6.6 Hz, 2H), 2.57 (ddd, J=14.2, 5.0, 3.2 Hz, 1H), 1.57–1.68 (m, 5H), 1.38 (m, 2H); $^{13}C$ NMR (62.9 MHz, $CDCl_3$) δ 23.5, 25.5, 28.4, 29.2, 36.7, 37.9, 68.1, 70.0, 71.4, 75.0, 75.2, 78.2, 79.3, 99.9, 113.6, 119.6, 123.1, 123.5, 124.7, 126.7, 127.7, 128.0, 128.4, 129.2, 131.1, 132.1, 133.6, 133.8, 135.1, 138.3, 138.5, 168.4; high resolution mass spectrum (Cl, $NH_3$) m/z 814.3287 ($M^+$; calcd for $C_{44}H_{50}SO_8N_2$: 814.3289).

AJ. 2-(1H-Indol-3-yl)ethyl 2-Deoxy-3,4-di-O-benzyl-6-O-(5-aminopentyl)-β-D-glucopyranoside (III-6)

A solution of hydrazine (0.2 M in MeOH, 6 ml) was added to III-36 (0.034 g, 0.043 mmol). After stirring for 16 h, the reaction mixture was concentrated in vacuo, the residue dissolved in ethanol (4 ml), and 5N NaOH (0.90 ml) added. The mixture was heated at reflux for 4 h, cooled, and extracted with dichloromethane (3×10 ml). The combined extracts were washed with brine, dried over magnesium sulfate, and concentrated in vacuo to an oil. Flash chromatogrphy (11% methanol/dichloromethane) afforded 6 (11 mg, 44%) as a pale yellow oil: $[\alpha]D^{25}$ −15° (c 0.62, $CHCl_3$); IR ($CHCl_3$) 3490 (m), 3345 (br, m), 3020 (m), 2945 (s), 2882 (s), 1625 (w), 1500 (w), 1459 (m), 1370 (m), 1230 (w), 1100 (s), 695 (w) $cm^{-1}$; $^1H$ NMR (500 MHz, $CDCl_3$) δ 8.80 (br s, 1H), 7.49 (d, J=7.9 Hz, 1H), 7.19–7.31 (m, 11H), 7.10 (t, J=7.1 Hz, 1H), 7.00 (t, J=8.0 Hz, 1H), 6.97 (s, 1H), 4.83 (d, J=11.1 Hz, 1H), 4.59 (d, J=11.7 Hz, 1H), 4.51 (d, J=11.0 Hz), 4.50 (d, J=11.7, 1H), 4.39 (d, J=9.7 Hz, 1H), 4.00 (apparent q, J=7.3 Hz, 1H), 3.67 (apparent q, J=7.3 Hz, 1H), 3.60 (d, J=9.0 Hz, 1H), 3.56 (m, 1H), 3.46 (dd, J=10.8, 5.3 Hz), 3.31 (m, 4H), 2.98 (t, J=7.2 Hz, 2H), 2.50 (t, J=7.3 Hz, 2H), 2.28 (m, 2H), 1.57 (q, J=10 Hz, 1H), 1.42 (m, 4H), 1.19 (m, 2H); $^{13}C$ NMR (62.9 MHz, $CDCL_3$) δ 138.3, 138.2, 136.2, 128.4, 128.0, 127.7, 127.5, 122.3, 121.8, 119.1, 118.7, 112.0, 111.4, 99.9, 79.3, 78.2, 74.9, 71.4, 71.0, 69.9, 69.8, 39.7, 36.7, 28.8, 27.6, 25.7, 23.1; high resolution mass spectrum (FAB, m-nitrobenzyl alcohol) m/z 573.3371 [$(M+H)^+$; calcd for $C_{35}H_{44}N_2O_5$: 573.3328].

AK. Methyl 2,3,6-Tri-O-benzoyl-4-deoxy-α-D-glucopyranoside (III-38)

A solution of III-37 (5.00 g, 9.87 mmol) in THF (100 ml) was cooled to −78° C. and treated with carbon disulfide (0.45 ml, 7.48 mmol) followed by sodium bis(trimethylsilyl) amide (1.0 M in THF, 10.5 ml, 51.8 mmol). After 20 min, methyl iodide (2.10 ml, 33.7 mmol) was added and the solution was stirred for 5 min at −78° C. and then at room temperature for 45 min. The reaction mixture was quenched with water (5 ml) and extracted with ethyl acetate. The organic layer was washed with brine, dried over sodium sulfate, filtered, and concentrated in vacuo, affording the crude xanthate as a pale yellow oil (5.70 g, 97% yield) which was used without purification in the next step. Purification of an analytical sample by flash chromatography (20% ethyl acetate/petroleum ether) gave white crystals: mp 72–73° C.; $[\alpha]D^{25}$ +140° (c 0.13, acetonitrile); $^{13}C$ NMR (125 MHz, $CDCl_3$) δ 166.10, 165.73, 165.53, 133.37, 133.13, 129.90, 129.75, 129.70, 129.21, 128.90, 128.37, 128.23, 96.94, 76.25, 71.83, 70.45, 67.36, 62.58, 55.60, 19.18; high resolution mass spectrum (FAB, m-nitrobenzyl alcohol) m/z 597.1286 [$(M+H)^+$; calcd for $C_{30}H_{28}O_9S_2$: 597.1253].

Tributyltin hydride (6.68 ml, 24.8 mmol) was added to a solution of the crude xanthate (5.70 g, 9.55 mmol) and AIBN (50 mg) in toluene (120 ml), and the reaction mixture was then heated to reflux for 4 h, cooled, and concentrated in vacuo. The residue was taken up in acetonitrile (200 ml) and extracted with petroleum ether (5×100 ml). The acetonitrile solution was dried over sodium sulfate, filtered, and concentrated in vacuo, affording a clear, colorless oil which solidified on standing. Flash chromatography (20% ethyl acetate/petroleum ether) yielded III-38 (3.60 g, 82% yield) as a white solid: mp 119–120° C.; $[\alpha]D^{25}$ +121° (c 0.17, acetonitrile); IR ($CHCl_3$) 3010 (m), 1730 (s), 1600 (w), 1580 (w), 1460 (m), 1270 (s), 1220 (s), 1110 (s), 1080 (m), 1060 (m), 1040 (m), 750 (s), 710 (s), 660 (m) $cm^{-1}$; $^1H$ NMR (500 MHz, $CDCl_3$) δ 8.08 (dd, J=8.3, 1.2 Hz, 2H), 8.05 (dd, J=8.3, 1.2 Hz, 2H), 8.00 (dd, J=8.4, 1.3 Hz, 2H), 7.51–7.35 (m, 9H), 5.78 (m, 1H), 5.31 (dd, J=10.2, 3.6 Hz, 1H), 5.15 (d, J=3.6 Hz, 1H), 4.45–4.43 (m, 3H), 3.44 (s, 3H), 2.47 (ddd, J=12.5, 5.2, 2.1, 1H), 1.89 (q, J=12 Hz, 1H); $^{13}C$ NMR (125 MHz, $CDCl_3$) δ 166.23, 166.09, 165.81, 133.22, 133.16, 133.09, 129.84, 129.67, 129.62, 129.41, 128.42, 128.35, 128.32, 97.82, 72.57, 68.38, 66.05, 65.33, 55.32, 33.16; high resolution mass spectrum (Cl, $NH_3$) m/z 536.1902 [$(M+NH_4)^+$; calcd for $C_{28}H_{30}N_1O_8$: 536.1919].

AL. Acetyl 2,3,6-Tri-O-benzoyl-4-deoxy-α-D-glucopyranoside (III-39)

A solution of glycoside III-38 (0.50 g, 1.1 mmol) in acetic anhydride (3.0 ml, 32 mmol) was cooled to 0° C. and treated with boron trifluoride etherate (0.1 ml). The reaction mixture was then stirred at room temperature for 4 h, diluted with ethyl acetate, and poured into ice-cold saturated sodium bicarbonate. The layers were separated and the aqueous layer was extracted with ethyl acetate. The combined extracts were washed with brine, dried over sodium sulfate, filtered, and concentrated in vacuo, affording III-39 (0.45 g, 85% yield) as a colorless oil which crystallized upon standing as white needles: mp 123–124° C.; $[\alpha]D^{25}$ +123° (c 0.19, acetonitrile); IR ($CHCl_3$) 3020 (s), 2400 (w), 1760 (m), 1730 (s), 1460 (w), 1280 (s), 1220 (s), 1110 (s), 930 (m) $cm^{-1}$; $^1H$ NMR (500 MHz, $CDCl_3$) δ 8.07–8.05 (m, 2H), 7.97–7.92 (m, 5H), 7.51–7.36 (m, 8H), 6.58 (d, J=3.7 Hz, 1H), 5.78 (m, 1H), 5.52 (m, 1H), 4.46 (m, 3H), 2.52 (ddd, J=12.5, 5.2, 2.1 Hz, 1H), 2.17 (s, 3H), 2.03 (m, 1H); $^{13}C$ NMR (125 MHz, $CDCl_3$) δ 168.87, 166.16, 165.54, 133.35, 133.29, 133.22, 129.71, 129.66, 129.58, 129.35, 129.02, 128.42, 128.39, 90.32, 71.59, 71.36, 70.78, 68.12, 68.05, 65.57, 32.76, 20.86, 20.80; high resolution mass spectrum (Cl, $NH_3$) m/z 536.1902 [$(M+NH_4)^+$; calcd for $C_{29}H_{26}O_9$: 536.1919].

AM. 2-(N-Phenylsulfonylindol-3-yl)ethyl 2,3,6-Tri-O-benzoyl-4-deoxy-β-D-glucopyranoside (III-40)

A stirred solution of acetate III-39 (0.137 g, 0.29 mmol) in dichloromethane (3 ml) was cooled to 0° C. and treated with 30% hydrogen bromide in acetic acid (0.07 ml, 0.33 mmol). The reaction mixture was stirred at room temperature for 4 h, diluted with ethyl acetate, washed with saturated aqueous sodium bicarbonate and brine, dried over sodium sulfate, filtered, and concentrated in vacuo, furnishing a colorless oil which solidified upon standing. Recrystallization (ether/petroleum ether) yielded the bromide (0.15 g, 100% yield) as white crystals: mp 134–135° C.; $[\alpha]D^{25}$ +114° (c 0.10, acetonitrile); $^{13}$C NMR (125 MHz, CDCl$_3$) δ 166.11, 165.64, 165.53, 133.65, 133.35, 133.32, 130.01, 129.78, 129.69, 129.49, 129.31, 128.75, 128.48, 128.42, 88.85, 71.54, 70.78, 68.63, 65.05, 32.16; high resolution mass spectrum (FAB, m-nitrobenzyl alcohol) m/z 539.0661 [(M+H)$^+$; calcd for C$_{27}$H$_{23}$O$_7$Br: 539.0705].

A solution of the above bromide (0.40 g, 0.814 mmol) in hexane and benzene (2:3, 17 ml) was added to a mixture of activated, powdered 4 Angstrom molecular sieves (0.83 g), protected tryptophol III-12 (0.37 g, 1.23 mmol) and silver(I) oxide (0.83 g, 3.58 mmol) in a flask wrapped with aluminum foil. The mixture was stirred at room temperature for two days, filtered through Celite, and concentrated in vacuo to furnish a colorless oil. Flash chromatography (50% ether/petroleum ether) then yielded III-40 (0.50 g, 81% yield) as a colorless solid: mp 76–78° C.; $[\alpha]D^{25}$ +28° (c 0.12, acetonitrile); UV (9.21×10$^{-5}$ M, acetonitrile) λmax 237.6 (ε 4.47×10$^3$), 198.8 (4.10×10$^3$) nm; IR (CHCl$_3$) 3010 (s), 1730 (s), 1455 (m), 1380 (m), 1320 (m), 1280 (m), 1220 (s), 1180 (s), 1120 (s), 1100 (m), 1075 (m), 1030 (m), 770 (s), 710 (s), 670 (s), cm$^{-1}$; $^1$H NMR (500 MHz, CDCl$_3$) δ 8.03–7.10 (m, 2 5H), 5.42 (m, 2H), 4.74 (d, J=7.5 Hz, 1H), 4.47 (m, 2H), 4.16–4.05 (m, 2H), 3.82 (m, 1H), 2.91 (m, 2H), 2.47 (ddd, J=12.5, 4.6, 1.9 Hz, 1 H), 1.90 (q, J=13.0 Hz, 1H); $^{13}$C NMR (125 MHz, CDCl$_3$) δ 166.20, 165.89, 165.42, 135.03, 133.55, 133.24, 133.22, 133.06, 130.86, 129.72, 129.67, 129.62, 129.49, 129.32, 129.12, 128.42, 128.37, 128.31, 126.67, 124.58, 123.43, 123.06, 119.42, 119.35, 113.56, 101.42, 72.53, 71.56, 69.75, 68.80, 65.81, 33.00, 25.60; high resolution mass spectrum (FAB, m-nitrobenzyl alcohol) m/z 759.2108 (M$^+$; calcd for C$_{43}$H$_{37}$NO$_{10}$S: 759.2138).

AN. 2-(N-Phenylsulfonylindol-3-yl)ethyl 4-Deoxy-β-D-glucopyranoside (III-41)

A solution of tribenzoate III-40 (120 mg, 0.158 mmol) in methanol (20 ml) was treated with sodium methoxide (0.027 g, 0.507 mmol) and then stirred for 16 h. The mixture was neutralized with Amberlyst® 15 ion exchange resin, filtered, and the filtrate was concentrated in vacuo to yield a tan solid. Flash chromatography (10% methanol/dichloromethane) yielded III-41 (65 mg, 91% yield) as a white solid: mp 64–65° C.; $[\alpha]D^{25}$ -29° (c 0.15, acetonitrile); UV (9.21× 10$^{-5}$ M, acetonitrile) λmax 253.2 (ε 1.55×10$^3$), 212.0 (2.58× 10$^4$) nm; IR (CHCl$_3$) 3420 (w), 3010 (m), 1455 (m), 1370 (m), 1280 (w), 1220 (s), 1180 (m), 1120 (m), 1075 (m), 760 (s), 690 (w), 670 (s) cm$^{-1}$; $^1$H NMR (500 MHz, CDCl$_3$) δ 7.99–7.22 (m, 10H), 4.22 (m, 2H), 3.82 (m, 1H), 3.69 (m, 2H), 3.61 (m, 2H), 3.24 (m, 1H), 2.97 (m, 2H), 2.76 (br s, 1H), 2.61 (br s, 1H), 1.89 (ddd, J=13.1, 5.1, 1.7 Hz, 1H), 1.56 (q, J=11.5 Hz, 1H); $^{13}$C NMR (125 MHz, CDCl$_3$) δ 138.19, 135.14, 133.74, 131.04, 129.23, 126.70, 124.83, 123.68, 123.22, 119.74, 119.31, 113.76, 102.92, 76.09, 72.75, 70.72, 68.72, 65.04, 33.75, 25.40; high resolution mass spectrum (FAB, m-nitrobenzyl alcohol) m/z 447.1389 (M$^+$; calcd for C$_{22}$H$_{25}$NO$_7$S: 447.1352).

AO. 2-(N-Phenylsulfonylindol-3-yl)ethyl 4-Deoxy-6-O-tert-butyldimethylsilyl-β-D-glucopyranoside (III-42)

A solution of triol III-41 (0.24 g, 0.536 mmol) in DMF (6 ml) was treated with imidazole (73 mg, 1.07 mmol) followed by tert-butyldiphenylsilyl chloride (0.17 ml, 0.643 mmol). The reaction mixture was then heated at 70° C. for 48 h, cooled, quenched with methanol (5 ml), and concentrated in vacuo. The residue was extracted with ethyl acetate and the extracts were washed with brine, dried over sodium sulfate, filtered and concentrated in vacuo. The resultant pale yellow oil was purified by flash chromatography (3% methanol/dichloromethane) to give III-42 (0.36 g, 97% yield) as a colorless oil: $[\alpha]D^{25}$ -24° (c 0.37, acetonitrile); UV (1.75×10$^{-4}$ M, acetonitrile) λmax 253.2 (ε 1.53×10$^3$), 212.0 (2.58×10$^3$) nm; IR (CHCl$_3$) 3440 (br), 3010 (m), 2960 (w), 2940 (m), 2870 (m), 1455 (m), 1430 (m), 1380 (m), 1280 (w), 1220 (s), 1180 (s), 1120 (s), 1070 (s), 1020 (w), 760 (s), 705 (m), 690 (m), 670 (m) cm$^{-1}$; $^1$H NMR (500 MHz, CDCl$_3$) δ 7.98 (d, J=8.4 Hz, 1H), 7.82 (m, 2H), 7.65 (m, 4H), 7.39–7.17 (m, 13H), 4.17 (d, J=7.7 Hz, 1H), 4.17–4.13 (m, 2H), 3.81–3.62 (m, 3H), 3.32 (t, J=8.0 Hz, 2H), 2.99–2.96 (m, 2H), 2.76 (br s, 1H), 2.59 (br s, 1H), 2.15–2.08 (ddd, J=13.1, 5.1. 1.7 Hz, 1H), 1.45 (q, J=12.7 Hz, 1H), 1.04 (s, 9H); $^{13}$C NMR (125 MHz, CDCl$_3$) δ 138.22, 135.55, 135.52, 133.64, 133.33, 129.69, 129.66, 129.16, 127.65, 126.65, 124.76, 123.49, 123.15, 119.75, 119.41, 113.71, 102.80, 76.24, 72.66, 70.82, 68.64, 66.09, 34.75, 26.75, 25.48, 19.20; high resolution mass spectrum (CI, NH$_3$) m/z 703.2929 [(M+NH$_4$)$^+$; calcd for C$_{38}$H$_{47}$N$_2$O$_7$SSi: 703.2873].

AP. 2-(N-Phenylsulfonylindol-3-yl)ethyl 2,3-Di-O-benzyl-4-deoxy-6-O-tert-butyldimethylsilyl-β-D-glucopyranoside (III-43)

A solution of diol III-42 (0.50 g, 0.729 mmol) in THF (7 ml) was added to a stirred suspension of sodium hydride (73.0 mg, 3.04 mmol, 60% oil dispersion) in THF (3 ml) at 0° C., and the reaction was stirred at room temperature for 30 min. The mixture was recooled to 0° C. and benzyl bromide (0.26 ml, 2.2 mmol) was added dropwise. After 3 days at room temperature, the reaction mixture was quenched with saturated aqueous ammonium chloride (10 ml) and extracted with ether. The extracts were washed with brine, dried over sodium sulfate, filtered, and concentrated in vacuo. Flash chromatography (33% ether/petroleum ether) afforded III-43 (0.73 g, 76% yield) as a colorless oil: $[\alpha]D^{25}$ -5.6° (c 0.16, acetonitrile); UV (1.44×10$^{-4}$ M, acetonitrile) λmax 252.8 (ε 2.27×10$^3$), 222.0 (2.63×10$^3$) nm; IR (CHCl$_3$) 3080 (w), 3010 (m), 2900 (m), 2850 (m), 1450 (m), 1430 (m), 1380 (m), 1220 (m), 1180 (m), 1100 (s), 750 (s), 700 (s), 660 (m) cm$^{-1}$; $^1$H NMR (500 MHz, CDCl$_3$) δ 7.98 (d, J=8.3 Hz, 1H), 7.80 (dd, J=8.1, 0.83 Hz, 2H), 7.64 (m, 4H), 7.32 (m, 23H), 4.67 (m, 4H), 4.33 (d, J=7.7 Hz, 1H), 4.14 (m, 1H), 3.81–3.77 (m, 2H), 3.62 (m, 1H), 3.57–3.48 (m, 2H), 3.47–3.29 (m, 1H), 3.29 (t, J=7.8 Hz, 1H), 2.99 (t, J=7.1 Hz, 1H), 2.13 (ddd, J=12.8, 5.2, 1.6 Hz, 1H), 1.40 (q, J=11.7 Hz, 1H), 1.08 (s, 9H); $^{13}$C NMR (125 MHz, CDCl$_3$) δ 138.64, 138.31, 135.58, 135.54, 135.19, 133.54, 133.46, 130.99, 129.70, 129.67, 129.10, 128.33, 128.20, 127.95, 127.66, 127.62, 127.54, 127.44, 126.62, 124.70, 123.42, 123.11, 119.74, 119.51, 113.69, 103.84, 82.95, 76.74, 74.89, 72.24, 68.55, 66.22, 33.66, 26.80, 25.80, 19.23; high resolution mass spectrum (CI, NH$_3$) m/z 883.3898 [(M+NH$_4$)$^+$; calcd for C$_{52}$H$_{59}$N$_2$O$_7$SSi: 883.3812].

AQ. 2-(N-Phenylsulfonylindol-3-yl)ethyl 2,3-Di-O-benzyl-4-deoxy-β-D-glucopyranoside (III-44)

A solution of silyl ether III-43 (0.37 g, 0.427 mmol) in THF (11 ml) was treated with tetrabutylammonium fluoride (1.33 ml, 1.0 M in THF, 1.33 mmol) and stirred at room temperature for 3 h. The solution was then diluted with ethyl acetate, washed with water and brine, dried over sodium sulfate, filtered, and concentrated in vacuo. Flash chromatography (33% petroleum ether/ethyl acetate) yielded III-44 (0.43 g, 85% yield) as a colorless oil: $[\alpha]D^{25}$ −4.4° (c 0.32, acetonitrile); IR (CHCl$_3$) 3600 (w), 3480 (br), 3010 (m), 2920 (m), 2890 (m), 1450 (m), 1380 (m), 1220 (s), 1180 (m), 1120 (m), 1100 (m), 760 (s), 700 (m), 690 (m), 670 (m) cm$^{-1}$; $^1$H NMR (500 MHz, CDCl$_3$) δ 7.98 (d, J=8.3 Hz, 1H), 7.83 (m, 2H), 7.52–7.04 (m, 12H), 4.74–4.66 (m, 5H), 4.41 (d, J=6.9 Hz, 1H), 4.19 (m, 1H), 3.88 (m, 1H), 3.67–3.50 (m, 4H), 3.31–3.27 (m, 1H), 2.99 (m, 2H), 2.08 (t, J=5.9 Hz, 1H), 1.98 (ddd, J=12.8, 5.2, 1.9 Hz, 1H), 1.56 (q, J=11.7 Hz, 1H); $^{13}$C NMR (125 MHz, CDCl$_3$)δ 138.54, 138.19, 135.14, 133.61, 130.99, 129.12, 128.32, 128.20, 127.92, 127.60, 127.56, 127.49, 126.63, 124.72, 123.58, 123.13, 119.69, 119.37, 113.69, 103.84, 82.74, 78.11, 74.93, 72.29, 72.19, 68.65, 65.12, 32.61, 25.65; high resolution mass spectrum (Cl, CH$_4$) m/z 645.2675 [(M+NH$_4$)$^+$; calcd for C$_{36}$H$_{41}$N$_2$O$_7$S: 645.2634].

AR. 2-(N-Phenylsulfonylindol-3-yl)ethyl 2,3-Di-O-benzyl-4-deoxy-6-O-(5-phthalimidopentyl)-β-D-glucopyranoside (III-45)

5-Phthalimidopentyl triflate was prepared as follows: A stirred solution of 5-phthalimido-1-pentanol (III-33) (39.1 mg, 0.168 mmol) and 2,6-di-tert-butyl-4-methylpyridine (34.5 mg, 0.168 mmol) in dry dichloromethane (1.5 ml) was treated with triflic anhydride (28.3 ml, 0.168 mmol). After 10 min at room temperature, the mixture was diluted with water (25 ml) and extracted with dichloromethane (2×50 ml). The combined extracts were washed with brine, dried over sodium sulfate, filtered, and concentrated in vacuo, affording a yellow solid which was used without purification in the next reaction. Sodium hydride (60% dispersion in oil, 51 mg, 1.3 mmol) was added to a solution of alcohol III-44 (150 mg, 0.240 mmol), 5-phthalimidopentyl triflate (1.37 mmol), and 2,6-di-tert-butyl-4-methylpyridine (282 mg, 1.39 mmol), in dichloromethane (1.5 ml) at 0° C. The reaction mixture was stirred for 48 h at room temperature, quenched with saturated aqueous ammonium chloride, and extracted with dichloromethane, and the organic layer was washed with brine, dried over sodium sulfate, filtered, and concentrated in vacuo. Flash chromatography (20% ethyl acetate/petroleum ether) gave III-45 (158 mg, 78% yield) as a colorless oil: $[\alpha]D^{25}$ −2.5° (c 0.36, acetonitrile); UV (2.14×10$^{-4}$ M, acetonitrile) λmax 283.6 (ϵ 710), 242.4 (808) nm; IR (CHCl$_3$) 2940 (m), 2860 (m), 1775(m), 1715 (s), 1450 (m), 1400 (s), 1370 (s), 1175 (m), 1120 (s), 1090 (s), 1050 (s), 745 (m), 720 (s), 700 (m) cm$^{-1}$; $^1$H NMR (500 MHz, CDCl$_3$) δ 7.96 (d, J=8.3 Hz, 1H), 7.84–7.80 (m, 4H), 7.69–7.64 (m, 2H), 7.50–7.17 (m, 12H), 4.69 (d, J=11.0 Hz, 1H), 4.67 (s, 2H), 4.64 (d, J=11.0 Hz, 1H), 4.36 (d, J=7.7 Hz, 1H), 4.21–4.17 (m, 1H), 3.86–3.81 (m, 1H), 3.66 (t, J=7.3 Hz, 2H), 3.60–3.39 (m, 6H), 3.28 (dd, J=7.8, 8.8 Hz, 1H), 3.00 (t, J=6.7 Hz, 2H), 2.12 (dd, J=5.4, 12.2 Hz, 1H), 1.71–1.58 (m, 5H), 1.47–1.36 (m, 3H); $^{13}$C NMR (125 MHz, CDCl$_3$) δ 168.37, 138.61, 138.31, 135.19, 133.83, 133.56, 132.13, 131.03, 129.11, 128.31, 128.19, 127.96, 127.63, 127.51, 127.44, 126.65, 124.68, 123.51, 123.12, 119.78, 119.49, 113.70, 103.85, 82.83, 78.23, 74.90, 73.10, 72.16, 71.39, 70.95, 68.68, 37.86, 33.94, 29.67, 29.11, 28.36, 25.75, 23.41; high resolution mass spectrum (FAB, m-nitrobenzyl alcohol) m/z 865.3201 [(M+Na)$^+$; calcd for C$_{49}$H$_{60}$N$_2$O$_9$SNa: 865.3134].

AS. 2-(1H-Indol-3yl)ethyl 2,3-Di-O-benzyl-6-O-(5-aminopentyl)-β-D-glucopyranoside (III-7)

Sodium methoxide (40 mg, 0.740 mmol) was added to a solution of III-45 (150 mg, 0.178 mmol) in methanol (8 ml) and the reaction mixture was then heated at reflux for 24 h, cooled, poured into water (100 ml), and extracted with dichloromethane (2×100 ml). The combined organic layers were washed with brine, dried over sodium sulfate, filtered, and concentrated in vacuo. Flash chromatography (10% methanol/dichloromethane) afforded III-7 (72.0 mg, 71% yield) as a colorless oil: $[\alpha]D^{25}$ +3.9° (c 1.8, acetonitrile); UV (1.57×10$^{-4}$ M, acetonitrile) λmax 280.0 (ϵ 1.41×10$^3$), 224.8 (1.66×10$^3$) nm; IR (CHCl$_3$) 3350 (br), 3060 (w), 2930 (m), 2860 (m), 1630 (m), 1590 (m), 1560 (m), 1450 (m), 1400 (m), 1270 (m), 1100 (s), 740 (s), 700 (s) cm$^{-1}$; $^1$H NMR (500 MHz, CDCl$_3$) δ 7.74 (br m, 1H), 7.48 (d, J=7.8 Hz, 1H), 7.36–6.93 (m, 1 5H), 4.62–4.49 (m, 4H), 4.32 (d, J=7.7 Hz, 1H), 4.11 (dt, J=9.4, 6.7 Hz, 1H), 3.78 (dt, J=9.2, 7.4 Hz, 1H), 3.52 (m, 4H), 3.26 (m, 2H), 3.22 (t, J=7.2 Hz, 1H), 3.13 (t, J=7.8 Hz, 1H), 3.00 (t, J=7.0 Hz, 2H), 2.00 (ddd, J=6.7, 5.2, 1.4 Hz, 1H), 1.29 (m, 9H); $^{13}$C NMR (125 MHz, CDCl$_3$) δ 140.11, 138.10, 130.75, 130.59, 129.31, 128.92, 128.84, 128.57, 128.44, 123.70, 122.24, 119.40, 112.82, 112.31, 105.01, 84.13, 79.55, 75.76, 74.12, 73.12, 72.53, 72.18, 71.29, 41.05, 34.54, 30.38, 29.90, 27.07, 24.72; high resolution mass spectrum (Cl, NH$_3$) m/z 573.3301 [(M+H)$^+$; calcd for C$_{35}$H$_{45}$N$_2$O$_5$: 573.3328].

AT. Methyl 2,3,4-Tri-O-benzyl-6-O-(5-azidopentyl)-β-D-glucopyranoside (III-47a)

At room temperature a solution of 5-azido-1-pentanol (0.18 g, 1.40 mmol) and 2,6-di-tert-butyl-4-methylpyridine (0.3 g, 1.46 mmol) in dichloromethane (10 ml) was treated dropwise with triflic anhydride (0.240 ml, 1.43 mmol). After 15 min the mixture was diluted with dichloromethane (40 ml) and poured into saturated aqueous sodium bicarbonate. The organic phase was washed with brine (2×20 ml), dried over magnesium sulfate, filtered, and concentrated, affording a light yellow solid which was used without purification. The alcohol III-46 (0.2 g, 0.429 mmol) and the crude triflate were dissolved in dichloromethane (2 ml) and treated with sodium hydride (0.025 g, 0.625 mmol, 60% dispersion in oil). The mixture was stirred for 48 h, diluted with dichloromethane (40 ml), and poured into saturated aqueous ammonium chloride (40 ml). The aqueous phase was extracted with dichloromethane (3×20 ml) and the combined organic solutions were washed with brine, dried over magnesium sulfate, filtered, and concentrated in vacuo. Flash chromatography (15% ethyl acetate/hexane) provided III-47a (0.126 g, 51% yield) as a white solid: $[\alpha]D^{25}$ +7.7° (c 0.75, CHCl$_3$); IR 3028 (m), 2921 (m), 2863 (m), 2110 (s), 1497 (w), 1462 (m), 1421 (m), 1356 (m), 1280 (s), 1070 (s), 732 (br) cm$^{-1}$; $^1$H NMR (500 MHz, CDCl$_3$) δ 7.35–7.23 (m, 15H), 4.92 (d, J=10.9 Hz, 1H), 4.91 (d, J=11.0 Hz, 1H), 4.86 (d, J=10.9 Hz, 1H), 4.78 (d, J=7.8 Hz, 1H), 3.70–3.50 (m, 6H), 3.56 (s, 3H), 3.44–3.40 (m, 3H), 3.23 (t, J=6.9 Hz, 2H), 1.63–1.40 (m, 6H); $^{13}$C NMR (125 MHz, CDCl$_3$) δ 138.59, 138.53, 138.27, 128.42, 128.35, 128.33, 128.07, 127.88, 127.83, 127.76, 127.60, 127.50, 104.73, 84.63, 82.32, 77.96, 75.67, 74.97, 74.84, 74.72, 71.41, 69.70, 57.08, 51.35, 29.22, 28.69, 23.44; high resolution mass spectrum (FAB, m-nitrobenzyl alcohol) m/z 598.2880 [(M+Na)$^+$; calcd for C$_{33}$H$_{39}$N$_3$O$_6$: 598.2893].

AU. Methyl 2,3,4-Tri-O-benzyl-6-O-(5-aminopentyl)-β-D-glucopyranoside (III-8a)

Azide III-47a (0.126 g, 0.219 mmol) was dissolved in THF (12 ml) and treated with water (0.096 ml, 5.33 mmol) followed by triphenylphosphine (0.114 g, 0.44 mmol). The mixture was then heated at 60° C. for 12 h, cooled, and concentrated in vacuo. Flash chromatography (10% methanol/dichloromethane) afforded III-8a (87.3 mg, 73% yield) as a white solid: $[\alpha]D^{25}$ +6.8° (c 1.85, CHCl$_3$); IR (CH$_2$Cl$_2$) 3700 (w), 3040 (s), 2980 (s), 2920 (s), 2860 (m), 1420 (s), 1350 (m), 1310 (m), 1260 (s), 1140(m), 1060 (s), 890(s), 700 (br) cm$^{-1}$; $^1$H NMR (500 MHz, CDCl$_3$) δ 7.35–7.25 (m, 15H), 4.92 (d, J=10.9 Hz, 1H), 4.91 (d, J=11.0 Hz, 1H), 4.85 (d, J=10.9 Hz, 1H), 4.78 (d, J=11.0 Hz, 1H), 4.70 (d, J=10.9 Hz, 1H), 4.61 (d, J=10.9 Hz, 1H), 4.29 (d, J=7.8 Hz, 1H), 3.70–3.40 (m, 8H), 3.56 (s, 3H), 2.66 (t, J=6.9 Hz, 2H), 1.61–1.56 (m, 4H), 1.46–1.35 (m, 4H); $^{13}$C NMR (125 MHz, CDCl$_3$) δ 138.58, 138.52, 138.25, 128.39, 128.31, 128.05, 127.85, 127.84, 127.73, 127.58, 127.55, 104.71, 84.61, 82.30, 77.94, 75.65, 74.95, 74.83, 74.70, 71.63, 69.61, 57.07, 42.02, 33.47, 29.48, 23.45; high resolution mass spectrum (FAB, m-nitrobenzyl alcohol) m/z 572.2997 [(M+Na)$^+$; calcd for C$_{33}$H$_{43}$O$_6$N: 572.2988].

AV. Methyl 2,3,4-Tri-O-benzyl-6-amino-6-deoxy-6-N-(5-hydroxypentyl)-β-D-glucopyranoside (III-8b)

A stirred solution of III-46 (800 mg, 1.71 mmol) and 2,6-di-tert-butyl-4-methyl pyridine (632 mg, 3.08 mmol) in dichloromethane (9 ml) was cooled to −78° C. and treated with triflic anhydride (0.345 ml, 2.05 mmol). After 15 min the mixture was warmed to room temperature over 20 min, poured into saturated aqueous sodium bicarbonate (20 ml), and extracted with ethyl acetate (50 ml). The organic layer was washed with additional bicarbonate solution and brine, dried over magnesium sulfate, filtered, and concentrated in vacuo, affording crude triflate which was used in the next step without further purification.

A solution of 5-trifluoroacetamido-1-pentanol (III-18a) (1.7 g, 8.6 mmol) in THF (35 ml) was added to a stirred suspension of sodium hydride (855 mg, 21.4 mmol, 60% oil dispersion) in THF (60 ml) at 0° C. After 10 min the suspension was warmed to room temperature, stirred for 1 h, and recooled to 0° C. A solution of the crude triflate (1.71 mmol) in dichloromethane (60 ml) was then added and stirring continued at 0° C. for 30 min and at room temperature for 24 h. The reaction mixture was quenched at 0° C. with saturated aqueous ammonium chloride and extracted with ethyl acetate, and the combined organic extracts were washed with water and brine, dried over magnesium sulfate, filtered, and concentrated in vacuo. Purification through a small plug of silica gel (30% ethyl acetate/petroleum ether) gave crude III-47b which was used immediately in the next step.

A stirred solution of the above crude III-47b in ethanol (10 ml) was treated with 5 N NaOH (3 ml, 15 mmol) at room temperature and then heated at reflux for 2 h, cooled, and concentrated in vacuo. The residue was diluted with dichloromethane and washed with 2 N HCl. The aqueous layer was extracted with dichloromethane (3×50 ml), and the combined organic solutions were washed with brine, dried over magnesium sulfate, filtered, and concentrated in vacuo. Recrystallization (ethyl acetate/petroleum ether) furnished pure III-8a (675 mg, 72% yield from 46) as a white solid: mp 95–95.5° C.; [α]D$^{25}$ +9.3° (c 0.15, acetonitrile); IR (film) 3280 (m), 3095 (w), 3065 (w), 3035 (w), 2935 (s), 2915 (s), 2860 (s), 1496 (w), 1454 (m), 1404 (w), 1393 (w), 1358 (m), 1214 (m), 1115 (s), 1072 (s), 1037 (m), 1027 (m), 1009 (m), 911 (w), 826 (w), 747 (s), 696 (s) cm $^{-1}$; $^1$H NMR (500 MHz, CDCl$_3$) δ 7.35–7.24 (m, 15H), 4.92 (d, J=7.5 Hz, 1H), 4.90 (d, J=7.6 Hz, 1H), 4.85 (d, J=11.0 Hz, 1H), 4.78 (d, J=11.0 Hz, 1H), 4.70 (d, J=11.0 Hz, 1H), 4.60 (d, J=11.0 Hz, 1H), 4.32 (d, J=7.8 Hz, 1H), 3.66–3.59 (m, 3H), 3.56 (s, 3H), 3.48–3.36 (m, 3H), 2.94 (dd, J=12.5, 2.1 Hz, 1H), 2.68 (dd, J=12.0, 6.8 Hz, 1H), 2.64–2.53 (m, 2H), 1.71 (s, 2H), 1.59–1.53 (m, 2H), 1.51–1.45 (m, 2H), 1.42–1.36 (m, 2H); $^{13}$C NMR (125 MHz, CDCl$_3$) δ 138.55, 138.47, 138.17, 128.39, 128.33, 128.03, 127.95, 127.85, 127.77, 127.60, 127.57, 104.72, 84.56, 82.45, 79.74, 75.66, 75.02, 74.74, 74.16, 62.62, 57.20, 50.69, 49.72, 32.49, 29.65, 23.37; high resolution mass spectrum (Cl, NH$_3$) m/z 550.3179 [(M+H)$^+$; calcd for C$_{33}$H$_{43}$O$_6$N: 550.3168].

AW. 2-(1H-Indol-3-yl)ethyl 2,3,4-Tri-O-benzyl-β-D-glucopyranoside (III-9)

A stirred solution of III-17 (100 mg, 0.136 mmol) in ethanol (3 ml) was treated with 5 N NaOH (1 ml) and then heated at reflux for 2 h, cooled, and concentrated in vacuo. The residue was diluted with dichloromethane and washed with 2 N HCl, and the aqueous layer was extracted with dichloromethane. The combined organic solutions were washed with brine, dried over magnesium sulfate, filtered, and concentrated in vacuo. Flash chromatography 3 0 (25% ethyl acetate/petroleum ether) furnished III-9 (68 mg, 85% yield) as a colorless oil: [α]D$^{25}$ −2.5° (c 1.37, acetonitrile); UV (2.89×10$^{-4}$ M, acetonitrile) λmax 289.6 (ε 3.56×10$^3$), 281.2 (4.24×10$^3$), 222.4 (1.01×10$^4$) nm; IR (film) 3575 (sh), 3435 (m), 3085 (sh), 3065 (w), 3035 (w), 2925 (m), 2880 (m), 1500 (w), 1455 (m), 1360 (w), 1310 (w), 1150 (sh), 1085 (s), 1030 (s), 920 (w), 810 (w), 740 (s), 700 (s) cm$^{-1}$; $^1$H NMR (500 MHz, CDCl$_3$) δ 7.83 (s, 1H), 7.59 (d, J=7.8 Hz, 1H), 7.33–7.24 (m, 15H), 7.20–7.17 (m, 2H), 7.11 (t, J=7.8 Hz, 1H), 7.01 (d, J=1.8 Hz, 1H), 4.91 (d, J=10.9 Hz, 1H), 4.85 (d, J=10.9 Hz, 1H), 4.80 (d, J=10.9 Hz, 1H), 4.79 (d, J=11.0 Hz, 1H), 4.64 (d, J=11.0 Hz, 1H), 4.63 (d, J=11.0 Hz, 1H), 4.49 (d, J=7.8 Hz, 1H), 4.22 (ddd, J=9.4, 6.7, 6.7 Hz, 1H), 3.90–3.82 (m, 2H), 3.72–3.67 (m, 1H), 3.65 (apparent t, J=9.1 Hz, 1H), 3.56 (apparent t, J=9.3 Hz, 1H), 3.42 (apparent t, J=8.1 Hz, 1H), 3.35 (ddd, J=9.5, 4.3, 2.8 Hz, 1H), 3.11 (t, J=7.0 Hz, 2H), 1.87 (dd, J=7.6, 5.9 Hz, 1H); $^{13}$C NMR (500 MHz, CDCl$_3$) δ 138.52, 138.44, 137.98, 136.17, 128.46, 128.36, 128.29, 128.05, 128.00, 127.89, 127.86, 127.60, 127.57, 127.45, 122.09, 122.01, 119.34, 118.68, 112.60, 111.13, 103.69, 84.49, 82.34, 77.57, 75.64, 75.04, 75.01, 74.75, 70.25, 62.04, 25.86; high resolution mass spectrum (Cl, NH$_3$) m/z 611.3043 [(M+NH$_4$)$^+$; calcd for C$_{37}$H$_{39}$O$_6$N: 611.3121].

AX. Methyl 2,3-Di-O-benzyl-4,6-di-O-isopropylidene-β-D-glucopyranoside (III-50)

A solution of glucoside III-49 (2.5 g, 10.7 mmol) in THF (100 ml) was added to a suspension of sodium hydride (0.94 g, 23.5 mmol) in THF (50 ml) at 0° C. The reaction was stirred at room temperature for 1 h and cooled to 0° C., and benzyl bromide (2.8 ml, 24 mmol) was then added dropwise, followed by tetrabutylammonium iodide (100 mg). The mixture was stirred at room temperature for 24 h, quenched with saturated aqueous ammonium chloride, extracted with ether, and the extracts washed with brine, dried over sodium sulfate, filtered, and concentrated in vacuo. Flash chromatography (10% ethyl acetate/petroleum ether) afforded III-50 as a colorless oil (4.02 g, 91% yield): [α]D$^{25}$ −2.0° (c 0.15, acetonitrile); UV (6.01×10$^{-4}$ M, acetonitrile) λmax 257.6 (ε 508) nm; IR (film) 3060 (m), 3000 (m), 2980 (m), 2900 (m), 1460 (m), 1390 (m), 1380 (m), 1310 (w), 1270 (s), 1210 (m), 1180 (m), 1100 (s), 1080 (s), 1050 (m), 1030 (m), 860 (m), 740 (s), 705 (s) cm$^{-1}$; $^1$H NMR (500 MHz, CDCl$_3$) δ 7.35–7.23 (m, 10H), 4.84 (d, J=11.3 Hz, 2H), 4.74 (dd, J=11.4, 9.2 Hz, 1H), 4.36 (d, J=7.6 Hz, 1H), 3.93 (dd, J=10.8, 5.4 Hz, 1H), 3.76 (t, J=10.5 Hz, 1H), 3.69 (t, J=9.3 Hz, 1H), 3.57 (m, 4 H), 3.37 (t, J=8.3 Hz, 1H), 3.23 (m, 1H), 1.48 (s, 3H), 1.42 (s, 3H); $^{13}$C NMR (125 MHz, CDCl$_3$) δ 138.81, 138.54, 128.26, 128.17, 127.98, 127.85, 127.58, 127.46, 105.16, 99.24, 82.14, 81.27, 75.19, 74.77, 74.27, 69.79, 62.25, 57.32, 29.14, 19.09; high resolution mass spectrum (Cl, NH$_3$) m/z 415.2137 [(M+H)$^+$; calcd for C$_{24}$H$_{31}$O$_6$: 415.2120].

AY. Methyl 2,3-Di-O-benzyl-β-D-glucopyranoside (III-51)

Amberlyst® 15 ion exchange resin (0.5 g) was added to a solution of III-50 (1.00 g, 2.4 mmol) in methanol (50 ml) and the mixture was stirred at room temperature for 4 h, filtered, and concentrated in vacuo. Flash chromatography (6% methanol/dichloromethane) yielded III-51 (0.75 g, 83% yield) as a white foam: $[\alpha]D^{25}$ +16° (c 0.15, acetonitrile); UV ($2.00\times10^{-4}$ M, acetonitrile) λmax 257.6 (ε 385.0) nm; IR (film) 3590 (w), 3410 (br), 3080 (m), 2910 (w), 2890 (w), 1500 (w), 1455 (m), 1270 (s), 1210 (w), 1065 (s), 1030 (s), 1000 (m), 900 (m), 740 (s), 700 (s) cm$^{-1}$; $^1$H NMR (500 MHz, CDCl$_3$) δ 7.34–7.23 (m, 10H), 4.91 (dd, J=15.6, 11.5 Hz, 2H), 4.69 (dd, J=11.5, 8.7 Hz, 2H), 4.34 (d, J=7.7 Hz, 1H), 3.87–3.83 (m, 1H), 3.77–3.72 (m, 1H), 3.58–3.54 (m, 4H), 3.44 (t, J=9.1 Hz, 1H), 3.37 (t, J=7.6 Hz, 1H), 3.31–3.27 (m, 1H), 2.84 (br s, 1H), 2.48 (br s, 1H); $^{13}$C NMR (125 MHz, CDCl$_3$) δ 138.48, 138.34, 128.49, 128.46, 128.30, 127.99, 127.83, 127.76, 127.62, 104.85, 83.82, 81.87, 75.13, 74.90, 74.57, 70.18, 62.30, 57.20; high resolution mass spectrum (Cl, NH$_3$) m/z 392.2043 [(M+NH$_4$)$^+$; calcd for C$_{21}$H$_{30}$NO$_6$: 392.2072].

BA. Methyl 2,3-Di-O-benzyl-6-O-tert-butyldiphenylsilyl-β-D-glucopyranoside (III-52)

A solution of III-51 (3.30 g, 8.81 mmol) and imidazole (0.84 g, 12.3 mmol) in a mixture of THF (150 ml) and DMF (25 ml) was treated with tert-butyldiphenylsilyl chloride (2.80 ml, 10.6 mmol) and heated at 50° C. for 24 h. The reaction mixture was quenched with methanol (5 ml) and concentrated in vacuo. The resultant oil was taken up in ethyl acetate and the solution was washed with water and brine, dried over sodium sulfate, filtered, and concentrated in vacuo. Flash chromatography (10% ethyl acetate/petroleum ether) furnished III-52 (5.40 g, 100% yield) as a colorless oil: $[\alpha]D^{25}$ +7.3 °(c 0.22, acetonitrile); UV ($1.79\times10^{-4}$ M, acetonitrile) λmax 258.8 (ε 836) nm; IR (film) 3500 (br), 3080 (w), 3030 (w), 2940 (m), 2860 (m), 1450 (w), 1430 (m), 1390 (w), 1360 (w), 1310 (w), 1270 (w), 1220 (w), 1190 (w), 1120 (s), 1070 (s), 830 (m), 805 (w), 740 (s), 700 (s) cm$^{-1}$; $^1$H NMR (500 MHz, CDCl$_3$) δ 7.71–7.69 (m, 4 H), 7.42–7.25 (m, 16H), 4.93 (d, J=11.5 Hz, 2H), 4.76 (d, J=11.4 Hz, 1H), 4.71 (d, J=11.1 Hz, 1H), 4.32 (d, J=7.6 Hz, 1H), 3.94–3.88 (m, 2H), 3.69–3.64 (m, 1H), 3.66 (s, 3H), 3.47 (t, J=9.1 Hz, 1H), 3.41–3.34 (m, 2H), 2.57 (br s, 1H), 1.06 (s, 9H); $^{13}$C NMR (125 MHz, CDCl$_3$) δ 138.71, 138.62, 135.69, 135.61, 129.73, 128.50, 128.34, 128.03, 127.99, 127.78, 127.72, 127.69, 127.62, 104.68, 84.22, 81.93, 75.30, 74.89, 74.67, 71.62, 64.44, 56.86, 26.79, 19.25; high resolution mass spectrum (Cl, NH$_3$) m/z 630.3296 [(M+NH$_4$)$^+$; calcd for C$_{37}$H$_{48}$NO$_6$Si: 630.3251].

BB. Methyl 2,3-Di-O-benzyl-4-deoxy-6-O-tert-butyldiphenylsilyl-β-D-glucopyranoside (III-53)

A solution of III-52 (0.33 g, 0.54 mmol) in THF (20 ml) was cooled to −78° C. and treated with sodium bis(trimethylsilyl)amide (0.66 ml, 1.0 M in THF, 0.66 mmol) followed by carbon disulfide (46 ml, 0.77 mmol). After 15 min, methyl iodide (137 ml, 2.20 mmol) was added, and the solution was stirred 15 min further at −78° C. and then at room temperature for 45 min. The reaction mixture was quenched with water (2 ml) and extracted with ether. The organic layer was washed with brine, dried over sodium sulfate, filtered, and concentrated in vacuo affording the crude xanthate as a yellow oil which was used without purification. A solution of crude xanthate (6.06 g, 8.62 mmol) and a catalytic amount of A/BN (ca. 50 mg) in toluene (350 ml) was treated with tributyltin hydride (7.0 ml, 26 mmol) and then heated at reflux for 3 h, cooled, and concentrated in vacuo. The residue was taken up in acetonitrile and extracted with petroleum ether (5×100 ml). The acetonitrile layer was dried over sodium sulfate, filtered, and concentrated in vacuo. Flash chromatography (8% ethyl acetate/petroleum ether) yielded III-53 (3.60 g, 78% yield for two steps) as a colorless oil: $[\alpha]D^{25}$ +2.7° (c 0.15, acetonitrile); UV ($1.26\times10^{-4}$ M, acetonitrile) λmax 258.4 (ε 976) nm; IR (film) 3080 (m), 2990 (w), 2880 (w), 1430 (w), 1270 (s), 1110 (m), 900 (w), 740 (s), 710 (s) cm$^{-1}$; $^1$H NMR (500 MHz, CDCl$_3$) δ 7.68–7.66 (m, 4H), 7.43–7.21 (m, 16H), 4.89 (d, J×11.1 Hz, 1H), 4.75 (d, J=10.2 Hz, 1H), 4.67 (dd, J=18.2, 11.9 Hz, 2H), 4.22 (d, J=7.6 Hz, 1H), 3.80 (dd, J=10.5, 5.7 Hz, 1H), 3.63 (dd, J=10.4, 5.4 Hz, 1H), 3.59–3.44 (m, 5H), 3.29 (t, J=8.9 Hz, 1H), 2.11 (ddd, J=12.8, 5.1, 1.5 Hz, 1H), 1.41 (q, J=11.8 Hz, 1H), 1.06 (s, 9H); $^{13}$C NMR (125 MHz, CDCl$_3$) δ 138.91, 138.65, 135.60, 135.55, 133.48, 133.44, 129.66, 128.29, 128.22, 127.95, 127.63, 127.60, 127.49, 127.43, 104.81, 82.99, 78.32, 74.82, 72.20, 72.15, 66.22, 56.73, 33.62, 26.78, 19.22; high resolution mass spectrum (Cl, NH$_3$) m/z 614.3256 [(M+NH$_4$)$^+$; calcd for C$_{37}$H$_{48}$NO$_5$Si: 614.3301].

BC. Methyl 2,3-Di-O-benzyl-4-deoxy-β-D-glucopyranoside (III-54)

A solution of III-53 (3.60 g, 6.02 mmol) in THF (125 ml) was treated with tetrabutylammonium fluoride (1.0 M in THF, 6.1 mmol, 6.1 ml) at room temperature, stirred for 4 h, poured into water, and extracted with ethyl acetate. The organic layer was dried over sodium sulfate, filtered, and concentrated in vacuo. Flash chromatography (50% ethyl acetate/petroleum ether) afforded III-54 (2.03 g, 94% yield) as a colorless oil: $[\alpha]D^{25}$ +8.0° (c 0.15, acetonitrile); UV ($2.09\times10^{-4}$ M, acetonitrile) λmax 257.6 (ε 177) nm; IR (film) 3450 (br), 3095 (w), 3060 (w), 3030 (w), 2920 (m), 2880 (m), 1500 (w), 1450 (m), 1380 (m), 1360 (m), 1300 (w), 1260 (w), 1210 (m), 1180 (w), 1070 (br), 910 (m), 740 (m), 700 (m) cm$^{-1}$; $^1$H NMR (500 MHz, CDCl$_3$) δ 7.38–7.25 (m, 10H), 4.89 (d, J=11.1 Hz, 1H), 4.76 (d, J=11.1 Hz, 1H), 4.67 (m, 2H), 4.28 (d, J=7.7 Hz, 1H), 3.73–3.49 (m, 7H), 3.29 (t, J=7.9 Hz, 1H), 2.08 (br s, 1H), 1.97 (ddd, J=12.9, 5.3, 1.9 Hz, 1H), 1.49 (dd, J=24.4, 11.7 Hz, 1H); $^{13}$C NMR (500 MHz, CDCl$_3$) δ 138.71, 138.47, 128.33, 128.28, 128.00, 127.62, 127.58, 127.55, 104.95, 82.81, 78.07, 74.92, 72.26, 72.13, 65.20, 57.19, 32.65; high resolution mass spectrum (Cl, NH$_3$) m/z 359.1827 [(M+H)$^+$; calcd for C$_{21}$H$_{27}$O$_5$: 359.1858].

BD. Methyl 2,3-Di-O-benzyl-4-deoxy-6-O-(5-phthalimidopentyl)-β-D-glucopyranoside (III-55)

A solution of 5-phthalimido-1-pentanol (0.66 g, 2.83 mmol) and 2,6-di-tert-butyl-4-methylpyridine (0.58 g, 2.83 mmol) in dry dichloromethane (21 ml) was treated with triflic anhydride (0.48 ml, 2.83 mmol) at room temperature, stirred for 10 min, poured into water, and extracted with dichloromethane. The organic layer was dried over sodium sulfate, filtered, and concentrated in vacuo. The freshly generated triflate was then dissolved in dry dichloromethane (21 ml), 2,6-di-tert-butyl-4-methylpyridine (0.58 g, 2.83 mmol) was added, and the solution was cooled to 0° C. A solution of III-54 (1.0 g, 2.79 mmol) in dichloromethane (21 ml) was introduced, followed after 20 min by sodium hydride (60% oil dispersion, 0.25 g, 6.25 mmol). The reaction mixture was stirred at room temperature for 24 h, quenched with saturated aqueous ammonium chloride, extracted with dichloromethane, and the combined extracts were washed with brine, dried over sodium sulfate, filtered, and concentrated in vacuo. Flash chromatography (50% ethyl acetate/petroleum ether) yielded III-55 (1.42 g, 89% yield) as a colorless oil: $[\alpha]D^{25}$ +11 ° (c 0.11, acetonitrile); UV ($9.60\times10^{-5}$ M, acetonitrile) λmax 290.8 (ε $3.20\times10^3$), 257.6 ($2.20\times10^3$), 241.2 ($1.69\times10^4$) nm; IR (film) 3480 (br), 3090 (w), 3040 (w), 3010 (w), 2940 (s), 2860 (s), 2250 (m), 1770 (m), 1715 (s), 1500 (w), 1470 (m), 1450 (m), 1430 (m), 1400 (s), 1370 (m), 1340 (w), 1300 (w), 1260 (w), 1210 (m), 1190 (m), 1170 (w), 1100 (br), 1000 (w), 910 (s), 730 (s), 720 (s), 700 (s), 650 (m) cm$^{-1}$; $^1$H NMR (500 MHz, CDCl$_3$) δ 7.84–7.68 (m, 4H), 7.38–7.24 (m, 10H), 4.88 (d, J=11.1 Hz, 1H), 4.75 (d, J=11.1 Hz, 1H), 4.67 (s, 2H), 4.24 (d, J=7.6 Hz, 1H), 3.68 (t, J=7.3 Hz, 2H), 3.61–3.41 (m, 9H), 3.28 (t, J=8.5 Hz, 1H), 2.10 (dd, J=12.6, 5.3 Hz, 1H), 1.73–1.59 (m, 5H), 1.45–1.37 (m, 2H); $^{13}$C NMR (125 MHz, CDCl$_3$) δ 168.38, 138.87, 138.64, 133.84, 132.17, 128.30, 128.25, 128.02, 127.63, 127.48, 123.14, 104.85, 82.91, 78.24, 74.86, 73.15, 72.19, 71.42, 70.92, 56.97, 37.90, 33.94, 29.15, 28.38, 23.44; high resolution mass spectrum (Cl, NH$_3$) m/z 591.3014 [(M+NH$_4$)$^+$; calcd for C$_{34}$H$_{43}$O$_7$N$_2$: 591.3070].

BE. Methyl 2,3-Di-O-benzyl-4-deoxy-6-O-(5-aminopentyl)-β-D-glucopyranoside (III-10)

A solution of phthalimide III-55 (0.79 g, 1.38 mmol) in methanol (100 ml) was treated with sodium methoxide (0.23 g, 4.26 mmol), heated at reflux for 4 h, cooled, and concentrated in vacuo. The residue was taken up in water and extracted with dichloromethane, and the organic layer was washed with brine, dried over sodium sulfate, filtered, and concentrated in vacuo. Flash chromatography (10% methanol/dichloromethane) furnished III-10 (0.46 g, 75% yield) as a white foam: [α]D$^{25}$ +8.9° (c 0.18, acetonitrile); UV (2.03×10$^{-4}$ M, acetonitrile) λmax 276.4 (ε 1.54×10$^3$), 257.6 (2.26×10$^3$) nm; IR (film) 3330 (br), 3080 (w), 3020 (w), 2930 (s), 2870 (s), 1650 (s), 1550 (m), 1450 (m), 1370 (m), 1300 (s), 1210 (m), 1185 (m), 1100 (br), 1000 (w), 900 (w), 740 (s), 700 (s), 670 (w), 640 (w) cm$^{-1}$; $^1$H NMR (500 MHz, CD$_3$OD) δ 7.76–7.74 (m, 1H), 7.35–7.13 (m, 9H), 4.74–4.49 (m, 4H), 4.14 (d, J=7.7 Hz, 1H), 3.53–3.36 (m, 9H), 3.20 (m, 2H), 3.07 (t, J=7.8 Hz, 1H), 1.99 (ddd, J=2.8, 5.3, 1.7 Hz, 1H), 1.50–1.18 (m, 9H); $^{13}$C NMR (125 MHz, CD3OD) δ 140.18, 139.99, 138.83, 131.94, 130.83, 130.49, 129.28, 129.18, 128.99, 128.83, 128.69, 128.55, 128.49, 105.98, 84.04, 79.56, 75.73, 74.05, 73.04, 72.49, 72.12, 57.24, 40.94, 34.53, 30.30, 29.81, 24.64; high resolution mass spectrum (Cl, NH$_3$) m/z 444.2783 [(M+H)$^+$; calcd for C$_{26}$H$_{38}$NO$_5$: 444.2749].

EXAMPLE 12

The affinity of a variety of compounds for the substance P receptor was determined employing the following procedure.

A. Receptor Expression in COS

To express the cloned human neurokinin-1 receptor (NK1R) transiently in COS, the cDNA for the human NK1R was cloned into the expression vector pCDM9 which was derived from pCDM8 (Invitrogen) by inserting the ampicillin resistance gene (nucleotide 1973 to 2964 from Bluescript SK+) into the Sac II site. Transfection of 20 μg of the plasmid DNA into 10 million COS cells was achieved by electroporation in 800 μl of the transfection buffer (135 mM CaCl$_2$, 1.2 mM MgCl$_2$, 2.4 mM K$_2$HPO$_4$, 0.6 mM KH2PO4, 10 nM glucose, 10 mM HEPES pH 7.4) at 260 V and 950 μF using the IBI Genezapper (IBI, New Haven, Conn.). The cells were incubated in 10% fetal calf serum, 2 mM glutamine, 100 U/ml penicillin-streptomycin, and 90% DMEM media (Gibco, Grand Island, N.Y.) in 5% CO$_2$ at 37° C. for three days before the binding assay.

B. Assay Protocol Using COS

The binding assay of human NK1R expressed in COS cells is based on the use of $^{125}$I-substance P ($^{125}$I-SP, from DuPont, Boston, Mass.) as a radioactively labeled ligand which competes with unlabeled substance P or any other ligand for binding to the human NK1R. Monolayer cell cultures of COS were dissociated by the non-enzymatic solution (Specialty Media, Lavallette, N.J.) and resuspended in appropriate volume of the bind buffer (50 mM Tris pH 7.5, 5 mM MnCl$_2$, 150 mM NaCl, 0.04 mg/ml bacitracin, 0.004 mg/ml leupeptin, 0.2 mg/ml BSA, 0.01 mM phosphoramidon) such that 200 μl of the cell suspension would give rise to about 10,000 cpm of specific $^{125}$I-SP binding (approximately 50,000 to 200,000 cells). In the binding assay, 200 μl of cells were added to a tube containing 20 μl of 1.5 to 2.5 nM of $^{125}$I-SP and 20 μl of unlabeled substance P or any other test compound. The tubes were incubated at 4° C. or at room temperature for 1 hour with gentle shaking. The bound radioactivity was separated from unbound radioactivity by GF/C filter (Brandel, Gaithersburg, Md.) which was pre-wetted with 0.1 polyethylenimine. The filter was washed with 3 ml of wash buffer (50 Tris pH 7.5, 5 mM MnCl$_2$, 150 mM NaCl) three times and its radioactivity was determined by gamma counter.

A variety of compounds were tested according to the COS cell procedure. The concentration of compound required to inhibit the binding of substance P to the human neurokinin-1 receptor by 50% was measured. The following data were obtained:

| Compound | IC$_{50}$ |
|---|---|
| III-4e | 120 nM |
| III-5c | 180 nM |
| III-4d | 56 nM |
| Methyl 6-O-(5-aminopentyl)-2,3,4-tri-O-benzyl-β-D-glucopyranoside | 840 Nm |
| Methyl 6-O-(5-aminopentyl)-2,3,4-tri-O-benzyl-β-D-glucopyranoside 2-Indol-3-yl-ethyl-2,3,-di-O-benzyl-4-deoxy-β-D-glucopyranoside | 400 nM |
| | 400 nM |
| III-46 | 1000 nM |

EXAMPLE 13

The affinity of a variety of compounds for the SRIF receptor was determined by studying the displacement of $^{125}$I-CGP-23996 from AtT-20 cells using the method generally in accordance with Raynor and Reisine, *Journal of Pharmacology and Experimental Therapeutics*, 1989, 251;2, 510. The following data were obtained:

| Compound | IC$_{50}$ |
|---|---|
| III-4e | 9500 nM |
| III-5c | 1300 nM |
| Methyl 6-O-(5-aminopentyl)-2,3,4-tri-O-benzyl-β-D-glucopyranoside | 40000 nM |
| III-46 | does not bind |
| SRIF | 9.3 nM |
| MK 678 | 60 nM |
| L-363,301 | 18.7 nM |

EXAMPLE 14

The affinity of a 2-(1-phenylsulfonyl-indol-3yl)ethyl-6-O-(5-aminopentyl)-2,3,4-tri-O-benzyl-β-D-glucopyranoside, structure (1) and methyl 6-O-(5-aminopentyl)-2,3,4-Tri-O-benzyl-β-D-glucopyranoside, structure (8) for a variety of G-protein-linked receptors was determined by studying the displacement of a variety of radioligands from AtT-20 and brain cells using the method disclosed by Reisine, et al., *Brain Research,* 1979, 117, 241. The following data was obtained ($^{125}$I-CYP=$^{125}$I-cyanopindolol; $^3$H-QNB=quinuclidinyl benzilate):

| Receptor | Radioligand | Binding Compound | Inhibition | Tissue |
|---|---|---|---|---|
| β-Adrenergic | $^{125}$I-CYP (0.1 nM) | III-4e | 70% | AtT-20 |
| | | III-4e | 45 | Brain |
| | | Methyl 6-O-(5-amino-pentyl)-2,3,4-tri-O-benzyl-β-D-glucopyranoside | 0 | AtT-20 |
| Opiate Receptor | $^3$H-naloxone (0.5 nM) | III-4e | 55 | Brain |
| Dopamine Receptor | $^3$H-spiperone (0.1 nM) | III-4e | 82 | Brain |
| Muscarinic cholingeric | $^3$H-QNB 0.1 (nM) | III-4e III-4e | 20 83 | AtT-20 Brain |

As can be seen from Examples 9–11, the peptide analogs of the present invention are selectively bound by certain receptors. For example, structure (1) exhibits approximately 14-fold greater selectivity than structure (8) for the substance P receptor, while structure (8) is bound by the substance P and SRIF receptors but does not bind the β-adrenergic receptor.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

EXAMPLE 15

Preparative Experiments: A Protocol for the Synthesis of Base-Sensitive Ethers

Glycosides such as IV-1 react with crude alkyl triflates to yield the desired ethers, when a mixture of the two compounds is dried in vacuo prior to the addition of solvent and base. It is believed that this reaction is not catalyzed by residual 2,6-di-t-butyl-4-methylpyridine since purification by silica gel column chromatography to remove the 2,6-di-t-butyl-4-methylpyridine was performed on representative triflates; use of triflates purified in this manner provided ethers in high yields. This method has been successfully applied to the synthesis of over 30 sugar based ligands including those in which a primary and/or a secondary alcohol acted as the reacting nucleophile. Preliminary investigations have revealed that benzyl alcohol may also serve as a nucleophile.

EXAMPLE 16

Representative Procedure for Etherification of Glycosides: Preparation of 2-(N-[Phenylsulfonyl] indol-3-yl)ethyl-2-O-triisopropylsilyl-3,4-di-O-benzyl-6-O-(5'-azidopentyl)-β-L-mannopyranoside [(+)-IV-2]

A solution of 5-azidopentanol (100 mg, 0.83 mmol) and 2,6-di-t- butyl-4-methylpyridine (170 mg, 0.83 mmol) in dichloromethane (5 ml) at 0° C. was treated with triflic anhydride (0.14 ml, 0.83 mmol). The reaction mixture was stirred at room temperature for 15 min, poured into water and extracted with dichloromethane (3×50 ml). The combined organic layers were dried over magnesium sulfate and concentrated in vacuo to afford 5-azidopentyl trifluoromethanesulfonate. Caution. Explosion hazard! Attempts to isolate neat azidoalkyl triflates have resulted in violent decomposition. These triflates should not be concentrated to dryness and should be used only in solution as described in this procedure.

To alcohol (+)-IV-1 (0.133 gram, 0.167 mmol) was added 5-azidopentyl trifluoromethanesulfonate (0.83 mmol) in 4 equal portions in dichloromethane (10 ml) over 12 hours. After addition of the first portion, the reaction mixture was concentrated in vacuo and placed under high vacuum. The process was repeated until all starting material was consumed as visualized by TLC. The residue was filtered through a plug of silica gel with ethyl acetate as eluant, concentrated in vacuo and purified by flash chromatography (10:1 to 7:3 hexanes/ethyl acetate). This afforded (+)-IV-2 (124 mg, 82% yield) as a clear oil and recovered (+)-IV-1 (21 mg). (See FIG. 24).

(+)-IV-2: $[a]^{20}{}_D$ +14.1° (c 1.41, CHCl$_3$); IR (CHCl$_3$) 3020 (m), 2950 (s), 2870 (s), 2100 (s), 1450 (s), 1370 (s), 1175 (s), 1120 (s), 690 (m), 590 (m) cm$^{-1}$; $^1$H NMR(500 MHz, CDCl$_3$) s 7.98 (d, J=8.3 Hz, 1H), 7.86 (d, J=8.4 Hz, 2H), 7.53–7.48(m, 2H), 7.42 (t, J=7.8 Hz, 2H), 7.38–7.22 (m, 13H), 4.89 (d, J=10.9 Hz, 1H), 4.74 (d, J=11.8 Hz, 1H), 4.62 (d, J=11.8 Hz, 1H), 4.61 (d, J=10.9 Hz, 1H), 4.27 (m, 2H), 4.14 (m, 1H), 3.90 (t, J=9.4 Hz, 1H), 3.71 (dd, J=16.6, 7.8 Hz, 1H), 3.66 (d, J=2.7 Hz, 2H), 3.57 (dt, J=6.3 Hz, 1H), 3.43 (m, 2H), 3.34 (m, 1H), 3.20 (t, J=6.9 Hz, 2H), 2.96 (m, 2H), 1.57 (m, 4H), 1.41 (m, 2H), 1.15–1.04 (m, 21H); $^{13}$C NMR (125 MHz, CDCl$_3$) s 138.5, 138.4, 135.2, 133.6, 131.0, 129.2, 128.3, 128.2, 128.1, 127.6, 127.4, 126.7, 124.7, 123.3, 123.1, 119.7, 119.4, 113.7, 100.8, 83.0, 75.8, 75.0, 74.6, 71.9, 71.3, 70.3, 70.2, 68.0, 51.4, 29.4, 28.8, 25.4, 23.4, 18.3 (2 C), 12.9; high resolution mass spectrum (FAB) m/z 933.4251 [(M+Na)$^+$; calcd for C$_{50}$H$_{66}$N$_4$O$_8$SSi: 933.4269].

EXAMPLE 17

2-(N-(Phenylsulfonyl)indol-3-yl)ethyl tetra-O-acetyl-β-L-glucopyranoside [(+)-IV-3]

To L-glucose pentacetate (−)-IV-3 (2.0 g, 5.12 mmol) was added HBr in acetic acid (6 mL, 31 mmol, 30%) at 0° C., stirred for 10 minutes, and allowed to warm to room temperature for 1 h. The reaction mixture was diluted with ether (50 mL) and poured into ice/saturated sodium bicarbonate. The layers were separated and the organic layer washed with saturated sodium bicarbonate (2×50 mL), water (50 mL), and brine (50 mL). The organic layer was dried over magnesium sulfate, filtered, and concentrated in vacuo to afford the crude bromide as a white solid.

2-(N-phenylsulfonyl)tryptophol (I-22) (1.54 g, 5.12 mmol), silver (I) oxide (4.87 g, 21 mmol), and powdered activated molecular sieves (4 Å, 2.6 g) in hexane/benzene (24 mL/8 mL) was added the above bromide in benzene (8 mL) and stirred in the absence of light for 3 d. The reaction was filtered through celite, concentrated in vacuo, and purified via flash chromatography (40% ethyl acetate/hexane) to afford (+)-IV-4 (2.23 g, 66% yield, 2 steps) as a clear oil: [x]_s(25,D)+16.6° (c 0.69, CHCl$_3$); IR (CHCl$_3$) 3020 (m), 1765 (s), 1455 (s), 1375 (s), 1240 (s), 1185 (s), 1050 (s) cm$^{-1}$; $^1$H NMR (500 MHz, CDCl$_3$) d 8.00 (m, 1H), 7.89 (m, 2H), 7.55 (tt, J=7.4, 1.2 Hz, 1H), 7.49–7.42 (m, 3H), 7.35–7.24 (m, 3H), 5.21 (t, J=9.4 Hz, 1H), 5.12 (t, J=9.4

Hz, 1H), 5.02 (dd, J=9.6, 7.9 Hz, 1H), 4.56 (d, J=7.9 Hz, 1H), 4.29 (dd, J=12.3, 4.8 Hz, 1H), 4.20–4.14 (m, 2H), 3.79 (dt, J=9.5, 6.9 Hz, 1H), 3.72 (ddd, J=9.9, 4.8, 2.5 Hz, 1H), 2.97 (t, J=5.3 Hz, 2H), 2.10 (s, 3H), 2.05 (s, 3H), 2.03 (s, 3H), 1.92 (s, 3H); $^{13}$C NMR (125 MHz, CDCl$_3$) d 170.5, 170.1, 169.3, 169.2, 138.2, 135.0, 133.6, 130.9, 129.1, 126.7, 124.7, 123.5, 123.1, 119.5, 119.4, 113.6, 100.6, 72.8, 71.8, 71.1, 68.6, 61.9, 25.2, 20.5, 20.5, 20.3; high resolution mass spectrum (Cl, NH$_3$) m/z 649.2055 [(M+NH$_4$)$^+$; calcd for C$_{30}$H$_{33}$NO$_{12}$S: 649.2066]. Anal. Calcd. for C$_{30}$H$_{33}$NO$_{12}$S: C 57.05; H 5.27; N 2.22. Found: C 56.98; H 5.12; N 2.12.

EXAMPLE 18

2-(N-(Phenylsulfonyl)indol-3-yl)ethyl β-L-glucopyranoside [(+)-IV-5]

A solution of acetate (+)-IV-4 (2.03 g, 3.21 mmol) in dry methanol (40 mL) was added sodium methoxide (100 μL, 5.4 M in methanol). The reaction mixture was stirred for 18 h, acidified with Amberlyst H-15 resin, and filtered. The filtrate was concentrated in vacuo and purified via flash chromatography (10% methanol/dichloromethane) to give (+)-IV-5 (1.37 g, 92% yield) as a white foam: $[\alpha]_D^{25}$+33° (c 0.79, CHCl$_3$); IR(CHCl$_3$) 3400 (br s), 3010 (m), 1450 (s), 1375 (m), 1175 (s) cm$^{-1}$; $^1$H NMR (500 MHz, CDCl$_3$) δ 7.90 (apparent d, J=8.4 Hz, 1H), 7.79 (apparent d, J=7.5 Hz, 2H), 7.52 (s, 1H), 7.33–7.07 (m, 6H), 5.40 (br s, 1H), 5.02 (br s, 1H), 4.65 (br s, 1H), 4.41 (d, J=7.6 Hz, 1H), 4.10 (apparent q, J=7.1 Hz, 1H), 3.88 (m, 2H), 3.76–3.65 (m, 4H), 3.55 (m, 1H), 3.33 (br d, J=9.2 Hz, 1H), 2.87 (br t, J=6.4 Hz, 2H); $^{13}$C NMR (125 MHz, CDCl$_3$) δ 138.0, 134.9, 133.6, 130.9, 129.1, 126.6, 124.7, 123.7, 123.2, 119.6, 119.4, 113.5, 102.8, 76.6, 75.7, 73.5, 69.5, 68.8, 61.4, 25.1; high resolution mass spectrum (Cl, NH$_3$) m/z 481.1649 [(M+NH$_4$)$^+$; calcd for C$_{22}$H$_{25}$NO$_8$S: 481.1644].

EXAMPLE 19

2-(N-(Phenylsulfonyl)indol-3-yl)ethyl 4,6-O-benzylidene-β-L-glucopyranoside [(+)-IV-6]

A solution of alcohol (+)-IV-5(1.87 g, 1.03 mmol), and pyridinium para-toluenesulfonate (100 mg) in DMF (10 mL) was added benzaldehyde dimethyl acetal (770 μL, 4.8 mmol). The reaction mixture was heated to 85° C. under an argon sweep for 2 h, cooled, and poured into water (100 mL). The water was extracted with ethyl acetate (3×50 mL) and the combined organic extracts were washed with water (50 mL), brine (50 mL), dried over magnesium sulfate, filtered, and concentrated in vacuo. Purification via flash chromatography (66% ethyl acetate/hexane) gave (+)-IV-6 (1.68 g, 76% yield) as a white foam: $[\alpha]_D^{25}$ +37.1° (c 0.63, CHCl$_3$); IR (CHCl$_3$) 3480 (m), 3005 (s), 2880 (m), 1725 (m), 1500 (s), 1370 (s), 1175(s), 1080 (s) cm$^{-1}$; $^1$H NMR (500 MHz, CDCl$_3$) d 7.97 (d, J=8.3 Hz, 1H), 7.86 (m, 2H), 7.46 (m, 4H), 7.38 (m, 2H), 7.32 (m, 5H), 7.21 (m, 1H), 5.49 (s, 1H), 4.38 (d, J=7.7 Hz, 1H), 4.30 (dd, J=10.5, 5.0 Hz, 1H), 4.16 (dt, J=9.5, 6.6 Hz, 1H), 3.82–3.72 (m, 3H), 3.51 (t, J=9.3 Hz, 1H), 3.48 (m, 1H), 3.39 (ddd, J=9.8, 5.0 Hz, 1H), 3.16 (br s, 1H), 2.96 (ddd, J=7.0, 3.5 Hz, 2H), 2.92 (apparent, J=2.6 Hz, 1H); $^{13}$C NMR (125 MHz, CDCl$_3$) d 138.3, 137.0, 135.2, 133.7, 131.1, 129.3, 128.3, 126.7, 126.3, 124.9, 123.7, 123.2, 119.6, 119.4, 113.8, 103.3, 101.9, 80.6, 77.3, 77.3, 73.3, 69.2, 68.7, 66.4, 25.4; high resolution mass spectrum (Cl, NH$_3$) m/z 552.1680 [(M+H)$^+$; calcd for C$_{29}$H$_{29}$NO$_8$S: 552.1692]. Anal. Calcd. for C$_{29}$H$_{29}$NO$_8$S.2H$_2$O: C 59.68; H 5.01; N 2.40. Found: C 59.97; H 4.56; N 2.12.

EXAMPLE 20

2-(N-(Phenylsulfonyl)indol-3-yl)ethyl 2,3-di-O-benzyl-4,6-O-benzylidene-β-L-glucopyranoside [(+)-IV-7]

A solution of alcohol (+)-IV-6 (415 mg, 0.75 mmol), benzyl bromide (270 μL, 2.3 mmol), and tetrabutylammonium hydrogen iodide (25 mg) in THF at 0° C. was added NaH (92 mg, 2.3 mmol, 65% in oil) and the reaction allowed to stir at room temperature for 3 d. Saturated ammonium hydrochloride was added and the reaction mixture poured into water (50 mL). The aqueous layer was extracted with ether (3×50 mL), and the combined organic extracts were dried over magnesium sulfate, filtered, and concentrated in vacuo. Purification via flash chromatography (20% ethyl acetate/hexane) gave (+)-IV-7 (200 mg, 40% yield) as a clear glass: $[\alpha]_D^{25}$+25.1° (c 0.43, CHCl$_3$); IR (CHCl$_3$) 3480 (m), 3005 (s), 2880 (m), 1725 (m), 1500 (s), 1370 (s), 1175 (s), 1080 (s) cm$^{-1}$; $^1$H NMR (500 MHz, CDCl$_3$) δ 8.01 (apparent d, 1H), 7.87 (m, 2H), 7.53–7.48 (m, 4H), 7.43–7.19 (m, 18H), 5.60 (s, 1H), 4.94 (d, J=11.5 Hz, 1H), 4.82 (d, J=11.5 Hz, 1H), 4.69 (dd, J=15.9, 11.0 Hz, 2H), 4.57 (d, J=7.6 Hz, 1H), 4.37 (dd, J=10.5, 5.0 Hz, 1H), 4.22 (dt, J=9.5, 7.0 Hz, 1H), 3.91 (dt, J=14.1, 7.6 Hz, 1H), 3.82 (t, J=10.3 Hz, 1H), 3.77 (m, 1H), 3.72 (t, J=9.1 Hz, 1H), 3.43 (m, 1H), 3.04 (t, J=6.7 Hz, 2H); $^{13}$C NMR (125 MHz, CDCl$_3$) S 138.5, 138.4, 138.3, 137.3, 135.2, 133.6, 130.9, 129.2, 128.9, 128.3, 128.2, 128.0, 128.0, 127.6, 127.6, 126.7, 126.0, 124.8, 123.5, 123.2, 119.5, 119.4, 113.8, 104.1, 101.2, 82.2, 81.5, 80.9, 75.3, 75.1, 69.1, 68.8, 66.1, 25.7; high resolution mass spectrum (FAB, m-nitrobenzyl alcohol) m/z 754.2473 [(M+Na)$^+$; calcd for C$_{43}$H$_{41}$NO$_8$S: 754.2450].

EXAMPLE 21

2-(N-(Phenylsulfonyl)indol-3-yl)ethyl 2,3,4-tri-O-benzyl-β-L-glucopyranoside [(+)-IV-8]

A solution of acetal (+)-IV-7 (213 mg, 0.29 mmol) in dichloromethane (8 mL) at 0° C. was added DIBALH (2.91 mL, 2.91 mmol, 1.0 M in toluene) and the reaction allowed to stir for 6 h. The reaction was quenched with saturated sodium-potassium tartate and diluted with water (10 mL). The aqueous layer was extracted with dichloromethane (3×35 mL), and the combined organic extracts were dried over magnesium sulfate, filtered, and concentrated in vacuo. Purification via flash chromatography (33% ethyl acetate/hexane) gave (+)-IV-8 (132 mg, 62% yield) as a clear glass: $[\alpha]_D^{25}$ +8.1° (c 0.8, CHCl$_3$); IR (CHCl$_3$) 3600 (w), 3010 (m), 2890 (m), 1450 (s), 1380 (s), 1180 (s), 1080 (s) cm$^{-1}$; $^1$H NMR (500 MHz, CDCl$_3$) δ 8.01 (d, J=8.3 Hz, 1H), 7.87 (apparent d, J=7.5 Hz, 2H), 7.56 (s, 1H), 7.51 (t, J=7.7 Hz, 2H), 7.41 (t, J=8.0 Hz, 2H), 7.36–7.21 (m, 17H), 4.96 (d, J=11.0 Hz, 1H), 4.89 (d, J=10.9 Hz, 1H), 4.85 (d, J=11.0 Hz, 1H), 4.78 (d, J=11.0 Hz, 1H), 4.69 (d, J=11.0 Hz, 1H), 4.66 (d, J=11.1 Hz, 1H), 4.52 (d, J=7.8 Hz, 1H), 4.23 (dt, J=9.4, 7.0 Hz, 1H), 3.95–3.89 (m, 2H), 3.77 (ddd, J=12.3, 8.1, 4.4 Hz, 1H), 3.72 (t, J=9.0 Hz, 1H), 3.64 (t, J=9.4 Hz, 1H), 3.44 (t, J=8.0 Hz, 1H), 3.39 (ddd, J=9.5, 4.2, 2.7 Hz, 1H), 3.02 (m, 2H), 2.02 (dd, J=8.0, 5.6 Hz, 1H); $^{13}$C NMR (125 MHz, CDCl$_3$) S 138.6, 138.3, 138.0, 135.2, 133.6, 131.0, 129.2, 128.5, 128.4, 128.3, 128.1, 128.0, 127.9, 127.8, 127.6, 126.7, 124.7, 123.7, 123.2, 119.6, 119.4, 113.8, 103.7, 84.5, 82.4, 77.5, 75.6, 75.2, 75.1, 68.7, 61.9, 25.7; high resolution mass spectrum (FAB, m-nitrobenzyl alcohol) m/z 756.2604 [(M+Na)$^+$; calcd for C$_{43}$H$_{43}$NO$_8$S: 756.2606]. Anal. Calcd. for C$_{43}$H$_{43}$NO$_8$S: C 70.38; H 5.91; N 1.91. Found: C 70.21; H 5.16; N 1.48.

EXAMPLE 22

2-(N-(Phenylsulfonyl)indol-3-yl)ethyl 2,3,4-tri-O-benzyl-6-O-(5'-azidopentyl)-β-L-glucopyranoside [(+)-IV-9]

To alcohol (+)-IV-8 (110 mg, 0.15 mmol) was added 5-azidopentyl triflate (1.2 mmol) in 3 equal portions over 12 hours. After addition of the first portion, the reaction mixture was concentrated in vacuo and placed under high vacuum (~1 mm Hg) and this process repeated until the starting material was consumed. The residue was filtered through a silica gel plug with ethyl acetate, concentrated in vacuo, and purified via flash chromatography (20% ethyl acetate/hexane) to furnish (+)-IV-9(80.3 mg, 64% yield) as a clear oil: $[\alpha]_D^{25}$ +2.8° (c 0.68, CHCl$_3$); IR (CHCl$_3$) 3005 (s), 2880 (m), 2100 (s), 1450 (s), 1370 (s), 1175 (s), 1070 (s) cm$^{-1}$; $^1$H NMR (500 MHz, CDCl$_3$) δ 8.01 (d, J=8.3 Hz, 1H), 7.87 (m, 2H), 7.50 (m, 3H), 7.42–7.24 (m, 18H), 7.20 (m, 1H), 4.94 (d, J=11.0 Hz, 1H), 4.89 (d, J=11.0 Hz, 1H), 4.82 (d, J=11.0 Hz, 1H), 4.77 (d, J=11.1 Hz, 1H), 4.64 (d, J=11.0 Hz, 1H), 4.64 (d, J=11.1 Hz, 1H), 4.45 (d, J=7.8 Hz, 1H), 4.23 (dt, J=9.5, 7.0 Hz, 1H), 3.88 (dt, J=9.6, 7.1 Hz, 1H), 3.71 (dd, J=10.6, 2.0 Hz, 1H), 3.65 (m, 2H), 3.61 (t, J=9.5 Hz, 1H), 3.54 (dt, J=9.4, 6.4 Hz, 1H), 3.46 (m, 3H), 3.22 (t, J=6.9 Hz, 2H), 3.05 (t, J=7.1 Hz, 2H), 1.60 (m, 4H), 1.46 (m, 2H); $^{13}$C NMR (125 MHz, CDCl$_3$) d 138.6, 138.4, 138.3, 135.2, 133.6, 131.0, 129.1, 128.4, 128.3, 128.3, 128.0, 127.9, 127.8, 127.8, 127.6, 126.7, 124.8, 123.5, 123.1, 119.7, 119.5, 113.8, 103.8, 84.7, 82.3, 78.0, 75.7, 75.0, 75.0, 74.7, 71.4, 69.8, 68.8, 51.3, 29.2, 28.7, 25.7, 23.4; high resolution mass spectrum (FAB, m-nitrobenzyl alcohol) m/z 867.3408 [(M+Na)$^+$; calcd for C$_{48}$H$_{52}$N$_4$O$_8$S: 867.3404].

EXAMPLE 23

2-(N-(Phenylsulfonyl)indol-3-yl)ethyl 2,3,4-tri-O-benzyl-6-O-(5'-aminopentyl)-β-L-glucopyranoside [(+)-IV-10]

A solution of azide (+)-IV-9 (77 mg, 0.09 mmol) in THF (5 mL) was added water (35 μL) followed by triphenylphosphine (50 mg, 0.18 mmol) and the reaction heated at 55° C. for 18 h. The mixture was concentrated in vacuo and purified directly by flash chromatography (5% methanol/dichloromethane then 2.5% methanol/ammoniacal chloroform) to give (+)-IV-10 (65 mg, 88% yield) as a colorless oil: $[\alpha]_D^{25}$ +2.8° (c 0.68, CHCl$_3$); IR (CHCl$_3$) 3010 (s), 2940 (s), 1450 (m), 1360 (s), 1180 (s), 1060 (s) cm$^{-1}$; $^1$H NMR (500 MHz, CDCl$_3$) δ 8.00 (d, J=8.3 Hz, 1H), 7.86 (m, 2H), 7.52–7.46 (m, 3H), 7.39–7.25 (m, 16H), 7.24 (m, 2H), 7.18 (m, 1H), 4.93 (d, J=11.0 Hz, 1H), 4.87 (d, J=11.0 Hz, 1H), 4.81 (d, J=11.0 Hz, 1H), 4.74 (d, J=11.1 Hz, 1H), 4.63 (d, J=11.0 Hz, 1H), 4.62 (d, J=11.1 Hz, 1H), 4.45 (d, J=7.8 Hz, 1H), 4.23 (dt, J=9.5, 6.9 Hz, 1H), 3.87 (dt, J=9.6, 7.1 Hz, 1H), 3.70 (dd, J=10.9, 1.9 Hz, 1H), 3.66 (m, 2H), 3.60 (t, J=9.4 Hz, 1H), 3.51 (dt, J=9.5, 6.4 Hz, 1H), 3.43 (m, 3H), 3.04 (t, J=6.9 Hz, 2H), 2.76 (br s, 2H), 1.57 (m, 4H), 1.35 (m, 2H); $^{13}$C NMR (125 MHz, CDCl$_3$) δ 138.6, 138.4, 138.3, 138.3, 135.2, 133.6, 131.0, 129.2, 128.4, 128.3, 128.3, 128.0, 127.9, 127.8, 127.8, 127.6, 126.7, 124.8, 123.5, 123.2, 119.7, 119.5, 113.7, 103.8, 84.7, 82.3, 78.0, 75.6, 75.0, 74.9, 74.7, 71.5, 69.7, 68.8, 29.2, 29.2, 25.7, 23.3; high resolution mass spectrum (FAB, m-nitrobenzyl alcohol) m/z 841.3523 [(M+Na)$^+$; calcd for C$_{46}$H$_{54}$N$_2$O$_8$S: 841.3499].

EXAMPLE 24

2-(1H-Indol-3-yl)ethyl 2,3,4-tri-O-benzyl-6-O-(5'-aminopentyl)-β-L-glucopyranoside [(−)-IV-11]

A solution of sulfonamide (+)-IV-10 (27 mg, 0.033 mmol) in methanol (2 mL) was added 5 M potassium hydroxide (200 μL) and the mixture heated at reflux for 48 h. The reaction was cooled, concentrated in vacuo, and purified by preparative plate chromatography (5% methanol/ammoniacal chloroform, 500 mm) to furnish (−)-IV-11 (15.0 mg, 67% yield) as a clear oil: $[\alpha]_D^{25}$ −14.7° (c 0.4, CHCl$_3$); IR (CHCl$_3$) 3490 (m), 3005 (s), 2630 (s), 1735 (m), 1455 (m), 1070 (s) cm$^{-1}$; $^1$H NMR (500 MHz, CDCl$_3$) δ 8.25 (br s, 1H), 7.63 (d, J=7.8 Hz, 1H), 7.32 (m, 15H), 7.24 (m, 1H), 7.21 (apparent t, J=7.1 Hz, 1H), 7.14 (apparent t, J=7.0 Hz, 1H), 7.09 (s, 1H), 4.94 (d, J=10.9 Hz, 1H), 4.88 (d, J=11.0 Hz, 1H), 4.86 (d, J=11.0 Hz, 1H), 4.81 (d, J=10.9 Hz, 1H), 4.69 (d, J=11.1 Hz, 1H), 4.64 (d, J=11.0 Hz, 1H), 4.47 (d, J=7.8 Hz, 1H), 4.27 (dt, J=9.4, 6.8 Hz, 1H), 3.90 (dt, J=9.4, 7.3 Hz, 1H), 3.71 (dd, J=10.9, 1.9 Hz, 1H), 3.68 (m, 2H), 3.61 (t, J=9.4 Hz, 1H), 3.55 (dt, J=9.4, 6.4 Hz, 1H), 3.46 (m, 3H), 3.15 (t, J=7.0 Hz, 2H), 2.66 (t, J=6.4 Hz, 2H), 1.62 (m, 4H), 1.47–1.37 (m, 4H); $^{13}$C NMR (125 MHz, CDCl$_3$) δ 138.7, 138.6, 138.3, 136.2, 128.4, 128.3, 128.3, 128.0, 127.9, 127.7, 127.6, 127.5, 122.2, 121.9, 119.2, 118.7, 112.8, 111.1, 103.7, 84.7, 82.4, 78.0, 75.7, 74.9, 74.9, 74.7, 71.7, 70.0, 69.7, 42.0, 29.7, 29.5, 25.8, 23.5; high resolution mass spectrum (Cl, NH$_3$) m/z 679.3739 [(M+H)$^+$; calcd for C$_{42}$H$_{50}$N$_2$O$_6$: 679.3747].

EXAMPLE 25

Tri-O-acetyl-L-glucal [(+)-IV-13]

L-glucose (−)-IV-12 (4.95 g, 27.4 mmol) was added acetic anhydride (25 mL) and HBr in acetic acid (5 mL, 33%) and stirred for 1 h until the solid dissolved. Another 25 mL of HBr in acetic acid was added and the reaction mixture stirred for 6 h. Concentration in vacuo with toluene and filtration through a silica gel plug (75% ether/hexanes) furnished pure bromo-α-L-glucopyranoside tetraacetate. The bromide was dissolved in ethyl acetate (140 mL), zinc (10.9 g, 166 mmol) added, and the mixture heated at reflux. N-methyl imidazole (2.21 mL, 27.7 mmol) was added in one portion and heating continued for 1 h. The mixture was concentrated in vacuo and purified by flash chromatography (33% ethyl acetate/hexane) to furnish (+)-IV-13 (5.89 g, 78% yield) as a clear oil: $[\alpha]_D^{25}$ −24.04° (c 1.4, CHCl$_3$); IR (CHCl$_3$) 3010 (m), 1745 (s), 1655 (s), 1375 (s), 1230 (s), 1050 (s) cm$^{-1}$; $^1$H NMR (500 MHz, CDCl$_3$) s 6.48 (dd, J=6.2, 1.3 Hz, 1H), 5.36 (m, 1H), 5.24 (dd, J=7.6, 5.9 Hz, 1H), 4.86 (dd, J=6.2, 3.3 Hz, 1H), 4.41 (dd, J=12.1, 5.7 Hz, 1H), 4.27 (m, 1H), 4.21 (dd, J=12.1, 3.2 Hz, 1H), 2.11 (s, 3H), 2.09 (s, 3H), 2.06 (s, 3H); $^{13}$C NMR (125 MHz, CDCl$_3$) s 170.5, 170.4, 169.5, 145.6, 99.0, 74.0, 67.4, 67.2, 61.4, 21.0, 20.8, 20.7; high resolution mass spectrum (Cl, NH$_3$) m/z 290.1243 [(M+NH$_4$)$^+$; calcd for C$_{12}$H$_{16}$O$_7$: 290.1239].

EXAMPLE 26

L-glucal [(−)-IV-14]

Triacetate (+)-IV-13 (2.61 g, 9.6 mmol) in methanol (65 mL) was added sodium methoxide (200 μL, 5.4 M in methanol) and the reaction mixture stirred 2 h, concentrated in vacuo and purified directly via flash chromatography (10% methanol/dichloromethane) to give (−)-IV-14 (1.36 g, 97% yield) as a clear oil: $[\alpha]_D^{25}$ −30.7° (c 1.33, MeOH); IR (CHCl$_3$) 3750–3200 (br s), 3010 (m), 1730 (w), 1220 (s), 1045 (s) cm$^{-1}$; $^1$H NMR (500 MHz, CD$_3$OD) δ 6.33 (dd, J=6.0, 1.7 Hz, 1H), 4.66 (dd, J=6.1, 2.4 Hz, 1H), 4.10 (dt, J=7.1, 2.0 Hz, 1H), 3.86 (dd, J=12.0, 2.6 Hz, 1H), 3.77 (dd, J=12.0, 5.4 Hz, 1H), 3.71 (ddd, J=9.6, 5.4, 2.5 Hz, 1H), 3.56 (dd, J=6.0, 1.7 Hz, 1H); $^{13}$C NMR (125 MHz, CD$_3$OD) δ 144.9, 104.5, 80.3, 70.9, 70.5, 62.2; high resolution mass spectrum (CI, NH$_3$) m/z 164.0927 [(M+NH$_4$)$^+$; calcd for C$_6$H$_{10}$O$_4$: 164.0923].

EXAMPLE 27

6-O-(Triisopropylsilyl)-L-glucal [(−)-IV-15]

Triol (−)-IV-14 (1.36 g, 9.3 mmol) in DMF/THF (1:6, 63 mL) was added imidazole (1.90 g, 28 mmol) and triisopropylsilyl chloride (1.94 mL, 11.1 mmol). The reaction mixture was heated at 55° C. for 20 h, cooled, and poured into water (100 mL). The aqueous layer was extracted with ethyl acetate (3×100 mL), and the combined organic extracts were dried over magnesium sulfate, filtered, concentrated in vacuo, and purified via flash chromatography (33% ethyl acetate/hexane) to give (−)-IV-15 (2.12 g, 75% yield) as a clear oil: [α]$_D^{25}$ −5.54° (c 0.92, CHCl$_3$); IR (CHCl$_3$) 3600 (br m), 3600–3200 (br s), 2950 (s), 2880 (s), 1650 (m), 1470 (m), 1225 (s), 1120 (s), 880 (s) cm$^{-1}$; $^1$H NMR (500 MHz, CHCl$_3$) δ 6.32 (dd, J=6.1, 1.8 Hz, 1H), 4.76 (dd, J=6.0, 2.3 Hz, 1H), 4.31 (m, 1H), 4.12 (m, 1H), 4.02 (m, 1H), 3.85 (m, 2H), 3.42 (br s, 1H), 2.50 (br s, 1H), 1.16 (m, 3H), 1.10 (m, 18H); $^{13}$C NMR (125 MHz, CD$_3$OD) δ 144.0, 102.5, 76.2, 73.0, 69.4, 64.7, 17.9, 17.8, 11.8; high resolution mass spectrum (CI, NH$_3$) m/z 320.2251 [(M+NH$_4$)$^+$; calcd for C$_{15}$H$_{30}$O$_4$Si: 320.2257]. Anal. Calcd. for C$_{15}$H$_{30}$O$_4$Si: C 59.56; H 10.00. Found: C 59.33; H 10.00.

EXAMPLE 28

3,4-Di-O-benzyl-6-O-(triisopropylsilyl)-L-glucal [(+)-IV-16]

A solution of glucal (−)-IV-15 (1.00 g, 3.3 mmol), benzyl bromide (1.2 mL, 10. mmol), and tetrabutylammonium iodide (10 mg) in THF (10 mL) at 0° C. was added sodium hydride (0.40 g, 10 mmol, 60% in oil) and the reaction mixture was stirred for 20 h. The reaction was quenched with water, diluted to 100 mL, and extracted with ether (3×100 mL). The combined organic extracts were dried over magnesium sulfate, filtered, concentrated in vacuo, and purified via flash chromatography (10% ethyl acetate/hexane) to give (+)-IV-16 (1.51 g, 95% yield) as a clear oil: [α]$_D^{25}$ +3.2° (c 0.8, CHCl$_3$); IR (CHCl$_3$) 2950 (s), 2875 (s), 1650 (m), 1450 (m), 1240 (m), 1100 (s), 880 (m) cm$^{-1}$; $^1$H NMR (500 MHz, CHCl$_3$) δ 7.40–7.29 (m, 10H), 6.42 (dd, J=6.1, 1.0 Hz, 1H), 4.88 (d, J=11.2 Hz, 1H), 4.86 (m, 1H), 4.79 (d, J=11.2 Hz, 1H), 4.76 (d, J=11.7 Hz, 1H), 4.61 (d, J=11.6 Hz, 1H), 4.23 (m, 1H), 4.05 (m, 2H), 3.96 (m, 2H), 1.13 (m, 3H), 1.10 (s, 12H), 1.09 (s, 6H); $^{13}$C NMR (125 MHz, CHCl$_3$) δ 144.8, 138.5, 138.5, 128.4, 127.9, 127.8, 127.7, 127.6, 127.6, 99.6, 78.2, 75.7, 74.1, 73.8, 70.6, 62.0, 18.0, 18.0, 12.0; high resolution mass spectrum (CI, NH$_3$) m/z 500.3187 [(M+NH$_4$)$^+$; calcd for C$_{29}$H$_{42}$O$_4$Si: 500.3196]. Anal. Calcd. for C$_{29}$H$_{42}$O$_4$Si: C 72.16; H 8.77. Found: C 71.90; H 8.49.

EXAMPLE 29

2-(N-(Phenylsulfonyl)indol-3-yl)ethyl 3,4-di-O-benzyl-6-O-(triisopropylsilyl)-β-L-glucopyranoside [(+)-IV-17]

A solution of glucal (+)-IV-16 (300 mg, 0.62 mmol) in dichloromethane (6 mL) at −10° C. was added dimethyldioxirane (14 mL, ~0.07 M in acetone) and the reaction stirred for 0.5 h at −10° C. Concentration in vacuo under an inert atmosphere afforded the crude epoxide which was added THF (2 mL) and the reaction vessel cooled to −78° C.

2-(N-phenylsulfonyl) tryptophol (I22) (187 mg, 0.62 mmol) in THF (2 mL) was added via cannula, followed by zinc chloride (1.37 mL, 1.37 mmol, 1.0 M in ether) and the reaction allowed to warm to room temperature slowly over several hours. The reaction was stirred for 48 h, poured into saturated sodium bicarbonate (25 mL), and extracted with ether (3×50 mL). The combined organic extracts were dried over magnesium sulfate, filtered, and concentrated in vacuo. Flash chromotagraphy (20% ethyl acetate/hexane) gave (+)-IV-17 (244 mg, 49% yield,) as a colorless oil: [α]$_D^{25}$ +7.6° (c 0.6, CHCl$_3$); IR (CHCl$_3$) 3600 (br m), 3005 (m), 2950 (s), 2875 (s), 1745 (m), 1450 (s), 1375 (s) cm$^{-1}$; $^1$H NMR (500 MHz, CHCl$_3$) δ 8.04 (d, J=8.4 Hz, 1H), 7.88 (m, 2H), 7.53 (m, 2H), 7.46–7.25 (m, 15H), 4.90 (m, 3H), 4.73 (d, J=10.9 Hz, 1H), 4.29 (d, J=7.6 Hz, 1H), 4.16 (m, 1H), 4.00 (dd, J=11.2, 1.9 Hz, 1H), 3.95 (dd, J=11.2, 4.2 Hz, 1H), 3.77 (dt, J=9.5, 7.3 Hz, 1H), 3.70 (t, J=9.1 Hz, 1H), 3.59 (t, J=9.1 Hz, 1H), 3.52 (apparent dt, J=7.7, 1.5 Hz, 1H), 3.35 (ddd, J=9.6, 4.1, 1.8 Hz, 1H), 3.02 (m, 2H), 2.17 (apparent d, J=1.9 Hz, 1H), 1.11 (m, 3H), 1.09 (s, 12H), 1.08 (s, 6H); $^{13}$C NMR (125 MHz, CHCl$_3$) δ 138.7, 138.3, 138.3, 135.2, 133.6, 131.0, 129.2, 128.5, 128.4, 128.0, 127.8, 127.8, 126.7, 124.8, 123.4, 123.1, 119.8, 119.5, 113.7, 102.5, 84.5, 76.4, 75.2, 75.0, 74.7, 68.4, 62.5, 25.6, 18.0, 17.9, 12.0; high resolution mass spectrum (FAB, m-nitrobenzyl alcohol) m/z 822.3487 [(M+Na)$^+$; calcd for C$_{45}$H$_{57}$NO$_8$SSi: 822.3471]. Anal. Calcd. for C$_{45}$H$_{67}$NO$_8$SSi: C 67.55; H 7.18; N 1.75. Found: C 67.22; H 6.87; N 1.56.

EXAMPLE 30

2-(N-(Phenylsulfonyl)indol-3-yl)ethyl 3,4-di-O-benzyl-6-O-(triisopropylsilyl)-β-L-mannopyranoside [(−)-IV-18]

A solution of (+)-IV-17 (231 mg, 0.29 mmol) in DMSO (8 mL) was added acetic anhydride (4 mL) and the reaction was stirred for 7 d. The reaction mixture was poured into ether (100 mL) and shaken with water (75 mL). The layers were separated and the aqueous layer further extracted with ether (2×75 mL). The combined organic extracts were dried over magnesium sulfate, filtered, and concentrated in vacuo. Flash chromatography (20% ethyl acetate/hexane) afforded the ketone as a mixture of hydrates.

The ketone was dissolved in ethanol/water (3.5:1, 18 mL), sodium borohydride (120 mg, 3.2 mmol) added, and the reaction heated at 60° C. for 1 h. Another portion of sodium borohydride (95 mg, 2.5 mmol) was added and the reaction heated again at 60° C. for 0.5 h. The reaction was cooled, poured into brine (40 mL), and extracted with ether (3×50 mL). The combined organic extracts were dried over magnesium sulfate, filtered, and concentrated in vacuo. Flash chromotagraphy (15% ethyl acetate/hexane then 25% ethyl acetate/hexane) afforded (−)-IV-18 (186 mg, 81% yield) as a colorless oil: [α]$_D^{25}$ −8.9° (c 0.8, CHCl$_3$); IR (CHCl$_3$) 3570 (m), 3010 (m), 2950 (s), 2875 (s), 1450 (s), 1370 (s), 1175 (s), 1000 (s) cm$^{-1}$; $^1$H NMR (500 MHz, CHCl$_3$) δ 8.01 (d, J=8.4 Hz, 1H), 7.88 (m, 2H), 7.53 (m, 2H), 7.42 (m, 4H), 7.38–7.24 (m, 11H), 4.94 (d, J=10.9 Hz, 1H), 4.80 (d, J=12.0 Hz, 1H), 4.70 (d, J=12.0 Hz, 1H), 4.69 (d, J=10.9 Hz, 1H), 4.43 (s, 1H), 4.18 (dt, J=9.6, 6.8 Hz, 1H), 4.07 (d, J=2.9 Hz, 1H), 4.00 (dd, J=10.0, 2.0 Hz, 1H), 3.94 (m, 2H), 3.77 (dt, J=9.6, 7.4 Hz, 1H), 3.54 (dd, J=9.1, 3.1 Hz, 1H), 3.27 (ddd, J=9.6, 4.7, 1.9 Hz, 1H), 3.02 (t, J=7.2 Hz, 2H), 2.30 (br s, 1H), 1.10 (m, 3H), 1.08 (s, 12H), 1.07 (s, 6H); $^{13}$C NMR (125 MHz, CHCl$_3$) δ 138.5, 138.3, 137.9, 135.2, 133.6, 131.0, 129.2, 128.5, 128.4, 128.1, 127.9, 127.8, 126.7, 126.7, 124.8, 123.4, 123.1, 119.7, 119.5, 113.7, 99.7, 81.5, 76.6, 75.2, 74.0, 71.5, 68.4, 68.3, 62.7, 25.5, 18.0, 17.9, 12.0; high resolution mass spectrum (FAB, m-nitrobenzyl alcohol) m/z 822.3463 [(M+Na)$^+$; calcd for $C_{45}H_{57}NO_8SSi$: 822.3471].

EXAMPLE 31

2-(N-(Phenylsulfonyl)indol-3-yl)ethyl 2,3,4-tri-O-benzyl-6-O-(triisopropylsilyl)-β-L-mannopyranoside [(+)-IV-19]

A solution of (−)-IV-18 (87.7 mg, 0.11 mmol), benzyl bromide (16 mL, 0.13 mmol), and tetrabutylammonium iodide (1 mg) in THF (5 mL) at −10° C. was added sodium hydride (9 mg, 0.22 mmol, 60% in oil) and the reaction was allowed to warm to room temperature and stir for 20 h. The reaction mixture was quenched with saturated ammonium chloride (20 mL) and extracted with ether (3×50 mL). The combined organic extracts were dried over magnesium sulfate, filtered, and concentrated in vacuo. Flash chromotagraphy (10% ethyl acetate/hexane) afforded (+)-IV-19 (58.3 mg, 60% yield) as a colorless oil: $[\alpha]_D^{25}$+26.9° (c 0.52, CHCl$_3$); IR (CHCl$_3$) 3005 (m), 2950 (s), 2880 (s), 1735 (w), 1450 (s), 1375 (s), 1175 (s), 1100 (s) cm$^{-1}$; $^1$H NMR (500 MHz, CHCl$_3$) δ 8.03 (apparent d, J=9.0 Hz, 1H), 7.85 (m, 2H), 7.53–7.22 (m, 22H), 4.95 (d, J=10.9 Hz, 1H), 4.92 (d, J=12.4 Hz, 1H), 4.80 (d, J=12.4 Hz, 1H), 4.67 (d, J=10.9 Hz, 1H), 4.57 (d, J=11.9 Hz, 1H), 4.50 (d, J=11.9 Hz, 1H), 4.39 (s, 1H), 4.24 (dt, J=9.5, 6.6 Hz, 1 H), 4.03 (apparent dt, J=10.9, 1.6 Hz, 1H), 3.95 (m, 2H), 3.87 (d, J=3.0 Hz, 1H), 3.72 (apparent q, J=7.2 Hz, 1H), 3.49 (dd, J=9.4, 3.0 Hz, 1H), 3.29 (ddd, J=9.6, 7.3, 1.6 Hz, 1H), 3.01 (t, J=6.8 Hz, 2H), 1.10 (m, 3H), 1.08 (s, 12H), 1.07 (s, 6H); $^{13}$C NMR (125 MHz, CHCl$_3$) δ 139.0, 138.6, 138.4, 138.3, 135.2, 133.6, 131.1, 129.8, 128.3, 128.3, 128.1, 128.0, 128.0, 127.6, 127.5, 127.2, 126.6, 124.7, 123.3, 123.1, 120.1, 75.1, 74.8, 74.3, 73.8, 71.4, 68.4, 63.2, 25.7, 18.0, 18.0, 12.0; high resolution mass spectrum (FAB, m-nitrobenzyl alcohol) m/z 912.3922 [(M+Na)$^+$; calcd for $C_{52}H_{63}NO_8SSi$: 912.3941].

EXAMPLE 32

2-(N-(Phenylsulfonyl)indol-3-yl)ethyl 2,3,4-tri-O-benzyl-β-L-mannopyranoside [(+)-IV-20]

A solution of (+)-IV-19 (55 mg, 0.06 mmol) in THF (2 mL) at 0° C. was added TBAF (90 L, 0.09 mmol, 1.0 M in THF) and the reaction was allowed to warm to room temperature and stir POR 15 h. The reaction was concentrated in vacuo and purified directly via flash chromotagraphy (33% ethyl acetate/hexane) to afford (+)-IV-20 (44.3 mg, 98% yield) as a colorless oil: $[\alpha]_D^{25}$ +37.3° (c 0.52, CHCl$_3$); IR (CHCl$_3$) 3600 (m), 3010 (m), 2890 (m), 1455 (s), 1370 (s), 1180 (s), 1090 (s) cm$^{-1}$; $^1$H NMR (500 MHz, CHCl$_3$) δ 8.02 (d, J=8.3 Hz, 1H), 7.87 (m, 2H), 7.55–7.24 (m, 22H), 4.97 (d, J=10.9 Hz, 1H), 4.90 (d, J=12.3 Hz, 1H), 4.81 (d, J=12.3 Hz, 1H), 4.68 (d, J=10.9 Hz, 1H), 4.55 (d, J=11.9 Hz, 1H), 4.49 (d, J=11.9 Hz, 1H), 4.44 (s, 1H), 4.27 (dt, J=9.4, 6.5 Hz, 1H), 3.98 (t, J=9.5 Hz, 1H), 3.91 (m, 2H), 3.80 (m, 2H), 3.50 (dd, J=9.5, 3.0 Hz, 1H), 3.32 (ddd, J=9.5, 5.2, 2.8 Hz, 1H), 3.04 (m, 2H), 2.21 (br s, 1H); $^{13}$C NMR (125 MHz, CHCl$_3$) δ 138.5, 138.3, 138.1, 135.2, 133.6, 131.0, 129.2, 128.4, 128.4, 128.2, 128.1, 128.1, 127.8, 127.6, 127.5, 127.5, 127.5, 126.7, 124.8, 123.7, 123.1, 119.7, 119.4, 113.7, 101.7, 82.1, 76.0, 75.3, 74.7, 74.3, 74.2, 71.5, 68.7, 62.4, 25.5; high resolution mass spectrum (FAB, m-nitrobenzyl alcohol) m/z 756.2592 [(M+Na)$^+$; calcd for $C_{43}H_{43}NO_8Si$: 756.2607].

EXAMPLE 33

N-(Phenylsulfonyl)indol-3-yl)ethyl 2,3,4-tri-O-benzyl-6-O-(5'-azidopentyl)-β-L-mannopyranoside [(+)-IV-21]

Alcohol (+)-IV-20 (41 mg, 0.056 mmol) was added 5-azidopentyl triflate (0.56 mmol) in 3 equal portions over 12 hours. After addition of the first portion, the reacton mixture was concentrated in vacuo and placed under high vacuum (~1 mm Hg) and this process repeated until the starting material was consumed. The residue was filtered through a silica gel plug with ethyl acetate, concentrated in vacuo, and purified via flash chromatography (20% ethyl acetate/hexane) to furnish (+)-IV-21 (31 mg, 75% yield, 87% conversion) as a colorless oil: $[\alpha]_D^{25}$+30.8° (c 0.36, CHCl$_3$); IR (CHCl$_3$) 3005 (w), 2940 (m), 2875 (m), 2100 (s), 1450 (s), 1370 (s), 1175 (s), 1100 (s) cm$^{-1}$; $^1$H NMR (500 MHz, CHCl$_3$) δ 8.02 (apparent d, J=8.3 Hz, 1H), 7.86 (m, 2H), 7.54 (apparent dt, J=7.8, 0.7 Hz, 1H), 7.48 (m, 2H), 7.41–7.23 (m, 19H), 4.97 (d, J=11.0 Hz, 1H, 4.91 (d, J=12.5 Hz, 1H), 4.80 (d, J=12.4 Hz, 1H), 4.63 (d, J=11.0 Hz, 1H), 4.52 (d, J=11.9 Hz, 1H), 4.45 (d, J=11.8 Hz, 1H), 4.38 (s, 1H), 4.27 (dt, J=9.5, 6.5 Hz, 1H), 3.87 (m, 2H), 3.77–3.69 (m, 3H), 3.55 (apparent dt, J=9.5, 6.3 Hz, 1H), 3.48 (m, 2H), 3.40 (ddd, J=9.7, 5.8, 1.9 Hz, 1H), 3.18 (t, J=7.0 Hz, 2H), 3.03 (t, J=6.8 Hz, 2H), 1.57 (m, 4H), 1.41 (m, 2H); $^{13}$C NMR (125 MHz, CHCl$_3$) δ 138.7, 138.5, 138.3, 138.1, 135.2, 133.6, 131.0, 129.2, 128.3, 128.2, 128.0, 127.9, 127.6, 127.6, 127.3, 126.7, 124.7, 123.5, 123.1, 119.9, 119.5, 113.7, 101.7, 82.2, 75.9, 75.1, 75.0, 74.4, 74.0, 71.4, 71.3, 70.3, 68.7, 51.3, 29.2, 28.6, 25.6, 23.4; high resolution mass spectrum (FAB, m-nitrobenzyl alcohol) m/z 867.3423 [(M+Na)$^+$; calcd for $C_{48}H_{52}N_4O_6Si$: 867.3405].

EXAMPLE 34

2-(1H-Indol-3-yl)ethyl 2,3,4-tri-O-benzyl-6-O-(5'-aminopentyl)-β-L-mannopyranoside [(+)-IV-22]

A solution of azide (+)-IV-20 (29 mg, 0.034 mmol) in THF (3 mL) was added water (25 μL) followed by triphenylphosphine (18 mg, 0.07 mmol) and the reaction heated at 55° C. for 20 h. The mixture was concentrated in vacuo and purified directly by flash chromatography (5% methanol/dichloromethane then 2.5% methanol/ammoniacal chloroform) to give the amine IV-21a (17 mg, 61% yield) as a colorless oil.

A solution of the above amine (16 mg, 0.021 mmol) in ethanol (2 mL) was added 5 M potassium hydroxide (200 μL) and the mixture heated at reflux for 18 h. The reaction was cooled, concentrated in vacuo, and purified by flash chromatography (5% methanol/dichloromethane then 2.5% methanol/ammoniacal chloroform) to furnish (+)-IV-22 (12.5 mg, 86% yield) as a colorless oil: $[\alpha]D^{25}$ +34.00 (c 0.24, CHCl$_3$); IR (CHCl$_3$) 3495 (w), 3010 (m), 2970 (m), 1735 (s), 1460 (m), 1375 (m), 1250 (s), 1100 (s) cm$^{-1}$; $^1$H NMR (500 MHz, CHCl$_3$) δ 8.44 (br s, 1H), 7.63 (d, J=7.9, 1H), 7.44–7.26 (m, 16H), 7.20 (m, 1H), 7.15 (m, 2H), 4.96 (d, J=12.3 Hz, 1H), 4.95 (d, J=10.9 Hz, 1H), 4.86 (d, J=12.3 Hz, 1H), 4.63 (d, J=10.9 Hz, 1H), 4.53 (d, J=11.8 Hz, 1H), 4.46 (d, J=11.8 Hz, 1H), 4.40 (s, 1H), 4.28 (dt, J=9.3, 7.0 Hz, 1H), 3.89 (m, 2H), 3.78 (dt, J=9.4, 7.0 Hz, 1H), 3.73 (m, 2H), 3.55 (dt, J=9.3, 6.5 Hz, 1H), 3.47 (m, 2H), 3.38 (ddd, J=9.7, 5.2, 2.2 Hz, 1H), 3.14 (m, 2H), 2.59 (t, J=6.8 Hz, 2H), 1.59 (m, 4H), 1.35 (m, 4H); $^{13}$C NMR (125 MHz, CHCl$_3$) δ 138.6, 138.5, 138.2, 136.2, 128.5, 128.3, 128.3, 128.2, 128.0, 127.7, 127.6, 127.6, 127.5, 122.5, 121.8, 119.1, 118.7, 112.7, 111.2, 101.6, 82.3, 75.7, 75.1, 74.8, 74.2, 74.1, 71.7, 71.5, 70.0, 29.1, 25.7, 23.3; high resolution mass spectrum (FAB, m-nitrobenzyl alcohol) m/z 679.3673 [(M+H)$^+$; calcd for $C_{42}H_{50}N_2O_6$: 679.3746].

EXAMPLE 35

Methyl 2-O-(tri-isopropylsilyl)-3-O-benzyl-4,6-O-benzylidene-β-D-glucopyranoside [(−)-IV-24]

A solution of methyl 3-O-benzyl-4,6-O-benzylidene-β-D-glucopyranoside (+)-IV-23 (0.64 g, 1.72 mmol) and 2,6-lutidine (0.60 mL, 5.2 mmol) in dichloromethane (15 mL) at 0° C. was added tri-isopropylsilyl triflate (0.70 mL, 2.6 mmol) dropwise via syringe. The reaction mixture was allowed to stand overnight at 0° C. The reaction mixture was quenched with saturated sodium bicarbonate, the layers separated, and the aqueous layer extracted with dichloromethane (3×50 mL). The combined organic extracts were dried over magnesium sulfate, filtered, and concentrated in vacuo. Flash chromatography (20% ethyl acetate/hexane) afforded (−)-IV-24 (0.90 g, 99% yield) as a colorless oil: $[α]_D^{25}$ −43.7° (c 1.35, CHCl$_3$); IR (CHCl$_3$) 2940 (s), 2870 (s), 1450 (m), 1365 (m), 1090 (s), 895 (s) cm$^{-1}$; $^1$H NMR (500 MHz, CDCl$_3$) δ 7.44–7.23 (m, 10H), 5.52 (s, 1H), 4.95 (d, J=11.3 Hz, 1H), 4.71 (d, J=11.3 Hz, 1H), 4.35 (dd, J=10.5, 5.0 Hz, 1H), 4.27 (d, J=7.2 Hz, 1H), 3.77 (t, J=10.3 Hz, 1H), 3.70 (m, 2H), 3.63 (apparent t, J=8.1 Hz, 1H), 3.50 (s, 3H), 3.45 (m, 1H), 1.10 (m, 3H), 1.05 (s, 18H); $^{13}$C NMR (125 MHz, CDCl$_3$) δ 138.8, 137.4, 128.9, 128.2, 128.0, 127.7, 126.0, 105.4, 101.1, 82.4, 82.0, 75.5, 74.7, 68.9, 65.7, 57.0, 18.1, 12.8; high resolution mass spectrum (Cl, CH$_4$) m/z 529.2981 [(M+H)$^+$; calcd for $C_{30}H_{44}O_6Si$: 529.2985]. Anal. Calcd. for $C_{30}H44O_6Si$: C 68.15; H 8.39. Found: C 68.27; H 8.48.

EXAMPLE 36

Methyl 2-O-(tri-isopropylsilyl)-3,4-di-O-benzyl-β-D-glucopyranoside [(−)-IV-25]

A stirred solution of silyl ether (+)-IV-24 (900 mg, 1.81 mmol) in dichloromethane (40 mL) at 0° C. was added DIBALH (19 mL, 19 mmol, 1.0 M in tol) dropwise. The reaction mixture was stirred at 0° C. for 6 h, quenched with saturated sodium-potassium tartrate, and diluted to 100 mL with water. The aqueous layer was extracted with ethyl acetate (3×100 mL), and the combined organic extracts were dried over magnesium sulfate, filtered, and concentrated in vacuo. Flash chromatography (20% ethyl acetate/hexane) gave (−)-IV-25 (950 mg, 98% yield) as a colorless oil: $[α]_D^{25}$ −26.9° (c =1.0, CHCl$_3$); IR (CHCl$_3$) 3590 (m), 3010 (m), 2950 (s), 2885 (s), 1450 (m), 1080 (s), 880 (s), 675 (s) cm$^{-1}$; $^1$H NMR (500 MHz, CDCl$_3$) δ 7.33–7.19 (m, 10H), 4.91 (d, J=11.4 Hz, 1H), 4.86 (d, J=11.4 Hz, 1H), 4.76 (d, J=10.9 Hz, 1H), 4.58 (d, J=10.9 Hz, 1H), 4.18 (d, J=7.4 Hz, 1H), 3.86 (br d, 1H), 3.67 (m, 2H), 3.54 (m, 2H), 3.48 (s, 3H), 3.38 (m, 1H), 1.86 (br s, 1H), 1.13 (m, 3H), 1.06 (s, 18H); $^{13}$C NMR (125 MHz, CDCl$_3$) δ 138.8, 138.0, 128.4, 128.2, 127.9, 127.8, 127.2, 127.1, 104.8, 86.1, 78.0, 75.8, 75.3, 74.9, 62.0, 56.7, 18.1, 13.1; high resolution mass spectrum (Cl, NH$_3$) m/z 548.3400 [(M+NH$_3$)$^+$; calcd for $C_{30}H_{46}O_6Si$: 548.3407]. Anal. Calcd. for $C_{30}H_{46}O_6Si$: C 67.89; H 8.74. Found: C 67.91; H 8.85.

EXAMPLE 37

Methyl 2-O-(tri-isopropylsilyl)-3,4-di-O-benzyl-6-O-(5'-azidopentyl)-β-D-glucopyranoside [(+)-IV-26]

Alcohol (+)-IV-25 (392 mg, 0.62 mmol) was added 5-azidopentyl triflate IV-26 (5.57 mmol) in 3 equal portions over 12 hours. After addition of the first portion, the reacton mixture was concentrated in vacuo and placed under high vacuum (~1 mm Hg) and this process repeated until the starting material was consumed. The residue was filtered through silica gel with dichloromethane, concentrated in vacuo, and purified via flash chromatography (5% ethyl acetate/hexane then 15% ethyl acetate/hexane) to furnish (+)-IV-26 (239 mg, 60% yield) as a colorless oil: $[α]_D^{25}$ −20.9° (c=1.41, CHCl$_3$); IR (CHCl$_3$) 2940 (s), 2865 (s), 2090 (s), 1060 (s), 905 (m) cm$^{-1}$; $^1$H NMR (500 MHz, CDCl$_3$) δ 7.32–7.19 (m, 10H), 4.91 (d, J=11.3 Hz, 1H), 4.83 (d, J=11.3 Hz, 1H), 4.76 (d, J=11.0 Hz, 1H), 4.55 (d, J=11.0 Hz, 1H), 4.11 (d, J=7.5 Hz, 1H), 3.69–3.66 (m, 2H), 3.60 (dd, J=17.7, 5.0 Hz, 1H), 3.55 (m, 3H), 3.46 (s, 3H), 3.44–3.36 (m, 2H), 3.23 (t, J=7.0 Hz, 2H), 1.63–1.50 (m, 4H), 1.46–1.39 (m, 2H) 1.17 (m, 2H); $^{13}$C NMR (125 MHz, CDCl$_3$) δ 138.9, 138.3, 128.4, 128.2, 127.7, 127.6, 127.2, 104.7, 86.4, 30 78.4, 75.8, 75.3, 74.8, 74.7, 71.4, 69.8, 56.5, 51.3, 29.2, 28.7, 18.2, 13.2; high resolution mass spectrum (FAB, m-nitrobenyl alcohol) m/z 664.3776 [(M+Na)$^+$; calcd for $C_{35}H_{55}N_3O_6Si$: 664.3758]. Anal. Calcd. for $C_{35}H_{55}N_3O_6Si$: C 65.49; H 8.64; N 6.55. Found: C 65.28; H 8.80; N 6.81.

EXAMPLE 38

Methyl 3,4-di-O-benzyl-6-O-(5'-azidopentyl)-β-D-glucopyranoside [(−)-IV-27]

A solution of silyl ether (+)-IV-26 (207 mg, 0.32 mmol) in THF (3 mL) at 0° C. was added TBAF (1.3 mL, 1.3 mmol, 1.0 M in THF) and the reaction allowed to stand at 0° C. overnight. The reaction was poured into water (25 mL), and extracted with ether (4×40 mL). The combined ether extracts were washed with water, dried over magnesium sulfate, filtered, and concentrated in vacuo. Flash chromatography (33% ethyl acetateihexane) gave (−)-IV-27 (143 mg, 91% yield) as a colorless oil: $[α]_D^{25}$ −6.22° (c =0.45, CHCl$_3$); IR (CHCl$_3$) 3600 (m), 3001 (m), 2940 (s), 2100 (s), 1455 (m), 1220 (m), 1120 (s), 1065 (s), 695 (m) cm$^{-1}$; $^1$H NMR (500 MHz, CDCl$_3$) δ 7.38–7.26 (m, 10H), 4.90 (d, J=11.3 Hz, 1H), 4.87 (d, J=11.5 Hz, 1H), 4.84 (d, J=11.6 Hz, 1H), 4.61 (d, J=11.0 Hz, 1H), 4.16 (d, J=7.6 Hz, 1H), 3.69 (dd, J=10.9, 5.0 Hz, 1H), 3.64 (dd, J=10.9, 4.6 Hz, 1H), 3.58 (m, 2H), 3.54 (s, 3H), 3.51 (m, 2H), 3.42 (m, 2H), 3.23 (t, J=8.9 Hz, 2H), 1.64 (m, 4H), 1.48 (m, 2H); $^{13}$C NMR (125 MHz, CDCl$_3$) δ 138.6, 138.2, 128.5, 128.4, 127.9, 127.8, 127.8, 127.7, 103.7, 84.4, 77.7, 77.7, 75.2, 75.1, 75.0, 74.6, 71.4, 69.6, 57.1, 51.3, 29.2, 28.7, 23.4; high resolution mass spectrum (Cl, CH$_4$) m/z 485.2508 [M$^+$; calcd for $C_{26}H_{35}N_6O_6$: 485.2526].

EXAMPLE 39

Methyl 2-O-(N-monomethoxytrityl-4'-methyleneimidazole)-3,4-di-O-benzyl-6-O-(5'-azidopentyl)-β-D-glucopyranoside [(−)-IV-28]

A stirred solution of alcohol (−)-IV-27 (51.0 mg, 0.105 mmol), N-(monomethoxytrityl)-4'-chloromethyl imidazole. (1–37) (0.15 mmol), and 15-Crown-5 (5 mg) in THF (2 mL) at 0° C. was added sodium hydride (12 mg. 0.31 mmol, 60% in oil). The reaction was allowed to warm to room temperature and stir overnight. The reaction mixture was quenched with water and extracted with ether (4×35 mL). The combined organic extracts were dried over magnesium sulfate, filtered, and concentrated in vacuo. Flash chromatography (33% ethyl acetate/hexane then 65% ethyl acetate/hexane then 75% ethyl acetate/hexane) gave (−)-IV-28 (76 mg, 86% yield) as a colorless oil: $[\alpha]_D^{25}$ −2.95° (c =0.48, CHCl$_3$); IR (CHCl$_3$) 3010 (s), 2940 (m), 2100 (s), 1530 (s), 1070 (s), 690 (s) cm$^{-1}$; $^1$H NMR (500 MHz, CDCl$_3$) δ 7.37 (br s, 1H), 7.33–7.22 (m, 13H), 7.16 (m, 3H), 7.07 (m, 4H), 6.99 (apparent d, J=8.9 Hz, 2H), 6.77 (m, 3H), 4.91 (apparent t, 2H), 4.84 (d, J=10.9 Hz, 1H), 4.67 (d, J=10.9 Hz, 1H), 4.62 (d, J=11.6, 1H), 4.57 (d, J=10.9 Hz, 1H), 4.27 (d, J=7.8 Hz, 1H), 3.78 (s, 3H), 3.66 (dd, J=10.9, 1.8 Hz, 1H), 3.60 (m, 2H), 3.50 (m, 2H), 3.49 (s, 3H), 3.38 (m, 3H), 3.22 (t, J=7.0, 2H), 1.58 (m, 4H), 1.44 (m, 2H); $^{13}$C NMR (125 MHz, CDCl$_3$) δ 158.9, 142.6, 138.7, 138.7, 138.4, 138.3, 134.4, 131.0, 129.6, 128.3, 128.0, 127.8, 127.8, 127.7, 127.6, 127.3, 119.9, 113.1, 104.5, 84.3, 82.2, 77.7, 75.3, 74.8, 74.8, 74.7, 71.3, 69.7, 68.6, 56.9, 55.1, 51.2, 29.1, 28.6, 23.3; high resolution mass spectrum (FAB, m-nitrobenzyl alcohol) m/z 860.3986 [(M+Na)$^+$; calcd for C$_{50}$H$_{55}$N$_5$O$_7$: 860.4000].

EXAMPLE 40

Methyl 2-O-(N-monomethoxytrityl-4'-methylene-imidazole)-3,4-di-O-benzyl-6-O-(5'-aminopentyl)-β-D-glucopyranoside [(−)-IV-29]

A solution of imidazole (−)-IV-28 (75.9 mg, 0.091 mmol) and water (20 μL) in THF (1 mL) was added triphenylphosphine (60 mg, 0.23 mmol) and the reaction mixture heated at 55° C. for 4 h. The reaction was concentrated in vacuo and purified directly via flash chromatography (5% methanol/dichloromethane then 5% methanol/ammoniacal chloroform) to give (−)-IV-29 (57.1 mg, 77% yield) as a colorless oil: $[\alpha]_D^{25}$ −3.47° (c =0.75, CHCl$_3$); IR (CHCl$_3$) 3675 (w), 3000 (s), 2925 (s), 1610 (w), 1515 (s), 1260 (s), 1065 (s), 690 (s) cm$^{-1}$; $^1$H NMR (500 MHz, CDCl$_3$) δ 7.36 (s, 1H), 7.32–7.22 (m, 13H), 7.16 (m, 3H), 7.10 (m, 4H), 7.00 (apparent d, 2H), 6.77 (apparent d, 3H), 4.90 (d, J=11.0 Hz, 1H), 4.87 (d, J=11.6 Hz, 1H), 4.83 (d, J=10.9 Hz, 1H), 4.67 (d, J=11.0 Hz, 1H), 4.62 (d, J=11.6 Hz, 1H), 4.57 (d, J=10.9 Hz, 1H), 4.27 (d, J=7.8 Hz, 1H), 3.77 (s, 3H), 3.66 (dd, J=11.0, 1.9 Hz, 1H), 3.60 (m 2H), 3.50 (m, 5H), 3.39 (m, 2H), 3.36 (dd, J=4.8, 1.8 Hz, 1H), 2.67 (t, J=7.0, 2H), 1.64 (s, 2H), 1.57 (m, 2H), 1.45 (m, 2H), 1.36 (m, 2H); $^{13}$C NMR (125 MHz, CDCl$_3$) δ 156.0, 142.7, 138.8, 138.8, 138.6, 138.4, 134.5, 131.1, 129.7, 128.3, 128.2, 128.1, 127.9, 127.8, 127.7, 127.3, 120.0, 113.2, 104.5, 84.4, 82.3, 77.8, 74.9, 74.8, 74.8, 71.6, 69.7, 68.7, 57.0, 55.2, 42.1, 29.5, 23.4; high resolution mass spectrum (FAB, m-nitrobenzyl alcohol) m/z 834.4073 [(M+Na)$^+$; calcd for C$_{50}$H$_{57}$N$_5$O$_7$: 834.4094].

EXAMPLE 41

Methyl 2-O-(4'-methylene-1H-imidazole)-3,4-di-O-benzyl-6-O-(5'-aminopentyl)-β-D-glucopyranoside [(+)-IV-30]

A solution of (−)-IV-29 (40 mg, 0.05 mmol) in dichloromethane (2 mL) was added TFA (50 μL, 0.62 mmol) and the reaction stirred for 5 minutes. The reaction was made basic with saturated sodium bicarbonate, diluted with brine, and extracted with dichloromethane (4×25 mL). The combined organic extracts were dried over sodium sulfate, filtered, and concentrated in vacuo to an oil. Purification via preparative plate chromatography (5% methanol/ammoniacal chloroform, 500 mm) afforded (+)-IV-30 (17.7 mg, 66% yield) as a colorless oil: $[\alpha]_D^{25}$+4.0° (c =0.43, MeOH); FT-IR (thin film) 3400 (s), 1510 (m), 1400 (m), 1100 (s), 1060 (s) cm$^{-1}$; $^1$H NMR (500 MHz, CD$_3$OD) δ 7.57 (s, 1H), 7.29–7.21 (m, 11H), 6.97 (s, 1H), 4.84 (apparent dd, 2H), 4.53 (d, J=11.1 Hz, 1H), 4.45 (d, J=5.0 Hz, 1H), 4.43 (d, J=5.0 Hz, 1H), 4.35 (d, J=11.1 Hz, 1H), 4.30 (d, J=7.8 Hz, 1H), 3.63 (m, 2H), 3.57 (t, J=8.9 Hz, 1H), 3.50 (s, 3H), 3.48 (apparent t, 2H), 3.40 (m, 2H), 3.32 (apparent t, 1H), 2.51 (t, J=7.0, 2H), 1.60 (m, 2H), 1.48 (m, 2H), 1.41 (m, 2H); $^{13}$C NMR (125 MHz, CD$_3$OD) δ 142.6, 142.3, 139.6, 131.8, 131.7, 131.4, 131.3, 131.2, 131.0, 108.4, 88.1, 85.4, 81.5, 78.9, 78.4, 74.9, 73.1, 59.8, 44.8, 35.7, 33.0, 27.1; high resolution mass spectrum (Cl, NH$_3$) m/z 540.3061 [M$^+$; calcd for C$_{30}$H$_{41}$N$_3$O$_6$: 540.3073].

EXAMPLE 42

Methyl 2-O-benzyl-3-O-(tert-butyldimethylsilyl)-4,6-O-benzylidene-β-D-glucopyranoside [(−)-IV-32]

A stirred solution of methyl 2-O-benzyl-4,6O-benzylidene-β-D-glucopyranoside (−)-IV-31 (1.03 g, 2.76 mmol) and 2,6-lutidine (0.97 mL, 8.3 mmol) in dichloromethane (15 mL) at 0° C. was added tert-butyldimethylsilyl triflate (0.95 mL, 4.15 mmol) dropwise via syringe. The reaction mixture was stirred for 10 minutes, saturated sodium bicarbonate added, and the layers separated. The aqueous layer was extracted with dichloromethane (3×100 mL) and the combined organic extracts were dried over magnesium sulfate, filtered, and concentrated in vacuo. Flash chromatography (25% ethyl acetate/hexane) afforded (−)-IV-32 (1.35 g, 100% yield) as a colorless oil: $[\alpha]_D^{25}$ −35.2° (c 0.63, CHCl$_3$); IR (CHCl$_3$) 3007 (m), 2940 (m), 2860 (m), 1455 (w), 1390 (m), 1230 (m), 1077 (s), 1000 (m), 838 (s), 695 (m) cm$^{-1}$; $^1$H NMR (500 MHz, CDCl$_3$) δ 7.47 (m, 2H), 7.26–7.36 (m, 8H), 5.49 (s, 1H), 4.87 (d, J=10.8 Hz, 1H), 4.70 (d, J=10.8 Hz, 1H), 4.38 (d, J=7.8 Hz, 1H), 4.33 (dd, J=5.0 Hz, 1H), 3.81 (t, J=8.8 Hz, 1H), 3.75 (t, J=10.2 Hz, 1H), 3.55 (s, 3H), 3.46 (t, J=9.3 Hz, 1H), 3.37 (ddd, J=10.0, 5.0, 1H), 3.29 (t, J=8.2 Hz, 1H), 0.84 (s, 9H), 0.02 (s, 3H), −0.01 (s, 3H); $^{13}$C NMR (62.5 MHz, CDCl$_3$) δ 138.4, 137.2, 128.8, 128.1, 128.0, 128.0, 127.4, 126.2, 105.3, 101.6, 83.1, 81.6, 75.1, 74.1, 68.7, 65.9, 57.3, 25.8, 18.2, −4.4, −4.6; high resolution mass spectrum (Cl, CH$_4$) m/z 487.2529 [M$^+$; calcd for C$_{27}$H$_{36}$O$_6$Si: 487.2516]. Anal. Calcd. for C$_{27}$H$_{38}$O$_6$Si: C 66.63; H 7.87. Found: C 66.73; H 8.00.

EXAMPLE 43

Methyl 2,4-di-O-benzyl-3-O-(tert-butyldimethylsilyl)-β-D-glucopyranoside [(−)-IV-34]

A stirred solution of silyl ether (−)-IV-32 (1.35 g, 2.77 mmol) in dichloromethane (15 mL) at 0° C. was added DIBALH (30 mL, 30 mmol, 1.0 M in tol) dropwise. The reaction mixture was stirred at 0° C. for 5 h, quenched with saturated sodium-potassium tartrate, and diluted to 100 mL with water. The aqueous layer was extracted with ethyl acetate (3×100 mL), and the combined organic extracts were dried over magnesium sulfate, filtered, and concentrated in vacuo. Flash chromatography (25% ethyl acetate/hexane) gave (−)-IV-34 (1.10 g, 81% yield) as a colorless oil: $[\alpha]_D^{25}$ −7.6° (c=1.0, CHCl$_3$); IR (CHCl$_3$) 3100 (m), 3020 (s), 2940 (s), 1460 (m), 1395 (m), 1260 (m), 1075 (s), 840 (s), 700 (m) cm$^{-1}$; $^1$H NMR (500 MHz, CDCl$_3$) δ 7.37–6.38 (m, 10H), 4.89 (d, J=11.6 Hz, 1H), 4.87 (d, J=12.1 Hz, 1H), 4.66 (d, J=11.0 Hz, 1H), 4.62 (d, J=11.4 Hz, 1H), 4.31 (d, J=7.7 Hz, 1H), 3.83 (dd, J=12.3, 2.8 Hz, 1H), 3.72 (t, J=8.9 Hz, 1H), 3.66 (dd, J=11.9, 4.4 Hz, 1H), 3.51 (s, 3H), 3.44 (t, J=9.2 Hz, 1H), 3.32 (ddd, J=9.2, 4.1, 2.6 Hz, 1H), 3.20 (t, J=8.1 Hz, 1H), 0.93 (s, 9H), 0.05 (s, 3H), 0.03 (s, 3H); $^{13}$C NMR (125 MHz, CDCl$_3$) δ 138.7, 138.1, 128.3, 128.1, 127.9, 127.6, 127.6, 127.4, 105.0, 82.5, 78.6, 76.5, 75.0, 75.0, 74.9, 74.5, 61.9, 57.2, 26.0, 18.1, −4.0, −4.2; high resolution mass spectrum (Cl, NH$_3$) m/z 457.2410 [(M-OMe)$^+$; calcd for C$_{27}$H$_{40}$C$_6$Si: 457.2428]. Anal. Calcd. for C$_{27}$H$_{40}$O$_6$Si: C 66.36; H 8.25. Found: C 66.16; H 8.34.

EXAMPLE 44

Methyl 2,4-di-O-benzyl-β-D-glucopyranoside [(+)-IV-33]

(0.20 g, 19% yield) as a crystalline solid: m.p. 104.0–105.0° C.; [α]$_D$$^{25}$ −23.4° (c=0.90, CHCl$_3$); IR (CHCl$_3$) 3595 (m), 3005 (s), 2890 (m), 1455 (m), 1260 (s), 1075 (s), 1030 (s), 695 (s) cm$^{-1}$; $^1$H NMR (500 MHz, CDCl$_3$) δ 7.35–7.24 (m, 10H), 4.91 (d, J=11.4 Hz, 1H), 4.87 (d, J=11.2 Hz, 1H), 4.65 (d, J=11.4 Hz, 1H), 4.63 (d, J=11.6 Hz, 1H), 4.32 (d, J=7.8 Hz, 1H), 3.87 (apparent dd, J=10.3 Hz, 1H), 3.75 (apparent t, J=9.0 Hz, 2H), 3.55 (s, 3H), 3.47 (t, J=9.5 Hz, 1H), 3.35 (ddd, J=9.6, 4.5, 2.8 Hz, 1H), 3.19 (dd J=9.2, 7.8 Hz, 1H), 2.42 (brs, 1H), 1.86 (br s, 1H); 13C NMR (125 MHz, CDCl$_3$) δ 138.3, 138.2, 128.5, 128.5, 128.1, 128.1, 128.0, 127.9, 104.3, 81.4, 77.3, 76.5, 74.9, 74.6, 74.4, 62.1, 57.1; high resolution mass spectrum (Cl, NH$_3$) m/z 392.2081 [(M+NH$_3$)$^+$; calcd for C$_{21}$H$_{26}$O$_6$: 392.2073].

EXAMPLE 45

Methyl 2,4-di-O-benzyl-3-O-(tert-butyldimethylsilyl)-6-O-(5'-azidopentyl)-β-D-glucopyranoside [(+)-IV-35]

Alcohol (+)-IV-34 (113 mg, 0.23 mmol) was added 5-azidopentyl triflouromethanesulfonate (1.4 mmol) in 3 equal portions over 12 hours. After addition of the first portion, the reaction mixture was concentrated in vacuo and placed under high vacuum (~1 mm Hg) and this process repeated until the starting material was consumed. The residue was filtered through silica gel with dichloromethane, concentrated in vacuo, and purified via flash chromatography (10% ethyl acetate/hexane) to furnish (+)-IV-35 (284 mg, 97% yield) as a colorless oil: [α]$_D$$^{25}$+15.6° (c =0.48, CHCl$_3$); IR (CHCl,) 3010 (s), 2940 (s), 2100 (s), 1460 (w), 1260 (m), 1075 (s), 840 (s) cm$^{-1}$; $^1$H NMR (500 MHz, CDCl$_3$) δ 7.37–7.26 (m, 10H), 4.89 (d, J=11.0 Hz, 1H), 4.85 (d, J=11.4 Hz, 1H), 4.63 (d. J=11.0 Hz, 1H), 4.59 (d, J=11.4 Hz, 1H), 4.24 (d, J=7.8 Hz, 1H), 3.68 (t, J=8.7 Hz, 1H), 3.62 (dd, J=10.9, 2.1 Hz, 1H), 3.58 (dd, J=10.9, 4.4 Hz, 1H), 3.50 (s, 3H), 3.48 (apparent t, J=6.4 Hz, 1H), 3.44–3.36 (m, 3H), 3.23 (t, J=6.9 Hz, 1H), 3.21 (m, 2H), 1.60 (m, 4H), 1.42 (m, 2H) 0.91 (s, 9H), 0.01 (s, 6H); $^{13}$C NMR (125 MHz, CDCl$_3$) δ 137.8, 137.4, 127.2, 127.1, 127.0, 126.4, 126.3, 126.2, 108.4, 81.4, 78.1, 75.6, 73.7, 73.6, 73.4, 70.3, 68.7, 56.0, 50.3, 28.1, 27.6, 25.0, 22.4, 17.0, −5.1, −5.3; high resolution mass spectrum (Cl, NH$_3$) m/z 617.3750 [(M+NH$_3$)$^+$; calcd for C$_{32}$H$_{49}$N$_3$O$_6$Si: 617.3750]. Anal. Calcd. for C$_{32}$H$_{49}$N$_3$O$_6$Si: C 64.08; H 8.23; N 7.01. Found: C 63.87; H 8.16; N 6.91.

EXAMPLE 46

Methyl 2,4-di-O-benzyl-6-O-(5'-azidopentyl)-β-D-glucopyranoside [(+)-IV-36]

A solution of silyl ether (+)-IV-35 (189 mg, 0.31 mmol) in THF (2 mL) at 0° C. was added TBAF (0.5 mL, 0.5 mmol, 1.0 M in THF) and the reaction allowed to stand at 0° C. overnight. The reaction was poured into water, and extracted with ether (3×50 mL). The combined ether extracts were washed with water (50 mL), dried over magnesium sulfate, filtered, and concentrated in vacuo. Flash chromatography (20% ethyl acetate/hexane) gave (+)-IV-36 (169 mg, 90% yield) as a colorless oil: [α]$_D$$^{25}$+18.0° (c=0.25, CHCl$_3$); IR (CHCl$_3$) 3600 (w), 3010 (m), 2940 (m), 2102 (s), 1460 (m), 1230 (m), 1070 (s), 690 (m) cm$^{-1}$; $^1$H NMR (500 MHz, CDCl$_3$) δ 7.41–7.26 (m, 10H), 4.93 (d, J=11.5 Hz, 1H), 4.87 (d, J=11.3 Hz, 1H), 4.65 (d, J=11.5 Hz, 1H), 4.63 (d, J=11.3 Hz, 1H), 4.27 (d, J=7.8 Hz, 1H), 3.72 (t, J=8.8 Hz, 1H), 3.70 (m, 1H), 3.61 (dd, J=10.9, 4.8 Hz, 1H), 3.55 (s, 3H), 3.52–3.40 (m, 4H), 3.24–3.21 (m, 3H), 2.41 (br s, 1H), 1.66–1.55 (m, 4H), 1.49–1.36 (m, 2H); $^{13}$C NMR (125 MHz, CDCl$_3$) δ 138.4, 138.4, 128.5, 128.4, 128.1, 128.0, 128.0, 127.8, 104.3, 81.3, 77.5, 76.6, 74.8, 74.5, 74.3, 71.4, 69.8, 60.0, 51.4, 29.2, 28.7, 23.4; high resolution mass spectrum (Cl, NH$_3$) m/z 503.2891 [(M+NH$_3$)$^+$; calcd for C$_{26}$H$_{35}$N$_3$O$_6$: 503.2870]. Anal. Calcd. for C$_{26}$H$_{35}$N$_3$O$_6$: C 64.31; H 7.27; N 8.60. Found: C 64.41; H 7.36; N 8.65.

EXAMPLE 47

Methyl 2,4-di-O-benzyl-3-O-(N-monomethoxytrityl-4'-methylene-imidazole)-6-O-(5'-azidopentyl)-β-D-glucopyranoside [(+)-IV-37]

A stirred solution of alcohol (+)-IV-36 (39.9 mg, 0.082 mmol), N-(monomethoxytrityl)-4'-chloromethyl imidazole (I-37) (45 mg, 0.12 mmol), and 15-crown-5 (3 mg) in THF (2 mL) at 0° C. was added sodium hydride (9.5 mg. 0.25 mmol, 60% in oil). The reaction was allowed to warm to room temperature and stir overnight. The reaction was quenched with water and extracted with ether (4×35 mL). The combined organic extracts were dried over magnesium sulfate, filtered and concentrated in vacuo. Flash chromatography (33% ethyl acetate/hexane) gave (+)-IV-37 (58.7 mg, 85% yield) as a colorless oil: [α]$_D$$^{25}$+7.1° (c=0.26, CHCl$_3$); IR (CHCl$_3$) 3010 (s), 2950 (s), 2100 (s), 1730 (w), 1510 (m), 1450 (m), 1260 (m), 1110 (s), 1070 (s), 690 (m) cm$^{-1}$; $^1$H NMR (500 MHz, CDCl$_3$) δ 7.38 (br s, 1H), 7.33–7.15 (m, 16H), 7.07 (brs, 4H), 7.04 (brs, 2H), 6.76 (m, 3H), 4.95 (d, J=11.2 Hz, 1H), 4.88 (d, J=11.2 Hz, 1H), 4.83 (d, J=11.0 Hz, 1H), 4.75 (d, J=12.4 Hz, 1H), 4.70 (d, J=11.0, 1H), 4.53 (d, J=11.0 Hz, 1H), 4.23 (d, J=7.8 Hz, 1H), 3.77 (s, 3H), 3.66 (dd, J=10.9, 1.7 Hz, 1H), 3.57 (apparent dd, J=10.7, 5.1 Hz, 2H), 3.53 (s, 3H), 3.51–3.47 (m, 2H), 3.43–3.35 (m, 3H), 3.23 (t, J=7.0 Hz, 2H), 1.54 (m, 4H), 1.40 (m, 2H); $^{13}$C NMR (125 MHz, CDCl$_3$) δ 158.9, 142.6, 138.9, 138.6, 138.4, 134.4, 131.1, 129.6, 128.2, 128.1, 128.1, 128.0, 127.9, 127.8, 127.5, 127.4, 119.8, 113.1, 104.5, 84.4, 82.1, 77.5, 74.8, 74.8, 74.6, 71.3, 69.8, 69.4, 57.0, 55.1, 51.3, 29.1, 28.6, 23.3; high resolution mass spectrum (FAB, m-nitrobenzyl alcohol) m/z 860.3971 [(M+Na)$^+$; calcd for C$_{50}$H$_{55}$N$_5$O$_7$: 860.4000].

EXAMPLE 48

Methyl 2,4-di-O-benzyl-3-O-(N-monomethoxytrityl-4'-methylene-imidazole)-6-O-(5'-aminopentyl)-β-D-glucopyranoside [(+)-IV-38]

A solution of azide (+)-IV-37 (58.7 mg, 0.07 mmol) and water (30 μL) in THF (1 mL) was added triphenylphosphine (46 mg, 0.17 mmol) and the reaction heated at 55° C. for 4 h. The reaction mixture was concentrated in vacuo and purified directly via flash chromatography (5% methanol/dichloromethane then 5% methanol/ammoniacal chloroform) to give (+)-IV-38 (50.7 mg, 89% yield) as a colorless oil: [α]$_D$$^{25}$+7.95° (c=1.12, CHCl$_3$); IR (CHCl$_3$), 3650 (w), 2950 (m), 1610 (m), 1515 (s), 1260 (s), 1070 (s), 825 (m), 700 (s) cm$^{-1}$; $^1$H NMR (500 MHz, CDCl$_3$) δ 7.37

(d, J=1.4 Hz, 1H), 7.32–7.18 (m, 26H), 7.07 (apparent dd, J=3.3, 1.4 Hz, 4H), 6.99 (d, J=9.0 Hz, 2H), 6.76 (m, 3H), 4.94 (d, J=10.9 Hz, 1H), 4.86 (d, J=11.3 Hz, 1H), 4.82 (d, J=11.0 Hz, 1H), 4.72 (apparent d, J=10.9 Hz, 2H), 4.53 (d, J=10.9 Hz, 1H), 4.24 (d, J=7.8 Hz, 1H), 3.76 (s, 3H), 3.66 (dd, J=10.9, 1.9 Hz, 1H), 3.66 (dd, J=10.9, 1.9 Hz, 1H), 3.62–3.54 (m, 5H), 3.53 (s, 3H), 2.67 (t, J=6.8, 2H), 1.69 (m, 2H), 1.57 (m, 2H), 1.45 (m, 2H), 1.36 (m, 2H); $^{13}$C NMR (125 MHz, CDCl$_3$) δ 159.0, 142.7, 138.9, 138.7 138.6, 138.5, 135.5, 131.1, 129.7, 128.3, 128.2, 128.1, 128.1, 127.9, 127.8, 127.5, 127.4, 119.9, 113.2, 104.6, 84.4, 82.2, 77.6, 74.9, 74.6, 71.6, 69.8, 69.5, 57.0, 55.2, 42.1, 33.5, 29.5, 23.4; high resolution mass spectrum (FAB, m-nitrobenzyl alcohol) m/z 834.4083 [(M+Na)$^+$; calcd for C$_{50}$H$_{57}$N$_5$O$_7$: 834.4094].

EXAMPLE 49

Methyl 2,4-di-O-benzyl-3-O-(4'-methylene-1H-imidazole)-6-O-(5'-aminopentyl)-β-D-glucopyranoside [(+)-IV-39]

A solution of (+)-IV-38 (50.7 mg, 0.062 mmol) in dichloromethane (2 mL) was added TFA (50 μL, 0.62 mmol) and the reaction stirred for 5 minutes. The reaction was made basic with saturated sodium bicarbonate, diluted with brine (20 mL), and extracted with dichloromethane (4×25 mL). The combined organic extracts were dried over sodium sulfate, filtered, and concentrated in vacuo to an oil. Reverse phase HPLC (water/acetonitrile) afforded (+)-IV-39 (14.8 mg, 44% yield) as a colorless oil: [α]$_D^{25}$+11.8° (c=0.25, MeOH); UV (MeOH) λ$_{max}$ 208 nm, e=13,000; FT-IR (thin film) 3300 (s), 1600 (m), 1490 (m), 1100 (s), 1020 (s) cm$^{-1}$; $^1$H NMR (500 MHz, CD$_3$OD) δ 8.40 (s, 1H), 7.29–7.21 (m, 11H), 6.93 (s, 1H), 4.90–4.78 (m, 4H), 4.72 (d, J=11.2 Hz, 1H), 4.59 (d, J=11.1 Hz, 1H), 4.34 (d, J=7.8 Hz, 1H), 3.67 (m, 3H), 3.60–3.44 (m, 3H), 3.53 (s, 3H), 3.35–3.27 (m, 2H), 2.90 (t, J=7.4, 2H), 1.71–1.60 (m, 4H), 1.52–1.42 (m, 2H); $^{13}$C NMR (125 MHz, CD$_3$OD) δ 140.0, 139.8, 132.5, 129.4, 129.4, 128.9, 128.7, 128.7, 128.6, 128.5, 128.5, 119.1, 106.0, 85.5, 83.0, 79.0, 75.8, 75.6, 75.3, 72.2, 70.5, 65.1, 57.4, 40.6, 30.1, 28.3, 24.1; high resolution mass spectrum (Cl, NH$_3$) m/z 540.3077 [M$^+$; calcd for C$_{30}$H$_{41}$N$_3$O$_6$: 540.3073].

EXAMPLE 50

2-(N-(Phenylsulfonyl)indol-3-yl)ethyl 2,3,4-tri-O-benzyl-6-N-(1',5'-diaminopentyl)-β-D-glucopyranoside [(+)-IV-41]

A solution of 2-(N-(Phenylsulfonyl)indol-3-yl)ethyl 2,3,4-tri-O-benzyl-β-D-glucopyranoside IV-40 (47 mg, 0.06 mmol) and 2,6-di-t-butyl-4-methyl pyridine (46 mg, 0.22 mmol) in dichloromethane (4 ml) at 0° C. was treated with trifluorosulfonic acid (2×15 1, 2×0.09 mmol). The reaction mixture was stirred for 30 min, during which the color changed to light pink. The mixture was diluted with ethyl acetate (50 ml) and poured into a saturated aqueous sodium bicarbonate solution (50 ml). The layers were separated and the aqueous layer was extracted with ethyl acetate (3×50 ml). The combined organic layers were washed with brine (100 ml), dried over magnesium sulfate, filtered and concentrated in vacuo. The crude triflate ester was dissolved in dichloromethane (5 ml). 1,5-Diaminopentane (150 μl, 1.27 mmol) in dichloromethane (1 ml) was added via a cannula and the reaction was stirred for 1 h at room temperature. The reaction mixture was concentrated in vacuo. Flash chromatography (dichloromethane to 10% methanol/ammoniacal chloroform) afforded (+)-IV-41 (46 mg, yield 88%); [α]$_D^{25}$+1.78° (c 1.52, CHCl$_3$); IR (CHCl$_3$) 3005 (s), 2930 (s), 2860 (s), 1450 (s), 1350 (s), 1150 (s), 1070 (s), 690 (s), 590 (s), 565 (s) cm$^{-1}$; $^1$H NMR (500 MHz, CD$_3$OD) δ 7.94 (d, J=8.3 Hz, 1H), 7.80 (d, J=7.2 Hz, 2H), 7.44 (m, 3H), 7.35–7.11 (m, 19H), 4.88 (d, J=11.0 Hz, 1H), 4.83 (d, J=11.0 Hz, 1H), 4.75 (d, J=11.0 Hz, 1H), 4.82 (d, J=11.0 Hz, 1H), 4.58 (d, J=10.0 Hz, 1H), 4.57 (t, J=10.9 Hz, 1H), 4.43 (d, J=7.8 Hz, 1H), 4.16 (ddd, J=9.5, 7.0, 6.5 Hz, 1H), 3.84 (dt, J=9.5, 7.0 Hz, 1H), 3.61 (t, J=8.8 Hz, 1H), 3.43 (m, 2H), 3.36 (t, J=7.9 Hz, 1H), 2.97 (t, J=6.8 Hz, 1H), 2.92 (dd, J=12.2, 2.2 Hz, 2H), 2.65 (m, 3H), 2.55 (m, 2H), 2.40 (s br, NH$_2$), 1.42 (m, 4H), 1.29 (m, 2H); $^{13}$C NMR (125 MHz, CDCl$_3$) δ 138.6, 138.3, 138.1. 135.2, 133.6, 130.9, 129.1, 128.4, 128.3 (2 C), 128.0, 127.9. 127.8, 127.6, 126.6, 124.8, 123.5, 123.2, 119.6, 119.4, 113.7, 103.6, 84.6, 82.4, 79.6, 75.6, 75.0, 74.8, 74.2, 68.8, 50.5, 49.7, 41.6, 32.3, 29.5, 25.7, 24.4; high resolution mass spectrum (FAB) m/z 818.3841 [(M+H)$^+$; calcd for C$_{48}$H$_{55}$N$_3$O$_7$S: 818.3839).

EXAMPLE 51

2-(1H-indol-3-yl)ethyl 2,3,4-tri-O-benzyl-6-N-(1',5'-diamino-pentyl)-β-D-glucopyranoside [(+)-IV-42]

A solution of (+)-IV-41 (18 mg, 0.022 mmol) in ethanol (2.4 ml) was treated with 5 M aqueous sodium hydroxide solution (390 μL) and heated to reflux for 16 h. The reaction mixture was cooled and concentrated in vacuo. Flash chromatography (10% methanol/dichloromethane to 10% methanol/ammoniacal chloroform) yielded (+)-IV-42 (11 mg, yield 72%); [α]$_D^{25}$+13.3° (c 0.27, CHCl$_3$); IR (CHCl$_3$) 3680 (w), 3480 (w), 3010 (m), 2940 (m), 2860 (m), 1450 (m), 1360 (m), 1230 (m), 1210 (m), 1070 (s), 690 (m) cm$^{-1}$; $^1$H NMR (500 MHz, CD$_3$OD) δ 8.19 (s br, 1H), 7.57 (d, J=7.9 Hz, 1H), 7.32–7.13 (m, 16H), 7.08 (dt, J=7.8, 0.6 Hz, 1H), 7.01 (s, 1H), 4.88 (d, J=11.0 Hz, 1H), 4.83 (d, J=11.1 Hz, 1H), 4.79 (d, J=11.1 Hz, 1H), 4.76 (d, J=11.0 Hz, 1H), 4.63 (d, J=11.0 Hz, 1H), 4.58 (d, J=11.1 Hz, 1H), 4.45 (d, J=7.8 Hz, 1H), 4.18 (dd, J=9.4, 6.8 Hz, 1H), 3.86 (dd, J=9.4, 7.4 Hz, 1H), 3.62 (t, J=8.8 Hz, 1H), 3.42 (m, 3H), 3.09 (t, J=7.1 Hz, 2H), 2.91 (dd, J=12.2, 2.2 Hz, 1H), 2.67–2.49 (m, 5H), 1.93 (s br., NH$_2$), 1.39 (m, 4H), 1.27 (m, 2H); $^{13}$C NMR (125 MHz, CDCl$_3$) δ 138.6, 138.5, 138.2, 136.2, 128.4, 128.3, 128.0 (2 C), 127.9, 127.8, 127.6, 127.5, 122.2, 121.9, 119.3, 118.7, 112.5, 111.2, 103.7, 84.7, 82.5, 79.7, 75.7, 75.0, 74.7, 74.1, 70.3, 50.6, 49.7, 41.7, 32.8, 29.7, 25.9, 24.5; high resolution mass spectrum (FAB) m/z [(M+H)$^+$; calcd for C$_4$H$_5$N$_3$O$_5$).

EXAMPLE 52

Dibromide (IV-44)

To a stirred solution of PPh$_3$ (3.7 g, 14.0 mmol) in dichloromethane (3 mL) at 0° C. in an argon atmosphere was added a solution of CBr$_4$ (2.3 g, 7.0 mmol) in CH$_2$Cl$_2$ (3 mL). The reaction stirred for 30 min before adding a solution of indole aldehyde IV-43 (1 g, 3.5 mmol) in dichloromethane (3 mL) dropwise. Reaction continued to stir at 0° C. for 30 min and then 1 h at room temperature. Hexanes were added to precipitate product which were removed from solvent by filtration. Recrystallization from ethanol yielded 1.36 g (88%) of pure IV-44 as beige needle like crystals; IR (CHCl$_3$) 3150 (w), 3010 (m), 1610 (w), 1540 (m), 1445 (s), 1375 (s), 1360 (m), 1280 (m), 1265 (m), 1170 (s), 1135 (s), 1090 (s), 970 (s), 870 (m), 660 (m), 600 (s), 570 (m), 560 (s), 540 (m) cm$^{-1}$; $^1$H NMR (500 MHz, CDCl$_3$) δ 8.28 (s, 1H), 7.99 (d, J=8.4 Hz, 1H), 7.89 (dd, J=8.3, 0.8 Hz, 2H), 7.56–7.51 (m, 3H), 7.45 (t, J=8.1 Hz, 2H), 7.36 (t, J=7.3 Hz, 1H), 7.28 (t, J=7.6 Hz, 1H) ppm; $^{13}$C NMR (125 MHz, CDCl$_3$) δ 137.9, 134.1, 134.0, 129.4, 126.8, 125.5, 125.0, 123.7, 118.9, 115.5, 113.7 high resolution mass spectrum (FAB) m/z 456.9228 [(M+NH$_4$)$^+$; calcd for C$_{16}$H$_{11}$Br$_2$NSO$_2$NH$_4$: 456.9221].

EXAMPLE 53

(+)-2-(1-Phenylsulfonyl-indol-3-yl)ethyne-1-deoxy-2,3,4-tri-O-benzyl-6-O-(tert-butyldiphenysilyl)-β-D-glucopyranoside (IV-46)

To a stirred solution of dibromide IV-44 (0.44 g, 1.0 mmol) in THF (3 mL) at –78° C. under argon was added n-butyl lithium (1.6M in hexanes, 1.33 mL, 2.12 mmol) dropwise. The mixture was stirred for 20 min and then transferred via cannula to a THF (2 mL) solution of lactone X-1 (0.9 g, 1.3 mmol). The reaction stirred for 1 h while the ice bath was allowed to slowly warm. Diethyl ether was added and the reaction was poured into sat. NH$_4$Cl and extracted. The organic layer was washed with water, brine, dried over and. MgSO$_4$, filtered and concentrated. Purification (hexanes/ethyl acetate, 9:1) yielded 0.62 g (63%) of IV-45A as a mixture of diastereomers.

Triethylsilane (0.2 mL, 1.2 mmol) was added to a –78° C. solution of lactols IV-45A (0.59 g, 0.6 mmol) in dichloromethane (3 mL) while stirring under argon. The solution was treated with BF$_3$.Et$_2$O (0.075 mL, 0.6 mmol), the reaction was warmed to room temperature and stirred for 15 min. Additional dichloromethane was added, the reaction was poured into sat. NaHCO$_3$ and extracted. The organic layer was washed with water, brine, dried over anh. Na$_2$SO$_4$, filtered and concentrated. Purification using flash silica gel chromatography (hexanes/ethyl acetate, 10:1) afforded (+)-IV-46 as a colorless oil; [α]$_D^{25}$ +1.4° (c 1.3, CHCl$_3$); IR (CHCl$_3$) 3010 (m), 2940 (m), 2860 (m), 1450 (s), 1380 (s), 1280 (m), 1230 (m), 1180 (s), 1100 (s), 905 (s), 820 (m), 690 (s) cm$^{-1}$; $^1$H NMR (500 MHz, CDCl$_3$) δ 7.91 (d, J=8.2 Hz, 1H), 7.81 (dd, J=8.2, 1.0 Hz, 2H), 7.72–7.71 (m, 2H), 7.66 (s, 1H), 7.64 (dd, J=7.8, 1.1 Hz, 2H), 7.53 (dd, J=7.8, 0.5 Hz, 1H), 7.49–7.45 (m, 1H), 7.36 (t, J=7.6 Hz, 2H), 7.32–7.14 (m, 23H), 4.99 (d, J=10.7 Hz, 1H), 4.87 (d, J=10.6 Hz, 1H), 4.85 (d, J=10.4 Hz, 1H), 4.83 (d, J=10.5 Hz, 1H), 4.81 (d, J=11.0 Hz, 1H), 4.68 (d, J=10.8 Hz, 1H), 4.22 (d, J=8.9 Hz, 1H), 3.89 (d, J=2.3 Hz, 2H), 3.79 (t, J=9.3 Hz, 1H), 3.67–3.61 (m, 2H), 3.31 (d, J=9.6 Hz, 1H), 1.01 (s, 9H) ppm; $^{13}$C NMR (125 MHz, CDCl$_3$) δ 138.5, 138.3, 138.1, 137.9, 136.1, 135.7, 134.3, 134.1, 133.8, 133.2, 130.7, 129.6, 129.5, 129.4, 129.3, 128.5, 128.5, 128.4, 128.1, 128.0, 127.8, 127.8, 127.7, 127.5, 126.9, 125.6, 123.9, 120.7, 113.6, 104.8, 91.2, 86.2, 82.8, 79.9, 77.6, 76.6, 75.9, 75.6, 75.2, 70.3, 62.9, 26.9, 19.4 ppm; high resolution mass spectrum (FAB) m/z 952.3718 [(M+Na)$^+$; calcd for C$_{59}$H$_{57}$NO$_7$SSiH: 952.3703].

EXAMPLE 54

(–)-2-(1-Phenylsulfonyl-indol-3-yl)ethyl-1-deoxy-2,3,4-tri-O-benzyl-6-O-(tert-butyldiphenysilyl)-β-D-glucopyranoside (IV-47)

A solution of alkyne (+)-IV-46 (0.19 g, 0.2 mmol) in ethyl acetate (1.5 mL) was treated with Pd(CaCO$_3$) (60 mg) at room temperature. The mixture was back flushed four times with H$_2$ and stirred for 36 h. Reaction was filtered through celite and concentrated. Flash silica gel chromatography (hexanes/ethyl acetate, 8:1) provided 154 mg (82% yield) of (–)-IV-4 as an oil; [α]$_D^{25}$ –3.4° (c 0.7, CHCl$_3$); IR (CHCl$_3$) 3020 (m), 3000 (s), 2930 (s), 2860 (s), 1450 (s), 1360 (s), 1270 (w), 1170 (s), 1100 (s), 690 (s), 590 (s), 570 (m) cm$^{-1}$; $^1$H NMR (500 MHz, CDCl$_3$) δ 7.99 (d, J=8.2 Hz, 1H), 7.81 (d, J=8.1 Hz, 2H), 7.75 (d, J=6.4 Hz, 2H), 7.70 (d, J=8.0 Hz, 2H), 7.47 (t, J=6.3 Hz, 1H), 7.39–7.23 (m, 26H), 7.16 (t, J=7.7 Hz, 1H), 4.95–4.88 (m, 4H), 4.78 (d, J=10.8 Hz, 1H), 4.64 (d, J=11.1 Hz, 1H), 3.96 (d, J=2.4 Hz, 2H), 3.82 (t, J=9.4 Hz, 1H), 3.67 (t, J=8.9 Hz, 1H), 3.13 (t, J=9.2 Hz, 1H), 3.27–3.20 (m, 2H), 2.87 (ddd, J=14.7, 9.9, 4.0 Hz, 1H), 2.69 (ddd, J=16.2, 9.5, 7.1 Hz, 1H), 2.19–2.14 (m, 1H), 1.73 (dddd, J=13.8, 9.6, 9.6, 4.4 Hz, 1H), 1.08 (s, 9H) $^{13}$C NMR (125 MHz, CDCl$_3$) δ 138.5, 138.4, 138.2, 135.9, 135.6, 135.5, 133.8, 133.5, 133.3, 131.2, 129.6, 129.1, 128.5, 128.4, 128.0, 127.9, 127.9, 127.8, 127.7, 127.6, 127.5, 126.6, 124.7, 123.5, 123.1, 122.5, 119.6, 113.8, 87.3, 82.3, 79.6, 78.4, 78.0, 75.7, 75.2, 75.1, 62.9, 31.2, 26.8, 20.8, 19.4 high resolution mass spectrum (FAB) m/z 978.3864 [(M+Na)$^+$; calcd for C$_{59}$H$_{61}$NO$_7$SSiNa: 978.3836].

EXAMPLE 55

(–)-2-(1-phenylsulfonyl-indol-3-yl)ethyl-1-deoxy-2,3,4-tri-O-benzyl-β-D-glucose ((+)-IV-48)

Neat silanol (–)-IV-47 (0.14 g, 0.15 mmol) was treated with a freshly prepared 9:1 CH$_3$CN/HF mixture (3 mL) at room temperature under argon. The reaction stirred for 8 h, was diluted with diethyl ether, poured into sat. NaHCO$_3$ and extracted. The organic layer was washed with brine, dried over MgSO$_4$, filtered and concentrated in vacuo. Flash silica gel chromatography (hexanes/ethyl acetate, 5:1) provided 81 mg (78% Yield) of (–)-IV-48 as a colorless oil; [α]$_D^{25}$ –5.7° (c 0.9, CHCl$_3$); IR (CHCl$_3$) 3600 (w), 300 (m), 2920 (w), 2870 (m), 1450(s), 1365 (s), 1260 (m), 1170 (s), 1140 (s), 1090 (s), 690 (m), 590 (m), 565 (w) cm$^{-1}$; $^1$H NMR (500 MHz, CDCl$_3$) δ 7.98 (d, J=8.6 Hz, 1H), 7.82 (d, J=7.7 Hz, 2H), 7.48 (app t, J=7.3 Hz, 1H), 7.42 (d, J=7.8 Hz, 1H), 7.38 (app t, J=7.9 Hz, 2H), 7.36–7.23 (m, 17H), 7.20 (t, J=7.6 Hz, 1H), 4.91 (d J=5.5 Hz, 2H), 4.88 (d, J=11.1 Hz, 1H), 4.87 (d, J=11.0 Hz, 1H), 4.67 (d, J=11.0 Hz, 1H), 4.61 (d, J=11.1 Hz, 1H), 3.86–3.83 (m, 1H), 3.70–3.65 (m, 2H), 3.55 (app t, J=9.4 Hz, 1H), 3.29–3.24 (m, 3H), 2.81 (ddd, J=14.9, 8.8, 4.7 Hz, 1H), 2.67 (ddd, J=15.9, 2.7, 7.0 Hz, 1H), 2.19–2.13 (m, 1H), 1.75 (br t, J=6.4 Hz, 1H), 1.68 (m, 1H) $^{13}$C NMR (125 MHz, CDCl$_3$) δ 138.5, 138.4, 138.0, 137.9, 135.4, 133.6, 131.0, 129.2, 128.5, 128.5, 128.5, 128.0, 128.0, 128.0, 127.9, 127.7, 127.7, 126.6, 124.7, 123.1, 123.1, 122.6, 119.5, 113.8, 87.1, 82.0, 78.9, 78.3, 75.6, 75.3, 75.0, 62.2, 31.0, 21.0 high resolution mass spectrum (FAB) m/z 740.2653 [(M+Na)$^+$; calcd for C$_{43}$H$_{43}$O$_7$NSNa: 740.2668].

EXAMPLE 56

(–)-2-(1-phenylsulfonyl-indol-3-yl)ethyl-1-deoxy-6-O-(5-azidopentyl)-2,3,4-tri-O-benzyl-β-D-glucose IV-49

Triflic anhydride (0.015 mL, 0.09 mmol) was added dropwise to a 0° C. dichloromethane (2 mL) solution of 5-azidopentanol (12 mg, 0.09 mmol) and 2,6-di-t-butyl-4-methylpyridine (18 mg, 0.09 mmol) while stirring under argon. The reaction stirred for 10 min, was diluted with dichloromethane (4 mL), poured into water and extracted. The organic layer was washed with brine, dried over anhydrous Na$_2$SO$_4$, filtered, and used without further purification in the next step.

To a round bottom flask containing dry alcohol (–)-IV-48 (20 mg, 0.03 mmol) was added a solution of above triflate (ca. 3 eq.) in dichloromethane. Solvent was removed in vacuo and the reaction flask was placed on a vacuum pump. Every 20 min. for the next 2.5 h, dichloromethane was added to the reaction vessel, reagents were solvated, and the solvent was again removed in vacuo prior to the reaction being placed on the vacuum pump. The azide (−)-IV-49 was purified using flash silica gel column chromatography (hexanes/ethyl acetate, 5:1) to yield 23 mg (98% yield) of a colorless oil; $[\alpha]_D^{25}$ −2.7° (c 0.3, CHCl$_3$); IR (CHCl$_3$) 3000 (m), 2940 (m), 2870 (m), 2100 (s), 1450 (s), 1370 (s), 1180 (s), 1120 (s), 1100 (s), 700 (m), 600 (m), 570 (m) cm$^{-1}$; $^1$H NMR (500 MHz, CDCl$_3$) δ 7.98 (d, J=8.3 Hz, 1H), 7.81 (d, J=8.7 Hz, 2H), 7.71–7.44 (m, 2H), 7.39–7.23 (m, 19H), 7.19 (t, J=7.6 Hz, 1H), 4.90–4.85 (m, 4H), 4.64 (d, J=11.0 Hz, 1H), 4.60 (d, J=11.0 Hz, 1H), 3.67–3.51 (m, 5H), 3.45–3.41 (m, 1H), 3.31–3.30 (m, 1H), 3.27 (t, J=9.0 Hz, 1H), 3.21 (app t, J=6.9 Hz, 2H), 3.16 (ddd, J=9.4, 9.4, 2.4 Hz, 1H), 2.83 (ddd, J=14.3, 9.6, 4.4 Hz, 1H), 2.71 (ddd, J=15.7, 7.9, 7.9 Hz, 1H), 2.17–2.11 (m, 1H), 1.74–1.67 (m, 1H), 1.65–1.57 (m, 4H), 1.49–1.40 (m, 2H) $^{13}$C NMR (125 MHz, CDCl$_3$) δ 138.6, 138.4, 138.4, 138.0, 135.4, 133.6, 131.2, 129.1, 128.4, 128.0, 127.90, 127.8, 127.7, 127.7, 126.6, 124.6, 123.2, 123.0, 122.7, 119.6, 113.8, 87.3, 82.1, 78.9, 78.8, 78.2, 75.6, 75.2, 74.9, 71.5, 70.0, 51.3, 30.9, 29.2, 28.7, 23.5, 20.8 high resolution mass spectrum (FAB) m/z 851.3450 [(M+Na)$^+$; calcd for C$_{48}$H$_{52}$N$_4$O$_7$SNa: 851.3454].

EXAMPLE 57

(−)-2-(1-phenylsulfonyl-indol-3-yl)ethyl-1-deoxy-6-O-(5-aminopentyl)-2,3,4-tri-O-benzyl-β-<u>D</u>-glucose (IV-51)

Triphenylphospine (16 mg, 0.06 mmol) was added to a solution (1.3 mL THF/0.02 mL H$_2$O) of azide (−)-IV-49 (23 mg, 0.027 mmol). The reaction was heated to 55° C. under argon and stirred for 3 h. Solvents were removed in vacuo and the amine was purified using flash silica gel column chromatography (100% ethyl acetate gradient to 10% methanol in dichloromethane) to yield 21 mg (97% Yield) of (−)-IV-50 as a colorless oil; $[\alpha]_D^{25}$ −6.8° (c 0.3, CH$_2$Cl$_2$); IR (CH$_2$Cl$_2$) 3650 (w), 3020 (m), 2940 (s), 2870 (s), 1450 (s), 1370 (s), 1160 (s), 1100 (vvs), 910 (w), 590 (m), 570 (m), 530 (w) cm$^{-1}$; $^1$H NMR (500 MHz, CDCl$_3$) δ 7.97 (d, J=8.3 Hz, 1H), 7.83–7.81 (m, 2H), 7.69–7.65 (m, 1H), 7.56–7.52 (m, 1H), 7.48–7.44 (m, 3H), 7.39–7.36 (m, 2H), 7.34–7.18 (m, 15H), 4.90–4.85 (m, 4H), 4.64 (d, J=11.0 Hz, 1H), 4.60 (d, J=11.0 Hz, 1H), 3.67 (dd, J=10.9, 1.8 Hz, 1H), 3.64–3.51 (m, 3H), 3.43 (app dt, J=9.5, 6.8 Hz, 1H), 3.32–3.30 (m, 1H), 3.27 (app t, J=9.0 Hz, 1H), 3.16 (app dt, J=9.4, 2.3 Hz, 1H), 2.83 (ddd, J=14.6, 9.6, 4.4 Hz, 1H), 2.74–2.66 (m, 3H), 2.16–2.10 (m, 1H), 1.74–1.55 (m, 6H), 1.48–1.33 (m, 4H) $^{13}$C NMR (125 MHz, CDCl$_3$) δ 138.6, 138.4, 138.0, 135.4, 133.5, 132.1, 132.1, 131.9, 131.2, 129.1, 128.5, 128.4, 128.0, 127.9, 127.8, 127.6, 126.6, 124.6, 123.2, 123.0, 122.7, 119.6, 113.7, 87.3, 82.1, 79.0, 78.8, 78.2, 75.6, 75.2, 74.9, 71.7, 70.0, 41.9, 30.9, 29.5 (2C), 23.5, 20.8 high resolution mass spectrum (FAB) m/z 803.3738 [(M+Na)$^+$; calcd for C$_{48}$H$_{54}$N$_2$O$_7$SNa: 803.3729].

EXAMPLE 58

(−)-2-(1H-indol-3-yl)ethyl-1-deoxy-6-O-(5-aminopentyl)-2,3,4-tri-O-benzyl-β-<u>D</u>-glucose (IV-50)

To a solution of amine (−)-IV-50 (27 mg, 0.03 mmol) in ethanol (4 mL) was added 5 <u>M</u> sodium hydroxide (0.65 mL). Reaction stirred for 15 h at reflux in an argon atmosphere. Solvents were removed in vacuo, residue was dissolved in dichloromethane and poured into water. After extraction, the organic layer was washed with brine, dried over anhydrous Na$_2$SO$_4$, filtered and concentrated. Purification using a 0.5 mm silica gel prep plate (100% ethyl acetate) afforded (−)-IV-51 (88% Yield) as a colorless oil; $[\alpha]_D^{25}$ −12.0° (c 0.2, CH$_2$Cl$_2$); IR (CHCl$_3$) 3490 (w), 3020 (w), 2920 (m), 2860 (m), 1450 (m), 1360 (m), 1090 (vs) cm$^{-1}$; $^1$H NMR (500 MHz, CDCl$_3$) δ 8.20 (s, 1H), 7.83–7.81 (m, 1H), 7.58 (d, J=7.8 Hz, 1H), 7.46 (app t, J=7.7 Hz, 1H), 7.37 (app t, J=7.5 Hz, 1H), 7.34–7.14 (m, 14H), 7.08 (app t, J=7.1 Hz, 1H), 6.97 (s, 1H), 4.88–4.82 (m, 4H), 4.64 (d, J=11.0 Hz, 1H), 4.61 (d, J=10.9 Hz, 1H), 3.71 (dd, J=10.9, 1.7 Hz, 1H), 3.65–3.53 (m, 3H), 3.51–3.46 (m, 1H), 3.39–3.35 (m, 1H), 3.30–3.27 (m, 2H), 2.97 (ddd, J=14.3, 8.9, 4.6 Hz, 1H), 2.90–2.85 (m, 1H), 2.67–2.65 (m, 2H), 2.28–2.23 (m, 1H), 1.82–1.74 (m, 4H), 1.63–1.59 (m, 2H), 1.58–1.35 (m, 4H) $^{13}$C NMR (125 MHz, CDCl$_3$) δ 138.7, 138.4, 138.2, 131.4, 133.5, 129.1, 128.4, 128.2, 127.9, 127.8, 127.7, 127.7, 127.6, 126.6, 124.6, 121.7, 121.5, 119.0, 116.1, 111.0, 87.3, 82.7, 79.0, 78.9, 78.4, 75.5, 75.2, 75.0, 71.7, 70.1, 41.9, 32.2, 29.5 (2C), 23.5, 20.9 high resolution mass spectrum (FAB) m/z 663.3784 [(M+H)$^+$; calcd for C$_{42}$H$_{51}$N$_2$O$_5$: 663.3797].

EXAMPLE 59

2-(N-(Phenylsulfonyl)indol-3-yl)ethyl 3-deoxy-4,6-O-benzylidene-β-D-glucopyranoside [(−)-IV-53]

A stirred solution of 2-(N-(phenylsulfonyl)indol-3-yl) ethyl 3-deoxy-β-D-glucopyranoside (−)-IV-52 (609 mg, 1.36 mmol) and p-toluenesulfonic acid (50 mg) in DMF (2 mL) was added benzaldehyde dimethyl acetal (201 µL, 1.36 mmol). The reaction mixture was heated at 45° C. under aspirator pressure (-MeOH) for 2 h, cooled, and saturated sodium bicarbonate (35 mL) was added. The aqueous layer was extracted with ethyl acetate (2×40 mL) and the combined organic extracts were dried over magnesium sulfate, filtered, and concentrated in vacuo. Flash chromatography (40% ethyl acetate/hexane) afforded [(−)-IV-53] (730 mg, 100% yield) as a colorless oil: $[\alpha]_D^{25}$ −8.2° (c 0.70, CHCl$_3$); IR (CHCl$_3$) 3600 (w), 3020 (m), 2880 (m), 1450 (m), 1370 (m), 1175 (s), 1100 (s), 1060 (s), 1000 (m), 720 (m) cm$^{-1}$; $^1$H NMR (500 MHz, CDCl$_3$) δ 8.04 (d, J=8.2 Hz, 1H), 7.90 (d, J=7.9 Hz, 2H), 7.55–7.27 (m, 12H), 5.56 (s, 1H), 4.35 (m, 2H), 4.25 (apparent dt, J=9.3, 6.5 Hz, 1H), 3.83 (m, 2H), 3.62 (m, 2H), 3.46 (m, 1H), 3.04 (m, 2H), 2.47 (dt, J=11.8, 4.4 Hz, 1H), 2.19 (br s, 1H), 1.75 (q, J=11.7 Hz, 1H); $^{13}$C NMR (125 MHz, CDCl$_3$) δ 138.2, 137.2, 135.1, 133.7, 130.9, 129.2, 129.1, 128.3, 126.6, 126.1, 124.8, 123.5, 123.2, 119.6, 119.2, 113.7, 105.4, 101.7, 76.0, 71.0, 69.0, 69.0, 68.9, 34.9, 25.4; high resolution mass spectrum (Cl, NH$_4$) m/z 536.1722 [(M+H)$^+$; calcd for C$_{29}$H$_{29}$NO$_7$S: 536.1743].Anal. Calcd. for C$_{29}$H$_{29}$NO$_7$S.1/2 H$_2$O: C 63.95; H 5.30; N 2.43. Found: C 63.56; H 5.30; N 2.43.

EXAMPLE 60

2-(N-(Phenylsulfonyl)indol-3-yl)ethyl 2-O-(tert-butyldimethylsilyl)-3-deoxy-4,6-O-benzylidene-β-D-glucopyranoside [(−)-IV-54]

A stirred solution of alcohol (−)-IV-54 (1.00 g, 1.87 mmol) and 2,6-lutidine (0.53 mL, 4.5 mmol) in dichloromethane (80 mL) at 0° C. was added tent-butyldimethylsilyl triflate (0.52 mL, 2.24 mmol) dropwise. The reaction mixture was allowed to stir 10 minutes, saturated sodium bicarbonate was added (25 mL), and the layers separated. The aqueous layer was extracted with dichloromethane (3×50 mL), and the combined organic extracts were dried over magnesium sulfate, filtered, and concentrated in vacuo. Flash chromatography (20% ethyl acetate/hexane) afforded (−)-IV-54 (1.21 g, 100% yield) as a colorless oil: $[\alpha]_D^{25}$−30.7° (c 0.50, CHCl$_3$); IR (CHCl$_3$) 3010 (m), 2950 (m), 2875 (m), 1730 (s), 1450 (s), 1375 (s), 1170 (s), 1085 (s); $^1$H NMR (500 MHz, CDCl$_3$) δ 8.03 (d, J=8.3 Hz, 1H), 7.90 (d, J=7.4 Hz, 2H), 7.56–7.30 (m, 11H), 7.27 (t, J=7.2 Hz, 1H), 5.56 (s, 1H), 4.41 (d, J=7.3 Hz, 1H), 4.35 (dd, J=10.5, 4.9 Hz, 1H), 4.16 (apparent q, J=7.9 Hz, 1H), 3.87 (apparent q, J=7.8 Hz, 1H), 3.80 (t, J=10.3 Hz, 1H), 3.70–3.59 (m, 2H), 3.46 (m, 1H), 3.05 (t, J=7.3 Hz, 2H), 2.41 (dt, J=12.0, 4.7 Hz, 1H), 1.82 (q, J=11.7 Hz, 1H), 0.93 (s, 9H), 0.12 (s, 3H), 0.11 (s, 3H); $^{13}$C NMR (125 MHz, CDCl$_3$) δ 138.4, 137.4, 135.2, 133.7, 131.0, 129.2, 129.1, 128.4, 126.8, 126.2, 124.8, 123.5, 123.2, 119.4, 119.4, 113.8, 105.8, 101.7, 76.0, 70.3, 70.0, 69.2, 69.0, 37.7, 25.7, 25.7, 18.2, −4.5, −4.9; high resolution mass spectrum (FAB, m-nitrobenzyl alcohol) m/z 672.2417 [(M+Na)$^+$; calcd for C$_{35}$H$_{43}$NO$_7$SSi: 672.2428].

EXAMPLE 61

2-(N-(Phenylsulfonyl)indol-3-yl)ethyl 2-O-(tert-butyldimethylsilyl)-3-deoxy-4-O-benzyl-β-D-glucopyranoside [(−)-IV-55]

A stirred solution of acetal (−)-IV-54 (1.21 g, 1.86 mmol) in dichloromethane (40 mL) at 0° C. was added DIBALH (18 mL, 18 mmol, 1.0 M in tol) dropwise. The reaction mixture was stirred at 0° C. for 3 h, quenched with saturated sodium-potassium tartrate, and diluted with water (50 mL). The aqueous layer was extracted with ethyl acetate (3×100 mL) and the combined organic extracts were dried over magnesium sulfate, filtered, and concentrated in vacuo. Flash chromatography (25% ethyl acetate/hexane) gave (−)-IV-55 (860 mg, 71% yield) as a colorless oil; $[\alpha]_D^{25}$−7.30° (c 0.50, CHCl$_3$); IR (CHCl$_3$) 3510 (w), 3010 (m), 2920 (m), 1445 (m), 1370 (m), 1170 (s), 1085 (s) cm$^{−1}$; $^1$H NMR (500 MHz, CDCl$_3$) δ 8.02 (d, J=8.2 Hz, 1H), 7.90 (d, J=7.6 Hz, 2H), 7.56–7.26 (m, 12H), 4.68 (d, J=11.4 Hz, 1H), 4.54 (d, J=11.4 Hz, 1H), 4.35 (d, J=7.4 Hz, 1H), 4.17 (q, J=7.7 Hz, 1H), 3.93 (dd, J=11.9, 2.8 Hz, 1H), 3.88 (apparent q, J=7.9 Hz, 1H), 3.80 (dd, J=11.8, 4.6 Hz, 1H), 3.59–3.44 (m, 3H), 3.02 (m, 2H), 2.44 (dt, J=12.3, 4.7 Hz, 1H), 2.15 (br s, 1H), 1.61 (q, J=11.6 Hz, 1H), 0.94 (s, 9H), 0.12 (s, 3H), 0.11 (s, 3H); $^{13}$C NMR (125 MHz, CDCl$_3$) δ 138.2, 137.9, 135.1, 133.6, 130.9, 129.1, 128.4, 127.8, 127.7, 126.6, 124.7, 123.5, 123.1, 119.5, 119.2, 113.6, 105.3, 78.3, 72.1, 71.3, 69.4, 68.4, 62.3, 37.6, 25.7, 25.5, 18.1, −4.5, −4.9; high resolution mass spectrum (FAB, m-nitrobenzyl alcohol) m/z 674.2589 [(M+Na)$^+$; calcd for C$_{35}$H$_{45}$NO$_7$SSi: 674.2584]. Anal. Calcd. for C$_{35}$H$_{45}$NO$_7$Si: C 64.49; H 6.96; N 2.15. Found: C 64.73; H 6.97; N 1.97.

EXAMPLE 62

2-(N-(Phenylsulfonyl)indol-3-yl)ethyl 2-O-(tert-butyldimethylsilyl)-3-deoxy-4-O-benzyl-6-O-(5'-azidopentyl)-β-D-glucopyranoside [(−)-IV-56]

Alcohol (−)-IV-55 (251 mg, 0.39 mmol) was converted according to the procedure described in example 16. The crude product was filtered through silica gel with ethyl acetate, concentrated in vacuo, and purified via flash chromatography (20% ethyl acetate/hexane) to furnish (−)-IV-56 (284 mg, 97% yield) as a colorless oil: $[\alpha]_D^{25}$−9.7° (c 0.72, (CHCl$_3$); IR (CHCl$_3$) 3010 (m), 2920 (m), 2850 (m), 2090 (s), 1730 (s), 1445 (s), 1380 (m), 1175 (s) cm$^{−1}$; $^1$H NMR (500 MH$_z$, CDCl$_3$) δ 8.00 (d, J=8.3 H$_z$, 1H), 7.89 (d, J=7.4 H$_z$, 2H), 7.55–7.24 (m, 12H), 4.65 (d, J=11.5 H$_z$, 1H), 4.50 (d, J=11.5 H$_z$, 1H), 4.27 (d, J=7.4 H$_z$, 1H), 4.14 (dt, J=8.3, 7.1 H$_z$, 1H), 3.81 (m, 2H), 3.62 (dd, J=10.8, 4.8 H$_z$, 1H), 3.51 (m, 6H), 3.19 (t, J=6.9 H$_z$, 2H), 3.02 (t, J=7.0 H$_z$, 2H), 2.40 (apparent dt, J=12.2, 4.6 H$_z$, 1H), 1.60 (m, 4H), 1.42 (m, 2H), 0.90 (s, 9H), 0.09 (s, 3H), 0.07 (s, 3H); $^{13}$C NMR (125 MH$_z$, CDCl$_3$) δ 138.4, 138.2, 135.2, 133.6, 131.0, 129.1, 128.4, 127.8, 127.7, 126.7, 124.7, 123.4, 123.1, 119.6, 119.4, 113.7, 105.4, 78.2, 72.3, 71.4, 71.3, 70.1, 69.4, 68.5, 51.3, 37.8, 29.2, 28.6, 25.7, 25.6, 23.4, 18.1, −4.4, −4.9; high resolution mass spectrum (FAB, m-nitrobenzyl alcohol) m/z 785.3356 [(M+Na)$^+$; calcd for C$_{40}$H$_{54}$N$_4$O$_7$SSi: 785.3381].

EXAMPLE 63

2-(N-(Phenylsulfonyl)indol-3-yl)ethyl 3-deoxy-4-O-benzyl-6-O-(5'-azidopentyl)-β-D-glucopyranoside [(−)-IV-57]

A stirred solution of silyl ether (−)-IV-56 (284 mg, 0.37 mmol) in THF (5 mL) at 0° C. was added TBAF (0.75 mL, 0.75 mmol, 1.0 M in THF) and the reaction mixture allowed to warm to room temperature. Stirring was continued for 20 hr, the reaction mixture was poured into water (50 mL), and extracted with ethyl acetate (3×50 mL). The combined organic extracts were dried over magnesium sulfate, filtered, and concentrated in vacuo. Purification via flash chromatography (40% ethyl acetate/hexane) furnished (−)-IV-57 (233 mg, 95% yield) as a colorless oil: $[\alpha]_D^{25}$−10.1° (c 1.14, CHCl$_3$); IR (CHCl$_3$) 3590 (w), 3010 (m), 2940 (s), 2890 (s), 2100 (s), 1440 (s), 1380 (s), 1175 (s) cm$^{−1}$; $^1$H NMR (500 MH$_z$, CDCl$_3$) δ 8.01 (d, J=8.3 Hz, 1H), 7.89 (apparent d, 2H), 7.55–7.24 (m, 12H0, 4.63 (d, J=11.6 Hz, 1H), 4.51 (d, J=11.0 Hz, 1H), 4.29 (d, J=7.0 Hz, 1H), 4.22 (dt, J=9.6, 6.5 Hz, 1H), 3.78 (dt, J=9.6, 6.9 Hz, 1H), 3.61–3.52 (m, 4H), 3.50–3.39 (m, 4H), 3.23 (t, J=6.9 Hz, 2H), 3.01 (ddd, J6.9, 3.3 Hz, 2H), 2.47 (dt, J=9.1, 4.5 Hz, 1 H), 1.71 (br s, 1H), 1.58 (m, 4H), 1.42 (m, 2H); $^{13}$C NMR (125 MHz, CDCl$_3$) δ 138.2, 137.9, 135.1, 133.6, 131.0, 129.1, 128.3, 127.7, 127.6, 126.6, 124.7, 123.4, 123.0, 119.8, 119.4, 113.7, 104.5, 77.7, 72.1, 71.2, 71.1, 70.0, 68.4, 68.2, 51.2, 33.9, 29.0, 28.5, 25.4, 25.3; high resolution mass spectrum (FAB, m-nitrobenzyl alcohol) m/z 671.2530 [(M+Na)$^+$; calcd for C$_{34}$H$_{40}$N$_4$O$_7$S:671.2516].

EXAMPLE 64

2-(N-(Phenylsulfonyl)indol-3-yl)ethyl 2-O-(N-monomethoxytrityl-4'-methylene-imidazole)-3-deoxy-4-O-(5'-azidopentyl)-β-D-glucopyranoside [(+)-IV-58]

A stirred solution of alcohol (−)-IV-57 (102 mg, 0.16 mmol) and N-(monomethoxytrityl)-4'-chloromethyl imidazole (I-37) (0.49 mmol) in THF (3 mL) was added tetrabutylammonium iodide (5 mg) and the reaction vessel cooled to −10° C. Sodium hydride (12 mg, 0.30 mmol), 60% in oil) was added in one portion and the reaction was allowed to warm to room temperature slowly. The reaction was stirred for 40 hr, poured into brine (20 mL), and extracted with ether (3×35 mL). The combined organic extracts were dried over magnesium sulfate, filtered, and concentrated in vacuo to an oil. Purification via flash chromatography (33% ethyl acetate then 50% ethyl acetate) gave (+)-IV-58(53.4 mg, 54% yield, 53% conversion of (−)-IV-57 as a colorless oil: $[\alpha]_D^{25}$+3.0° (c 0.24, CHCl$_3$); IR (CHCl$_3$) 3010 (s), 2930 (m), 2885 (m), 2100 (s), 1740 (s), 1510 (m), 1455 (m) cm$^{−1}$; $^1$H NMR (500 MHz, CDCl$_3$) δ 8.00 (d, 1H), 7.87 (m, 2H), 7.51–7.25 (m, 22H), 7.24–7.12 (m, 2H), 7.06 (m, 2H), 6.84 (m, 2H), 4.69 (d, J=12.2 Hz, 1H), 4.62 (d, J-11.5 Hz, 1H), 4.52 (d, J=12.2 Hz, 1H), 4.44 (d, J 11.5 Hz, 1H), 4.41 (d, J=7.6 Hz, 1H), 4.15 (dt, J=9.6, 7.0 Hz, 1H), 3.81 (m, 2H), 3.80 (s, 3H), 3.61 (dd, J=10.8, 5.0 Hz, 1H), 3.55–3.43 (m, 4H), 3.38 (ddd, J=12.1, 11.2, 6.2 Hz, 2H), 3.20 (t, J=6.9 Hz, 2H), 2.96 (5, J=7.0 Hz, 2H), 2.60 (dt, J=12.3, 4.4 Hz, 1H), 1.59 (m, 4H), 1.41 (m, 2H); $^{13}$C NMR (125 MHz, CDCl$_3$) δ 159.1, 142.7, 138.9, 138.4, 138.4, 138.1, 135.2, 134.4, 133.6, 131.1, 131.1, 129.7, 129.1, 128.4, 128.0, 127.9, 127.7, 127.7, 127.0, 124.6, 123.6, 123.0, 120.0, 119.9, 119.5, 113.7, 113.3, 105.1, 78.0, 75.2, 72.4, 71.4, 71.1, 70.1, 68.3, 66.8, 55.2, 51.3, 34.9, 29.2, 28.7, 25.6, 23.4; high resolution mass spectrum (FAB, m-nitrobenzyl alcohol) m/z 1023.4083 [(M+Na)$^+$; calcd for $c_{58}H_{60}N_6O_8S$: 1023.4041].

EXAMPLE 65

2-(N-(phenylsulfonyl)indol-3-yl)ethyl 2-O-(N-monomethoxytrityl-4'-methylene-imidazole)-3-deoxy-4-O-benzyl-6-O-(5'-aminopentyl)-β-D-glucopyranoside [(+)-IV-59]

A solution of azide (+)-IV-58 (43 mg, 0.043 mmol) in THF (4 mL) was added water (20 μL) followed by triphenylphosphine (28 mg, 0.11 mmol) and the reaction heated at 55° C. for 20 h. The mixture was concentrated in vacuo and purified directly by flash chromatography (5% methanol/dichloromethane then 1% methanol/ammoniacal chloroform) to give (+)-IV-59 (30.1 mg, 73% yield) as a colorless oil: $[\alpha]_D^{25}$+2.7° (c 0.52, CHCl$_3$); IR (CHCl$_3$) 3400 (s), 3010 (m), 2935 (m), 2860 (w), 1450 (s), 1385 (m), 1185 (s) cm$^{-1}$; $^1$H NMR (500 MHz, CDCl$_3$) δ 7.98 (d, J=7.5 Hz, 1H), 7.87 (m, 2H), 7.52–7.27 (m, 21H), 7.20–7.14 (m, 2H), 7.10 (m, 3H), 6.85 (m, 2H), 4.70 (d, J=12.1 Hz, 1H), 4.63 (d, J-11.4 Hz, 1H), 4.53 (d, J=12.1 Hz, 1H), 4.46 (d, J=11.4 Hz, 1H), 4.42 (d, J-7.6 Hz, 1H), 4.17 (dt, J=9.6, 7.1 Hz, 1H), 3.80 (m, 2H), 3.80 (s, 3H), 3.61 (dt, J=10.7, 5.1 Hz, 1H), 3.50 (m, 4H0, 3.40 (ddd, J=14.0, 7.5, 5.1 Hz, 2H), 2.97 (5, J=6.5 Hz, 2H), 2.65 (5, J=6.8 Hz, 2H), 2.60 (dt, J=12.6 4.5 Hz, 1H), 1.61 (m, 2H), 1.50 (br s, 2H), 1.39 (m, 4H); $^{13}$C NMR (125 MHz, CDCl$_3$) δ 159.1, 142.8, 139.0, 138.6, 138.4, 138.1, 135.2, 134.5, 133.6, 131.2, 131.1, 129.7, 129.1, 128.4, 128.0, 127.9, 127.7, 127.7, 126.7, 124.6, 123.6, 123.1, 120.0, 119.9, 119.5, 113.7, 113.2, 105.1, 78.1, 75.2, 72.4, 71.6, 71.1, 70.1, 68.4, 66.9, 55.2, 42.1, 34.9, 33.6, 29.5, 25.6, 23.4; high resolution mass spectrum (FAB, m-nitrobenzyl alcohol) m/z 975.4379 ([(M+H)$^+$; calcd for $C_{58}H_{62}N_4O_8S$: 975.4366].

EXAMPLE 66

2-(1H-Indol-3-yl)ethyl 2-O-(4'-methylene-1H-imidazole)-3-deoxy-4-O-benzyl-6-O-(5'-aminopentyl)-β-D-glucopyranoside [(+)-IV-60]

A solution of sulfonamide (+)-IV-59 (21 mg, 0.022 mmol) in methanol (2 mL) was added 5 M potassium hydroxide (200 μL) and the mixture heated at reflux for 20 h. the reaction was cooled, concentrated in vacuo, and purified by flash chromatography (5% methanol/dichloromethane then 2.5% methanol/ammoniacal chloroform) to give the disulphonated indole (18 mg, 100% yield). A solution of the above indole (0.022 mmol) in dichloromethane (1 mL) was added TFA (20 μL, 0.26 mmol) and the reaction stirred for 15 minutes. The reaction was made basic with saturated sodium bicarbonate, dried azeotropically with 1:1 ethanol/benzene, and concentrated in vacuo to an oil. Flash chromatography (5% methanol/dichloromethane then 5% methanol/ammoniacal chloroform) afforded (+)-IV-60 (8 mg, 64% yield, 2 steps) as a colorless oil: $[\alpha]_D^{25}$+8.0 (c 0.20, CHCl$_3$); IR (CHCl$_3$) 3400 (s), 3005 (s), 2940 (m), 1730 (m), 1675 (m), 1210 (s), 1020 (s) cm$^{-1}$; $^1$H NMR (500 MHz, CD$_3$OD) δ 7.58 (s, 1H), 7.55 (d, J=8.1 Hz, 1H), 7.30 (m, 7H), 7.09 (s, 1H), 7.07 (dt, J=7.0, 1.0 Hz, 1H), 7.00 (dt, J=7.1, 1.0 Hz, 1H), 6.81 (s, 1H), 4.58 (d, J=11.7 Hz, 1H), 4.56 (d, J=12.1 Hz, 1H), 4.47 (d, J=12.2 Hz, 1H), 4.42 (d, J=11.6 Hz, 1H), 4.39 (d, J=7.6 Hz, 1H), 4.14 (dt, J=9.5, 6.8 Hz, 1H), 3.84 (dt, J=9.5, 7.4 Hz, 1H), 3.68 (d, J=10.9 Hz, 1H), 3.55 (dt, J=10.9, 4.8 Hz, 1H), 3.50 (m, 5H), 3.26 (ddd, J=11.9, 7.5, 5.1 Hz, 1H), 3.07 (5, J=7.1 Hz, 2H), 2.66 (t, J=7.5 Hz, 2H), 2.46 (dt, J=12.3, 4.4 Hz, 1H), 1.52 (m, 4H), 1.37 (m, 2H); $^{13}$C NMR (125 MHz, CD$_3$OD) δ 139.7, 138.1, 136.7, 131.8, 129.4, 128.9, 128.8, 25.0, 123.7, 122.2, 119.5, 119.4, 112.8, 112.2, 106.4, 79.2, 75.9, 73.4, 72.5, 72.2, 72.0, 71.0, 42.1, 35.9, 32.5, 30.4, 27.0, 24.5, 19.0; high resolution mass spectrum (Cl, NH$_3$) m/z 563.3251 [(M+H)$^+$; calcd for $C_{32}H_{42}N_4O_5$; 563.3233].

EXAMPLE 67

2-(N-(phenylsulfonyl)indol-3-yl)ethyl 2,4,6-tri-o-acetyl-3-o-benzyl-β-I-gluco-pyranoside [(+)-IV-62]

Hydrobromic acid (30% in acetic acid, 10 ml, 50 mmol) was added to 1,2,4,6-tetra-D-acetyl-(3-)-benzyl-α,β-L-glucose (+)-IV-61 (1.84 g, 4.21 mmol) in dichloromethane (5 ml) at 0° C., followed by 10 min. of stirring. The reaction mixture was carefully poured into a mixture of ice and saturated aqueous sodium bicarbonate (100 mL). An additional 100 ml dichloromethane was added and the layers were separated. The organic layer was washed with saturated aqueous sodium bicarbonate until neutral, with water, brine, dried over MgSO$_4$, filtered and concentrated in vacuo. Flash chromatography with 7:3 hexanes/ethyl acetate as eluant gave the crude bromide (1.13 g, 58%) which was immediately used in the next step. To a mixture of N-(benzenesulfonyl)tryptophol (1.62 gram, 6.14 mmol), mercury(II) oxide (0.53 gram, 2.5 mmol), mercuric(I) bromide (18 mg, 0.05 mmol) and drierite (1.2 gram) in 3 ml dichloromethane was added via a cannula a solution of the crude bromide in 5 ml dichoromethane. The reaction was stirred for 16 h. at room temperature. Flash chromatography with 7:3 hexanes/ethyl acetate as eluant afforded (+)-IV-62 (1.44 g, yield 87%) as a colorless oil; $[\alpha]_D^{25}$+5.6° (c 1.15, CHCl$_3$); IR (CHCl$_3$) 3010 (m), 2950 (w), 2930 (w), 1750 (s), 1450 (m), 1379 (s), 1230 (s), 1170 (s), 1120 (s), 1080 (s), 1040 (s), 590 (m) cm$^{-1}$; $^1$H NMR (500 MHz, CDCl$_3$) δ 8.00 (d, J=8.2 Hz, 1H), 7.89 (d, J=7.4 Hz, 2H), 7.54 (t, J=7.4 Hz, 1H), 7.52–7.42 (m, 4H), 7.36–7.25 (m, 7H), 5.15 (t, J=9.5 Hz, 1H), 5.09 (t, J=9.4 Hz, 1H), 4.62 (dd, J=11.6 Hz, 2H), 4.48 (d, J=7.9 Hz, 1H), 4.24 (dd, J=12.3, 5.1 Hz, 1H), 4.16 (m, 2H), 3.77 (dt, J=9.5, 7.0 Hz, 1H), 3.72 (t, J=9.4 Hz, 1H), 3.62 (m, 1H), 2.96 (t, J=6.6 Hz, 2H), 2.09 (s, 3H), 2.00 (s, 3H), 1.91 (s, 3H); $^{13}$C NMR (125 MHz, CDCl$_3$) δ 170.7, 169.3, 169.2, 138.2, 137.7, 135.1, 133.7, 130.9, 129.2, 128.4, 127.8, 127.8, 126.7, 124.7, 123.6, 123.2, 119.7, 119.4, 113.6, 100.9, 80.1, 73.8, 72.3, 72.2, 69.6, 68.3, 62.3, 25.3, 20.7 (2 C), 20.6; high resolution mass spectrum (FAB m-nitrobenzyl alcohol) m/z 702.1998 [(M+Na)$^+$; calcd for $C_{35}H_{37}NO_{11}S$: 702.1985].

EXAMPLE 68

2-(N-(Phenylsulfonyl)indol-3-yl)ethyl 3-O-Benzyl-β-L-glucopyranoside [(+)-IV-63]

To a solution of acetate (+)-IV-62 (1.44 g, 2.11 mmol) in dry methanol (60 ml) was added sodium methoxide ( 0.5 ml, 5.4 M in methanol). The reaction mixture was stirred for 5 h, concentrated in vacuo and purified via flash chromatography (5% methanol/dichloromethane) to give (+)-IV-63 (1.18 g, yield 99%); $[\alpha]_D^{25}$+35.8° (c 1.48, CHCl$_3$); IR (CHCl$_3$) 3590 (m), 3450 (br. w), 3050 (m), 2920(s), 2880 (m), 1450(s), 1370 (s), 1170 (s), 1120 (s), 1090 (s), 1030 (s), 680 (m), 590 (m) cm$^{-1}$; $^1$H NMR (500 MHz, CDCl$_3$) δ 8.00 (d, J=8.2 Hz, 1H), 7.87 (d, J =8.1 Hz, 2H), 7.52, (s, 1H), 7.50–7.26 (m, 5H), 7.26 (dt, J=8.0, 0.8 Hz, 1H), 4.98 (d, J=11.7 Hz, 1H), 4.76 (d, 11.7 Hz, 1H), 4.33 (d, J=7.7 Hz, 1H), 4.21 (dt, J=9.5, 6.6 Hz, 1H), 3.90–3.76 (series of multiplets, 3H), 3.62 (dt, J=9.4, 2.2 Hz, 1H), 3.49 (dt, J=7.5, 1.7 Hz, 1H), 3.40 (t, J=9.0 Hz, 1H), 3.35 (ddd, J=9.5, 4.6, 3.5 Hz, 1H), 2.98 (t, J=6.5 Hz, 2H), 2.49 (br. s, 1H), 2.27 (br. s, 1H), 2.19 (br. s, 1H); $^{13}$C NMR (125 MHz, CDCl$_3$) δ 138.5, 138.2, 135.2, 133.7, 131.0, 129.2, 128.6, 128.0, 126.7, 124.8, 123.7, 123.2, 119.7, 119.3, 113.8, 103.0, 83.6, 75.3, 74.7, 74.5, 70.1, 68.9, 62.4, 25.4; high resolution mass spectrum (FAB m-notrobenzyl alcohol) m/z 576.1660 [(M+Na)$^+$; calcd for C$_{29}$H$_{31}$NO$_8$S: 576.1668].

EXAMPLE 69

2-(N-(Phenylsulfonyl)indol-3-yl)ethyl 3-O-Benzyl-4,6-O-benzylidene-β-L-glucopyranoside [(+)-IV-64]

A solution of (+)-# (1.21 gram, 2.19 mmol), camphor sulfonic acid (25 mg) and benzaldehyde dimethyl acetal (0.8 ml, 5.4 mmol) in chloroform (50 ml) was heated to reflux for 4 h. The reaction mixture was concentrated in vacuo. Flash chromatography with 10:1 to 1:1 hexanes/ethyl acetate as eluant gave (+)-IV-64 (1.20 g, yield 86%) as a colorless oil; $[\alpha]_D^{25}$+20.4° (c 0.81, CHCl$_3$); IR (CHCl$_3$) 3480 (w), 3010 (m), 2890 (m), 1450 (m), 1370 (m), 1320 (m), 1270 (s), 1220 (s), 1200 (s), 1130 (m), 1100 (m), 780 (w), 690 (m) cm$^{-1}$; $^1$H NMR (500 MHz, CDCl$_3$) δ 7.99 (d, J=8.4 Hz, 1H), 7.87 (m, 2H), 7.52–7.48 (m, 5H), 7.42–7.23 (m, 12H), 5.58 (s, 1H), 4.97 (d, J=11.7 Hz, 1H), 4.80 (d, J=11.7 Hz, 1H), 4.43 (d, J=7.7 Hz, 1H), 4.34 (dd, J=10.5, 5.0 Hz, 1H), 4.19 (dt, J=9.5, 6.6 Hz, 1H), 3.83 (dt, J=9.5, 7.0 Hz, 1H), 3.80 (t, J=10.3 Hz, 1H), 3.71 (t, J=9.1 Hz, 1H), 3.65 (t, J=9.1 Hz, 1H), 3.57 (t, J=8.1 Hz, 1H), 3.44 (dt, J=9.7, 5.0 Hz, 1H), 3.01 (dt, J=7.1, 1.5 Hz, 2H), 2.27 (br. s, OH); $^{13}$C NMR (125 MHz, CDCl$_3$) δ 138.4, 138.3, 137.3, 135.2, 133.7, 131.0, 129.2, 129.0, 128.5, 128.3, 128.0, 127.8, 126.7, 126.0, 124.8, 123.7, 123.2, 119.5, 119.4, 113.8, 103.4, 101.3, 81.4, 80.2, 74.6, 69.1, 68.7, 66.5, 25.4; high resolution mass spectrum (FAB, m-notrobenzyl alcohol) m/z 664.2078 [(M+Na)$^+$; calcd for C$_{36}$H$_{35}$NO$_8$S: 664.2081].

EXAMPLE 70

2-(N-(Phenylsulfonyl)indol-3-yl)ethyl 3-O-Benzyl-4,6-O-benzylidene-β-L-mannopyranoside [(+)-IV-65]

To a solution of (+)-IV-64 (0.243 g, 0.38 mmol) in 8 ml DMSO was added 4 ml acetic anhydride and the reaction was stirred for 4 d at room temperature. The reaction mixture was poured into water (150 ml) and extracted with ether (3×100 ml). The combined organic layers were dried over magnesium sulfate, filtered and concentrated in vacuo. Flash chromatography with 7:3 to 1:1 hexanes/ethyl acetate as eluant afforded the crude ketone (0.205 g, 0.32 mmol), which was immediately used for the next step. The ketone (0.205 g, 0.32 mmol) was dissolved in ethanol/water (3.5:1, 13 ml) and treated with sodium borohydride (140 mg, 3.7 mmol). After heating the reaction mixture at 60° C. for 1 h, another portion of sodium boro hydride (140 mg, 3.7 mmol) was added. The reaction mixture was heated for another hour. The reaction was cooled, poured into brine (30 ml) and extracted with ether (3×50 ml). The combined organic extracts were dried over magnesium sulfate, filtered and concentrated in vacuo. Flash chromatography (7:3 to 1:1 hexanes/ethyl acetate) gave and (+)-IV-64 (32 mg, undesired isomer yield 13%) and (+)-IV-65 (165 mg, yield 68%) as a colorless oil; $[\alpha]_D^{25}$+13.4° (c 1.51, CHCl$_3$); IR (CHCl$_3$) 3580 (w), 3010 (s), 2880 (m), 1450 (s), 1370 (s), 1170 (s), 1090 (s), 690 (m), 590 (m) cm$^{-1}$; $^1$H NMR (500 MHz, CDCl$_3$) δ 8.00 (d, J=8.3 Hz, 1H), 7.87 (d, J=8.1 Hz, 2H), 7.52–7.16 (m, 17H), 5.61 (s, 1H), 4.87 (d, J=12.3 Hz, 1H), 4.79 (d, J=12.3 Hz, 1H), 4.50 (s, 1H), 4.33 (dd, J=10.5, 4.9 Hz, 1H), 4.21 (dt, J=9.5, 6.8 Hz, 1H), 4.16 (t, J=9.5 Hz, 1H), 4.09 (d, J=3.1 Hz, 1H), 3.89 (t, J=10.3 Hz, 1H), 3.81 (dt, J=9.5, 7.1 Hz, 1H), 3.63 (dd, J=9.5, 3.6 Hz, 1H), 3.33 (ddd, J=9.8, 4.9 Hz, 1H), 3.02 (t, J=6.9 Hz, 2H), 2.53 (s, 1H); $^{13}$C NMR (125 MHz, CDCl$_3$) δ 138.3, 137.9, 137.4, 135.2, 133.7, 130.9, 129.2, 129.0, 128.9, 128.4, 128.2, 127.9, 127.8, 126.7, 126.0, 124.8, 123.5, 123.2, 119.5, 119.4, 113.7, 101.5, 100.5, 78.4, 76.6, 72.5, 69.9, 68.9, 68.6, 66.9, 25.4; high resolution mass spectrum(FAB, m-nitrobenzyl alcohol) m/z 659.2445 [(M+NH$_4$)$^+$; calcd for C$_{36}$H$_{35}$NO$_8$S: 659.2427].

EXAMPLE 71

2-(N-(Phenylsulfonyl)indol-3-yl)ethyl 2-O-Triisopropylsilyl-3-O-benzyl-4,6-O-benzylidene-β-L-mannopyranoside (+)-IV-66]

To a solution of (+)-IV-65 (94 mg, 0.15 mmol) and 2,6-lutidine (43 μl, 0.36 mmol) in dichloromethane (3 ml) was added triisopropylsilyl trifluoromethanesulfonate (47 μl, 0.18 mmol). The reaction was stirred at room temperature for 16 h and concentrated in vacuo. Flash chromatography with 7:3 to 1:1 hexanes/ethyl acetate as eluant gave recovered starting material (+)-IV-65 (28 mg) and (+)-IV-66 (51 mg, yield 62% borsm) as a clear oil; $[\alpha]_D^{25}$+24.0° (c 1.65, CHCl$_3$); IR (CHCl$_3$) 3020 (m), 2950 (s), 2870 (s), 1450 (s), 1370 (s), 1170(s), 1100 (s), 1050 (m), 880 (m), 670 (m), 590 (m), 560 (m) cm$^{-1}$; $^1$H NMR (500 MHz, CDCl$_3$) δ 8.00 (d, J=8.3 Hz, 1H), 7.86 (d, J=7.9 Hz, 2H), 7.53–7.48 (m, 3H), 7.43–7.24 (series of m, 15H). 5.62 (s, 1H), 4.82 (d, J=12.2 Hz, 1H), 4.74 (d, J=12.2 Hz, 1H), 4.37 (s, 1H), 4.32 (dd, J=10.4, 4.8 Hz, 1H), 4.29 (d, J=2.7 Hz, 1H), 4.16 (t, J=9.4 Hz, 1H), 4.13 (m, 1H), 3.87 (t, J=10.2 Hz, 1H), 3.75 (dt, J=9.4, 7.8 Hz. 1H), 3.51 (dd, J=9.6, 2.7 Hz, 1H), 3.30 (dd, J=9.7, 4.8 Hz, 1H), 2.97 (m, 2H), 1.18–1.07 (m, 21H); $^{13}$C NMR (125 MHz, CDCl$_3$) δ 138.5, 138.4, 137.7, 135.2, 133.7, 130.9, 129.2, 128.8, 128.1, 127.9, 127.4, 128.7, 126.1, 124.8, 123.3, 123.1, 119.5, 119.3, 113.7, 101.8, 101.5, 79.2, 78.0, 72.5, 72.0, 68.9, 68.4, 67.7, 25.4, 18.3, 17.7, 12.9; high resolution mass spectrum (FAB, m-notrobenzyl alcohol) m/z 820.3356 [(M+Na)$^+$; calcd for C$_{45}$H$_{55}$NO$_8$SSi: 820.3315].

EXAMPLE 72

2-(N-(Phenylsulfonyl)indol-3-yl)ethyl 2-O-Triisopropylsilyl-3,4-di-O-benzyl-β-L-mannopyranoside [(+)-IV-67]

A solution of acetal (+)-IV-66 (51 mg, 0.06 mmol) in dichloromethane (3 ml) at 0° C. was treated with DIBALH (0.65 ml, 0.64 mmol, 1.0 M in toluene). The reaction was allowed to stir for 1.5 h at room temperature. The reaction was quenched with saturated sodium-potassium tartrate and diluted with water (15 ml). The mixture was extracted with dichloromethane (3×40 ml). The combined organic layers were dried over magnesium sulfate, filtered and concentrated in vacuo. Flash chromatography with 7:3 hexanes/ethyl acetate as eluant afforded (+)-IV-67 (30 mg, yield 50%); $[\alpha]_D^{25}$+20.5° (c 1.33, CHCl$_3$); IR (CHCl)$_3$ 3580 (w), 3020 (m), 2950 (s), 2870 (s), 1450 (s), 1370 (s), 1270 (s), 1100 (s), 1080 (s), 880 (m), 680 (m), 590 (m) cm$^{-1}$; $^1$H NMR (500 MHz, CDCl$_3$) δ 7.98 (d, J=8.3 Hz, 1H), 7.86 (m, 2H), 7.51 (m, 1H), 7.47 (d, J=7.7 Hz, 1H), 7.42 (m, 3H), 7.38–7.23 (x series of m, 12H), 4.91 (d, J=10.9 Hz, 1H), 4.75 (d, J=11.8 Hz, 1H), 4.64 (d, J=10.9 Hz, 1H), 4.63 (d, J=11.7 Hz, 1H), 4.34 (s, 1H), 4.27 (d, J=2.3 Hz, 1H), 4.13 (ddd, J=9.4, 7.5, 6.5 Hz, 1H), 4.00 (t, J=9.5 Hz, 1H), 3.85 (ddd, J=11.7, 4.8, 2.8 Hz, 1H), 3.77–3.70 (m, 2H), 3.43 (dd, J=9.4, 2.4 Hz, 1H), 3.28 (ddd, J=9.5, 3.9, 2.9 Hz, 1H), 2.02 (dd, J=8.5, 4.8 Hz, 1H), 1.47 (m, 2H), 1.16–11.06 (m, 21H); $^{13}$C NMR (125 MHz, CDCl$_3$) δ 138.4, 138.3, 135.2, 133.7, 130.9, 129.2, 128.4, 128.2 (2 C), 127.7, 127.6, 127.5, 126.7, 124.8, 123.4, 123.1, 119.6, 119.3, 113.7, 100.9, 83.9, 75.6. 75.2, 74.0, 71.9, 70.3, 68.1, 62.2, 25.4, 18.3, 18.2, 12.9; high resolution mass spectrum (FAB m-nitrobenzyl alcohol) m/z 822.3451 [(M+Na)$^+$; calcd for C$_{45}$H$_{57}$NO$_8$SSi: 822.3471].

EXAMPLE 73

2-(N-(Phenylsulfonyl)indol-3-yl)ethyl 2-O-Triisopropylsilyl-3,4-di-O-benzyl-6-O-(5'-azidopentyl)-β-L-mannopyranoside [(+)-IV-68]

A solution of 5-azidopentanol (100 mg, 0.83 mmol) and 2,6-di-t-butyl-4-methyl pyridine (170 mg, 0.83 mmol) in dichloromethane (5 ml) at 0° C. was treated with triflic anhydride (0.14 ml, 0.83 mmol). Reaction mixture was stirred at room temperature for 15 min, poured into water and extracted with dichloromethane (3×50 ml). The combined organic layers were dried over magnesium sulfate and concentrated in vacuo to afford 5-azidopentyl trifluoromethanesulfonate.

To alcohol (+)-IV-67 (0.133 gram, 0.167 mmol) was added 5-azidopentyl trifluoromethanesulfonate (0.83 mmol) in 4 equal portions in dichloromethane (10 ml) over 12 hours. After addition of the first portion, the reaction mixture was concentrated in vacuo and placed under high vacuum. The process was repeated until all starting material was consumed. The residue was filtered over a plug of silica gel with ethyl acetate, concentrated in vacuo and purified by flash chromatography with 10:1 to 7:3 hexanes/ethyl acetate as eluant. This afforded starting material (+)-IV-67 (21 mg) and (+)-IV-68 (124 mg, yield 82%;based on recovered starting material yield 97%) as a clear oil; $[\alpha]_D^{25}$+14.1° (c 1.41, CHCl$_3$); IR (CHCl$_3$) 3020 (m), 2950 (s), 2870 (s), 2100 (s), 1450 (s), 1370 (s), 1175 (s), 1120 (s), 690 (m), 590 (m) cm$^{-1}$; $^1$H NMR (500 MHz, CDCl$_3$) δ 7.98 (d, J=8.3 Hz, 1H), 7.86 (d, J=8.4 Hz, 2H), 7.53–7.48 (m, 2H), 7.42 (t, J=7.8 Hz, 2H), 7.38–7.22 (m, 13H), 4.89 (d, J=10.9 Hz, 1H), 4.74 (d, J=11.8 Hz, 1H), 4.62 (d, J=11.8 Hz, 1H), 4.61 (d, J=10.9 Hz, 1H), 4.27 (m, 2H), 4.14 (m, 1H), 3.90 (t, J=9.4 Hz, 1H), 3.71 (dd, J=16.6 , 7.8 Hz, 1H), 3.66 (d, J=2.7 Hz, 2H), 3.57 (dt, J=9.3, 6.3 Hz, 1H), 3.43 (m, 2H), 3.34 (m, 1H), 3.20 (t, J=6.9 Hz, 2H), 2.96 (m, 2H), 1.57 (m, 4H), 1.41 (m, 2H), 1.15–1.04 (m, 21H); $^{13}$C NMR (125 MHz, CDCl$_3$) δ 138.5, 138.4, 135.2, 133.6, 131.0, 129.2, 128.3, 128.2, 128.1, 127.6, 127.4, 126.7, 124.7, 123.3, 123.1, 119.7, 119.4, 113.7, 100.8, 83.0, 75.8, 75.0, 74.6, 71.9, 71.3, 70.3, 70.2, 68.0, 51.4, 29.4, 28.8, 25.4, 23.4, 18.3 (2 C), 12.9; high resolution mass spectrum (FAB m-nitrobenzyl alcohol) m/z 933.4251 [(M+Na)$^+$; calcd for C$_{50}$H$_{66}$N$_4$O$_6$SSi: 933.4269].

EXAMPLE 74

2-(N-(Phenylsulfonyl)indol-3-yl)ethyl 3,4-di-O-Benzyl-6-O-(5'-azidopentyl)-β-L-mannopyranoside [(+)-IV-69]

A solution of (+)-IV-68 (24 mg, 0.026 mmol) in dichloromethane (2 ml) was treated with tetrabutylammonium fluoride (106 ml, 0.106 mmol). The reaction mixture was stirred at room temperature for 2.5 h and concentrated in vacuo. Flash chromatography with 7:3 to 1:1 hexanes/ethyl acetate as eluant afforded (+)-IV-69 (20 mg, yield 99%) as a clear oil; $[\alpha]_D^{25}$+9.4° (c 1.04, CHCl$_3$); IR (CHCl$_3$) 3570 (w), 3050 (m), 2920 (m), 2880 (m), 2100 (s), 1450 (m), 1370 (m), 1170 (s), 1120 (s), 1100 (s), 690 (m), 590 (m) cm$^{-1}$; $^1$H NMR (500 MHz, CDCl$_3$) δ 7.99 (d, J=8.4 Hz, 1H), 7.87 (d, J=8.2 Hz, 2H); 7.52–7.49 (m, 2H), 7.44–7.22 (m, 15H), 4.93 (d, J=11.0 Hz, 1H), 4.76 (d, J=11.9 Hz, 1H), 4.67 (d, J=11.9 Hz, 1H), 4.62 (d, J=11.0 Hz, 1H), 4.40 (s, 1H), 4.21 (dt, J=9.5, 6,8 Hz, 1H), 4.06 (d, J=2.4 Hz, 1H), 3.85 (t, J=9.4 Hz, 1H), 3.78 (dt, J=9.4, 7.2 Hz, 1H), 3.70 (dd, J=10,9, 1.8 Hz, 1H), 3.66 (dd, 10.9, 5.2 Hz, 1H), 3.52 (m, 2H), 3.43 (dt, J=9.4, 6.6 Hz, 1H), 3.37 (ddd, J=9.6, 5.2, 1.9 Hz, 1H), 3.18 (t, J=6.9 Hz, 2H), 3.00 (t, J=6.9 Hz, 2H), 2.35 (s, OH), 1.60–1.53 (m, 4H), 1.43–1.37 (m, 2H); $^{13}$C NMR (125 MHz, CDCl$_3$) δ 138.4, 138.3, 137.8, 135.2, 133.7, 131.0, 129.2, 128.5, 128.4, 127.9 (3 C), 127.8, 126.7, 124.8, 123.5, 123.1, 119.7, 119.5, 113.7, 99.9, 81.5, 75.4, 75.2, 74.4, 71.5, 71.4, 70.0, 68.6, 68.3, 51.3, 29.2, 28.7, 25.5, 23.4; high resolution mass spectrum (FAB, m-nitrobenzyl alcohol) m/z 777.2926 [(M+Na)$^+$; calcd for C$_{41}$H$_{46}$N$_4$O$_8$Si: 777.2935].

EXAMPLE 75

2-(N-(Phenylsulfonyl)indol-3-yl)ethyl 2-O-(N-monomethoxytrityl-4'-methylene-imidazole)-3,4-di-O-benzyl-6-O-(5'-azidopentyl)-b-L-Mannopyranoside [(+)-IV-70]

A mixture of alcohol (+)-IV-69 (100 mg, 0.13 mmol) and N-(monomethoxytrityl)-4'-chloro methyl imidazole I-37 was azeotroped with benzene and put under high vacuum for 2 h. The mixture was dissolved in THF (8 ml) and tetrabutylammonium iodide (2 mg) was added. The vessel was cooled to −10° C. Sodium hydride (6 mg, 0.15 mmol, 60% in mineral oil) was added, followed by stirring for 20 h. More sodium hydride (5 mg, 0.13 mmol) was added and the reaction was stirred for another 20 h. The reaction mixture was poured into water (25 ml) and extracted with ether (3×40 ml). The combined organic layers were dried over magnesium sulfate, filtered and concentrated in vacuo. Flash chromatography with 20:1 to 1:1 hexanes/ethyl acetate as eluant afforded (+)-IV-70 (61 mg, yield 49%) as a colorless oil; $[\alpha]_D^{25}$+17.6° (c 1.39, CHCl$_3$); IR (CHCl$_3$) 3010 (s), 2940 (s), 2870 (s), 2100 (s), 1515 (s), 1450 (s), 1370 (s), 1260 (s), 1180 (s), 1120 (s), 690 (s), 590 (m) cm$^{-1}$; $^1$H NMR (500 MHz, CDCl$_3$) δ 7.96 (d, J=8.2 Hz, 1H), 7.84 (d, J=7.5 Hz, 2H), 7.47 (t, J=7.5 Hz, 1H), 7.39 (m, 4H), 7.31–7.21 (m, 18H), 7.18 (t, J=7.5 Hz, 1H), 7.09 (m, 4H), 7.01 (m, 3H), 6.75 (m, 2H), 4.87 (m, 3H), 4.58 (d, J=12.0 Hz, 1H), 4.51 (d, J=10.9 Hz, 1H), 4.35 (m, 2H), 4.22 (d, J=3.0 Hz, 1H), 4.11 (m, 1H), 3.71 (m, 2H), 3.72 (s, 3H), 3.61 (m, 2H), 3.46 (m, 2H), 3.39 (m, 1H), 3.33 (m, 1H), 3.12 (t, J=6.9 Hz, 2H), 2.84 (m, 2H), 1.55–1.47 (m, 4H), 1.37–1.27 (m, 2H); $^{13}$C NMR (125 MHz, CDCl$_3$) δ 159.0, 142.8, 139.0, 138.6, 138.3, 138.1, 135.1, 134.6, 133.6, 131.2, 131.0, 129.7, 129.2, 128.3, 127.9 (2 C), 127.8, 127.6, 127.5, 126.7, 124.7, 123.5, 123.1, 120.7, 119.7, 119.6, 113.6, 113.2, 101.7, 81.6, 75.8, 75.1, 74.9 (2 C), 73.0, 71.3, 70.7, 70.5, 68.9, 68.0, 55.2, 51.3, 29.2, 28.6, 25.5, 23.4; high resolution mass spectrum (FAB, m-nitrobenzyl alcohol) m/z 1129.4531 [(M+Na)$^+$; calcd for C$_{65}$H$_{66}$N$_6$O$_9$S: 1129.4511].

EXAMPLE 76

2-(N-(Phenylsulfonyl)indol-3-yl)ethyl 2-O-(N-monomethoxytrityl-4'-methylene-imidazole)-3,4-di-O-benzyl-6-O-(5'-aminopentyl)-β-L-mannopyranoside [(+)-IV-71]

To a mixture of azide (+)-IV-70 (52 mg, 0.047 mmol) and water (21 μl, 1.2 mmol) in THF (4.5 ml) was added triphenylphosphine (33 mg, 0.12 mmol). Reaction mixture was heated at 55–60° C. for 16 h, cooled and concentrated in vacuo. Flash chromatography (10% methanol/dichloromethane to ammoniacal chloroform) yielded (+)-IV-71 (33 mg, yield 66%) as a clear oil; $[\alpha]_D^{25}$ +24.0° (c 0.30, CHCl$_3$); IR (CHCl$_3$) 3010 (s), 2970 (s), 2870 (m), 1515 (m), 1450 (s), 1370 (s), 1260 (m), 1190 (s), 1180 (s), 1120 (s), 690 (m) cm$^{-1}$; $^1$H NMR (500 MHz, CDCl$_3$) δ 7.96, (dd, J=8.2, 0.6 Hz, 1H), 7.85 (m, 2H), 7.49–7.46 (m, 2H), 7.43–7.36 (m, 7H), 7.32–7.17 (series of m, 16H), 7.11 (m, 4H), 7.02 (dd, J=9.0, 1.6 Hz, 3H), 6.75 (dd, J=9.0, 1.6 Hz, 2H), 4.88 (d, J=10.9 Hz, 1H), 4.89 (s, 2H), 4.58 (d, J=12.0 Hz, 1H), 4.52 (d, J=10.9 Hz, 1H), 4.36 (d, J=11.9 Hz, 1H), 4.35 (s, 1H), 4.22 (d, J=2.6 Hz, 1H), 4.12 (m, 1H), 3.75 (m, 1H), 3.73 (s, 3H), 3.69 (dd, J=10.8, 1.5 Hz, 1H), 3.61 (m, 2H), 3.43 (m, 3H), 3.29 (m, 2H), 2.85 (m, 2H), 2.57 (t, J=6.9 Hz, 2H), 1.55–1.49 (m, 2H), 1.42–1.12 (m, 4H); $^{13}$C NMR (125 MHz, CDCl$_3$) δ 159.0, 142.9, 139.0, 138.6, 138.3, 138.1, 135.1, 134.6, 133.6, 131.1, 131.0, 129.7, 129.2, 128.3, 127.9, 127.9, 127.8, 127.6, 127.5, 123.5, 123.1, 120.7, 119.8, 119.6, 113.6, 113.2, 101.7, 81.6, 75.8, 75.1, 75.0, 74.9, 73.1, 71.5, 70.7, 70.4, 68.9, 68.0, 55.2, 42.1, 33.6, 29.5, 25.5, 23.5; high resolution mass spectrum (FAB, m-nitrobenzyl alcohol) m/z 1081.4770 [(M+H)$^+$; calcd for C$_{65}$H$_{68}$N$_4$O$_9$S: 1081.4785].

EXAMPLE 77

2-(1H-indol-3-yl)ethyl 2-O-(4'-methylene-1H-imidazole)-3,4-di-O-benzyl-6-O-(5'-amino-pentyl)-β-L-mannopyranoside [(+)-IV-72]

To a solution of (+)IV-71 (36 mg, 0.033 mmol) in methanol (3 ml) was added 5 M aqueous sodium hydroxide solution (300 μL). The reaction mixture was refluxed for 44 h, followed by stirring at room temperature for 48 h. Reaction mixture was concentrated in vacuo and purified by flash chromatography (5% methanol/dichloromethane to 10% methanol/ammoniacal chloroform). This afforded the deprotected indole sugar, which was immediately dissolved in 1 ml dichloromethane, followed by addition of freshly distilled trifluoroacetic acid (20 μl). The color of the solution turned orange. After stirring for 15 min at room temperature, the reaction mixture was treated with saturated aqueous sodium bicarbonate until basic. The mixture was azeotroped with ethanol and benzene until dry. Flash chromatography (10% methanol/dichloromethane to 10% methanol/ammoniacal chloroform) afforded (+)-IV-72 (11.6 mg, yield 90%); $[\alpha]_D^{25}$ +15.4° (c 0.59, CHCl$_3$); IR (CHCl$_3$) 3480 (m), 3350 (br. m), 3000 (s), 2940 (s), 2870 (s), 1450 (m), 1360 (m), 1230 (m), 1100 (s) cm$^{-1}$; $^1$H NMR (500 MHz, CD$_3$OD) δ 7.56 (d, J=8.0 Hz, 1H), 7.49 (s, 1H), 7.33 (d, J=8.1 Hz, 1H), 7.30–7.23 (m, 10H), 7.09 (s, 1H), 7.08 (dt, J=7.0, 1.0 Hz, 1H), 6.99 (dt, J=7.0, 0.9 Hz, 1H), 6.91 (s, 1H), 4.81 (d, J=10.9 Hz, 1H), 4.77 (d, J=12.7 Hz, 1H), 4.73 (d, J=12.6 Hz, 1H0), 4.55 (d, J=11.1 Hz, 1H), 4.49 (s, 1H), 4.44 (d, J=11.6 Hz, 1H), 4.39 (d, J=11.6 Hz, 1H), 4.16 (dt,J 9.6, 6.7 Hz, 1H), 3.95 (d, J=3.0 Hz, 1H), 3.81 (dt,J 9.6, 7.1 Hz, 1H), 3.71 (t, J=9.6 Hz, 1H), 3.64 (dd, J=10.9, 2.0 Hz, 1H), 3.60 (dd, J=10.9, 5.1 Hz, 1H), 3.52–3.40 (series of m, 3H), 3.35–3.31 (m, 1H), 3.07 (t, J=6.9 Hz, 2H), 2.54–2.50 (m, 2H), 1.57–1.51 (m, 2H), 1.44–1.39 (m, 2H), 1.37–1.30 (m, 2H); $^{13}$C NMR (125 MHz, CDCl$_3$) δ 138.4, 137.8, 136.3, 135.4, 128.6, 128.4, 128.3, 127.9 (2 C), 127.8, 127.7, 127.4, 122.4, 122.0, 119.3, 118.6, 112.4, 111.3, 101.2, 82.3, 75.7, 75.2, 74.9, 74.8, 72.3, 71.5, 69.7, 69.6, 65.5, 41.7, 32.9, 29.2, 25.8, 23.4; high resolution mass spectrum (FAB, m-nitrobenzyl alcohol) m/z 669.3640 [(M+H)$^+$; calcd for C$_{39}$H$_{48}$N$_4$O$_6$: 669.3652].

EXAMPLE 78

(−)--2-(1-phenylsulfonyl-indol-3-yl)ethyl-2,4,6-tri-O-acetyl-3-O-benzyl-β-D-glucopyranoside (IV-74)

To a flame-dried flask containing stir bar and crushed 4 Å molecular sieves (4.5 g) was added silver(I)oxide (2.6 g, 11.2 mmol) and dry hexanes (24 mL). A benzene (16 mL) solution of 2,4,6-tri-O-acetyl-3-O-benzyl-α-D-glucopyranosyl bromide IV-73 (1.16 g, 2.54 mmol) and N-phenylsulfonylindole (0.92 g, 3.05 mmol) was added via cannula. The reaction stirred at room temperature, protected from light, under argon for 48 h. Subsequent to filtering the reaction through celite, the triacetate (−)-IV-74 was purified using flash silica gel chromatography (hexanes/ethyl acetate, 10:1) yielding (−)-IV-74 (1.67, 94% yield) of a colorless oil; $[\alpha]_D^{25}$ −7.8° (c 1.0, CHCl$_3$); IR (CCl$_4$) 2870 (w), 1750 (s), 1450 (m), 1375 (s), 1220 (s), 1175 (m), 1120 (m), 1040 (m), 710 (w), 675 (w), 590 (m), 560 (w) cm$^{-1}$; $^1$H NMR (500 MHz,CDCl$_3$) δ 7.95 (d, J=8.3 Hz, 1H), 7.85 (d, J=8.3 Hz, 1H), 7.84 (s, 1H), 7.52–7.49 (m, 1H), 7.46–7.39 (m, 4H), 7.33–7.21 (m, 7H), 5.11 (t, J=9.7 Hz, 1H), 5.05 (dd, J=9.4, 8.1 Hz, 1H), 4.57 (dd, J=11.6, 4.1 Hz, 2H), 4.44 (d, J=7.9 Hz, 1H), 4.21–4.10 (m, 3H), 3.73 (dt, J=9.5, 6.9 Hz, 1H), 3.67 (t, J=9.4 Hz, 1H), 3.58 (ddd, J=9.8, 5.0, 2.5 Hz, 1H), 2.93 (t, J=6.8 Hz, 1H), 2.05 (s, 3H), 1.96 (s, 3H), 1.87 (s, 3H) $^{13}$C NMR (125 MHz, CDCl$_3$) δ 170.7, 169.3, 169.2, 138.2, 137.7, 135.1, 133.7, 130.9, 129.2, 128.4, 127.8, 127.7, 126.7, 124.7, 123.6, 123.2, 119.7, 119.4, 113.6, 100.9, 80.1, 73.8, 72.3, 72.2, 69.6, 68.3, 62.3, 25.3, 20.7, 20.7, 20.6 high resolution mass spectrum (FAB, m-nitrobenzyl alcohol) m/z 702.1978 [(M+Na)$^+$; calcd for C$_{35}$H$_{37}$NO$_{11}$SNa: 702.1985]. Anal. Calcd for C$_{35}$H$_{37}$NO$_{11}$S: C, 61.89; H, 5.49. Found: C, 61.57; H, 5.30.

EXAMPLE 79

(−)-2-(1-phenylsulfonyl-indol-3-yl)ethyl-3-O-benzyl-β-D-glucopyranoside (IV-75)

Solid sodium methoxide (600 mg, 11.2 mmol) was added to a methanolic (15 mL) solution of triacetate (−)-IV-74 (1.67 g, 2.46 mmol) at ambient temperature. Reaction stirred under argon for 16 h. Solvent was removed in vacuo with diethylether (3×50 ml). The solution was poured into water and extracted. The organic layer was washed with brine, dried over MgSO$_4$, filtered and concentrated. Purification using flash silica gel column chromatography (hexanes/ethyl acetate, 7:3) as a colorless oil; (1.27 g, 93% yield) $[\alpha]_D^{25}$ −29.7° (c 3.1, CHCl3); IR (CHCl$_3$) 3590(m), 3000 (w), 2780 (w), 1450 (s), 1370 (s), 1275 (w), 1175 (s), 1100(s), 905 (m), 590 (m), 560 (m) cm$^{-1}$; $^1$H NMR (500 MHz, CDCl$_3$) δ 7.98 (d, J=8.3 Hz, 1H), 7.87–7.85 (m, 2H), 7.51–7.47 (m, 3H), 7.42–7.22 (m, 9H), 4.98 (d, J=11.7, 1H), 4.74 (d, J=11.7 Hz, 1H), 4.32 (d, J=7.7 Hz, 1H), 4.20 (dt, J=9.5, 6.5 Hz, 1H), 3.88 (dd, J=11.9, 3.4 Hz, 1H), 3.82 (dt, J=9.5, 6.6 Hz, 1H), 3.77 (dd, J=12.0, 4.8 Hz, 1H), 3.61 (t, J=9.2 Hz, 1H), 3.48 (dd, J=9.1, 7.7 Hz, 1H), 3.39 (t, J=9.0 Hz, 1H), 3.35 (ddd, J=8.3, 4.7, 3.5 Hz, 1H), 2.98 (app. t, J=6.5 Hz, 2H), 2.16 (br s, 1H), 2.03 (br s, 2H) $^{13}$C NMR 138.5, δ 138.3, 135.2, 133.7, 131.0, 129.2, 128.7, 128.0, 127.9, 126.7, 124.8, 123.7, 123.2, 119.7, 119.3, 113.8, 103.0, 83.6, 75.4, 74.7, 74.5, 70.1, 68.8, 62.5, 25.4 ppm; high resolution mass spectrum (FAB, m-nitrobenzyl alcohol) m/z 576.1679 [(M+Na)$^+$; calcd for C$_{29}$H$_{31}$O$_8$NSNa: 576.1668].

EXAMPLE 80

(−)-2-(1-Phenylsulfonyl-indol-3-yl)ethyl-3-O-benzyl-4,6-O-benzylidene-β-D-glucopyranoside (IV-76)

Fresh benzaldehyde (0.203 mL, 2.0 mmol) was added to a flask containing flame-dried ZnCl$_2$ (61 mg, 0.45 mmol).

The reaction mixture was stirred in an argon atmosphere at ambient temperature until a thick paste formed (10 minutes). A solution of triol (−)-IV-75 (165 mg, 0.3 mmol) in benzaldehyde (1.0 mL) was added to the paste via cannula and the reaction stirred for 14 h. The reaction was poured into water and extracted with dichloromethane (3×50 ml). The organic layer was washed with brine, dried over MgSO$_4$, filtered and concentrated in vacuo. Flash silica gel chromatography (petroleum ether/ethyl acetate, 10:1) provided of (−)-IV-76 (177 mg, 92% yield) as an oil: $[\alpha]_D^{25}$ −25.3° (c 1.1, CHCl$_3$); IR (CCl$_4$) 3500 (w), 3060 (w), 3025 (w), 2870 (m), 1450 (s), 1360 (s), 1160 (s), 1100 (s), 1050 (m), 990 (m), 690 (m), 590 (m), 565 (m) cm$^{-1}$; $^1$H NMR (500 MHz, CDCl$_3$) δ 7.98 (d, J=8.3 Hz, 1H), 7.87–7.85 (m, 2H), 7.51–7.22 (m, 17H), 5.57 (s, 1H), 4.96 (d, J=11.7 Hz, 1H), 4.79 (d, J=11.7 Hz, 1H), 4.42 (d, J=7.6 Hz, 1H), 4.33 (dd, J=10.5, 5.0 Hz, 1H), 4.18 (dt, J=9.5, 6.6 Hz, 1H), 3.85–3.77 (m, 2H), 3.70 (t, J=9.1 Hz, 1H), 3.64 (t, J=8.7 Hz, 1H), 3.56 (t, J=7.8 Hz, 1H), 3.43 (dt, J=9.2, 5.0 Hz, 1H), 3.01–2.98 (m, 2H), 2.29 (br s, 1H); $^{13}$C NMR (125 MHz, CDCl$_3$) δ 138.4, 138.3, 137.2, 135.2, 133.7, 131.0, 129.2, 129.0, 128.4, 128.3, 128.0, 127.8, 126.7, 126.0, 124.8, 123.7, 123.2, 119.5, 119.3, 113.8, 103.3, 101.3, 81.4, 80.2, 74.6, 74.3, 69.1, 68.7, 66.5, 25.4; high resolution mass spectrum (FAB, m-nitrobenzyl alcohol) m/z 664.1970 [(M+Na)$^+$; calcd for C$_{36}$H$_{35}$NO$_8$SNa: 664.1981] .Anal. Calcd for C$_{36}$H$_{35}$NO$_8$S: C, 67.43; H, 5.50. Found: C, 67.08; H, 5.27.

EXAMPLE 81

(−)-2-(1-Phenylsulfonyl-indol-3-yl)ethyl-3-O-benzyl-4,6-O-benzylidene-2-O-(2-naphthyl)methyl-β-$\underline{D}$-glucopyranoside (IV-77)

A solution of alcohol (−)-IV-76 (111 mg, 0.17 mmol) in THF (0.850 mL) was cooled to 0° C. in an argon atmosphere. Sodium hydride (60% in oil, 10 mg, 0.26 mmol) was added and the reaction stirred for 20 min. Tetrabutylammonium iodide (2 mol %) and 2-methylnaphthylbromide (42 mg, 0.19 mmol) were added to the reaction mixture, solution was warmed to room temperature and allowed to stir for 15 h. Diethyl ether (25 ml) was added and the reaction was quenched with water. The organic layer was washed with brine, dried over MgSO$_4$, filtered and concentrated in vacuo. Flash silica gel chromatography (hexanes/ethyl acetate, 10:1) provided IV-77 as a colorless oil (133 mg, 99% yield); $[\alpha]_D^{25}$ −8.8° (c 0.8, CHCl$_3$); IR (CHCl$_3$) 3060 (m), 2870 (m), 1450 (s), 1380 (s), 1270 (m), 1175 (s), 1090 (s), 990 (m), 715 (w), 690 (m), 585 (m), 560 (m) cm$^{-1}$; $^1$H NMR (500 MHz, CDCl$_3$) δ 7.98 (d, J=8.3 Hz, 1H), 7.82–7.80 (m, 3H), 7.77–7.67 (m, 2H), 7.56 (s, 1H), 7.50–7.20 (m, 20H), 5.57 (s, 1H), 4.92 (d, J=11.4 Hz, 1H), 4.81 (d, J=11.4 Hz, 1H), 4.79 (d, J=2.8 Hz, 2H), 4.56 (d, J=7.7 Hz, 1H), 4.34 (dd, J=10.5, 5.0 Hz, 1H), 4.21 (dt, J=9.4, 7.0 Hz, 1H), 3.88 (dt, J=9.4, 7.0 Hz, 1H), 3.81–3.75 (m, 2H), 3.70 (t, J=9.2 Hz, 1H), 3.50 (dd, J=8.4, 7.9 Hz, 1H), 3.41 (ddd, J=9.9, 9.9, 5.0 Hz, 1H), 3.0 (t, J=7.0 Hz, 2H) $^{13}$C NMR (125 MHz, CDCl$_3$) δ 138.5, 138.4, 137.3, 135.8, 135.2, 133.6, 133.3, 133.0, 131.0, 129.1, 129.0, 128.3, 128.3, 128.0, 127.9, 127.6, 126.7, 126.6, 126.1, 126.0, 125.9, 125.8, 124.8, 123.6, 123.2, 119.5, 119.5, 113.8, 104.2, 101.2, 82.2, 81.6, 80.9, 75.3, 75.1, 69.1, 68.8, 66.1, 25.7 high resolution mass spectrum (FAB, m-nitrobenzylalcohol) m/z 804.2618 [(M+Na)$^+$; calcd for C$_{47}$H$_{43}$O$_8$NSNa: 804.2607].

EXAMPLE 82

(+)-2-(1-phenysulfonyl-indol-3-yl)ethyl-3,4-di-O-benzyl-2-O-(2-naphthyl)methyl-β-$\underline{D}$-glucopyranoside (IV-78)

To a solution of acetal (−)-IV-77 (450 mg, 0.58 mmol) in dichloromethane (3 mL) at 0° C. was added DIBAL (5.2 mL, 1 M in toluene) dropwise. The reaction stirred under argon for 30 min before quenching with Rochelle's salt. Additional dichloromethane (50 ml)was added and the layers were separated. The organic layer was washed with water, brine, dried over MgSO$_4$, filtered and concentrated in vacuo. The crude alcohol was purified using flash silica gel column chromatography (hexanes/ethyl acetate, 13:1) to yield IV-78 as a colorless oil (260 mg, 58% yield); $[\alpha]_D^{25}$+2.3° (c 1.4, CHCl$_3$); IR (CHCl$_3$) 3580 (w), 3005 (m), 2900 (m), 1450 (m), 1365 (m), 1170 (s), 1070 (s), 905 (m), 680 (w), 590 (w), 570 (w) cm$^{-1}$; $^1$H NMR (500 MHz, CDCl$_3$) δ 7.98 (d, J=8.3 Hz, 1H), 7.84–7.78 (m, 3H), 7.69 (d, J=8.5 Hz, 1H), 7.68–7.66 (m, 2H), 7.59 (s, 1H), 7.54 (s, 1H), 7.50–7.21 (m, 18H), 4.96 (d, J=11.1 Hz, 1H), 4.88 (d, J=12.0 Hz, 1H), 4.88 (d, J=10.4 Hz, 1H), 4.85 (d, J=11.1 Hz, 1H), 4.77 (d, J=11.4 Hz, 1H), 4.67 (d, J=10.0 Hz, 1 H), 4.53 (d, J=7.8 Hz, 1H), 4.23 (app dt, J=9.4, 6.8 Hz, 1H), 3.92 (app dt, J=9.4, 6.5 Hz, 1H), 3.89–3.86 (m, 1H), 3.78–3.73 (m, 1H), 3.70 (app t, J=9.0 Hz, 1H), 3.63 (app t, J=9.4 Hz, 1H), 3.47 (dd, J=8.9, 7.7 Hz, 1H), 3.40–3.37 (m, 1H), 3.05–2.94 (m, 2H), 2.03 (s, 1H) $^{13}$C NMR (125 MHz, CDCl$_3$) δ 138.6, 138.2, 138.0, 135.8, 135.2, 133.6, 133.3, 132.9, 131.0, 129.1, 128.5, 128.4, 128.0, 128.0, 127.9, 127.9, 127.7, 127.6, 127.6, 126.6, 126.1, 125.9, 125.8, 124.8, 123.6, 123.2, 119.7, 119.4, 113.7, 103.7, 84.5, 82.3, 77.5, 75.6, 75.2, 75.1, 74.8, 68.7, 61.9, 25.6 high resolution mass spectrum (FAB) m/z 783.2743 [(M+Na)$^+$; calcd for C$_{47}$H$_{45}$O$_8$NSNa: 783.2769].

EXAMPLE 83

(+)-2-(1H-indol-3-yl)ethyl-3,4-di-O-benzyl-6-O-(4-fluorobenzyl)-2-O-(2-naphthyl)methyl-β-$\underline{D}$-glucopyranoside (IV-79)

A solution of alcohol (+)-IV-78 (21 mg, 0.027 mmol) in THF (1.0 mL) at 0° C. was treated with sodium hydride (60% in oil, 2 mg, 0.041 mmol). After 15 min, 4-fluorobenzylbromide (0.004 mL, 0.029 mmol) and a catalytic amount of tetrabutylammonium iodide (2 mol %) were added. The reaction stirred is for 14 h before being quenched with water and diluted with diethyl ether (50 ml). The organic layer was washed with brine, dried over anhydrous MgSO$_4$, filtered and concentrated in vacuo. The sugar IV-78A was purified using flash silica gel column chromatography (hexanes/ethyl acetate, 10:1) to yield 16 mg (67%) of a mixture of protected and deprotected indoles.

A solution of mixture IV-78A (24 mg, ca. 0.03 mmol) in EtOH (2.2 mL) was treated with 5 M sodium hydroxide (0.360 μL). Reaction stirred for 15 h at reflux (25 ml). Solvents were removed in vacuo, residue was dissolved in dichloromethane and poured into water (25 ml). After extraction, the organic layer was washed with brine, dried over anhydrous Na$_2$SO$_4$, filtered and concentrated. The sugar (+)-IV-79 was purified using flash silica gel column chromatography (hexanes/ethyl acetate, 10:1) to yield 16 mg (67% yield) of a colorless oil; $[\alpha]_D^{25}$ +16.8° (c 0.3, CH$_2$Cl$_2$); IR (CH$_2$Cl$_2$) 3490 (m), 3025 (m), 2900 (m), 1605 (w), 1510 (s), 1455 (w), 1360 (m), 1230 (s), 1080 (vs), 850 (w), 820 (m) cm$^{-1}$; $^1$H NMR (500 MHz, CDCl$_3$) δ 7.81–7.79 (m, 1H), 7.77 (br s, 1H), 7.71–7.67 (m, 2H), 7.62–7.61 (m, 2H), 7.47–7.44 (m, 2H), 7.38–7.26 (m, 14H), 7.20–7.08 (m, 2H), 7.02–7.00 (m, 1H), 6.99–6.93 (m, 2H), 4.96–4.93 (m, 2H), 4.85–4.77 (m, 3H), 4.57–4.53 (m, 2H), 4.51–4.48 (m, 2H), 4.29 (app dt, J=9.4, 6.7 Hz, 1H), 3.89 (app dt, J=9.6, 7.4 Hz, 1H), 3.72 (dd, J=10.8, 1.9 Hz, 1H), 3.70–3.63 (m, 2H), 3.60 (app t, J=9.4 Hz, 1H), 3.52 (app t, J=7.9 Hz, 1H), 3.48 (ddd, J=9.8, 4.8, 1.9 Hz, 1H), 3.15 (appt, J=7.0 Hz, 2H) $^{13}$C NMR (125 MHz, CDCl$_3$) δ 162.3 (d, J=249.6 Hz), 138.6, 138.1, 136.2, 136.0, 134.0, 133.3, 133.0, 129.5, 129.4, 128.4, 128.3, 127.9, 127.9, 127.8, 127.7, 127.7, 127.6, 127.5, 126.7, 126.2, 126.0, 125.8, 122.1, 122.0, 119.3, 118.7, 115.2, 115.1, 112.9, 111.1, 103.7, 84.7, 82.3, 78.0, 75.7, 75.0, 74.9, 74.7, 72.7, 70.1, 69.0, 25.8 ppm; high resolution mass spectrum (FAB, m-nitrobenzyl alcohol) m/z 752.3382 [(M+Na)$^+$; calcd for $C_{48}H_{46}FO_6NNa$: 752.3387].

EXAMPLE 84

(+)-2-(1-Phenylsulfonyl-indol-3-yl)ethyl-3,4-di-O-benzyl-6-O-(4-fluorophenyl)-2-O-(2-naphthyl) methyl-β-D-glucopyranoside (IV-80)

Triflic anhydride (0.015 mL, 0.09 mmol) was added dropwise to a 0° C. dichloromethane (3 mL) solution of (+)-IV-78 (35 mg, 0.044 mmol) and 2,6-di-t-butyl-4-methylpyridine (18 mg, 0.09 mmol) while stirring under argon. The reaction stirred for 10 min, was diluted with dichloromethane (5 mL), poured into water and extracted. The organic layer was washed with brine, dried over anhydrous $Na_2SO_4$, filtered, and used without further purification in the next step.

To a solution containing the triflate formed above and 4-fluorophenol (12 mg, 0.1 mmol) in THF (2 mL) at 0° C. was added solid NaH (60% in oil, 4 mg, 0.1 mmol). The reaction stirred for 1 h before being quenched with water and diluted with diethyl ether (50 ml). The organic layer was washed with 1 M NaOH, brine, dried over anhydrous $MgSO_4$, filtered and concentrated in vacuo. The sugar (+)-IV-80 was purified using flash silica gel column chromatography (hexanes/ethyl acetate, 10:1) to yield 20 mg (51% yield) of a colorless oil; $[\alpha]_D^{25}$+17.0° (c 0.1, $CH_2Cl_2$); IR ($CH_2Cl_2$) 3050 (m), 2920 (m), 2880 (m), 1520 (m), 1450 (m), 1370 (s), 1220 (s), 1180 (s), 1100 (vs), 910 (w), 830 (w), 590 (w) cm$^{-1}$; $^1$H NMR (500 MHz, CDCl$_3$) δ 7.97 (d, J=8.4 Hz, 1H), 7.80–7.78 (m, 2H), 7.72–7.66 (m, 2H), 7.58 (s, 1H), 7.46–7.43 (m, 3H), 7.40–7.37 (m, 1H), 7.31–7.25 (m, 14H), 7.24–7.17 (m, 3H), 6.95–6.91 (m, 2H), 6.83–6.79 (m, 2H), 4.97 (d, J=11.0 Hz, 1H), 4.87 (d, J=11.4 Hz, 1H), 4.86 (d, J=11.0 Hz, 1H), 4.83 (d, J=11.0 Hz, 1H), 4.76 (d, J=11.4 Hz, 1H), 4.55 (d, J=11.0 Hz, 1H), 4.50 (d, J=7.7 Hz, 1H), 4.20 (app dt, J=9.6, 6.8 Hz, 1H), 4.15 (dd, J=10.4, 1.9 Hz, 1H), 4.05 (dd, J=10.4, 4.9 Hz, 1H), 3.86 (app dt, J=9.5, 7.2 Hz, 1 H), 3.73–3.69 (m, 2H), 3.63–3.60 (m, 1H), 3.56–3.52 (m, 1H), 3.00 (app t, J=6.9 Hz, 2H) $^{13}$C NMR (125 MHz, CDCl$_3$) δ 157.4 (d, J=238.5 Hz), 154.8, 138.5, 138.3, 137.9, 135.8, 135.2, 133.5, 133.3, 133.0, 131.0, 129.1, 128.5, 128.4, 128.1, 128.0, 128.0, 127.9, 127.8, 127.8, 127.6, 126.7, 126.6, 126.1, 125.9, 125.8, 124.8, 123.5, 123.2, 119.6, 119.4, 119.3, 115.8, 115.8, 115.6, 113.7, 103.8, 84.7, 82.2, 77.5, 75.7, 75.1, 74.8, 73.9, 68.9, 67.6, 25.7 high resolution mass spectrum (FAB, m-nitrobenzyl alcohol) m/z 900.2995 [(M+Na)$^+$; calcd for $C_{53}H_{48}FO_8NSNa$: 900.2982].

EXAMPLE 85

(+)-2-(1H-indol-3-yl)ethyl-3,4-di-O-benzyl-6-O-(4-fluorophenyl)-2-O-(2-naphthyl)methyl-β-D-glucopyranoside (IV-81)

A solution of the indole (+)-IV-86 (29 mg, 0.033 mmol) in EtOH (4 mL) was treated with 5 M sodium hydroxide (0.650 mL). Reaction mixture was refluxed for 15 h. Solvents were removed in vacuo, residue was dissolved in dichloromethane (50 ml) and poured into water (50 ml). After extraction, the organic layer was washed with brine, dried over anhydrous $Na_2SO_4$, filtered and concentrated. The sugar (+)-IV-81 was purified using a 0.5 mm $SiO_2$ prep plate (7:3 hexanes/ethyl acetate) to yield 20 mg (82% yield) of a colorless oil; $[\alpha]_D^{25}$+26.8° (c 0.3, $CH_2Cl_2$); IR ($CH_2Cl_2$) 3490 (m), 3025 (m), 2620 (m), 2580 (m), 1510 (s), 1450 (m), 1360 (w), 1210 (s), 1080 (vs), 820 (m) cm$^{-1}$; $^1$H NMR (500 MHz, CDCl$_3$) δ 7.81–7.78 (m, 1H), 7.74 (br s, 1H), 7.71–7.67 (m, 2H), 7.60–7.58 (m, 2H), 7.46–7.44 (m, 3H), 7.32–7.23 (m, 9H), 7.19–7.16 (m, 3H), 7.11–7.08 (m, 1H), 7.00 (s, 1H), 6.95–6.91 (m, 2H), 6.82–6.79 (m, 2H), 4.96 (d, J=11.1 Hz, 1H), 4.93 (d, J=12.4 Hz, 1H), 4.86 (d, J=11.0 Hz, 1H), 4.82 (d, J=11.0 Hz, 1H), 4.79 (d, J=11.2 Hz, 1H), 4.54 (d, J=11.0 Hz, 1H), 4.51 (d, J=7.8 Hz, 1H), 4.25 (app dt, J=9.4, 6.6 Hz, 1H), 4.15–4.09 (m, 1H), 4.03 (dd, J=10.4, 4.8 Hz, 1H), 3.87 (app dt, J=9.4, 7.4 Hz, 1H), 3.74–3.64 (m, 2H), 3.60–3.48 (m, 2H), 3.12 (app t, J=6.9 Hz, 2H) $^{13}$C NMR (125 MHz, CDCl$_3$) δ 157.4 (J=239.5 Hz), 154.9, 138.6, 138.0, 136.2, 136.0, 133.3, 133.0, 128.5, 128.4, 128.2, 128.0, 127.9, 127.9, 127.7, 127.6, 127.6, 126.7, 126.3, 126.0, 125.8, 122.1, 122.0, 119.4, 118.8, 115.9, 115.8, 115.8, 115.7, 112.8, 111.1, 103.8, 84.7, 82.3, 77.6, 75.7, 75.2, 74.8, 73.9, 70.2, 67.7, 25.8 high resolution mass spectrum (FAB, m-nitrobenzyl alcohol) m/z 760.3072 [(M+Na)$^+$; calcd for $C_{47}H_{44}FO_6NNa$: 760.3050].

EXAMPLE 86

(−)-2-(1-phenylsulfonyl-indol-3-yl)ethyl-3-O-benzyl-4,6-O-benzylidene-2-O-(4-fluorobenzyl)-β-D-glucopyranoside (IV-82)

A solution of alcohol (−)-IV-76 (164 mg, 0.26 mmol) in THF (6 mL) was cooled to 0° C. in an argon atmosphere. Sodium hydride (60% in oil, 15 mg, 0.38 mmol) was added and the reaction stirred for 20 min. Tetrabutylammonium iodide (2 mol %) and 4-fluorobenzylbromide (0.035 mL, 0.28 mmol) were added to the reaction mixture, solution was warmed to room temperature and allowed to stir for 15 h. Diethyl ether was added and the reaction was quenched with water. The organic layer was washed with brine, dried over $MgSO_4$, filtered and concentrated in vacuo. Flash silica gel chromatography (hexanes/ethyl acetate, 10:1) provided IV-82 as a colorless oil (135 mg, 71% yield); $[\alpha]_D^{20}$ −24.3° (c 4.5, CHCl$_3$); IR (CHCl$_3$) 2880 (w), 1605 (w), 1515 (w), 1450 (m), 1370 (m), 1175 (s), 1090 (s), 910 (s), 695 (w), 650 (m), 595 (w), 570 (w) cm$^{-1}$; $^1$H NMR (500 MHz, CDCl$_3$) δ 8.04 (d, J=8.4 Hz, 1H), 7.88 (d, J=7.9 Hz, 2H), 7.55–7.53 (m, 4H), 7.48–7.25 (m, 13H), 7.11–7.08 (m, 2H), 6.94–6.91 (m, 2H), 5.62 (s, 1H), 4.97 (d, J=11.5 Hz, 1H), 4.81 (d, J=11.5 Hz, 1H), 4.61(s, 2H), 4.57 (d, J=7.7 Hz, 1H), 4.40 (dd, J=10.5, 5.0 Hz, 1H), 4.25 (dt, J=9.5, 6.6 Hz, 1H), 3.93 (dt, J=9.4, 7.0 Hz, 1H), 3.84 (t, J=10.3 Hz, 1H), 3.80–3.72 (m, 2H), 3.47 (t, J=7.8 Hz, 2H), 3.06 (t, J=6.7 Hz, 2H) $^{13}$C NMR (125 MHz, CDCl$_3$) δ 162.2 (d, J=243.5 Hz), 138.4, 138.2, 137.2, 135.1, 133.9, 133.9, 133.6, 130.8, 129.7, 129.6, 129.1, 128.8, 128.2, 128.1, 127.9, 127.6, 126.6, 125.9, 124.7, 123.5, 123.1, 119.5, 119.4, 115.0, 114.8, 113.7, 103.9, 101.1, 81.8, 81.5, 80.7, 77.2, 74.9, 74.3, 68.9, 68.7, 65.9, 25.6 high resolution mass spectrum (FAB, m-nitrobenzyl alcohol) m/z 772.2352 [(M+Na)$^+$; calcd for $C_{43}H_{40}FO_8NSNa$: 772.2356].

EXAMPLE 87

(−)-2-(1-phenylsulfonyl-indol-3-yl)ethyl-3,4-di-O-benzyl-2-O-(4-fluorobenzyl)-β-D-glucopyranoside (IV-83)

To a solution of acetal (−)-IV-82 (94 mg, 0.13 mmol) in dichloromethane (0.625 mL) at 0° C. was added DIBAL (1 mL, 1M in toluene) dropwise. The reaction stirred under argon for 30 min before quenching with Rochelle's salt. Additional dichloromethane (50 ml) was added and the layers were separated. The organic layer was washed with water, brine, dried over $MgSO_4$, filtered and concentrated in vacuo. The crude alcohol was purified using flash silica gel column chromatography (hexanes/ethyl acetate, 13:1) to yield IV-83 as a colorless oil; (56 mg, 60% yield) $[\alpha]_D^{20}$ −5.8° (c 1.9, $CHCl_3$); IR ($CHCl_3$) 3590 (w, br), 3000 (m), 2880 (m), 1605 (m), 1510 (s), 1450 (s), 1370 (s), 1175 (s), 1075 (s), 820 (w), 690 (w), 595 (m), 570 (m) $cm^{-1}$; $^1H$ NMR (500 MHz, $CDCl_3$) δ 7.97 (d, J=8.3 Hz, 1H), 7.85–7.83 (m, 2H), 7.53 (s, 1H), 7.49–7.45 (m, 2H), 7.39–7.22 (m, 14H), 7.08–7.05 (m, 2H), 6.89–6.86 (m, 2H), 4.85–4.69 (m, 3H), 4.65 (t, J=10.9 Hz, 2H), 4.53 (d, J=11.0 Hz, 1H), 4.46 (d, J=7.8 Hz, 1H), 4.21 (dt, J=9.4, 6.6 Hz, 1H), 3.92–3.86 (m, 2H), 3.73 (dd, J=12.1, 4.2 Hz, 1H), 3.65–3.58 (m, 2H), 3.38–3.34 (m, 2H), 2.99 (dt, J=11.5, 5.7 Hz, 2H), 1.98 (br s, 1H) $^{13}C$ NMR (125 MHz, $CDCl_3$) δ 162.3 (d, J=245.3 Hz), 138.5, 138.3, 137.9, 135.2, 134.0, 133.9, 133.7, 130.9, 129.7, 129.6, 129.2, 128.5, 128.4, 128.1, 127.9, 127.7, 127.6, 126.7, 124.8, 123.6, 123.2, 119.6, 119.3, 115.2, 115.0, 113.7, 103.6, 84.4, 82.1, 77.5, 75.6, 75.2, 75.1, 74.0, 68.6, 61.9, 25.6 high resolution mass spectrum (FAB, m-nitrobenzyl alcohol) m/z 774.2531 [(M+Na)$^+$; calcd for $C_{43}H_{42}FO_8NSNa$: 774.2513].

EXAMPLE 88

(+)-2-(1H-inclol-3-yl) ethyl-3, li-di-O-Benzyl 2-O-(4-fluorobenzyl)-B-D-glucopyranoside (IV-84)

A solution of alcohol (−)-IV-83 (15 mg, 0.02 mmol) in THF (1 mL) at 0° C. was treated with sodium hydride (60% in oil, 1 mg, 0.03 mmol) while stirring under argon. After 15 min, 2-methylnaphthylbromide (0.5 mg, 0.02 mmol) and a catalytic amount of tetrabutylammonium iodide (2 mol %) were added. The reaction stirred for 14 h before being quenched with water and diluted with diethyl ether (50 ml). The organic layer was washed with brine, dried over anhydrous $MgSO_4$, filtered and concentrated in vacuo. A mixture of naphthyl alkylated product as the protected indole and deprotected indole was obtained.

The above mixture (17 mg) in EtOH (2.2 mL) was treated with 5 M sodium hydroxide (0.360 mL). Reaction was refluxed for 15 h (25 ml). Solvents were removed in vacuo, residue was dissolved in dichloromethane and poured into water. After extraction, the organic layer was washed with brine, dried over anhydrous $Na_2SO_4$, filtered and concentrated. The sugar (+)-IV-84 was purified using flash silica gel column chromatography (hexanes/ethyl acetate, 10:1) to yield 7.2 mg (50% yield, 2 steps) of a colorless oil; $[\alpha]^{20}$+ 8.0° (c 1.0, $CHCl_3$); IR ($CHCl_3$) $cm^{-1}$; $^1H$ NMR (500 MHz, $CDCl_3$) δ 7.84 (br s, 1H), 7.82–7.80 (m, 1H), 7.78–7.76 (m, 3H), 7.63 (d, J=8.0 Hz, 1H), 7.48–7.44 (m, 3 H), 7.34–7.27 (m, 7H), 7.22–7.16 (m, 3H), 7.13 (d,J=7.1 Hz, 1H), 7.11–7.07 (m, 4H), 7.02 (d, J=2.2 Hz, 1H), 6.91–6.88 (m, 2H), 4.88 (d, J=11.1 Hz, 1H), 4.81 (d, J=10.8 Hz, 1H), 4.80 (d, J=11.0 Hz, 1H), 4.78 (d, J=12.3 Hz, 1H), 4.73 (d, J=10.9 Hz, 1H), 4.71 (d, J=12.3 Hz, 1H), 4.57 (J=11.0 Hz, 1H), 4.53 (d, J=10.8 Hz, 1H), 4.45 (d, J=7.8 Hz, 1H), 4.30 (app dt, J=9.4, 6.6 Hz, 1H), 3.89 (app dt, J=9.4, 7.4 Hz, 1H), 3.79 (dd, J=10.8, 2.0 Hz, 1H), 3.73 (dd, J=10.7, 4.8 Hz, 1H), 3.64–3.62 (m, 2H), 3.51–3.44 (m, 2H), 3.15 (app t, J=7.0 Hz, 2H) $^{13}C$ NMR (125 MHz, $CDCl_3$) δ 162.3 (d, J=245.5 Hz), 138.6, 138.0, 136.2, 135.6, 134.3, 134.3, 133.2, 133.0, 129.9, 129.8, 128.3, 128.3, 128.2, 127.9, 127.8, 127.7, 127.6, 127.6, 126.5, 126.1, 125.9, 125.8, 122.0, 122.0, 119.3, 118.8, 115.1, 114.9, 112.8, 111.1, 103.7, 84.7, 82.1, 77.9, 75.6, 75.0, 74.9, 73.8, 73.6, 70.0, 68.9, 25.9 high resolution mass spectrum (CI) m/z 769.3658 [(M+NH$_4$)$^+$; calcd for $C_{48}H_{50}FN_2O_6$: 769.3652].

EXAMPLE 89

(−)-2-(1-phenylsulfonyl-indol-3-yl)ethyl-6-O-(5-azidopentyl)-3,4-di-O-benzyl-2-O-(4-fluorobenzyl)-β-D-glucopyranoside (IV-85)

To a round bottomed flask containing dry alcohol (−)-IV-83 (55 mg, 0.07 mmol) was added a solution of 5-azidopentanoltrifluoro-methane-sulfhonate (ca. 10 eq.) in dichloromethane. Solvent was removed in vacuo and the reaction flask was placed on a vacuum pump. Every 20 min. for the next 2.5 h, dichloromethane was added to the reaction vessel, reagents were solvated, and the solvent was again removed in vacuo prior to the reaction being placed on the vacuum pump. The azide (−)-IV-85 was purified using flash silica gel column chromatography (hexanes/ethyl acetate, 5:1) to yield 30 mg (50% yield) of a colorless oil; $[\alpha]_D^{20}$ −3.3° (c 1.0, $CHCl_3$); IR (CHCl,) 3000 (s), 2920 (s), 2880 (s), 2100 (vs), 1600 (m), 1510 (s), 1450 (s), 1370 (s), 1170 (s), 1100 (s), 900 (s), 690 (w), 590 (m), 560 (m) $cm^{-1}$; $^1H$ NMR (500 MHz, $CDCl_3$) δ 7.97 (d, J=7.9 Hz, 1H), 7.85–7.83 (m, 2H), 7.50–7.44 (m, 3H), 7.38–7.21 (m, 14H), 7.06–7.02 (m, 2H), 6.88–6.83 (m, 2H), 4.86 (d, J=11.1 Hz, 1H), 4.85 (d, J=10.9 Hz, 1H), 4.79 (d, J=11.1 Hz, 1H), 4.62 (d, J=11.0 Hz, 1H), 4.61 (d, J=10.9 Hz, 1H), 4.51 (d, J=11.1 Hz, 1H), 4.40 (d, J=7.8 Hz, 1H), 4.21 (app dt, J=9.5, 6.6, 6.6 Hz, 1H), 3.84 (app dt, J=9.6, 7.1, 7.1 Hz, 1H), 3.68 (dd, J=10.9, 2.0 Hz, 1H), 3.63 (dd, J=10.8, 4.8 Hz, 1H), 3.61–3.56 (m, 2H), 3.51 (app dt, J=9.4, 6.3, 6.3 Hz, 1H), 3.44–3.36 (m, 3H), 3.19 (app t, J=6.9 Hz, 2H), 3.01 (app t, J=7.2 Hz, 2H), 1.62–1.54 (m, 4H), 1.46–1.38 (m, 2H) $^{13}C$ NMR (125 MHz, $CDCl_3$) δ 162.3 (d, J=245.8 Hz), 138.6, 138.3, 138.2, 135.2. 134.1, 133.6, 131.0, 129.8, 129.7, 129.1, 128.4, 128.3, 127.8, 127.8, 127.7, 127.6, 126.7, 124.8, 123.5, 123.1. 119.7, 119.4, 115.1, 115.0, 113.7, 103.7, 84.6, 82.0, 78.0, 75.6, 75.0, 74.9, 73.9, 71.4, 69.7, 68.7, 51.3, 29.2, 28.7, 25.7, 23.4 high resolution mass spectrum (FAB) m/z 885.3513 [(M+Na)$^+$; calcd for $C_{48}H_{51}FO_8N_4SNa$: 885.3529].

EXAMPLE 90

(−)-2-(1-phenylsulfonyl-indol-3-yl)ethyl-6-O-(5-aminopentyl)-3,4-di-O-benzyl-2-O-(4-fluorobenzyl)-β-D-glucopyranoside (IV-86)

Triphenylphospine (21 mg, 0.08 mmol) was added to a solution (1.96 mL THF/0.04 mL $H_2O$) of azide (−)-IV-85 (30 mg, 0.035 mmol). The reaction was heated to 55° C. under argon and stirred for 5 h. Solvents were removed in vacuo and the amine was purified using flash silica gel column chromatography (100% ethyl acetate gradient to 10% methanol in dichloromethane) to yield (−)-IV-86 as a colorless oil; 26.2 mg, 90% yield $[\alpha]_D^{20}$ −5.5° (c 0.2, $CHCl_3$); IR ($CHCl_3$) 3005 (m), 2930 (s), 2870 (m), 1610 (w), 1510 (m), 1450 (s), 1370 (s), 1225 (m), 1170 (s), 1120 (m), 1070 (s), 590 (m), 560 (w) $cm^{-1}$; $^1H$ NMR (500 MHz, $CDCl_3$) δ 7.96 (d, J=8.2 Hz, 1H), 7.84–7.82 (m, 2H), 7.48 (d, J=7.4 Hz, 1H), 7.47–7.39 (m, 2H), 7.36 (d, J=7.8 Hz, 1H), 7.35 (d, J=7.7 Hz, 1H), 7.32–7.20 (m, 12H), 7.03 (d, J=8.4 Hz, 1H), 7.02 (d, J=8.3 Hz, 1H), 6.85 (d, J=8.6 Hz, 1H), 6.83 (d, J=8.7 Hz, 1H), 4.85 (d, J=11.0 Hz, 1H), 4.83 (d, J=10.9 Hz, 1H), 4.78 (d, J=11.0 Hz, 1H), 4.60 (d, J=10.9 Hz, 2H), 4.49 (d, J=11.0 Hz, 1H), 4.38 (d, J=7.7 Hz, 1H), 4.21 (app dt, J=9.4, 6.7, 6.7 Hz, 1H), 3.83 (app dt, J=9.3, 7.0, 7.0 Hz, 1H), 3.67 (dd, J=10.9, 1.7 Hz, 1H), 3.62 (dd, J=10.7, 4.8 Hz. 1H), 3.60–3.55 (m, 2H), 3.49 (app dt, J=9.3, 6.4, 6.4 Hz, 1H), 3.43–3.36 (m, 3H), 3.00 (app t, J=6.8 Hz, 2H), 2.65 (app t, J=7.0 Hz, 2H), 2.21 (br s, 2H), 1.60–1.52 (m, 2H), 1.51–1.41 (m, 2H), 1.39–1.31 (m, 2H) $^{13}$C NMR (125 MHz, CDCl$_3$) δ 162.2 (d, J=245.1 Hz), 138.6, 138.3, 138.2, 135.2, 134.1, 133.6, 131.0, 129.8, 129.7, 129.1, 128.4, 128.4, 127.9, 127.8, 127.7, 127.6, 126.7, 124.8, 123.5, 123.2, 119.7, 119.5, 115.1, 115.0, 113.7, 103.7, 84.6, 82.0, 78.0, 75.6, 75.0, 74.9, 73.9, 71.6, 69.6, 68.7, 41.7, 29.7, 29.4, 25.7, 23.4 ppm; high resolution mass spectrum (FAB, m-nitrobenzyl alcohol) m/z 837.3584 [(MH)$^+$; calcd for C$_{48}$H$_{54}$FO$_8$N$_2$S: 837.3584].

EXAMPLE 91

(−)-2-(1-phenylsulfonyl-indol-3-yl)ethyl-6-O-(N-acetyl-5-aminopentyl)-3,4-O-dibenzyl-2-O-(4-fluorobenzyl)-β-D-glucopyranoside (IV-87)

To a solution of amine (−)-IV-86 (26.2 mg, 0.031 mmol) in dichloromethane (1 mL) was added acetic anhydride (0.003 mL, 0.031 mmol) and pyridine (0.01 mL). Reaction stirred for 15 min at ambient temperature in an argon atmosphere. Solvents were removed in vacuo and the residue was azeotroped dry with toluene (3×5 mL). Purification using flash silica gel column chromatography (100% ethyl acetate) afforded (−)-IV-87 (97% yield) as a colorless oil; [α]$_D^{20}$ −15.0° (c 0.2, CHCl$_3$); IR (CHCl$_3$) 3460 (w), 3010 (m), 2940 (m), 2870 (m), 1670 (s), 1610 (w), 1510 (s), 1450 (s), 1370 (s), 1175 (m), 1080 (vs), 590 (m), 570 (w) cm$^{-1}$; $^1$H NMR (500 MHz, CDCl$_3$) δ 7.96 (d, J=8.2 Hz, 1H), 7.83 (d, J=7.6 Hz, 2H), 7.50–7.45 (m, 3H), 7.37 (app t, J=8.0 Hz, 2H), 7.33–7.21 (m 12H), 7.06–7.04 (m, 2H), 6.87–6.83 (m, 2H), 5.44 (brs, 1H), 4.86 (d, J=11.0 Hz, 1H), 4.84 (d, J=10.8 Hz, 1H), 4.78 (d, J=11.0 Hz, 1H), 4.62 (app t, J=11.3 Hz, 1H), 4.51 (d, J=11.1 Hz, 1H), 4.39 (d, J=7.8 Hz, 1H), 4.21 (app dt, J=9.5, 6.7, 6.7 Hz, 1H), 3.85 (app dt, J=9.5, 7.0, 7.0 Hz, 1H), 3.67 (dd, J=10.7, 1.7 Hz, 1H), 3.63–3.55 (m, 3H), 3.50 (app dt, J=9.4, 6.3, 6.3 Hz, 1H), 3.43–3.35 (m, 3H), 3.21–3.11 (m, 2H), 3.00 (app t, J=6.8 Hz, 2H), 1.91 (s, 3H), 1.59–1.51 (m, 2H), 1.49–1.43 (m, 2H), 1.40–1.31 (m, 2H) $^{13}$C NMR (125 MHz, CDCl$_3$) δ 170.0, 162.2 (d, J=245.7 Hz), 138.6, 138.3, 138.2, 135.2, 134.1, 133.7, 131.0, 129.8, 129.7, 129.2, 128.5, 128.4, 127.9, 127.8, 127.7, 127.7, 126.7, 124.8, 123.5, 123.2, 119.8, 119.5, 115.2, 115.0, 113.8, 103.7, 84.7, 82.1, 78.0, 75.7, 75.0, 75.0, 73.9, 71.5, 69.7, 68.7, 39.5, 29.3, 29.3, 25.7, 23.6, 23.3 ppm; high resolution mass spectrum (FAB, m-nitorbenzyl alcohol) m/z 901.3736 [(M+Na)$^+$; calcd for C$_{50}$H$_{55}$FO$_9$N$_2$SNa: 901.3714].

EXAMPLE 92

(−)-2-(1H-indol-3-yl)ethyl-6-O-(N-acetyl-5-aminopentyl)-3,4-di-O-benzyl-2-O-(4-fluorobenzyl)-β-D-glucopyranoside (IV-88)

To a solution of amide (−)-IV-87 (26.3 mg, 0.03 mmol) in ethanol (3 mL) was added 5 M sodium hydroxide (0.5 mL). Reaction was refluxed for 15 h (50 ml). Solvents were removed in vacuo, residue was dissolved in dichloromethane (50 ml) and poured into water. After extraction, the organic layer was washed with brine, dried over anhydrous Na$_2$SO$_4$, filtered and concentrated. Purification using a 0.5 mm silica gel prep plate (100% ethyl acetate) afforded (−)-IV-88 (67% yield) as a colorless oil; [α]$_D^{20}$ −1.7° (c 0.2, CHCl$_3$); IR (CHCl$_3$) 3490 (m), 3000 (m), 2920 (m), 1460 (s), 1510 (m), 1360 (s), 1220 (w), 1070 (s), 590 (m) cm$^{-1}$; $^1$H NMR (500 MHz, CDCl$_3$) δ 8.26 (br s, 1H), 7.59 (d, J=7.9 Hz, 1H), 7.35–7.25 (m, 11H), 7.19–7.15 (m, 3H), 7.12–7.09 (m, 3H), 7.04 (d, J=2.2 Hz, 1H), 6.91–6.87 (m, 2H), 5.39 (br s, 1H), 4.86 (d, J=11.0 Hz, 1H), 4.84 (d, J=11.0 Hz, 1H), 4.78 (d, J=11.0 Hz, 1H), 4.73 (d, J=11.0 Hz, 1H), 4.59 (d, J=10.8 Hz, 1H), 4.57 (d, J=10.9 Hz, 1H), 4.42 (d, J=7.8 Hz, 1H), 4.22 (app dt, J=9.4, 6.8 Hz, 1H), 3.86 (app dt, J=9.4, 7.5 Hz, 1H), 3.67 (dd, J=10.9, 1.8 Hz, 1H), 3.63–3.38 (m, 7H), 3.18–3.10 (m, 4H), 1.92 (s, 3H), 1.58–1.53 (m, 2H), 1.47–1.42 (m, 2H), 1.36–1.30 (m, 2H) $^{13}$C NMR (125 MHz, CDCl$_3$) δ 170.0, 162.3 (d, J=246.0 Hz), 138.6, 138.2, 136.3, 134.3, 132.1, 129.9, 129.8, 128.4, 128.4, 127.9, 127.8, 127.7, 127.6, 127.5, 122.1, 121.9, 119.2, 118.7, 115.1, 115.0, 112.6, 111.2, 103.7, 84.7, 82.1, 78.1, 75.7, 75.0, 74.9, 73.9, 71.5, 70.0, 69.7, 39.6, 29.3, 29.3, 25.8, 23.6, 23.3 high resolution mass spectrum (FAB, m-nitrobenzylalcohol) m/z 756.4043 [(M+NH$_4$)$^+$; calcd for C$_{44}$H$_{55}$FO$_7$N$_3$: 756.4024].

EXAMPLE 93

(+)-2-(1-phenylsulfonyl-indol-3-yl)ethyl-6-O-(5-azidopentyl)-3,4-di-O-benzyl-2-O-(2-naphthyl)methyl-β-D-glucopyranoside (IV-89)

The alcohol (+)-IV-78 was converted to azide IV-78 using the representative procedure of example 16 azide (+)-IV-89 was purified using flash silica gel column chromatography (hexanes/ethyl acetate, 8:1) to yield 67 mg (96% yield) of a colorless oil; [α]$_D^{20}$ +9.8° (c 1.1, CHCl$_3$); IR (CHCl$_3$) 3010 (m), 2935 (m), 2865 (m), 2100 (s), 1730 (w), 1605 (vw), 1450 (m), 1375 (s), 1180 (s), 1120 (m), 1090(m), 1070 (m), 695 (w), 595 (w), 570 (w) cm$^{-1}$; $^1$H NMR (500 MHz, CDCl$_3$) δ 7.98 (d, J=8.4 Hz, 1H), 7.82 (d, J=7.6 Hz, 2H), 7.79–7.77 (m, 1H), 7.68–7.65 (m, 2H), 7.57 (s, 1H), 7.49–7.20 (m, 20H), 4.94 (d, J=11.0 Hz, 1H), 4.87 (dd, J=11.0, 3.9 Hz, 2H), 4.81 (d, J=11.0 Hz, 1H), 4.75 (d, J=11.4 Hz), 4.63 (d, J=11.0 Hz, 1H), 4.46 (d, J=7.8 Hz, 1H), 4.23 (dt, J=9.5, 6.8 Hz, 1H), 3.87 (dt, J=9.5, 7.0 Hz, 1H), 3.71–3.58 (m, 4H), 3.53–3.42 (m, 4H), 3.19 (t, J=6.9 Hz, 2H), 3.02 (t, J=6.9 Hz, 2H), 1.61–1.54 (m, 4H), 1.45–1.39 (m, 2H) $^{13}$C NMR (125 MHz, CDCl$_3$) d 138.6, 138.3, 138.2, 135.8, 135.2, 133.5, 133.3, 132.9, 131.0, 129.1, 128.4, 128.3, 128.0, 127.9, 127.8, 127.7, 127.6, 127.5, 126.6, 126.1, 124.7, 123.5, 123.1, 119.7, 119.4, 113.7, 103.8, 84.7, 82.3, 78.0, 75.6, 74.9, 74.7, 71.4, 69.7, 68.7, 51.3, 29.2, 28.7, 25.7, 23.4 high resolution mass spectrum (FAB, m-nitrobenzylalcohol) m/z 917.3579 [(M+Na)$^+$; calcd for C$_{52}$H$_{54}$O$_8$N$_4$SNa: 917.3560].

EXAMPLE 94

(+)-2-(1-phenylsulfonyl-indol-3-yl)ethyl-6-O-(5-aminopentyl)-3,4-di-O-benzyl-2-O-(2-naphthyl)methyl-β-D-glucopyranoside (IV-90)

Triphenylphospine (18.8 mg, 0.07 mmol) was added to a solution (1.76 mL THF/0.04 mL H$_2$O) of azide (+)-IV-89 (28 mg, 0.031 mmol). The reaction was heated to 55° C. under argon and stirred for 5 h. Solvents were removed in vacuo and the amine was purified using flash silica gel column chromatography (100% ethyl acetate gradient to 10% methanol in dichloromethane) to yield (+)-IV-90 as a colorless oil; (22.9 mg, 85% yield) [α]$_D^{20}$ +4.2° (c 0.6, CH$_2$Cl$_2$); IR (CH$_2$Cl$_2$) 3020 (m), 2930 (s), 2760 (s), 1450 (s), 1370 (s), 1180 (s), 1120 (s), 1080 (vs), 910 (m), 590 (m), 570 (m) cm$^{-1}$; $^1$H NMR (500 MHz, CDCl$_3$) δ 7.97 (d, J=8.4 Hz, 1H), 7.82–7.80 (m, 2H), 7.80–7.77 (m, 1H), 7.77–7.63 (m, 2H), 7.56 (s, 1H), 7.48–7.38 (m, 5H), 7.33–7.15 (m, 15H), 4.93 (d, J=11.0 Hz, 1H), 4.86 (d, J=10.9 Hz, 1H), 4.85

(d, J=11.4 Hz, 1H), 4.80 (d, J=11.0 Hz, 1H), 4.73 (d, J=11.4 Hz, 1H), 4.62 (d, J=10.9 Hz, 1H), 4.44 (d, J=7.8 Hz, 1H), 4.23 (app dt, J=9.5, 6.8 Hz, 1H), 3.86 (app dt, J=9.5, 7.1 Hz, 1H), 3.69 (dd, J=10.9, 1.9 Hz, 1H), 3.68–3.62 (m, 2H), 3.60 (app t, J=9.4 Hz, 1H), 3.54–3.40 (m, 4H), 3.01 (app t, J=7.0 Hz, 2H), 2.63 (br s, 2H), 1.60–1.56 (m, 2H), 1.43–1.33 (m, 6H) $^{13}$C NMR (125 MHz, CDCl$_3$) δ 138.6, 138.3, 138.3, 135.9, 135.2, 133.5, 133.3, 132.9, 131.0, 129.1, 129.0, 128.4, 128.3, 128.2, 128.0, 127.9, 127.8, 127.8, 127.6, 127.5, 126.6, 126.6, 126.1, 125.9, 124.7, 123.5, 123.1, 119.7, 119.5, 113.7, 103.8, 84.7, 82.3, 78.0, 75.6, 75.0 (2C), 74.8, 71.7, 69.7, 68.7, 42.1, 33.5, 29.5, 25.7, 23.5 ppm; high resolution mass spectrum (FAB) m/z 891.3632 [(M+Na)$^+$; calcd for C$_{52}$H$_{56}$O$_8$N$_2$SNa: 891.3655].

EXAMPLE 95

(+)-2-(1-phenylsulfonyl-indol-3-yl)ethyl-6-O-(N-acetyl-5-aminopentyl)-3,4-di-O-benzyl-2-O-(2-naphthyl)methyl-β-D-glucopyranoside (IV-91)

To a solution of amine (+)-IV-90 (22 mg, 0.025 mmol) in dichloromethane (1 mL) was added acetic anhydride (0.003 mL, 0.031 mmol) and pyridine (0.01 mL). Reaction stirred for 15 min at ambient temperature in an argon atmosphere. Solvents were removed in vacuo and the residue was azeotroped dry with toluene (3×5 mL). Purification using flash silica gel column chromatography (100% ethyl acetate) afforded (+)-IV-91 (100% yield) as a colorless oil; [α]$_D^{20}$ +4.1° (c 0.8, CHCl$_3$); IR (CHCl$_3$) 3980 (w), 3005 (m), 2920 (m), 2860 (m), 1670 (s), 1510 (w), 1450 (m), 1370 (s), 1170 (s), 1120 (s), 1080 (s), 910 (m), 680 (w), 590 (w), 570 (w) cm$^{-1}$; $^1$H NMR (500 MHz, CDCl$_3$) δ 7.98–7.96 (m, 1H), 7.82–7.81 (m, 2H), 7.80–7.76 (m, 1H), 7.68–7.63 (m, 2H), 7.57 (s, 1H), 7.48–7.36 (m, 5H), 7.34–7.20 (m, 15H), 5.46 (brs, 1H), 4.93 (d, J=11.0 Hz, 1H), 4.87 (d, J=11.4 Hz, 1H), 4.86 (d, J=11.0 Hz, 1H), 4.80 (d, J=11.0 Hz, 1H), 4.75 (d, J=11.4 Hz, 1H), 4.61 (d, J=11.0 Hz, 1H), 4.45 (d, J=7.8 Hz, 1H), 4.22 (app dt, J=9.5, 6.8 Hz, 1H), 3.87 (app dt, J=9.6, 7.1 Hz, 1H), 3.68 (dd, J=10.6, 2.1 Hz, 1H), 3.66–3.57 (m, 3H), 3.51–3.39 (m, 4H), 3.19–3.11 (m, 2H), 3.01 (app t, J=7.0 Hz, 2H), 1.91 (s, 3H), 1.59–1.54 (m, 2H), 1.49–1.43 (m, 2H), 1.39–1.31 (m, 2H) $^{13}$C NMR (125 MHz, CDCl$_3$) δ 170.0, 138.6, 138.3, 135.9, 135.2, 133.6, 133.3, 133.0, 131.1, 129.2, 129.1, 128.5, 128.4, 128.2, 128.0, 128.0, 127.9, 127.8, 127.6, 127.6, 126.7, 126.6, 126.2, 126.0, 125.8, 124.8, 123.5, 123.2, 119.8, 119.5, 113.8, 103.8, 84.7, 82.3, 78.0, 75.7, 75.0 (2C), 74.8, 71.5, 69.7, 68.8, 39.5, 29.3, 29.3, 25.7, 23.6, 23.3 high resolution mass spectrum (FAB, m-nitrobenzylalcohol) m/z 933.3786 [(M+Na)$^+$; calcd for C$_{54}$H$_{58}$O$_9$N$_2$SNa: 933.3761].

EXAMPLE 96

(+)-2-(1H-indol-3-yl)ethyl-6-O-(N-acetyl-5-aminopentyl)-3,4-di-O-benzyl-2-O-(2-naphthyl)methyl-β-D-glucopyranoside (IV-92)

To a solution of amide (+)-IV-91 (23 mg, 0.03 mmol) in ethanol (3 mL) was added 5 M sodium hydroxide (0.5 mL). Reaction was refluxed for 15 h. Solvents were removed in vacuo, residue was dissolved in dichloromethane and poured into water. After extraction, the organic layer was washed with brine, dried over anhydrous Na$_2$SO$_4$, filtered and concentrated. Purification using a 0.5 mm silica gel prep plate (100% ethyl acetate) afforded (+)-IV-92 (62% yield) as a colorless oil; [α]$_D^{20}$+7.2° (c 0.3, CHCl$_3$); IR (CHCl$_3$) 3480 (w), 3445 (w), 3010 (s), 2940 (m), 2870 (m), 1670 (s), 1520 (m), 1455 (m), 1365 (m), 1170 (m), 695 (m) cm$^{-1}$; $^1$H NMR (500 MHz, CDCl$_3$) δ 8.15 (br s, 1H), 7.80–7.66 (m, 5H), 7.63 (s, 1H), 7.58 (d, J=7.9 Hz, 1H), 7.47–7.42 (m, 9H), 7.39–7.24 (m, 3H), 7.17 (dt, J=8.0, 1.0 Hz, 1H), 7.09 (dt, J=7.9, 0.9 Hz, 1H), 7.03 (d, J=2.3 Hz, 1H), 5.37 (s, 1H), 4.96 (d, J=11.3 Hz, 1H), 4.93 (d, J=11.0 Hz, 1H), 4.85 (d, J=11.0 Hz, 1H), 4.80 (d, J=11.3 Hz, 1H), 4.79 (d, J=11.0 Hz, 1H), 4.59 (d, J=11.0 Hz, 1H), 4.47 (d, J=7.8 Hz, 1H), 4.24 (dt, J=9.4, 6.8 Hz, 1H), 3.88 (dt, J=9.4, 7.5 Hz, 1H), 3.69–3.41 (m, 8H), 3.16–3.12 (m, 4H), 1.91 (s, 3H), 1.59–1.50 (m, 2H), 1.48–1.43 (m, 2H), 1.38–1.29 (m, 2H), $^{13}$C NMR (125 MHz, CDCl$_3$) δ 170.1, 138.6, 138.3, 136.2, 136.1, 133.3, 132.9, 132.1, 132.0, 128.6, 128.4, 128.3, 127.9, 127.8, 127.8, 127.8, 127.6, 127.5, 126.7, 126.2, 125.9, 125.8, 122.2, 121.8, 119.2, 118.6, 112.6, 111.2, 103.7, 84.7, 82.3, 78.1, 75.7, 74.9, 74.7, 71.4, 70.1, 69.8, 39.6, 29.7, 29.3, 25.8, 23.6, 23.2 ppm; high resolution mass spectrum (FAB, m-nitrobenzylalcohol) m/z 793.3821 [(M+Na)$^+$; calcd for C$_{48}$H$_{54}$O$_7$N$_2$Na: 793.3828].

EXAMPLE 97

(−)-2-(1-phenysulfonyl-indol-3-yl)ethyl-4,6-di-O-acetyl-2,3-di-O-benzyl-β-D-glucopyranoside (IV-94)

To a flame-dried flask containing stir bar and crushed 4 Å molecular sieves (10 g) was added silver(I)oxide (5.1 g, 7.0 mmol) and dry hexanes (40 mL) under argon. A benzene (30 mL) solution of 4,6-di-O-acetyl-2,3-di-O-benzyl-β-D-glucopyranosyl bromide IV-93 (2.4 g, 5.0 mmol) and N-phenylsulfonylindole (2.3 g, 7.0 mmol) was added via cannula. The reaction stirred at room temperature, protected from light, under argon for 36 h. Subsequent to filtering the reaction through celite, the diacetate (−)-IV-94 was purified using flash silica gel chromatography (hexanes/ethyl acetate, 10:1) yielding 3.4 g IV-94 (94% yield) of a colorless oil; [α]$_D^{20}$−18.8° (c 0.2, CHCl$_3$); IR (CHCl$_3$) 3010 (m), 2910 (w), 1745 (s), 1450 (m), 1370 (s), 1230 (s), 1175 (s), 1120 (s), 1090 (s), 1040 (s), 690 (m), 590 (m), 560 (m) cm$^{-1}$; $^1$H NMR (500 MHz, CDCl$_3$) δ 7.98 (d, J=8.3 Hz, 1H), 7.84–7.82 (m, 2H), 7.51–7.44 (m, 3H), 7.38–7.21 (m, 12H), 7.16–7.14 (m, 2H), 5.03 (t, J=9.7 Hz, 1H), 4.80 (d, J=11.6 Hz, 1H), 4.68 (d, J=11.0 Hz, 1H), 4.59 (d, J=11.6 Hz, 1H), 4.57 (d, J=11.1 Hz, 1H), 4.44 (d, J=7.7 Hz, 1H), 4.24–4.17 (m, 2H), 4.08 (dd, J=12.2, 2.4 Hz, 1H), 3.84 (dt, J=9.5, 7.2 Hz, 1H), 3.57 (t, J=9.2 Hz, 1H), 3.53 (ddd, J=10.0, 5.1, 2.4 Hz, 1H), 3.47 (t, J=7.8 Hz, 1H), 3.02 (t, J=7.0 Hz, 2H), 2.05 (s, 3H), 1.91 (s, 3H) $^{13}$C NMR (125 MHz, CDCl$_3$) δ 170.8, 169.5, 138.3, 138.2, 138.0, 135.2, 133.6, 130.9, 129.1, 128.3, 128.3, 128.0, 127.8, 127.7, 127.6, 126.7, 124.8, 123.5, 123.1, 119.4, 119.4, 113.7, 103.7, 81.9, 81.5, 75.1, 74.9, 71.9, 69.7, 69.0, 62.4, 25.7, 20.8, 20.7 high resolution mass spectrum (CI) m/z 745.2781 [(M+NH$_4$)$^+$; calcd for C$_{40}$H$_{45}$N$_2$O$_{10}$S: 745.2795].

EXAMPLE 98

(−)-2-(1-phenylsulfonyl-indol-3-yl)ethyl-2,3-di-O-benzyl-b-D-glucopyranoside (IV-95)

Solid sodium methoxide (0.6 g, 11.7 mmol) was added to a methanolic (100 mL) solution of diacetate (−)-IV-94 (3.4 g, 0.5 mmol) at ambient temperature. Reaction stirred under argon for 16 h. Solvent was removed in vacuo, diethyl ether was added and the solution was poured into water and extracted. The organic layer was washed with brine, dried over MgSO$_4$, filtered and concentrated. Purification using flash silica gel column chromatography (hexanes/ethyl acetate, 7:3) afforded -IV-95 as a colorless oil (1.0 gram, 31% yield); [α]$_D^{20}$ −14.3° (c 0.4, CHCl$_3$); IR (CHCl$_3$)

3600–3400 (br, w), 3010 (s), 2920 (m), 2880 (m), 1450 (s), 1370 (s), 1180 (s), 1060 (s), 910 (m), 690 (m), 595 (m), 565 (m) cm$^{-1}$; $^1$H NMR (500 MHz, CDCl$_3$) δ 7.97 (d, J=8.2 Hz, 1H), 7.85–7.83 (m, 2H), 7.51 (s, 1H), 7.49–7.45 (m, 2H), 7.38–7.18 (m, 14H), 4.95 (d, J=11.6 Hz, 1H), 4.75 (d, J=11.1 Hz, 1H), 4.67 (d, J=11.5 Hz, 1H), 4.60 (d, J=11.1 Hz, 1H), 4.48 (d, J=7.5 Hz, 1H), 4.20 (dt, J=9.4, 6.9 Hz, 1H), 3.91–3.81 (m, 2H), 3.79–3.76 (m, 1H), 3.60–3.56 (m, 1H), 3.46–3.37 (m, 2H), 3.34–3.31 (m, 1H), 3.05–2.95 (m, 2H), 2.36 (br s, 1H), 2.15 (br s, 1H) $^{13}$C NMR δ 138.5, 138.3, 138.2, 135.2, 133.6, 130.9, 129.2, 128.6, 128.3, 128.0, 127.9, 127.9, 127.7, 126.7, 124.8, 123.6, 123.2, 119.6, 119.4, 113.8, 103.8, 83.9, 81.9, 75.2, 75.1, 74.7, 70.3, 68.8, 62.5, 25.7 high resolution mass spectrum (Cl) m/z 661.2586 [(M+NH$_4$)$^+$; calcd for C$_{36}$H$_{41}$N$_2$O$_8$S: 661.2586].

EXAMPLE 99

(−)-2-(1-phenylsulfonyl-indol-3-yl)ethyl-6-O-(5-azidopentyl)-2,3-di-O-benzyl-β-<u>D</u>-glucopyranoside (IV-96)

To a round bottomed flask containing dry alcohol (−)-IV-95 (228 mg, 0.35 mmol) was added a solution of 5-azido pentnol trifluoro methane sulfonate (<1 eq.) in dichloromethane. Solvent was removed in vacuo and the reaction flask was placed on a vacuum pump. Every 20 min. for the next 2.5 h, dichloromethane was added to the reaction vessel, reagents were solvated, and the solvent was again removed in vacuo prior to the reaction being placed on the vacuum pump. The azide (−)-IV-96 was purified using flash silica gel column chromatography (hexanes/ethyl acetate,) to yield 137 mg (60%) of recovered starting material and 64 mg (24% yield) of (−)-IV-96 as a colorless oil; [α]$_D^{20}$ −35.8° (c 0.1, CHCl$_3$); IR (CHCl$_3$) 3500 (br w), 3000 (m), 2940 (m), 2860 (m), 2100 (s), 1450 (s), 1370 (s), 1170 (s), 1120 (s), 1060 (s), 910 (s), 690 (m), 590 (m), 560 (m) cm$^{-1}$; $^1$H NMR (500 MHz, CDCl$_3$) δ 7.97 (d, J=8.3 Hz, 1H), 7.84–7.82 (m, 2H), 7.49–7.44 (m, 3H), 7.38–7.16 (m, 14H), 4.91 (d, J=11.4 Hz, 1H), 4.73 (d, J=11.5 Hz, 1H), 4.72 (d, J=11.1 Hz, 1H), 4.59 (d, J=11.1 Hz, 1H), 4.43 (d, J=7.8 Hz, 1H), 4.19 (dt, J=9.5, 6.9 Hz, 1H), 3.83 (dt, J=9.5, 7.1 Hz, 1H), 3.69 (ddd, J=10.4, 10.4, 6.1 Hz, 1H), 3.66 (ddd, J=10.4, 10.4, 5.2 Hz, 1H), 3.58 (t, J=8.4 Hz, 1H), 3.54–3.37 (m, 5H), 3.22 (t, J=6.9 Hz, 2H), 3.00 (t, J=7.0 Hz, 2H), 2.62 (s, 1H), 1.61–1.56 (m, 4H), 1.43–1.37 (m, 2H) $^{13}$C NMR (125 MHz, CDCl$_3$) δ 138.6, 138.3, 138.3, 135.2, 133.6, 131.0, 129.1, 128.5, 128.3, 128.0, 127.9, 127.8, 127.6, 126.7, 124.8, 123.5, 123.1, 119.6, 119.4, 113.8, 103.8, 84.0, 81.7, 75.3, 74.7, 73.8, 71.9, 71.6, 71.1, 68.8, 51.3, 29.1, 26.6, 25.7, 23.3 high resolution mass spectrum (Cl) m/z 772.3386 [(M+NH$_4$)$^+$; calcd for C$_{41}$H$_{50}$N$_5$O$_8$S: 772.3380].

EXAMPLE 100

(−)-2-(1-phenylsulfonyl-indol-3-yl)ethyl-6-O-(5-aminopentyl)-2,3-di-O-benzyl-β-<u>D</u>-glucopyranoside (IV-97)

Triphenylphosphine (33 mg, 0.13 mmol) was added to a solution (2.3 mL THF/0.04 mL H$_2$O) of azide (−)-IV-96 (36 mg, 0.5 mmol). The reaction was heated to 55° C. for 5 h. Solvents were removed in vacuo and the amine was purified using flash silica gel column chromatography (100% ethyl acetate gradient to 10% methanol in dichloromethane) to yield (−)-IV-97 as a colorless oil (28 mg, 73% yield); [α]$_D^{20}$ −7.4° (c 1.1, CHCl$_3$); IR (CHCl$_3$) 3500 (w), 3000 (m), 2940 (m), 2880 (m), 1450 (m), 1370 (s), 1170 (s), 1140 (s), 1060 (s), 590 (w), 570 (w) cm$^{-1}$; $^1$H NMR (500 MHz, CDCl$_3$) δ 7.97 (d, J=8.3 Hz, 1H), 7.84–7.82 (m, 2H), 7.49–7.43 (m, 3H), 7.37–7.20 (m, 12H), 7.18–7.16 (m, 2H), 4.89 (d, J=11.3 Hz, 1H), 4.75 (d, J=11.3 Hz, 1H), 4.71 (d, J=11.1 Hz, 1H), 4.59 (d, J=11.1 Hz, 1H), 4.42 (d, J=7.7 Hz, 1H), 4.19 (dt, J=9.5, 7.0 Hz, 1H), 3.82 (dt, J=9.5, 7.2 Hz, 1H), 3.68 (d, J=4.1 Hz, 2H), 3.66 (t, J=9.3 Hz, 1H), 3.56 (dt, J=9.6, 6.1 Hz, 1H), 3.46–3.36 (m, 4H), 3.00 (t, J=6.8 Hz, 2H), 2.65 (t, J=6.2 Hz, 2H), 2.19 (br s, 3H), 1.60–1.53 (m, 2H), 1.47–1.31 (m, 4H) $^{13}$C NMR (125 MHz, CDCl$_3$) δ 138.8, 138.4, 138.3, 135.2, 133.6, 131.0, 129.1, 128.4, 128.3, 128.0, 127.9, 127.7, 127.5, 126.7, 124.7, 123.5, 123.1, 119.7, 119.4, 113.7, 103.8, 84.5, 81.8, 75.4, 74.7, 74.2, 71.3, 71.0, 70.4, 68.7, 41.5, 32.2, 28.8, 25.7, 23.1 high resolution mass spectrum (Cl) m/z 746.3200 [(M+NH$_4$)$^+$; calcd for C$_{41}$H$_{52}$N$_3$O$_8$S: 746.3208].

EXAMPLE 101

(+)-2-(1H-indol-3-yl)ethyl-6-O-(5-aminopentyl)-2,3-di-O-benzyl-β-<u>D</u>-glucopyranoside (IV-98)

To a solution of amine (−)-IV-97 (26 mg, 0.04 mmol) in ethanol (4.4 mL) was added 5 M sodium hydroxide (0.72 mL). Reaction mixture was refluxed for 6 h. Solvents were removed in vacuo, residue was dissolved in dichloromethane (50 ml) and poured into water. After extraction, the organic layer was washed with brine, dried over anhydrous Na$_2$SO$_4$, filtered and concentrated. Purification using a 0.5 mm silica gel prep plate (dichloromethane/methanol, 9:1) afforded (+)-IV-98 (%) as a colorless oil; [α]$_D^2$+1.6° (c 0.3, CHCl$_3$); IR (CHCl$_3$) 3490 (m), 3400–3200 (vw), 3000 (s), 2960 (s), 2870 (s), 1455 (m), 1360 (m), 1230 (s), 1060 (vs), 1005 (s), 695 (m) cm$^{-1}$; $^1$H NMR (500 MHz, CDCl$_3$) δ 8.03 (s, 1H), 7.58 (d, J=7.8 Hz, 1H), 7.32–7.31 (m, 5H), 7.29–7.25 (m, 4H), 7.21–7.18 (m, 2H), 7.16 (d, J=7.8 Hz, 1H), 7.10 (t, J=7.3 Hz, 1H), 7.03 (s, 1H), 4.90 (d, J=11.3 Hz, 1H), 4.79 (d, J=11.1 Hz, 1H), 4.74 (d, J=11.3 Hz, 1H), 4.63 (d, J=11.1 Hz, 1H), 4.45 (d, J=7.3 Hz, 1H), 4.23 (app dt, J=9.4, 6.7 Hz, 1H), 3.84 (app dt, J=9.3, 7.4 Hz, 1H), 3.68 (d, J=4.2 Hz, 2H), 3.65 (t, J=8.8 Hz, 1H), 3.56 (app dt, J=9.6, 6.0 Hz, 1H), 3.47–3.36 (m, 5H), 3.11 (app t, J=7.0 Hz, 2H), 2.65 (br t, J=7.0 Hz, 2H), 2.16–1.92 (br s, 2H), 1.59–1.56 (m, 2H), 1.45–1.34 (m, 4H) $^{13}$C NMR (125 MHz, CDCl$_3$) δ 138.9, 138.6, 136.2, 128.4, 128.3, 128.0, 127.9, 127.7, 127.5, 127.5, 122.2, 121.9, 119.2, 118.7, 111.1, 103.8, 84.5, 81.9, 75.3, 74.8, 74.6, 74.2, 71.4, 71.1, 70.6, 70.0, 41.6, 32.4, 28.9, 25.8, 23.2 high resolution mass spectrum (Cl) m/z [(M+H)$^+$; calcd for C$_{35}$H$_{45}$N$_2$O$_6$:]

EXAMPLE 102

(−)-2-(1H-indol-3-yl)ethyl-6-O-(N-acetyl-5-aminopentyl)-2,3-di-O-benzyl-β-<u>D</u>-glucopyranoside (IV-99)

To a solution of amine (+)-IV-98 (7.5 mg, 0.013 mmol) in CH$_2$Cl$_2$ (1.5 mL) was added acetic anhydride (0.001 mL) and pyridine (0.001 mL). Reaction stirred for 10 min at room temperature. Solvents were removed in vacuo, residue was dissolved in dichloromethane and poured into water. After extraction, the organic layer was washed with brine, dried over anhydrous Na$_2$SO$_4$, filtered and concentrated. Purification using a 0.5 mm silica gel prep plate (dichloromethanelmethanol, 9:1) afforded 8.1 mg (−)-IV-99 (100% yield) as a colorless oil; [α]$_D^{20}$ −11.3° (c 0.2, CHCl$_3$); IR (CHCl$_3$) 3490 (br w), 3000 (m), 2920 (m), 2810 (m), 1665 (s), 1520 (m), 1450 (m), 1360 (m), 1230 (s), 1060 (s), 750 (w), 690 (m) cm$^{-1}$; $^1$H NMR (500 MHz, CDCl$_3$) δ 8.11 (s, 1H), 7.59 (d, J=7.9 Hz, 1H), 7.38–7.21 (m, 11H), 7.17 (app t, J=7.6 Hz, 7.10 (app t, J=7.4 Hz, 1H), 7.03 (d, J=2.2 Hz, 1H), 5.41 (s, 1H), 4.92 (d, J=11.4 Hz, 1H), 4.82 (d, J=11.0 Hz, 1H), 4.73 (d, J=11.4 Hz, 1H), 4.65 (d, J=11.0 Hz, 1H), 4.46 (d, J=7.3 Hz, 1H), 4.42 (dt, J=9.4, 6.9 Hz, 1H), 3.86 (dt, J=9.4, 7.5 Hz, 1H), 3.70 (dd, J=10.5, 3.9 Hz, 1H), 3.63 (dd, J=10.5, 5.4 Hz, 1H), 3.57 (t, J=8.2 Hz, 1H), 3.53–3.37 (m, 5H), 3.17 (app dt, J=13.1, 7.0 Hz, 2H), 3.11 (app t, J=7.2 Hz, 2H), 2.73 (d, J=1.9 Hz, 1H), 1.93 (s, 3H), 1.60–1.54 (m, 2H), 1.49–1.44 (m, 2H), 1.38–1.33 (m, 2H) $^{13}$C NMR (125 MHz, CDCl$_3$) δ 170.1, 138.7, 138.5, 136.2, 128.5, 128.3, 128.1, 128.0, 127.8, 127.6, 127.5, 122.2, 121.9, 119.2, 118.7, 112.6, 111.2, 103.8, 84.2, 81.8, 75.3, 74.6, 73.9, 71.8, 71.6, 71.0, 70.1, 39.6, 29.3, 29.1, 25.8, 23.5, 23.3 high resolution mass spectrum (CI) m/z 648.3656 [(M+NH$_4$)$^+$; calcd for C$_{37}$H$_{50}$N$_3$O$_7$: 648.3649]

EXAMPLE 104

The Use of Nonpeptide Peptidomimetics to Elucidate the Bioactive Conformation of L-363,301 (99)

Somatostatin, a cyclic tetradecapeptide, has attracted attention for its therapeutic potential. [Brazeau et al., Science 1973, 179, 77–79. Brazeau et al., Can. J. Biochem. 1974, 52, 1067–1072; Rivier et al., J. Am. Chem. Soc. 1974, 96, 2986–2992; ] Hirschmann et al. "Some Recent Developments in the Chemistry and Biology of Somatostatin-Related Peptides". In Chemistry of Natural Products: The Proceedings of Sino-American Symposium on Chemistry of Natural Products; Yu, W., Ed.; Gordon and Breach, Science Publishers: New York, 1982; pp 44–54 and references cited therein. Indeed the parenteral peptidal drug octreotide has been approved for clinical use; see: Bauer, W.; Briner, U.; Doepfner, W.; Haller, R.; Huguenin, R.; Marbach, P.; Petcher, T. J.; Pless, J. Life Sciences 1982, 31, 1133–1140. Lamberts, S. W.; van der Lely, A.-J.; de Herder, W. W.; Hofland, L. J. Octreotide. New Engl. J. Med. 1996, 334, 246–254. Sassolas, G. Eur. J. Endocrinology 1995, 133, 675–677. It has been demonstrated that Phe$^7$ of somatostatin has an axial disposition. Ueber, D. F.; Holly, F. W.; Paleveda, W. J.; Nutt, R. F.; Berg Strand, S. J.; Torchiana, M.; Glitzer, M. S.; Saper-Stein, R.; Hirschmann, R. Proc. Natl. Acad. Sci U.S.A. 1978, 75, 2636–2640. Arison, B. H.; Hirschmann, R.; Ueber, D. F. Bioorg. Chem, 1978, 7, 447–451. Arison, B. H.; Hirschmann, R.; Paleveda, W. J.; Brady, S. F.; Ueber, D. F. Biochem. Biophys. Res. Common 1981, 100, 1148–1153.

Similarly, several bicyclic, conformationally constrained peptidal SRIF analogs, containing an axial Phe$^7$, were found to be potent ligands. Veber et al, "Conformationally Restricted Bicyclic Analogs of Somatostatin" Proc. Natl. Acad. Sci. U.S.A. 1978, 75, 2636–2640. Freidinger, R., Merck Research Laboratories, private communication. It was determined that 2-benzyl group of III-4a mimics Phe$^7$ of the cyclic hexapeptide 1, so the mannose scaffold, with its axial C(2) hydroxyl, was used to gain information about the conformation of Phe$^7$ of the peptide 1.

The design of an appropriate mannose derivative required use of an L-sugar, in order to maintain the side chain in the 2 position in the same orientation as that of the Phe$^7$ of somatostatin. It was first demonstrated that the L-glucose based enantiomer of III-4a (IV-11) can bind the SRIF receptors on AtT-20 cells, although with somewhat lower affinity than III-4a (Table 1).

An L-mannose derivative IV-22 was then prepared. It was pleasing that the mannoside IV-22 bound the SRIF receptor on AtT-20 cells with an affinity about twice that of III-4a (Table 1). These results show that an axial substituent in the 2 position of the sugar enhances potency at SRIF receptors, and suggest that the Phe$^7$ in L-363,301 (1), the point of departure for the glycoside mimetics of the invention, is also axial (FIG. 39). X-ray crystallography of octreotide revealed that it, too, has an axial Phe$^7$: Pohl et al., "Acta Crystallogr., Sect. D 1995, 51, 48–59.

These results are consistent with the work of Goodman and Veber; see: (a) He, Y.-B.; Huang, Z.; Raynor, K.; Reisine, T.; Goodman, M.; J. Am. Chem. Soc. 1993, 115, 8066–8072. (b) Huang, Z.; Probstl, A.; Spencer, J. R.; Yamazaki, T.; Goodman, M. Int. J. Pept. Protein Res. 1993, 42, 352–365. (c) Huang, Z.; He, Y.-B.; Raynor, K.; Tallent, M.; Reisine, T.; Goodman, M. J. Am. Chem. Soc. 1992, 114, 9390–9401. (d) Brady, S. F.; Paleveda, Jr., W. J.; Arison, B. H.; Saperstein, R.; Brady, E. J.; Raynor, K.; Reisine, T.; Veber, D. F.; Freidinger, R. M. Tetrahedron 1993, 49, 3449–3466. This result demonstrates that the flow of information between peptide and peptidomimetic can be bidirectional, [Hirschmann, R.; Yao, W.; Cascieri, M. A.; Strader, C. D.; Maechier, L.; Cichy-Knight, M. A.; Hynes, Jr., J.; van Rijn, R. D.; Sprengeler, P. A.; Smith, A. B., III. J. Med. Chem. 1996, 39, 2441–2448], and provides evidence that the stereochemical diversity of readily available monosaccharides represents an important advantage of carbohydrate based scaffolds over hydrocarbon scaffolds. In a recent paper, Papageorgiou and collaborators sought to improve on the β-D-glucose scaffold through the synthesis of a furanoside. The resultant compound, though no more potent than III-5a, exemplifies the use of yet another sugar scaffold: Papageorgiou, C.; Haltiner, R.; Bruns, C.; Petcher, T. J. Bioorg. Med. Chem. Lett. 1992, 2, 135–140. Also, Nicolaou and coworkers have recently used pyranosides as potential mimics of the α$_v$β$_3$ antagonist cRGDFV albeit with limited success: Nicolaou, K. C.; Trujillo, J. I.; Chibale, K. Tetrahedron 1997, 53, 8751–8778.

EXAMPLE 105

Alternate Binding Mode of Monosaccharide III-8 at the SRIF Receptor

SARs in the SRIF-derived cyclic hexapeptides parallel those of the β-D-glycosides at the AtT-20 receptors, but it has now been shown that an L- or D-Trp residue in position 8 of SRIF and of the c-hexapeptides (SRIF numbering) is required for activity. Indeed, III-8 was synthesized as a negative control. This compound, in which a methoxy group replaced the Trp-mimicking side chain in III-4a, proved to be one of the more potent ligands at AtT-20 cell membranes (IC$_{50}$=5.9 μM for III-8a vs. 15.0 μM for III-4a). It appears that III-8a binds the SRIF receptors on AtT-20 cells in a manner different from our other active glycosides. In this alternate binding mode the 4-benzyloxy group would replace the indole ring.

Replacement of Phe$^7$ by His in cyclic hexapeptides and replacement of the 2-benzyl of III-5b by the imidazole moiety enhanced potency by factors of 1.6 and 3.5, respectively. Hirschmann, R.; Nicolaou, K. C.; Pietranico, S.; Leahy, E. M.; Salvino, J.; Arison, B.; Cichy, M. A.; Spoors, P. G.; Shakespeare, W. C.; Sprengeler, P. A.; Hamley, P.; Smith, A. B., III; Reisine, T.; Raynor, K.; Maechler, L.; Donaldson, C.; Vale, W.; Freidinger, R. M.; Cascieri, M. A.; Strader, C. D. De J. Am. Chem. Soc. 1993, 115, 12550–12568. If III-8a binds the SRIF receptors like the other sugars, then introduction of the imidazole residue in the 2 position should enhance activity. In fact this analog, III-10 proved to be inactive. If, on the other hand, the alternate binding mode hypothesis is correct, one would expect the isomeric 3-imidazole analog at least to retain comparable activity. This proved to be the case; IV-3g had an $IC_{50}$ of 5.6 µM, identical with that of III-8a (5.9 µM).

TABLE 1

Binding affinities of sugar analogs at AtT-20 receptors.

| Compound | AtT-20 cells $IC_{50}$ (µM) |
|---|---|
| III-4a | 15.0 |
| III-5a | 8.4 |
| III-5b | 7.0 |
| IV-11 | 47.0 |
| IV-22 | 8.0 |
| III-8a | 5.9 |
| III-10 | DNB |
| IV-30 | DNB |
| IV-39 | 5.6 |

DNB = Did Not Bind

The observed binding affinities of III-3, IV-30 and IV-39 at AtT-20 cells support the alternate binding made hypothesis. The orientation of the C(4) benzyl group relative to the Lys-mimicking side chain in the X-ray structure of the only crystalline intermediate (III-47a), the azido precursor of III-8a, is also consistent with the hypothesis.

EXAMPLE 106

The Role of the $Lys^9$-Mimicking Side Chain in SRIF Receptor Binding

Isomers of III-4a and III-5b in which the lysine mimicking side chain is linked via nitrogen rather than oxygen (i.e., III-4e and III-5c; Table 2) have affinities for the SRIF receptor that were about the same as those of III-4a and III-5b. Hirschmann, R.; Nicolaou, K. C.; Pietranico, S.; Leahy, E. M.; Salvino, J.; Arison, B.; Cichy, M. A.; Spoors, P. G.; Shakespeare, W. C.; Sprengeler, P. A.; Hamley, P.; Smith, A. B., III; Reisine, T.; Raynor, K.; Maechler, L.; Donaldson, C.; Vale, W.; Freidinger, R. M.; Cascieri, M. A.; Strader, C. D. *J. Am. Chem. Soc.* 1993, 115, 12550–12568.

TABLE 2

Binding affinities of sugar analogs at AtT-20 receptors.

| Compound | AtT-20 cells $IC_{50}$ (µM) |
|---|---|
| III-4e | 14.0 |
| III-5c | 5.1 |
| IV-42 | DNB |
| IV-51 | 13.0 |

DNB = Did Not Bind

The possibility that the primary hydroxyls of III-4e and III-5c replace the binding interactions normally provided by the primary amines of III-4a and III-5b. This interpretation became unattractive when it was found that the cyclic hexapeptide 9a, in which the e-amino group of lysine is replaced by a hydroxyl, and the N-acylated III-4d are both inactive. We believe therefore that it is the secondary amines of III-4e and III-5c that make possible the binding of these two compounds to the SRIF receptors. For cyclic hexapeptides such as L-363,301 (99), the lysine binding region is postulated to be on transmembrane helix #3 (TM3) at $Asp^{122}$. Underwood, D. Merck Research Laboratories, private communication. This raises the question whether the amines of the N-linked sugars (III-4e and III-5c) interact with the same functionality (i.e., $Asp^{122}$) of the receptor, as the primary amines of III-4a and III-5b, or whether the secondary amines III-4e and III-5c interact with a dibasic amino acid other than $Asp^{122}$. To address this question diamine IV-42 was synthesized. Since this ligand did not result in an increase in affinity, we suggest that $Asp^{122}$ is positioned so it can form a salt bridge either with the primary amines of III-4a and III-5a, or with the secondary amines of III-4e and III-5c.

EXAMPLE 107

The Unsolved Problem of the Indole-Mimicking Side Chain in SRIF Receptor Binding A combination of $^1H$ NMR and biological studies has established a direct relationship between potency of peptidal SRIF analogs and the observed shielding of the γ-methylene protons of $Lys^9$ by $Trp^8$. Arison, B. H.; Hirschmann, R.; Veber, D. F. *Biorg. Chem.* 1978, 7, 447–451. That D-Trp replacement enhances the potency of SRIF by an order of magnitude and also generates a dramatic upfield shift in the γ-methylene protons serves as an example. Rivier, J.; Brown, M.; Vale, W. *Biochem. Biophys. Res. Commun.* 1975, 65, 746–751. Arison, B. H.; Hirschmann, R.; Veber, D. F. NMR Studies. *Biorg. Chem.* 1978, 7, 447–451. None of the sugars showed such a shielding effect suggesting that the spatial relationship of the Trp- and Lys-mimicking side chains is not optimal. In the initial design of the sugars, typified by III-4a and III-5a, an ethylene group was inserted between the anomeric oxygen and the indole ring to prevent gramine fragmentation. To enhance affinity, the deoxy analog IV-51 was synthesized. This compound is not subject to gramine fragmentation. IV-51 did not improve the affinity ($IC_{50}$=22 µM) at AtT-20 cells, and failed to display the desired chemical shift in the $^1H$ NMR. Optimization of the interactions of the side chains in positions 99 and IV-11 of the sugars remains an important objective, if we are to achieve subnanomolar affinities.

EXAMPLE 108

Binding Affinities at Human SRIF Receptor Subtypes

It has been suggested that the affinity of SRIF for the mixture of SRIF receptors present on AtT-20 cells may depend in part on the subclone of the AtT-20 cell line and on the radioactive ligand employed. [Hirschmann, R.; Nicolaou, K. C.; Pietranico, S.; Leahy, E. M.; Salvino, J.; Arison, B.; Cichy, M. A.; Spoors, P. G.; Shakespeare, W. C.; Sprengeler, P. A.; Hamley, P.; Smith, A. B., III; Reisine, T.; Raynor, K.; Maechler, L.; Donaldson, C.; Vale, W.; Freidinger, R. M.; Cascieri, M. A.; Strader, C. D. *J. Am. Chem. Soc.* 1993, 115, 12550–12568. Sreedharan, S. P.; Kodama, K. T.; Peterson, K. E.; Goetzl, E. J. *J. Biol. Chem.* 1989, 264, 949–952. (b) He, H.-T.; Johnson, K.; Thermos, K.; Reisine, T. *Proc. Natl. Acad. Sci. U.S.A.* 1989, 86, 1480–1484. Kimura, N.; Hayafuji, C.; Kimura, N. Characterization of 17-b-estradiol-dependent and -independent somatostatin receptor subtypes in rat anterior pituitary. *J. Biol. Chem.* 1989, 264, 7033–7040. Rens-Domiano, S.; Law, S. F.; Yamada, Y.; Seino, S.; Bell, G. I.; Reisine, T. *Mol. Pharmacol.* 1992, 42, 28–34. Thus SRIF had an $IC_{50}$ of 0.83 nM against $^{125}I$-$Tyr^{11}$-SRIF and of 9.3 nM when $^{125}I$-CGP-23996 (des-$Ala^1$, $Gly^2$-desamino-$Cys^3$[$Tyr^{11}$]dicarba$^{3,4}$-somatostatin) was employed as the radio ligand. Nicolaou, K. C.; Salvino, J. M.; Raynor, K.; Pietranico, S.; Reisine, T.;

Freidinger, R. M.; Hirschmann, R. In *Peptides—Chemistry, Structure and Biology: Proceedings of the 11th American Peptide Symposium;* Rivier, J. E., Marshall, G. R., Eds.; ESCOM: Leiden, 1990; pp 881–884]. Since the AtT-20 cells are derived from transformed mouse cells they may contain receptor subtypes which have no counterparts among the five known human SSTRs. SRIF-14 had $K_i$'s ranging from 0.07 nM for hSSTR2 to 2.7 nM for hSSTR5 when $^{125}$I-Tyr$^{11}$-SRIF was the radioligand. This represents an attractive biological profile, because it has been suggested that SSTR2 controls the inhibition of the release of growth hormone (GH) and glucagon, whereas SRIF agonists inhibit insulin release via SSTR5. Inhibition of the release of GH and of glucagon, but not of insulin, is thought to be desirable for the treatment of adult onset diabetes. Hirschmann, R. Chemistry of Natural Products: The proceedings of Sino-American Symposium on Chemistry of Natural Products Yu W. ed.; Gordon and Breach, Science Publishers; New York, 1982, pp 44–54 and references cited therein. The affinity of SRIF for the five hSSTRs decreases in the order SSTR2>>SSTR1>SSTR3>SSTR4 and SSTR5. It is of interest to compare the profiles of III-4a, III-5a, and IV-22 with each other and with that of SRIF. Raynor, K.; Murphy, W. A.; Coy, D. H.; Taylor, J. E.; Moreau, J.-P.; Yasuda, K.; Bell, G. I.; Reisine, T. *Mol. Pharmacol.* 1993, 43, 838–842. Rossowski, W. J.; Coy, D. H. *Biochem. Biophys. Res. Commun.* 1994, 205, 341–346. Prior to the availability of receptor subtypes, only juvenile diabetics, who lack insulin, were thought to be likely to benefit from SRIF therapy. The dominant feature of the receptor subtype profile of SRIF is its high affinity for SSTR2. The profile of the three glycosides resemble each other more than they resemble SRIF, although both SRIF and the three peptidomimetics have the lowest affinity for hSSTR5. The most striking feature of all the glycosides reported herein is that they have a preference for SSTR4. To our knowledge no SRIF receptor ligand has heretofore revealed this property. This fact may make these glycosides useful tools for gaining an understanding of the function of this receptor subtype. The affinity profiles of glycoside III-4a, its 3-deoxy analog III-5a, and of the diastereomeric congener IV-22 at the five receptor subtypes resemble each other. Interestingly, IV-11, the enantiomer of III-4a, shares with III-4a, III-5a and IV-22, high affinities for hSSTR2 and hSSTR4 and a low affinity for SSTR1, but IV-22 in its binding affinity profile except for the fact that, like IV-11, it has an atypically high affinity for hSSTR5.

It was of particular interest to determine the profile of III-8a. This compound, also displays the highest affinity for hSSTR4, but differs markedly from all of the other glycosides at the other receptor subtypes. This latter result is consistent with the alternate binding mode hypothesis.

The glycoside IV-42, in which a secondary amino nitrogen replaces the C(6) oxygen, has a general profile that resembles that of III-4a. Moreover the average $K_i$'s for III-4a and IV-42 are 2.7 mM and 1.0 mM, respectively, indicating that the presence of two nitrogens in the C(6) side chains does enhance affinity but not sufficiently so to suggest the presence of a second salt bridge (see above). It is also of considerable interest that IV-42 displays submicromolar affinities at SSTRs 2, 3 and 4.

The most significant profile is that of IV-72 with $K_i$'s of 100 nM, 300 nM, 800 nM and 900 nM at SSTRs 4, 1, 2 and 3, respectively. Interestingly, IV-72 failed to bind SSTR5, a very appealing feature (see above). The $IC_{50}$'s of SRIF at AtT-20 receptors and the average affinity at the five hSSTRs are about the same (0.83 nM and 1.05 nM) when $^{125}$I-Tyr$^{11}$-SRIF is used as the radioactive ligand. It is important to note that the glycosidic peptidomimetics display higher affinities at selected human receptor subtypes than at the mutated mouse receptors of AtT-20 cells. That $K_i$'s of 100 nM are obtainable provides validation of our underlying design and shows that free rotation of the side chains does not preclude submicromolar affinities as has been suggested by others. [In a recent paper, Papageorgiou and collaborators sought to improve on the β-D-glucose scaffold through the synthesis of a furanoside. The resultant compound, though no more potent than III-5a, exemplifies the use of yet another sugar scaffold: Papageorgiou, C.; Haltiner, R.; Bruns, C.; Petcher, T. J. Design, Synthesis, and Binding Affinity of a Nonpeptide Mimic of Somatostatin. *Bioorg. Med. Chem. Lett.* 1992, 2, 135–140. Also, Nicolaou and coworkers have recently used pyranosides as potential mimics of the $a_vb_3$ antagonist cRGDFV albeit with limited success: Nicolaou, K. C.; Trujillo, J. I.; Chibale, K. Design, Synthesis and Biological Evaluation of Carbohydrate-Based Mimetics of cRGDFV. *Tetrahedron* 1997, 53, 8751–8778]. In addition, all of the results reported herein demonstrate that subtle changes in the sugar scaffold can change the biological profiles.

TABLE 3

Comparison of binding affinities of selected sugar analogs at AtT-20 and human SRIF subtype receptors

| Compound | AtT-20I $C_{50}$ ($\mu$M) | hSSTR 1$K_i$ ($\mu$M) | hSSTR 2$K_i$ ($\mu$M) | hSSTR 3$K_i$ ($\mu$M) | hSSTR 4$K_i$ ($\mu$M) | hSSTR 5$K_i$ ($\mu$M) |
| --- | --- | --- | --- | --- | --- | --- |
| III-4a | 15.0 | 4.0 | 1.8 | 2.8 | 1.1 | 3.7 |
| III-5a | 8.4 | 4.1 | 3.1 | 3.3 | 1.7 | 5.1 |
| IV-11 | 47.0 | 4.4 | 2.7 | 6.4 | 2.0 | 3.4 |
| IV-22 | 8.0 | 4.0 | 2.6 | 3.3 | 1.9 | 3.9 |
| III-8a | 5.9 | 2.4 | 4.6 | 3.0 | 2.0 | 3.0 |
| IV-42 | 13.0 | 2.1 | 0.6 | 0.6 | 0.5 | 1.3 |
| IV-60 | 4.1 | 6.8 | 4.6 | 6.2 | 3.0 | 4.0 |
| IV-72 | — | 0.3 | 0.8 | 0.9 | 0.1 | DNB |

DNB = Did Not Bind; refers to compounds with $K_i$'s >10,000 nM at hSSTR's

IV-11 differs in that it has a higher relative affinity for SSTR5 and a lesser relative affinity for SSTR3 than the other three glycosides. This demonstrates that subtle changes in the scaffold affect the biological profile. Compound IV-60, which possesses an imidazole substituent at C(2) mimicking the mutation Phe$^7$His in SRIF, resembles III-4a, III-5a and

EXAMPLE 109

Divergent SARs at SRIF and NK-1 Receptors

Compounds III-4a and III-5a are potent antagonist ligands for the NK-1 receptor subtype of substance P, and that these ligands also bind the $\beta_2$-adrenergic receptor as antagonists. Hirschmann, R.; Nicolaou, K. C.; Pietranico, S.; Salvino, J.;

Leahy, E. M.; Sprengeler, P. A.; Furst, G.; Smith, A. B., III; Strader, C. D.; Cascieri, M. A.; Candelore, M. R.; Donaldson, C.; Vale, W.; Maechler, L. *J. Am. Chem. Soc.* 1992, 114, 9217–9218. In contrast, SRIF and L-363,301 do not bind either the NK-1 or the $\beta_2$-adrenergic receptors. $\beta$-D-glycosides such as III-4a or III-5a provided the first direct evidence that peptides such as SRIF and nonpeptidal ligands, typified by catecholamines, bind G-protein coupled receptors in an analogous manner and that the binding sites of the SRIF, NK-1, and the $\beta_2$-adrenergic receptors have much in common. It was shown that this is indeed the case, since the potent c-hexapeptide SRIF agonist L-363,301 (9a) can be converted into the potent (2 nM) NK-1 receptor antagonist IV-100 with remarkable ease. Hirschmann, R.; Yao, W.; Cascieri, M. A.; Strader, C. D.; Maechler, L.; Cichy-Knight, M. A.; Hynes, Jr., J.; van Rijn, R. D.; Sprengeler, P. A.; Smith, A. B., III *J. Med. Chem.* 1996, 39, 2441–2448.These experiments demonstrated that peptidomimetics can provide valuable information about structural similarities between different receptors which cannot be obtained through studies with their endogenous ligands. To explore the relationship between peptidal and glycosidic ligands further, sugars designed and sugars related to IV-100 and IV-101 were synthesized ($IC_{50}$ 2 nM and 65 nM, respectively). Glycoside IV-92 was found to bind the NK-1 receptor with an $IC_{50}$ of 209 nM, whereas analogs IV-79, IV-81, IV-84 and IV-92, containing a $\beta$-naphthyl substituent did not bind the NK-1 receptors.

EXAMPLE 110

Summary of Biological Results

The N-acylated derivative of III-4a, compound III-4d, had an $IC_{50}$ of 60 nM at the NK-1 receptor. Hirschmann, R.; Nicolaou, K. C.; Pietranico, S.; Salvino, J.; Leahy, E. M.; Sprengeler, P. A.; Furst, G.; Smith, A. B., III; Strader, C. D.; Cascieri, M. A.; Candelore, M. R.; Donaldson, C.; Vale, W.; Maechler, L. *J. Am. Chem. Soc.* 1992, 114, 9217–9218. More recently the 4-unsubstituted analog IV-99 was prepared and found it to possess the highest affinity of any of our sugars for the NK-1 receptor (27 nM). Compound III-4d did not bind some sixty-five other receptors including the SRIF and $\beta_2$-adrenergic receptors. This result demonstrates that the monosaccharides can be both highly potent and highly specific. Results obtained with the $\beta$-D-glucosides had provided the first demonstration that the Trp mimicking side chains can enhance affinity in nonpeptidal ligands at the NK-1 receptors. Hirschmann, R.; Nicolaou, K. C.; Pietranico, S.; Salvino, J.; Leahy, E. M.; Sprengeler, P. A.; Furst, G.; Smith, A. B., III; Strader, C. D.; Cascieri, M. A.; Candelore, M. R.; Donaldson, C.; Vale, W.; Maechler, L. *J. Am. Chem. Soc.* 1992, 114, 9217–9218.

That seemingly small changes in the sugar scaffold can affect very differently the biological profile at the SRIF and NK-1 receptors is also exemplified by the finding that whereas IV-11 retained much of the activity of III-4a at the AtT-20 receptor, at the NK-1 receptor the former had an $IC_{50}$ of 150 nM but the latter did not bind. Thus switching from the D- to the L-glucose scaffold had a dramatic effect on binding affinities at the NK-1 but less so at the SRIF receptors. Similarly, going from the $\beta$-D-glucose scaffold (i.e., III-4a) to the L-mannose scaffold enhanced affinity at the somatostatin receptors on AtT-20 cells by a factor of two, but reduced the affinity at the NK-1 receptor from 150 nM to 1 nM. Finally, changing to the C-glycoside IV-51 did not significantly alter affinity at the SRIF receptor, but blocked binding at the NK-1 receptor.

What is claimed is:
1. A compound having the structure:

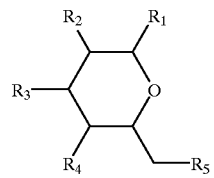

(3)

wherein;
$R_1$, $R_2$, $R_3$, $R_4$, and $R_5$ are, independently, H, OH, $OCH_3$, O—$(CH_2)_n NH_2$, O—$(CH_2)_n OH$, O—$(CH_2)_n NHC(O)$ $CH_3$, O—$(CH_2)_n$-indole, O-(benzyl), O—$(CH_2)_n$ (imidazole), pyridine, p-fluoro-benzyl, $CH_2$-$\beta$-naphthyl, $CH_2$-$\alpha$-naphthyl, —$(CH_2)_n$-indole, —$CH_2$Ph-OH,—$CH_2$-picolyl, —$NH(CH_2)_5 NH_2$, —$NH(CH_2)_3 NH(CO)CH_3$, or —$NH(CH_2)_5 OH$, —$NH(CH_2)_6 OH$, at least one of $R_2$, $R_3$, and $R_4$, is $OCH_3$, O—$(CH_2)_n NH_2$, O—$(CH_2)_n OH$, O—$(CH_2)_n NHC(O)CH_3$, O—$(CH_2)_n$-indole, O—$(CH_2)$(imidazole), pyridine, p-fluoro-benzyl, $CH_2$-$\beta$-naphthvl, $CH_2$-$\alpha$-naphthyl, —$(CH_2)_n$-indole, —$CH_2$Ph-OH,—$CH_2$-picolyl, —$NH(CH_2)_5 NH_2$, —$NH(CH_2)_3 NH(CO)CH_3$, or —$NH(CH_2)_5 OH$, —$NH(CH_2)_6 OH$, and n is 1, 2, 3, 4, 5, or 6.

2. A compound having the structure:

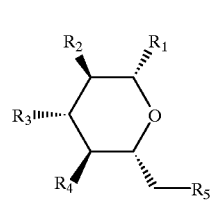

(4)

wherein:
$R_1$ is $OCH_3$, $R_2$ is O-(benzyl), $R_3$ is $O(CH_2)$(imidazole), and $R_4$ is O-(benzyl); or $R_1$ is O—$(CH_2)_2$(indole), $R_2$ is O—$(CH_2)$imidazole, $R_3$ is H, $R_4$ is O-(benzyl), and $R_5$ is $O(CH_2)_5 NH_2$; or $R_1$ is O—$(CH_2)_2$(indole) $R_2$ is O-(P-fluorobenzyl), $R_3$ is O-(benzyl), $R_4$ is O-(benzyl), and $R_5$ is $O(CH_2)_5 NHC(O)CH_2$; or $R_1$ is $O(CH_2)_2$(indole), $R_2$ is O-(benzyl), $R_3$ is O-(benzyl), $R_4$ is OH, and $R_5$ is $O(CH_2)_5 NHC(O)CH_3$; or $R_1$ is —$OCH_3$, $R_2$ is O-(benzyl), $R_3$ is O—$CH_2$(indole), $R_4$ is O-(benzyl) and $R_5$ is $O(CH_2)_5 NH_2$; or $R_1$ is O—$(CH_2)_2$(indole), $R_2$ is O-(p-fluorobenzyl), $R_3$ is O-(benzyl), $R_4$ is O-(benzyl), and $R_5$ is $(CH_2)_5 NHA_C$; or $R_1$, is $O(CH_2)_2$indole, $R_2$ is O—$(CH_2)$(imidazole), $R_3$ is O-(benzyl), $R_4$ is O-(benzyl), $R_5$ is $O(CH_2)_5 NH_2$.

3. The compound of claim 2 wherein $R_1$ is $OCH_3$, $R_2$ is O-(benzyl), $R_3$ is $O(CH_2)$ (imidazole), and $R_4$ is O-(benzyl).

4. The compound of claim 2 wherein $R_1$ is O—$(CH_2)_2$ (indole), $R_2$ is O—$(CH_2)$ imidazole, $R_3$ is H, $R_4$ is O-(benzyl), and $R_5$ is $O(CH_2)_5 NH_2$.

5. The compound of claim 2 wherein $R_1$ is O—$(CH_2)_2$ (indole), $R_2$ is O-(p-fluorobenzyl), $R_3$ is O-(benzyl), $R_4$ is O-(benzyl), and $R_5$ is $O(CH_2)_5 NHC(O)CH_2$.

6. The compound of claim 2 wherein $R_1$ is —OCH$_3$, $R_2$ is O-(benzyl), $R_3$ is O—CH$_2$(indole), $R_4$ is O-(benzyl) and $R_5$ is O(CH$_2$)$_6$NH$_2$.

7. The compound of claim 2 wherein $R_1$ is O—(CH$_2$)$_2$(indole), $R_2$ is O-(p-fluorobenzyl), $R_3$ is O-(benzyl), $R_4$ is O-(benzyl), and $R_5$ is (CH$_2$)$_5$NHA$_C$.

8. A compound having the structure:

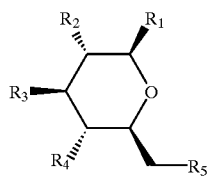

(5)

wherein:

$R_1, R_2, R_3, R_4$, and $R_5$ are H, OH, OCH$_3$, O—(CH$_2$)$_n$NH$_2$, O—(CH$_2$)$_n$OH, O—(CH$_2$)$_n$NHC(O)CH$_2$, O—(CH$_2$)$_n$-indole, O-(benzyl), pyridine, p-fluoro-benzyl, CH$_2$-β-naphthyl, O—(CH$_2$)$_n$(imidazole), CH$_2$-α-naphthyl, —(CH$_2$)$_n$-indole, —CH$_2$Ph-OH, —CH$_2$-picolyl, —NH(CH$_2$)$_5$NH$_2$, —NH(CH$_2$)$_3$NH(CO)CH$_3$, —NH(CH$_2$)$_5$OH, or —NH(Ch$_2$)$_6$OH, at least one of $R_2, R_3$, and $R_4$ is OCH$_3$, O—(CH$_2$)$_n$NH$_2$, O—(CH$_2$)$_n$OH, O—(CH$_2$)$_n$NHC(O)CH$_2$, O—(CH$_2$)$_n$-indole, pyridine, p-fluoro-benzyl, CH$_2$-β-naphthyl, O—(CH$_2$)$_n$(imidazole), CH$_2$-α-naphthyl, —(CH$_2$)$_n$-indole, —CH, Ph-OH, —CH$_2$-picolyl, —NH(CH$_2$)$_5$NH$_2$, —NH(CH$_2$)$_3$NH(CO)CH$_3$, —NH(CH$_2$)$_5$OH, or —NH(Ch$_2$)$_6$OH, and n is 1, 2, 3, 4, 5, or 6.

9. A compound having the structure:

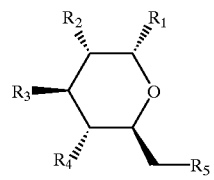

(6)

wherein:

$R_1, R_2, R_3, R_4$, and $R_5$ are H, OH, OCH$_3$, O—(CH$_2$)$_n$NH$_2$, O—(CH$_2$)$_n$OH, O—(CH$_2$)$_n$NHC(O)CH$_3$, O—(CH$_2$)$_n$-indole, O-(benzyl), O—(CH$_2$)$_n$(imidazole), pyridine, p-fluoro-benzyl, O—CH$_2$-β-naphthyl, O—CH$_2$-α-naphthyl, O—(CH$_2$)$_n$-indole, —CH$_2$Ph-OH, —CH$_2$-picolyl, —NH(CH$_2$)$_5$NH$_2$, —NH(CH$_2$)$_3$NH(CO)CH$_3$, or —NH(CH$_2$)$_5$OH, —NH(CH$_2$)$_6$OH;

at least one of $R_2, R_3$, and $R_4$ is OCH$_3$, O—(CH$_2$)$_n$NH$_2$, O—(CH$_2$)$_n$OH, O—(CH$_2$)$_n$NHC(O)CH$_3$, O—(CH$_2$)$_n$-indole, O—(CH$_2$)$_n$(imidazole), pyridine, p-fluorobenzyl, O—CH$_2$-β-naphthyl, O—CH$_2$-α-naphthyl, O—(CH$_2$)$_n$-indole, —CH, Ph-OH, —CH$_2$-picolyl, —NH(CH$_2$)$_5$NH$_2$, —NH(CH$_2$)$_3$NH(CO)CH$_3$, or —NH(CH$_2$)$_5$OH, —NH(CH$_2$)$_6$OH, and n is 1, 2, 3, 4, 5, or 6.

10. A compound having the structure:

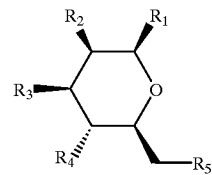

(7)

wherein:

$R_1, R_2, R_3, R_4$, and $R_5$ are H, OH, OCH$_3$, O—(CH$_2$)$_n$NH$_2$, O—(CH$_2$)$_n$OH, O—(CH$_2$)$_n$NHC(O)CH$_2$, O—(CH$_2$)$_n$-indole, O-(benzyl), pyridine, p-fluoro-benzyl, CH$_2$-β-naphthyl, CH$_2$-α-naphthyl, —(CH$_2$)$_n$-indole, —CH$_2$Ph-OH, —CH$_2$-picolyl, —NH(CH$_2$)$_5$NH$_2$, —NH(CH$_2$)$_3$NH(CO)CH$_3$, —NH(CH$_2$)$_5$OH, or —NH(CH$_2$)$_6$OH, at least one of $R_2, R_3$, and $R_4$ is OCH$_3$, O—(CH$_2$)$_n$NH$_2$, O—(CH$_2$)$_n$OH, O—(CH$_2$)$_n$NHC(O)CH$_2$, O—(CH$_2$)$_n$-indole, pyridine, p-fluoro-benzyl, CH$_2$-β-naphthyl, CH$_2$-α-naphthyl, —(CH$_2$)$_n$-indole, —CH$_2$Ph-OH, —CH$_2$-picolyl, —NH(CH$_2$)$_5$NH$_2$, —NH(CH$_2$)$_3$NH(CO)CH$_3$, —NH(CH$_2$)$_5$OH, or —NH(CH$_2$)$_6$OH, and n is 1, 2, 3, 4, 5, or 6.

11. A compound of claim 10 wherein $R_1$, is O(CH$_2$)$_2$indole, $R_2$ is O—(CH$_2$)(imidazole), $R_3$ is O-(benzyl), $R_4$ is O-(benzyl), $R_5$ is O(CH$_2$)$_5$NH$_2$.

12. A compound having the structure:

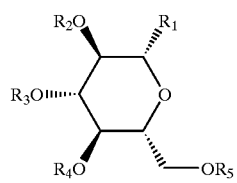

(8)

wherein:

$R_1$ is H, OH, OCH$_3$, O—(CH$_2$)$_n$NH$_2$, O—(CH$_2$)$_n$OH, O—(CH$_2$)$_n$NHC(O)CH$_3$, O—(CH$_2$)-indole, O-(benzyl), pyridine, p-fluoro-benzyl, CH$_2$-β-naphthyl, O—(CH$_2$)$_n$imidazole; CH$_2$-α-naphthyl, —(CH$_2$)$_n$-indole, —CH$_2$Ph-OH, —CH$_2$-picolyl, —NH(CH$_2$)$_5$NH$_2$, —NH(CH$_2$)$_3$NH(CO)CH$_3$, $R_2, R_3, R_4, R_5$ are, independently, H, CH$_3$, (CH$_2$)$_n$NH$_2$, (CH$_2$)$_n$OH, (CH$_2$)$_n$(imidazole), (CH$_2$)NHC(O)CH$_2$, (CH$_2$)-indole, benzyl, pyridine, p-fluoro-benzyl, CH$_2$-β-naphthyl; CH$_2$-α-naphthyl, —(CH$_2$)$_n$-indole, —CH$_2$Ph-OH, —CH$_2$-picolyl, —NH(CH$_2$)$_5$NH$_2$, —NH(CH$_2$)$_3$NH(CO)CH$_3$, NH(CH$_2$)$_5$OH, or —NH(CH$_2$)$_6$OH, at least one of $R_2, R_3$, and $R_4$, is CH$_3$, (CH$_2$)$_n$NH$_2$, (CH$_2$)$_n$OH, (CH$_2$)$_n$(imidazole), (CH$_2$)NHC(O)CH$_3$, (CH$_2$)-indole, pyridine, p-fluoro-benzyl, CH$_2$-β-naphthyl; CH$_2$-α-naphthyl, —(CH$_2$)$_n$-indole —CH$_2$Ph-OH, —CH$_2$-picolyl, —NH(CH$_2$)$_5$NH$_2$, —NH(CH$_2$)$_3$NH(CO)CH$_3$, NH(CH$_2$)$_5$OH, or —NH(CH$_2$)$_6$OH, n is 0, 1, 2, 3, 4, 5, or 6.

13. A compound having the structure:

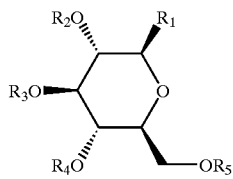

(9)

wherein:
- $R_1$ is H, OH, $OCH_3$, $O-(CH_2)_nNH_2$, $O-(CH_2)_nOH$, $O-(CH_2)_nNHC(O)CH_3$, $O-(CH_2)$-indole, O-(benzyl), pyridine, p-fluoro-benzyl, $CH_2$-β-naphthyl, and $(CH_2)_n$(imidazole);
- $R_2$, $R_3$, $R_4$, $R_5$ are H, $CH_3$, $(CH_2)_nNH_2$, $(CH_2)_nOH$, $(CH_2)_nNHC(O)CH_3$, $(CH_2)_n$-indole, benzyl, pyridine, p-fluoro-benzyl, $CH_2$-β-naphthyl, $(CH_2)_n$(imidazole); $CH_2$-α-naphthyl, $-(CH_2)_n$-indole, $-CH_2Ph$-OH, $-CH_2$-picolyl, $-NH(CH_2)_5NH_2$, $-NH(CH_2)_3NH(CO)CH_3$, or $-NH(CH_2)_5OH$, $-NH(CH_2)_6OH$;
- at least one of $R_2$, $R_3$, and $R_4$, is $CH_3$, $(CH_2)_nNH_2$, $(CH_2)_nOH$, $(CH_2)_nNHC(O)CH_3$, $(CH_2)_n$-indole, pyridine, p-fluoro-benzyl, $CH_2$-β-naphthyl, $(CH_2)_n$(imidazole); $CH_2$-α-naphthyl, $-(CH_2)_n$-indole, $-CH_2Ph$-OH, $-CH_2$-picolyl, $-NH(CH_2)_5NH_2$, $-NH(CH_2)_3NH(CO)CH_3$, or $-NH(CH_2)_5OH$, $-NH(CH_2)_6OH$; and
- n is 0, 1, 2, 3, 4, 5, or 6.

14. A compound having the structure:

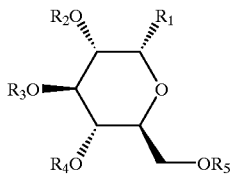

(10)

wherein:
- $R_1$, $R_2$, $R_3$, $R_4$, and $R_5$ are H, OH, $OCH_3$, $O-(CH_2)_nNH_2$, $O-(CH_2)_nOH$, $O-(CH_2)_nNHC(O)CH_3$, $O-(CH_2)$-indole, O-(benzyl), pyridine, p-fluoro-benzyl, $CH_2$-β-naphthyl, $CH_2$-α-naphthyl, $-(CH_2)_n$-indole, $-CH_2Ph$-OH, $-CH_2$-picolyl, $-NH(CH_2)_5NH_2$, $-NH(CH_2)_3NH(CO)CH_3$, $-NH(CH_2)_5OH$, $-NH(CH_2)_6OH$,
- at least one of $R_2$, $R_3$, and $R_4$ is $OCH_3$, $O-(CH_2)_nNH_2$, $O-(CH_2)_nOH$, $O-(CH_2)_nNHC(O)CH_3$, $O-(CH_2)$-indole, pyridine, p-fluoro-benzyl, $CH_2$-β-naphthyl, $CH_2$-α-naphthyl, $-(CH_2)_n$-indole, $-CH_2$ Ph-OH, $-CH_2$-picolyl, $-NH(CH_2)_5NH_2$, $-NH(CH_2)_3NH(CO)CH_3$, $-NH(CH_2)_5OH$, $-NH(CH_2)_6OH$, and
- n is 1, 2, 3, 4, 5, or 6.

15. A compound having the structure:

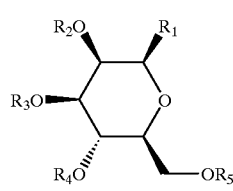

(11)

wherein:
- $R_1$, $R_2$, $R_3$, $R_4$, and $R_5$ are H, OH, $OCH_3$, $O-(CH_2)_nNH_2$, $O-(CH_2)_nOH$, $O-(CH_2)_nNHC(O)CH_3$, $O-(CH_2)$-indole, O-(benzyl), pyridine, p-fluoro-benzyl, $CH_2$-β-naphthyl, $CH_2$-α-naphthyl, $-(CH_2)_n$-indole, $-CH_2Ph$-OH, $-CH_2$-picolyl, $-NH(CH_2)_5NH_2$, $-NH(CH_2)_3NH(CO)CH_3$, $-NH(CH_2)_5OH$, $-NH(CH_2)_6OH$,
- at least one of $R_2$, $R_3$, and $R_4$ is $OCH_3$, $O-(CH_2)_nNH_2$, $O-(CH_2)_nOH$, $O-(CH_2)_nNHC(O)CH_3$, $O-(CH_2)$-indole, pyridine, p-fluoro-benzyl, $CH_3$-β-naphthyl, $CH_2$-α-naphthyl, $-(CH_2)_n$-indole, $-CH_2Ph$-OH, $-CH_2$-picolyl, $-NH(CH_2)_5NH_2$, $-NH(CH_2)_3NH(CO)CH_3$, $-NH(CH_2)_5OH$, $-NH(CH_2)_6OH$, and
- n is 1, 2, 3, 4, 5, or 6.

* * * * *